US008324264B1

(12) United States Patent
Eldridge et al.

(10) Patent No.: US 8,324,264 B1
(45) Date of Patent: Dec. 4, 2012

(54) INHIBITORS OF BACTERIAL BIOFILMS AND RELATED METHODS

(75) Inventors: Gary R. Eldridge, St. Louis, MO (US); Ronald Neil Buckle, Delmar, NY (US); Michael Ellis, Clifton Park, NY (US); Zhongping Huang, Voorheesville, NY (US); John Edward Reilly, Voorheesville, NY (US)

(73) Assignee: Sequoia Sciences, Inc., St. Louis, MO (US)

( * ) Notice: Subject to any disclaimer, the term of this patent is extended or adjusted under 35 U.S.C. 154(b) by 0 days.

(21) Appl. No.: 13/188,790

(22) Filed: Jul. 22, 2011

(51) Int. Cl.
*A61K 31/416* (2006.01)
*C07D 231/54* (2006.01)

(52) U.S. Cl. .................................... 514/406; 548/358.1
(58) Field of Classification Search .................. 514/406; 548/358.1
See application file for complete search history.

(56) References Cited

U.S. PATENT DOCUMENTS

| | | | |
|---|---|---|---|
| 3,996,132 A | 12/1976 | Mateos et al. |
| 4,606,911 A | 8/1986 | Hayashi et al. |
| 4,897,268 A | 1/1990 | Tice et al. |
| 4,929,365 A | 5/1990 | Clark et al. |
| 5,075,109 A | 12/1991 | Tice et al. |
| 5,312,813 A | 5/1994 | Costerton et al. |
| 5,462,644 A | 10/1995 | Woodson |
| 5,789,239 A | 8/1998 | Eyers et al. |
| 5,834,437 A | 11/1998 | Jew et al. |
| 5,882,916 A | 3/1999 | Wiersma et al. |
| 5,906,825 A | 5/1999 | Seabrook et al. |
| 5,985,601 A | 11/1999 | Ni et al. |
| 6,080,323 A | 6/2000 | Yu et al. |
| 6,264,926 B1 | 7/2001 | Farooqi et al. |
| 6,267,897 B1 | 7/2001 | Robertson et al. |
| 6,267,979 B1 | 7/2001 | Raad et al. |
| 6,369,101 B1 | 4/2002 | Carlson |
| 6,395,189 B1 | 5/2002 | Fabri et al. |
| 6,399,115 B2 | 6/2002 | Revel |
| 6,410,256 B1 | 6/2002 | Ceri et al. |
| 6,423,219 B1 | 7/2002 | Chandler |
| 6,455,031 B1 | 9/2002 | Davies et al. |
| 6,468,549 B1 | 10/2002 | Dupuis et al. |
| 6,498,862 B1 | 12/2002 | Pierson et al. |
| 6,555,055 B1 | 4/2003 | Cisar et al. |
| 6,585,961 B1 | 7/2003 | Stockel |
| 6,596,505 B2 | 7/2003 | Ceri et al. |
| 6,669,929 B1 | 12/2003 | Boyd et al. |
| 6,762,160 B2 | 7/2004 | Barbeau et al. |
| 6,946,124 B2 | 9/2005 | Arnaud-Sebillotte et al. |
| 7,098,227 B2 | 8/2006 | Dunkel et al. |
| 7,326,542 B2 | 2/2008 | Bassler et al. |
| 7,604,978 B2 | 10/2009 | Eldridge |
| 7,612,045 B2 | 11/2009 | Eldridge |
| 2002/0037260 A1 | 3/2002 | Budny et al. |
| 2002/0110530 A1 | 8/2002 | Harper et al. |
| 2003/0113742 A1 | 6/2003 | Whiteley et al. |
| 2003/0225126 A1 | 12/2003 | Markham et al. |
| 2004/0033548 A1 | 2/2004 | Bassler et al. |
| 2004/0033549 A1 | 2/2004 | Greenberg et al. |
| 2004/0136203 A1 | 7/2004 | Boyd et al. |
| 2005/0137259 A1 | 6/2005 | Matsuyama et al. |
| 2005/0143428 A1 | 6/2005 | Dunkel et al. |
| 2006/0014285 A1 | 1/2006 | Eldridge et al. |
| 2006/0014290 A1 | 1/2006 | Eldridge |
| 2006/0228384 A1 | 10/2006 | Eldridge |
| 2006/0264411 A1 | 11/2006 | Eldridge |
| 2007/0014739 A1 | 1/2007 | Eldridge et al. |
| 2008/0145322 A1 | 6/2008 | Eldridge |

FOREIGN PATENT DOCUMENTS

| | | |
|---|---|---|
| WO | WO 98/08091 A1 | 2/1998 |
| WO | WO 2006/010147 A2 | 1/2006 |
| WO | WO 2006/019881 A2 | 2/2006 |
| WO | WO 2006/019926 A2 | 2/2006 |
| WO | WO 2006/031943 A1 | 3/2006 |
| WO | WO 2006/102255 A1 | 9/2006 |

OTHER PUBLICATIONS

U.S. Appl. No. 11/479,095, filed Jun. 30, 2006, Eldridge, Gary R.
U.S. Appl. No. 12/327,349, filed Dec. 3, 2008, Eldridge et al.
Abe, F., et al., Ursolic acid as a trypanocidal constituent in rosemary, Biol. Pharm. Bull., Nov. 2002, 25(11): 1485-1487.
Adler and Epstein, Phosphotransferase-System Enzymes as Chemoreceptors for Certain Sugars in *Escherichia coli* Chemotax, Proc. Nat. Acad. Sci. USA, Jul. 1974, 71(7): 2895-2899.
Adnyana et al., J. Nat. Prod., 2001, vol. 64, pp. 360-363 (Abstract).
Akamatsu, H. et al., The inhibition of free radical generation by human neutrophils through the synergistic effects of metronidazole with palmitoleic acid: a possible mechanism of action of metronidazole in rosacea and acne, Archives of Dermatological Research, 1990, 282: 449-454.
Anderson et al., Intracellular Bacterial Biofilm-Like Pods in Urinary Tract Infections, www.sciencemag.org, Jul. 4, 2003, pp. 105-107.
Ando, E. et al., Biofilm Formation Among Methicillin-Resistant *Staphylococcus aureus* Isolates from Patients with Urinary Tract Infection, Acta Med. Okayama, 2004, 58(4): 207-214.
Arevalo-Ferro, C. et al., Biofilm Formation of *Pseudomonas putida* IsoF: the role of quorum sensing as assessed by proteomics, Systematic and Applied Microbiology, 2005, vol. 28, 87-114.
Auger, S. et al., Global Expression Profile of *Bacillus subtilis* Grown in the Presence of Sulfate or Methionine, Journal of Bacteriology, Sep. 2002, 184(18): 5179-5186.
Ballesta-Acosta, M. C. et al., A New 24-nor-Oleanase Triterpenoid from *Salvia darduacea*, J. Nat. Prod., 2002, 65: 1513-1515.
Bannon, C.D., et al., Chlorination of Olean-12-Enes, Database Accession No. 1976:44437 Abstract & Australian Journal of Chemistry, 1976, pp. 2649-2654, vol. 28, No. 12.

(Continued)

*Primary Examiner* — Rebecca Anderson
*Assistant Examiner* — Samantha Shterengarts
(74) *Attorney, Agent, or Firm* — McNeely Hare & War; Christopher Casieri

(57) ABSTRACT

Certain multi-cyclic compounds and compositions thereof are useful for reducing or inhibiting the growth of bacterial biofilms and for controlling bacterial biofilm infections. Such compounds and compositions are also useful in methods for reducing or inhibiting the growth of biofilms and for controlling bacterial biofilm infections involving biofilms.

62 Claims, 1 Drawing Sheet

OTHER PUBLICATIONS

Begum, S. at al., Chemical Constituents From the Leaves of *Psidium guajava*, Database Accession No. 2004:177767 Abstract & Natural Product Research, 2004, pp. 135-140, vol. 18, No. 2.

Begum et al, Triterpenoids from the Leaves of *Eucalyptus camaldulensis* var. obtusa, J. Nat. Prod. 1997, 60, pp. 20-23 (Abstract).

Beloin, C., et al., Finding gene-expression patterns in bacterial biofilms, Trends in Microbiology, Jan. 2005, pp. 16-19, vol. 13, No. 1, Elsevier Science Ltd.

Boddicker, J. D. et al., Differential binding to and biofilm formation on, HEp-2 cells by *Salmonella enterica* Serovar Typhimurium is dependent upon allelic variation in the fimH gene of the fim gene cluster, Molecular Microbiology, 2002, 45(5): 1255-1265.

Borum, P. R. and Monty, K. J., Regulatory Mutants and Control of Cysteine Biosynthetic Enzymes in *Salmonella typhimurium*; Journal of Bacteriology, Jan. 1976, pp. 94-101, vol. 125, No. 1, USA.

Both, D., at al., Liposome-encapsulated ursolic acid increases ceramides and collagen in human skin cells, Arch Dermatol. Res., 2002, 293: 569-575.

Bowden et al., Abstract & Database Crossfire Beilstein, Beilstein Institut zur Forderung der Chemischen Wissenschaften, Frankfurt am Main, DE, 1975, pp. 91-103, Database Accession No. BRN 2189905, Australian J. Chem., vol. 28.

Brieskorn, C. H. et al., and Escehelbach Glykamine Von ORsol— Und 18Beta-Glycyrrhetinsaure, Archiv Der Pharmazie, VCH Verlagsgesellschaft MBH, Weinhelm, DE, Sep. 1, 1979, pp. 752-762, vol. 312, No. 9.

Burkhart, Craig N. et al., Microbiology's principle of biofilms as a major factor in the pathogenesis of acne vulgaris, International J. of Dermatology, 2003, 42: 925-927.

Byrne, C., et al., DNA Sequences of the cysK Regions of *Salmonella typhimurium* and *Escherichia coli* and Linkage of the cysK Regions to ptsH, Journal of Bacteriology, Jul. 1988, 170(7): 3150-3157.

Cardenas, C. et al., Effects of ursolic acid on different steps of the angiogenic process, Biochem. Biophys. Res. Commun., Jul. 23, 2004, 320: 402-408.

Centers for Disease Control and Prevention, Update: Investigation of Bioterrorism-Related Anthrax and Interim Guidelines for Exposure Management and Antimicrobial Therapy, Oct. 26, 2001, MMWR 2001, 50 (42): 909-919.

Centers for Disease Control and Prevention, Guidelines for the Prevention of Intravascular Catheter-Related Infections, MMWR, 2002, 51: No. RR-10.

Chambers 21st Century Dicitonary, Chambers Harrap Publishers Limited 2001, Retrieved Jul. 7, 2008, from http:// www.credoreference.com/entry/1215201.

Chaturvedula et al., A New Ursane Triterpene from Monochaetum Vulcenicum that Inhibits DNA Polymerase βLyase, J. Nat. Prod. 2004, 67, pp. 889-901 (Abstract).

Coldren, C. et al., Gene Expression Changes in the Juman Fibroblast Induced by *Centella asiatica* Triterpenoids, Planta Med., 2003, 69: 725-732.

Conley, J. et al., Biofilm Formation by Group A *Streptococci*: Is There a Relationship with Treatment Failure?, J. Clin. Microbiol., Sep. 2003, 41(9): 4043-4048.

Corey E. J. and Lee, J.; Enantioselective Total Synthesis of Oleanolic Acid, Erythrodiol, β-Amyrin, and Other Pentacyclic Triterpenes from a Common Intermediate, J. Am. Chem. Soc., 1993, 115: 8873-8874.

Cortés, G. et al., Role of Lung Epithelial Cells in Defense against *Klebsiella pneumoniae* Pneumonia, Infect. and immun., Mar. 2002, 70(3): 1075-1080.

Cossart P. and Sansonetti, P. J., Bacterial Invasion: The Paradigms of Enteroinvasive Pathogens, Science, Apr. 9, 2004, 304: 242-248.

Costerton, J. W. et al., Bacterial Biofilms: A Common Cause of Persistent Infections, Science, May 21, 1999, 284: 1318-1322.

Cremin P. A. and Zeng, L., High-Throughput Analysis of Natural Product Compound Libraries by Parallel LC-MS Evaporative Light Scattering Detection, Anal. Chem., Nov. 1, 2002, 74(21): 5492-5500.

Cywes, C. et al., Group A *Streptococcus* tissue invasion by CD44-mediated cell signaling, Nature, 2001, 414, pp. 648-652.

Darouiche, R. et al., A Comparison of Two Antimicrobial-impregnated Central Venous Catheters, New Engl. Jour. Med., 1999, 340(1), pp. 1-8.

Datsenko and Wanner, One-step inactivation of chromosomal genes in *Escherichia coli* K-12 using PCR products, PNAS, Jun. 6, 2000, 97(12), pp. 6640-6645.

Demuth, D. et al., Discrete Protein Determinant Directs the Species-Species Adherence of *Porphyromonas gingivalis* to Oral *Streptococci*, Infection and Immunity, 2001, 69(9), pp. 5736-5741.

Ding, H. and Demple, B., Thiol-Mediated Disassembly and Reassembly of [2Fe-2S] Clusters in the Redox-Regulated Transcription Factor SoxR; American Chemical Society, 1998, pp. 17280-17286, vol. 37, published on Web Nov. 19, 1998.

Dolan, Rodney M. et al,, Biofilms: Survival mechanisms of clinically relevant microorganisms, Clinical Microbiology Reviews, Apr. 2002, vol. 15, No. 2: 167-193.

Drefahl, G. and Huneck, S., Ober Reduktionsprodukte verschiedener Triterpenoxime und Triterpensaureamids, Chemische Berichte, Verlag Chemie GMBH Weinheim, DE, 1960, pp. 1967-1975.

Drefahl, G. and Huneck, S., Abstract Database Crossfire Beilstein, Beilstein Institut zur Forderung der Chemischen Wissenschaften, Frankfurt am Main, DE, Database Accession No. BRN 2824441, 4114508, 2825723, Chem. Ber., 1961, pp. 1145-1150, vol. 94.

Edwards, J. et al., The role of lipooligosaccharide in *Neisseria gonorrhoeae* pathogenisis of cervical epithelia: lipid A serves as a C3 acceptor molecule, Cellular Micro., 2002, 4(9), pp. 585-598.

Edwards, R. and Harding, K.G., Bacteria and wound healing, Curr. Opin. Infect. Dis., 2004, 17: 91-96.

Eldridge, G. et al., High-throughput method for the production and analysis of large natural product libraries for drug discover, Analytical Chemistry., Aug. 15, 2002, vol. 74, No. 16, pp. 3963-3971.

Elsinghorst, Eric A., Measurement of Invasion by Gentamicin Resistance, Methods Enzymology, 1994, 236, pp. 405-420.

Elvers et al., Biofilms and Biofouling, Encyclopedia of Microbiology, 2000, vol. 1, 2nd edition, pp. 478-485.

Farina, C. et al., Synthesis and Anti-Ulcer Activity of New Derivatives of Glycyrrhetic, Oleanolic and Ursolic Acids, II Farmaco, 1998, 53, pp. 22-32.

Finlay, B.B. and Cossart, P., Exploitation of Mammalian Host Cell Funtions by Bacterial Pathogens, Science, May 2, 1997, 276, pp. 718-725.

Fried et al., J. Structure-Activity Relationship in the Field of Antibacterial Steroid Acid, J. Med. Chem., 1965, vol. 8, No. 3, pp. 279-282.

Frimodt-Moller, Niels, Correlation Between Pharmacokinetic/ Pharmacodynamic Parameters and Efficacy for Antibiotics in the Treatment of Urinary Track Infection, International Journal of Antimicrobial Agents, 2002, 19, pp. 546-553.

Gallardo-Madueno, R., et al., In Vivo Transcription of nrdAB Operon and of grxA and fpg Genes I Triggered in *Escherichia coli* Lacking both Thioredoxin and Glutaredoxin 1 or Thioredoxin and Glutathione, Respectively; Journal of Biologica Chemistry, Jul. 17, 1998, pp. 18382-18388, vol. 273, No. 29, The American Society for Biochemistry and Molecular Biology, Inc. U.S.A.

Gao, Ze-Li et al., Effect of Sea buckthorn on liver fibrosis: A clinical study, World J. Gastroenterol, Jul. 15, 2003, vol. 9, No. 7, pp. 1615-1617.

Garcia-Granados, A., Epoxides, Cyclic Sulfites, and Sulfate from Natural Pentacyclic Triterpenoids: Theoretical Calculations and Chemical Transformations, J. Org. Chem., 2003, pp. 4833-4844, vol. 68, No. 12.

Greiner, L. et al., Biofilm Formation by *Neisseria gonorrhoeae*, Infect. and Immun., Apr. 2005, vol. 73, No. 4, pp. 1964-1970.

Greiner, L. et al., Nontypeable *Haemophilus influenzae* Strain 2019 Produces a Biofilm Containing N-Acetylneuraminic Acid that may mimic Sialylated 0-Linked Glycans, Infect. and Immun., Jul. 2004, vol. 72, No. 7, ppl 4249-4260.

Hall-Stoodley, Luanne, et al., Bacterial biofilms: Form the natural environment to infectious diseases, Nature Reviews Microbiology, Feb. 2004, Bol. 2, No. 2, pp. 95-108.

Hanna, H.A. at al., Antibiotic-Impregnated Catheters Associated with Significant Decrease in Nosocomial and Multidrug-Resistant Bacteremias in Critically III Patients, Chest, Sep. 2003, vol. 124, No. 3, pp. 1030-1038.

Hardy, G. et al., The Pathogenesis of Disease Due to Nontypeable *Haemophilus Influenzae*, Methods Mol. Med., 2007, vol. 71, M. Herbort © Humana Press Inc., Totawa, NJ, USA, pp. 1-28.

Harrison-Balestra, C. et al., A Wound-isolated *Pseudomonas aeruginosa* Grows a Biofilm In Vitro Within 10 Hours and Is Visualized by Light Micro Dermatol. Surg. 29, 631-635, 2003.

Hesse, H. et al., Molecular analysis and control of cysteine biosynthesis: integration of nitrogen and sulphur metabolism, J. Exp. Bot., Jun. 2004, vol. 55, No. 401, pp. 1283-1292.

Hichri, Faycal et al., Antibacterial Activities of a Few Prepared Derivatives of Oleanic Acid and of Other Natural Triterpenic Compounds, Comptes Rendus Chimie, 2003, vol. 6, No. 4, pp. 473-483.

Hogema, B.M., at al., Inducer exclusion in *Escherichia coli* by non-PTS substrates: the role of the PEP to pyruvate ratio in determining the phosphorylation state of enzyme IIA Glc, Molecular Microbiology, 1998, vol. 30, No. 3, Blackwell Science Ltd.

Honda, T. et al., Design and Synthesis of 2-Cyano-3, 12-Dioxoolean-1, 9-Dien-28-Oic Acid, A Novel and Highly Active Inhibitor of Nitric Oxide Production in Mouse Macrophages, Bioorganic & Medicinal Chemistry Letters, 1998, vol. 8, pp. 2711-2714.

Honda, T. et al., New Enone Derivatives of Oleanolic Acid and Ursolic Acid as Inhibitors of Nitric Oxide Production in Mouse Macrophages, Bioorganic & Medicinal Chemistry Letters, 1997, vol. 7, No. 13, pp. 1623-1628.

Honda, T. et al., Novel Synthetic Oleanane Triterpenoids: A Series of Highly Active Inhibitors of Nitric Oxide Production in Mouse Macrophages; Bioorganic & Medicinal Chemistry Letters 9, Elseview Science Ltd., 1999, pp. 3429-3434.

Howell-Jones, R.S. et al., A review of the microbiology, antibiotic usage and resistance in chronic skin wounds, J. Antimicrob. Ther., Jan. 2005, vol. 55, No. 2, pp. 143-149.

Hsu, H. et al., Methods of Decocting and Administering Herbal Drugs, and 382. Centellae Herba, Oriental Materia Medica: A Concise Guide, Oriental Healing Arts Institute, 1986, 39-40 and 443-444.

Hsu, Y. at al., Proliferative inhibition, cell-cycle dysregulation, and induction of apoptosis by ursolic acid in human non-small cell lung cancer A549 cells, Life Sciences 75, Sep. 24, 2004, pp. 2303-2316.

Hu, J.F. et al., Antibacterial, Partially Acetylated Obigorhamnosides from Cleistopholis patens, J. Nat. Prod., American Chemical Society and American Society of Pharmacognosy, 2006, vol. 69, No. 4, pp, 585-590.

Hu, J.F. et al., Cyclolignans from *Scyphocephalium ochocoa* via high-throughput natural product chemistry methods; Phytochemistry, 2005, 66, pp. 1077-1082.

Hu, J.F. et al., Application of Capillary-scale NMR for the Structure Determination of Phytochemicais, Phytochem. Anal., 2005, 16, pp. 127-133.

Hu, J.F. et al., Miniaturization of the Structure Elucidation of Novel Natural Products—Two Trace Antibacterial Acylated Caprylic Alcohol Gylcosides from *Arctostaphylosis pumila*, Planta Med., 2005, 71, pp. 176-180.

Huang, A.X. et al., An Exceptionally Short and Simple Enantioselective Total Synthesis of Pentacyclic Triterpenes of the β-Amyrin Family, J. Am. Chem. Soc., 1999, vol. 121, No. 43, pp. 9999-10003.

Ikuta, A. et al., Ursane- and Oleannane-Type Triterpenes from *Ternstroemia gymnanthera* Callus Tissues, J. Nat. Prod., 2003, 66, pp. 1051-1054.

Isobe, T. et al., Studies on the Constituents of Leucoseptrum Stellipillum, STN Database Accession No. 1989:404216 Abstract & Natural Product Research 1989, vol. 109, No. 3, pp. 175-178.

Jackson, D.W. et al., Biofilm Formation and Dispersal under the Influence of the Global Regulator CsrA of *Escherichia coli*, Journal of Bacteriology, Jan. 2002, vol. 184, No. 1, pp. 290-301.

Jackson, D.W. et al., Catabolite Repression of *Escherichia coli* Biofilm Formation, Journal of Bacteriology, Jun. 2002, vol. 184, No. 12, pp. 3406-3410.

Jain, S.M., Atal, C.K., & Abstract Database Crossfire Beilstein, Beilstein Institut zur Forderung der Chemischen Wissenschaften, Frankfurt am Main, DE, Database Accession No. BRN, 5692755, 5775629, Indian J. Chem., 1986, vol. 25, Sect. B, pp. 427-428.

Jarrett, C.O. et al., Transmission of *Yersinia pestis* from an Infectious Biofilm in the Flea Vector, JID, Aug. 15, 2004, vol. 190, pp. 783-792.

Jones, S.M. et al., Effect of vancomycin and rifampicin on methicillin-resistant *Staphylococcus aureus* biofilms, The Lancet, 2001, vol. 357, pp. 40-41.

Justice, S. et al., Differentiation and developmental pathways of uropathogenic *Escherichia coli* in urinary tract pathogenesis, PNAS, Feb. 3, 2004, vol. 101, No. 5, pp. 1333-1338.

Kaplan, J.B., Methods for the treatment and prevention of bacterial biofilms, Expert Opinion on Therapeutic Patents, Ashley Publications, GB, 2005, vol. 15, No. 8, pp. 995-965.

Karting, T., Clinical Applications of *Centella asiatica* (L.) Urb., Herbs, Spices and Medicinal Plants, Oryx Press, Arizona, USA 1998, vol. 3, pp. 145-173.

Kaufman, P.B. at al., Phytochemicals: The Chemical Components of Plants and Bioseparation of Compounds, Chapters 1 and 7, Natural Products from Plants, CRC Press LLC, Boca Raton, USA, 1999, pp. 1-36 and 207-240.

Kiley, P.J. and Beinert, H., The role of Fe-S proteins in sensing and regulations in bacteria, Current Opinion in Microbiology, 2003, pp. 181-185, vol. 6, www.currentopinion.com.

Konoike, T. et al., Synthesis of [2-13C] Oleanolic Acid and [2-13C]-Myricerone, Tetrahedron, 1999, vol. 55, pp. 14901-14914.

Landa, A.S. et al., Efficacy of Ophthalmic Solutions to Detach Adhering *Pseudomonas aeruginosa* from Contact Lenses, 1998, Cornea, vol. 17, No. 2, pp. 293-300.

Lavender, H.F. et al., Biofilm Formation In Vitro and Virulence In Vivo of Mutants of *Klebsiella pneumonia*, Infect. and Immun., Aug. 2004, vol. 72, No. 8, pp. 4888-4890.

Leroy-Dudal, J. et al., Role of αvβ5 integrins and vitronectin in *Pseudomonas aeruginosa* PAK interaction with A549 respiratory cells, Microbes and infection 6, 2004, pp. 875-881.

Leyh, T. et al., The DNA Sequence of the Sulfate Activation Locus form *Escherichia coli* K-12, The Journal of Biological Chemistry, May 25, 1992, vol. 267, No. 15, pp. 10405-10410.

Li, Yung-Hua, et al., Natural Genetic Transformation of *Streptococcus* mutans Growing in Biofilms, J. Bacteriol., Feb. 2001, vol. 183, No. 3, pp. 897-908.

Liaw, Shwu-Jen et al., Modulation of swarming and virulence by fatty acids through the RsbA Protein in *Proteus mirabilis*, Infect. Immun., Dec. 2004, vol. 72, No. 12, pp. 6836-6845.

Lilic, M. at al., Identification of the CysB-regulated gene, hslJ, related to the *Escherichia coli* novobiocin resistance phenotype, FEMS Microbiology Letters 224, 2003, pp. 239-246.

Linde, H., Zur Synthese Eliniger Stickstoffhaltiger Oleanol- und Ursolsaurederivate, Arch. Pharm., 1979, vol. 312, pp. 832-837.

Lipsky, Benjamin A., Medical Treatment of Diabetic Foot Infections, CID, 2004, 39 (Suppl 2), pp. S104-S114.

Lochowska, A. et al., Identification of activating region (AR) or *Escherichia coli* LysR-type transcription factor CysB and CysB contact site on RNA polymerase alpha subunit at the cysP promoter, Molecular Microbiology, 2004, vol. 53, No. 3, pp. 791-806.

Lochowska, A. et al., Functional Dissection of the LysR-type CysB Transcriptional Regulator, The Journal of Biological Chemistry, Jan. 19, 2001, vol. 276, No. 3, pp. 2098-2107.

Ma, Chao-Mei et al., Chemical Modification of Oleanene Type Triterpenes and their Inhibitory Activity Against HIV-1Protease Dimerization, Chemical & Pharmaceutical Bulletin, 2000, vol. 48, No. 11, pp. 1681-1688.

Mah Thien-Fah, C. et al., Mechanism of biofilm resistance to antimicrobial agents, Trends in Microbiology, Jan. 2001, vol. 9, No. 1, pp. 34-39.

Maki, D. G. at al., Prevention of Central Venous Catheter-Related Bloodstream Infection by Use of an Antiseptic-Impregnated Catheter, Ann. Int. Med., 1997, vol. 127, No. 4, pp. 257-266.

Martinez, J. J. at al., Type 1 pilus-mediated bacterial invasion of bladder epithelial cells, The EMBO Journal, 2000, vol. 19, No. 12, pp. 2803-2812.

Martinez, J.J. and Hultgren, S,J., Requirement of Rho-family GTPases in the invasion of Type 1-piliated uropathogenic *Escherichia coli*, Cellular Microbiology, 2002, vol. 4, No. 1, pp. 19-28.

McLaughlin-Borlace, L. et. al., Bacterial biofilm on contact lenses and in lens storage cases in wearers with microbial keratitis, J. of Applied Microbiology, 1998, vol. 84, pp. 827-838.

Menzies, B.E., The role of fibronectin binding proteins in the pathogenesis of *Staphylococcus aureus* infections, Curr. Opin. Infect. Dis., 2003, 16, pp. 225-229.

Mi, Y. et al., Total Synthesis of (+)-α-Onocerin in Four Steps via Four-Component Coupling and Tetracyclization Steps, J. Am. Chem. Soc., 2002, 124, pp. 11290-11291.

Miranda-Vizuete, A. et al., The Levels of Ribonucleotide Reductase, Thioredoxin, Glutaredoxin 1, and GSH are balanced in *Escherichia coli* K12, The Journal of Biological Chemistry, Aug. 9, 1996, pp. 19099-19103, vol. 271, No. 32, The American Society for biochemistry and Molecular Biology, Inc., USA.

Mulvey, M.A. et al., Induction and Evasion of Host Defenses by Type 1-Piliated Uropathogenic *Escherichia coli*, Science, Nov. 20, 1998, 282, pp. 1494-1497.

Murphy, K. and Campellone, K.G., Lambda Red-mediated recombinogenic engineering of enterohemorrhagic and enteropathogenic *E. coli*, BMC Molecular Biology, 2003, 4, pp. 1-12.

Murakami, S. et al., Ursolic acid, an antagonist for transforming growth factor (TGF) beta 1, FEBS Lett., May 21, 2004, 566, pp. 55-59.

Nishimura, K. et al., Activity-Guided Isolation of Triterpenold Acyl CoA Cholestryl Acyl Transferase (ACAT) Inhibitors from Ilex kudincha, J. Nat. Prod., 1999, 62, pp. 1061-1064.

Nociari, M.M. et al., A novel one-step, highly sensitive fluorometric assay to evaluate cell-mediated cytotoxicity, J. Immunol. Met., 1998, 213, pp. 157-167.

Ojinnaka, C.M., et al., The Chemical Constituents of *Musanga Cecropioides*, Database Accession No. 1985:419849, Abstract & Journal of Natural Products, 1985, vol. 48, No. 2, pp. 337.

Olofsson, A-C. et al., N-Acetyl-L-Cysteine Affects Growth, Extracellar Polysaccharide Productions, and Bacterial biofilm Formation on Solid Surfaces, Applied and Environmental Microbiology, Aug. 2003, vol. 69, No. 8, pp. 4814-4822.

Osawa, K. et al., Antibacterial and Antihemolytic Activity of Triterpenes and beta-Sitosterol Isolated from Chinese Quince (Chaenomeles Sinesis), Database CA 'Online! Chemical Abstracts Service, Columbus, Ohio, US, STN Database accession No. 1997:741679 abstract & Natural Medicines, 1997, pp. 365-367, Tokyo.

Parry, J. and Clark, D., Identification of a CysB-regulated gene involved in glutathione transport in *Escherichia coli*, FEMS Microbiology Letters, 2002, 209, pp. 81-85.

Pendland, S.L. et al., In vitro synergy testing of levofloxacin, ofloxacin, and ciprofloxacin in combination with aztreonam, ceftazidime, or piperacillin against *Pseudomonas aeruginosa*, Diagnostic Microbiology and Infectious Disease, 2002, 42, pp. 75-78.

Perez-Giraldo, C. et al., Influence of N-acetylcysteine on the formation of biofilm by *Staphylococcus epidermidis*, Journal of Antimicrobial Chemotherapy, The British Society for Antimicrobial Chemotherapy, 1997, vol. 267, pp. 643-646.

Pirzada, O.M. et al., Improved lung function and body mass index associated with long-term use of Macrolide antibiotics, J. Cystic Fibrosis, 2003, 2, pp. 69-71.

Pratt, L. and Kolter, R., Genetic analysis of *Escherichia coli* biofilm formation: roles of flagella, motility, chemotaxis and type I pili, Molecular Microbiology, Oct. 1998, vol. 30, No. 2, pp. 285-293.

Prieto-Alamo, M-J. et al., Transcriptional Regulation of Glutaredoxin and Thioredoxin Pathways and Related Enzymes in Response to Oxidative Stress, The American Society for biochemistry and Molecular Biology, Inc., May 5, 2000, vol. 275, No. 18, pp. 13398-13405, USA.

Price, L.B. et al., In vitro selection and characterization of *Bacillus anthracis* mutants with high-level resistance to ciprofloxacin, Antimicrobial Agents Chemotherapy, Jul. 2003, vol. 47, No. 7, pp. 2362-2365.

Quan, J. et al., Regulation of carbon utilization by sulfur availability in *Escherichia coil* and *Salmonella typhimurium*, Microbiology, 2002, 148, pp. 123-131.

Raad, I. et al., Central Venous Catheters Coated with Minocycline and Rifampin for the Prevention of Catheter-Related Colonization and Bloodstream Infections, Ann. Int. Med., Aug. 15, 1997, vol. 127, Issue 4, pp. 267-274.

Ramage, G. et al., Formation of Propionibacterium acnes biofilms on orthopaedic biomaterials and their susceptibility to antimicrobials, Biomaterials, 2003, 24, pp. 3221-3227.

Ramsey, B.W. at al., Intermittent Administration of Inhaled Tobramycin in Patients with Cystic Fibrosis, New England J. Medicine, 1999, vol. 340, No. 1, pp. 23-30.

Rashid, M.H. et al., Polyphosphate kinase is essential for biofilm development, quorum sensing, and virulence of *Pseudomonas aeruginosa*, Proc. Natl. Acad. Sci., 10.107283397, Aug. 15, 2000, vol. 97. No. 17, pp. 9636-9641.

Ren, D. et al., Stationary-Phase Quorum-Sensing Signals Affect Autoinducer-2 and Gene Expression in *Escherichia coli*, Applied and Environmental Microbiology, Apr. 2004, vol. 70, No. 4, pp. 2038-2043.

Ren, D. et al., Differential Gene Expression for Investigation of *Escherichia coli* Biofilm Inhibition by Plant Extract Ursolic Acid, Applied and Environmental Microbiology, Jul. 2005, vol. 71, No. 7, pp, 4022-4034.

Russo, T.A. and Johnson, J.R., Medical and economic impact of extrainstestinal infections due to *Escherichia coli*: focus on an increasingly important endemic problem, Microbes and Infection 5, 2003, pp. 449-456.

Saiman, L., The use of macrolide antibiotics in patients with cystic fibrosis, Curr. Opin. Pulm. Med., 2004, 10, pp. 515-523.

Sauer, K. et al., Characterization of Nutrient-Induced Dispersion in *Psuedomonas aeruginosa* PA01 Biofilm, Journal of Bacteriology, Nov. 2004, vol. 186, No. 21, pp. 7312-7326.

Sauer, K. and Camper, A.K., Characterization of Phenotypic Changes in *Pseudomonas putida* in Response to Surface-Associated Growth, J. Bacteriol., Nov. 2001, vol. 183, No. 22, pp. 6579-6589.

Schembri, M. et al., An attractive surface: gram-negative bacterial biofilms, Science's Stke, May 2002, vol. 2002, No. 132, pp. 1-8.

Schwab, U.E. et al., Role of Actin Filament Network in *Burkholderia multivorans* Invasion in Well-Differentiated Human Airway Epithelia, Infect. and Immun., Nov. 2003, vol. 71, No. 11, pp. 6607-6609.

Silverman, R.B., The Organic Chemistry of Drug Design and Drug Action, 2nd Ed., Elsevier Academy Press, 2004.

Singh, P.K. et al., A component of innate immunity prevents bacterial biofilm development; Nature, May 30, 2002, vol. 417, Nature Publishing Group, pp. 552-555.

Slack, J.M. Stem Cells in Epithelial Tissues, (Review) Science, 2000, vol. 287, No. 25, pp. 1431-1433.

Stanley, N. et al., Identification of Catabolite Repression as a Physiological Regulator of Biofilm Formation by *Bacillus subtilis* by Use of DNA Microarrays, Journal of Bacteriology, Mar. 2003, vol. 185, No. 6, pp. 1951-1957.

Sturgill, G. et al., Role of CysE in Production of an Extracellular Signaling Molecule in *Providencia stuartli* and *Excherichia coli*: Loss of cysE Enhances Biofilm Formation in *Escherichia coli*, J. Bacteriol., Nov. 2004, vol. 186, No. 22, pp. 7610-7617.

Takai, T. et al, Effects of temperature and volatile fatty acids on nitrification-denitrification activity in small-scale anaerobic-aerobic recirculation biofilm process, Water Sci. Techno. , 1997, vol. 35, No. 6, pp. 101-108.

Takechi, M. et al., Structure—Activity Relationships of Synthetic Methyl Ursolate Glycosides, Phytochemistry, 1993, vol. 34, No. 3, pp. 657-677.

Tamura, Y. et al., Antimicrobial Activities of Saponins of Pericarps of *Sapindus mukurossi* on Dermatophytes, STN Database Accession No. 2001:412378 Abstract & Natural Medicines, 2001 vol. 55, No. 1, pp. 11-16 Tokyo, Japan.

Tran, Q.H., et al., Role of glutathione in the formation of the active form of the oxygen sensor FNR ([4Fe-4S]-FNR) and in control of FNR function, Eur. J. Biochem., 2000, vol. 267, pp. 4817-4824.

Utaisincharoen, P. et al., *Burkholderia pseudomallei* invasion and activation of epithelial cells requires activation of p38 mitogen-activated protein kinase, Microbial Pathgenesis 38, 2005, pp. 107-112.

Van Der Ploeg, J. et al.,. Functional analysis of the *Bacillus subtilis* cysK and cysJI genes, FEMS Microbiology Letters 201, 2001, pp. 29-35.

Veeh, R.H. et al., Detection of *Staphylococcus aureus* Biofilm on Tampons and Menses Component, JID, Aug. 15, 2003, 188, pp. 519-530.

Vergauwen, B. et al., Exogenous Glutathione Completes the Defense against Oxidative Stress in *Haemophilus influenzae*, Journal of Bacteriology, Mar. 2003, vol. 185, No. 5, pp. 1572-1581.

Verschueren, K., et al., Crystallization of full-length CysB of *Klebsiella aerogenes*, a LysT-type transcriptional regulator, Acta Cryst., 2001, D57, pp. 260-262.

Wang, M., et al., Studies of Chemical Constituents from Root of Rubus, STN Database Accession No. 2003:597250 Abstract & Zhongcaoyao, 2003, vol. 34, No. 4, pp. 295-297.

Wei, Y. et al., Journal of Bacteriology, 2001, vol. 183, No. 2, pp. 545-556.

Wein, L.M. et al., Emergency response to an anthrax attack, PNAS, Apr. 1, 2003, vol. 100, No. 7, pp. 4346-4351.

Wille, J.J. et al., Palmitoleic Acid Isomer (C16:1Δ6) in Human Skin Sebum Is Effective against Gram-Positive Bacteria, Skin Pharmacol. Appl. Skin Physiol., 2003, 16, pp. 176-187.

Wrzeciono et al., Abstract & Database Crossfire Beilstein, Beilstein Institut zur Forderung der Chemischen Wissenschaften, Fankfurt am Main, DE, Database Accession No. BRN 3041373, 3040548, 3040547, 2923199, Rocz. Chem., 1973, Vol, 47, pp. 955-961.

Xavier, K. and Bassler, B., LuxS quorum sensing: more than just a numbers game, Current Opinion in Microbiology, 2003, 6, pp. 191-197.

Xie, H. et al., Intergeneric Communication in Dental Plaque Biofilms (Notes), J. Bacteriol., Dec. 2000, vol. 182, No. 24), pp. 7067-7069.

Yang, B. et al., Effects of dietary supplementation with sea buckthorn (*Hippophae rhamnoides*) seed and pulp oils on atopic dermatitis, J. Nutr. Biochem., 1999, 10, pp. 622-630.

Yoo, H-D. et al., Suaveolindole, a New Mass-Limited Antibacterial Indolosesquiterpene from Greenwayodendron suaveolens Obtained via High-Throughput Natural Products Chemistry Methods, American Chemical Society and American Society of Pharmacognosy, J. Nat. Prod., published on web Jan. 8, 2005, vol. 68, No. 1, pp. 122-124.

Yoshida, M. et al., Antiproliferative Constituents from Umbeliiferae Plants VII. 1) Active Triterpenes and Rosmarinic Acid from *Centella asiatica*, Biol. Pharm. Bull, 2005, vol. 28, No. 1, pp. 173-175.

"Antibacterial Program" from Sequoia Sciences' website located at www.sequoiasciences.com/Antibacterials.htm, Oct. 26, 2004, pp. 1-2.

Blast search of the cysB gene at the Microbial Genomics database at the National Center for Biotechnology Information (NCBI) of the National Institutes of Health (NIH), http://www.ncbi.nim.nih.gov/sutils/genom_table.cgi, Sep. 26, 2007.

Results of search performed by NERAC for scientific articles regarding Biofilm, Jan. 28, 2005, pp. 1-40.

European Search Report for Application No. 0579135 dated Jun. 29, 2007, Publication No. EP1771558A2.

European Search Report for Application No. 05791709.8 dated Oct. 10, 2007, Publication No. EP1773313A2.

International Search Report for PCT/US2005/24946 (WO/2006/1010147), Jan. 26, 2006.

International Search Report for PCT/US2005/25016 (WO/2006/019926 A2), Feb. 23, 2006.

International Search Report for PCT/US2005/24945 (WO/2006/019881), Feb. 23, 2006.

International Preliminary Report on Patentability completed on Feb. 21, 2006 for PCT/US05/24946 (WO06/010147).

International Preliminary Report on Patentability completed on Jun. 5, 2007 for PCT/US05/32874 (WO06/031943).

International Preliminary Report on Patentability completed on Oct. 18, 2006 for PCT/US0524945 (WO06/019881).

International Preliminary Report on Patentability completed on Oct. 1, 2006 for PCT/US05/25016 (WO06/019926).

International Preliminary Report on Patentability completed on Aug. 7, 2006 for PCT/US06/10088 (WO06/102255).

Written Opinion of the International Search Authority completed on Feb. 16, 2006 for PCT/US05/32874 (WO06/031943).

Written Opinion of the International Search Authority completed on Feb. 6, 2006 for PCT/US05/25016 (WO06/019926).

Written Opinion of the International Search Authority completed on Jan. 23, 2006 for PCT/US05/24045 (WO06/019881.

Written Opinion of the International Search Authority completed on Feb. 21, 2006 for PCT/US05/24946 (WO06/010147).

Written Opinion of the International Search Authority completed on Sep. 25, 2007 for PCT/US06/10088 (WO06/102255).

Office Action issued by the United States Patent and Trademark Office for U.S. Appl. No. 11/181,556 dated Oct. 6, 2008.

Anderson, K.J. et al., Biochemical and Molecular Action of Nutrients-Walnut Polyphenolics Inhibit in Vitro Human Plasma and LDL Oxidation 1, 2, The Journal of Nutrition, Nov. 2001, 131, pp. 2837-2842.

Byrn et al., Hydrates and Solvates, Solid-State Chemistry of Drugs, 1999, 2nd Edition, Chapter 10, pp. 232-247.

Delic-Attree et al., Cloning, Sequence and Mutagenesis of the Structural gene of *Pseudomonas aeruginosa* CysB, which can activate algD transcription, 1997, 24(6), pp. 1275-1284.

Ettmayer et al., Lessons Learned from Marketed and Investigational Prodrugs, Journal of Medical Chemistry, May 6, 2004, vol. 47, No. 10, pp. 2393-2404.

Little, et al., Age Alterations in Extent and Severity of Experimental Intranasal Infection with *Chamydophila pneumoniae* in BALB/c Mice, Infection and Immunity, Mar. 2005, vol. 73, No. 3, pp. 1723-1734.

Morissette, et al., High-throughput crystallization: polymorphs, salts, co-crystals and solvates of pharmaceutical solids, Advance Drug Delivery Reviews, 2004, 56, pp. 275-300.

Rakonjac et al., cysB and cysE mutants of *Escherichia coli* K12 show increased resistance to novobiocin, Mol Gen Genet, 1991, 228, pp. 307-311.

Schuhly et al., New Triterpenoids with Antibacterial Activity from *Zizyphus joazeiro*, Planta Medica, 1999, 65, pp. 740-743.

Testa, Bernard, Prodrug research: futile or fertile? Biochemical Pharmacology, 2004, 68, pp. 2097-2106.

Vippagunta et al., Crystalline Solids, Advanced Drug Delivery Reviews, 2001, 48, pp. 3-26.

Weiss, Lucinda, Researcher's Work on Bacteria, Biofilms has Range of Applications, Jan. 24, 2005, pp. 1-3.

Wolff at al., Burger's Medicinal Chemistry and Drug Discovery, 1994, 5th Edition, vol. 1, pp. 975-977.

Office Action issued by the U.S. Patent and Trademark Office for U.S. Appl. No. 11/085,279 dated May 3, 2007.

Final Office Action issued by the U.S. Patent and Trademark Office for U.S. Appl. No. 11/085,279 dated Apr. 3, 2008.

Office Action issued by the U.S. Patent and Trademark Office for U.S. Appl. No. 11/081,240 dated Apr. 9, 2009.

Wilson et al., Bacterial Disease Mechanisms, An Introduction to cellular microbiology, 2002.

Office Action issued by the United States Patent and Trademark Office for U.S. Appl. No. 11/479,095 dated Nov. 22, 2009.

Figure 1. Biofilm Growth Assay
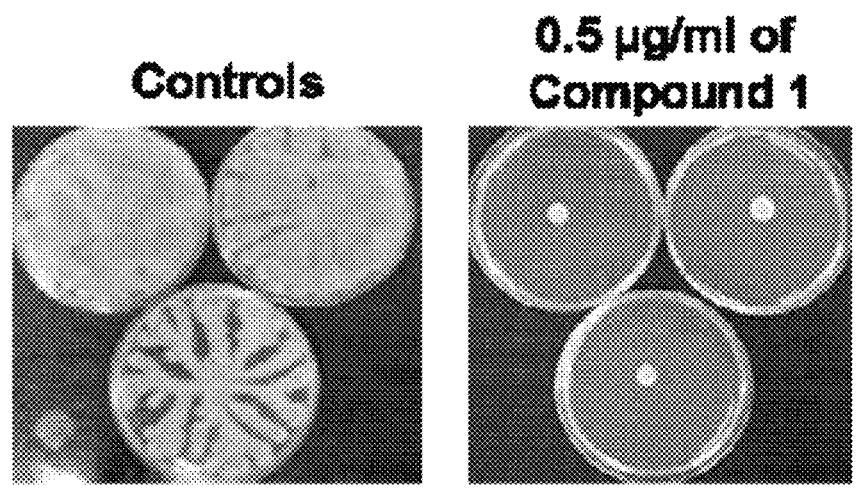
Figure 2. Biofilm Growth Assay using *P. aeruginosa* with and without colistin (antibiotic) 10 µg disks and Compound 1 at a concentration of 0.125 µg/ml.
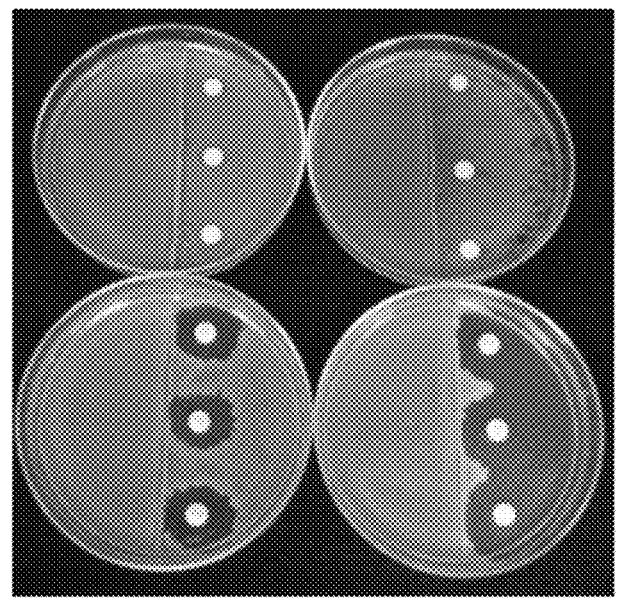

INHIBITORS OF BACTERIAL BIOFILMS AND RELATED METHODS

FIELD OF THE INVENTION

The present invention generally relates to compounds and compositions useful for reducing or inhibiting the growth of a biofilm. The present invention also relates to compounds useful for reducing or inhibiting the formation of a biofilm and for controlling or treating a chronic bacterial infection involving biofilms.

BACKGROUND

Bacterial biofilms exist in natural, medical, and engineering environments. The biofilms offer a selective advantage to a microorganism to ensure its survival, or allow it a certain amount of time to exist in a dormant state until growth conditions arise. Unfortunately, this selective advantage poses serious threats to animal health, especially human health.

Chronic infections involving biofilms are serious medical problems throughout the world. For example, biofilms are involved in 65% of human bacterial infections. Biofilms are involved in prostatitis, biliary tract infections, urinary tract infections, cystitis, lung infections, sinus infections, ear infections, acne, rosacea, dental caries, periodontitis, nosocomial infections, open wounds, and chronic wounds.

Compounds that modify biofilm formation would have a substantial medical impact by treating many chronic infections, reducing catheter- and medical device-related infections, and treating lung and ear infections. The potential market for biofilm inhibitors could be enormous given the sheer number of cases in which biofilms contribute to medical problems. The inhibitors may be used to cure, treat, or prevent a variety of conditions, such as, but are not limited to, arterial damage, gastritis, urinary tract infections, pyelonephritis, cystitis, otitis media, otitis externa, leprosy, tuberculosis, benign prostatic hyperplasia, chronic prostatitis, chronic lung infections of humans with cystic fibrosis, osteomyelitis, bloodstream infections, skin infections, open or chronic wound infections, cirrhosis, and any other acute or chronic infection that involves or possesses a biofilm.

In the United States, the market for antibiotics is greater than $10 billion. The antibiotic market is fueled by the continued increase in resistance to conventional antibiotics. Approximately 70% of bacteria found in hospitals resist at least one of the most commonly prescribed antibiotics. Because biofilms appear to reduce or prevent the efficacy of antibiotics, co-administration of biofilm inhibitors could significantly boost the antibiotic market.

Using the protection of biofilms, microbes can resist antibiotics at a concentration ranging from 1 to 1.5 thousand times higher than the amount used in conventional antibiotic therapy. During an infection, bacteria surrounded by biofilms are rarely resolved by the immune defense mechanisms of the host. It has been proposed that in a chronic infection, a biofilm gives bacteria a selective advantage by reducing the penetration of an antibiotic into the depths of the tissue needed to completely eradicate the bacteria's existence (Costerton, J. W. et al., *Science.* 1999 May 21; 284(5418):1318-22).

Traditionally, antibiotics are discovered using the susceptibility test methods established by the Clinical Laboratory and Standards Institute (CLSI). The methods identify compounds that specifically affect growth or death of bacteria. These methods involve inoculation of a bacterial species into a growth medium, followed by the addition of a test compound, and then plot of the bacterial growth over a time period post-incubation. Unfortunately these antibiotics derived from the CLSI methods would not be effective therapeutics against chronic infections involving biofilms because the methods do not test compounds against bacteria in a biofilm. Consistently, numerous publications have reported a difference in gene transcription in bacteria living in biofilms from bacteria in suspension, which further explains the failure of conventional antibiotics to eradicate biofilm infections (Sauer, K. et al. *J. Bacteriol.* 2001, 183: 6579-6589).

Biofilm inhibitors can provide an alternative treatment approach for certain infections. Biofilm inhibitors, on the other hand, act on the biological mechanisms that provide bacteria protection from antibiotics and from a host's immune system. Biofilm inhibitors may be used to "clear the way" for the antibiotics to penetrate the affected cells and eradicate the infection. Traditionally, treatment of nosocomial infections requires an administration of a combination of products, such as amoxicillin/clavulanate and quinupristin/dalfopristin, or an administration of two antibiotics simultaneously. In one study of urinary catheters, rifampin was unable to eradicate methicillin-resistant *Staphylococcus aureus* in a biofilm but was effective against planktonic, or suspended cells (Jones, S. M., et. al., "Effect of vancomycin and rifampicin on methicillin-resistant *Staphylococcus aureus* biofilms", *Lancet* 357:40-41, 2001).

Bacteria have no known resistance to biofilm inhibitors. Biofilm inhibitors are not likely to trigger growth-resistance mechanisms or affect the growth of the normal human flora. Thus, biofilm inhibitors could potentially extend the product life of antibiotics.

*Pseudomonas aeruginosa* in the lungs of cystic fibrosis (CF) patients is resistant to high doses of antibiotics because it forms biofilms. Biofilms are complex, heterogeneous communities of bacterial cells encased in extrapolymeric substances (EPS). These EPS are composed of polysaccharides, proteins, and extracellular DNA. EPS provide frameworks for communities of bacteria to exist and enhance attachment to themselves and surfaces. Bacteria within biofilms differentiate into stratified communities of phenotypically diverse cells that offer competitive advantages for different environmental conditions. One of these advantages is increased tolerance to antibiotics, which enables bacteria like *P. aeruginosa* to persist in chronic infections despite antibiotic therapy. While residing within these EPS, one hypothesis is that *P. aeruginosa* reduces its metabolism, which prevents its death from antibiotics. As antibiotic concentrations are reduced, specific populations of *P. aeruginosa* within the EPS increase their metabolism and spread. This cycle continuously repeats, enabling the spread of *P. aeruginosa* bacteria within the lungs of CF patients.

Chronic wound infection represents another illness that is difficult to eradicate. Examples of the most common types of chronic wounds are diabetic foot ulcers, venous leg ulcers, arterial leg ulcers, and pressure ulcers. Diabetic foot ulcers appear to be the most prevalent. These wounds are typically colonized by multiple species of bacteria including *Staphylococcus* spp., *Streptococcus* spp., *Pseudomonas* spp. and Gram-negative bacilli (Lipsky, B. Medical Treatment of Diabetic Foot Infections. *Clin. Infect. Dis.* 2004, 39, p. S104-14).

Based on clinical evidence, microorganisms cause or contribute to chronic wound infections. Only recently have biofilms been implicated in these infections (Harrison-Balestra, C. et al. A Wound-isolated *Pseudomonas aeruginosa* Grow a Biofilm In Vitro Within 10 Hours and Is Visualized by Light Microscopy, *Dermatol Surg* 2003, 29; 631-635; Edwards, R. et al. Bacteria and wound healing. *Curr Opin Infect Dis,* 2004, 17; 91-96). Approximately 140,000 amputations occur each year in the United States due to chronic wound infections that could not be treated with conventional antibiotics. Unfortunately, treating these infections with high doses of antibiotics over long periods of time contributes to the development of antibiotic resistance (Howell-Jones, R. S., et al. A review of the microbiology, antibiotic usage and resistance in chronic skin wounds. *J. Antimicrob. Ther.* January 2005). Biofilm inhibitors in a combination therapy with antibiotics may provide an effective alternative to the treatment of chronic wounds.

Recent publications describe the cycles of the pathogenesis of numerous species of bacteria involving biofilms. For example, *Escherichia coli*, which cause recurrent urinary tract infections, undergo a cycle of binding to and then invading a host's bladder epithelial cells. *E. coli* form a biofilm intracellularly, modify its morphology, and then burst out of the host cells to repeat the cycle of pathogenesis (Justice, S. et al. Differentiation and development pathways of uropathogenic *Escherichia coli* in urinary tract pathogenesis, *PNAS* 2004, 101(5): 1333-1338). The authors suggest that this repetitive cycle of pathogenesis of *E. coli* may explain the recurrence of the infection. In 1997, Finlay, B. et al. reported that numerous bacteria, including Staphylococci, Streptococci, *Bordetella pertussis*, *Neisseria* spp., *Helicobactor pylori*, and *Yersinia* spp., adhere to mammalian cells during their pathogenesis. The authors hypothesized that the adherence would lead to an invasion of the host cell. Later publications confirm this hypothesis (Cossart, P. *Science*, 2004, 304; 242-248; see additional references infra). Other publications presented similar hypotheses to Mulvey, M. et al. (Mulvey, M. et al. "Induction and Evasion of Host Defenses by Type 1-Piliated Uropathogenic *E. coli*" *Science* 1998, 282 p. 1494-1497). In particular, Mulvey, M. et al. stated invasion of *E. coli* into epithelial cells provide protection from the host's immune response to allow a build up of a large bacterial population.

Cellular invasion and biofilm formation appear to be integral to the pathogenesis of most, if not all bacteria. *P. aeruginosa* have been shown to invade epithelial cells during lung infections (Leroy-Dudal, J. et al. Microbes and Infection, 2004, 6, p. 875-881). *P. aeruginosa* are the principal infectious organisms found in the lungs of cystic fibrosis patients, and the bacteria exist within a biofilm. Antibiotics like tobramcyin, and other current antibacterial compounds, do not provide effective treatment against biofilms of chronic infections, perhaps because antibiotic therapy fails to eradicate the biofilm.

The pathogenesis of cellular invasion and biofilm formation gram-negative bacteria follow conserved mechanisms. For example, *Haemophilus influenzae* invade epithelial cells and form biofilms (Hardy, G. et al., Methods Mol. Med., 2003, 71; 1-18; Greiner, L. et al., *Infection and Immunity*, 2004, 72(7); 4249-4260). *Burkholderia* spp. invade epithelial cells and form biofilm (Utaisincharoen, P. et al., *Microb Pathog.* 2005, 38(2-3); 107-112; Schwab, U. et al. Infection and Immunity, 2003, 71(11); 6607-6609). *Klebsiella pneumoniae* invade epithelial cells and form biofilm (Cortes, G et al. *Infection and Immunity.* 2002, 70(3); 1075-1080; Lavender, hours. et al., *Infection and Immunity.* 2004, 72(8); 4888-4890). *Salmonella* spp. invade epithelial cells and form biofilms (Cossart, P. Science, 2004, 304; 242-248; Boddicker, J. et al., *Mol. Microbiol.* 2002, 45(5); 1255-1265). *Yersinia pestis* invade epithelial cells and form biofilms (Cossart, P. Science, 2004, 304; 242-248; Jarrett, C. et al. *J. Infect. Dis.*, 2004, 190; 783-792). *Neisseria gonorrhea* invade epithelial cells and form biofilms (Edwards, J. et al., *Cellular Micro.*, 2002, 4(9); 585-598; Greiner, L. et al., *Infection and Immu-* *nity.* 2004, 73(4); 1964-1970). *Burkholderia* spp. are another important class of gram-negative bacterial pathogens. *Chlamydia* spp., including *Chlamydia pneumoniae* is an intracellular, gram-negative pathogen implicated in respiratory infections and chronic diseases such as atherosclerosis and Alzheimer's disease (Little, C. S. et al., *Infection and Immunity.* 2005, 73(3); 1723-34).

These Gram-negative bacteria cause lung, ear, and sinus infections, gonorrhoeae, plague, diarrhea, typhoid fever, and other infectious diseases. *E. coli* and *P. aeruginosa* are two of the most widely studied Gram-negative pathogens. Researchers believe that the pathogenesis of these bacteria involves invasion of host cells and formation of biofilms. These models have enabled those skilled in the art to understand the pathogenesis of other Gram-negative bacteria.

Accordingly, for the reasons discussed above and others, there exists an unmet need for compounds that serve as biofilm inhibitors and/or that would be useful for reducing or inhibiting the formation or growth of bacterial biofilms and bacterial infections involving biofilms.

SUMMARY OF INVENTION

The present invention provides compounds of the following chemical Structure I

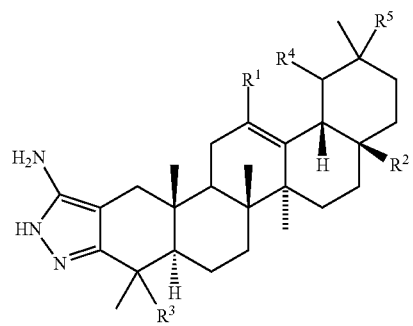

wherein $R^1$ is selected from the group consisting of hydrogen, methyl, halide, lower haloalkyl, nitrile, lower alkyl nitrile, lower alkyl, substituted lower alkyl, lower alkenyl, substituted lower alkenyl, lower alkynyl, lower cycloalkyl, lower cycloalkenyl, substituted lower alkynyl, aryl, substituted aryl, heteroaryl, and substituted heteroaryl; $R^2$ is selected from the group consisting of carboxyl, amide, hydroxyamide, methylamide, —$CH_2N(CH_3)_2$, —$CH_2NR^6R^7$,

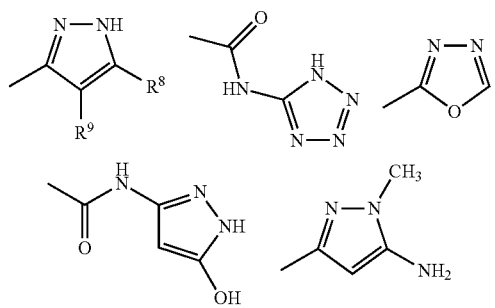

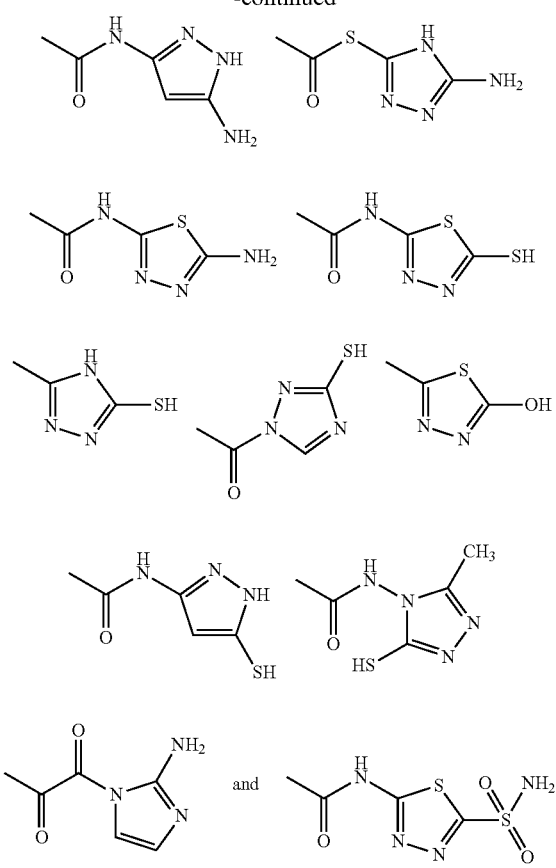

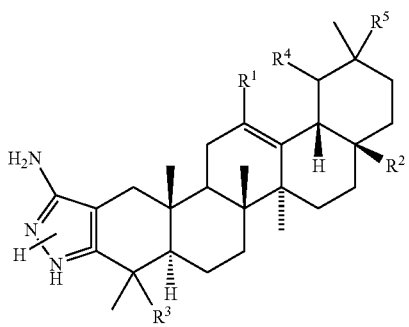 AND/OR

Or a 3-aminopyrazole of any structure of the invention may be as follows:

$R^3$ is selected from the group consisting of hydrogen or methyl; one of $R^4$ and $R^5$ is hydrogen and the other is methyl; $R^6$ and $R^7$ are independently selected from the group consisting of hydrogen, methyl, ethyl, propyl, isopropyl, and butyl; $R^8$ selected from the group consisting of hydroxyl, amino, —N(CH$_3$)$_2$, and —NHCH$_3$; and wherein $R^9$ is selected from the group consisting of hydrogen, halide, lower alkyl, lower alkenyl, lower alkynyl, morpholinyl, piperazinyl, lower alkyl piperazinyl, heterocycloalkyl, lower cycloalkyl, lower cycloalkenyl; and lower alkyl, lower alkenyl, and lower alkynyl substituted with moieties selected from the group consisting of hydroxyl, amino, lower aminoalkyl, halide, lower alkoxy, lower alkoxyalkyl, lower alkoxycarbonyl, lower alkylcarbonylamino, carboxyl, amide, hydroxyamide, —CONHCH$_3$, —NHCONH$_2$, —SO$_2$NH$_2$, —SO$_2$CH$_3$, —NHCOCH$_3$, —NHCSNH$_2$, and —NHSO$_2$CH$_3$. Salts are also contemplated by the present invention as described in the examples.

A number of the compounds of the invention and intermediates may exist in different tautomeric forms. All such tautomeric forms are within the scope of the invention. The depiction of any tautomer herein is not intended to limit the scope of the invention to one specific tautomer. For example, the following is within the scope of the invention.

Those skilled in the art will understand that Structure I may exist as a tautomer envisioned as the following. In any respect, 3-aminopyrazole of any structure of the invention may be as follows:

These tautomeric depictions are within the scope of the invention.

Furthermore, the hydroxypyrazole of compound 68 as described herein may exist as tautomers. These tautomers are within the scope of the invention.

Compositions containing the compounds described above and a pharmaceutically acceptable carrier are also contemplated by this invention. Such compositions containing the compounds described above optionally include an antimicrobial agent. As demonstrated herein such compositions are useful in reducing or inhibiting the formation or growth of biofilms.

This invention also provides methods for reducing or inhibiting the formation or growth of biofilms comprising contacting the biofilm or cell capable of biofilm formation with an effective amount of a composition or a compound of the preceeding chemical Structure I wherein $R^1$ is selected from the group consisting of hydrogen, methyl, halide, lower haloalkyl, nitrile, lower alkyl nitrile, lower alkyl, substituted lower alkyl, lower alkenyl, substituted lower alkenyl, lower alkynyl, substituted lower alkynyl, lower cycloalkyl, lower cycloalkenyl, aryl, substituted aryl, heteroaryl, and substituted heteroaryl; $R^2$ is selected from the group consisting of carboxyl, amide, hydroxyamide, methylamide, —$CH_2N(CH_3)_2$, —$CH_2NR^6R^7$,

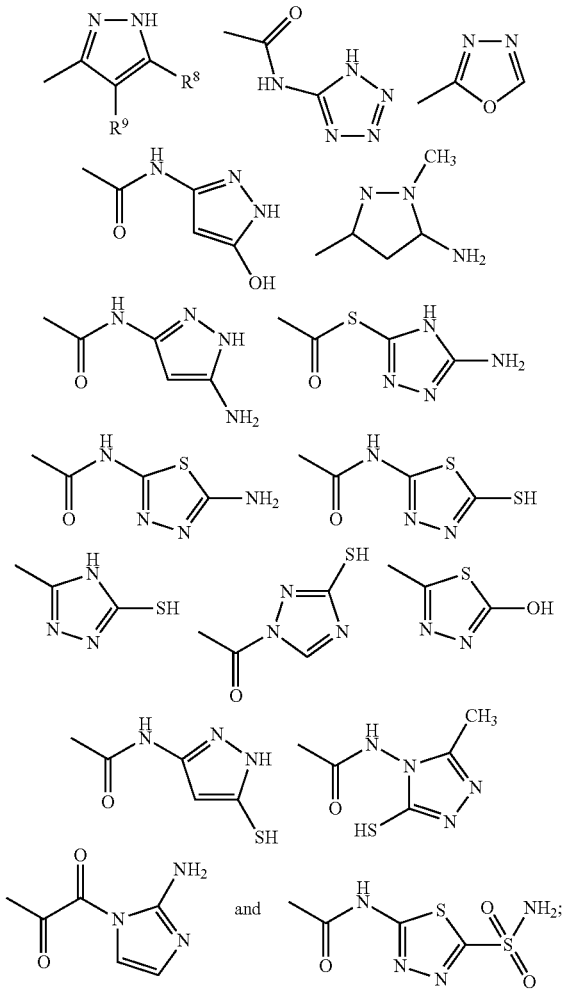

$R^3$ is selected from the group consisting of hydrogen or methyl; one of $R^4$ and $R^5$ is hydrogen and the other is methyl; $R^6$ and $R^7$ are independently selected from the group consisting of hydrogen, methyl, ethyl, propyl, isopropyl, and butyl; $R^8$ selected from the group consisting of hydroxyl, amino, —$N(CH_3)_2$, and —$NHCH_3$; and $R^9$ is selected from the group consisting of hydrogen, halide, lower alkyl, lower alkenyl, lower alkynyl, morpholinyl, piperazinyl, lower alkyl piperazinyl, heterocycloalkyl, lower cycloalkyl, lower cycloalkenyl; and lower alkyl, lower alkenyl, and lower alkynyl substituted with moieties selected from the group consisting of hydroxyl, amino, lower aminoalkyl, halide, lower alkoxy, lower alkoxyalkyl, lower alkoxycarbonyl, lower alkylcarbonylamino, carboxyl, amide, hydroxyamide, —$CONHCH_3$, —$NHCONH_2$, —$SO_2NH_2$, —$SO_2CH_3$, —$NHCOCH_3$, —$NHCSNH_2$, and —$NHSO_2CH_3$. Salts are also contemplated by the present invention as described in the examples.

Inhibition or reduction of the formation or growth of biofilms may be effected either in vivo or in vitro. Compositions used to inhibit or reduce the formation or growth of biofilms may further include an antimicrobial agent, biocide, or antibiotic. The methods also provide for inhibiting or reducing the formation or growth of biofilms on a variety of substrates.

Inhibition or reduction of the formation or growth of biofilms reduces virulence of gram-negative bacteria. Adhesion, biofilm growth, invasion, and the secretion of enzymes or toxins contribute to virulence of gram-negative bacteria. It is well known to those skilled in the art that biofilms increase the virulence of gram-negative bacteria and an upregulation of virulence factors (i.e. enzymes, toxins) has been demonstrated in gram-negative bacterial biofilms. The compounds of the invention reduce virulence of gram-negative bacteria.

Compound 1 as described herein modulates cysB and genes under its control as described in U.S. Pat. No. 7,604,978 incorporated herein in its entirety by this reference. It is anticipated that all of the compounds described herein modulate cysB and genes under its control.

BRIEF DESCRIPTION OF THE DRAWINGS

FIG. 1 is a set of photographs of the Biofilm Growth Assay for Compound 1, as described in Example I, below, wherein the round plates on the left are negative controls, in which the agar in the plates does not contain Compound 1, and wherein, as shown in the negative control plates, P. aeruginosa spread out from the inoculation point in the center of the plate during overnight incubation at 37° C. and covered the entire plate, whereas the agar in the plates on the right contained 0.5 µg/ml of Compound 1 of the invention, which prevented the growth of the spreading P. aeruginosa biofilm.

FIG. 2 is a set of photographs of the Biofilm Growth Assay for Compound 1 in the presence of colistin (antibiotic) disks as described in Example VIII, below, wherein the top left plate was a negative control plate with paper disks without antibiotic and the top right plate had 0.125 µg/ml of Compound 1 in the agar on the right side of the plate with paper disks without antibiotic (and 0.125 µg/ml of Compound 1 was two dilutions below its optimal working concentration of 0.5 µg/ml), and the bottom left plate had colistin 10 µg disks, while the bottom right plate had 0.125 µg/ml of Compound 1 in the agar on the right side of the plate with colistin 10 µg disks, the inhibition of the growth of P. aeruginosa biofilm in the bottom right plate demonstrating that Compound 1 and colistin (antibiotic) are synergistic at preventing the growth of P. aeruginosa biofilms.

DESCRIPTION OF THE INVENTION

Definitions

"Acceptable carrier" refers to a carrier that is not deleterious to the other ingredients of the composition and is not deleterious to material to which it is to be applied.

"Pharmaceutically acceptable carrier" refers to a carrier that is not deleterious to the other ingredients of the composition and is not deleterious to the human or other animal recipient thereof. "Agriculturally acceptable carrier" refers to a carrier that is not deleterious to the other ingredients of the composition and is not deleterious to the plant recipient thereof. In the context of the other ingredients of the composition, "not deleterious" means that the carrier will not react with or degrade the other ingredients or otherwise interfere with their efficacy. Interference with the efficacy of an ingredient does not encompass mere dilution of the ingredient. In the context of the animal or plant host, "not deleterious" means that the carrier is not injurious or lethal to the plant or animal.

"Administration" refers to any means of providing a compound or composition to a subject. Non-limiting examples of administration means include oral, topical, rectal, percutaneous, parenteral injection, intranasal and inhalation delivery.

"Biofilm" refers to an extracellular matrix in which microorganisms are dispersed and/or form colonies. The biofilm typically is made of polysaccharides and other macromolecules.

"Biofilm Growth Assay" refers to an assay performed on semi-solid agar surface where the bacteria collectively move out from an inoculation point. To those skilled in the art, the act of bacteria collectively moving out from an inoculation point on a semi-solid surface may be referred to as swarming or a spreading biofilm. (Anderson, et al *Microbiology*, 2003, 149, 37-46; Daniels, et al. FEMS Microbiology Reviews, 2004, 28, 261-289). The procedure to perform this assay is described in detail in the Examples. This type of surface motility by bacteria has been reported in the literature by those skilled in the art. (Shrout, et al. Molecular Microbiology, 2006, 62(5), 1264-1277; Kim, et al. J. Bacteriology, 2003, 185(10), 3111-3117; Lai, et al. Environmental Microbiology, 2009, 11(1), 126-136; Overhage, et al. J. Bacteriology, 2008, 190(8), 2671-2679) These literature references also demonstrate a link to this type of surface motility and increased antibiotic tolerance. These references are incorporated herein by reference in their entirety.

"Commercial source" refers to a vendor that provides the desired compound.

"Direct synthesis" refers to production of the desired compound by reacting appropriate compound precursors under appropriate conditions to obtain the desired compound.

"Effective amount" refers to the amount of compound or composition that, in the case of biofilm formation, will reduce the size or volume of existing biofilms; reduce the rate at which bacteria are capable of producing biofilm; or will inhibit or prevent the formation of biofilm by one or more microorganisms. In the context of treating a bacterial infection, an "effective amount" refers the amount of a compound or composition that will reduce the degree of an existing infection or will inhibit or prevent an infection from occurring.

"Essentially pure preparation" refers to a preparation in which the concentration of the desired ingredient is at least 95% or more of the preparation by weight. In the context of this processes used in this invention, the antimicrobial agents and compounds of the invention typically and preferably make up 99% or more by weight of the preparation and are referred to herein as "highly pure" preparations.

"In vivo", in the context of biofilm formation, refers to effects mediated in or upon living organisms or subjects. Effects mediated on biofilms associated with medical devices such as central venous catheters, urinary catheters, endotracheal tubes, mechanical heart valves, pacemakers, vascular grafts, stents, and prosthetic joints located within a living organism or subject are considered as "in vivo" uses of the compounds and compositions described herein.

"In vitro", in the context of biofilm formation, refers to effects mediated on substrates located outside of an organism that are potential sites of biofilm formation. Non-limiting examples of substrates include vessel hulls, cars, airplanes, industrial equipment, devices, membranes, filters, microtiter plates, continuous flow chambers, bioreactors, fermentors, chemostats and machinery.

"Is one that permits" as it relates to a pharmaceutically acceptable carrier that has characteristics that enable the preparation to be used for a given mode of administration of the composition. For example, pharmaceutically acceptable carriers that permit parenteral administration to an animal are liquids that are not injurious or lethal to the animals when so injected. Such carriers often comprise sterile water, which may be supplemented with various solutes to increase solubility. Sterile water or sterile water supplemented with solutes is thus a pharmaceutically acceptable carrier that permits parental administration.

As used herein, all agar percentages are expressed in terms of weight/volume; all formulation percentages are expressed in terms of weight/weight.

"Reducing or inhibiting" in reference to a biofilm refers to the inhibiting or reducing of biofilm formation or growth, a reduction in the rate of biofilm formation or growth, reduction or removal of preformed or existing biofilm, as well as the partial or complete inhibition of biofilm formation or growth. This definition includes but is not limited to the biofilm growth that also occurs on semi-solid surfaces like 0.4% to 1.0% agar, but is not limited to these surfaces, as described in the Examples of the invention. This type of surface motility, which is also referred to as swarming or spreading biofilms and conducted on the same semi-solid agar plates independent of terminology, demonstrates mechanistic relationships between attached biofilms and gram-negative bacteria spreading across semi-solid agar plates as known to those skilled in the art. Michael Givskov and colleagues defined the movement of a *Pseudomonas* spp. across a 0.6% Bacto agar plate as surface motility with biofilm structures instead of swarming (Anderson, et al Microbiology, 2003, 149, 37-46). Jan Michiels and colleagues defined swarming as a biofilm spreading over a semi-solid surface (Daniels, et al. FEMS Microbiology Reviews, 2004, 28, 261-289). Even though terminology is evolving as more investigations are reported, all of these data have been generated examining the movement of gram-negative bacteria on 0.4% to 0.7% agar surfaces.

"Subject in need thereof" refers to living organism that would benefit from either prevention or reductions in the degree of a bacterial infection. Subjects may include animals or more specifically, mammals or humans. Subjects may also include plants.

"Substrate" refers to any material to which the compound or a composition containing the compound may be applied.

The term "lower alkyl" as used herein refers to a saturated hydrocarbon chain having one, two, three, four, or five carbon atoms. Lower alkyl groups may be optionally substituted with one or more substituents as defined herein to form substituted lower alkyl groups. Lower alkyl groups may be straight or branched. Examples of lower alkyl groups include methyl, ethyl, propyl, isopropyl, butyl, isobutyl, t-butyl, pentyl, and isopentyl.

The phrase "substituted lower alkyl" as used herein, refers to a lower alkyl group, as previously defined, substituted by independent replacement of one, two, or three of the hydrogen atoms thereon with substituents including halide, nitrile, aryl, heteroaryl, substituted heteroaryl, lower cycloalkyl, lower cycloalkenyl, —SH, and lower thioalkyl.

The term "lower alkenyl" as used herein refers to an unsaturated hydrocarbon chain having one, two, three, four, or five carbon atoms and having one or more carbon-carbon double bonds within the chain. The lower alkenyl groups may be straight or branched and may be optionally substituted with one or more substituents as defined herein to form substituted lower anlkenyl groups.

The phrase "substituted lower alkenyl" as used herein, refers to a lower alkenyl group, as previously defined, substituted by independent replacement of one, two or three of the hydrogen atoms thereon with substituents including halide, nitrile, aryl, heteroaryl, substituted heteroaryl, lower cycloalkyl, lower cycloalkenyl, —SH, and lower thioalkyl.

The term "lower alkynyl" as used herein refers to an unsaturated hydrocarbon chain having one, two, three, four, or five carbon atoms and having one or more carbon-carbon triple bonds within the chain. The lower alkynyl groups may be straight or branched and may be optionally substituted with one or more substituents as defined herein to form substituted lower alkynyl groups.

The phrase "substituted lower alkynyl" as used herein refers to a lower alkynyl group, as previously defined, substituted by independent replacement of one, two, or three of the hydrogen atoms thereon with substituents including halide, nitrile, aryl, heteroaryl, substituted heteroaryl, lower cycloalkyl, lower cycloalkenyl, —SH, and lower thioalkyl.

The phrase "lower alkyl ethers" as used herein refers to ethers of the formula R'OR", wherein R' is a lower alkyl, lower alkenyl or lower alkynyl, and R" is a lower alkyl, lower alkenyl, lower alkynyl, or aryl, heteroaryl or heterocycloalkyl.

The term "lower alkoxy," as used herein by itself or as part of another substituent, means a radical of the formula —OR, wherein R is a lower alkyl, lower alkenyl, lower cycloalkyl, or lower cycloalkenyl group as defined herein. Representative examples of lower alkoxy groups include, but are not limited to, methoxy, ethoxy, propoxy, isopropoxy, butoxy, tert-butoxy, cyclopropyloxy, cyclopentyloxy, and the like.

The term "lower alkoxyalkyl" as used herein refers to a lower alkyl moiety as defined herein with one carbon atom replaced with an oxygen atom. Examples include —$CH_2CH_2OCH_3$ and —$CH_2OCH_2CH_2CH_3$.

The term "lower alkoxycarbonyl" as used herein by itself or as part of another substituent, refers to a radical of the formula —C(O)-(lower alkoxy), wherein lower alkoxy is as defined herein.

The phrase "lower alkyl nitrile" as used herein refers to lower alkyl or lower alkenyl with one nitrile group replacing one terminal carbon atom in the unbranched or branched chain. Lower alkyl nitrile includes, but is not limited to, —$CH_2CN$ and —$CH_2CH_2CN$.

The term "lower aminoalkyl" as used herein refers to lower alkyl or lower alkenyl with one nitrogen atom replacing one carbon atom in the unbranched or branched chain. Lower aminoalkyl includes, but is not limited to, —$NHCH_2CH_2CH_3$, —$CH_2CH_2$—$NHCH_3$, —$CH_2N(CH_3)_2$, —$N(CH_3)_2$, and —$CH_2CH_2NH_2$.

The term "lower alkylcarbonylamino" as used herein refers to lower alkyl with a carbonylamino or aminocarbonyl replacing two carbon atoms in the unbranched or branched chain. Lower alkylcarbonylamino includes, but is not limited to, —$NHCOCH_2CH_3$, —$CH_2CONHCH_3$, —$CON(CH_3)_2$, and —$CONHCH_3$ (methylamide).

The terms "halo" and "halogen," as used herein, mean an atom selected from fluorine, chlorine, bromine and iodine and the term "halide" and used herein means the corresponding anion.

The term "lower haloalkyl" as used herein refers to a lower alkyl group wherein one or more hydrogen atoms attached to a member atom within the lower alkyl group is replaced with 1, 2, 3, or 4 halide atoms. Lower haloalkyl includes, but are not limited to, fluoromethyl, —$CF_3$, difluoroethyl, and trifluoromethyl.

The term "lower hydroxyalkyl" as used herein refers to lower alkyl or lower alkenyl wherein one or more hydrogen atoms attached to a member atom within the lower alkyl or lower alkenyl group is replaced with one or two hydroxyls. Lower hydroxyalkyl includes, but is not limited to, —$CH_2CH_2$—OH and —$CH_2CH$(—OH)$CH_3$, and the like.

The term "aryl" as used herein, means mono- or bicyclic carbocyclic ring systems comprising 6 to 12 carbon atoms, which consist of one or two aromatic rings, specifically including phenyl, naphthyl, tetrahydronaphthyl, indanyl, and idenyl; and specifically substitutions to these aryls by independent replacement of one two, or three of the hydrogen atoms thereon with substituents specifically selected from the group consisting of halide, lower haloalkyl, amino, hydroxyl, lower alkoxy, lower aminoalkyl, lower hydroxyalkyl, nitrile, lower alkyl nitrile, lower alkyl, lower alkenyl, lower alkynyl, nitro, carboxyl, amide, hydroxyamide, lower alkyl ethers, lower alkoxyalkyl, lower alkoxycarbonyl, lower alkylcarbonylamino, —SH, and lower thioalkyl.

The phrase "substituted aryl," as used herein, means a aryl group, as previously defined, substituted by independent replacement or one or two of the hydrogen atoms thereon with substituents specifically selected from the group consisting of —$(CH_2)_{0-3}$-lower cycloalkyl, —$(CH_2)_{0-3}$-aryl, —$(CH_2)_{0-3}$-lower cycloalkenyl, —$(CH_2)_{0-3}$-heteroaryl, —$(CH_2)_{0-3}$-heterocycloalkyl, —NH-lower cycloalkyl, —NH-aryl, —NH-lower cycloalkenyl, —NH-heteroaryl, —NH—heterocycloalkyl, —O-aryl, —O-heteroaryl, —O— heterocycloalkyl, —C(O)-lower alkyl, —C(O)-lower alkenyl, —C(O)-lower alkynyl, —C(O)-lower cycloalkyl, —C(O)-aryl, —C(O)-lower cycloalkenyl, —C(O)-heteroaryl, —C(O)— heterocycloalkyl, —$CONH_2$, —CONH-lower alkyl, —CONH-lower alkenyl, —CONH-lower alkynyl, —CONH-lower cycloalkyl, —CONH-aryl, —CONH-lower cycloalkenyl, —CONH-heteroaryl, —CONH-heterocycloalkyl, —$OCO_2$-lower alkyl, —$OCO_2$-lower alkenyl, —$OCO_2$-lower alkynyl, —$OCO_2$-lower cycloalkyl, —$OCO_2$-aryl, —$OCO_2$-lower cycloalkenyl, —$OCO_2$-heteroaryl, —$OCO_2$— heterocycloalkyl, —$OCONH_2$, —OCONH-lower alkyl, —OCONH-lower alkenyl, —OCONH-lower alkynyl, —OCONH-lower cycloalkyl, —OCONH-aryl, —OCONH-lower cycloalkenyl, —OCONH-heteroaryl, —OCONH— heterocycloalkyl, —NHC(O)-lower alkyl, —NHC(O)-lower alkenyl, —NHC(O)-lower alkynyl, —NHC(O)-lower cycloalkyl, —NHC(O)-aryl, —NHC(O)-lower cycloalkenyl, —NHC(O)-heteroaryl, —NHC(O)-heterocycloalkyl, —$NHCO_2$-lower alkyl, —$NHCO_2$-lower alkenyl, —$NHCO_2$-lower alkynyl, —$NHCO_2$-lower cycloalkyl, —$NHCO_2$-aryl, —$NHCO_2$-lower cycloalkenyl, —$NHCO_2$-heteroaryl, —$NHCO_2$— heterocycloalkyl, —$NHC(O)NH_2$, —NHC(O)NH-lower alkyl, —NHC(O)NH-lower alkenyl, —NHC(O)NH-lower alkynyl, —NHC(O)NH-lower cycloalkyl, —NHC(O)NH-aryl, —NHC(O)NH-lower cycloalkenyl, —NHC(O)NH-heteroaryl, —NHC(O)NH— heterocycloalkyl, —$NHC(S)NH_2$, —NHC(S)NH-lower alkyl, —NHC(S)NH-lower alkenyl, —NHC(S)NH-lower alkynyl, —NHC(S)NH-lower cycloalkyl, —NHC(S)NH-aryl, —NHC(S)NH-lower cycloalkenyl, —NHC(S)NH-heteroaryl, —NHC(S)NH— heterocycloalkyl, —S(O)-lower alkyl, —S(O)-lower alkenyl, —S(O)-lower alkynyl, —S(O)-lower cycloalkyl, —S(O)-aryl, —S(O)-lower cycloalkenyl, —S(O)-heteroaryl, —S(O)— heterocycloalkyl, —$CH_2SO_2CH_3$, —$SO_2NH_2$, —$SO_2NH$-lower alkyl, —$SO_2NH$-lower alkenyl, —$SO_2NH$-lower alkynyl, —$SO_2NH$-lower cycloalkyl, —$SO_2NH$-aryl, —$SO_2NH$-lower cycloalkenyl, —$SO_2NH$-heteroaryl, —$SO_2NH$— heterocycloalkyl, —$NHSO_2$-lower alkyl, —$NHSO_2$-lower alkenyl, —$NHSO_2$-lower alkynyl, —$NHSO_2$-lower cycloalkyl, —$NHSO_2$-aryl, —$NHSO_2$-lower cycloalkenyl, —$NHSO_2$-heteroaryl, —$NHSO_2$— heterocycloalkyl, —S-lower alkenyl, —S-lower alkynyl, —S-lower cycloalkyl, —S-aryl, —S-heteroaryl, —S-heterocycloalkyl, or methylthiomethyl.

The phrase "lower cycloalkyl," as used herein, means a saturated carbocyclic ring compound specifically including cyclopropyl, cyclobutyl, cyclopentyl, cyclohexyl, norbornane, and adamantine; and specifically substitutions to these lower cycloalkyls by independent replacement of one or two of the hydrogen atoms thereon with substituents specifically selected from the group consisting of halide, lower haloalkyl, amino, hydroxyl, lower alkoxy, lower aminoalkyl, lower hydroxyalkyl, nitrile, lower alkyl nitrile, lower alkyl, lower alkenyl, lower alkynyl, nitro, carboxyl, amide, hydroxyamide, lower alkyl ethers, lower alkoxyalkyl, lower alkoxycarbonyl, lower alkylcarbonylamino, —SH, and thioalkyl.

The term "lower cycloalkenyl" as used herein specifically refers to an unsaturated hydrocarbon ring with five or six carbons; and specifically substitutions to these lower cycloalkenyls by independent replacement of one or two of the hydrogen atoms thereon with substituents specifically selected from the group consisting of halide, lower haloalkyl, amino, hydroxyl, lower alkoxy, lower aminoalkyl, lower hydroxyalkyl, nitrile, lower alkyl nitrile, lower alkyl, lower alkenyl, lower alkynyl, nitro, carboxyl, amide, hydroxyamide, lower alkyl ethers, lower alkoxyalkyl, lower alkoxycarbonyl, lower alkylcarbonylamino, —SH, and thioalkyl.

The term "heteroaryl" as used herein specifically refers to pyrrolyl, pyrazolyl, imidazolyl, oxazolyl, isoxazolyl, oxadiazolyl, thiazolyl, isothiazolyl, thienyl, furanyl, furazanyl, pyridinyl, pyrimidinyl, pyridazinyl, indolyl, 3H-indolyl, isoindolyl, indolinyl, indolizinyl, indazolyl, dihydroindolyl, tetrahydroindolyl, purinyl, pyrazinyl, quinolinyl, isoquinolinyl, tetrahydroisoquinolinyl, quinoxalinyl, quinazolinyl, cinnolinyl, pteridinyl, benzimidazolyl, benzopyranyl, benzoxazolyl, benzisoxazolyl, benzofuranyl, isobenzofuranyl, benzothiazolyl, benzisothiazolyl, benzothienyl, furopyridinyl, phthalazinyl, napthyridinyl, pyrazolopyridyl, pyrazolopyrimidinyl; specifically their partially reduced forms as known to those skilled in the art like as tetrahydroisoquinolinyl is to isoquinolinyl; and specifically a heteroaryl (as defined herein) of 6 members or less fused with an aryl (as defined herein) of 6 members or less OR separately two heteroaryls (as defined herein) of 6 members or less fused together as known to those skilled in the art like as in pyrrolopyridinyl and its partially reduced form dihydropyrrolopyridinyl; and specifically substitutions to these heteroaryls by independent replacement of one two, or three of the hydrogen atoms thereon with substituents specifically selected from the group consisting of halide, lower haloalkyl, amino, hydroxyl, lower alkoxy, lower aminoalkyl, lower hydroxyalkyl, nitrile, lower alkyl nitrile, lower alkyl, lower alkenyl, lower alkynyl, nitro, carboxyl, amide, hydroxyamide, lower alkyl ethers, lower alkoxyalkyl, lower alkoxycarbonyl, lower alkylcarbonylamino, —SH, and thioalkyl; and heteroaryls as defined herein with substitutions by independent replacement of a hydrogen atom on a ring nitrogen specifically selected from the group consisting of lower alkyl, lower alkenyl, and lower haloalkyl.

The phrase "substituted heteroaryl," as used herein, means a heteroaryl group as previously defined, substituted by independent replacement or one or two of the hydrogen atoms thereon with substituents specifically selected from the group consisting of —$(CH_2)_{0-3}$-lower cycloalkyl, —$(CH_2)_{0-3}$-aryl, —$(CH_2)_{0-3}$-lower cycloalkenyl, —$(CH_2)_{0-3}$-heteroaryl, —$(CH_2)_{0-3}$— heterocycloalkyl, —NH-lower cycloalkyl, —NH-aryl, —NH-lower cycloalkyl, —NH-heteroaryl, —NH— heterocycloalkyl, —O-aryl, —O-heteroaryl, —O-heterocycloalkyl, —C(O)-lower alkyl, —C(O)-lower alkenyl, —C(O)-lower alkynyl, —C(O)-lower cycloalkyl, —C(O)-aryl, —C(O)-lower cycloalkenyl, —C(O)-heteroaryl, —C(O)-heterocycloalkyl, —$CONH_2$, —CONH-lower alkyl, —CONH-lower alkenyl, —CONH-lower alkynyl, —CONH-lower cycloalkyl, —CONH-aryl, —CONH-lower cycloalkenyl, —CONH-heteroaryl, —CONH— heterocycloalkyl, —$OCO_2$-lower alkyl, —$OCO_2$-lower alkenyl, —$OCO_2$-lower alkynyl, —$OCO_2$-lower cycloalkyl, —$OCO_2$-aryl, —$OCO_2$-lower cycloalkenyl, —$OCO_2$-heteroaryl, —$OCO_2$— heterocycloalkyl, —$OCONH_2$, —OCONH-lower alkyl, —OCONH-lower alkenyl, —OCONH-lower alkynyl, —OCONH-lower cycloalkyl, —OCONH-aryl, —OCONH-lower cycloalkenyl, —OCONH-heteroaryl, —OCONH— heterocycloalkyl, —NHC(O)-lower alkyl, —NHC(O)-lower alkenyl, —NHC(O)-lower alkynyl, —NHC(O)-lower cycloalkyl, —NHC(O)-aryl, —NHC(O)-lower cycloalkenyl, —NHC(O)-heteroaryl, —NHC(O)— heterocycloalkyl, —$NHCO_2$-lower alkyl, —$NHCO_2$-lower alkenyl, —$NHCO_2$-lower alkynyl, —$NHCO_2$-lower cycloalkyl, —$NHCO_2$-aryl, —$NHCO_2$-lower cycloalkenyl, —$NHCO_2$-heteroaryl, —$NHCO_2$— heterocycloalkyl, —$NHC(O)NH_2$, —NHC(O)NH-lower alkyl, —NHC(O)NH-lower alkenyl, —NHC(O)NH-lower alkynyl, —NHC(O)NH-lower cycloalkyl, —NHC(O)NH-aryl, —NHC(O)NH-lower cycloalkenyl, —NHC(O)NH-heteroaryl, —NHC(O)NH— heterocycloalkyl, —$NHC(S)NH_2$, —NHC(S)NH-lower alkyl, —NHC(S)NH-lower alkenyl, —NHC(S)NH-lower alkynyl, —NHC(S)NH-lower cycloalkyl, —NHC(S)NH-aryl, —NHC(S)NH-lower cycloalkenyl, —NHC(S)NH-heteroaryl, —NHC(S)NH-heterocycloalkyl, —S(O)-lower alkyl, —S(O)-lower alkenyl, —S(O)-lower alkynyl, —S(O)-lower cycloalkyl, —S(O)-aryl, —S(O)-lower cycloalkenyl, —S(O)-heteroaryl, —S(O)-heterocycloalkyl, —$CH_2SO_2CH_3$, —$SO_2NH_2$, —$SO_2NH$-lower alkyl, —$SO_2NH$-lower alkenyl, —$SO_2NH$-lower alkynyl, —$SO_2NH$-lower cycloalkyl, —$SO_2NH$-aryl, —$SO_2NH$-lower cycloalkenyl, —$SO_2NH$-heteroaryl, —$SO_2NH$— heterocycloalkyl, —$NHSO_2$-lower alkyl, —$NHSO_2$-lower alkenyl, —$NHSO_2$-lower alkynyl, —$NHSO_2$-lower cycloalkyl, —$NHSO_2$-aryl, —$NHSO_2$-lower cycloalkenyl, —$NHSO_2$-heteroaryl, —$NHSO_2$— heterocycloalkyl, —S-lower alkenyl, —S-lower alkynyl, —S-lower cycloalkyl, —S-aryl, —S-heteroaryl, —S-heterocycloalkyl, or methylthiomethyl.

The term "heterocycloalkyl" as used herein specifically refers to azetidinyl, [1,3]dioxolane, pyrazolinyl, pyrrolidinyl, 2-pyrrolinyl, 3-pyrrolinyl, tetrahydrofuranyl, dihydrofuranyl, pyranyl, tetrahydropyranyl, dihydropyranyl, tetrahydrothienyl, imidazolinyl, imidazolidinyl, pyrazolidinyl, oxazolidinyl, isoxazolidinyl, thiazolidinyl, isothiazolidinyl, piperidinyl, homopiperidinyl, quinuclidinyl, piperazinyl, lower alkyl piperazinyl, morpholinyl, thiamorpholinyl, 1-pyrazolidinyl, azepinyl; and heterocycloalkyls as defined herein with substitutions by independent replacement of a hydrogen atom on a ring nitrogen specifically selected from the group consisting of lower alkyl, lower alkenyl, and lower haloalkyl; and specifically substitutions to these heterocycloalkyls by independent replacement of one or two of the hydrogen atoms thereon with substituents specifically selected from the group consisting of halide, lower haloalkyl, amino, hydroxyl, lower alkoxy, lower aminoalkyl, lower hydroxyalkyl, nitrile, lower alkyl nitrile, lower alkyl, lower alkenyl, lower alkynyl, carboxyl, amide, hydroxyamide, lower alkoxyalkyl, lower alkoxycarbonyl, lower alkylcarbonylamino, —SH, and thioalkyl. For example, substitutions to pyrrolidinyl may include hydroxyl-pyrrolidinyl, chloropyrrolidinyl, methoxy-pyrrolidinyl, nitrile-pyrrolidinyl, methyl-pyrrolidinyl, and amino-pyrrolidinyl.

The term "heteroatom" as used herein refers to a nitrogen, sulfur, or oxygen atom.

The term "lower thioalkyl" as used herein by itself or as part of another substituent, means a radical of the formula —SR, wherein R is a lower alkyl or lower cycloalkyl group as defined herein. Examples of lower alkylthio groups include, but are not limited to, methylthio, ethylthio, propylthio, isopropylthio, butylthio, and tert-butylthio.

The term "carboxy," as used herein, means a group of formula —COOH.

The term "hydroxy," as used herein, means a group of formula —OH.

The phrase "hydroxy protecting group," as used herein, means a labile chemical moiety which is known in the art to protect a hydroxyl group against undesired reactions during synthetic procedures. Following such procedures, the hydroxy protecting group may be selectively removed. Examples of hydroxy protecting groups include, but are not limited to, methylthiomethyl, tert-butyldimethylsilyl, tertbutyldiphenylsilyl, acyl substituted with an aromatic group, and the like.

The phrase "protected hydroxy," as used herein, means a hydroxy group protected with a hydroxy protecting group, as defined above, including benzoyl, acetyl, trimethylsilyl, triethylsilyl, methoxymethyl groups, for example.

The phrase "amino protecting group," as used herein, means a labile chemical moiety which is known in the art to protect an amino group against undesired reactions during synthetic procedures. Following such procedures, the amino protecting group may be selectively removed. Examples of amino protecting groups include, but are not limited to, t-butoxycarbonyl, 9-fluorenylmethoxycarbonyl, benzyloxycarbonyl, and the like.

The phrase "protected amino," as used herein, means an amino group protected with an amino protecting group as defined above.

In accordance with the present invention, compounds as disclosed herein are surprisingly effective at inhibiting or reducing the formation or growth of biofilms. Furthermore, it is also disclosed that the co-administration to a bacterial biofilm of compounds described herein with an antimicrobial agent, antibiotic, or biocide provides increased susceptibility of the bacteria within the biofilm to the antimicrobial agent, antibiotic, or biocide. The instant invention thus provides for novel compounds, compositions, compositions comprising biofilm inhibitors and antimicrobial agents or antibiotics or biocides, and various methods of using the compositions containing the biofilm inhibitors of the invention to reduce or inhibit the formation or growth of bacterial biofilms.

The compounds of the invention may be prepared by the techniques described in the examples below, starting from the ursane or oleanane triterpene scaffolds like ursolic acid and oleanolic acid. While a typical starting chemical compound in the semi-synthetic preparation of the compounds of the invention may be ursolic acid, oleanolic acid, corosolic acid, asiatic acid, or madecassic acid, oleanolic acid and ursolic acid are preferred staring compounds. In designing semi-synthetic strategies to prepare analogs of the starting chemical compound, modifications at certain positions of the scaffold of the basic chemical compound prove to be important for modulating biofilm inhibition, while other modifications at positions can improve the bioavailability of the compound. Many of these modifications or optimizations are taught in the literature known to those skilled in the art, including The Organic Chemistry of Drug Design and Drug Action, $2^{nd}$ Edition, by Richard B. Silverman, incorporated herein in its entirety by this reference. Improvement of the bioavailability of the compound expands the therapeutic range of the compounds by reducing certain cellular toxicities in the subject.

Compounds of this invention include:

| Compound | Chemical Structure |
|---|---|
| 1 | 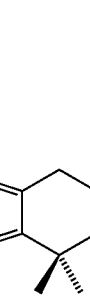 |
| 2 | 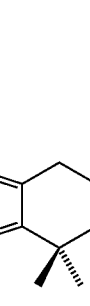 |
| 3 | 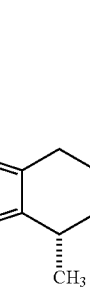 |
| 4 | 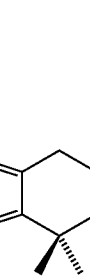 |

| Compound | Chemical Structure |
|---|---|
| 5 | 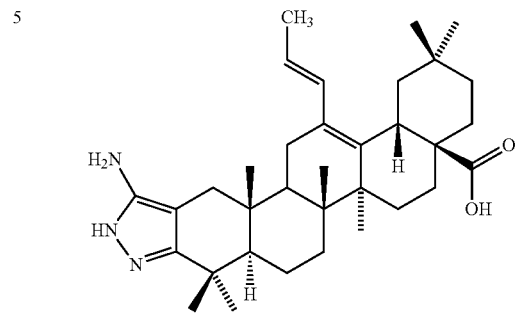 |
| 6 | 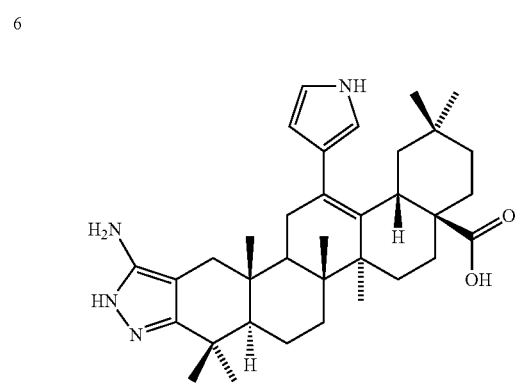 |
| 7 | 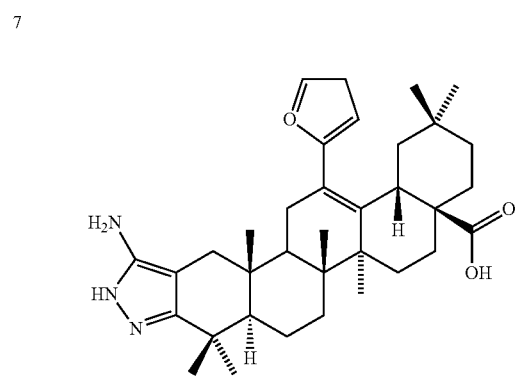 |
| 8 | 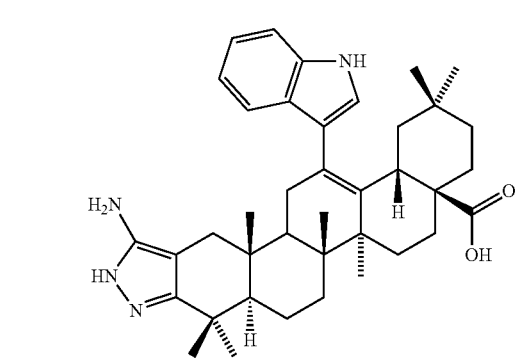 |
| 9 | 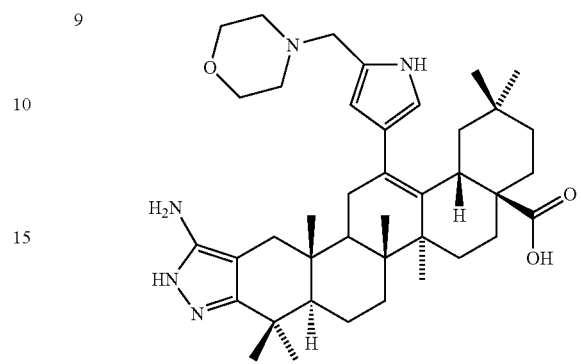 |
| 10 | 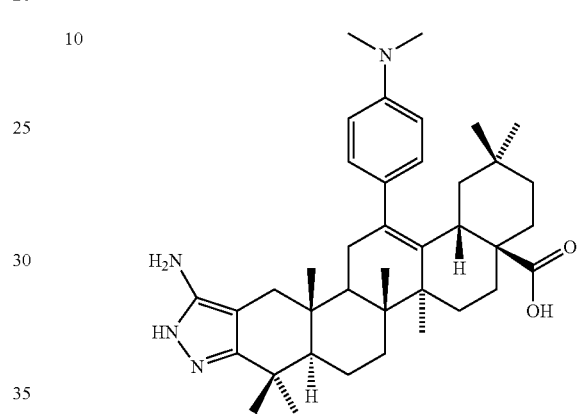 |
| 11 | 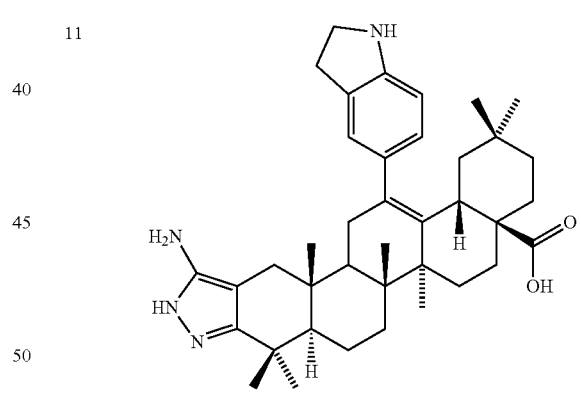 |
| 12 | 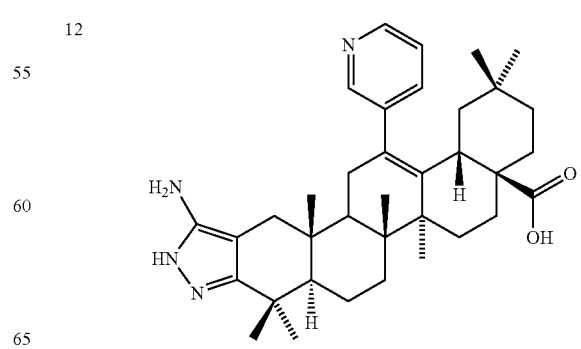 |

-continued

| Compound | Chemical Structure |
|---|---|
| 62 | 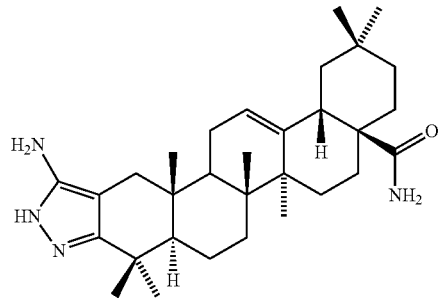 |
| 64 | 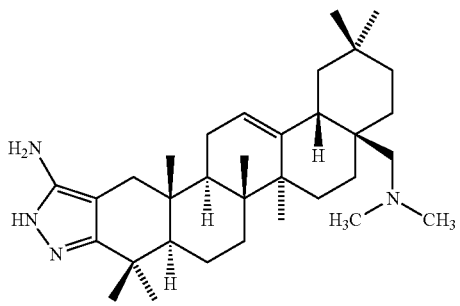 |
| 65 | 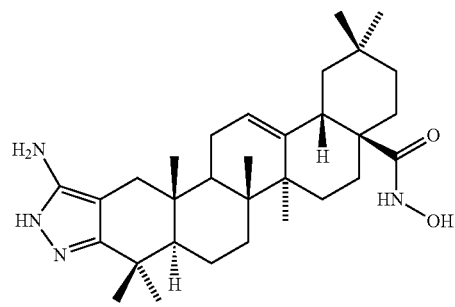 |
| 68 | 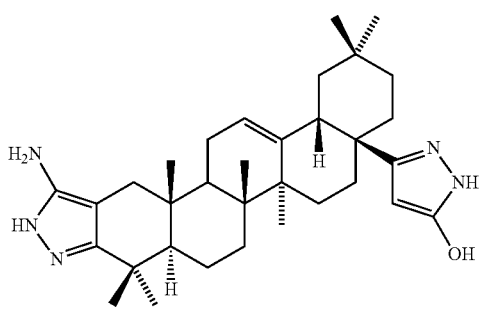 |
| 84 | 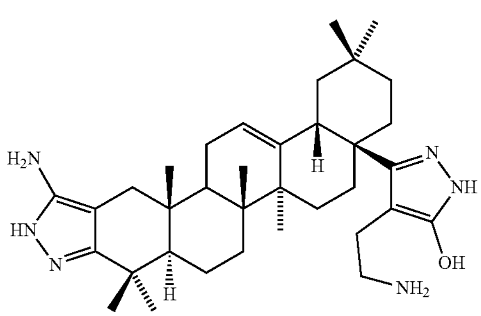 |

-continued

| Compound | Chemical Structure |
|---|---|
| 88 | 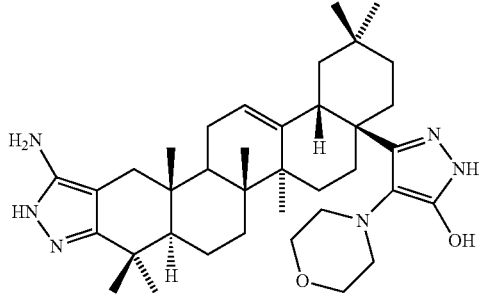 |
| 90 | 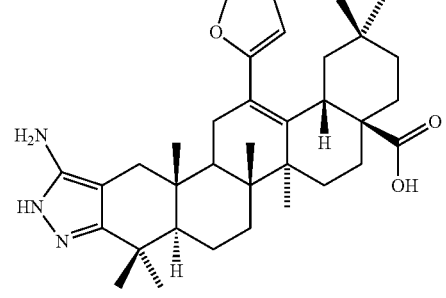 |
| 92 | 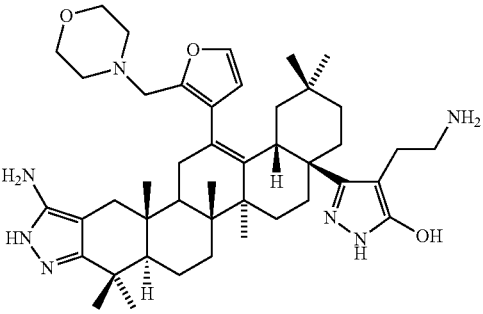 |

The invention especially teaches the remarkable discovery as demonstrated by the examples that the following Structure II

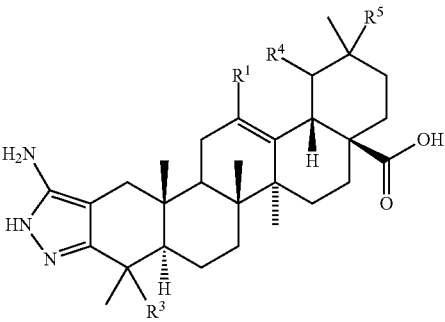

may contain a diverse variety of moieties and structures at $R^1$ and retain the ability to inhibit or reduce the formation or growth of biofilms. The examples demonstrate that a diverse group of aryl, substituted aryl, heteroaryl, and substituted heteroaryl moieties and structures may be added at $R^1$ and retain potent activity to reduce or inhibit the formation or growth of biofilms. A few representative chemical structures prepared semi-synthetically and described herein including the examples are as follows:

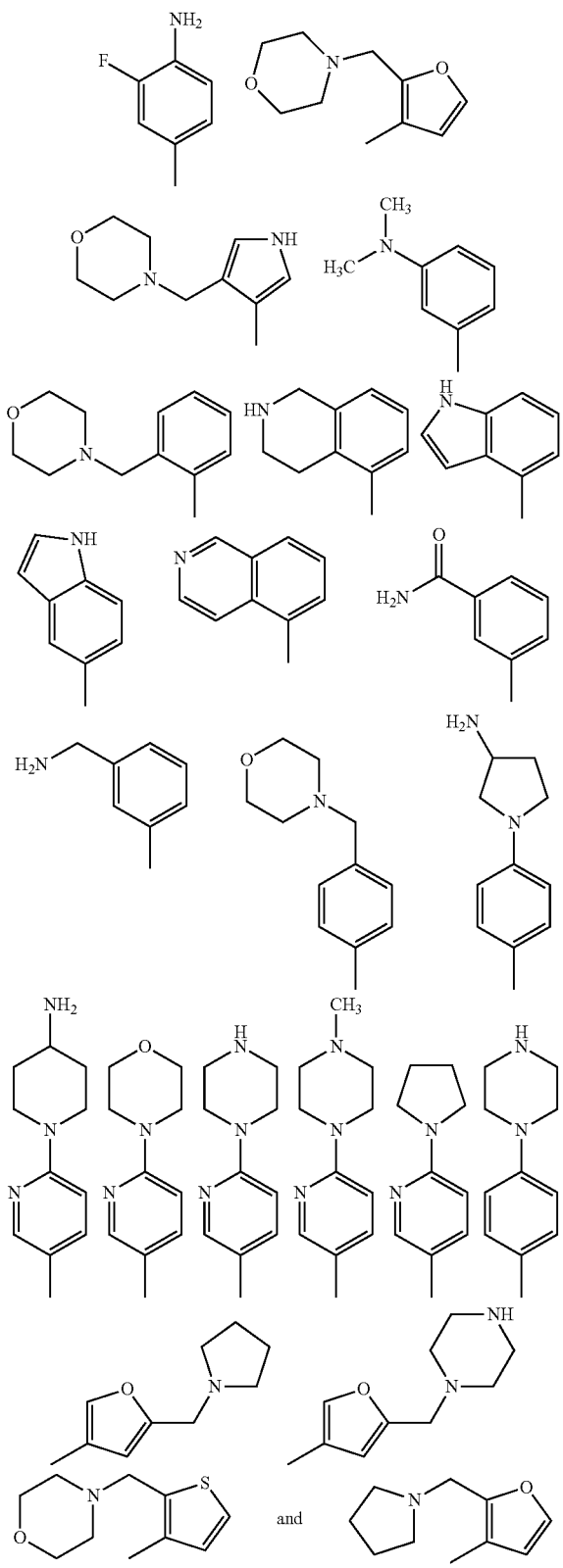

The present invention also includes compounds of the following chemical Structure III:

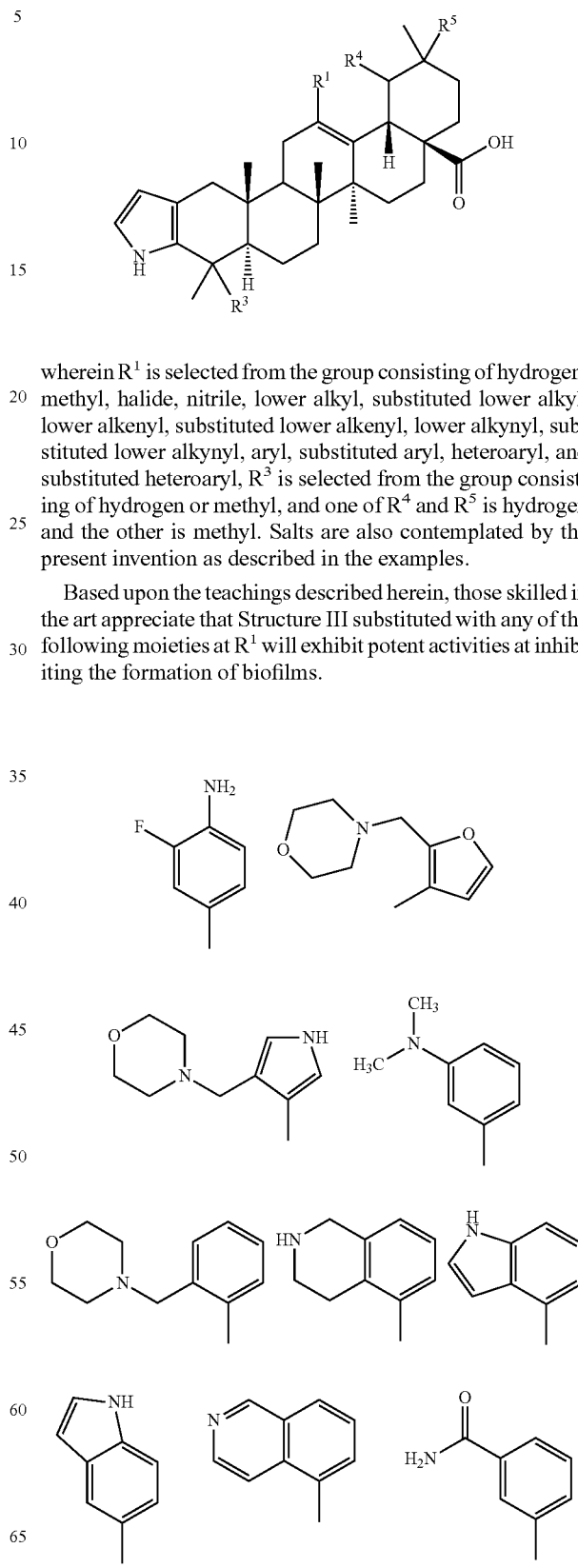

wherein $R^1$ is selected from the group consisting of hydrogen, methyl, halide, nitrile, lower alkyl, substituted lower alkyl, lower alkenyl, substituted lower alkenyl, lower alkynyl, substituted lower alkynyl, aryl, substituted aryl, heteroaryl, and substituted heteroaryl, $R^3$ is selected from the group consisting of hydrogen or methyl, and one of $R^4$ and $R^5$ is hydrogen and the other is methyl. Salts are also contemplated by the present invention as described in the examples.

Based upon the teachings described herein, those skilled in the art appreciate that Structure III substituted with any of the following moieties at $R^1$ will exhibit potent activities at inhibiting the formation of biofilms.

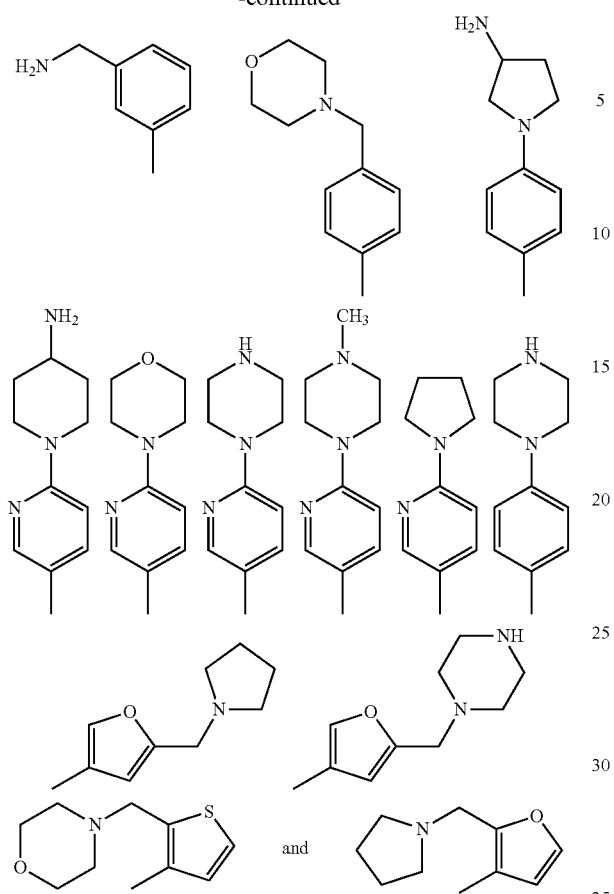

The present invention provides compounds of the following chemical Structure IV

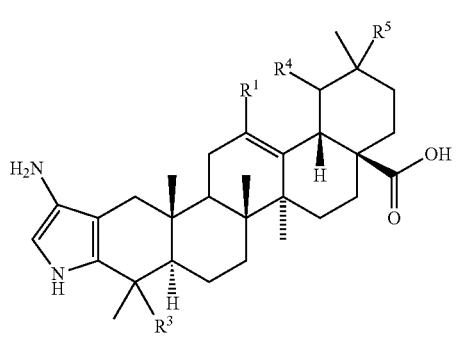

wherein $R^1$ is selected from the group consisting of hydrogen, methyl, halide, nitrile, lower alkyl, substituted lower alkyl, lower alkenyl, substituted lower alkenyl, lower alkynyl, substituted lower alkynyl, aryl, substituted aryl, heteroaryl, and substituted heteroaryl, wherein $R^3$ is selected from the group consisting of hydrogen or methyl; wherein one of $R^4$ and $R^5$ is hydrogen and the other is methyl. Salts are also contemplated by the present invention as described in the examples.

Based upon the teachings described herein, those skilled in the art appreciate that Structure IV substituted with the following moieties at $R^1$ would exhibit potent activities at inhibiting the formation of biofilms:

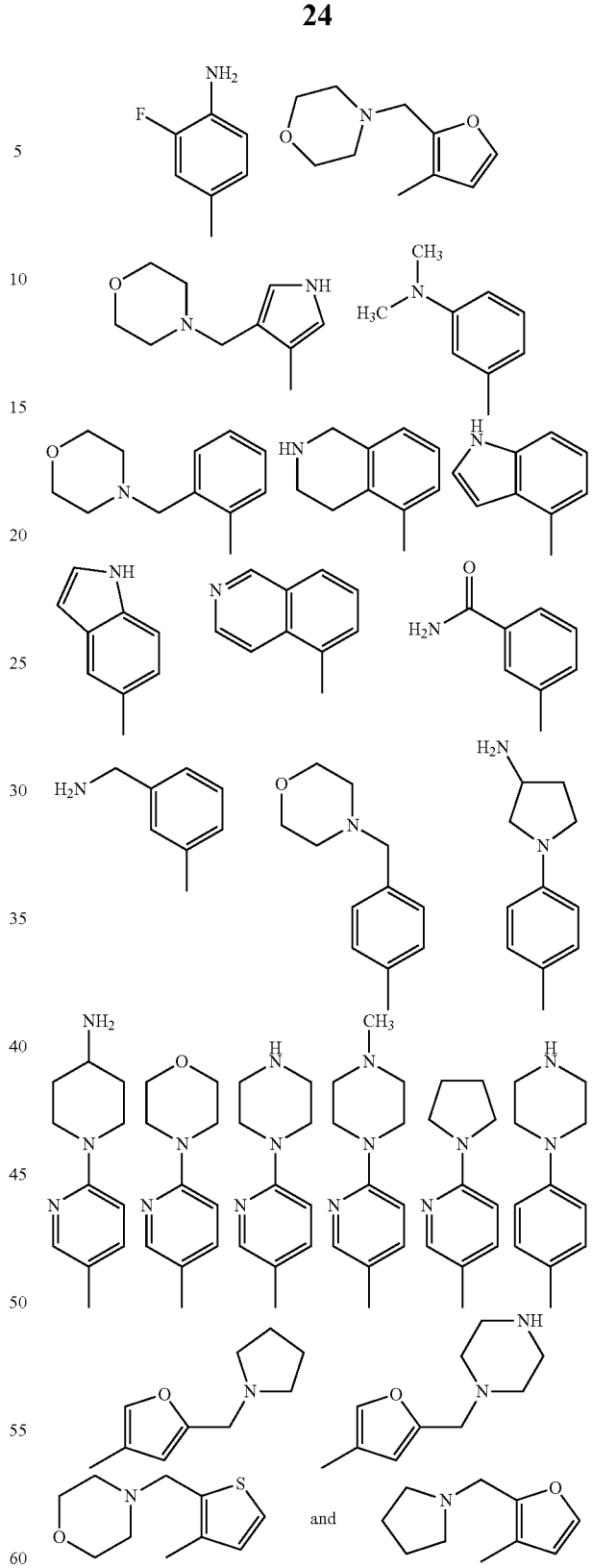

Various pharmaceutical compositions contemplated by the present invention, including the compounds of the invention and the specific examples described herein, further including pharmaceutically acceptable derivable prodrugs or prodrugs thereof. A "pharmaceutically acceptable derivable prodrug or prodrug" means any pharmaceutically acceptable salt, ester, salt of an ester, or other derivable prodrug of a compound of this invention which, upon administration to a patient, is capable of providing (directly or indirectly) a compound used in this invention. It will be recognized that the efficacy of the compounds of this invention is related to localized reaction sites on the compounds. Accordingly, as illustrated by the examples below, a wide variety of substitutions therefore may be made at various sites on the compounds spacially remote from the localized reaction sites that do not significantly interfere with the efficacy of the compounds Likewise, substitutions to form pharmaceutically acceptable salts, esters, salts of esters, and other such derivable prodrugs of the compounds of this invention are are contemplated herein as well. Thus, compounds with such innocuous substitutions do no depart from the scope of the invention.

On the other hand, however, certain moieties have been found to be so significant in size or reactivity as to interfere significantly with the efficacy of the compounds. Thus, highly reactive, polar, ionic or large substituents such as those shown in the examples below as having a deleterious affect on the activity of the compound are are excluded from the most preferred embodiments of the invention.

Compounds useful in the present invention may, optionally, be converted to their therapeutically-active non-toxic acid salt forms by treatment with appropriate acids. Such acids include inorganic acids, e.g., hydrochloric and hydrobromic acids, sulfuric acid, nitric acid, phosphoric acid and like acids; or organic acids, such as acetic, propanoic, hydroxyacetic, 2-hydroxypropanoic, 2-oxo-propanoic, ethanedioic, propanedioic and like acids. Of course, the salt forms may be converted into the free base form by treatment with alkali. The pharmaceutically-acceptable acid salts of the present invention also comprise the solvates that the compositions of the present invention may form, which, of course, are included within the scope of the present invention. Non-limiting examples of such solvates are hydrates, alcoholates and the like.

Such pharmacologic compositions may be formulated in various ways known in the art for administration purposes. Pharmaceutical compositions of the present invention can be prepared by combining an effective amount of the particular compound of this invention, typically in base or acid salt form, as the active ingredient with one or more pharmaceutically-acceptable carriers and delivery vehicles. Numerous pharmaceutically acceptable carriers and delivery vehicles exist that are readily accessible and well-known in the art, which may be employed to generate the preparation desired (i.e. that permit administration of the pharmaceutical composition orally, topically, rectally, percutaneously, by parenteral injection, intranasally or by inhalation). Representative examples of pharmaceutically acceptable carriers and delivery vehicles include aluminum stearate, lecithin, serum proteins, such as human serum albumin; buffer substances such as the various phosphates, glycine, sorbic acid, potassium sorbate, partial glyceride mixtures of saturated vegetable fatty acids; water, salts or electrolytes, such as protamine sulfate, disodium hydrogen phosphate, potassium hydrogen phosphate, sodium chloride, and zinc salts; colloidal silica, magnesium trisilicate, polyvinyl pyrrolidone, cellulose-based substances, polyethylene glycol, sodium carboxymethylcellulose, polyarylates, waxes, polyethylene, polyoxypropylene-block polymers, polyethylene glycol and wool fat, and the like. Other constituents, such as aids for taste, color, tableting, and so forth, may be combined with the active ingredient and carrier for any of the many known purposes of such additives. Examples of such additives are discussed below.

The pharmacologic compositions described herein may further be prepared in unitary dosage form for administration orally, percutaneously, by parenteral injection (including subcutaneous, intramuscular, intravenous and intradermal), topically, intranasally, by inhalation, or for application to a medical device, such as an implant, catheter, or other device. In preparing the compositions that permit administration of an oral dosage, for example, any of the pharmaceutically acceptable carriers known in the art may be used, such as water, glycols, oils, alcohols and the like in the case of carriers that permit oral delivery of liquid preparations such as suspensions, syrups, elixirs and solutions. When solid pharmaceutically acceptable carriers are desired that permit oral or rectal administration, starches, sugars, kaolin, lubricants, binders, cellulose and its derivable prodrugs, and disintegrating agents and the like may be used to prepare, for example, powders, pills, capsules and tablets.

For pharmaceutically acceptable carriers that permit parenteral administration, the pharmaceutically acceptable carriers often comprise sterile water, which may be supplemented with various solutes to, for example, increase solubility. Injectable solutions may be prepared in which the pharmaceutically acceptable carrier comprises saline solution, glucose solution, or a mixture thereof, which may include certain well-known anti-oxidants, buffers, bacteriostats, and other solutes that render the formulation isotonic with the blood of the intended patient.

For pharmaceutically acceptable carriers that permit intranasal administration, the pharmaceutically acceptable carriers often comprise poly acrylic acids such as Carbopol® 940, a hydrogenated castor oil such as Cremophor® RH40, glycerol, vinylpyrrolidones such as PVP-K90® or PVP K30®, polyethylene glycols such as PEG 1450®, benzyl alcohol, Edetate sodium, hydroxycellulose, potassium chloride, potassium phosphate, and sodium phosphate. Compositions used for intranasal administration also commonly include benzalkonium chloride as an anti-microbial preservative.

For pharmaceutically acceptable carriers that permit administration by inhalation, the pharmaceutically acceptable carriers often comprise solvent/carrier/water mixtures that are easily dispersed and inhaled via a nebulizer or inhaler. For example, a mixture of ethanol/propylene glycol/water in the ratio of about 85:10:5 (parts ethanol: parts propylene glycol: parts water) can be used to administer the compounds and compositions of the invention via inhalation. Ratios as expressed herein are based on parts by weight.

For pharmaceutically acceptable carriers that permit percutaneous administration, the pharmaceutically acceptable carrier may, optionally, comprise a penetration enhancing agent and/or a wetting agent.

Dosage forms that permit topical or transdermal administration of a compound of this invention include ointments, pastes, creams, lotions, gels, powders, solutions, sprays, inhalants or patches. The active compound or compounds is/are mixed under sterile conditions with a pharmaceutically acceptable carrier and optionally one or more preservatives and/or buffers. In the context of certain embodiments of this invention, the active compound is a pentacyclic acid triterpene. In the context of other embodiments of this invention, the pentacyclic acid triterpene is combined in the composition with another active compound that is an antimicrobial agent or antibiotic.

The ointments, pastes, creams and gels may contain, in addition to an active compound or compounds according to the present invention, pharmaceutically acceptable carriers that permit topical or transdermal administration such as animal and vegetable fats, oils, waxes, paraffins, starch, tragacanth, cellulose derivable prodrugs, polyethylene glycols, silicones, bentonites, silicic acid, talc and zinc oxide, or mixtures thereof.

In some cases, the pH of the pharmaceutical formulations contemplated herein may be adjusted with acceptable acids, bases or buffers to enhance the stability of one or more of the active compounds present or their delivery forms. In the context of certain embodiments of this invention, the active compound is a pentacyclic acid triterpene. In the context of other embodiments of this invention, the pentacyclic acid triterpene is combined in the composition with another active compound that is an antimicrobial agent or antibiotic.

Still further, in order to prolong the anti-bacterial effect of a compound disclosed herein, it may be desirable to slow the absorption of the compound from subcutaneous or intramuscular injection. This may be accomplished using a liquid suspension of crystalline or amorphous material with poor water solubility. The rate of absorption of the compound then depends upon its rate of dissolution, which, in turn, may depend upon crystal size and crystalline form. Alternatively, delayed absorption of a parenterally administered drug form may be accomplished by dissolving or suspending the compound in an oil vehicle.

Injectable depot forms are made, e.g., by forming microencapsule matrices of one or more compounds of the present invention in biodegradable polymers such as polylactide-polyglycolide. Depending upon the ratio of active(s) to polymer and the nature of the particular polymer employed, the rate at which such active(s) is released may be controlled. Examples of other biodegradable polymers include poly (orthoesters) and poly(anhydrides). Depot injectable formulations are also prepared by entrapping the compound in liposomes or microemulsions that are compatible with body tissues.

The pharmaceutical composition may also be a dentifrice. In the present invention, "dentifrice" is understood to broadly include compositions suitable for administering to the oral cavity, especially, for example, to the gingival/mucosal tissue or to the teeth. Thus, the dentifrice may include toothpastes, toothpowders, liquid dentifrices, mouth detergents, mouthwashes, troches, chewing gums, dental or gingival massage creams, dental strips, dental gels, and gargle tablets.

When the pharmaceutical composition of this invention is a dentifrice such as tooth paste, a tooth or gum adherence promoting substance selected from the group consisting of copolymers of methyl vinyl ether and maleic anhydride, copolymers of vinyl pyrrolidone and vinyl acetate, and cyclodextrins may also be included in the composition. Copolymers of methyl vinyl ether and maleic anhydride useful in this invention may have molecular weights ranging from 200,000 to 2,000,000 kD and may be free acids, mixed sodium and calcium salts, or half ester derivable prodrugs. Representative commercial sources of the copolymers of methyl vinyl ether and maleic anhydride include GANTREZ® AN(CAS #9011-16-9) GANTREZ® S (CAS #25153-40-69) GANTREZ® MS (CAS#62386-95-2) GANTREZ® ES (CAS#25087-06-3 or CAS#25119-68-0) and can be obtained from International Specialty Products Wayne, N.J. Copolymers of vinyl pyrrolidone and vinyl acetate useful in the invention typically have a molecule weight of approximately 27,000 kD and are water soluble. Representative commercial sources of the copolymers of vinyl pyrrolidone and vinyl acetate PLASDONE® S-630 and can be obtained from International Specialty Products Wayne, N.J. Cyclodextrins useful in the invention are cyclic oligosaccharides composed of either 6, 7 or 8 glucose units (a-, b- and g-cyclodextrin, respectively). Representative commercial sources of the cyclodextrins useful in this invention include CAVAMAX® W6 Pharma, CAVAMAX® W7 Pharma and CAV AMAXW8 Pharma (a-, b- and g-cyclodextrin, respectively) and can be obtained from International Specialty Products Wayne, N.J.

When the composition of this invention is a dentifrice, an antimicrobial agent is selected from the group consisting of triclosan, metronidazole, tetracyclines, quinolones, plant essential oils, camphor, thymol, carvacrol, menthol, eucalyptol, and methyl salicylate may also be included. Pharmaceutically acceptable carriers that permit administration of the pentacyclic acid triterpene compounds of this application as dentifrices include sorbitol, glycerin, silica, sodium lauryl sulfate and Xanthum gum. The dentifrices of this invention may also include sodium fluoride.

Reducing or Inhibiting Bacterial Biofilms in Plants

Finally, bacterial biofilms also may be reduced or inhibited by the application or administration of compositions containing compounds disclosed herein when the subject is a plant. Thus, the compound or a composition containing an active compound described herein may be administered to a plant, such as a surface of a plant to reduce or inhibit the formation of a biofilm on the plant.

It is believed that the methods described herein are applicable to reducing or inhibiting a variety of bacterial biofilms in plants. Pseudomonadaceae, Rhizobiaceae, Enterobacteriaceae, Corynebacteriaceae and Streptomycetaceae bacteria are all economically significant plant pathogens that may be controlled by the present invention. Non-limiting examples of specific plant pathogens involving biofilms that may be effectively inhibited by the methods described herein include: *Xanthomonas* species, such as, for example, *Xanthomonas campestris* pv. *oryzae*; *Pseudomonas* species, such as, for example, *Pseudomonas syringae* pv. *lachrymans*; and *Erwinia* species, such as, for example, *Erwinia amylovora*. It is also believed that the compositions used in the methods of reducing or inhibiting bacterial biofilms of plants described herein can further comprise antimicrobial agents such as bronopol, dichlorophen, nitrapyrin, nickel dimethyldithiocarbamate, kasugamycin, octhilinone, furancarboxyl, oxytetracyclin, probenazole, streptomycin, tecloftalam, copper sulphate and other copper preparations.

Methods of reducing or inhibiting bacterial biofilms described herein can be used to treat all plants and parts of plants. By reference to "plants," what is meant here is all plants and plant populations such as desired and undesired wild plants or crop plants (including naturally occurring crop plants). Crop plants can be plants obtainable by conventional breeding and optimization methods or by biotechnological and genetic engineering methods or combinations of these methods, and include the transgenic plants and the plant varieties that can or cannot be protected by varietal property rights. The phrase "parts of plants" as used herein is to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example, seedlings, tubers, rhizomes, cuttings and seeds.

The treatment of the plants and the parts of plants with the active compounds according to the invention is carried out directly or by action on their surroundings, habitat or storage space, according to customary treatment methods, for example by dipping, spraying, evaporating, atomizing, broadcasting, spreading-on and, in the case of propagation material, in particular in the case of seeds, furthermore by one- or multi-layer coating.

Agriculturally Acceptable Carriers and Compositions

Depending on their particular physical and/or chemical properties, the compounds and compositions described herein can be converted to the customary formulations, such as solutions, emulsions, suspensions, powders, foams, pastes, granules, aerosols and microencapsulations in polymeric substances and in coating compositions for seeds, and ULV cool and warm fogging formulations.

The following examples illustrate various aspects of the present invention and are not intended to limit the scope of the present invention. Those of skill in the art should, in light of the present disclosure, appreciate that many changes can be made in the specific embodiments which are disclosed and still obtain a like or similar result without departing from the spirit and scope of the invention.

EXAMPLE I

Specificity of the Biofilm Growth Assay

Table 1, below, shows experimental results illustrating remarkable properties of Compound 1 to inhibit the spreading of clinical isolates of *P. aeruginosa* and *E. coli* biofilms as determined in a biofilm growth assay. The related scaffolds and analogs shown in Table 1 have been found to exhibit significantly less inhibitory activities than does Compound 1 in the biofilm growth assay even though certain of the compounds consist of chemical structures similar to that of Compound 1. These data demonstrate the novel and unique aspects of Compound 1 and its discovery and the specificity of the biofilm growth assay to identify Compound 1 as a potent inhibitor of spreading gram-negative bacterial biofilms.

The biofilm growth assay was carried out to measure swarming or biofilm spreading on semi-solid agar media in round plates (for example, 100×15 mm), also referred to as Petri dishes. For *E. coli*, the plates contained LB medium with 0.6% agar and 0.5% glucose. *P. aeruginosa* plates were made with M8 agar supplemented with 0.2% glucose, 100 µM CaCl$_2$, 1 mM MgSO$_4$, and 0.5% Casamino acids. The agar plates of this assay consisted of 0.4% to 0.7% agar (Bacto or Noble agar), although other media may also be used as described in the literature and known to those skilled in the art. Test compounds at the desired concentration were added to the cooled, autoclaved media. Portions of the media were then poured into the plates (20 mL/plate), and the plates allowed to dry at room temperature for approximately 3 to 4 hours. Alternatively, however, plates may be dried in a laminar flow hood for approximately fifteen to twenty minutes. Overnight cultures were grown in a 37° C. shaker in LB (*E. coli*) or TSB (*P. aeruginosa*). Plates were inoculated by placing 5 µL of the appropriate overnight culture in the centers of the plates. The plates then were incubated overnight at 37° C. The area of the zone of spreading bacteria was then measured and replicates are averaged. Percent inhibition was calculated as 100×(area without compound−area with compound)/(area without compound). An active compound was considered that which reduces the area of the spreading biofilm compared to negative controls by greater than or equal to 85%. The values shown in Table 1 are the concentrations of compounds (µg/ml) tested in the biofilm growth assay that reduce the area of the spreading biofilm compared to negative controls by greater than or equal to 85% unless noted differently in Table 1. A > ("greater than" symbol) as used in Table 1 is well understood to those skilled in the art as an indication that the listed concentration was not effective at this concentration.

This example demonstrates the reduction of virulence of gram-negative bacteria. Inhibition or reduction of the growth of biofilms reduces virulence of gram-negative bacteria. Adhesion, biofilm growth, invasion, and the secretion of enzymes or toxins contribute to virulence of gram-negative bacteria. It is well known to those skilled in the art that biofilms increase the virulence of gram-negative bacteria and an upregulation of virulence factors (i.e. enzymes, toxins) has been demonstrated in gram-negative bacterial biofilms. The compounds of the invention reduce virulence of gram-negative bacteria.

TABLE 1

Related Scaffolds and Analogs of Compound 1

| COMPOUND | STRUCTURE | *P. aeruginosa* (µg/ml) | *E. coli* (µg/ml) |
| --- | --- | --- | --- |
| Compound 1 | 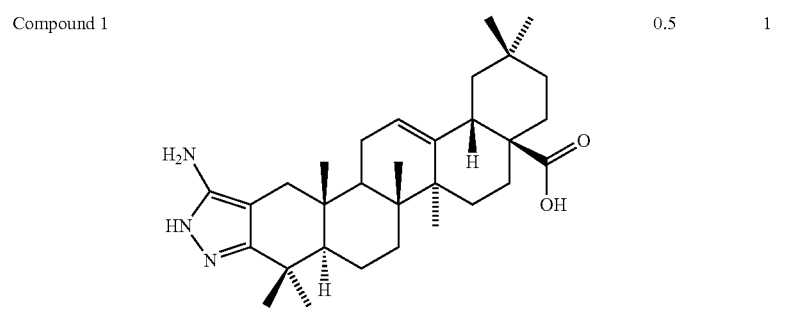 | 0.5 | 1 |

TABLE 1-continued

Related Scaffolds and Analogs of Compound 1

| COMPOUND | STRUCTURE | P. aeruginosa (µg/ml) | E. coli (µg/ml) |
|---|---|---|---|
| Uvaol | 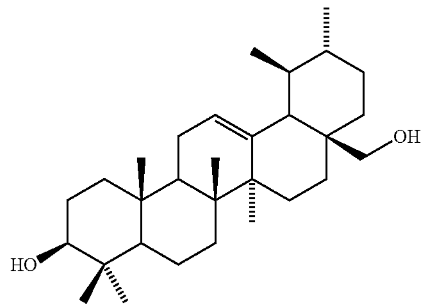 | >128 | >8 |
| alpha-Amyrin | 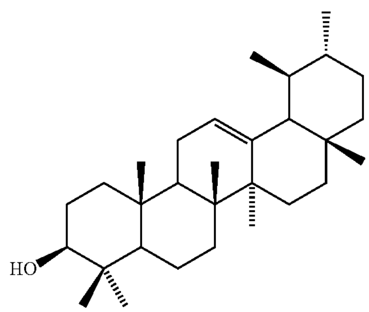 | >32 | Not tested |
| Lupeol | 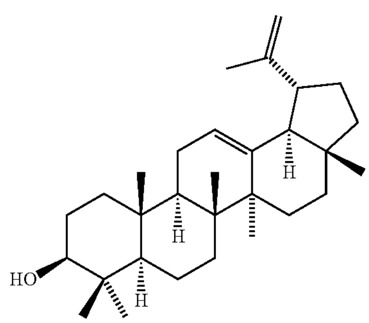 | >16 | >8 |
| Betulin | 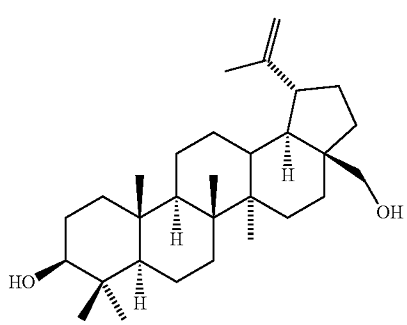 | 16 | >16 |

TABLE 1-continued

Related Scaffolds and Analogs of Compound 1

| COMPOUND | STRUCTURE | P. aeruginosa (µg/ml) | E. coli (µg/ml) |
| --- | --- | --- | --- |
| Betulinic acid | 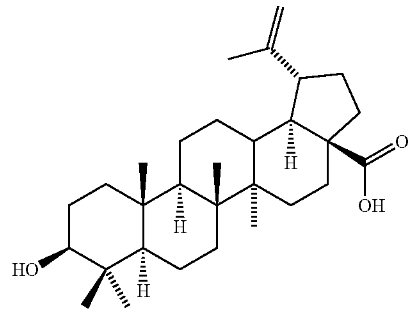 | >16 | >16 |
| Oleanolic acid methyl ester | 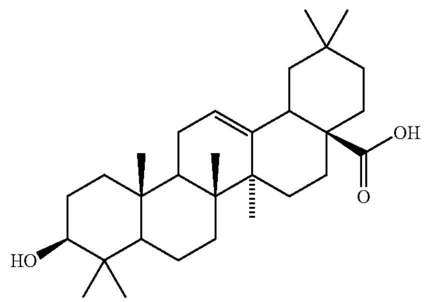 | 4 | >8 |
| Ursolic acid | 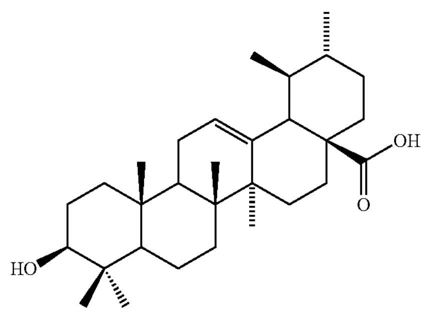 | 8 | 8 |
| Oleanolic acid | 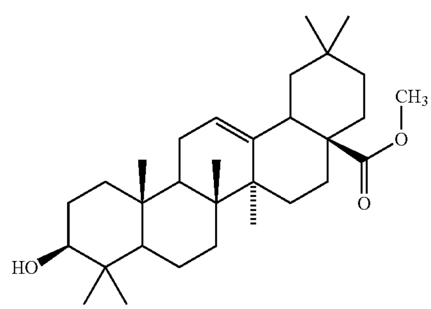 | >16 | >16 |
| Corosolic acid | 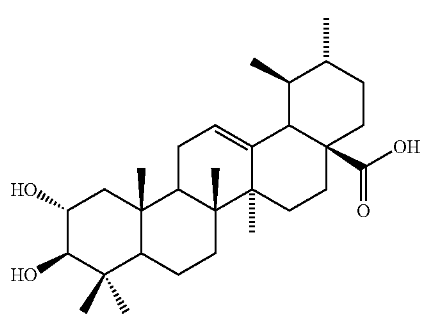 | 4 | Not tested |

TABLE 1-continued

Related Scaffolds and Analogs of Compound 1

| COMPOUND | STRUCTURE | P. aeruginosa (µg/ml) | E. coli (µg/ml) |
|---|---|---|---|
| Maslinic acid | 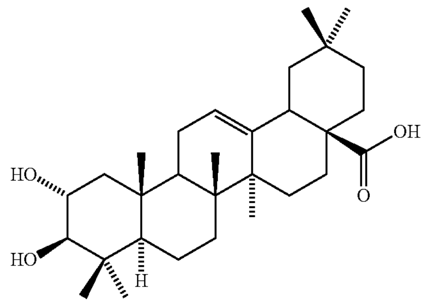 | 4 | Not tested |
| A | 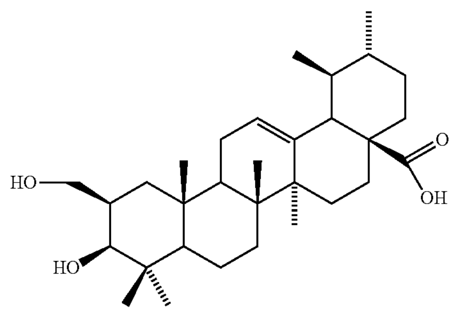 | 8 | >8 |
| B | 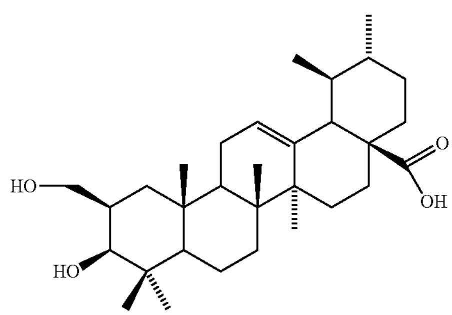 | 4 | 8 |
| C | 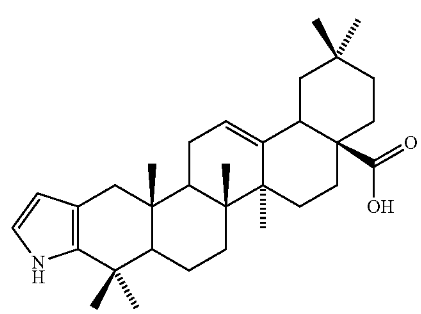 | 0.5 | 0.5 |

TABLE 1-continued

Related Scaffolds and Analogs of Compound 1

| COMPOUND | STRUCTURE | P. aeruginosa (μg/ml) | E. coli (μg/ml) |
|---|---|---|---|
| D | 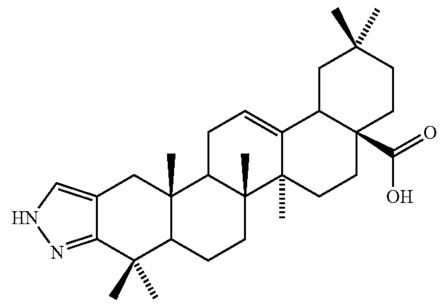 | 1 | 4 |
| E | 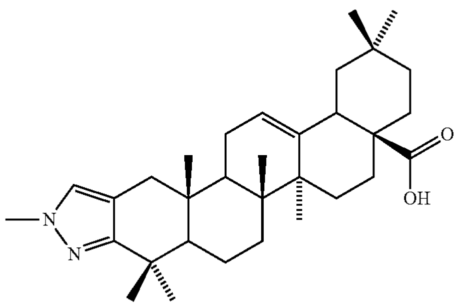 | 2 | >16 |
| F | 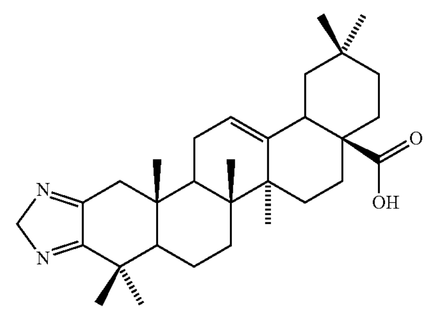 | 4 | >8 |
| G | 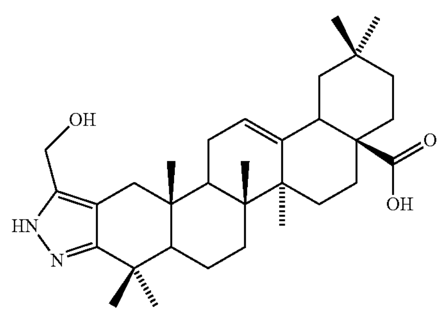 | >8 | >8 |
| H | 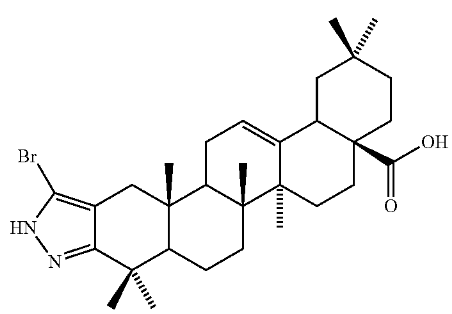 | 8 | >8 |

TABLE 1-continued

Related Scaffolds and Analogs of Compound 1

| COMPOUND | STRUCTURE | P. aeruginosa (µg/ml) | E. coli (µg/ml) |
|---|---|---|---|
| I | 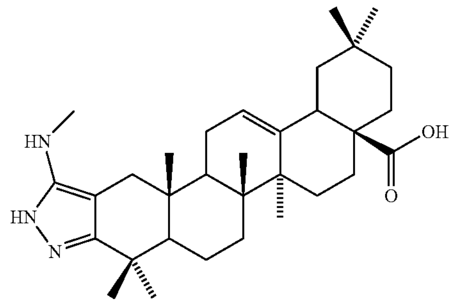 | >16 | 8 |
| J | 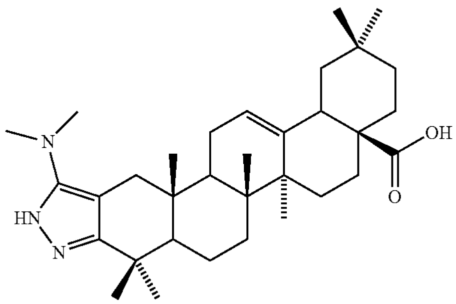 | >16 | >16 |
| K | 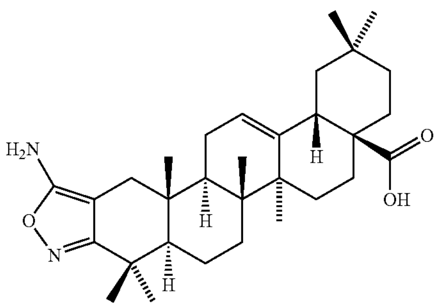 | >8 | >8 |
| L | 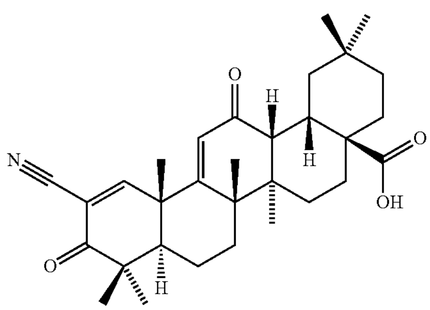 | >16 | >16 |
| M | 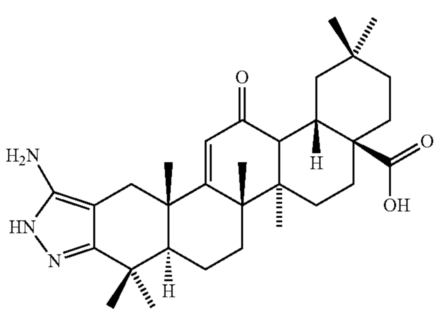 | 8 | 8 |

TABLE 1-continued

Related Scaffolds and Analogs of Compound 1

| COMPOUND | STRUCTURE | P. aeruginosa (µg/ml) | E. coli (µg/ml) |
|---|---|---|---|
| N | [structure] | 8 | 8 |

EXAMPLE II

All of the compounds shown in Tables 2, 3, 4, and 5, below, were prepared semi-synthetically from oleanolic acid, except for Compounds 2 and 3. Compound 2 was prepared from ursolic acid. Compound 3 was prepared from hederagenin, but could also be prepared from an oleanolic acid analog with a hydroxyl at $C_{23}$ or $C_{24}$. These compounds were tested in the spreading biofilm assay according to the methods detailed in Example I, above. The values shown in Tables 2, 3, 4, and 5 are the concentrations of compounds tested in the biofilm growth assay that reduce the area of the spreading biofilm compared to negative controls by greater than or equal to 85%.

TABLE 2

Compound 1 and its Analogs and their inhibitory concentrations in the biofilm growth assay as detailed in Example I, above

| COMPOUND | Chemical Structure | P. aeruginosa (µg/ml) | E. coli (µg/ml) |
|---|---|---|---|
| 1 | [structure] | 0.5 | 1 |
| 2 | [structure] | 0.5 | 1 |

TABLE 2-continued

Compound 1 and its Analogs and their inhibitory concentrations in the biofilm growth assay as detailed in Example I, above

| COMPOUND | Chemical Structure | P. aeruginosa (µg/ml) | E. coli (µg/ml) |
|---|---|---|---|
| 3 | 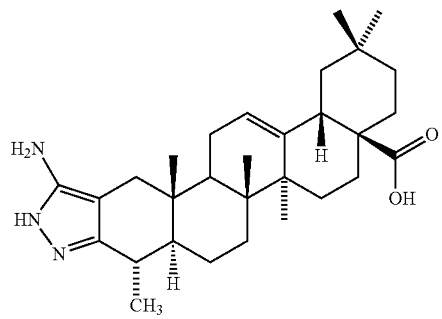 | 0.5 | 1 |
| 4 | 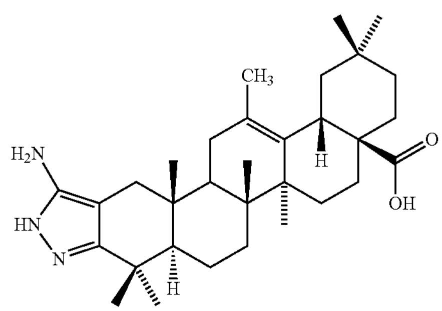 | 0.25 | 1 |
| 5 | 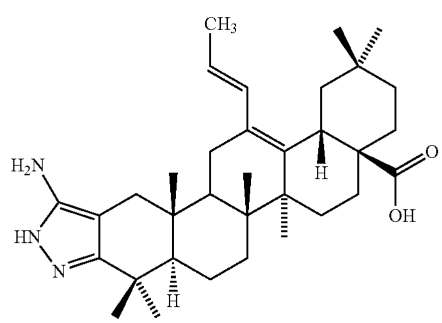 | 0.5 | 1 |
| 6 | 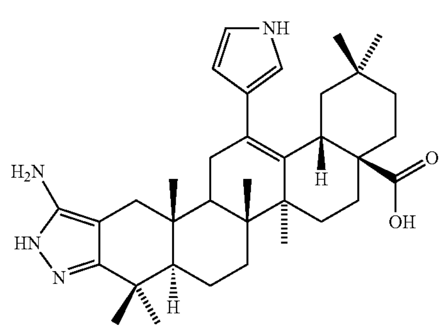 | 0.125 | 0.25 |

TABLE 2-continued

Compound 1 and its Analogs and their inhibitory concentrations in the biofilm growth assay as detailed in Example I, above

| COMPOUND | Chemical Structure | P. aeruginosa (µg/ml) | E. coli (µg/ml) |
|---|---|---|---|
| 7 | 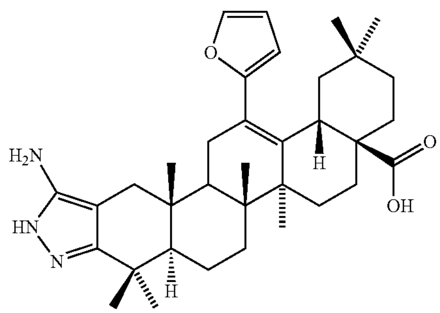 | 0.25 | 1 |
| 8 | 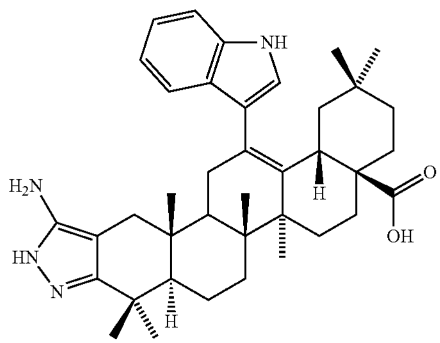 | 0.25 | 1 |
| 9 | 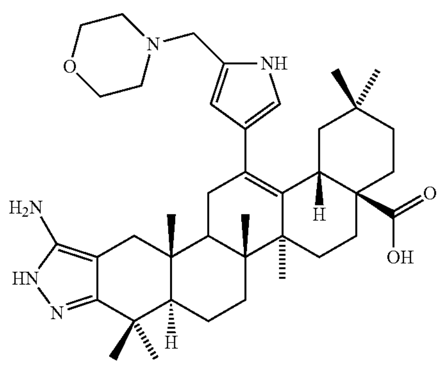 | 0.5 | 1 |
| 10 | 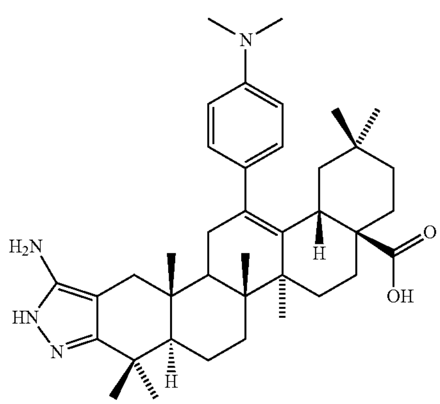 | 0.5 | 1 |

TABLE 2-continued

Compound 1 and its Analogs and their inhibitory concentrations in the biofilm growth assay as detailed in Example I, above

| COMPOUND | Chemical Structure | P. aeruginosa (µg/ml) | E. coli (µg/ml) |
|---|---|---|---|
| 11 | [structure with indoline substituent] | 0.5 | 0.5 |
| 12 | [structure with pyridyl substituent] | 0.5 | 1 |

TABLE 3

Analogs of Compound 1

Chemical Structure

[core structure with R₁ substituent]

| COMPOUND | R₁ | P. aeruginosa (µg/ml) | E. coli (µg/ml) |
|---|---|---|---|
| 13 | —CH=CH₂ | 0.5 | 1 |
| 14 | —CH₂CH₃ | 0.5 | 2 |
| 15 | 3-aminophenyl | 0.25 | 1 |
| 16 | 3-hydroxyphenyl | 1 | 2 |

TABLE 3-continued

Analogs of Compound 1

Chemical Structure

[core structure with R₁ substituent]

| COMPOUND | R₁ | P. aeruginosa (µg/ml) | E. coli (µg/ml) |
|---|---|---|---|
| 17 | 3-fluorophenyl | 0.5 | >2 |
| 18 | 3-methylbenzylamine | 0.5 | 1 |

TABLE 3-continued

Analogs of Compound 1

| COMPOUND | R₁ | P. aeruginosa (µg/ml) | E. coli (µg/ml) |
|---|---|---|---|
| 19 | 3-carbamoylphenyl (H₂N-C(=O)-C₆H₄-) | 1 | 1 |
| 20 | 2-amino-5-methylphenyl (H₂N, CH₃ substituted) | 0.5 | 2 |
| 21 | 3-(dimethylamino)phenyl | 0.5 | >2 |
| 22 | 6-(dimethylamino)-4-methylpyridin-2-yl | 1 | >2 |
| 23 | 2-aminophenyl | 1 | 2 |
| 24 | —Cl | 0.5 | 1 |
| 25 | —Br | 0.5 | >2 |
| 26 | 3-methylfuran-2-yl | 0.25 | 1 |
| 27 | 4-methyl-1H-pyrazol-3-yl | 1 | >2 |
| 28 | 1,4-dimethyl-1H-pyrazol-3-yl | 1 | 2 |
| 29 | 4-methylpyridin-3-yl | 1 | 1 |
| 30 | 5-methylpyrimidin-4-yl | 2 | 1 |
| 31 | 2-amino-3-fluoro-5-methylphenyl | 0.5 | 1 |
| 32 | (morpholinomethyl)-3-methylfuran-2-yl | 0.5 | 1 |
| 33 | (morpholinomethyl)-4-methyl-1H-pyrrol-3-yl | 2 | 4 |
| 34 | (morpholinomethyl)-3-methylthiophen-2-yl | 1 | 1 |
| 35 | (piperazin-1-ylmethyl)-3-methylfuran-2-yl | >1 | 1 |
| 36 | (4-methylpiperazin-1-ylmethyl)-3-methylfuran-2-yl | >1 | 2 |

TABLE 3-continued

Analogs of Compound 1

| COMPOUND | R₁ | P. aeruginosa (μg/ml) | E. coli (μg/ml) |
|---|---|---|---|
| 37 | pyrrolidin-1-ylmethyl-3-methylfuran | >1 | 1 |
| 38 | (4-methylfuran-2-yl)methyl-pyrrolidine | 1 | 2 |
| 39 | (4-methylfuran-2-yl)methyl-piperazine | 1 | 2 |
| 40 | (4-methylfuran-2-yl)methyl-morpholine | 0.5 | 2 |
| 41 | 2-amino-5-methylpyridine | 1 | 2 |
| 42 | 2-methoxy-5-methylpyridine | 0.25 | 1 |
| 43 | N-methyl-5-methylpyridin-2-amine | 1 | 1 |
| 44 | N,N-dimethyl-5-methylpyridin-2-amine | 0.5 | 2 |
| 45 | 1-(5-methylpyridin-2-yl)pyrrolidine | 0.5 | 1 |
| 46 | 5-methylisoquinoline | 0.5 | 1 |
| 47 | 5-methyl-1,2,3,4-tetrahydroisoquinoline | 0.5 | 1 |
| 48 | 4-methyl-1H-indole | 0.5 | 1 |
| 49 | 5-methyl-1H-indole | 0.5 | >1 |

TABLE 3-continued

Analogs of Compound 1

Chemical Structure

| COMPOUND | R₁ | P. aeruginosa (µg/ml) | E. coli (µg/ml) |
|---|---|---|---|
| 50 | 4-(4-methylphenyl)piperazin-1-yl (NH linker) | 2 | 1 |
| 51 | 4-(4-methylphenyl)morpholin-4-yl | 0.5 | 2 |
| 52 | 4-((4-methylphenyl)methyl)morpholin-4-yl | 1 | 2 |
| 53 | 1-methyl-4-(4-methylphenyl)piperidin-4-yl | 0.5 | 2 |
| 54 | 4-(5-methylpyridin-2-yl)morpholin-4-yl | 1 | 2 |
| 55 | 1-(5-methylpyridin-2-yl)piperazin-4-yl (NH) | >1 | 2 |
| 56 | 1-methyl-4-(5-methylpyridin-2-yl)piperazin-4-yl | 1 | 2 |
| 57 | 4-amino-1-(5-methylpyridin-2-yl)piperidin-4-yl | >2 | 1 |

TABLE 3-continued

Analogs of Compound 1

Chemical Structure

[Structure: triterpenoid core with aminopyrazole fused ring and R₁ substituent on carboxylic acid group]

| COMPOUND | R₁ | P. aeruginosa (µg/ml) | E. coli (µg/ml) |
|---|---|---|---|
| 58 | 3-amino-1-(5-methylpyridin-2-yl)pyrrolidine | 1 | 2 |
| 59 | 4-(2-methylbenzyl)morpholine | 0.5 | >1 |

TABLE 4

Analogs of Compound 1

CHEMICAL STRUCTURE

[Structure: triterpenoid core with aminopyrazole fused ring and R₁ substituent]

| COMPOUND | R₁ | P. aeruginosa (µg/ml) | E. coli (µg/ml) |
|---|---|---|---|
| 60 | 5-methyl-3-amino-1H-pyrazole | 0.5 | 1 |
| 61 | N-(1H-tetrazol-5-yl)acetamide | 0.5 | 0.5 |
| 62 | acetamide | 1 | 1 |
| 63 | ethylamine | 4 | 1 |

TABLE 4-continued

Analogs of Compound 1

CHEMICAL STRUCTURE

[Structure: triterpenoid core with aminopyrazole fused ring and R₁ substituent]

| COMPOUND | R₁ | P. aeruginosa (µg/ml) | E. coli (µg/ml) |
|---|---|---|---|
| 64 | N,N-dimethyl-N-ethylamine | 0.5 | 1 |
| 65 | N-hydroxyacetamide | 0.25 | 0.25 |
| 66 | N-(5-hydroxy-1H-pyrazol-3-yl)acetamide | 0.25 | 1 |
| 67 | 2-methyl-1,3,4-oxadiazole | 1 | 2 |
| 68 | 3-methyl-5-hydroxy-1H-pyrazole | 0.5 | 0.5 |
| 69 | N-(5-amino-1H-pyrazol-3-yl)acetamide | 1 | 1 |
| 70 | S-(5-amino-1H-1,2,4-triazol-3-yl) ethanethioate | 0.5 | 2 |
| 71 | N-(5-amino-1,3,4-thiadiazol-2-yl)acetamide | 0.5 | 2 |
| 72 | 5-amino-1,3-dimethyl-1H-pyrazole | 1 | >2 |
| 73 | 1-(2-amino-1H-imidazol-1-yl)ethanone | 1 | 1 |

TABLE 4-continued

Analogs of Compound 1

CHEMICAL STRUCTURE

| COMPOUND | R₁ | P. aeruginosa (µg/ml) | E. coli (µg/ml) |
|---|---|---|---|
| 74 | acetamido-thiadiazole-SH | 1 | >2 |
| 75 | methyl-triazole-SH | 0.5 | 1 |
| 76 | acetyl-triazole-SH | 0.5 | 2 |
| 77 | acetamido-methyl-triazole-SH | 1 | 2 |
| 78 | methyl-thiadiazole-OH | >1 | 1 |
| 79 | acetamido-pyrazole-SH | 0.25 | 0.5 |
| 80 | acetamido-thiadiazole-SO₂NH₂ | 1 | 1 |
| 81 | hydroxy-methyl-pyrazole-ethanol | 0.5 | 1 |
| 82 | hydroxy-methyl-pyrazole-CH₃ | 0.5 | 1 |
| 83 | hydroxy-methyl-pyrazole-F | 0.25 | 0.5 |
| 84 | hydroxy-methyl-pyrazole-ethyl-NH₂ | 0.125 | 0.5 |
| 85 | hydroxy-methyl-pyrazole-ethyl-N(CH₃)₂ | 0.5 | 1 |
| 86 | hydroxy-methyl-pyrazole-ethyl-NHCH₃ | 0.5 | 2 |
| 87 | hydroxy-methyl-pyrazole-ethyl-NH-C(O)NH₂ | 0.5 | 1 |
| 88 | hydroxy-methyl-pyrazole-morpholine | 0.25 | 0.5 |

TABLE 4-continued

Analogs of Compound 1

| COMPOUND | CHEMICAL STRUCTURE R₁ | P. aeruginosa (µg/ml) | E. coli (µg/ml) |
|---|---|---|---|
| 89 | (pyrazole-OH with N-methylpiperazine) | 1 | 1 |
| 90 | (pyrazole-OH with piperazine-NH) | 0.5 | 1 |

TABLE 5

Analogs of Compound 1.
Compounds 91 and 92 demonstrate that combined modifications at the $R^1$ and $R^2$ positions can be prepared and retain potent inhibitory activities against biofilms.

| COMPOUND | CHEMICAL STRUCTURE | P. aeruginosa (µg/ml) | E. coli (µg/ml) |
|---|---|---|---|
| 91 | (structure with pyridine and thio-triazole-amine) | 1 | 1 |
| 92 | (structure with morpholinomethyl-furan and aminoethyl-pyrazole-OH) | 0.5 | 2 |

EXAMPLE III

Semi-Synthesis Procedures for the Compounds Shown in Example II

Preparative HPLC: Preparative HPLC was conducted using a SunFire Prep C18 OBD Column, 5 µm, 19×100 mm eluting with a gradient from 90:10 (water:acetonitrile, both with 0.05% trifluoroacetic acid) to 10:90 (water:acetonitrile, both with 0.05% trifluoroacetic acid) over 14 minutes followed by a 2 minute hold at 10:90 (water:acetonitrile, both with 0.05% trifluoroacetic acid) with a flow rate at 25 mL/min.

CMA: CMA=80:18:2 Methylene Chloride/Methanol/concentrated Ammonium Hydroxide

Preparation of Common Intermediate I

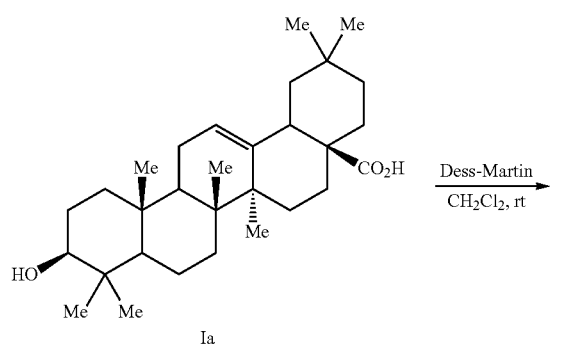

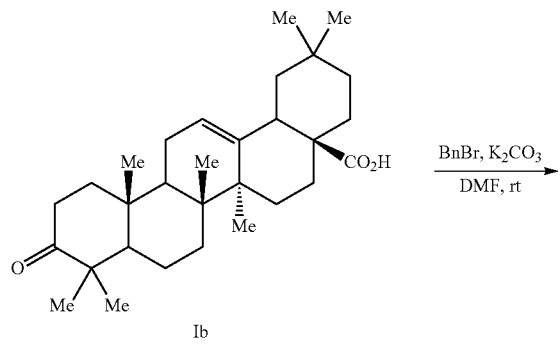

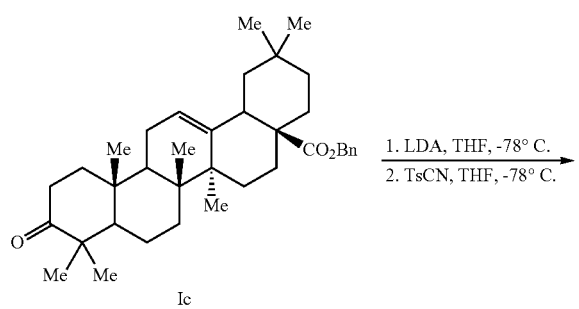

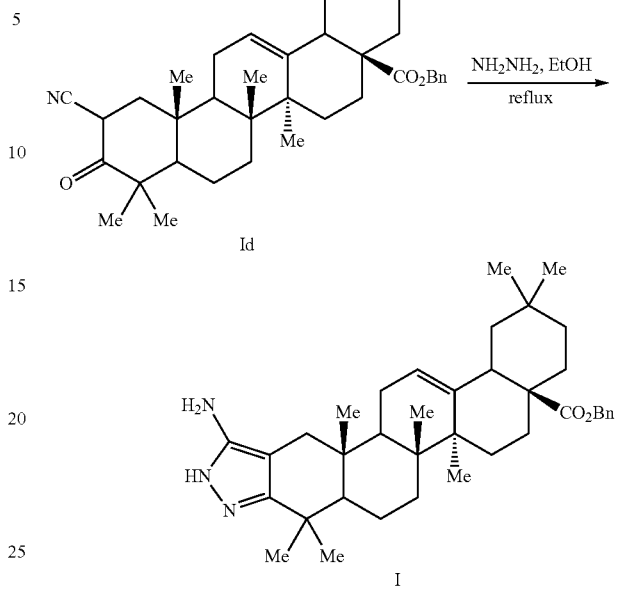

(i) Preparation of Ib: (4aS,6aS,6bR,12aR)-2,2,6a,6b,9,9,12a-Heptamethyl-10-oxo-1,2,3,4,4a,5,6,6a,6b,7,8,8a,9,10,11,12,12a,12b,13,14b-icosahydropicene-4-a-carboxylic acid To a mixture of oleanolic acid (Ia, 5.0 g, 10.9 mmol) and $CH_2Cl_2$ (200 mL) was added the Dess-Martin reagent (6.0 g, 14.2 mmol) under nitrogen at room temperature. After stirring at room temperature for 1 hour, the starting material was consumed, as indicated by TLC (1:1 hexanes:diethyl ether). The reaction mixture was quenched with the addition of a solution of sodium thiosulfate and $NaHCO_3$ (50 g sodium thiosulfate in 200 mL saturated $NaHCO_3$ solution). The mixture was stirred at room temperature for 10 minutes. The layers were separated and the aqueous layer was extracted with EtOAc (3×250 mL).

The combined organics were dried ($Na_2SO_4$), filtered and concentrated under reduced pressure. The residue was purified by column chromatography (silica, 3:1 hexanes/diethyl ether) to provide the sub-title compound (4.9 g, 99%) as a white foam.

$^1$H NMR (300 MHz, $CDCl_3$) δ 0.81 (s, 3H), 0.90-2.05 (m, 39H), 2.42-2.44 (m, 1H), 2.59-2.61 (m, 1H), 2.83-2.85 (m, 1H), 5.29-5.31 (m, 1H). ESI MS m/z 455 $[C_{30}H_{46}O_3+H]^+$.

(ii) Preparation of Ic: (4aS,6aS,6bR,12aR)-Benzyl 2,2,6a,6b,9,9,12a-heptamethyl-10-oxo-1,2,3,4,4a,5,6,6a,6b,7,8,8a,9,10,11,12,12a,12b,13,14b-icosahydropicene-4-a-carboxylate A mixture of Ib (4.9 g, 10.8 mmol), benzyl bromide (1.9 mL, 16.2 mmol), $K_2CO_3$ (2.2 g, 16.2 mmol) and DMF (185 mL) was stirred at room temperature for 2.5 hours. The solvent then was removed under reduced pressure and the residue was partitioned between $H_2O$ (250 mL) and EtOAc (250 mL). The layers were separated and the aqueous layer was extracted with EtOAc (200 mL). The combined organics were dried ($Na_2SO_4$) and filtered. The solvent was removed under reduced pressure and the residue was purified by column chromatography (silica, 3:1 hexanes/diethyl ether) to provide the sub-title compound (4.7 g, 81%) as a white solid.

¹H NMR (300 MHz, CDCl₃) δ 0.65 (s, 3H), 0.89 (s, 3H), 0.92 (s, 3H), 1.09-2.05 (m, 32H), 2.36-2.38 (m, 1H), 2.49-2.51 (m, 1H), 2.87-2.89 (m, 1H), 5.07-5.09 (m, 2H), 5.29-5.31 (m, 1H), 7.29-7.38 (m, 5H). ESI MS m/z 545 $[C_{37}H_{52}O_3+H]^+$.

(iii) Preparation of Id: (4aS,6aS,6bR,12aR)-Benzyl 11-cyano-2,2,6a,6b,9,9,12a-heptamethyl-10-oxo-1,2,3,4,4a,5,6,6a,6b,7,8,8a,9,10,11,12,12a,12b,13,14b-icosahydropicene-4-a-carboxylate A solution of diisopropylamine (31.8 mL, 227 mmol) and THF (250 mL) was cooled to −78° C. under nitrogen. A solution of n-butyllithium (2.5 M in hexanes, 100 mL, 251 mmol) was slowly added, maintaining the internal temperature below −70° C. The solution was allowed to stir for 30 min and was then slowly added to a solution of Ic (65.0 g, 120 mmol) and THF (1.4 L) at −78° C. under nitrogen. This solution was stirred for 30 min after which time a suspension of p-toluenesulfonyl cyanide (43.3 g, 239 mmol) and THF (200 mL) was added over 45 min. The solution was stirred for 10 min and then quenched by the addition of saturated ammonium chloride solution (250 mL) at −78° C. The mixture was allowed to warm to room temperature overnight. The organic layer was separated and the aqueous layer was extracted with EtOAc. The combined organic layers were dried (Na₂SO₄) and filtered. The solvent was removed under reduced pressure and the residue was purified by column chromatography (silica, 1:1 hexanes/EtOAc) to provide the sub-title compound (58g, 85%) as a white solid.

¹H NMR (300 MHz, CDCl₃) δ 0.65 (s, 3H), 2.14-2.16 (m, 39H), 2.93-2.95 (m, 1H), 5.06-5.08 (m, 2H), 5.29-5.31 (m, 1H), 7.29-7.37 (m, 5H).

(iv) Preparation of I: (4aS,6aS,6bR,13aR)-Benzyl 12-amino-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylate A solution of Id (2.0 g, 3.5 mmol) and hydrazine (0.33 mL, 10.6 mmol) in EtOH (18 mL) was heated at reflux for 16 hours. The solvent and excess hydrazine were removed under reduced pressure. The residue was purified by column chromatography (silica, 0-7% MeOH in CH₂Cl₂) to provide the title compound (1.8 g, 88%) as an off-white solid.

¹H NMR (300 MHz, CDCl₃) δ 0.69 (s, 3H), 0.85-2.03 (m, 37H), 2.24-2.35 (m, 1H), 2.92-2.98 (m, 1H), 5.06-5.08 (m, 2H), 5.22-5.24 (m, 1H), 7.28-7.37 (m, 5H).

APCI MS m/z 584 $[C_{38}H_{53}N_3O_2+H]^+$.

Preparation of Common Intermediate II

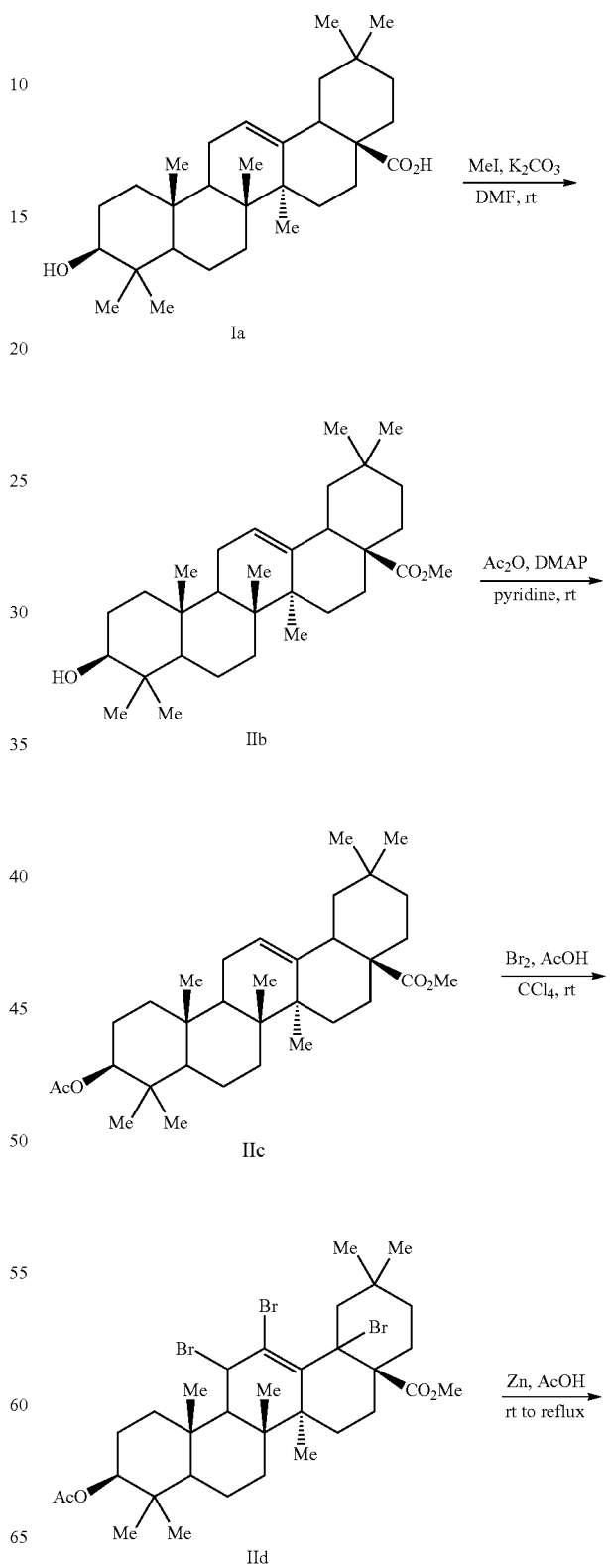

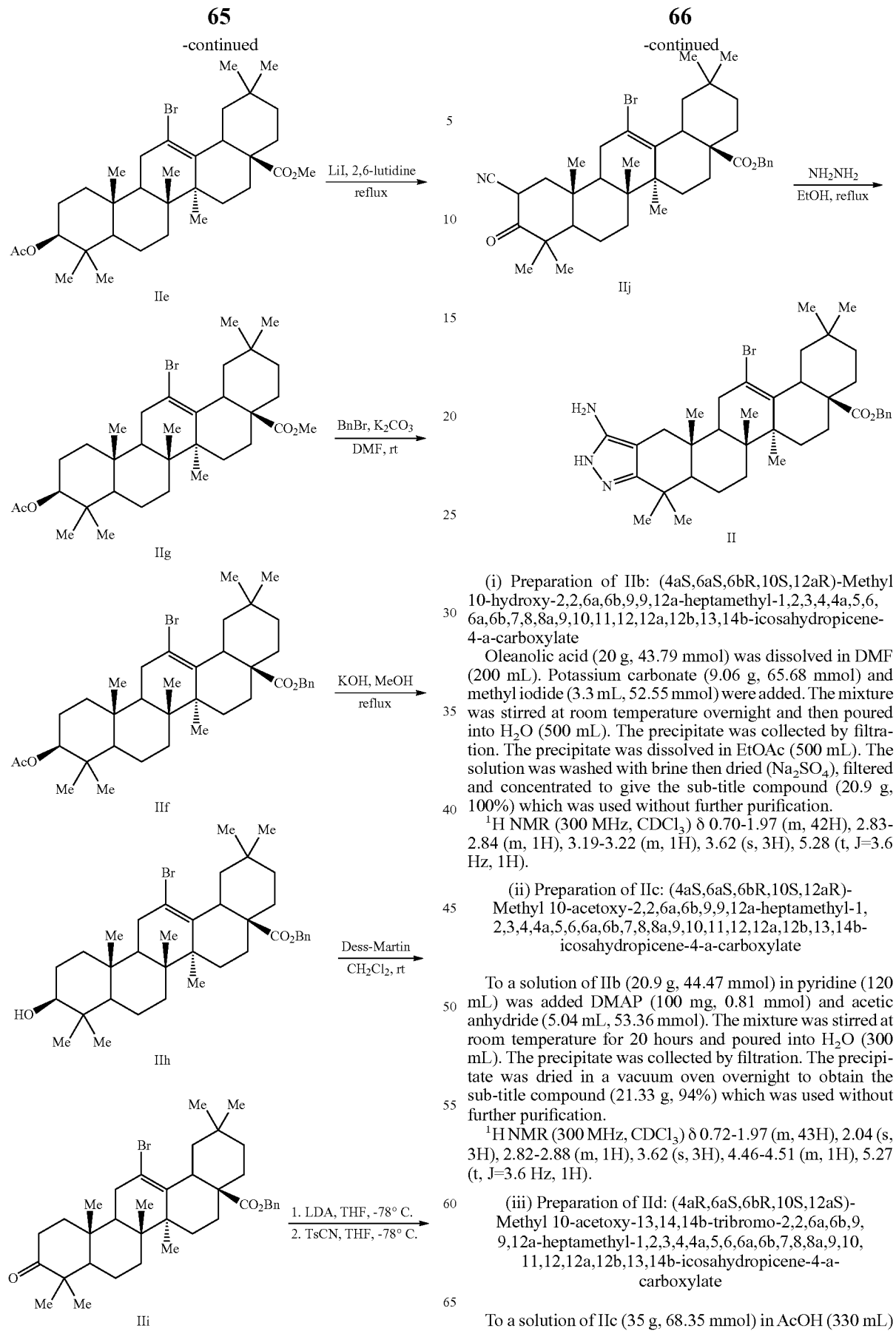

(i) Preparation of IIb: (4aS,6aS,6bR,10S,12aR)-Methyl 10-hydroxy-2,2,6a,6b,9,9,12a-heptamethyl-1,2,3,4,4a,5,6,6a,6b,7,8,8a,9,10,11,12,12a,12b,13,14b-icosahydropicene-4-a-carboxylate Oleanolic acid (20 g, 43.79 mmol) was dissolved in DMF (200 mL). Potassium carbonate (9.06 g, 65.68 mmol) and methyl iodide (3.3 mL, 52.55 mmol) were added. The mixture was stirred at room temperature overnight and then poured into $H_2O$ (500 mL). The precipitate was collected by filtration. The precipitate was dissolved in EtOAc (500 mL). The solution was washed with brine then dried ($Na_2SO_4$), filtered and concentrated to give the sub-title compound (20.9 g, 100%) which was used without further purification.

$^1$H NMR (300 MHz, $CDCl_3$) δ 0.70-1.97 (m, 42H), 2.83-2.84 (m, 1H), 3.19-3.22 (m, 1H), 3.62 (s, 3H), 5.28 (t, J=3.6 Hz, 1H).

(ii) Preparation of IIc: (4aS,6aS,6bR,10S,12aR)-Methyl 10-acetoxy-2,2,6a,6b,9,9,12a-heptamethyl-1,2,3,4,4a,5,6,6a,6b,7,8,8a,9,10,11,12,12a,12b,13,14b-icosahydropicene-4-a-carboxylate To a solution of IIb (20.9 g, 44.47 mmol) in pyridine (120 mL) was added DMAP (100 mg, 0.81 mmol) and acetic anhydride (5.04 mL, 53.36 mmol). The mixture was stirred at room temperature for 20 hours and poured into $H_2O$ (300 mL). The precipitate was collected by filtration. The precipitate was dried in a vacuum oven overnight to obtain the sub-title compound (21.33 g, 94%) which was used without further purification.

$^1$H NMR (300 MHz, $CDCl_3$) δ 0.72-1.97 (m, 43H), 2.04 (s, 3H), 2.82-2.88 (m, 1H), 3.62 (s, 3H), 4.46-4.51 (m, 1H), 5.27 (t, J=3.6 Hz, 1H).

(iii) Preparation of IId: (4aR,6aS,6bR,10S,12aS)-Methyl 10-acetoxy-13,14,14b-tribromo-2,2,6a,6b,9,9,12a-heptamethyl-1,2,3,4,4a,5,6,6a,6b,7,8,8a,9,10,11,12,12a,12b,13,14b-icosahydropicene-4-a-carboxylate To a solution of IIc (35 g, 68.35 mmol) in AcOH (330 mL) and $CCl_4$ (160 mL) was added bromine (14.05 mL, 273.4 mmol) slowly. The mixture was stirred at room temperature for 17 hours. The CCl$_4$ was removed under reduced pressure and the reaction mixture was poured into H$_2$O (1 L). The precipitate was collected by filtration and then dissolved in EtOAc (1 L). The solution was washed with brine then dried (Na$_2$SO$_4$), filtered and concentrated to give the sub-title compound (50.5 g, 98%) which was used without further purification.

$^1$H NMR (300 MHz, CDCl$_3$) δ 0.75-1.75 (m, 38H), 2.04 (s, 3H), 2.40-2.43 (m, 2H), 2.57 (t, J=12.6 Hz, 1H), 3.63 (s, 3H), 4.44-4.50 (m, 1H), 4.58-4.64 (m, 1H).

(iv) Preparation of IIe: (4aS,6aS,6bR,10S,12aR)-Methyl 10-acetoxy-14-bromo-2,2,6a,6b,9,9,12a-heptamethyl-1,2,3,4,4a,5,6,6a,6b,7,8,8a,9,10,11,12,12a,12b,13,14b-icosahydropicene-4-a-carboxylate Zinc dust (21.8 g, 335.7 mmol) was added to a solution of IId (50.5 g, 67.15 mmol) and AcOH (450 mL). The mixture was stirred at room temperature overnight and then heated at reflux for 2 hours. The reaction mixture was cooled to room temperature and then poured into H$_2$O (600 mL). The precipitate was collected by filtration and then dissolved in EtOAc (1 L). The solution was washed with brine then dried (Na$_2$SO$_4$), filtered and concentrated. The residue was purified by column chromatography (silica, 0-10% EtOAc in hexanes) to obtain the sub-title compound (21.5 g, 54%).

$^1$H NMR (300 MHz, CDCl$_3$) δ 0.75-1.78 (m, 40H), 1.93-1.95 (m, 1H), 2.04 (s, 3H), 2.41 (m, 2H), 3.54 (m, 1H), 3.63 (s, 3H), 4.48 (m, 1H).

(v) Preparation of IIf: (4aS,6aS,6bR,10S,12aR)-10-Acetoxy-14-bromo-2,2,6a,6b,9,9,12a-heptamethyl-1,2,3,4,4a,5,6,6a,6b,7,8,8a,9,10,11,12,12a,12b,13,14b-icosahydropicene-4-a-carboxylic acid To a solution of IIe (21.5 g, 36.31 mmol) in 2,6-lutidine (300 mL) was added lithium iodide (72.9 g, 544.7 mmol). The mixture was heated at 143° C. overnight and then cooled to room temperature. The mixture was acidified (pH≈4) with aqueous HCl and extracted with EtOAc (300 mL×3). The combined extracts were washed with H$_2$O and brine then dried (Na$_2$SO$_4$), filtered and concentrated to afford the sub-title compound (22.8 g, 109%) which was used without further purification.

$^1$H NMR (300 MHz, CDCl$_3$) δ 0.80-1.82 (m, 42H), 2.04 (s, 3H), 2.41 (m, 2H), 3.51 (m, 1H), 4.48 (m, 1H).

(vi) Preparation of IIg: (4aS,6aS,6bR,10S,12aR)-Benzyl 10-acetoxy-14-bromo-2,2,6a,6b,9,9,12a-heptamethyl-1,2,3,4,4a,5,6,6a,6b,7,8,8a,9,10,11,12,12a,12b,13,14b-icosahydropicene-4-a-carboxylate To a solution of IIf (21.2 g, 36.67 mmol) and DMF (350 mL) was added K$_2$CO$_3$ and BnBr (as used herein, "Bn" represents benzyl). The reaction mixture was stirred overnight at room temperature and then poured into H$_2$O (1 L). The precipitate was collected by filtration and then dissolved in EtOAc (1 L). The solution was washed with H$_2$O and brine then dried (Na$_2$SO$_4$), filtered and concentrated to afford the sub-title compound (24.5 g, 100%) which was used without further purification.

$^1$H NMR (300 MHz, CDCl$_3$) δ 0.57-2.00 (m, 41H), 2.04 (s, 3H), 2.34 (d, J=8.7 Hz, 2H), 3.59 (dd, J=4.8, 4.2 Hz, 1H), 4.49 (m, 1H), 5.08 (s, 2H), 7.29-7.38 (m, 5H).

(vii) Preparation of IIh: (4aS,6aS,6bR,10S,12aR)-Benzyl 14-bromo-10-hydroxy-2,2,6a,6b,9,9,12a-heptamethyl-1,2,3,4,4a,5,6,6a,6b,7,8,8a,9,10,11,12,12a,12b,13,14b-icosahydropicene-4-a-carboxylate To a solution of IIg (24.5 g, 36.67 mmol) in MeOH (500 mL) was added potassium hydroxide (8.2 g, 146.7 mmol) and the mixture was heated at reflux for 2.5 hours. The resulting mixture was concentrated and the residue was dissolved in EtOAc (1 L). The solution was washed with H$_2$O and brine then dried (Na$_2$SO$_4$), filtered and concentrated. The residue was purified by column chromatography (silica, 0-30% EtOAc in hexanes) to afford the sub-title compound (21.3 g, 93%).

$^1$H NMR (300 MHz, CDCl$_3$) δ 0.58-1.81 (m, 41H), 2.01 (m, 1H), 2.37 (d, J=9.3 Hz, 2H), 3.21 (m, 1H), 3.58 (dd, J=4.8, 4.1 Hz, 1H), 5.08 (s, 2H), 7.29-7.38 (m, 5H).

(viii) Preparation of IIi: (4aS,6aS,6bR,12aR)-Benzyl 14-bromo-2,2,6a,6b,9,9,12a-heptamethyl-10-oxo-1,2,3,4,4a,5,6,6a,6b,7,8,8a,9,10,11,12,12a,12b,13,14b-icosahydropicene-4-a-carboxylatelate To a solution of IIh (21.3 g, 34.02 mmol) in CH$_2$Cl$_2$ (400 mL) was added the Dess-Martin reagent (18.76 g, 44.23 mmol). The mixture was stirred at room temperature for 5 hours, quenched with aqueous sodium thiosulfate and NaHCO$_3$ and then extracted with EtOAc (3×300 mL). The organic solution was washed with H$_2$O and brine then dried (Na$_2$SO$_4$), filtered and concentrated. The residue was purified by column chromatography (silica, 0-15% EtOAc in hexanes) to afford the sub-title compound (19.3 g, 90%).

$^1$H NMR (300 MHz, CDCl$_3$) δ 0.24-2.27 (m, 40H), 2.94 (d, J=8.7 Hz, 1H), 3.44 (dd, J=4.8, 4.2 Hz, 1H), 5.13-5.15 (m, 2H), 7.33-7.35 (m, 5H).

(ix) Preparation of IIj: (4aS,6aS,6bR,12aR)-Benzyl 14-bromo-11-cyano-2,2,6a,6b,9,9,12a-heptamethyl-10-oxo-1,2,3,4,4a,5,6,6a,6b,7,8,8a,9,10,11,12,12a,12b,13,14b-icosahydropicene-4-a-carboxylate To a solution of diisopropylamine (0.64 mL, 4.5 mmol) in THF (15 mL) was added n-butyl lithium (2.5 M; 1.9 mL, 4.8 mmol) at −78° C. The mixture was stirred at −78° C. for 10 min. The LDA solution was added to a solution of IIi (1.5 g, 2.4 mmol) in THF (40 mL) pre-cooled to −78° C. The mixture was stirred at −78° C. for 1 hour. A solution of 4-methylbenzenesulfonyl cyanide (815 mg, 4.5 mmol) in THF (5 mL) was added and stirred for 30 min at −78° C. The reaction mixture was warmed to −20° C. over 1 hour. The reaction mixture was quenched with saturated NH$_4$Cl solution and extracted with EtOAc (3×50 mL). The organic layer was washed with H$_2$O and brine then dried (Na$_2$SO$_4$), filtered and concentrated. The residue was purified by column chromatography (silica, 0-20% EtOAc in hexanes) to afford the sub-title compound (1.2 g, 77%).

$^1$H NMR (300 MHz, CDCl$_3$) δ 0.56-2.42 (m, 41H), 3.61-3.89 (m, 2H), 5.08 (s, 2H), 7.35 (m, 5H).

(x) Preparation of II: (4aS,6aS,6bR,13aR)-Benzyl 12-amino-15-bromo-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylate To a solution of IIj (6.4 g, 9.89 mmol) and EtOH (30 mL) was added hydrazine (0.62 mL, 19.78 mmol). The solution was heated at reflux overnight. The reaction mixture was concentrated and then the residue was purified by column chromatography (silica, 0-10% MeOH in CH$_2$Cl$_2$) to afford the title compound (5.0 g, 76%).

$^1$H NMR (300 MHz, CDCl$_3$) δ 0.63-2.06 (m, 38H), 2.29 (d, J=14.7 Hz, 1H), 2.45 (d, J=9.0 Hz, 2H), 3.65 (dd, J=4.4, 4.2 Hz, 1H), 5.08 (s, 2H), 7.29-7.39 (m, 5H).

APCI MS (Positive Mode) m/z 662 [C$_{38}$H$_{52}$BrN$_3$O$_2$+H]$^+$.

Preparation of Common Intermediate III

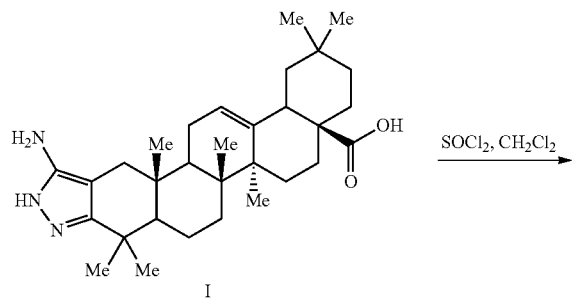

(i) Preparation of III: (4aS,6aS,6bR,13aR)-12-Amino-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carbonyl chloride To a suspension of 1 (as defined above) (3.0 g, 6.08 mmol) in CH$_2$Cl$_2$ was added thionyl chloride (4.4 mL, 60.85 mmol) at room temperature. The mixture was stirred for 2.5 hours, after which time the solvent was removed under reduced pressure. The residue was dried in a high vacuum to provide the title compound (3.2 g, >100%). The material was used without further purification. APCI MS (Positive Mode) m/z 512 [C$_{31}$H$_{46}$ClN$_3$O+H]$^+$.

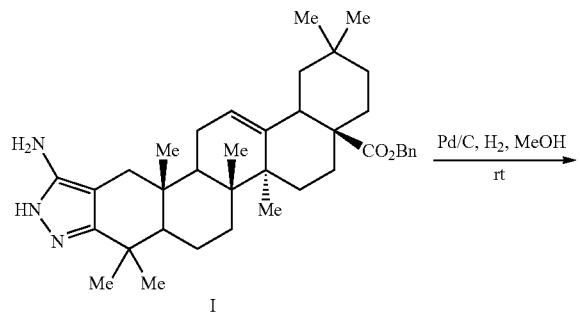

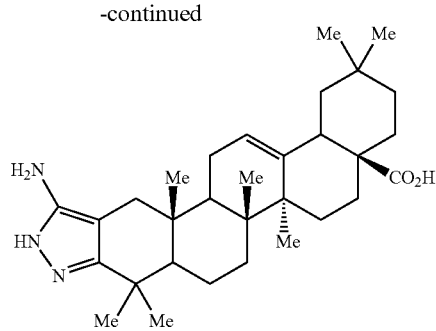

(i) Preparation of 1: (4aS,6aS,6bR,13aR)-12-Amino-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylic acid A suspension of I (as defined above)(1.8 g, 3.1 mmol), 10% Pd/C (1.0 g) and MeOH (100 mL) was stirred under hydrogen at atmospheric pressure for 2 hours. The catalyst was removed by filtration through diatomaceous earth and the filtrate was concentrated under reduced pressure to provide the title compound (1.4 g, 88%) as an off-white solid.

R$_f$ 0.37 (9:1 Methylene Chloride/Methanol) m.p. 263-266° C.

$^1$H NMR (500 MHz, CD$_3$OD) δ 0.82-0.98 (m, 9H), 1.12-1.31 (m, 15H), 1.39-1.87 (m, 13H), 2.01-2.10 (m, 3H), 2.35-2.42 (m, 1H), 2.87-2.91 (m, 1H), 5.28-5.33 (m, 1H).

ESI MS m/z 494 [C$_{31}$H$_{47}$N$_3$O$_2$+H]$^+$. HPLC 98.8% (area %), t$_R$=16.2 min.

EXAMPLE 2

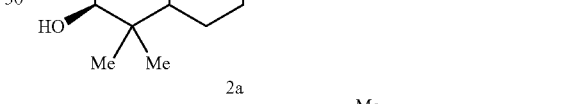

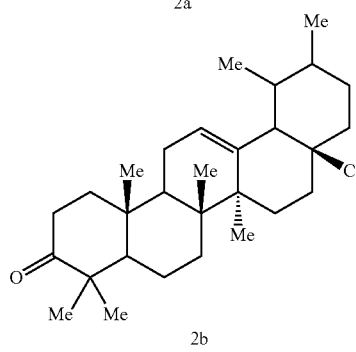

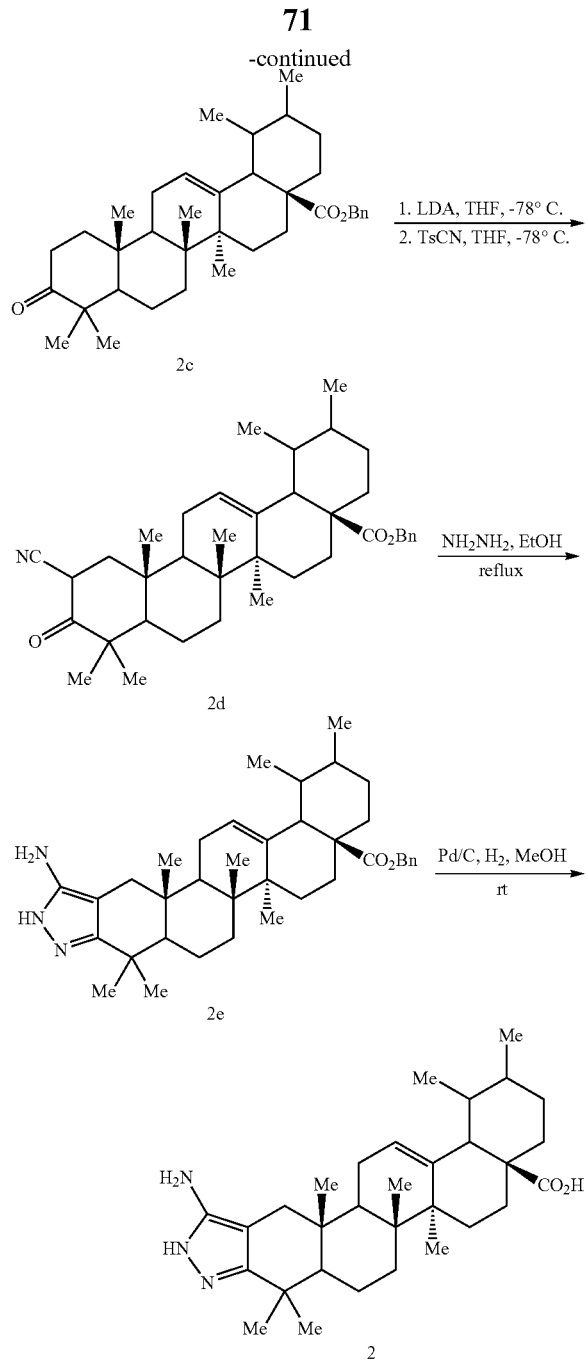

(i) Preparation of 2b: (4aS,6aS,6bR,12aR)-1,2,6a,6b,9,9,12a-Heptamethyl-10-oxo-1,2,3,4,4a,5,6,6a,6b,7,8,8a,9,10,11,12,12a,12b,13,14b-icosahydropicene-4-a-carboxylic acid To a mixture of ursolic acid (2a, 1.0 g, 2.18 mmol) and CH$_2$Cl$_2$ (55 mL) was added the Dess-Martin reagent (1.2 g, 2.83 mmol) under nitrogen at room temperature. After stirring at room temperature for 2.5 hours, the starting material was consumed as indicated by TLC (1:1 hexanes:diethyl ether). The reaction mixture was quenched with the addition of a solution of sodium thiosulfate and NaHCO$_3$ (6.3 g sodium thiosulfate in 25 mL saturated NaHCO$_3$ solution). The mixture was stirred at room temperature for 10 minutes. The layers were separated and the aqueous layer was extracted with EtOAc (3×250 mL). The combined organics were dried (Na$_2$SO$_4$), filtered and concentrated under reduced pressure. The residue was purified by column chromatography (silica, 3:1 hexanes/diethyl ether) to provide the sub-title compound (924 mg, 92%) as a white foam solid.

(ii) Preparation of 2c: (4aS,6aS,6bR,12aR)-Benzyl 1,2,6a,6b,9,9,12a-heptamethyl-10-oxo-1,2,3,4,4a,5,6,6a,6b,7,8,8a,9,10,11,12,12a,12b,13,14b-icosahydropicene-4-a-carboxylate A mixture of 2b (924 mg, 2.03 mmol), benzyl bromide (0.31 mL, 0.64 mmol), K$_2$CO$_3$ (393 mg, 2.84 mmol) and DMF (50 mL) was stirred at room temperature for 12 hours. The solvent was then removed under reduced pressure and the residue was partitioned between H$_2$O (150 mL) and EtOAc (150 mL). The layers were separated and the aqueous layer was extracted with EtOAc (50 mL). The combined organics were dried (Na$_2$SO$_4$) and filtered. The solvent was removed under reduced pressure and the residue was purified by column chromatography (silica, 1:1 hexanes/diethyl ether) to provide the sub-title compound (1.0 g, 92%) as a white solid.

$^1$H NMR (300 MHz, CDCl$_3$) δ 0.68 (s, 3H), 0.84 (d, J=6.3 Hz, 3H), 0.92 (d, J=6.0 Hz, 3H), 1.02 (s, 3H), 1.03 (s, 3H), 1.08 (s, 6H), 1.20-2.05 (m, 20H), 2.26 (d, J=15.0 Hz, 1H), 2.30 (m, 1H), 2.50 (m, 1H), 4.96 (m, 2H), 5.24 (m, 1H), 7.30-7.35 (m, 5H).

(iii) Preparation of 2d: (4aS,6aS,6bR,12aR)-Benzyl 11-cyano-1,2,6a,6b,9,9,12a-heptamethyl-10-oxo-1,2,3,4,4a,5,6,6a,6b,7,8,8a,9,10,11,12,12a,12b,13,14b-icosahydropicene-4-a-carboxylate A solution of diisopropylamine (0.45 mL, 3.24 mmol) and THF (5 mL) was cooled to −78° C. under nitrogen. A solution of n-butyllithium (2.5 M in hexanes, 1.43 mL, 3.56 mmol) was slowly added, maintaining the internal temperature below −70° C. The solution was allowed to stir for 30 min and was then slowly added to a solution of 2c (880 mg, 1.62 mmol) and THF (10 mL) at −78° C. under nitrogen. This solution was stirred for 30 min after which time a suspension of p-toluenesulfonyl cyanide (587 mg, 3.24 mmol) and THF (2 mL) was added over 45 min. The solution was stirred for 10 min and then quenched by the addition of saturated ammonium chloride solution (3 mL) at −78° C. The mixture was allowed to warm to room temperature overnight. The organic layer was separated and the aqueous layer was extracted with EtOAc. The combined organic layers were dried (Na$_2$SO$_4$) and filtered. The solvent was removed under reduced pressure and the residue was purified by column chromatography (silica, 3:1 hexanes/Et$_2$O) to provide the sub-title compound (600 mg, 65%) as a white foam solid.

(iv) Preparation of 2e: (4aS,6aS,6bR,13aR)-Benzyl 12-amino-1,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylate A solution of 2d (303 mg, 0.53 mmol) and hydrazine (0.050 mL, 1.59 mmol) in EtOH (5 mL) was heated at reflux for 12 hours. The solvent and excess hydrazine were removed under reduced pressure. The residue was purified by column chromatography (silica, 0-10% MeOH in CH$_2$Cl$_2$) to provide the sub-title compound (234 mg, 75%) as a white foam solid.

$^1$H NMR (300 MHz, CDCl$_3$) δ 0.69 (s, 3H), 0.86 (d, J=5.7 Hz, 3H), 0.88 (s, 3H), 0.93 (d, J=6.0 Hz, 3H), 1.09 (s, 3H), 1.13 (s, 3H), 1.22 (s, 3H), 1.38-2.05 (m, 19H), 2.28 (m, 1H), 2.30 (d, J=14.7 Hz, 1H), 4.96 (q, J=12.6 Hz, 2H), 5.29 (s, 1H), 7.32 (m, 5H).

(v) Preparation of 2: (4aS,6aS,6bR,13aR)-12-Amino-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylic acid A suspension of 2e (234 mg, 0.40 mmol), 10% Pd/C (60 mg) and MeOH (6 mL) was stirred under hydrogen at atmospheric pressure for 9 hours. The catalyst was removed by filtration and the filtrate was concentrated under reduced pressure. The residue was purified by column chromatography (silica, 0-15% MeOH in CH₂Cl₂) to provide the title compound (103 mg, 52%) as an off-white solid.

$R_f$ 0.16 (89:18:2 Methylene Chloride/Methanol/concentrated Ammonium Hydroxide).

m.p. 258-278° C. $^1$H NMR (300 MHz, CD₃OD) δ 0.89 (s, 9H), 0.91 (s, 3H), 1.15 (s, 6H), 1.19 (s, 3H), 2.05-2.10 (m, 19H), 2.22 (m, 1H), 2.40 (m, 1H), 5.30 (s, 1H). ESI MS m/z 494 [C₃₁H₄₇N₃O₂+H]⁺.

EXAMPLE 3

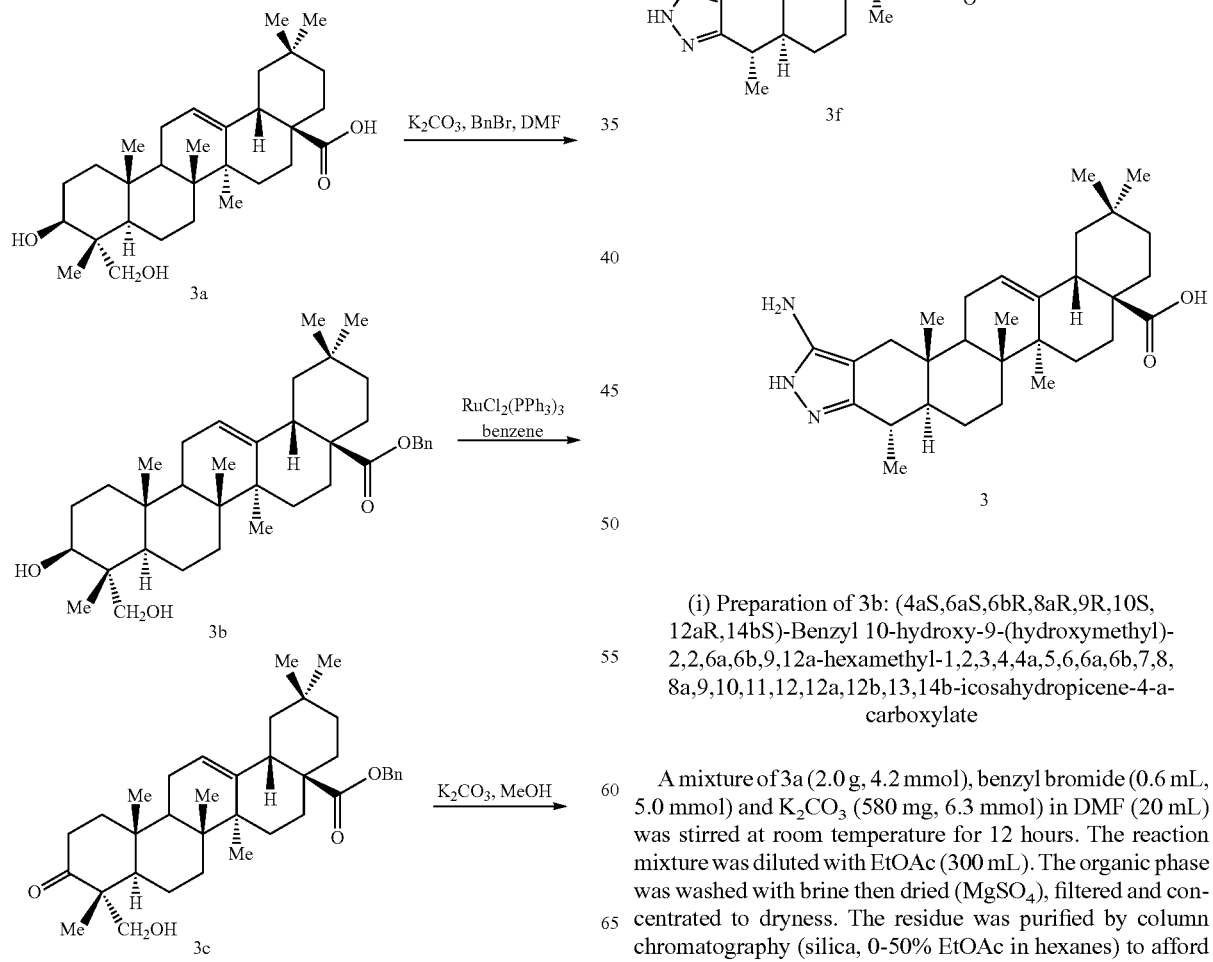

(i) Preparation of 3b: (4aS,6aS,6bR,8aR,9R,10S,12aR,14bS)-Benzyl 10-hydroxy-9-(hydroxymethyl)-2,2,6a,6b,9,12a-hexamethyl-1,2,3,4,4a,5,6,6a,6b,7,8,8a,9,10,11,12,12a,12b,13,14b-icosahydropicene-4-a-carboxylate A mixture of 3a (2.0 g, 4.2 mmol), benzyl bromide (0.6 mL, 5.0 mmol) and K₂CO₃ (580 mg, 6.3 mmol) in DMF (20 mL) was stirred at room temperature for 12 hours. The reaction mixture was diluted with EtOAc (300 mL). The organic phase was washed with brine then dried (MgSO₄), filtered and concentrated to dryness. The residue was purified by column chromatography (silica, 0-50% EtOAc in hexanes) to afford the sub-title compound (2.3 g, 95%).

(ii) Preparation of 3c: (4aS,6aS,6bR,8aR,9R,12aR, 14bS)-Benzyl 9-(hydroxymethyl)-2,2,6a,6b,9,12a-hexamethyl-10-oxo-1,2,3,4,4a,5,6,6a,6b,7,8,8a,9,10, 11,12,12a,12b,13,14b-icosahydropicene-4-a-carboxylate To a solution of 3b (400 mg, 0.71 mmol) in benzene (20 mL) was added $RuCl_2(PPh_3)_3$ (682 mg, 0.71 mmol). The mixture was stirred at room temperature for 12 hours. The reaction was not complete. An additional amount of $RuCl_2(PPh_3)_3$ (341 mg, 0.36 mmol) was added and the reaction mixture was continued to stir for 8 hours. The reaction mixture was diluted with EtOAc (150 mL). The organic phase was washed with brine then dried ($MgSO_4$), filtered and concentrated to dryness. The residue was purified by column chromatography (silica, 0-50% EtOAc in hexanes) to afford the sub-title compound (150 mg, 38%).

(iii) Preparation of 3d: (4aS,6aS,6bR,8aS,9S,12aS, 14bS)-Benzyl 2,2,6a,6b,9,12a-hexamethyl-10-oxo-1, 2,3,4,4a,5,6,6a,6b,7,8,8a,9,10,11,12,12a,12b,13,14b-icosahydropicene-4-a-carboxylate A mixture of 3c (150 mg, 0.26 mmol) and $K_2CO_3$ (44 mg, 0.32 mmol) in MeOH (10 mL) was stirred at room temperature for 24 hours. The reaction mixture was diluted with EtOAc (150 mL) and washed with brine then dried ($MgSO_4$), filtered and concentrated to dryness. The residue was purified by column chromatography (silica, 0-30% EtOAc in hexanes) to afford the sub-title compound (70 mg, 49%).

(iv) Preparation of 3e: (4aS,6aS,6bR,8aS,9S,12aS, 14bS)-Benzyl 11-cyano-2,2,6a,6b,9,12a-hexamethyl-10-oxo-1,2,3,4,4a,5,6,6a,6b,7,8,8a,9,10,11,12,12a, 12b,13,14b-icosahydropicene-4-a-carboxylate To a solution of diisopropylamine (0.073 mL, 0.52 mmol) in THF (4 mL) was added n-butyllithium (0.22 mL, 2.5 M in hexanes, 0.54 mmol) at −78° C. The solution was stirred for 30 min. The LDA solution was added to 3d (150 mg, 0.27 mmol) in THF (5 mL). The mixture was allowed to warm to −40° C. for 5 min and cooled to −78° C. A suspension of p-toluene sulfonyl cyanide (98 mg, 0.54 mmol) in THF (2 mL) was added. The reaction mixture was allowed to warm to −40° C. over 1.5 hours. The reaction was quenched by saturated $NH_4Cl$ (3 mL) and extracted with EtOAc (100 mL). The organic phase was washed with brine then dried ($MgSO_4$), filtered and concentrated to dryness. The residue was purified by column chromatography (silica, 0-30% EtOAc in hexanes) to afford the sub-title compound (90 mg, 58%).
$^1$H NMR (300 MHz, $CDCl_3$) δ 0.65 (s, 3H), 0.86 (s, 3H), 0.88 (s, 3H), 1.0-2.0 (m, 28H), 2.35 (m, 2H), 2.92 (m, 1H), 3.61 (m, 1H), 5.15 (s, 2H), 5.30 (m, 1H), 7.30 (s, 5H).

(v) Preparation of 3f: (4aS,6aS,6bR,8aS,9S,13aS, 15bS)-Benzyl 12-amino-2,2,6a,6b,9,13a-hexamethyl-2,3,4,4a,5,6,6a,6b,7,8,8a,9,11,13,13a,13b,14, 15b-octadecahydro-1H-chryseno[1,2-f]indazole-4-a-carboxylate A mixture of 3e (90 mg, 0.15 mmol) and hydrazine (0.025 mL) in EtOH (3 mL) was heated at reflux overnight. The reaction mixture was concentrated to dryness under reduced pressure. The residue was purified by column chromatography (silica, 0-10% MeOH in $CH_2Cl_2$) to afford the sub-title compound (60 mg, 65%).

(v) Preparation of 3: (4aS,6aS,6bR,8aS,9S,13aS, 15bS)-12-Amino-2,2,6a,6b,9,13a-hexamethyl-2,3,4, 4a,5,6,6a,6b,7,8,8a,9,11,13,13a,13b,14,15b-octa-decahydro-1H-chryseno[1,2-f]indazole-4-a-carboxylic acid A mixture of 3f (60 mg, 0.10 mmol) and 10% $Pd(OH)_2/C$ (60 mg) in MeOH (5 mL) and EtOAc (5 mL) was stirred under hydrogen balloon for 5 hours. The reaction mixture was filtered through a pad of diatomaceous earth and washed with CMA (25 mL). The filtrate was concentrated to dryness under reduced pressure. The residue was purified by column chromatography (silica, 0-60% CMA in $CH_2Cl_2$) to afford the title compound (32 mg, 68%) as a brown solid.

$R_f$ 0.40 (80:18:2 Methylene Chloride/Methanol/concentrated Ammonium Hydroxide).

$^1$H NMR (300 MHz, DMSO-$d_6$) δ 0.78 (s, 3H), 0.80 (s, 3H), 0.91 (s, 6H), 1.05 (s, 3H), 1.10-2.0 (m, 25H), 2.15 (m, 1H), 2.25 (d, J=15.0 Hz, 1H), 2.80 (m, 1H), 5.24 (s, 1H), 11.4 (bs, 1H). mp >300° C. ESI MS (Positive Mode) m/z 478 $[C_{30}H_{45}N_3O_2+H]^+$.

EXAMPLE 4

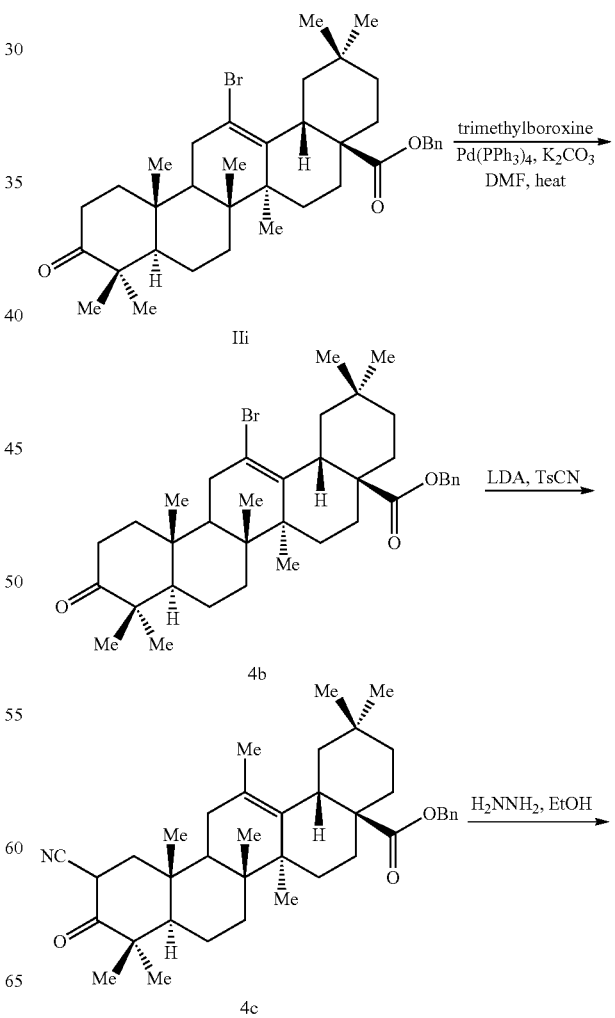

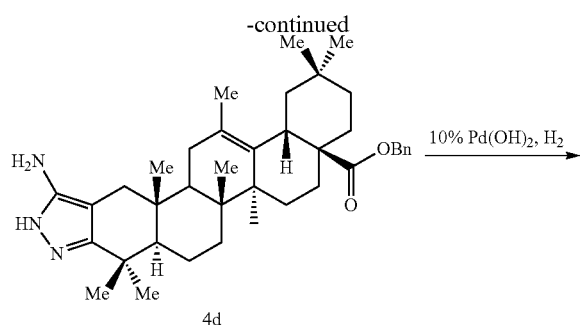

4d

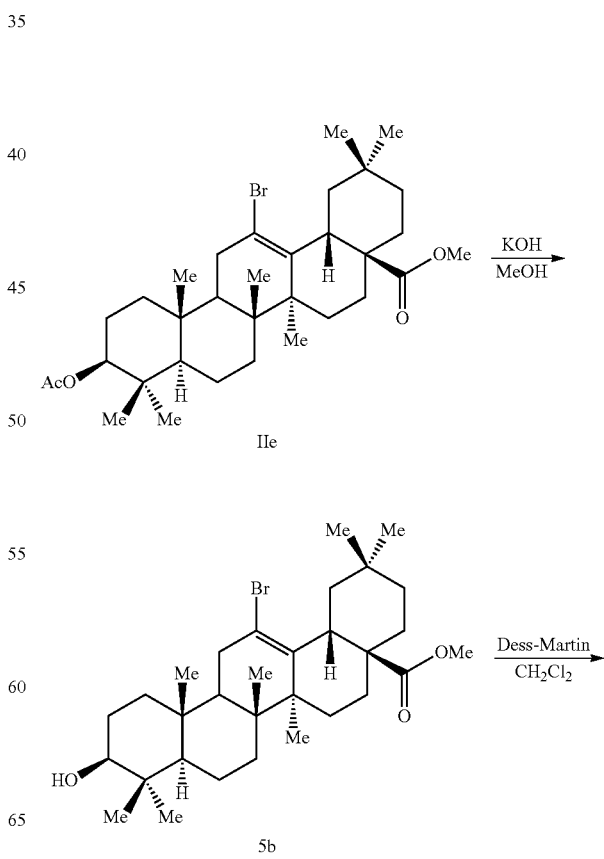

4

(i) Preparation of 4b: (4aS,6aS,6bR,8aR,12aR,14bS)-Benzyl 2,2,6a,6b,9,9,12a,14-octamethyl-10-oxo-1,2,3,4,4a,5,6,6a,6b,7,8,8a,9,10,11,12,12a,12b,13,14b-icosahydropicene-4-a-carboxylate A mixture of Hi (300 mg, 0.48 mmol), trimethylboroxine (0.3 mL, 2.15 mmol), Pd(PPh$_3$)$_4$ (60 mg, 0.048 mmol) and K$_2$CO$_3$ (300 mg, 2.17 mmol) in DMF (9 mL) was heated at 100° C. for 12 hours. The reaction mixture was diluted with EtOAc (100 mL). The organic phase was washed with brine then dried (MgSO$_4$), filtered and concentrated to dryness. The residue was purified by column chromatography (silica, 0-10% EtOAc in hexanes) to afford the sub-title compound (220 mg, 82%).

(ii) Preparation of 4c: (4aS,6aS,6bR,8aR,12aR,14bS)-Benzyl 11-cyano-2,2,6a,6b,9,9,12a,14-octamethyl-10-oxo-1,2,3,4,4a,5,6,6a,6b,7,8,8a,9,10,11,12,12a,12b,13,14b-icosahydropicene-4-a-carboxylate To a solution of diisopropylamine (0.15 mL, 1.07 mmol) in THF (5 mL) was added n-butyllithium (0.45 mL, 2.5 M in hexanes, 1.1 mmol) at −78° C. The solution was stirred for 30 min. The LDA solution was added to 4b (315 mg, 0.56 mmol) in THF (5 mL). The mixture was allowed to warm to −40° C. for 5 min and cooled to −78° C. A suspension of p-toluene sulfonyl cyanide (203 mg, 1.1 mmol) in THF (2 mL) was added. The reaction mixture was allowed to warm to −40° C. over 1.5 hours. The reaction was quenched by saturated NH$_4$Cl (3 mL) and extracted with EtOAc (100 mL). The organic phase was washed with brine then dried (MgSO$_4$), filtered and concentrated to dryness. The residue was purified by column chromatography (silica, 0-20% EtOAc in hexanes) to afford the sub-title compound (215 mg, 66%).

(iii) Preparation of 4d: (4aS,6aS,6bR,8aR,13aR,15bS)-Benzyl 12-amino-2,2,6a,6b,9,9,13a,15-octamethyl-2,3,4,4a,5,6,6a,6b,7,8,8a,9,11,13,13a,13b,14,15b-octadecahydro-1H-chryseno[1,2-f]indazole-4-a-carboxylate A mixture of 4c (215 mg, 0.36 mmol) and hydrazine (0.060 mL, 1.85 mmol) in EtOH (3 mL) was heated at reflux overnight. The reaction mixture was concentrated to dryness under reduced pressure. The residue was purified by column chromatography (silica, 0-10% MeOH in CH$_2$Cl$_2$) to afford the sub-title compound (180 mg, 84%).

ESI MS (Positive Mode) m/z 598 [C$_{39}$H$_{55}$N$_3$O$_2$+H]$^+$.

(iv) Preparation of 4: (4aS,6aS,6bR,8aR,13aR,15bS)-12-Amino-2,2,6a,6b,9,9,13a,15-octamethyl-2,3,4,4a,5,6,6a,6b,7,8,8a,9,11,13,13a,13b,14,15b-octadecahydro-1H-chryseno[1,2-f]indazole-4-a-carboxylic acid A mixture of 4d (180 mg, 0.30 mmol) and 10% Pd(OH)$_2$/C (100 mg) in MeOH (15 mL) and EtOAc (2 mL) was stirred under hydrogen balloon for 12 hours. The reaction mixture was filtered through a pad of diatomaceous earth and washed with CMA (25 mL). The filtrate was concentrated to dryness under reduced pressure. The residue was purified by column chromatography (silica, 0-50% CMA in CH$_2$Cl$_2$) followed by preparative HPLC to provide the title compound (28 mg, 18%) as an off-white solid.

R$_f$ 0.62 (80:18:2 Methylene Chloride/Methanol/concentrated Ammonium Hydroxide).

$^1$H NMR (300 MHz, CD$_3$OD) δ 0.85 (s, 3H), 0.90 (s, 3H), 0.93 (s, 3H), 0.99 (s, 3H), 1.20 (s, 3H), 1.23 (s, 3H), 1.38 (s, 3H), 1.40-2.05 (m, 23H), 2.39 (d, J=14.7 Hz, 1H).

mp >300° C. ESI MS (Positive Mode) m/z 508 [C$_{32}$H$_{49}$N$_3$O$_2$+H]$^+$.

EXAMPLE 5

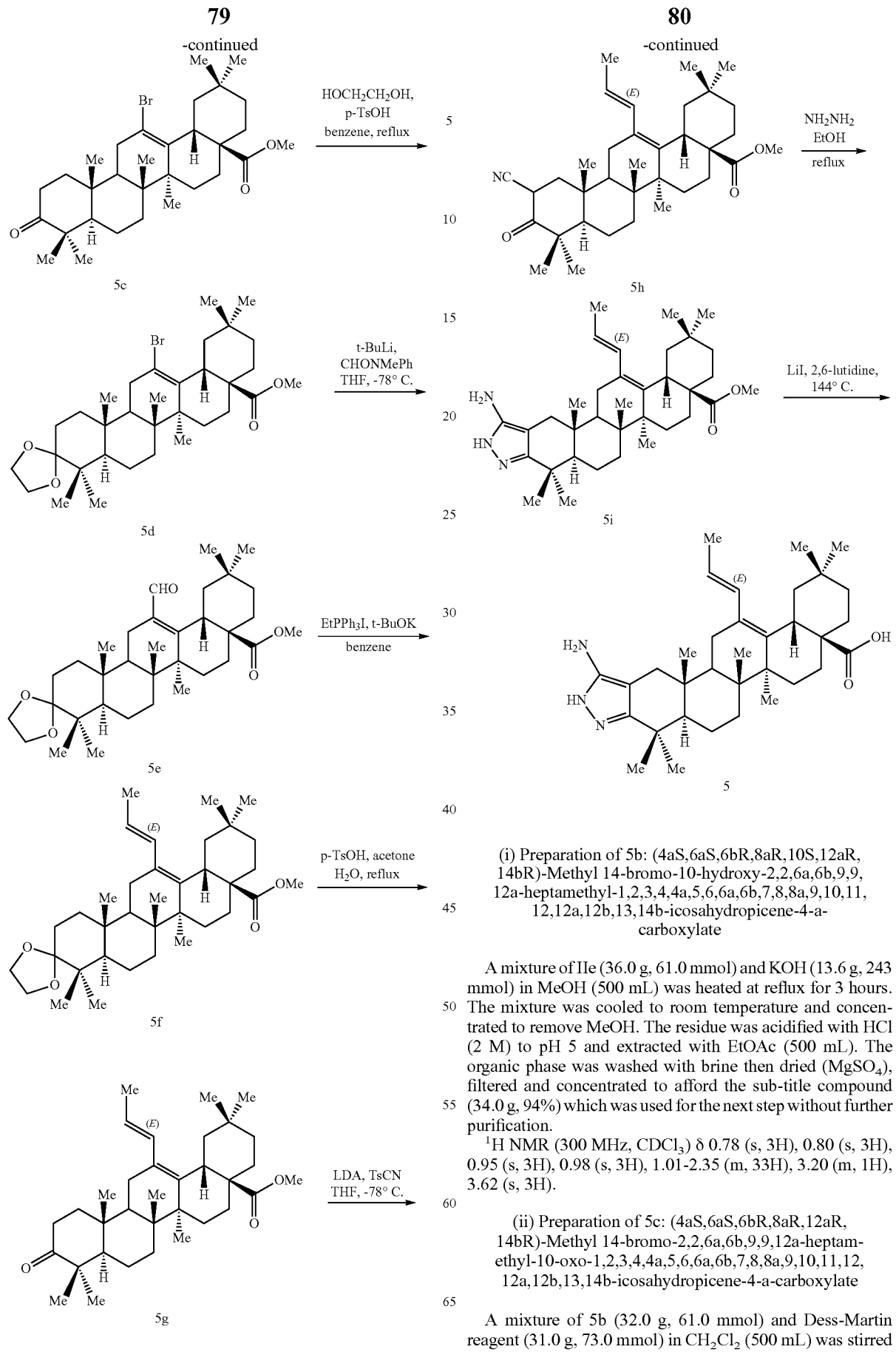

(i) Preparation of 5b: (4aS,6aS,6bR,8aR,10S,12aR,14bR)-Methyl 14-bromo-10-hydroxy-2,2,6a,6b,9,9,12a-heptamethyl-1,2,3,4,4a,5,6,6a,6b,7,8,8a,9,10,11,12,12a,12b,13,14b-icosahydropicene-4-a-carboxylate A mixture of IIe (36.0 g, 61.0 mmol) and KOH (13.6 g, 243 mmol) in MeOH (500 mL) was heated at reflux for 3 hours. The mixture was cooled to room temperature and concentrated to remove MeOH. The residue was acidified with HCl (2 M) to pH 5 and extracted with EtOAc (500 mL). The organic phase was washed with brine then dried (MgSO$_4$), filtered and concentrated to afford the sub-title compound (34.0 g, 94%) which was used for the next step without further purification.

$^1$H NMR (300 MHz, CDCl$_3$) δ 0.78 (s, 3H), 0.80 (s, 3H), 0.95 (s, 3H), 0.98 (s, 3H), 1.01-2.35 (m, 33H), 3.20 (m, 1H), 3.62 (s, 3H).

(ii) Preparation of 5c: (4aS,6aS,6bR,8aR,12aR,14bR)-Methyl 14-bromo-2,2,6a,6b,9,9,12a-heptamethyl-10-oxo-1,2,3,4,4a,5,6,6a,6b,7,8,8a,9,10,11,12,12a,12b,13,14b-icosahydropicene-4-a-carboxylate A mixture of 5b (32.0 g, 61.0 mmol) and Dess-Martin reagent (31.0 g, 73.0 mmol) in CH$_2$Cl$_2$ (500 mL) was stirred at room temperature for 4 hours. The mixture was quenched with saturated sodium thiosulfate (50 mL) and NaHCO₃ (50 mL) and extracted with EtOAc (500 mL). The organic phase was washed with brine then dried (MgSO₄), filtered and concentrated to dryness under reduced pressure. The residue was purified by column chromatography (silica, 5-10% EtOAc in hexanes) to afford the sub-title compound (26.0 g, 81%).

$^1$H NMR (300 MHz, CDCl₃) δ 0.80 (s, 3H), 0.90 (s, 3H), 0.98 (s, 3H), 1.02 (s, 3H), 1.05 (s, 6H), 1.06-2.55 (m, 26H), 3.62 (s, 3H).

(iii) Preparation of 5d: (4a'R,6a'R,6b'S,8a'S,12a'R, 14b'R)-Methyl 13'-bromo-4',4',6a',6b',11',11',14b'- heptamethyl-2',4',4a',5',6',6a',6b',7',8',8a',9',10',11', 12',12a',14',14a',14b'-octadecahydro-1'H-spiro[[1,3] dioxolane-2,3'-picene]-8a'-carboxylate A flask equipped with a Dean-Stark trap was charged 5c (26.0 g, 47.4 mmol), ethylene glycol (7.9 mL, 142.3 mmol) and p-toluenesulfoinc acid monohydrate (894 mg, 4.7 mmol) in benzene (500 mL). The mixture was heated at reflux overnight. The reaction mixture was cooled to room temperature and diluted with EtOAc (500 mL). The organic phase was washed with saturated NaHCO₃ (50 mL) and brine (200 mL) then dried (MgSO₄), filtered and concentrated to dryness. The residue was purified by column chromatography (silica, 0-10% EtOAc in hexanes) to afford the sub-title compound (18.0 g, 64%).

$^1$H NMR (300 MHz, CDCl₃) δ 0.74 (s, 3H), 0.83 (s, 3H), 0.92 (s, 3H), 0.94 (s, 3H), 0.97 (s, 3H), 0.99 (s, 3H), 1.14 (s, 3H), 1.15-2.05 (m, 21H), 2.39 (d, J=9.0 Hz, 1H), 3.57 (m, 1H), 3.63 (s, 3H), 3.93 (m, 4H).

(iv) Preparation of 5e: (4a'R,6a'R,6b'S,8a'S,12a'S, 14b'R)-Methyl 13'-formyl-4',4',6a',6b',11',11',14b'- heptamethyl-2',4',4a',5',6',6a',6b',7',8',8a',9',10',11', 12',12a',14',14a',14b'-octadecahydro-1'H-spiro[[1,3] dioxolane-2,3'-picene]-8a'-carboxylate To a solution of 5d (3.0 g, 5.1 mmol) in THF (60 mL) was added tert-butyllithium (10 mL, 1.5 M in heptane, 15.0 mmol) at −78° C. The mixture was stirred for 20 min. n-Methylformanilide (1.8 mL, 15.2 mmol) was added. The reaction mixture was allowed to warm to −10° C. over 1 hour. The reaction mixture was quenched by saturated NH₄Cl (10 mL) and extracted with EtOAc (200 mL). The organic phase was washed with brine (200 mL) then dried (MgSO₄), filtered and concentrated to dryness. The residue was purified by column chromatography (silica, 0-10% EtOAc in hexanes) to afford the sub-title compound (2.0 g, 73%).

$^1$H NMR (300 MHz, CDCl₃) δ 0.65 (s, 3H), 0.81 (s, 3H), 0.90 (s, 6H), 0.92 (s, 3H), 0.99 (s, 3H), 1.12 (s, 3H), 1.25-2.18 (m, 19H), 2.65 (s, 3H), 3.85 (m, 4H), 10.3 (s, 1H).

(v) Preparation of 5f: (4a'R,6a'R,6b'S,8a'S,12a'S, 14b'R)-Methyl 4',4',6a',6b',11',11',14b'-heptamethyl- 13'-(prop-1-enyl)-2',4',4a',5',6',6a',6b',7',8',8a',9',10', 11',12',12a',14',14a',14b'-octadecahydro-1'H-spiro [[1,3]dioxolane-2,3'-picene]-8a'-carboxylate To a suspension of ethyltriphenylphosphonium iodide (1.2 g, 2.96 mmol) in benzene (20 mL) was added potassium tert-butoxide (332 mg, 2.96 mmol). The mixture was stirred at room temperature for 1 hour. A solution of 5e (400 mg, 0.74 mmol) in THF (5 mL) was added. The mixture was stirred at room temperature for 1.5 hours. The reaction mixture was diluted with EtOAc (100 mL). The organic phase was washed with brine then dried (MgSO₄), filtered and concentrated to dryness. The residue was purified by column chromatography (silica, 0-10% EtOAc in hexanes) to afford the sub-title compound (380 mg, 93%) as a mixture of cis- and trans-isomers.

(vi) Preparation of 5g: (4aS,6aS,6bR,8aR,12aR, 14bS)-Methyl 2,2,6a,6b,9,9,12a-heptamethyl-10- oxo-14-(prop-1-enyl)-1,2,3,4,4a,5,6,6a,6b,7,8,8a,9, 10,11,12,12a,12b,13,14b-icosahydropicene-4-a- carboxylate A mixture of 5f (571 mg, 0.92 mmol) and p-toluenesulfonic acid monohydrate (176 mg, 0.92 mmol) in acetone (20 mL) and H₂O (2 mL) was stirred at room temperature for 1.5 hours. The reaction mixture was concentrated to remove acetone under reduced pressure and extracted with EtOAc (100 mL). The organic phase was washed with brine then dried (MgSO₄), filtered and concentrated to dryness. The residue was purified by column chromatography (silica, 0-10% EtOAc in hexanes) to afford the sub-title compound (500 mg, 95%).

$^1$H NMR (300 MHz, CDCl₃) δ 0.72 (s, 1.8H), 0.81 (s, 1.2H), 0.89 (s, 3H), 0.91 (s, 3H), 1.0-2.50 (m, 38H), 3.65 (s, 3H), 5.40-5.70 (m, 1H), 6.05 (d, J=12.0 Hz, 0.4H), 6.53 (d, J=15.0 Hz, 0.6H).

(vii) Preparation of 5h: (4aS,6aS,6bR,8aR,12aR, 14bS)-Methyl 1'-cyano-2,2,6a,6b,9,9,12a-heptam- ethyl-10-oxo-14-(prop-1-enyl)-1,2,3,4,4a,5,6,6a,6b, 7,8,8a,9,10,11,12,12a,12b,13,14b-icosahydropicene- 4-a-carboxylate To a solution of diisopropylamine (0.26 mL, 1.87 mmol) in THF (5 mL) was added n-butyllithium (0.78 mL, 2.5 M in hexanes, 1.96 mmol) at −78° C. The solution was stirred for 30 min. The LDA solution was added to 5g (500 mg, 0.98 mmol) in THF (5 mL). The mixture was allowed to warm to −40° C. for 5 min and cooled to −78° C. A suspension of p-toluene sulfonyl cyanide (339 mg, 1.87 mmol) in THF (2 mL) was added. The reaction mixture was allowed to warm to −40° C. over 1.5 hours. The reaction was quenched by saturated NH₄Cl (3 mL) and extracted with EtOAc (100 mL). The organic phase was washed with brine then dried (MgSO₄), filtered and concentrated to dryness. The residue was purified by column chromatography (silica, 0-20% EtOAc in hexanes) to afford the sub-title compound (210 mg, 40%).

$^1$H NMR (300 MHz, CDCl₃) δ 0.65-2.01 (m, 44H), 2.42-2.80 (m, 1H), 3.60 (s, 3H), 4.21 (m, 1H), 5.41-5.70 (m, 1H), 6.01 (m, 1H).

(viii) Preparation of 51: (4aS,6aS,6bR,8aR,13aR, 15bS)-Methyl 12-amino-2,2,6a,6b,9,9,13a-heptam- ethyl-15-((E)-prop-1-enyl)-2,3,4,4a,5,6,6a,6b,7,8,8a, 9,11,13,13a,13b,14,15b-octadecahydro-1H-chryseno [1,2-f]indazole-4-a-carboxylate A mixture of 5h (200 mg, 0.37 mmol) and hydrazine (0.014 mL, 0.45 mmol) in EtOH (3 mL) was heated at reflux overnight. The reaction mixture was concentrated to dryness under reduced pressure. The residue was purified by column chromatography (silica, 0-10% MeOH in CH₂Cl₂) to afford the sub-title compound (130 mg, 64%).

$^1$H NMR (300 MHz, CDCl₃) δ 0.71 (s, 1.8H), 0.81 (s, 1.2H), 0.88 (s, 3H), 0.89 (s, 6H), 0.98 (s, 1.8H), 1.02 (s, 1.2H), 1.05 (s, 3H), 1.12 (s, 3H), 1.16-2.35 (m, 27H), 3.65 (s, 3H), 5.50 (m, 0.4H), 5.70 (m, 0.6H), 6.05 (d, J=12.0 Hz, 0.4H), 6.55 (d, J=15.0 Hz, 0.6H).

(ix) Preparation of 5: (4aS,6aS,6bR,8aR,13aR, 15bS)-12-Amino-2,2,6a,6b,9,9,13a-heptamethyl-15-((E)-prop-1-enyl)-2,3,4,4a,5,6,6a,6b,7,8,8a,9,11,13, 13a,13b,14,15b-octadecahydro-1H-chryseno[1,2-f]indazole-4-a-carboxylic acid A mixture of 5h (90 mg, 0.16 mmol) and lithium iodide (330 mg, 2.47 mmol) in 2,6-lutidine (3 mL) was heated to 144° C. for 6 hours. The reaction mixture was cooled to room temperature and neutralized with HCl (2 M) and extracted with $CH_2Cl_2$/i-PrOH (3:1). The organic phase was dried ($MgSO_4$), filtered and concentrated to dryness under reduced pressure. The residue was purified by column chromatography (silica, 0-40% CMA in $CH_2Cl_2$) followed by preparative HPLC to provide the title compound (20 mg, 23%) as an off-white solid.

$R_f$ 0.85 (80:18:2 Methylene Chloride/Methanol/concentrated Ammonium Hydroxide).

$^1$H NMR (300 MHz, $CD_3OD$) δ 0.80 (s, 3H), 0.90 (s, 6H), 1.02 (s, 3H), 1.18 (s, 3H), 1.20 (s, 3H), 1.28 (s, 3H), 1.30-2.30 (m, 22H), 2.52 (d, J=15.0 Hz, 1H), 3.63 (m, 1H), 5.68 (dd, J=6.0, 15.0 Hz, 1H), 6.59 (d, J=15.0 Hz, 1H). mp >300° C. ESI MS (Positive Mode) m/z 534 $[C_{34}H_{51}N_3O_2+H]^+$.

EXAMPLE 6

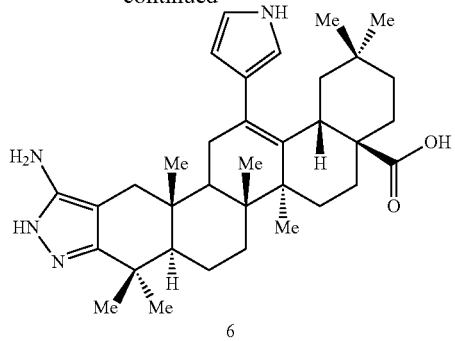

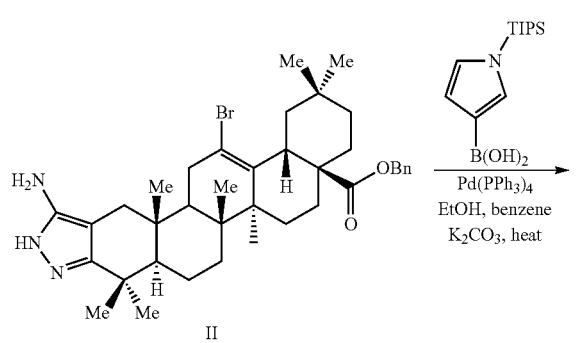

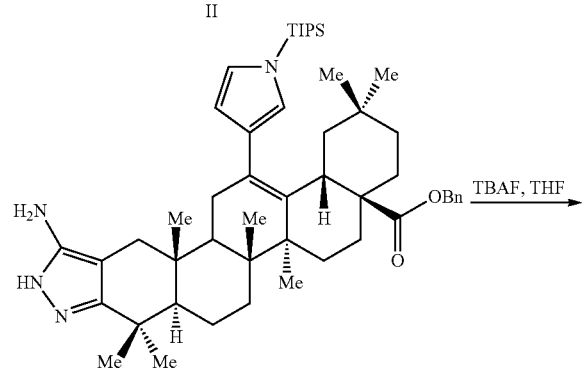

wherein TIPS refers to triisopropylsilyl.

(i) Preparation of 6b: (4aS,6aS,6bR,8aR,13aR, 15bS)-Benzyl 12-amino-2,2,6a,6b,9,9,13a-heptamethyl-15-(1-(triisopropylsilyl)-1H-pyrrol-3-yl)-2,3,4, 4a,5,6,6a,6b,7,8,8a,9,11,13,13a,13b,14,15b-octadecahydro-1H-chryseno[1,2-f]indazole-4-a-carboxylate A mixture of II (250 mg, 0.37 mmol), 1-(triisopropylsilyl)-1H-pyrrol-3-ylboronic acid (303 mg, 1.13 mmol), $Pd(PPh_3)_4$ (43 mg, 0.037 mmol) and $K_2CO_3$ (203 mg, 1.47 mmol) in benzene (3.5 mL) and EtOH (1.5 mL) was sealed and heated to 120° C. by microwave for 1 hour. The reaction mixture was diluted with EtOAc (100 mL). The organic phase was washed with brine then dried ($MgSO_4$), filtered and concentrated to dryness. The residue was purified by column chromatography (silica, 0-10% MeOH in $CH_2Cl_2$) to afford the sub-title compound (130 mg, 43%). APCI MS (Positive Mode) m/z 805 $[C_{51}H_{76}N_4O_2Si+H]^+$.

(ii) Preparation of 6c: (4aS,6aS,6bR,8aR,13aR, 15bS)-Benzyl 12-amino-2,2,6a,6b,9,9,13a-heptamethyl-15-(1H-pyrrol-3-yl)-2,3,4,4a,5,6,6a,6b,7,8,8a, 9,11,13,13a,13b,14,15b-octadecahydro-1H-chryseno [1,2-f]indazole-4-a-carboxylate To a solution of 6b (130 mg, 0.16 mmol) in THF (2 mL) was added tetrabutylammonium fluoride (0.49 mL, 1 M in THF, 0.49 mmol). The mixture was stirred at room temperature for 2 hours. The reaction mixture was diluted with EtOAc (100 mL). The organic phase was washed with brine then dried ($MgSO_4$), filtered and concentrated to dryness. The residue was purified by column chromatography (silica, 0-10% MeOH in $CH_2Cl_2$) to afford the sub-title compound (90 mg, 87%). APCI MS (Positive Mode) m/z 649 $[C_{42}H_{56}N_4O_2+H]^+$.

(iii) Preparation of 6: (4aS,6aS,6bR,8aR,13aR, 15bS)-12-Amino-2,2,6a,6b,9,9,13a-heptamethyl-15-(1H-pyrrol-3-yl)-2,3,4,4a,5,6,6a,6b,7,8,8a,9,11,13, 13a,13b,14,15b-octadecahydro-1H-chryseno[1,2-f]indazole-4-a-carboxylic acid A mixture of 6c (90 mg, 0.13 mmol) and 10% $Pd(OH)_2$/C (50 mg) in MeOH (12 mL) and EtOAc (3 mL) was stirred under a hydrogen balloon for 5 hours. The reaction mixture was filtered through a pad of diatomaceous earth and washed with CMA (25 mL). The filtrate was concentrated to dryness under reduced pressure. The residue was purified by column chromatography (silica, 0-50% CMA in $CH_2Cl_2$) to afford the title compound (18 mg, 25%) as a brown solid.

$R_f$ 0.26 (9:1 Methylene Chloride/Methanol).

$^1$H NMR (400 MHz, $CD_3OD$) δ 0.50 (s, 3H), 0.80 (s, 3H), 0.86 (s, 3H), 0.95 (s, 3H), 1.14 (s, 3H), 1.21 (s, 3H), 1.24 (s, 3H), 1.25-2.18 (m, 19H), 2.26 (s, 1H), 2.36 (d, J=14.8 Hz, 1H), 3.62 (m, 1H), 6.08 (s, 1H), 6.65 (s, 1H), 9.91 (s, 1H). mp >300° C. APCI MS (Positive Mode) m/z 559 $[C_{35}H_{50}N_4O_2+H]^+$.

EXAMPLE 7

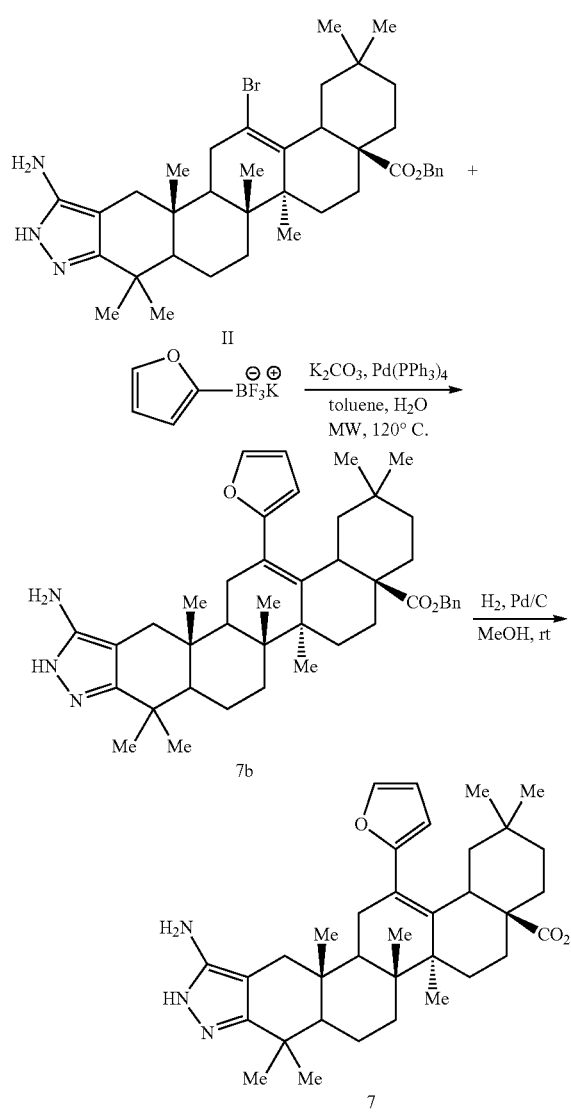

(i) Preparation of 7b: (4aS,6aS,6bR,13aR)-Benzyl 12-amino-15-(furan-2-yl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylate To a mixture of II (250 mg, 0.377 mmol) and potassium 2-furantrifluoroborate (196 mg, 1.12 mmol) in toluene (4.5 mL) and $H_2O$ (0.5 mL) was added $K_2CO_3$ (207 mg, 1.5 mmol). The mixture was sparged with nitrogen and then $Pd(PPh_3)_4$ (86 mg, 0.074 mmol) was added. The reaction mixture was heated at 120° C. for 1 hour using microwave irradiation. The solvent was concentrated under reduced pressure. The residue was taken up in EtOAc (40 mL) and washed with brine (3×15 mL). The organic layer was dried ($Na_2SO_4$), filtered and concentrated. The residue was purified by column chromatography (silica, 0-10% MeOH in $CH_2Cl_2$) to afford the sub-title compound (200 mg, 81%). APCI MS m/z 650 $[C_{42}H_{55}N_3O_3+H]^+$.

(ii) Preparation of 7: (4aS,6aS,6bR,13aR)-12-Amino-15-(furan-2-yl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylic acid A solution of 7b (200 mg, 0.308 mmol) and MeOH (15 mL) was flushed with nitrogen and then 10% Pd/C (200 mg) was added. The mixture was flushed with nitrogen followed by hydrogen. The mixture was stirred under hydrogen at atmospheric pressure overnight.

The catalyst was removed by filtration through diatomaceous earth and the filtrate was concentrated. The residue was purified by column chromatography (silica, 0-10% MeOH in $CH_2Cl_2$) followed by preparative HPLC to afford the title compound (19 mg, 11%).

$R_f$ 0.20 (90:9:1 Methylene Chloride/Methanol/concentrated Ammonium Hydroxide).

$^1$H NMR (400 MHz, $CD_3OD$) δ 0.78 (s, 3H), 0.86-2.50 (m, 42H), 3.74 (d, J=12.1 Hz, 1H), 6.38 (s, 2H), 7.41 (s, 1H). APCI MS m/z 560 $[C_{39}H_{49}N_3O_3+H]^+$. m.p. 250-270° C. dec. HPLC (Method A) 98.3% (214 nm) $t_R$=16.6 min.

EXAMPLE 8

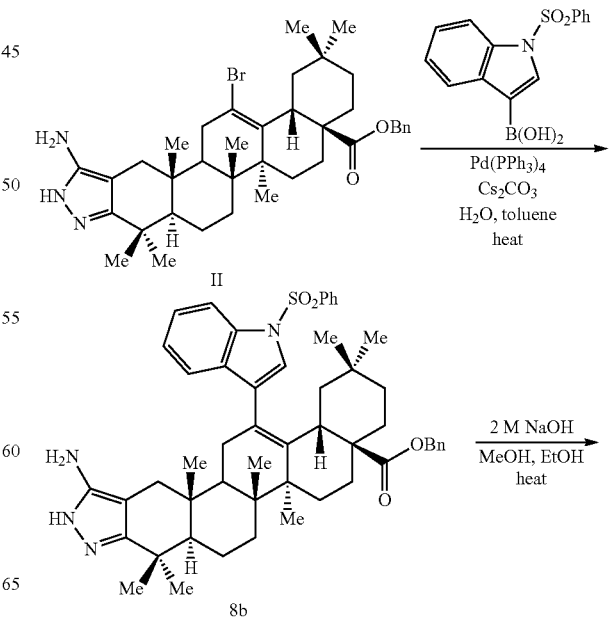

-continued

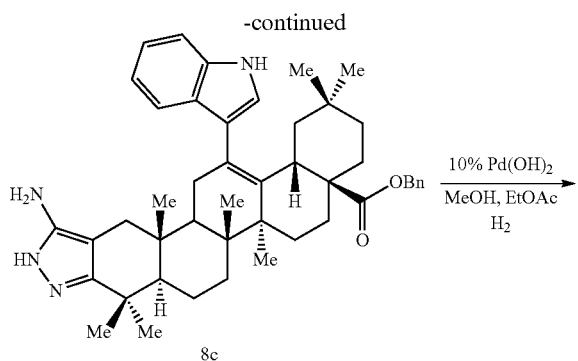

(i) Preparation of 8b: (4aS,6aS,6bR,8aR,13aR, 15bS)-Benzyl 12-amino-2,2,6a,6b,9,9,13a-heptamethyl-15-(1-(phenylsulfonyl)-1H-indol-3-yl)-2,3,4, 4a,5,6,6a,6b,7,8,8a,9,11,13,13a,13b,14,15b-octadecahydro-1H-chryseno[1,2-f]indazole-4-a-carboxylate A mixture of II (250 mg, 0.37 mmol), 1-(phenylsulfonyl)-1H-indol-3-ylboronic acid (341 mg, 1.13 mmol), Pd(PPh$_3$)$_4$ (43 mg, 0.037 mmol) and cesium carbonate (491 mg, 1.50 mmol) in toluene (4.0 mL) and H$_2$O (1.0 mL) was sealed and heated to 120° C. by microwave for 1 hour. The reaction mixture was diluted with EtOAc (100 mL). The organic phase was washed with brine then dried (MgSO$_4$), filtered and concentrated to dryness. The residue was purified by column chromatography (silica, 0-5% MeOH in CH$_2$Cl$_2$) to afford the sub-title compound (264 mg, 83%). APCI MS (Positive Mode) m/z 839 [C$_{52}$H$_{62}$N$_4$O$_4$S+H]$^+$.

(ii) Preparation of 8c: (4aS,6aS,6bR,8aR,13aR, 15bS)-Benzyl 12-amino-15-(1H-indol-3-yl)-2,2,6a, 6b,9,9,13a-heptamethyl-2,3,4,4a,5,6,6a,6b,7,8,8a,9, 11,13,13a,13b,14,15b-octadecahydro-1H-chryseno [1,2-f]indazole-4-a-carboxylate A mixture of 8b (260 mg, 0.30 mmol) and NaOH (15 mL, 2.0 M) in MeOH (10 mL) and EtOH (30 mL) was heated at reflux for 24 hours. The reaction mixture was extracted with EtOAc (100 mL). The organic phase was washed with brine then dried (MgSO$_4$), filtered and concentrated to dryness. The residue was purified by column chromatography (silica, 0-5% MeOH in CH$_2$Cl$_2$) to afford the sub-title compound (115 mg, 53%).

(iii) Preparation of 8: (4aS,6aS,6bR,8aR,13aR, 15bS)-12-Amino-15-(1H-indol-3-yl)-2,2,6a,6b,9,9, 13a-heptamethyl-2,3,4,4a,5,6,6a,6b,7,8,8a,9,11,13, 13a,13b,14,15b-octadecahydro-1H-chryseno[1,2-f] indazole-4-a-carboxylic acid A mixture 8c (115 mg, 0.16 mmol) and 10% Pd(OH)$_2$/C (60 mg) in MeOH (15 mL) and EtOAc (5 mL) was stirred under a hydrogen balloon for 12 hours. The reaction mixture was filtered through a pad of diatomaceous earth and washed with CMA (25 mL). The filtrate was concentrated to dryness under reduced pressure. The residue was purified by column chromatography (silica, 0-40% CMA in CMA) to afford the title compound (56 mg, 76%) as a brown solid.

R$_f$ 0.75 (80:18:2 Methylene Chloride/Methanol/concentrated Ammonium Hydroxide).

$^1$H NMR (400 MHz, CD$_3$OD) δ 0.14 (s, 3H), 0.65 (s, 3H), 0.88 (s, 3H), 1.09 (s, 3H), 1.16 (s, 3H), 1.26 (s, 3H), 1.34 (s, 3H), 1.35-2.20 (m, 19H), 2.30 (d, J=14.4 Hz, 1H), 2.40 (m, 1H), 6.96 (t, J=8.0 Hz, 1H), 7.05 (t, J=8.0 Hz, 1H), 7.07 (s, 1H), 7.31 (d, J=8.0 Hz, 1H), 7.42 (d, J=8.0 Hz, 1H). mp >300° C. dec. APCI MS (Positive Mode) m/z 609 [C$_{39}$H$_{52}$N$_4$O$_2$+H]$^+$.

EXAMPLE 9

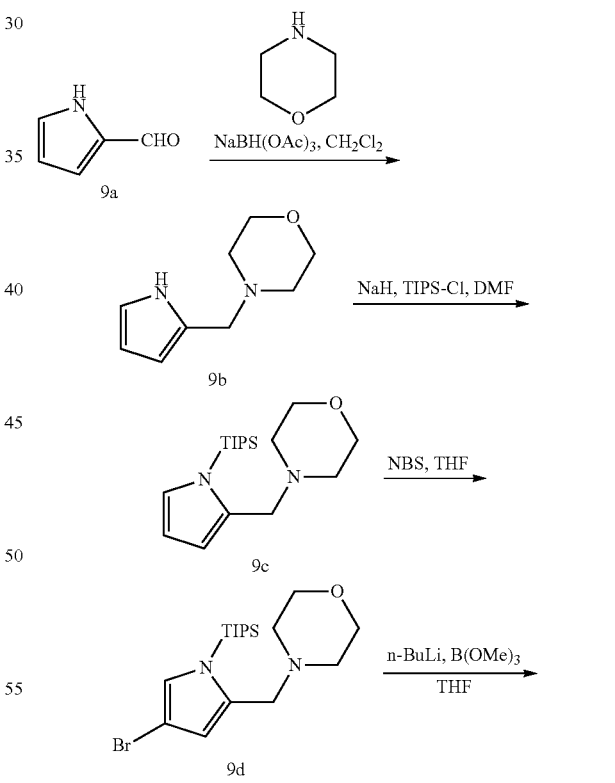

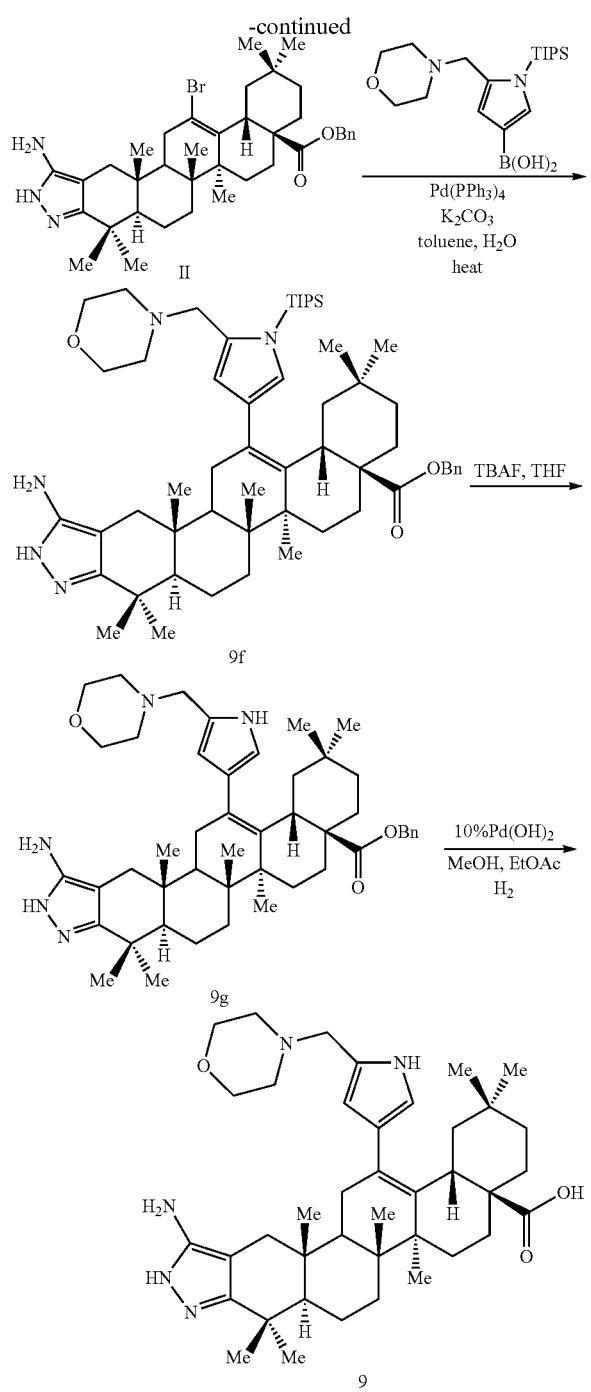

¹H NMR (400 MHz, CDCl₃) δ 2.40 (s, 4H), 3.42 (s, 2H), 3.70 (m, 4H), 6.03 (s, 1H), 6.09 (s, 1H), 6.74 (s, 1H), 8.30 (bs, 1H).

(ii) Preparation of 9c: 4-((1-(Triisopropylsilyl)-1H-pyrrol-2-yl)methyl)morpholine To a solution of 9b (5.3 g, 31.9 mmol) in DMF (60 mL) was added sodium hydride (60% in mineral oil, 1.4 g, 35.1 mmol) in an ice bath. The mixture was stirred for 5 min. Chlorotriisopropylsilane (7.4 mL, 35.1 mmol) was added. The reaction mixture was stirred at room temperature for 12 hours. The reaction mixture was diluted with EtOAc (200 mL). The organic phase was washed with brine then dried (MgSO₄), filtered and concentrated to dryness. The residue was purified by column chromatography (silica, 0-20% EtOAc in hexanes) to afford the sub-title compound (10.0 g, 98%).
¹H NMR (400 MHz, CDCl₃) δ 1.10 (d, J=2.5 Hz, 18H), 1.62 (m, 3H), 2.40 (s, 4H), 3.42 (s, 2H), 3.70 (m, 4H), 6.20 (s, 2H), 6.80 (s, 1H).

(iii) Preparation of 9d: 4-((4-Bromo-1-(triisopropylsilyl)-1H-pyrrol-2-yl)methyl)morpholine To a solution of 9c (1.0 g, 3.1 mmol) in THF (10 mL) was added N-bromosuccinimide (552 mg, 3.1 mmol) at −78° C. The mixture was stirred at −78° C. for 2 hours and warmed to room temperature for 1 hour. The reaction was quenched with H₂O (5 mL) and extracted with EtOAc (100 mL). The organic phase was washed with brine then dried (MgSO₄), filtered and concentrated to dryness. The residue was purified by column chromatography (silica, 0-10% EtOAc in hexanes) to afford the sub-title compound (1.0 g, 83%).
¹H NMR (400 MHz, CDCl₃) δ 1.15 (d, J=2.5 Hz, 18H), 1.58 (m, 3H), 2.40 (m, 4H), 3.32 (s, 2H), 3.68 (m, 4H), 6.20 (s, 1H), 6.72 (s, 1H).

(iv) Preparation of 9e: 5-(Morpholinomethyl)-1-(triisopropylsilyl)-1H-pyrrol-3-ylboronic acid To a solution of 9d (200 mg, 0.49 mmol) in THF (5 mL) was added n-butyllithium (2.5 M in hexanes, 0.30 mL, 0.74 mmol) at −78° C. The mixture was stirred at −78° C. for 20 min. Trimethyl borate (0.28 mL, 2.45 mmol) was added. The reaction mixture was stirred at −78° C. for 1 hour and quenched with MeOH (4 mL). The reaction mixture was warmed to room temperature for 1 hour and extracted with EtOAc (100 mL). The organic phase was washed with brine then dried (MgSO₄), filtered and concentrated to dryness. The residue was purified by column chromatography (silica, 0-10% MeOH in CH₂Cl₂) to afford the sub-title compound (70 mg, 39%).
¹H NMR (400 MHz, CDCl₃) δ 1.15 (d, J=2.5 Hz, 18H), 1.58 (m, 3H), 2.40 (m, 4H), 3.32 (s, 2H), 3.68 (m, 4H), 6.35 (s, 1H), 7.15 (s, 1H).

(v) Preparation of 9f: (4aS,6aS,6bR,8aR,13aR, 15bS)-Benzyl 12-amino-2,2,6a,6b,9,9,13a-heptamethyl-15-(5-(morpholinomethyl)-1-(triisopropylsilyl)-1H-pyrrol-3-yl)-2,3,4,4a,5,6,6a,6b,7,8,8a,9,11, 13,13a,13b,14,15b-octadecahydro-1H-chryseno[1,2-f]indazole-4-a-carboxylate A mixture of II (220 mg, 0.33 mmol), 9e (310 mg, 0.84 mmol), Pd(PPh₃)₄ (60 mg, 0.052 mmol) and K₂CO₃ (184 mg, 1.32 mmol) in toluene (4.0 mL) and H₂O (0.5 mL) was sealed and heated to 120° C. by microwave for 1 hour. The reaction mixture was diluted with EtOAc (100 mL). The organic phase was washed with brine then dried (MgSO₄), filtered and concentrated to dryness. The residue was purified by column (i) Preparation of 9b: 4-((1H-Pyrrol-2-yl)methyl)morpholine To a solution of 1H-pyrrole-2-carbaldehyde (5.0 g, 52.5 mmol) and morpholine (5.0 mL, 57.8 mmol) in CH₂Cl₂ (160 mL) was added sodium triacetoxyborohydride (12.2 g, 57.8 mmol). The mixture was stirred at room temperature for 4 hours. The reaction mixture was diluted with EtOAc (200 mL). The organic phase was washed with aqueous NaHCO₃ and brine then dried (MgSO₄), filtered and concentrated to dryness. The residue was purified by column chromatography (silica, 0-10% MeOH in CH₂Cl₂) to afford the sub-title compound (5.3 g, 61%).

chromatography (silica, 0-10% MeOH in CH₂Cl₂) to afford the sub-title compound (250 mg, 83%).

¹H NMR (300 MHz, CDCl₃) δ 0.42 (s, 3H), 0.73 (s, 3H), 0.78 (s, 3H), 0.85 (s, 3H), 1.11-2.40 (m, 55H), 3.43 (s, 3H), 3.60 (m, 6H), 5.02 (m, 2H), 6.08 (s, 1H), 6.68 (s, 1H), 7.33 (m, 5H). APCI MS (Positive Mode) m/z 904 [$C_{56}H_{85}N_5O_3Si$+H]⁺.

(vi) Preparation of 9g: (4aS,6aS,6bR,8aR,13aR, 15bS)-Benzyl 12-amino-2,2,6a,6b,9,9,13a-heptamethyl-15-(5-(morpholinomethyl)-1H-pyrrol-3-yl)-2, 3,4,4a,5,6,6a,6b,7,8,8a,9,11,13,13a,13b,14,15b-octadecahydro-1H-chryseno[1,2-f]indazole-4-a-carboxylate To a solution of 9f (250 mg, 0.27 mmol) in THF (5 mL) was add tetrabutylammonium fluoride (0.83 mL, 1 M in THF, 0.83 mmol). The mixture was stirred at room temperature for 2 hours. The reaction mixture was diluted with EtOAc (100 mL). The organic phase was washed with brine then dried (MgSO₄), filtered and concentrated to dryness. The residue was purified by column chromatography (silica, 0-10% MeOH in CH₂Cl₂) to afford the sub-title compound (176 mg, 87%). APCI MS (Positive Mode) m/z 748 [$C_{47}H_{65}N_5O_3$+H]⁺.

(vii) Preparation of 9: (4aS,6aS,6bR,8aR,13aR, 15bS)-12-Amino-2,2,6a,6b,9,9,13a-heptamethyl-15-(5-(morpholinomethyl)-1H-pyrrol-3-yl)-2,3,4,4a,5,6, 6a,6b,7,8,8a,9,11,13,13a,13b,14,15b-octadecahydro-1H-chryseno[1,2-f]indazole-4-a-carboxylic acid A mixture of 9g (176 mg, 0.23 mmol) and 10% Pd(OH)₂/C (100 mg) in MeOH (15 mL) and EtOAc (5 mL) was stirred under a hydrogen balloon for 12 hours. The reaction mixture was filtered through a pad of diatomaceous earth and washed with CMA (25 mL). The filtrate was concentrated to dryness under reduced pressure. The residue was purified by column chromatography (silica, 0-60% CMA in CH₂Cl₂) to afford the title compound (25 mg, 17%) as an off-white solid.

$R_f$ 0.50 (80:18:2 Methylene Chloride/Methanol/concentrated Ammonium Hydroxide).

¹H NMR (400 MHz, CD₃OD) δ 0.55 (s, 3H), 0.78 (s, 3H), 0.86 (s, 3H), 0.94 (s, 3H), 1.12 (s, 3H), 1.21 (s, 3H), 1.24 (s, 3H), 1.25-2.18 (m, 19H), 2.26 (m, 1H), 2.36 (d, J=14.8 Hz, 1H), 3.49 (m, 4H), 3.52 (m, 3H), 3.67 (m, 6H), 6.03 (m, 1H), 6.63 (s, 1H).

mp 270-280° C. dec. ESI MS (Positive Mode) m/z 659 [$C_{40}H_{59}N_5O_3$+H]⁺.

EXAMPLE 10

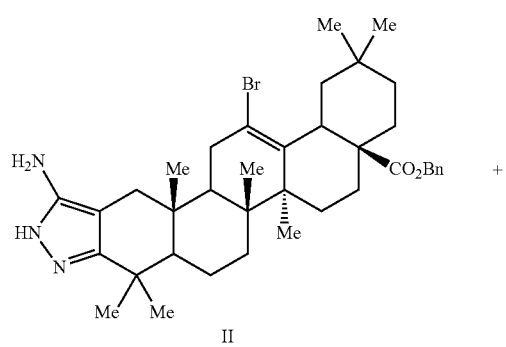

II

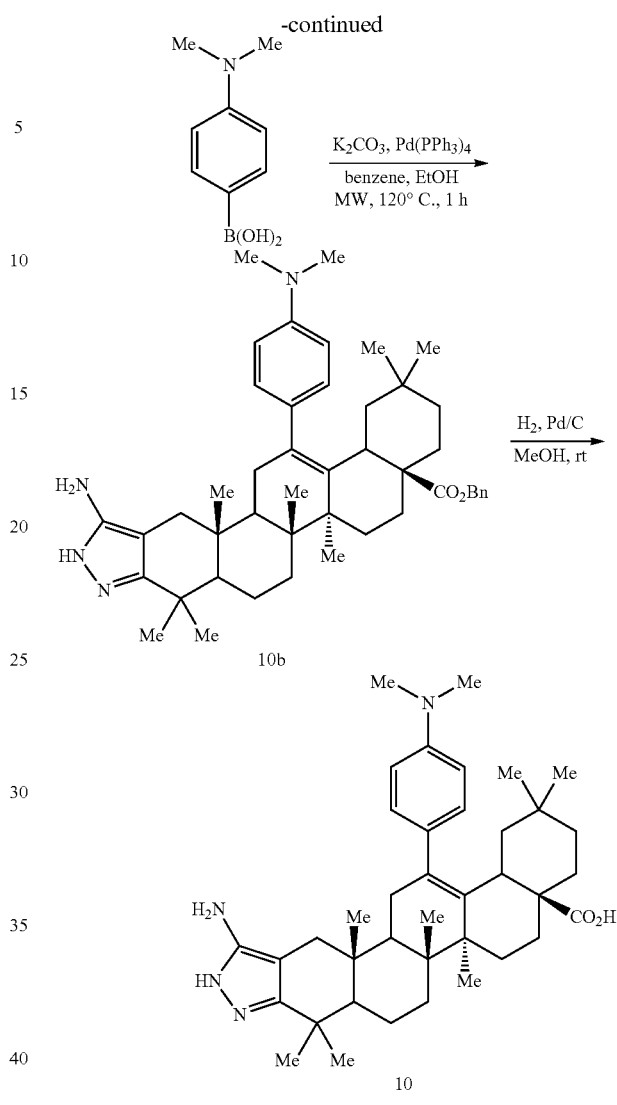

10b

10

(i) Preparation of 10b: (4aS,6aS,6bR,13aR)-Benzyl 12-amino-15-(4-(dimethylamino)phenyl)-2,2,6a,6b, 9,9,13a-heptamethyl-2,3,4,4a,5,6,6a,6b,7,8,8a,9,11, 13,13a,13b,14,15b-octadecahydro-1H-chryseno[1,2-f]indazole-4-a-carboxylate To a solution of II (300 mg, 0.45 mmol), 4-(dimethylamino)phenylboronic acid (223 mg, 1.35 mmol), benzene (4 mL) and EtOH (1 mL) was added K₂CO₃ (249 mg, 1.80 mmol).

The mixture was sparged with nitrogen and then Pd(PPh₃)₄ (104 mg, 0.08 mmol) was added. The reaction mixture was heated at 120° C. for 1 hour using microwave irradiation and then concentrated under reduced pressure. The residue was dissolved in EtOAc (20 mL) and the solution was washed with brine then dried (Na₂SO₄), filtered and concentrated. The residue was purified (silica, 0-5% MeOH in CH₂Cl₂) to afford the sub-title compound (254 mg, 79%).

¹H NMR (300 MHz, CDCl₃) δ 0.32-2.31 (m, 41H), 2.89 (s, 6H), 3.15 (m, 1H), 5.08 (m, 2H), 6.63 (d, J=8.7 Hz, 2H), 7.03 (d, J=8.7 Hz, 2H), 7.34-7.37 (m, 5H).

APCI MS m/z 703 [$C_{46}H_{62}N_4O_2$+H]⁺.

(ii) Preparation of 10: (4aS,6aS,6bR,13aR)-12-Amino-15-(4-(dimethylamino)phenyl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylic acid A solution of 10b (248 mg, 0.35 mmol) and MeOH (20 mL) was flushed with nitrogen and then 10% Pd/C (150 mg) was added. The mixture was flushed with nitrogen followed by hydrogen. The mixture was stirred under hydrogen at atmospheric pressure overnight. The catalyst was removed by filtration and the filtrate was concentrated. Purification by column chromatography (silica, 0-50% CMA in $CH_2Cl_2$) afforded the title compound (40 mg, 19%).

$R_f$ 0.32 (90:9:1 Methylene Chloride/Methanol/concentrated Ammonium Hydroxide).

$^1$H NMR (300 MHz, $CD_3OD$) δ 0.31-2.37 (m, 41H), 2.88 (s, 6H), 3.18 (m, 1H), 6.81 (d, J=8.7 Hz, 2H), 7.13 (d, J=8.4 Hz, 2H). APCI MS m/z 613 $[C_{39}H_{56}N_4O_2+H]^+$. m.p. >300° C. HPLC (Method A) 97.0% (214 nm) $t_R$=13.2 min.

EXAMPLE 11

(i) Preparation of 11b: (4aS,6aS,6bR,13aR)-Benzyl 12-amino-15-(1H-indol-5-yl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylate To a solution of II (200 mg, 0.302 mmol), 1H-indol-5-ylboronic acid (145 mg, 0.90 mmol), toluene (4.5 mL) and $H_2O$ (0.5 mL) was added cesium carbonate (391 mg, 1.20 mmol). The mixture was sparged with nitrogen and then $Pd(PPh_3)_4$ (69 mg, 0.06 mmol) was added. The reaction mixture was heated at 120° C. for 1 hour using microwave irradiation and then concentrated under reduced pressure. The residue was dissolved in EtOAc (30 mL) and the solution was washed with brine then dried ($Na_2SO_4$), filtered and concentrated. The residue was purified by column chromatography (silica, 0-5% MeOH in $CH_2Cl_2$) to afford the title compound (195 mg, 92%). APCI MS m/z 699 $[C_{46}H_{58}N_4O_2+H]^+$.

(ii) Preparation of 11: (4aS,6aS,6bR,13aR)-12-Amino-15-(indolin-5-yl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylic acid A solution of 11b (192 mg, 0.274 mmol), MeOH (12 mL) and EtOAc (3 mL) was flushed with nitrogen and then 10% Pd/C (228 mg) was added. The mixture was flushed with nitrogen followed by hydrogen. The mixture was stirred under hydrogen at atmospheric pressure overnight. The catalyst was removed by filtration and the filtrate was concentrated. The residue was purified by column chromatography (silica, 0-50% CMA in $CH_2Cl_2$) followed by preparative HPLC to afford the title compound (7.5 mg, 5%) as a solid.

$R_f$ 0.15 (90:9:1 Methylene Chloride/Methanol/concentrated Ammonium Hydroxide).

$^1$H NMR (400 MHz, $CD_3OD$) δ 0.30 (s, 3H), 0.77-2.39 (m, 43H), 2.99-3.03 (m, 1H), 3.34 (t, J=7.75 Hz, 2H), 3.85 (t, J=7.75 Hz, 2H), 7.35-7.44 (m, 3H).

APCI MS m/z 611 $[C_{39}H_{54}N_4O_2+H]^+$. m.p. 170-190° C. dec. HPLC (Method A) 97.7% (214 nm) $t_R$=12.6 min.

EXAMPLE 12

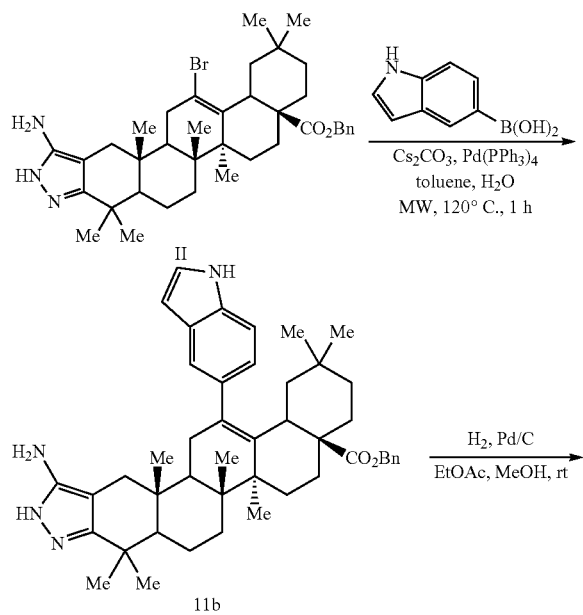

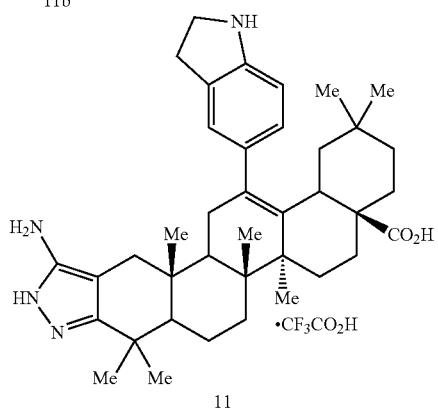

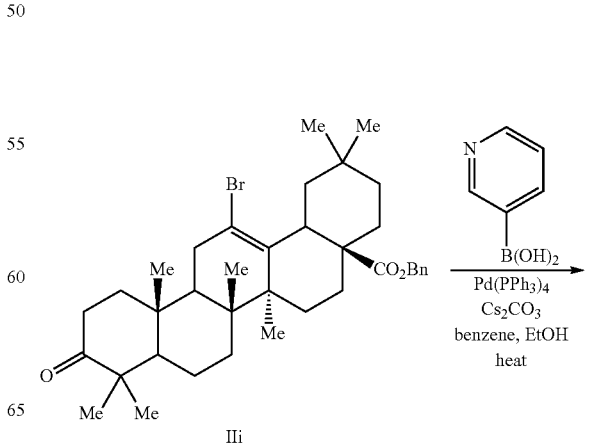

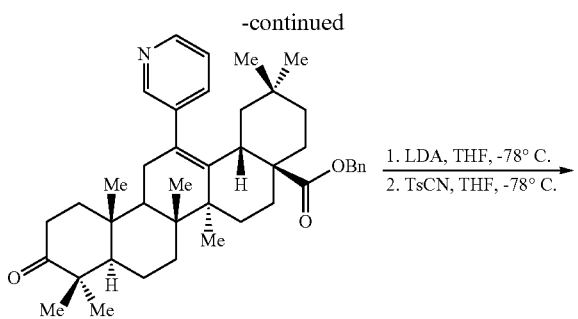

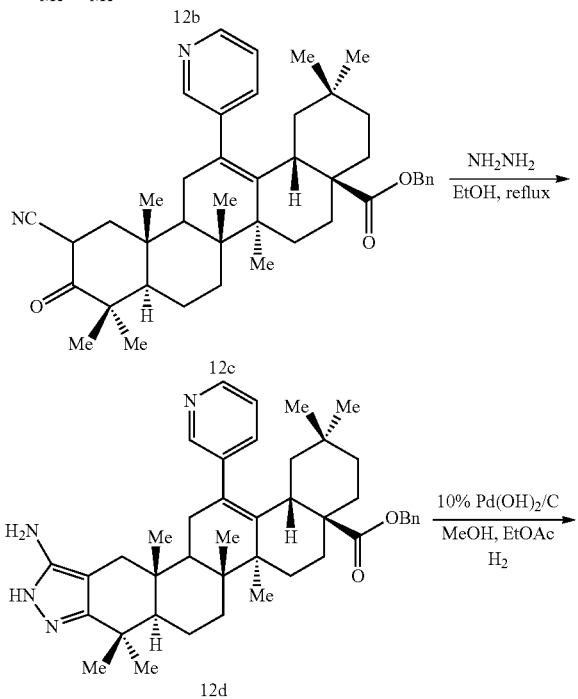

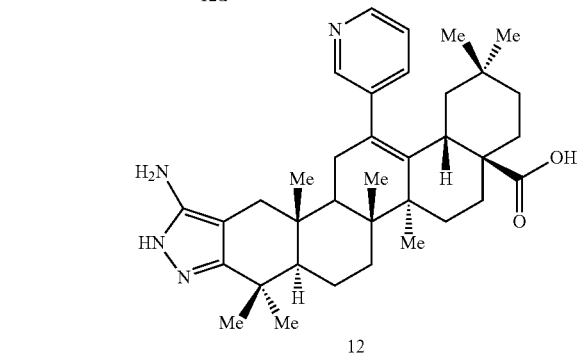

(i) Preparation of 12b: (4aS,6aS,6bR,8aR,12aR, 14bS)-Benzyl 2,2,6a,6b,9,9,12a-heptamethyl-10-oxo-14-(pyridin-3-yl)-1,2,3,4,4a,5,6,6a,6b,7,8,8a,9, 10,11,12,12a,12b,13,14b-icosahydropicene-4-a-carboxylate A mixture of 11i (400 mg, 0.64 mmol), pyridin-3-ylboronic acid (237 mg, 1.93 mmol), Pd(PPh$_3$)$_4$ (74 mg, 0.064 mmol) and cesium carbonate (629 mg, 1.93 mmol) in benzene (15 mL) and EtOH (5 mL) was heated at reflux for 12 hours. The reaction mixture was diluted with EtOAc (100 mL). The organic phase was washed with brine then dried (MgSO$_4$), filtered and concentrated to dryness. The residue was purified by column chromatography (silica, 0-50% EtOAc in hexanes) to afford the sub-title compound (200 mg, 48%).

$^1$H NMR (300 MHz, CDCl$_3$) δ 0.25 (s, 3H), 0.75 (s, 3H), 0.83 (s, 3H), 1.02 (s, 3H), 1.04 (s, 3H), 1.09 (s, 3H), 1.22 (s, 3H), 1.23-2.02 (m, 20H), 2.30-2.50 (m, 2H), 2.90 (m, 1H), 5.05 (m, 2H), 7.14 (m, 1H), 7.37 (m, 5H), 7.48 (m, 1H), 8.42 (m, 2H).

(ii) Preparation of 12c: (4aS,6aS,6bR,8aR,12aR, 14bS)-Benzyl 11-cyano-2,2,6a,6b,9,9,12a-heptamethyl-10-oxo-14-(pyridin-3-yl)-1,2,3,4,4a,5,6,6a,6b, 7,8,8a,9,10,11,12,12a,12b,13,14b-icosahydropicene-4-a-carboxylate To a solution of diisopropylamine (0.085 mL, 0.61 mmol) in THF (3 mL) was added n-butyllithium (0.26 mL, 2.5 M in hexanes, 0.64 mmol) at −78° C. The solution was stirred for 30 min. The LDA solution was added to 12b (200 mg, 0.32 mmol) in THF (5 mL). The mixture was allowed to warm to −40° C. for 5 min and cooled to −78° C. A suspension of p-toluene sulfonyl cyanide (116 mg, 0.64 mmol) in THF (2 mL) was added. The reaction mixture was allowed to warm to −40° C. over 1.5 hours. The reaction was quenched by saturated NH$_4$Cl (3 mL) and extracted with EtOAc (100 mL). The organic phase was washed with brine then dried (MgSO$_4$), filtered and concentrated to dryness. The residue was purified by column chromatography (silica, 0-50% EtOAc in hexanes) to afford the sub-title compound (80 mg, 39%).

$^1$H NMR (300 MHz, CDCl$_3$) δ 0.25 (s, 3H), 0.75 (s, 3H), 0.83 (s, 3H), 1.08 (s, 3H), 1.13 (s, 3H), 1.15 (s, 3H), 1.21 (s, 3H), 1.23-2.25 (m, 20H), 2.90 (m, 1H), 3.82 (m, 1H), 5.04 (m, 2H), 7.14 (m, 1H), 7.37 (m, 5H), 7.48 (m, 1H), 8.43 (m, 2H).

(iii) Preparation of 12d: (4aS,6aS,6bR,8aR,13aR, 15bS)-Benzyl 12-amino-2,2,6a,6b,9,9,13a-heptamethyl-15-(pyridin-3-yl)-2,3,4,4a,5,6,6a,6b,7,8,8a,9, 11,13,13a,13b,14,15b-octadecahydro-1H-chryseno [1,2-f]indazole-4-a-carboxylate A mixture of 12c (80 mg, 0.12 mmol) and hydrazine (0.020 mL) in EtOH (2 mL) was heated at reflux overnight. The reaction mixture was concentrated to dryness under reduced pressure. The residue was purified by column chromatography (silica, 0-50% CMA in CH$_2$Cl$_2$) to afford the sub-title compound (74 mg, 93%). ESI MS (Positive Mode) m/z 661 [C$_{43}$H$_{56}$N$_4$O$_2$+H]$^+$.

(iv) Preparation of 12: (4aS,6aS,6bR,8aR,13aR, 15bS)-12-Amino-2,2,6a,6b,9,9,13a-heptamethyl-15-(pyridin-3-yl)-2,3,4,4a,5,6,6a,6b,7,8,8a,9,11,13,13a, 13b,14,15b-octadecahydro-1H-chryseno[1,2-f] indazole-4-a-carboxylic acid A mixture of 12d (74 mg, 0.11 mmol) and 10% Pd(OH)$_2$/C (60 mg) in MeOH (10 mL) and EtOAc (2 mL) was stirred under a hydrogen balloon for 5 hours. The reaction mixture was filtered through a pad of diatomaceous earth and washed with CMA (25 mL). The filtrate was concentrated to dryness under reduced pressure. The residue was purified by column chromatography (silica, 0-70% CMA in CH$_2$Cl$_2$) to afford the title compound (25 mg, 40%) as a brown solid.

R$_f$ 0.30 (80:18:2 Methylene Chloride/Methanol/concentrated Ammonium Hydroxide).

$^1$H NMR (300 MHz, CD$_3$OD) δ 0.55 (s, 3H), 0.81 (s, 3H), 0.87 (s, 3H), 0.97 (s, 3H), 1.03 (s, 3H), 1.08 (s, 6H), 1.25-2.10

(m, 19H), 2.10 (d, J=14.8 Hz, 1H), 2.75 (m, 1H), 7.18 (t, J=7.8 Hz, 1H), 7.56 (d, J=7.2 Hz, 1H), 8.16 (d, J=4.8 Hz, 1H), 8.26 (s, 1H).

mp >300° C. APCI MS (Positive Mode) m/z 571 $[C_{36}H_{50}N_4O_2+H]^+$.

EXAMPLE 13

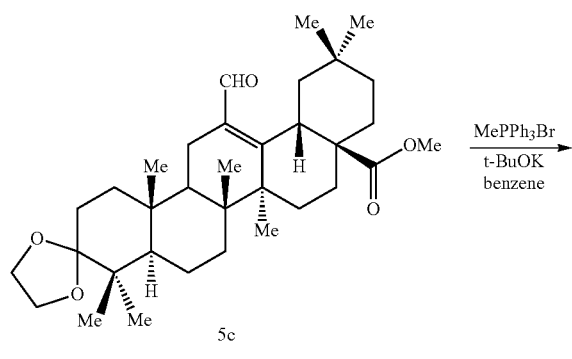

5c

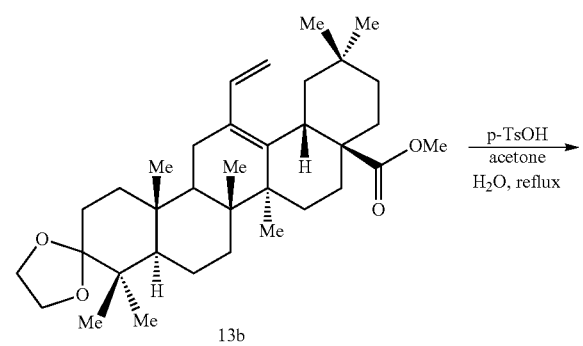

13b

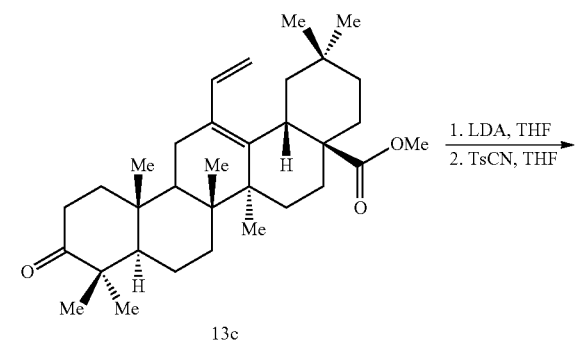

13c

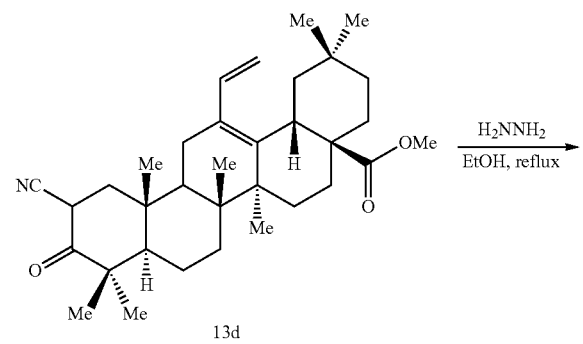

13d

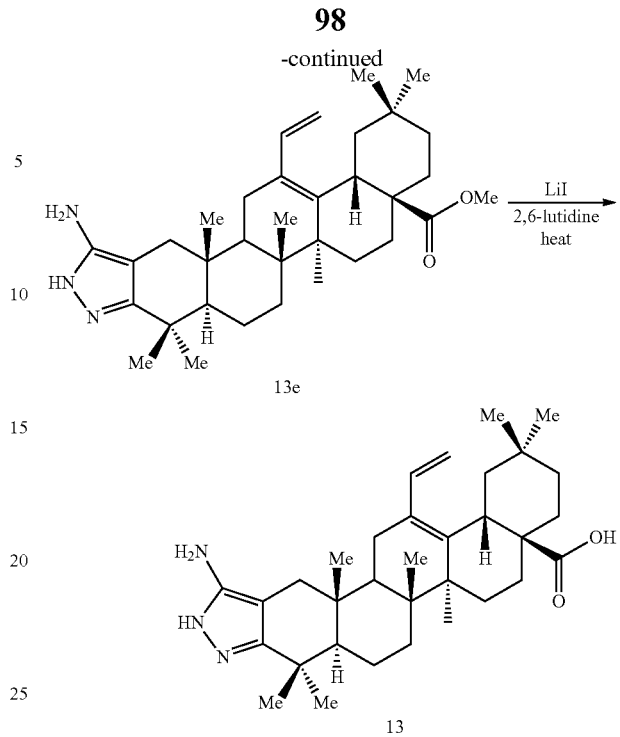

(i) Preparation of 13b: (4a'R,6a'R,6b'S,8a'S,12a'S, 14b'R)-Methyl 4',4',6a',6b',11',11',14b'-heptamethyl-13'-vinyl-2',4',4a',5',6',6a',6b',7',8',8a',9',10',11',12', 12a',14',14a',14b'-octadecahydro-1'H-spiro[[1,3] dioxolane-2,3'-picene]-8a'-carboxylate To a suspension of methyltriphenylphosphonium iodide (808 mg, 2.0 mmol) in benzene (30 mL) was added potassium tert-butoxide (224 mg, 2.0 mmol). The mixture was stirred at room temperature for 1 hour. A solution of 5c (600 mg, 1.11 mmol) in THF (5 mL) was added. The mixture was stirred at room temperature for 1.5 hours. The reaction mixture was diluted with EtOAc (100 mL). The organic phase was washed with brine then dried (MgSO$_4$), filtered and concentrated to dryness. The residue was purified by column chromatography (silica, 0-15% EtOAc in hexanes) to afford the sub-title compound (490 mg, 82%).

$^1$H NMR (300 MHz, CDCl$_3$) δ 0.63 (s, 3H), 0.85 (s, 3H), 0.89 (s, 3H), 0.91 (s, 3H), 0.94 (s, 3H), 0.97 (s, 3H), 0.99 (s, 3H), 1.11 (s, 3H), 1.15-2.05 (m, 22H), 3.60 (s, 3H), 3.95 (m, 4H), 4.95 (m, 1H), 4.95 (d, J=9.3 Hz, 2H), 5.09 (d, J=16.2 Hz, 1H).

(ii) Preparation of 13c: (4aS,6aS,6bR,8aR,12aR, 14bS)-Methyl 2,2,6a,6b,9,9,12a-heptamethyl-10-oxo-14-vinyl-1,2,3,4,4a,5,6,6a,6b,7,8,8a,9,10,11,12, 12a,12b,13,14b-icosahydropicene-4-a-carboxylate A mixture of 13b (600 mg, 1.11 mmol) and p-toluenesulfonic acid monohydrate (211 mg, 1.11 mmol) in acetone (20 mL) and H$_2$O (2 mL) was heated at reflux for 4 hours. The reaction mixture was concentrated to remove acetone under reduced pressure and extracted with EtOAc (100 mL). The organic phase was washed with brine then dried (MgSO$_4$), filtered and concentrated to dryness. The residue was purified by column chromatography (silica, 0-15% EtOAc in hexanes) to afford the sub-title compound (500 mg, 91%).

¹H NMR (300 MHz, CDCl₃) δ 0.72 (s, 1.8H), 0.81 (s, 1.2H), 0.89 (s, 3H), 0.91 (s, 3H), 1.0-2.50 (m, 38H), 3.65 (s, 3H), 5.40-5.70 (m, 1H), 6.05 (d, J=12.0 Hz, 0.4H), 6.53 (d, J=15.0 Hz, 0.6H).

(iii) Preparation of 13d: (4aS,6aS,6bR,8aR,12aR,14bS)-Methyl 11-cyano-2,2,6a,6b,9,9,12a-heptamethyl-10-oxo-14-vinyl-1,2,3,4,4a,5,6,6a,6b,7,8,8a,9,10,11,12,12a,12b,13,14b-icosahydropicene-4-a-carboxylate To a solution of diisopropylamine (0.27 mL, 1.92 mmol) in THF (6 mL) was added n-butyllithium (0.81 mL, 2.5 M in hexanes, 2.02 mmol) at −78° C. The solution was stirred for 30 min. The LDA solution was added to 13c (500 mg, 1.01 mmol) in THF (10 mL). The mixture was allowed to warm to −40° C. for 5 min and cooled to −78° C. A suspension of p-toluene sulfonyl cyanide (329 mg, 1.82 mmol) in THF (3 mL) was added. The reaction mixture was allowed to warm to −40° C. over 1.5 hours. The reaction was quenched by saturated NH₄Cl (3 mL) and extracted with EtOAc (100 mL). The organic phase was washed with brine then dried (MgSO₄), filtered and concentrated to dryness. The residue was purified by column chromatography (silica, 0-15% EtOAc in hexanes) to afford the sub-title compound (200 mg, 38%).

(iv) Preparation of 13e: (4aS,6aS,6bR,8aR,13aR,15bS)-Methyl 12-amino-2,2,6a,6b,9,9,13a-heptamethyl-15-vinyl-2,3,4,4a,5,6,6a,6b,7,8,8a,9,11,13,13a,13b,14,15b-octadecahydro-1H-chryseno[1,2-f]indazole-4-a-carboxylate A mixture of 13d (200 mg, 0.38 mmol) and hydrazine (0.015 mL, 0.46 mmol) in EtOH (3 mL) was heated at reflux overnight. The reaction mixture was concentrated to dryness under reduced pressure. The residue was purified by column chromatography (silica, 0-10% MeOH in CH₂Cl₂) to afford the sub-title compound (180 mg, 89%). ESI MS (Positive Mode) m/z 534 [C₃₄H₅₁N₃O₂+H]⁺.

(v) Preparation of 13: (4aS,6aS,6bR,8aR,13aR,15bS)-12-Amino-2,2,6a,6b,9,9,13a-heptamethyl-15-vinyl-2,3,4,4a,5,6,6a,6b,7,8,8a,9,11,13,13a,13b,14,15b-octadecahydro-1H-chryseno[1,2-f]indazole-4-a-carboxylic acid A mixture of 13e (80 mg, 0.15 mmol) and lithium iodide (300 mg, 2.25 mmol) in 2,6-lutidine (3 mL) was heated to 144° C. for 5 hours. The reaction mixture was cooled to room temperature and neutralized with HCl (2 M) and extracted with CH₂Cl₂/i-PrOH (3:1). The organic phase was dried (MgSO₄), filtered and concentrated to dryness under reduced pressure. The residue was purified by column chromatography (silica, 0-50% CMA in CH₂Cl₂) followed by preparative HPLC to provide the title compound (6 mg, 8%) as an off-white solid.

R$_f$ 0.35 (80:18:2 Methylene Chloride/Methanol/concentrated Ammonium Hydroxide).

¹H NMR (300 MHz, CD₃OD) δ 0.81 (s, 3H), 0.91 (s, 3H), 0.94 (s, 3H), 1.01 (s, 3H), 1.17 (s, 3H), 1.22 (s, 3H), 1.25 (m, 3H), 1.30-2.30 (m, 19H), 2.53 (d, J=15.0 Hz, 1H), 3.53 (m, 1H), 4.98 (d, J=12.3 Hz, 1H), 5.18 (d, J=19.2 Hz, 1H), 6.95 (dd, J=12.3, 19.2 Hz, 1H). mp >300° C. ESI MS (Positive Mode) m/z 520 [C₃₃H₄₉N₃O₂+H]⁺.

EXAMPLE 14

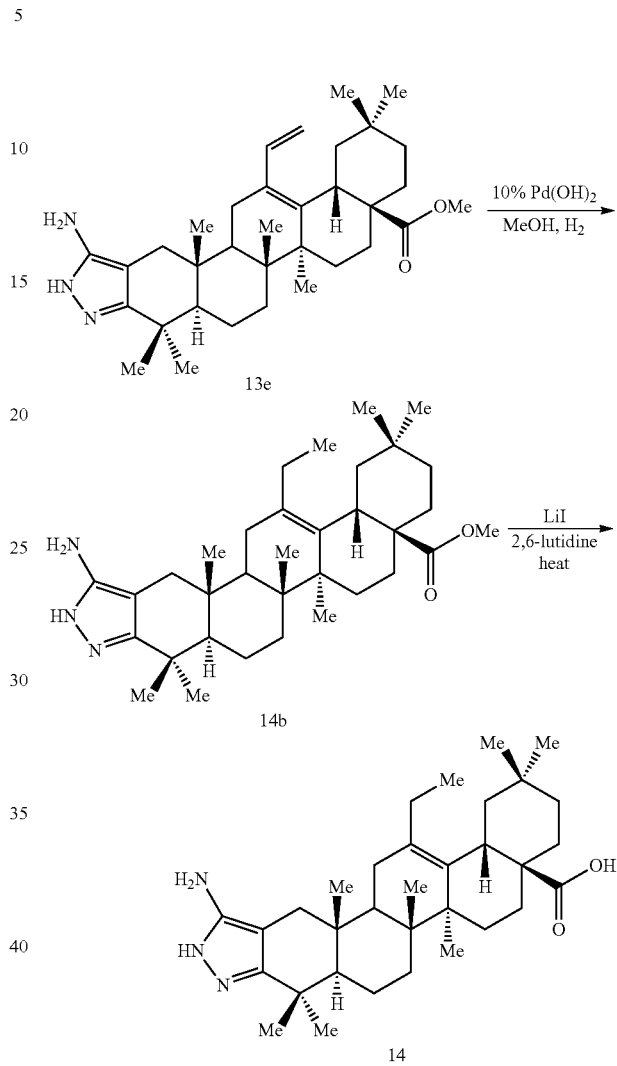

(i) Preparation of 14b: (4aS,6aS,6bR,8aR,13aR,15bS)-Methyl 12-amino-15-ethyl-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylate A mixture of 13e (80 mg, 0.15 mmol) and 10% Pd(OH)₂/C (30 mg) in MeOH (10 mL) was stirred under a hydrogen balloon for 12 hours. The reaction mixture was filtered through a pad of diatomaceous earth and washed with CMA (20 mL). The filtrate was concentrated to dryness and the residue purified by column chromatography (silica, 0-10% MeOH in CH₂Cl₂) to afford the sub-title compound (70 mg, 87%). ESI MS (Positive Mode) m/z 536 [C₃₄H₅₃N₃O₂+H]⁺.

(ii) Preparation of 14: (4aS,6aS,6bR,8aR,13aR,15bS)-12-Amino-15-ethyl-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylic acid A mixture of 14b (70 mg, 0.13 mmol) and lithium iodide (263 mg, 1.96 mmol) in 2,6-lutidine (3 mL) was heated to 144° C. for 5 hours. The reaction mixture was cooled to room temperature and neutralized with HCl (2 M) and extracted with CH₂Cl₂/i-PrOH (3:1). The organic phase was dried (MgSO₄), filtered and concentrated to dryness under reduced pressure. The residue was purified by column chromatography (silica, 0-50% CMA in CH₂Cl₂) followed by preparative HPLC to provide the title compound (13 mg, 19%) as an off-white solid.

$R_f$ 0.80 (80:18:2 Methylene Chloride/Methanol/concentrated Ammonium Hydroxide).

$^1$H NMR (300 MHz, CD₃OD) δ 0.83 (s, 3H), 0.92 (s, 6H), 0.99 (s, 3H), 1.11 (s, 3H), 1.21 (s, 3H), 1.29 (s, 3H), 1.30-2.30 (m, 25H), 2.44 (d, J=15.0 Hz, 1H). mp >300° C. ESI MS (Positive Mode) m/z 522 [C₃₃H₅₁N₃O₂+H]⁺.

EXAMPLE 15

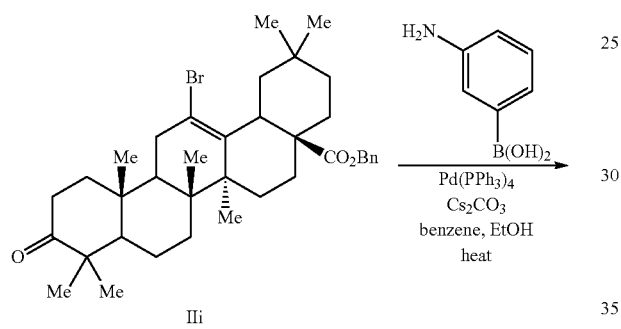

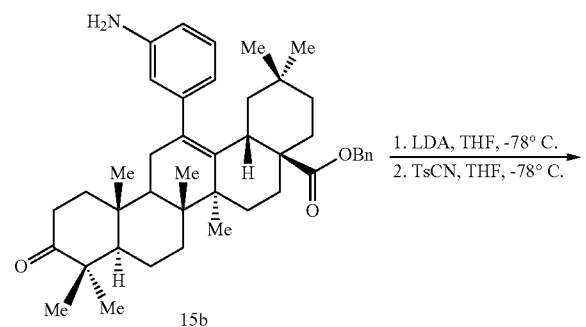

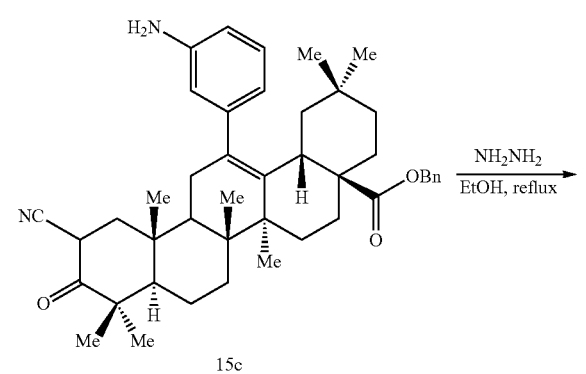

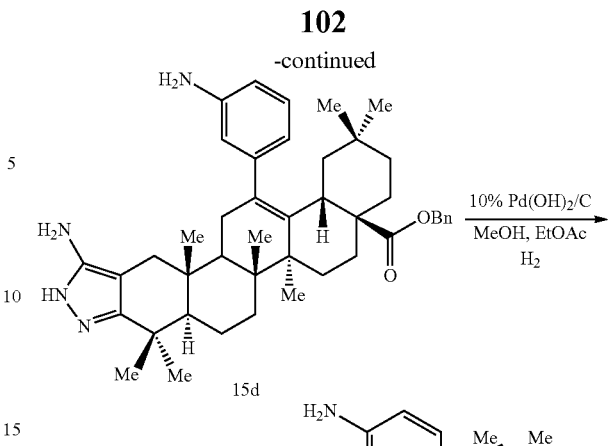

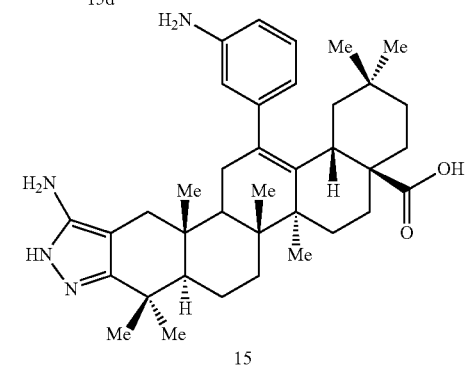

(i) Preparation of 15b: (4aS,6aS,6bR,8aR,12aR, 14bS)-Benzyl 14-(3-aminophenyl)-2,2,6a,6b,9,9, 12a-heptamethyl-10-oxo-1,2,3,4,4a,5,6,6a,6b,7,8,8a, 9,10,11,12,12a,12b,13,14b-icosahydropicene-4-a-carboxylate A mixture of IIi (600 mg, 0.96 mmol), 3-aminophenylboronic acid (362 mg, 2.66 mmol), Pd(PPh₃)₄ (104 mg, 0.09 mmol) and K₂CO₃ (353 mg, 2.56 mmol) in benzene (16 mL) and EtOH (5 mL) was heated at reflux for 12 hours. The reaction mixture was diluted with EtOAc (100 mL). The organic phase was washed with brine then dried (MgSO₄), filtered and concentrated to dryness. The residue was purified by column chromatography (silica, 0-40% EtOAc in hexanes) to afford the sub-title compound (400 mg, 65%).

$^1$H NMR (300 MHz, CDCl₃) δ 0.30 (s, 3H), 0.76 (s, 3H), 0.86 (s, 3H), 1.04 (s, 3H), 1.06 (s, 3H), 1.08 (s, 3H), 1.19 (s, 3H), 1.20-2.50 (m, 24H), 3.12 (m, 1H), 5.02 (m, 2H), 6.48 (m, 3H), 7.01 (m, 1H), 7.33 (m, 5H).

(ii) Preparation of 15c: (4aS,6aS,6bR,8aR,12aR, 14bS)-Benzyl 14-(3-aminophenyl)-11-cyano-2,2,6a, 6b,9,9,12a-heptamethyl-10-oxo-1,2,3,4,4a,5,6,6a,6b, 7,8,8a,9,10,11,12,12a,12b,13,14b-icosahydropicene-4-a-carboxylate To a solution of diisopropylamine (0.22 mL, 1.57 mmol) in THF (5 mL) was added n-butyllithium (0.64 mL, 2.5 M in hexanes, 1.61 mmol) at −78° C. The solution was stirred for 30 min. The LDA solution was added to 15b (400 mg, 0.62 mmol) in THF (5 mL). The mixture was allowed to warm to −40° C. for 5 min and cooled to −78° C. A suspension of p-toluene sulfonyl cyanide (285 mg, 1.57 mmol) in THF (3 mL) was added. The reaction mixture was allowed to warm to −40° C. over 1.5 hours. The reaction was quenched by saturated NH₄Cl (3 mL) and extracted with EtOAc (100 mL). The organic phase was washed with brine then dried (MgSO₄), filtered and concentrated to dryness. The residue was purified by column chromatography (silica, 0-20% EtOAc in hexanes) to afford the sub-title compound (100 mg, 25%).

$^1$H NMR (300 MHz, CDCl$_3$) δ 0.32 (s, 3H), 0.76 (s, 3H), 0.86 (s, 3H), 0.87-2.30 (m, 32H), 3.12 (m, 1H), 3.30 (s, 2H), 3.82 (m, 1H), 5.02 (m, 2H), 6.48 (m, 3H), 7.01 (m, 1H), 7.33 (m, 5H).

(iii) Preparation of 15d: (4aS,6aS,6bR,8aR,13aR, 15bS)-Benzyl 12-amino-15-(3-aminophenyl)-2,2,6a, 6b,9,9,13a-heptamethyl-2,3,4,4a,5,6,6a,6b,7,8,8a,9, 11,13,13a,13b,14,15b-octadecahydro-1H-chryseno [1,2-f]indazole-4-a-carboxylate A mixture of 15c (100 mg, 0.15 mmol) and hydrazine (0.020 mL) in EtOH (2 mL) was heated at reflux overnight. The reaction mixture was concentrated to dryness under reduced pressure. The residue was purified by column chromatography (silica, 0-30% CMA in CH$_2$Cl$_2$) to afford the sub-title compound (70 mg, 69%). APCI MS (Positive Mode) m/z 675 [C$_{44}$H$_{58}$N$_4$O$_2$+H]$^+$.

(iv) Preparation of 15: (4aS,6aS,6bR,8aR,13aR, 15bS)-12-Amino-15-(3-aminophenyl)-2,2,6a,6b,9,9, 13a-heptamethyl-2,3,4,4a,5,6,6a,6b,7,8,8a,9,11,13, 13a,13b,14,15b-octadecahydro-1H-chryseno[1,2-f] indazole-4-a-carboxylic acid A mixture of 15d (70 mg, 0.10 mmol) and 10% Pd(OH)$_2$/C (35 mg) in MeOH (12 mL) was stirred under a hydrogen balloon for 12 hours. The reaction mixture was filtered through a pad of diatomaceous earth and washed with CMA (25 mL). The filtrate was concentrated to dryness under reduced pressure. The residue was purified by column chromatography (silica, 0-80% CMA in CH$_2$Cl$_2$) followed by preparative HPLC to provide the title compound (32 mg, 55%) as a brown solid.

R$_f$ 0.70 (80:18:2 Methylene Chloride/Methanol/concentrated Ammonium Hydroxide).

$^1$H NMR (300 MHz, DMSO-d$_6$) δ 0.30 (s, 3H), 0.78 (s, 3H), 0.85 (s, 3H), 0.96 (s, 3H), 1.18 (s, 3H), 1.31 (s, 6H), 1.32-2.28 (m, 19H), 2.26 (d, J=14.7 Hz, 1H), 3.0 (m, 1H), 7.16 (m, 4H). mp >300° C. APCI MS (Positive Mode) m/z 585 [C$_{37}$H$_{52}$N$_4$O$_2$+H]$^+$.

EXAMPLE 16

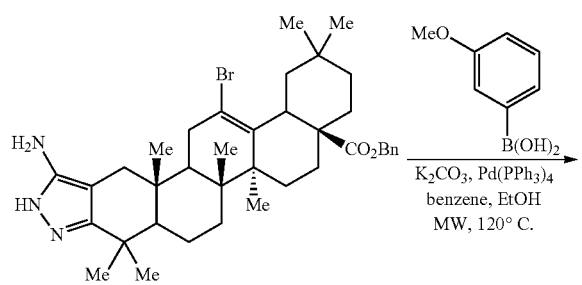

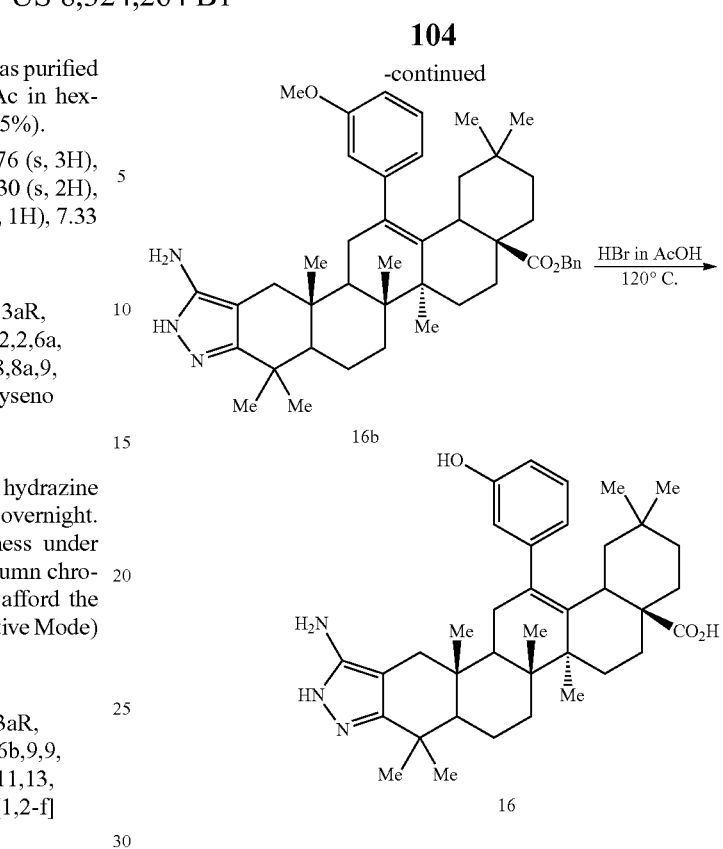

(i) Preparation of 16b: (4aS,6aS,6bR,13aR)-Benzyl 12-amino-15-(3-methoxyphenyl)-2,2,6a,6b,9,9,13a-heptamethyl-2,3,4,4a,5,6,6a,6b,7,8,8a,9,11,13,13a, 13b,14,15b-octadecahydro-1H-chryseno[1,2-f]indazole-4-a-carboxylate To a mixture of II (200 mg, 0.30 mmol) and 3-methoxyphenylboronic acid (92 mg, 0.60 mmol) in benzene (4 mL) and EtOH (1 mL) was added K$_2$CO$_3$ (125 mg, 0.90 mmol). The mixture was sparged with nitrogen and then Pd(PPh$_3$)$_4$ (70 mg, 0.06 mmol) was added. The reaction mixture was heated at 120° C. for 1 hour using microwave irradiation and then concentrated. The residue was dissolved in EtOAc (20 mL) and the solution was washed with brine then dried (Na$_2$SO$_4$), filtered and concentrated under reduced pressure. The residue was purified by column chromatography (silica, 0-30% CMA in CH$_2$Cl$_2$) to afford the sub-title compound (179 mg, 86%).

$^1$H NMR (300 MHz, CDCl$_3$) δ 0.30-2.25 (m, 39H), 3.11 (m, 1H), 3.40 (s, 2H), 3.82 (s, 3H), 5.08 (d, J=12.6 Hz, 1H), 5.20 (d, J=12.3 Hz, 1H), 6.75 (m, 1H), 6.78 (s, 1H), 7.15 (t, J=7.8 Hz, 1H), 7.31-7.36 (m, 5H). APCI MS m/z 690 [C$_{45}$H$_{59}$N$_3$O$_3$+H]$^+$.

(ii) Preparation of 16: (4aS,6aS,6bR,13aR)-12-Amino-15-(3-hydroxyphenyl)-2,2,6a,6b,9,9,13a-heptamethyl-2,3,4,4a,5,6,6a,6b,7,8,8a,9,11,13,13a, 13b,14,15b-octadecahydro-1H-chryseno[1,2-f] indazole-4-a-carboxylic acid A mixture of 16b (179 mg, 0.25 mmol) and HBr (2 mL, 33% in AcOH) was heated at 120° C. for 1 hour. The reaction mixture was concentrated under reduced pressure and the residue was purified by column chromatography (silica, 0-80% CMA in CH$_2$Cl$_2$) to afford the title compound (20 mg, 13%).

$R_f$ 0.30 (40:9:1 Methylene Chloride/Methanol/concentrated Ammonium Hydroxide).

$^1$H NMR (300 MHz, CD$_3$OD) δ 0.34-2.37 (m, 41H), 3.15 (d, J=10.8 Hz, 1H), 6.61-6.70 (m, 3H), 7.11 (t, J=7.8 Hz, 1H). APCI MS m/z 586 [C$_{37}$H$_{51}$N$_3$O$_3$+H]$^+$. m.p. 260-280° C. dec. HPLC (Method A) 92.4% (214 nm) $t_R$=15.6 min.

EXAMPLE 17

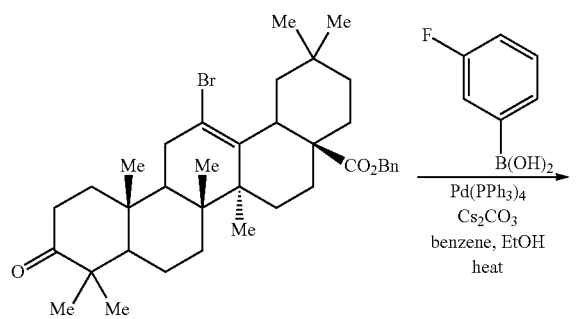

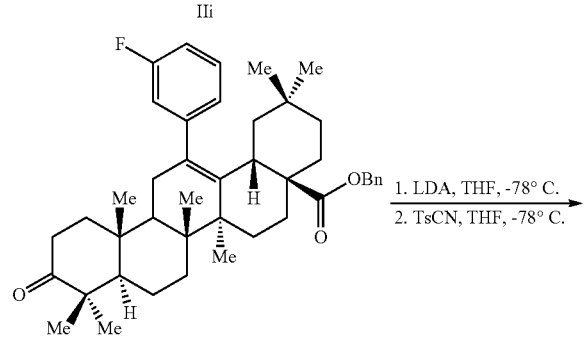

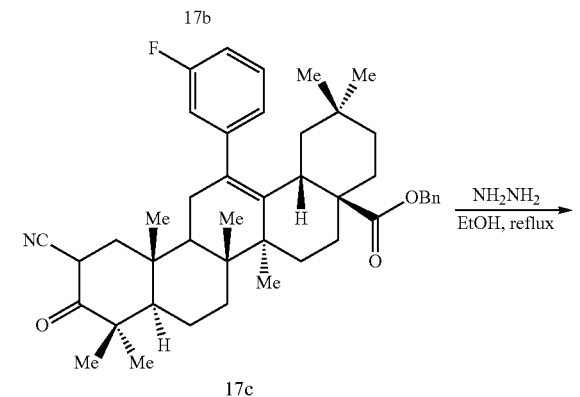

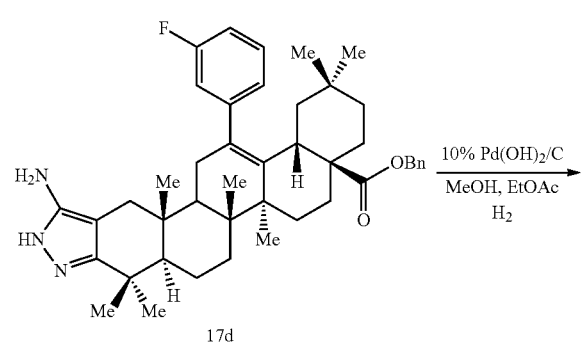

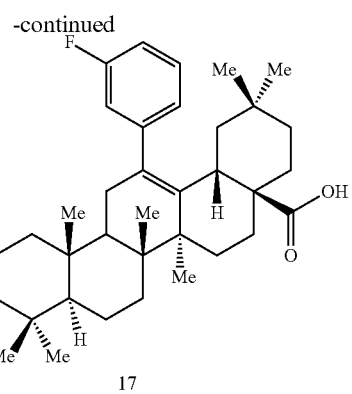

(i) Preparation of 17b: (4aS,6aS,6bR,8aR,12aR, 14bS)-Benzyl 14-(3-fluorophenyl)-2,2,6a,6b,9,9, 12a-heptamethyl-10-oxo-1,2,3,4,4a,5,6,6a,6b,7,8,8a, 9,10,11,12,12a,12b,13,14b-icosahydropicene-4-a-carboxylate A mixture of IIi (300 mg, 0.48 mmol), 3-fluorophenylboronic acid (100 mg, 0.72 mmol), Pd(PPh$_3$)$_4$ (55 mg, 0.048 mmol) and cesium carbonate (469 mg, 1.44 mmol) in benzene (15 mL) and EtOH (5 mL) was heated at reflux for 12 hours. The reaction mixture was diluted with EtOAc (100 mL). The organic phase was washed with brine then dried (MgSO$_4$), filtered and concentrated to dryness. The residue was purified by column chromatography (silica, 0-10% EtOAc in hexanes) to afford the sub-title compound (250 mg, 82%).

$^1$H NMR (300 MHz, CDCl$_3$) δ 0.25 (s, 3H), 0.78 (s, 3H), 0.83 (s, 3H), 1.05 (s, 3H), 1.07 (s, 3H), 1.12 (s, 3H), 1.21 (s, 3H), 1.23-2.55 (m, 22H), 3.01 (m, 1H), 5.04 (m, 2H), 6.87 (m, 3H), 7.15 (m, 1H), 7.34 (m, 5H).

(ii) Preparation of 17c: (4aS,6aS,6bR,8aR,12aR, 14bS)-Benzyl 11-cyano-14-(3-fluorophenyl)-2,2,6a, 6b,9,9,12a-heptamethyl-10-oxo-1,2,3,4,4a,5,6,6a,6b, 7,8,8a,9,10,11,12,12a,12b,13,14b-icosahydropicene-4-a-carboxylate To a solution of diisopropylamine (0.17 mL, 1.22 mmol) in THF (6 mL) was added n-butyllithium (0.51 mL, 2.5 M in hexanes, 1.28 mmol) at −78° C. The solution was stirred for 30 min. The LDA solution was added to 17b (408 mg, 0.64 mmol) in THF (4 mL). The mixture was allowed to warm to −40° C. for 5 min and cooled to −78° C. A suspension of p-toluene sulfonyl cyanide (232 mg, 1.28 mmol) in THF (3 mL) was added at −78° C. The reaction mixture was allowed to warm to −40° C. over 1.5 hours. The reaction was quenched by saturated NH$_4$Cl (3 mL) and extracted with EtOAc (100 mL). The organic phase was washed with brine then dried (MgSO$_4$), filtered and concentrated to dryness. The residue was purified by column chromatography (silica, 0-20% EtOAc in hexanes) to afford the sub-title compound (280 mg, 66%).

$^1$H NMR (300 MHz, CDCl$_3$) δ 0.25 (s, 3H), 0.78 (s, 3H), 0.83 (s, 3H), 1.05 (s, 3H), 1.07 (s, 3H), 1.12 (s, 3H), 1.22 (s, 3H), 1.23-2.30 (m, 20H), 3.01 (m, 1H), 3.83 (m, 1H), 5.04 (m, 2H), 6.87 (m, 3H), 7.15 (m, 1H), 7.34 (m, 5H).

(iii) Preparation of 17d: (4aS,6aS,6bR,8aR,13aR, 15bS)-Benzyl 12-amino-15-(3-fluorophenyl)-2,2,6a, 6b,9,9,13a-heptamethyl-2,3,4,4a,5,6,6a,6b,7,8,8a,9, 11,13,13a,13b,14,15b-octadecahydro-1H-chryseno [1,2-f]indazole-4-a-carboxylate A mixture of 17c (280 mg, 0.42 mmol) and hydrazine (0.053 mL) in EtOH (5 mL) was heated at reflux overnight. The reaction mixture was concentrated to dryness under reduced pressure. The residue was purified by column chromatography (silica, 0-10% MeOH in $CH_2Cl_2$) to afford the sub-title compound (230 mg, 81%). ESI MS (Positive Mode) m/z 678 $[C_{44}H_{56}FN_3O_2+H]^+$.

(iv) Preparation of 17: (4aS,6aS,6bR,8aR,13aR, 15bS)-12-Amino-15-(3-fluorophenyl)-2,2,6a,6b,9,9, 13a-heptamethyl-2,3,4,4a,5,6,6a,6b,7,8,8a,9,11,13, 13a,13b,14,15b-octadecahydro-1H-chryseno[1,2-f] indazole-4-a-carboxylic acid A mixture of 17d (230 mg, 0.34 mmol) and 10% Pd(OH)$_2$/C (100 mg) in MeOH (6 mL) and EtOAc (6 mL) was stirred under a hydrogen balloon for 12 hours. The reaction mixture was filtered through a pad of diatomaceous earth and washed with CMA (25 mL). The filtrate was concentrated to dryness under reduced pressure. The residue was purified by column chromatography (silica, 0-50% CMA in $CH_2Cl_2$) to afford the title compound (110 mg, 55%) as a white solid.

$R_f$ 0.75 (4:1 Methylene Chloride/Methanol).

$^1$H NMR (300 MHz, $CD_3OD$) δ 0.30 (s, 3H), 0.75 (s, 3H), 0.87 (s, 3H), 0.99 (s, 3H), 1.16 (s, 3H), 1.19 (s, 3H), 1.25 (s, 3H), 1.26-2.25 (m, 19H), 2.30 (d, J=14.7 Hz, 1H), 3.15 (m, 1H), 6.91 (t, J=8.4 Hz, 1H), 7.01 (m, 2H), 7.28 (q, J=8.1 Hz, 1H). mp >300° C.

APCI MS (Positive Mode) m/z 588 $[C_{37}H_{50}FN_3O_2+H]^+$.

EXAMPLE 18

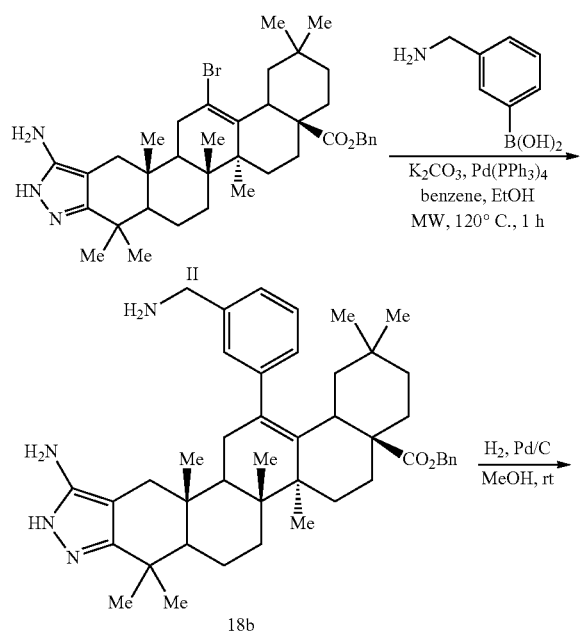

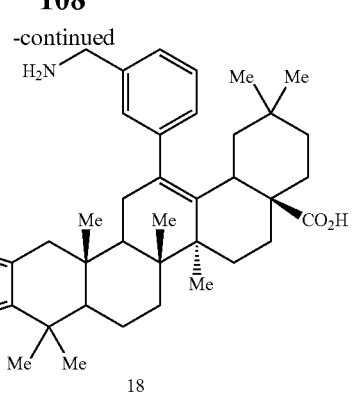

(i) Preparation of 18b: (4aS,6aS,6bR,13aR)-Benzyl 12-amino-15-(3-(aminomethyl)phenyl)-2,2,6a,6b,9, 9,13a-heptamethyl-2,3,4,4a,5,6,6a,6b,7,8,8a,9,11,13, 13a,13b,14,15b-octadecahydro-1H-chryseno[1,2-f] indazole-4-a-carboxylate To a mixture of II (200 mg, 0.30 mmol) and 3-(aminomethyl)phenylboronic acid (169 mg, 0.90 mmol) in benzene (4 mL) and EtOH (1 mL) was added $K_2CO_3$ (166 mg, 1.20 mmol). The mixture was sparged with nitrogen and then Pd(PPh$_3$)$_4$ (70 mg, 0.06 mmol) was added. The reaction mixture was heated at 120° C. for 1 hour using microwave irradiation and then concentrated. The residue was dissolved in EtOAc (20 mL) and the organic layer was washed with brine then dried (Na$_2$SO$_4$), filtered and concentrated under reduced pressure. The residue was purified by column chromatography (silica, 0-40% CMA in $CH_2Cl_2$) to afford the sub-title compound (170 mg, 82%).

$^1$H NMR (300 MHz, CDCl$_3$) δ 0.23-2.25 (m, 45H), 3.05 (m, 1H), 3.40 (s, 1H), 3.82 (s, 2H), 5.06 (d, J=12.6 Hz, 1H), 5.23 (d, J=12.3 Hz, 1H), 7.06-7.20 (m, 4H), 7.33-7.38 (m, 5H). APCI MS m/z 689 $[C_{45}H_{60}N_4O_2+H]^+$.

(ii) Preparation of 18: (4aS,6aS,6bR,13aR)-12-Amino-15-(3-(aminomethyl)phenyl)-2,2,6a,6b,9,9, 13a-heptamethyl-2,3,4,4a,5,6,6a,6b,7,8,8a,9,11,13, 13a,13b,14,15b-octadecahydro-1H-chryseno[1,2-f] indazole-4-a-carboxylic acid A solution of 18b (160 mg, 0.23 mmol) and MeOH (20 mL) was flushed with nitrogen and then 10% Pd/C (100 mg) was added. The mixture was flushed with nitrogen followed by hydrogen. The mixture was stirred under hydrogen at atmospheric pressure overnight. The catalyst was removed by filtration and the filtrate was concentrated under reduced pressure. The residue was purified by column chromatography (silica, 0-70% CMA in $CH_2Cl_2$) followed by preparative HPLC to afford the title compound (48 mg, 35%) as a solid.

$R_f$ 0.13 (40:9:1 Methylene Chloride/Methanol/concentrated Ammonium Hydroxide).

$^1$H NMR (300 MHz, $CD_3OD$) δ 0.27-2.34 (m, 41H), 2.99 (d, J=11.1 Hz, 1H), 4.13 (s, 2H), 7.30-7.44 (m, 4H). APCI MS m/z 599 $[C_{38}H_{54}N_4O_2+H]^+$. m.p. 270-290° C. dec.

HPLC (Method A)>99% (214 nm) $t_R$=12.4 min.

EXAMPLE 19

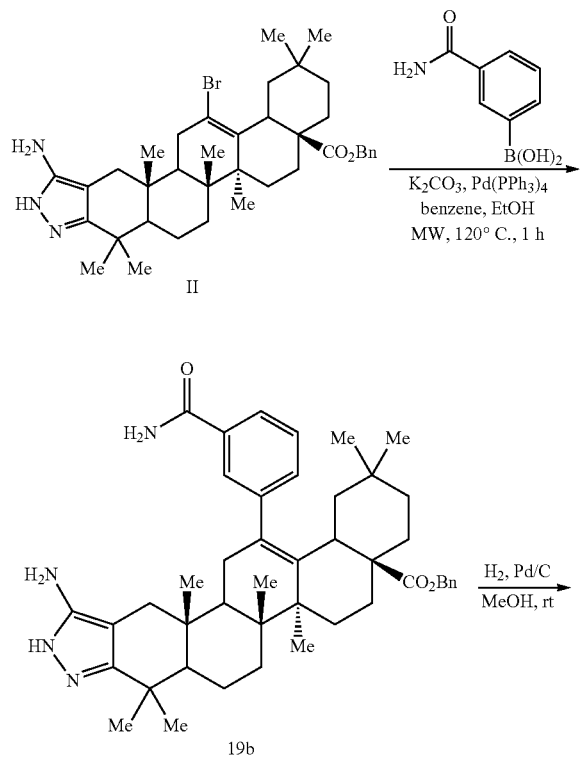

(i) Preparation of 19b: (4aS,6aS,6bR,13aR)-Benzyl 12-amino-15-(3-carbamoylphenyl)-2,2,6a,6b,9,9, 13a-heptamethyl-2,3,4,4a,5,6,6a,6b,7,8,8a,9,11,13, 13a,13b,14,15b-octadecahydro-1H-chryseno[1,2-f] indazole-4-a-carboxylate To a mixture of II (200 mg, 0.30 mmol) and 3-carbamoylphenylboronic acid (99 mg, 0.64 mmol) in benzene (4 mL) and EtOH (1 mL) was added $K_2CO_3$ (125 mg, 0.90 mmol). The mixture was sparged with nitrogen and then $Pd(PPh_3)_4$ (69 mg, 0.06 mmol) was added. The reaction mixture was heated at 120° C. for 1 hour using microwave irradiation and then concentrated. The residue was dissolved in EtOAc (20 mL) and the solution was washed with brine then dried ($Na_2SO_4$), filtered and concentrated under reduced pressure. The residue was purified by column chromatography (silica, 0-40% CMA in $CH_2Cl_2$) to afford the sub-title compound (170 mg, 80%). APCI MS m/z 703 $[C_{45}H_{58}N_4O_3+H]^+$.

(ii) Preparation of 19: (4aS,6aS,6bR,13aR)-12-Amino-15-(3-carbamoylphenyl)-2,2,6a,6b,9,9,13a-heptamethyl-2,3,4,4a,5,6,6a,6b,7,8,8a,9,11,13,13a, 13b,14,15b-octadecahydro-1H-chryseno[1,2-f] indazole-4-a-carboxylic acid A solution of 19b (170 mg, 0.24 mmol) and MeOH (20 mL) was flushed with nitrogen and then 10% Pd/C (100 mg) was added. The mixture was flushed with nitrogen followed by hydrogen. The mixture was stirred under hydrogen at atmospheric pressure overnight. The catalyst was removed by filtration through diatomaceous earth and the filtrate was concentrated under reduced pressure. The residue was purified by column chromatography (silica, 0-60% CMA in $CH_2Cl_2$) to afford the title compound (60 mg, 40%).

$R_f$ 0.22 (40:9:1 Methylene Chloride/Methanol/concentrated Ammonium Hydroxide).

$^1$H NMR (300 MHz, $CD_3OD$) δ 0.24-2.38 (m, 41H), 3.02 (d, J=11.4 Hz, 1H), 7.42-7.45 (m, 2H), 7.73-7.76 (m, 2H). APCI MS m/z 613 $[C_{38}H_{52}N_4O_3+H]^+$.m.p. >300° C.

HPLC (Method A)>99% (214 nm) $t_R$=14.1 min.

EXAMPLE 20

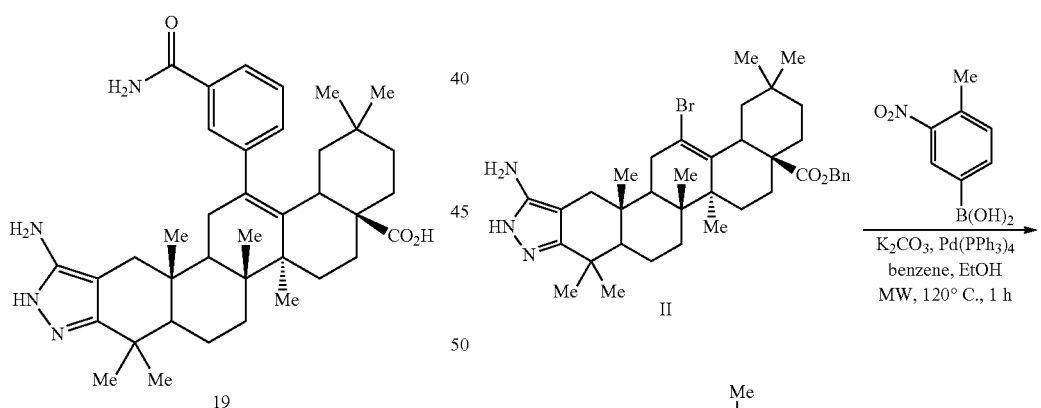

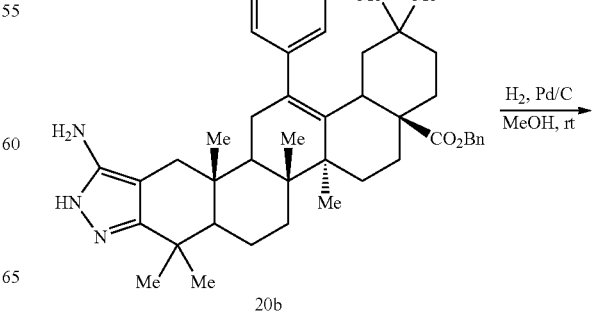

EXAMPLE 21

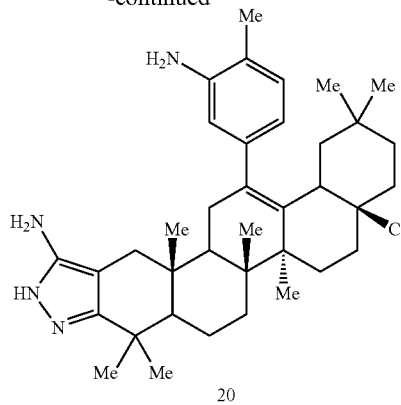

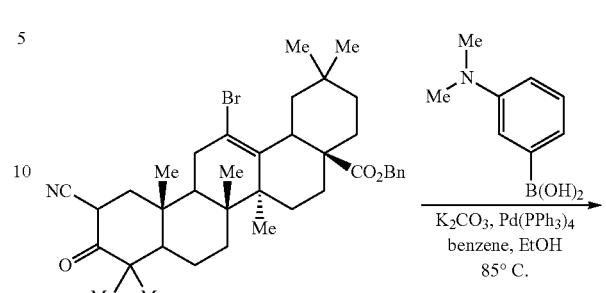

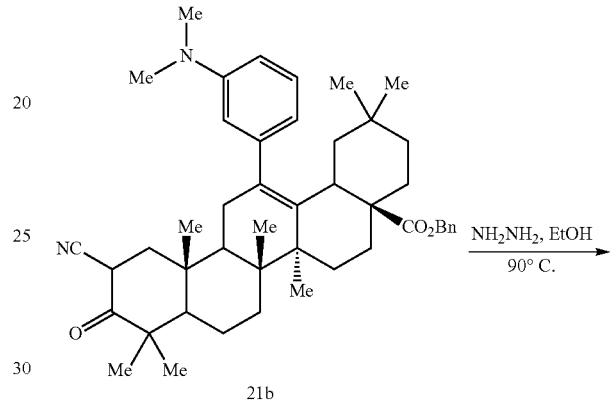

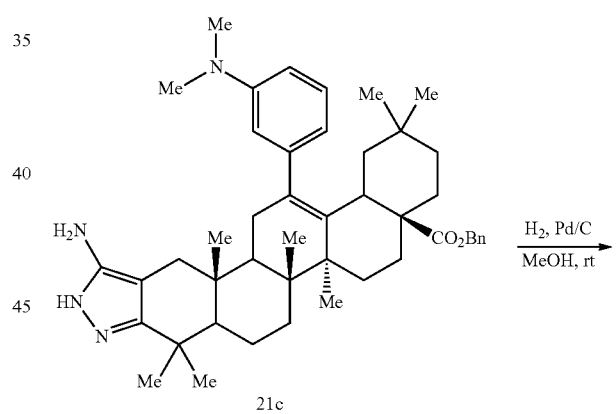

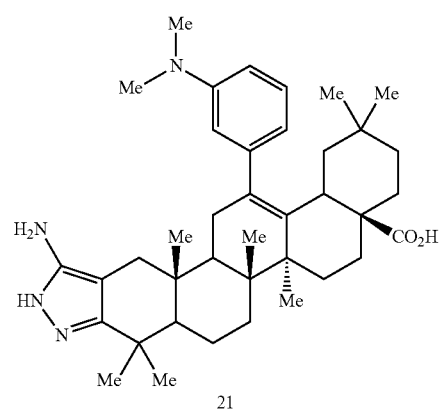

(i) Preparation of 20b: (4aS,6aS,6bR,13aR)-Benzyl 12-amino-2,2,6a,6b,9,9,13a-heptamethyl-15-(4-methyl-3-nitrophenyl)-2,3,4,4a,5,6,6a,6b,7,8,8a,9,11,13,13a,13b,14,15b-octadecahydro-1H-chryseno[1,2-f]indazole-4-a-carboxylate To a mixture of II (250 mg, 0.37 mmol) and 4-methyl-3-nitrophenylboronic acid (136 mg, 0.75 mmol) in benzene (4 mL) and EtOH (1 mL) was added $K_2CO_3$ (156 mg, 1.13 mmol). The mixture was sparged with nitrogen and then $Pd(PPh_3)_4$ (87 mg, 0.07 mmol) was added. The reaction mixture was heated at 120° C. for 1 hour using microwave irradiation. The solvent was removed under reduced pressure and then the residue was dissolved in EtOAc (20 mL). The solution was washed with brine then dried ($Na_2SO_4$), filtered and concentrated under reduced pressure. The residue was purified by column chromatography (silica, 0-40% CMA in $CH_2Cl_2$) to afford the sub-title compound (186 mg, 69%).

$^1$H NMR (300 MHz, $CD_3OD$) δ 0.26-2.34 (m, 41H), 2.51 (s, 3H), 3.01 (m, 1H), 5.05 (d, J=12.0 Hz, 1H), 5.23 (d, J=12.0 Hz, 1H), 7.22-7.37 (m, 7H), 7.80 (s, 1H). APCI MS m/z 719 $[C_{45}H_{58}N_4O_4+H]^+$.

(ii) Preparation of 20: (4aS,6aS,6bR,13aR)-12-Amino-15-(3-amino-4-methylphenyl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylic acid A solution of 20b (180 mg, 0.25 mmol) and MeOH (20 mL) was flushed with nitrogen and then 10% Pd/C (180 mg) was added. The mixture was flushed with nitrogen followed by hydrogen. The mixture was stirred under hydrogen at atmospheric pressure overnight. The catalyst was removed by filtration through diatomaceous earth and the filtrate was concentrated under reduced pressure. The residue was purified by column chromatography (silica, 0-40% CMA in $CH_2Cl_2$) followed by preparative HPLC to afford the title compound (16 mg, 10%) as a solid.

$R_f$ 0.23 (90:9:1 Methylene Chloride/Methanol/concentrated Ammonium Hydroxide).

$^1$H NMR (300 MHz, $CD_3OD$) δ 0.31-2.27 (m, 41H), 2.36 (s, 3H), 2.99 (d, J=10.5 Hz, 1H), 7.14-7.32 (m, 3H). APCI MS m/z 599 $[C_{38}H_{54}N_4O_2+H]^+$. m.p. 220-240° C. dec.

HPLC (Method A)>99% (214 nm) $t_R$=12.4 min.

(i) Preparation of 21b: (4aS,6aS,6bR,12aR)-Benzyl 11-cyano-14-(3-(dimethylamino)phenyl)-2,2,6a,6b,9,9,12a-heptamethyl-10-oxo-1,2,3,4,4a,5,6,6a,6b,7,8,8a,9,10,11,12,12a,12b,13,14b-icosahydropicene-4-a-carboxylate To a mixture of IIj (300 mg, 0.46 mmol) and 3-(dimethylamino)phenylboronic acid (458 mg, 2.78 mmol) in benzene (10 mL) and EtOH (5 mL) was added $K_2CO_3$ (511 mg, 3.70 mmol). The mixture was sparged with nitrogen and then $Pd(PPh_3)_4$ (107 mg, 0.09 mmol) was added. The mixture was heated at 85° C. overnight and then concentrated under reduced pressure. The residue was dissolved in EtOAc (50 mL) and the solution was washed with brine then dried ($Na_2SO_4$), filtered and concentrated under reduced pressure. The residue was purified by column chromatography (silica, 0-10% EtOAc in hexanes) to afford the sub-title compound (270 mg, 84%).

$^1$H NMR (300 MHz, $CDCl_3$) δ 0.29-2.30 (m, 41H), 2.95 (s, 6H), 3.13 (d, J=10.5 Hz, 1H), 3.81-3.91 (m, 1H), 5.07 (d, J=12.3 Hz, 1H), 5.17 (d, J=15.3 Hz, 1H), 6.51 (d, J=6.9 Hz, 1H), 6.51 (d, J=6.9 Hz, 1H), 7.03-7.09 (m, 1H), 7.34-7.36 (m, 5H).

(ii) Preparation of 21c: (4aS,6aS,6bR,13aR)-Benzyl 12-amino-15-(3-(dimethylamino)phenyl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylate To a solution of 21b (266 mg, 0.38 mmol) and EtOH (4 mL) was added hydrazine (60 µL, 1.93 mmol). The mixture was heated at 90° C. overnight and then concentrated under reduced pressure. The residue was purified by column chromatography (0-30% EtOAc in hexanes and 50% CMA in $CH_2Cl_2$) to afford the sub-title compound (191 mg, 70%).

$^1$H NMR (300 MHz, $CD_3OD$) δ 0.27-2.36 (m, 42H), 2.89 (s, 6H), 5.05 (m, 1H), 5.22 (m, 1H), 6.49-7.06 (m, 4H), 7.35-7.7.36 (m, 5H). APCI MS m/z 703 $[C_{46}H_{62}N_4O_2+H]^+$.

(iii) Preparation of 21: (4aS,6aS,6bR,13aR)-12-Amino-15-(3-(dimethylamino)phenyl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylic acid A solution of 21c (180 mg, 0.25 mmol) and MeOH (20 mL) was flushed with nitrogen and then 10% Pd/C (90 mg) was added. The mixture was flushed with nitrogen followed by hydrogen. The mixture was stirred under hydrogen at atmospheric pressure overnight. The catalyst was removed by filtration through diatomaceous earth and the filtrate was concentrated. The residue was purified by column chromatography (silica, 0-40% CMA in $CH_2Cl_2$) followed by preparative HPLC to afford the title compound (36 mg, 23%) as a solid.

$R_f$ 0.44 (90:9:1 Methylene Chloride/Methanol/concentrated Ammonium Hydroxide).

$^1$H NMR (300 MHz, $CD_3OD$) δ 0.27-2.43 (m, 41H), 3.04 (d, J=9.6 Hz, 1H), 3.18 (s, 6H), 7.16-7.47 (m, 4H). APCI MS m/z 613 $[C_{39}H_{56}N_4O_2+H]^+$. m.p. >300° C. HPLC (Method A) 98.1% (214 nm) $t_R$=12.0 min.

EXAMPLE 22

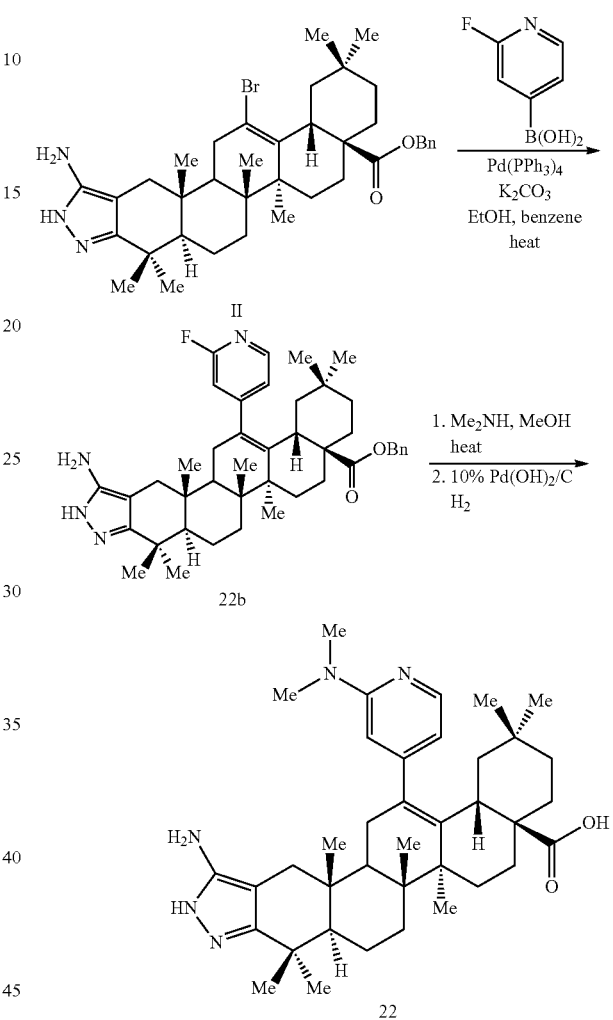

22

(i) Preparation of 22b: (4aS,6aS,6bR,8aR,13aR,15bS)-Benzyl 12-amino-15-(2-fluoropyridin-4-yl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylate A mixture of II (500 mg, 0.75 mmol), 2-fluoropyridin-4-ylboronic acid (210 mg, 1.50 mmol), $Pd(PPh_3)_4$ (80 mg, 0.075 mmol) and $K_2CO_3$ (310 mg, 2.25 mmol) in benzene (4.0 mL) and EtOH (1.0 mL) was sealed and heated to 120° C. by microwave for 1 hour. The reaction mixture was diluted with EtOAc (100 mL). The organic phase was washed with brine then dried ($MgSO_4$), filtered and concentrated to dryness. The residue was purified by column chromatography (silica, 0-10% MeOH in $CH_2Cl_2$) to afford the sub-title compound (448 mg, 88%) as a brown solid. APCI MS (Positive Mode) m/z 679 $[C_{43}H_{55}FN_4O_2+H]^+$.

(ii) Preparation of 22: (4aS,6aS,6bR,8aR,13aR, 15bS)-12-Amino-15-(2-(dimethylamino)pyridin-4-yl)-2,2,6a,6b,9,9,13a-heptamethyl-2,3,4,4a,5,6,6a,6b, 7,8,8a,9,11,13,13a,13b,14,15b-octadecahydro-1H-chryseno[1,2-f]indazole-4-a-carboxylic acid A mixture of 22b (150 mg, 0.22 mmol) and dimethylamine (4.0 mL, 2 M in MeOH, 8.0 mmol) was sealed and heated to 140° C. by microwave for 5 hours. The mixture was concentrated to dryness. The residue and 10% Pd(OH)$_2$/C (50 mg) in MeOH (12 mL) was stirred under a hydrogen balloon for 5 hours. The reaction mixture was filtered through a pad of diatomaceous earth and washed with CMA (25 mL). The filtrate was concentrated to dryness under reduced pressure. The residue was purified by column chromatography (silica, 0-10% MeOH in CH$_2$Cl$_2$) followed by preparative HPLC to provide the title compound (25 mg, 19%) as an off-white solid.

R$_f$ 0.65 (80:18:2 Methylene Chloride/Methanol/concentrated Ammonium Hydroxide).

$^1$H NMR (300 MHz, CD$_3$OD) δ 0.50 (s, 3H), 0.82 (s, 3H), 0.90 (s, 3H), 0.98 (s, 3H), 1.22 (s, 3H), 1.31 (s, 6H), 1.35-2.20 (m, 24H), 2.28 (m, 1H), 2.31 (d, J=14.8 Hz, 1H), 3.05 (m, 1H), 6.90 (s, 1H), 7.31 (s, 1H), 7.90 (s, 1H). mp >300° C. APCI MS (Positive Mode) m/z 614 [C$_{38}$H$_{55}$N$_5$O$_2$+H]$^+$.

EXAMPLE 23

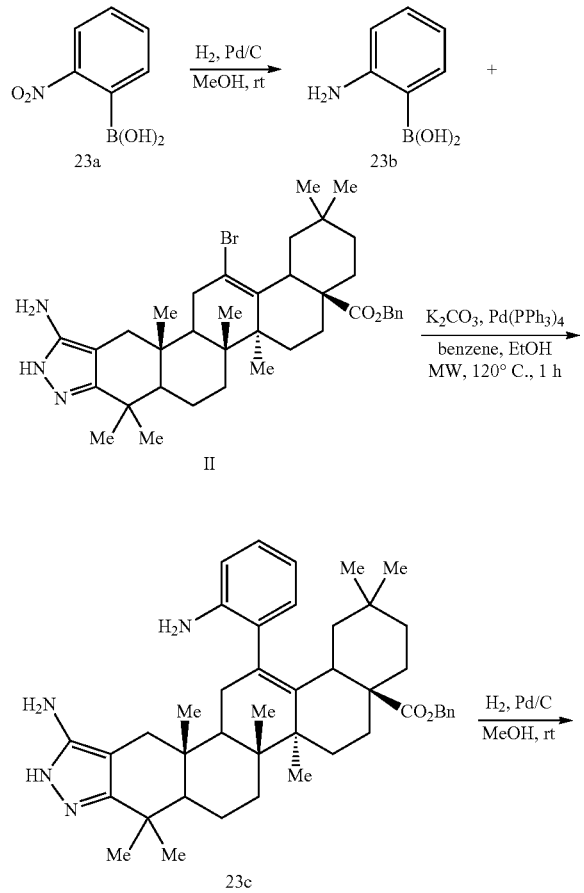

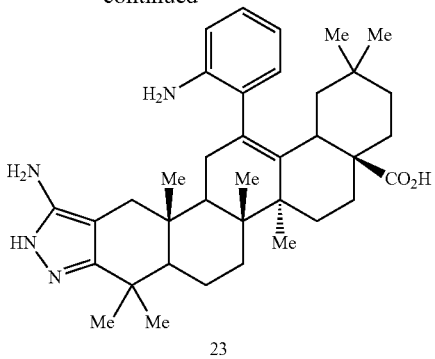

23

(i) Preparation of 23b: 2-Aminophenylboronic acid

To a solution of 2-nitrophenylboronic acid (500 mg, 2.99 mmol) and MeOH (10 mL) was added 10% Pd/C (250 mg). The mixture was stirred under hydrogen at atmospheric pressure for 2 hours. The catalyst was removed by filtration through diatomaceous earth and the filtrate was concentrated under reduced pressure. The residue was purified by column chromatography (silica, 0-50% CMA in CH$_2$Cl$_2$) to afford the sub-title compound (182 mg, 44%).

$^1$H NMR (300 MHz, CD$_3$OD) δ 6.69-7.75 (m, 4H).

(ii) Preparation of 23c: (4aS,6aS,6bR,13aR)-Benzyl 12-amino-15-(2-aminophenyl)-2,2,6a,6b,9,9,13a-heptamethyl-2,3,4,4a,5,6,6a,6b,7,8,8a,9,11,13,13a, 13b,14,15b-octadecahydro-1H-chryseno[1,2-f]indazole-4-a-carboxylate To a mixture of II (150 mg, 0.22 mmol) and 23b (77 mg, 0.56 mmol) in benzene (4 mL) and EtOH (1 mL) was added K$_2$CO$_3$ (124 mg, 0.90 mmol). The mixture was sparged with nitrogen and then Pd(PPh$_3$)$_4$ (52 mg, 0.04 mmol) was added. The reaction mixture was heated at 120° C. for 1 hour using microwave irradiation and then concentrated under reduced pressure. The residue was dissolved in EtOAc (20 mL). The organic solution was washed with brine then dried (Na$_2$SO$_4$), filtered and concentrated. The residue was purified by column chromatography (silica, 0-40% CMA in CH$_2$Cl$_2$) to afford the sub-title compound (190 mg, 75%).

APCI MS m/z 675 [C$_{44}$H$_{58}$N$_4$O$_2$+H]$^+$.

(iii) Preparation of 23: (4aS,6aS,6bR,13aR)-12-Amino-15-(2-aminophenyl)-2,2,6a,6b,9,9,13a-heptamethyl-2,3,4,4a,5,6,6a,6b,7,8,8a,9,11,13,13a,13b, 14,15b-octadecahydro-1H-chryseno[1,2-f]indazole-4-a-carboxylic acid A solution of 23c (180 mg, 0.26 mmol) and MeOH (20 mL) was flushed with nitrogen and then 10% Pd/C (150 mg) was added. The mixture was flushed with nitrogen followed by hydrogen. The mixture was stirred under hydrogen at atmospheric pressure overnight. The catalyst was removed by filtration through diatomaceous earth and the filtrate was concentrated under reduced pressure. The residue was purified by column chromatography (silica, 0-100% CMA in CH$_2$Cl$_2$) followed by preparative HPLC to afford the title compound (17 mg, 10%) as a solid.

R$_f$ 0.28 (40:9:1 Methylene Chloride/Methanol/concentrated Ammonium Hydroxide).

¹H NMR (300 MHz, CD₃OD) δ 0.20-2.47 (m, 48H), δ 7.29 (d, J=7.2 Hz, 1H), δ 7.41-7.42 (m, 3H). APCI MS m/z 585 [C₃₇H₅₂N₄O₂+H]⁺. m.p. 210-230° C. dec. HPLC (Method A)>99% (214 nm) $t_R$=12.7 min.

EXAMPLE 24

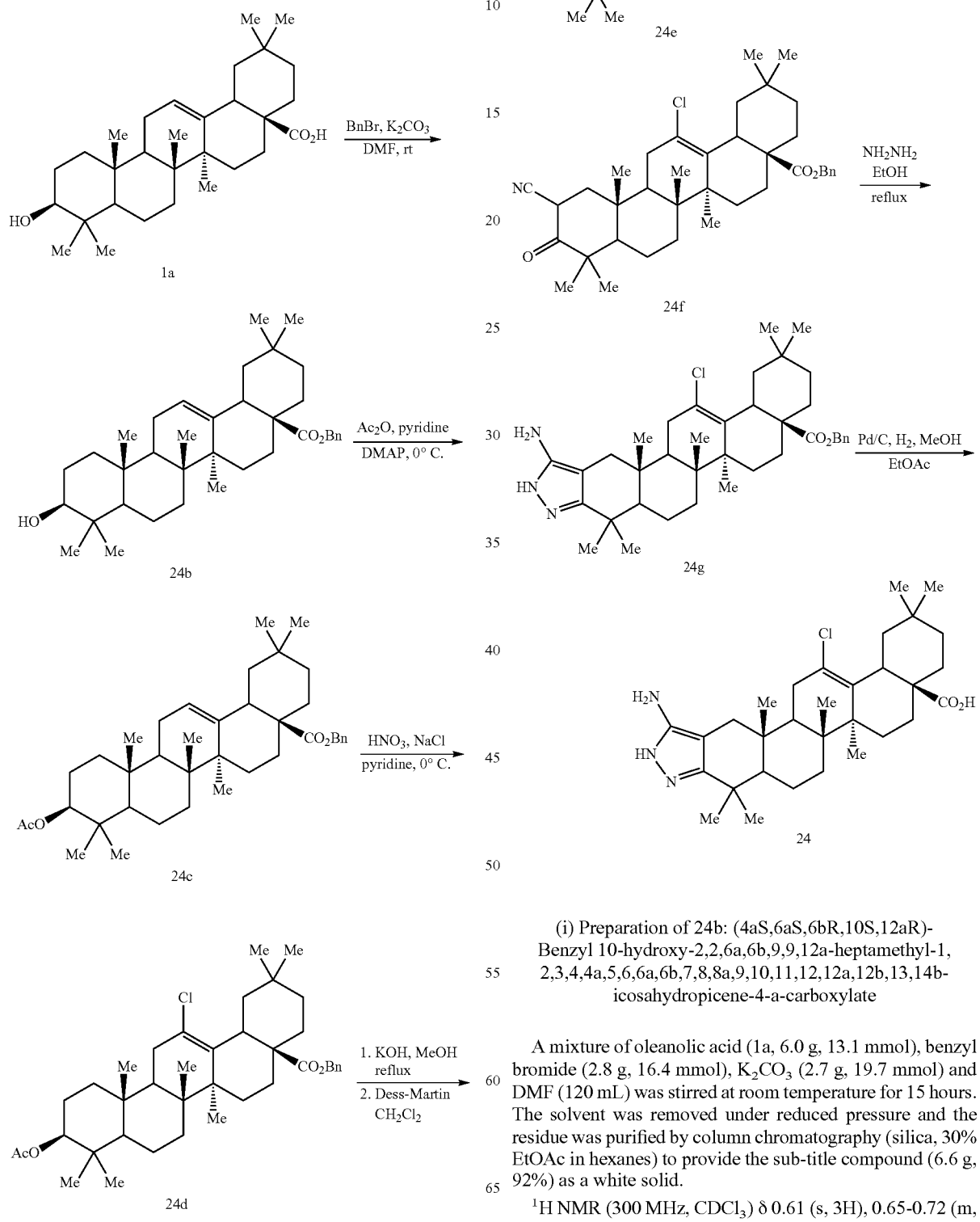

(i) Preparation of 24b: (4aS,6aS,6bR,10S,12aR)-Benzyl 10-hydroxy-2,2,6a,6b,9,9,12a-heptamethyl-1,2,3,4,4a,5,6,6a,6b,7,8,8a,9,10,11,12,12a,12b,13,14b-icosahydropicene-4-a-carboxylate A mixture of oleanolic acid (1a, 6.0 g, 13.1 mmol), benzyl bromide (2.8 g, 16.4 mmol), K₂CO₃ (2.7 g, 19.7 mmol) and DMF (120 mL) was stirred at room temperature for 15 hours. The solvent was removed under reduced pressure and the residue was purified by column chromatography (silica, 30% EtOAc in hexanes) to provide the sub-title compound (6.6 g, 92%) as a white solid.

¹H NMR (300 MHz, CDCl₃) δ 0.61 (s, 3H), 0.65-0.72 (m, 1H), 0.78 (s, 3H), 0.87-1.00 (m, 10H), 1.05-1.46 (m, 12H), 1.49-1.72 (m, 12H), 1.81-2.05 (m, 3H), 2.86-2.91 (m, 1H), 3.15-3.27 (m, 1H), 5.02-5.11 (m, 2H), 5.43-5.45 (m, 1H), 7.31-7.49 (m, 5H).

(ii) Preparation of 24c: (4aS,6aS,6bR,10S,12aR)-Benzyl 10-acetoxy-2,2,6a,6b,9,9,12a-heptamethyl-1,2,3,4,4a,5,6,6a,6b,7,8,8a,9,10,11,12,12a,12b,13,14b-icosahydropicene-4-a-carboxylate To a solution of 24b (6.6 g, 12.1 mmol), DMAP (200 mg) and pyridine (65 mL) was slowly added acetic anhydride (1.5 g, 14.5 mmol) at 0° C. under nitrogen. The mixture was allowed to slowly warm to room temperature overnight and was quenched by pouring into one liter of $H_2O$. The precipitate was collected by filtration and dried in a vacuum oven at 40° C. to provide the sub-title compound (6.6 g, 93%) as a white solid.

$^1$H NMR (300 MHz, $CDCl_3$) δ 0.61 (s, 3H), 0.77-0.94 (m, 16H), 0.98-1.75 (m, 21H), 1.84-2.02 (m, 3H), 2.04 (s, 3H), 2.85-2.95 (m, 1H), 4.46-4.51 (m, 1H), 5.01-5.08 (m, 2H), 5.27-5.29 (m, 1H), 7.29-7.35 (m, 5H).

(iii) Preparation of 24d: (4aS,6aS,6bR,10S,12aR)-Benzyl 10-acetoxy-14-chloro-2,2,6a,6b,9,9,12a-heptamethyl-1,2,3,4,4a,5,6,6a,6b,7,8,8a,9,10,11,12,12a,12b,13,14b-icosahydropicene-4-a-carboxylate To a suspension of 24c (3.0 g, 5.13 mmol) and pyridine (65 mL) at 0° C. was added chlorine gas which was generated by addition of nitric acid to sodium chloride. After 20 min at 0° C., the mixture was poured into $H_2O$ and the solid was collected by filtration. The crude material was purified by column chromatography (silica, 20% diethyl ether in hexanes) to provide the sub-title compound (1.3 g, 40%).

$^1$H NMR (500 MHz, $CDCl_3$) δ 0.82-0.91 (m, 12H), 1.00 (s, 3H), 1.12-1.79 (m, 22H), 1.88-2.33 (m, 9H), 3.63-3.74 (m, 1H), 4.45-4.52 (m, 1H), 5.11-5.21 (m, 2H), 7.31-7.44 (m, 5H).

(iv) Preparation of 24e: (4aS,6aS,6bR,12aR)-Benzyl 14-chloro-2,2,6a,6b,9,9,12a-heptamethyl-10-oxo-1,2,3,4,4a,5,6,6a,6b,7,8,8a,9,10,11,12,12a,12b,13,14b-icosahydropicene-4-a-carboxylate A mixture of 24d (1.0 g, 1.62 mmol), KOH (360 mg, 4.86 mmol) and MeOH (70 mL) was heated at reflux for 96 hours. The solvent was removed and the residue was partitioned between $H_2O$ (50 mL) and $CH_2Cl_2$ (50 mL). The organic layer was separated then dried ($Na_2SO_4$), filtered and concentrated under reduced pressure. The crude product was dissolved in $CH_2Cl_2$ (40 mL) and the Dess-Martin reagent (900 mg, 2.1 mmol) was added at room temperature. The mixture was stirred for 14 hours before quenching with a solution of sodium thiosulfate (12.5 g) and saturated $NaHCO_3$ (50 mL). After stifling 30 min, the layers were separated and the aqueous layer was extracted with $CH_2Cl_2$ (50 mL). The combined organic layers were dried ($Na_2SO_4$), filtered and concentrated under reduced pressure. The residue was purified by column chromatography (silica, 0-25% EtOAc in hexanes) to provide the sub-title compound (785 mg, 100%) as a white solid.

$^1$H NMR (300 MHz, $CDCl_3$) δ 0.64 (s, 3H), 0.89-1.18 (m, 21H), 1.22-2.07 (m, 15H), 2.23-2.41 (m, 3H), 2.47-2.61 (m, 1H), 3.62-3.75 (m, 1H), 5.05-5.16 (m, 2H), 7.29-7.41 (m, 5H).

(v) Preparation of 24f: (4aS,6aS,6bR,12aR)-Benzyl 14-chloro-11-cyano-2,2,6a,6b,9,9,12a-heptamethyl-10-oxo-1,2,3,4,4a,5,6,6a,6b,7,8,8a,9,10,11,12,12a,12b,13,14b-icosahydropicene-4-a-carboxylate A solution of diisopropylamine (0.2 mL, 1.46 mmol) and THF (7 mL) was cooled to −78° C. under nitrogen. A solution of n-butyllithium (2.5 M in hexanes, 0.65 mL, 1.63 mmol) was slowly added, maintaining the internal temperature below −70° C. The solution was allowed to stir for 45 min and was then slowly added to a solution of 24e (500 mg, 0.86 mmol) and THF (10 mL) at −78° C. under nitrogen. This solution was stirred for 30 min after which time a suspension of p-toluenesulfonyl cyanide (310 mg, 1.72 mmol) and THF (3 mL) was added over 15 min. The solution was stirred for 30 min and then quenched by addition of saturated ammonium chloride solution (10 mL) at −78° C. The mixture was allowed to warm to room temperature overnight. The organic layer was separated and the aqueous layer was extracted with EtOAc. The combined organic layers were dried ($Na_2SO_4$) and filtered. The solvent was removed under reduced pressure and the residue was purified by column chromatography (silica, 0-25% EtOAc in hexanes) to provide the sub-title compound (350 mg, 67%).

$^1$H NMR (500 MHz, $CD_3OD$) δ 0.59 (s, 3H), 0.82-2.29 (m, 39H), 3.63-3.74 (m, 1H), 5.03-5.15 (m, 2H), 7.31-2.7.45 (m, 5H).

(vi) Preparation of 24g: (4aS,6aS,6bR,13aR)-Benzyl 12-amino-15-chloro-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylate A solution of 24f (350 mg, 0.58 mmol) and hydrazine (74 mg, 2.32 mmol) in EtOH (10 mL) was heated at reflux for 16 hours. The solvent and excess hydrazine were removed under reduced pressure. The residue was purified by column chromatography (silica, 0-50% CMA in $CH_2Cl_2$) to provide the sub-title compound (175 mg, 50%).

$^1$H NMR (300 MHz, $CDCl_3$) δ 0.61 (s, 3H), 0.88 (s, 3H), 0.91 (s, 3H), 0.98 (s, 3H), 1.09-2.06 (m, 27H), 2.23-2.35 (m, 3H), 3.66-3.78 (m, 1H), 5.02-5.14 (m, 2H), 7.29-7.41 (m, 5H).

(vii) Preparation of 24: (4aS,6aS,6bR,13aR)-12-Amino-15-chloro-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylic acid A suspension of 24g (150 mg, 0.24 mmol), 10% Pd/C (100 mg) and EtOAc/MeOH (20% MeOH, 25 mL) was stirred under hydrogen at atmospheric pressure for 23 hours. The catalyst was removed by filtration through diatomaceous earth and the filtrate was concentrated under reduced pressure. The residue was purified by column chromatography (silica, 50-100% CMA in $CH_2Cl_2$) to provide the title compound (48 mg, 38%) as an off-white solid.

$^1$H NMR (300 MHz, $CD_3OD$) δ 0.89-1.01 (m, 12H), 1.12-1.30 (m, 12H), 1.34-2.10 (m, 15H), 2.33-2.41 (m, 3H), 3.62-3.70 (m, 1H). APCI MS m/z 528 $[C_{31}H_{46}ClN_3O_2+H]^+$.

HPLC >99% (area %), $t_R$=15.9 min.

EXAMPLE 25

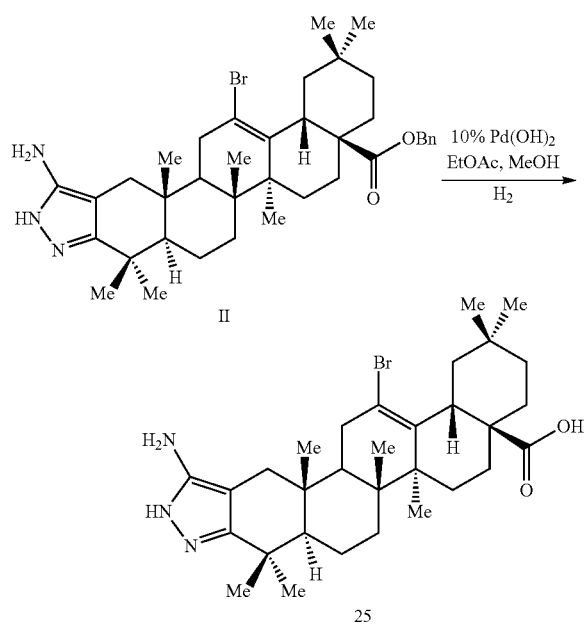

(i) Preparation of 25: (4aS,6aS,6bR,8aR,13aR, 15bR)-12-Amino-15-bromo-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylic acid A mixture of II (75 mg, 0.11 mmol) and 10% Pd(OH)$_2$/C (75 mg) in EtOAc (10 mL) and MeOH (2 mL) was stirred under a hydrogen balloon for 12 hours. The reaction mixture was filtered through a pad of diatomaceous earth and washed with CMA (25 mL). The filtrate was concentrated to dryness under reduced pressure. The residue was purified by column chromatography (silica, 0-60% CMA in CH$_2$Cl$_2$) to afford the title compound (20 mg, 32%) as a brown solid.

R$_f$ 0.40 (80:18:2 Methylene Chloride/Methanol/concentrated Ammonium Hydroxide).

$^1$H NMR (300 MHz, CD$_3$OD) δ 0.91 (s, 6H), 0.93 (s, 3H), 1.0 (s, 3H), 1.12 (s, 3H), 1.15 (s, 3H), 1.21 (s, 3H), 1.32-2.28 (m, 20H), 2.35 (d, J=14.4 Hz, 1H), 2.53 (d, J=8.7 Hz, 2H), 3.53 (m, 1H). mp 268-270° C. ESI MS (Positive Mode) m/z 572 [C$_{31}$H$_{46}$BrN$_3$O$_2$+H]$^+$.

EXAMPLE 26

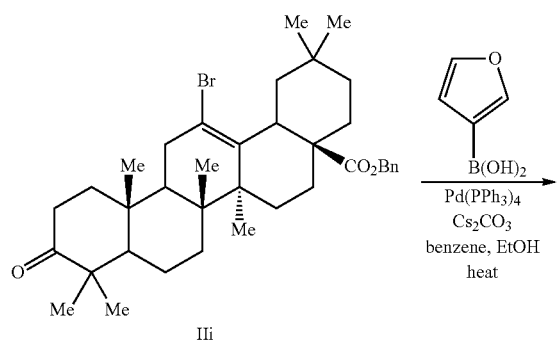

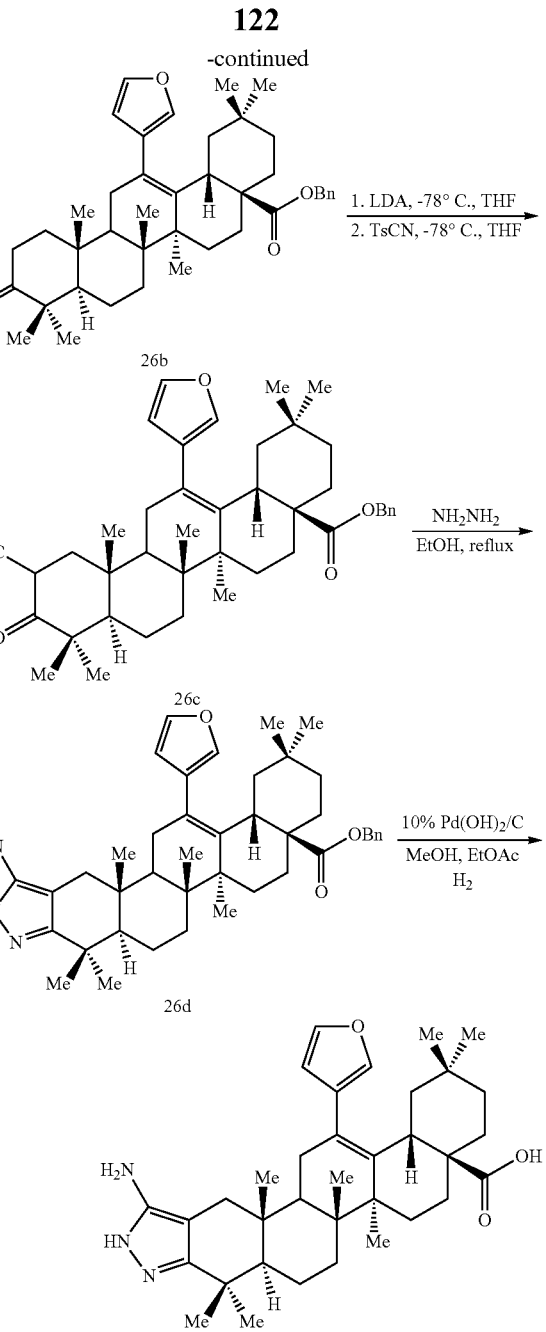

(i) Preparation of 26b: (4aS,6aS,6bR,8aR,12aR, 14bS)-benzyl 14-(furan-3-yl)-2,2,6a,6b,9,9,12a-heptamethyl-10-oxo-1,2,3,4,4a,5,6,6a,6b,7,8,8a,9,10,11,12,12a,12b,13,14b-icosahydropicene-4-a-carboxylate A mixture of IIi (360 mg, 0.57 mmol), furan-3-ylboronic acid (194 mg, 1.73 mmol), Pd(PPh$_3$)$_4$ (66 mg, 0.057 mmol) and cesium carbonate (564 mg, 1.73 mmol) in benzene (15 mL) and EtOH (4 mL) was heated at reflux for 12 hours. The reaction mixture was diluted with EtOAc (100 mL). The organic phase was washed with brine then dried (MgSO$_4$), filtered and concentrated to dryness. The residue was purified by column chromatography (silica, 0-20% EtOAc in hexanes) to afford the sub-title compound (340 mg, 97%).

<sup>1</sup>H NMR (300 MHz, CDCl<sub>3</sub>) δ 0.57 (s, 3H), 0.77 (s, 3H), 0.81 (s, 3H), 1.05 (s, 3H), 1.07 (s, 3H), 1.12 (s, 3H), 1.22 (s, 3H), 1.23-2.55 (m, 22H), 3.31 (m, 1H), 5.04 (m, 2H), 6.32 (s, 1H), 7.20 (s, 1H), 7.31 (m, 6H).

(ii) Preparation of 26c: (4aS,6aS,6bR,8aR,12aR, 14bS)-benzyl 11-cyano-14-(furan-3-yl)-2,2,6a,6b,9, 9,12a-heptamethyl-10-oxo-1,2,3,4,4a,5,6,6a,6b,7,8, 8a,9,10,11,12,12a,12b,13,14b-icosahydropicene-4-a-carboxylate To a solution of diisopropylamine (0.12 mL, 0.84 mmol) in THF (5 mL) was added n-butyllithium (0.35 mL, 2.5 M in hexanes, 0.88 mmol) at −78° C. The solution was stirred for 30 min. The LDA solution was added to 26b (270 mg, 0.44 mmol) in THF (5 mL). The mixture was allowed to warm to −40° C. for 5 min and cooled to −78° C. A suspension of p-toluene sulfonyl cyanide (203 mg, 1.12 mmol) in THF (2 mL) was added. The reaction mixture was allowed to warm to −40° C. over 1.5 hours. The reaction was quenched by saturated NH<sub>4</sub>Cl (3 mL) and extracted with EtOAc (100 mL). The organic phase was washed with brine then dried (MgSO<sub>4</sub>), filtered and concentrated to dryness. The residue was purified by column chromatography (silica, 0-20% EtOAc in hexanes) to afford the sub-title compound (150 mg, 54%).

<sup>1</sup>H NMR (300 MHz, CDCl<sub>3</sub>) δ 0.51 (s, 3H), 0.62 (s, 3H), 0.65 (s, 3H), 1.03 (s, 3H), 1.04 (s, 3H), 1.07 (s, 3H), 1.16 (s, 3H), 1.23-2.55 (m, 21H), 3.32 (m, 1H), 5.02 (m, 2H), 6.32 (s, 1H), 7.20 (s, 1H), 7.31 (m, 6H).

(iii) Preparation of 26d: (4aS,6aS,6bR,8aR,13aR, 15bS)-Benzyl 12-amino-15-(furan-3-yl)-2,2,6a,6b,9, 9,13a-heptamethyl-2,3,4,4a,5,6,6a,6b,7,8,8a,9,11,13, 13a,13b,14,15b-octadecahydro-1H-chryseno[1,2-f] indazole-4-a-carboxylate A mixture of 26c (150 mg, 0.23 mmol) and hydrazine (0.030 mL) in EtOH (3 mL) was heated at reflux overnight. The reaction mixture was concentrated to dryness under reduced pressure. The residue was purified by column chromatography (silica, 0-10% MeOH in CH<sub>2</sub>Cl<sub>2</sub>) to afford the sub-title compound (110 mg, 71%).

ESI MS (Positive Mode) m/z 650 [C<sub>42</sub>H<sub>55</sub>N<sub>3</sub>O<sub>3</sub>+H]<sup>+</sup>.

(iv) Preparation of 26: (4aS,6aS,6bR,8aR,13aR, 15bS)-12-Amino-15-(furan-3-yl)-2,2,6a,6b,9,9,13a-heptamethyl-2,3,4,4a,5,6,6a,6b,7,8,8a,9,11,13,13a, 13b,14,15b-octadecahydro-1H-chryseno[1,2-f] indazole-4-a-carboxylic acid A mixture of 26d (110 mg, 0.17 mmol) and 10% Pd(OH)<sub>2</sub>/C (50 mg) in MeOH (6 mL) and EtOAc (6 mL) was stirred under a hydrogen balloon for 12 hours. The reaction mixture was filtered through a pad of diatomaceous earth and washed with CMA (25 mL). The filtrate was concentrated to dryness under reduced pressure. The residue was purified by column chromatography (silica, 0-50% CMA in CH<sub>2</sub>Cl<sub>2</sub>) to afford the title compound (20 mg, 21%) as a brown solid.

R<sub>f</sub> 0.45 (80:18:2 Methylene Chloride/Methanol/concentrated Ammonium Hydroxide).

<sup>1</sup>H NMR (300 MHz, DMSO-d<sub>6</sub>) δ 0.53 (s, 3H), 0.78 (s, 3H), 0.80 (s, 3H), 0.84 (s, 3H), 1.05 (s, 3H), 1.16 (s, 6H), 1.26-2.25 (m, 19H), 2.25 (d, J=14.7 Hz, 1H), 6.48 (s, 1H), 7.48 (s, 1H), 7.59 (s, 1H). mp >300° C. APCI MS (Positive Mode) m/z 560 [C<sub>35</sub>H<sub>49</sub>N<sub>3</sub>O<sub>3</sub>+H]<sup>+</sup>.

EXAMPLE 27

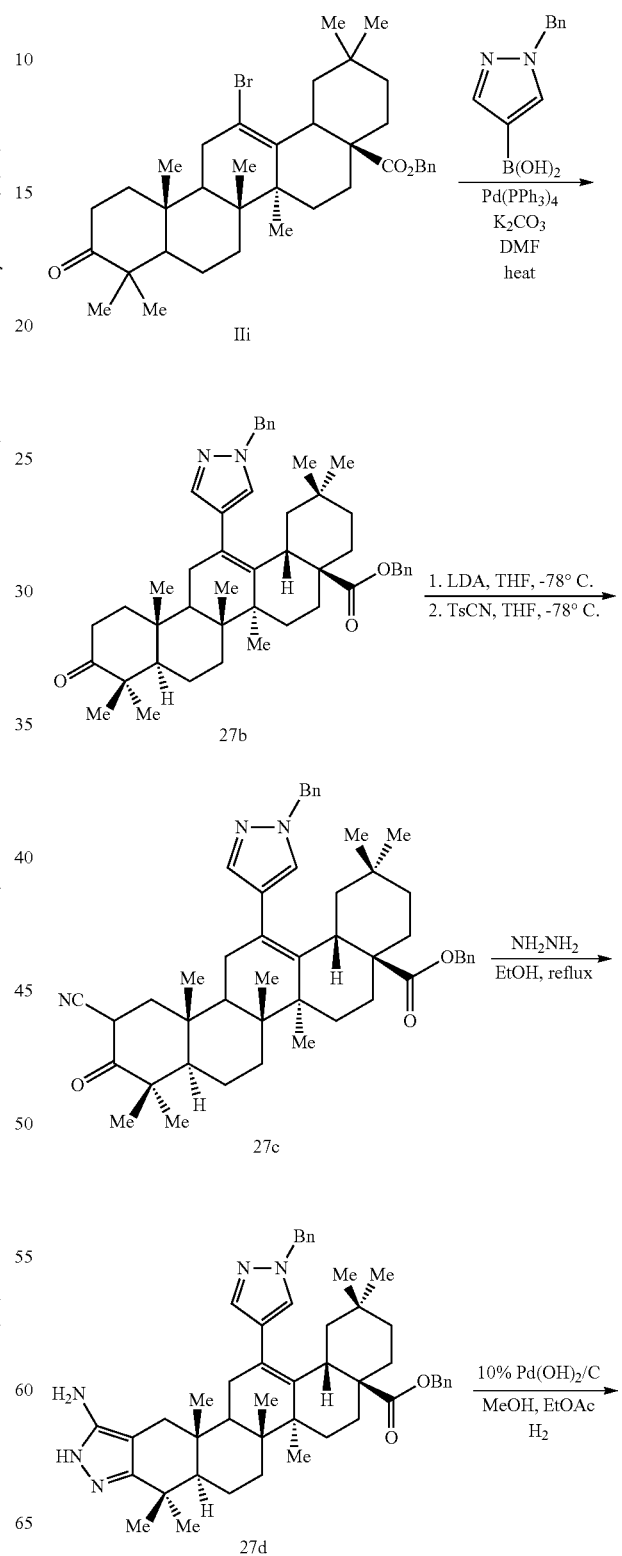

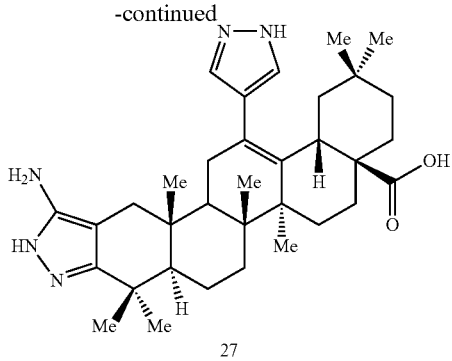

27

(i) Preparation of 27b: (4aS,6aS,6bR,8aR,12aR, 14bS)-Benzyl 14-(1-benzyl-1H-pyrazol-4-yl)-2,2,6a, 6b,9,9,12a-heptamethyl-10-oxo-1,2,3,4,4a,5,6,6a,6b, 7,8,8a,9,10,11,12,12a,12b,13,14b-icosahydropicene-4-a-carboxylate carboxylate A mixture of IIi (300 mg, 0.48 mmol), 1-benzyl-1H-pyrazol-4-ylboronic acid (291 mg, 1.44 mmol), Pd(PPh$_3$)$_4$ (60 mg, 0.048 mmol) and K$_2$CO$_3$ (198 mg, 1.44 mmol) in DMF (9 mL) was heated at 100° C. for 24 hours. The reaction mixture was diluted with EtOAc (100 mL). The organic phase was washed with brine then dried (MgSO$_4$), filtered and concentrated to dryness. The residue was purified by column chromatography (silica, 0-20% EtOAc in hexanes) to afford the sub-title compound (280 mg, 83%).

$^1$H NMR (300 MHz, CDCl$_3$) δ 0.43 (s, 3H), 0.76 (s, 3H), 0.77 (s, 3H), 0.78-2.53 (m, 37H), 3.32 (m, 1H), 5.02 (m, 4H), 7.15 (m, 4H), 7.31 (m, 8H).

(ii) Preparation of 27c: (4aS,6aS,6bR,8aR,12aR, 14bS)-Benzyl 14-(1-benzyl-1H-pyrazol-4-yl)-11-cyano-2,2,6a,6b,9,9,12a-heptamethyl-10-oxo-1,2,3, 4,4a,5,6,6a,6b,7,8,8a,9,10,11,12,12a,12b,13,14b-icosahydropicene-4-a-carboxylate To a solution of diisopropylamine (0.13 mL, 0.95 mmol) in THF (5 mL) was added n-butyllithium (0.4 mL, 2.5 M in hexanes, 1.0 mmol) at −78° C. The solution was stirred for 30 min. The LDA solution was added to 27b (350 mg, 0.50 mmol) in THF (5 mL). The mixture was allowed to warm to −40° C. for 5 min and cooled to −78° C. A suspension of p-toluene sulfonyl cyanide (181 mg, 1.0 mmol) in THF (2 mL) was added. The reaction mixture was allowed to warm to −40° C. over 1.5 hours. The reaction was quenched by saturated NH$_4$Cl (3 mL) and extracted with EtOAc (100 mL). The organic phase was washed with brine then dried (MgSO$_4$), filtered and concentrated to dryness. The residue was purified by column chromatography (silica, 0-20% EtOAc in hexanes) to afford the sub-title compound (160 mg, 44%).

(iii) Preparation of 27d: (4aS,6aS,6bR,8aR,13aR, 15bS)-Benzyl 12-amino-15-(1-benzyl-1H-pyrazol-4-yl)-2,2,6a,6b,9,9,13a-heptamethyl-2,3,4,4a,5,6,6a,6b, 7,8,8a,9,11,13,13a,13b,14,15b-octadecahydro-1H-chryseno[1,2-f]indazole-4-a-carboxylate A mixture of 27c (160 mg, 0.22 mmol) and hydrazine (0.10 mL, 0.69 mmol) in EtOH (3 mL) was heated at reflux overnight. The reaction mixture was concentrated to dryness under reduced pressure. The residue was purified by column chromatography (silica, 0-40% CMA in CH$_2$Cl$_2$) to afford the sub-title compound (60 mg, 62%). APCI MS (Positive Mode) m/z 740 [C$_{41}$H$_{55}$N$_5$O$_2$+H]$^+$.

(iv) Preparation of 27: (4aS,6aS,6bR,8aR,13aR, 15bS)-12-Amino-2,2,6a,6b,9,9,13a-heptamethyl-15-(1H-pyrazol-4-yl)-2,3,4,4a,5,6,6a,6b,7,8,8a,9,11,13, 13a,13b,14,15b-octadecahydro-1H-chryseno[1,2-f] indazole-4-a-carboxylic acid A mixture of 27d (60 mg, 0.082 mmol) and 10% Pd(OH)$_2$/C (60 mg) in MeOH (12 mL) and EtOAc (2 mL) was stirred under a hydrogen balloon for 12 hours. The reaction mixture was filtered through a pad of diatomaceous earth and washed with CMA (25 mL). The filtrate was concentrated to dryness under reduced pressure. The residue was purified by column chromatography (silica, 0-80% CMA in CH$_2$Cl$_2$) to afford the title compound (8 mg, 18%) as a brown solid.

R$_f$ 0.20 (80:18:2 Methylene Chloride/Methanol/concentrated Ammonium Hydroxide).

$^1$H NMR (300 MHz, CD$_3$OD+CDCl$_3$) δ 0.52 (s, 3H), 0.77 (s, 3H), 0.88 (s, 3H), 0.95 (s, 3H), 1.16 (s, 3H), 1.24 (s, 6H), 1.32-2.28 (m, 20H), 2.32 (d, J=14.7 Hz, 1H), 7.57 (s, 1H), 7.82 (s, 1H). mp >300° C. APCI MS (Positive Mode) m/z 560 [C$_{34}$H$_{49}$N$_5$O$_2$+H]$^+$.

EXAMPLE 28

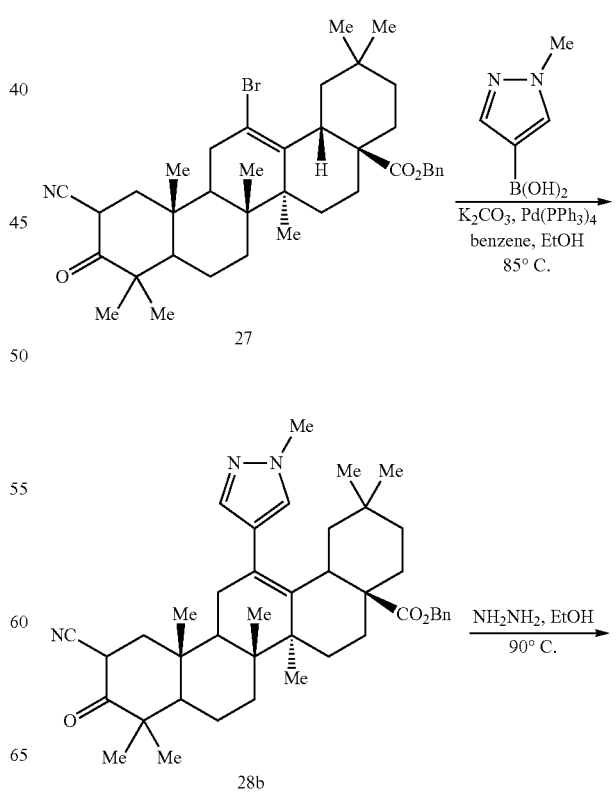

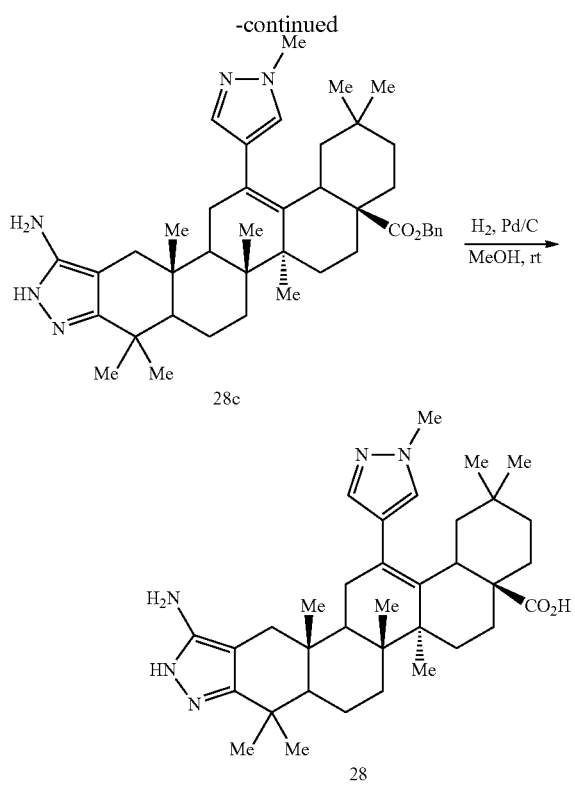

(i) Preparation of 28b: (4aS,6aS,6bR,8aR,12aR, 14bS)-Benzyl 11-cyano-2,2,6a,6b,9,9,12a-heptamethyl-14-(1-methyl-1H-pyrazol-4-yl)-10-oxo-1,2,3,4, 4a,5,6,6a,6b,7,8,8a,9,10,11,12,12a,12b,13,14b-icosahydropicene-4-a-carboxylate A mixture of IIj (100 mg, 0.15 mmol), 1-methyl-1H-pyrazol-4-ylboronic acid (75.0 mg, 0.60 mmol), Pd(PPh₃)₄ (34 mg, 0.030 mmol) and K₂CO₃ (184 mg, 1.33 mmol) in benzene (3.5 mL) and EtOH (1.5 mL) was sealed and heated to 120° C. by microwave for 1 hour. The reaction mixture was diluted with EtOAc (100 mL). The organic phase was washed with brine then dried (MgSO₄), filtered and concentrated to dryness. The residue was purified by column chromatography (silica, 0-30% EtOAc in hexanes) to afford the sub-title compound (60 mg, 61%).

$^1$H NMR (300 MHz, CDCl₃) δ 0.54 (s, 3H), 0.76 (s, 3H), 0.80 (s, 3H), 0.81-2.05 (m, 32H), 3.32 (m, 1H), 3.77 (s, 3H), 3.85 (m, 1H), 5.02 (m, 2H), 7.10 (s, 1H), 7.33 (m, 6H).

(ii) Preparation of 28c: (4aS,6aS,6bR,8aR,13aR, 15bS)-Benzyl 12-amino-2,2,6a,6b,9,9,13a-heptamethyl-15-(1H-pyrrol-3-yl)-2,3,4,4a,5,6,6a,6b,7,8,8a, 9,11,13,13a,13b,14,15b-octadecahydro-1H-chryseno [1,2-f]indazole-4-a-carboxylate A mixture of 28b (60 mg, 0.09 mmol) and hydrazine (0.05 mL) in EtOH (1.5 mL) was heated at reflux overnight. The reaction mixture was concentrated to dryness under reduced pressure. The residue was purified by column chromatography (silica, 0-30% CMA in CH₂Cl₂) to afford the sub-title compound (33 mg, 54%). APCI MS (Positive Mode) m/z 664 [C₄₂H₅₇N₅O₂+H]⁺.

(iii) Preparation of 28: (4aS,6aS,6bR,8aR,13aR, 15bS)-12-Amino-2,2,6a,6b,9,9,13a-heptamethyl-15-(1-methyl-1H-pyrazol-4-yl)-2,3,4,4a,5,6,6a,6b,7,8, 8a,9,11,13,13a,13b,14,15b-octadecahydro-1H-chryseno[1,2-f]indazole-4-a-carboxylic acid A mixture of 28c (33 mg, 0.05 mmol) and 10% Pd(OH)₂/C (16 mg) in MeOH (12 mL) was stirred under a hydrogen balloon for 5 hours. The reaction mixture was filtered through a pad of diatomaceous earth and washed with CMA (25 mL). The filtrate was concentrated to dryness under reduced pressure. The residue was purified by column chromatography (silica, 0-50% CMA in CH₂Cl₂) to afford the title compound (20 mg, 71%) as a brown solid.

R$_f$ 0.64 (9:1 Methylene Chloride/Methanol).

$^1$H NMR (300 MHz, CD₃OD) δ 0.55 (s, 3H), 0.81 (s, 3H), 0.87 (s, 3H), 0.93 (s, 3H), 1.15 (s, 3H), 1.23 (s, 3H), 1.24 (s, 3H), 1.25-2.18 (m, 19H), 2.36 (d, J=14.8 Hz, 1H), 3.34 (m, 1H), 7.45 (s, 1H), 7.52 (s, 1H). mp >300° C. APCI MS (Positive Mode) m/z 574 [C₃₅H₅₁N₅O₂+H]⁺.

EXAMPLE 29

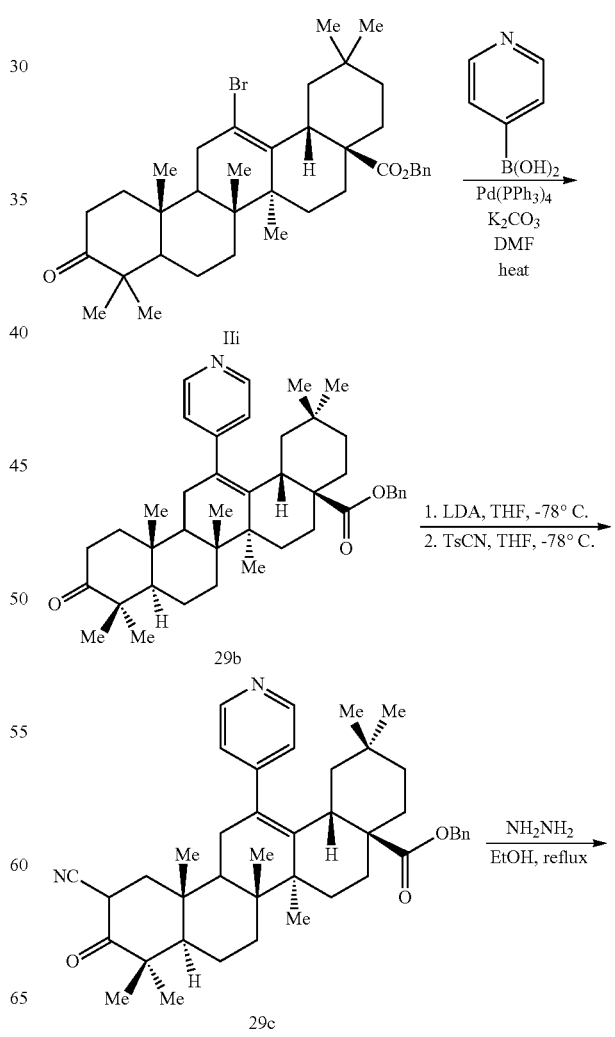

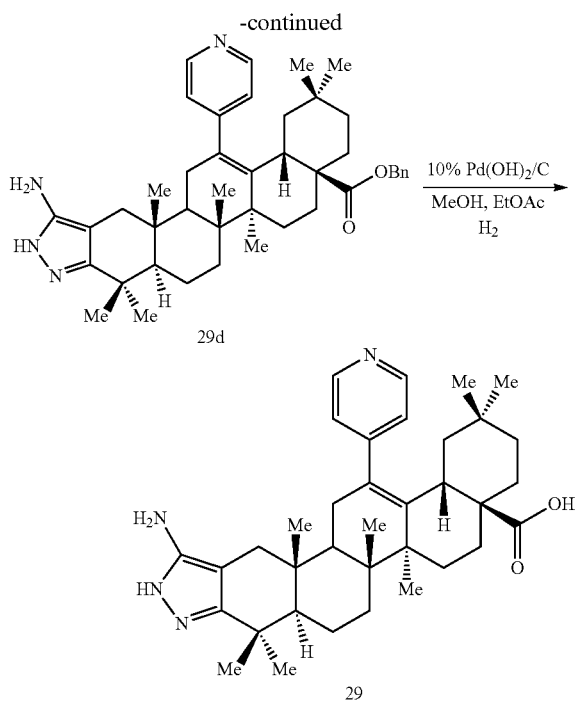

(i) Preparation of 29b: (4aS,6aS,6bR,8aR,12aR, 14bS)-Benzyl 2,2,6a,6b,9,9,12a-heptamethyl-10-oxo-14-(pyridin-4-yl)-1,2,3,4,4a,5,6,6a,6b,7,8,8a,9, 10,11,12,12a,12b,13,14b-icosahydropicene-4-a-carboxylate A mixture of IIi (400 mg, 0.64 mmol), pyridine-4-ylboronic acid (395 mg, 3.21 mmol), Pd(PPh₃)₄ (222 mg, 0.19 mmol) and K₂CO₃ (443 mg, 3.21 mmol) in DMF (10 mL) was heated at 100° C. for 24 hours. The reaction mixture was diluted with EtOAc (100 mL). The organic phase was washed with brine then dried (MgSO₄), filtered and concentrated to dryness. The residue was purified by column chromatography (silica, 0-30% EtOAc in hexanes) to afford the sub-title compound (185 mg, 46%).

$^1$H NMR (300 MHz, CDCl$_3$) δ 0.32 (s, 3H), 0.75 (s, 3H), 0.89 (s, 3H), 1.02 (s, 3H), 1.04 (s, 3H), 1.10 (s, 3H), 1.23 (s, 3H), 1.32-2.05 (m, 20H), 2.30 (m, 1H), 2.45 (m, 1H), 2.98 (m, 1H), 5.10 (m, 2H), 7.10 (d, J=5.7 Hz, 2H), 7.30 (m, 5H), 8.35 (d, J=5.7 Hz, 2H).

(ii) Preparation of 29c: (4aS,6aS,6bR,8aR,12aR, 14bS)-Benzyl 1'-cyano-2,2,6a,6b,9,9,12a-heptamethyl-10-oxo-14-(pyridin-4-yl)-1,2,3,4,4a,5,6,6a,6b, 7,8,8a,9,10,11,12,12a,12b,13,14b-icosahydropicene-4-a-carboxylate To a solution of diisopropylamine (0.16 mL, 1.16 mmol) in THF (5 mL) was added n-butyllithium (0.48 mL, 2.5 M in hexanes, 1.2 mmol) at −78° C. The solution was stirred for 30 min. The LDA solution was added to 29b (326 mg, 0.52 mmol) in THF (5 mL). The mixture was allowed to warm to −40° C. for 5 min and cooled to −78° C. A suspension of p-toluene sulfonyl cyanide (188 mg, 1.0 mmol) in THF (2 mL) was added. The reaction mixture was allowed to warm to −40° C. over 1.5 hours. The reaction was quenched by saturated NH₄Cl (3 mL) and extracted with EtOAc (100 mL). The organic phase was washed with brine then dried (MgSO₄), filtered and concentrated to dryness. The residue was purified by column chromatography (silica, 0-30% EtOAc in hexanes) to afford the sub-title compound (171 mg, 51%).

$^1$H NMR (300 MHz, CDCl$_3$) δ 0.25 (s, 3H), 0.75 (s, 3H), 0.82 (s, 3H), 1.09 (s, 3H), 1.13 (s, 3H), 1.15 (s, 3H), 1.17 (s, 3H), 1.18-2.25 (m, 20H), 2.95 (m, 1H), 3.85 (m, 1H), 5.04 (m, 2H), 7.06 (m, 2H), 7.37 (m, 5H), 8.44 (m, 2H).

(iii) Preparation of 29d: (4aS,6aS,6bR,8aR,13aR, 15bS)-Benzyl 12-amino-2,2,6a,6b,9,9,13a-heptamethyl-15-(pyridin-4-yl)-2,3,4,4a,5,6,6a,6b,7,8,8a,9, 11,13,13a,13b,14,15b-octadecahydro-1H-chryseno[1,2-f]indazole-4-a-carboxylate A mixture of 29c (171 mg, 0.26 mmol) and hydrazine (0.025 mL, 0.80 mmol) in EtOH (3 mL) was heated at reflux overnight. The reaction mixture was concentrated to dryness under reduced pressure. The residue was purified by column chromatography (silica, 0-10% MeOH in CH₂Cl₂) to afford the sub-title compound (143 mg, 83%).

ESI MS (Positive Mode) m/z 661 [C₄₃H₅₆N₄O₂+H]⁺.

(iv) Preparation of 29: (4aS,6aS,6bR,8aR,13aR, 15bS)-12-Amino-2,2,6a,6b,9,9,13a-heptamethyl-15-(pyridin-4-yl)-2,3,4,4a,5,6,6a,6b,7,8,8a,9,11,13,13a, 13b,14,15b-octadecahydro-1H-chryseno[1,2-f] indazole-4-a-carboxylic acid A mixture of 29d (143 mg, 0.21 mmol) and 10% Pd(OH)₂/C (50 mg) in MeOH (15 mL) was stirred under a hydrogen balloon for 12 hours. The reaction mixture was filtered through a pad of diatomaceous earth and washed with CMA (25 mL). The filtrate was concentrated to dryness under reduced pressure. The residue was purified by column chromatography (silica, 0-50% CMA in CH₂Cl₂) to afford the title compound (85 mg, 72%) as a brown solid.

R$_f$ 0.24 (80:18:2 Methylene Chloride/Methanol/concentrated Ammonium Hydroxide).

$^1$H NMR (300 MHz, CD₃OD) δ 0.32 (s, 3H), 0.75 (s, 3H), 0.89 (s, 3H), 0.98 (s, 3H), 1.10 (s, 3H), 1.19 (s, 3H), 1.25 (s, 3H), 1.32-2.28 (m, 20H), 2.32 (d, J=14.7 Hz, 1H), 3.0 (m, 1H), 7.40 (d, J=5.7 Hz, 2H), 8.47 (d, J=5.7 Hz, 1H). mp >300° C. ESI MS (Positive Mode) m/z 571 [C₃₆H₅₆N₄O₂+H]⁺.

EXAMPLE 30

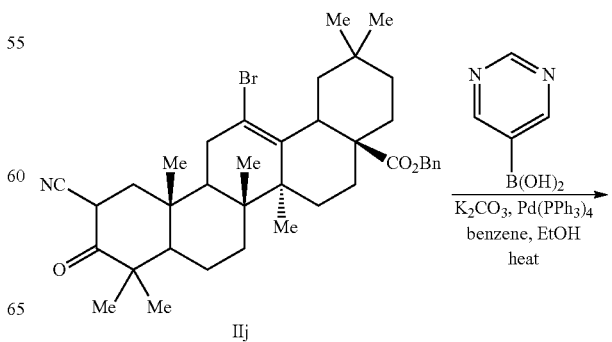

-continued

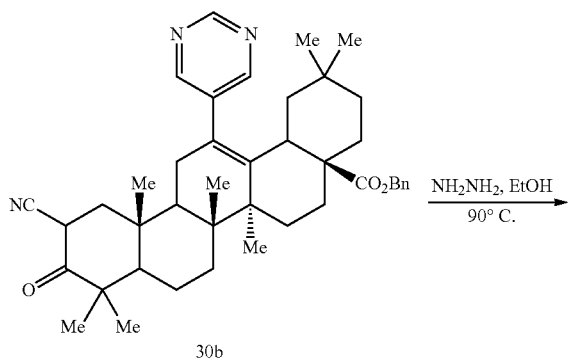

30b

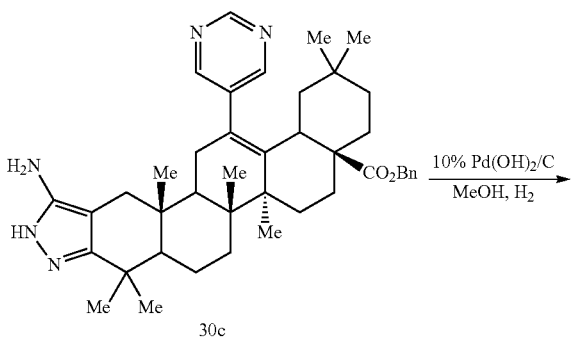

30c

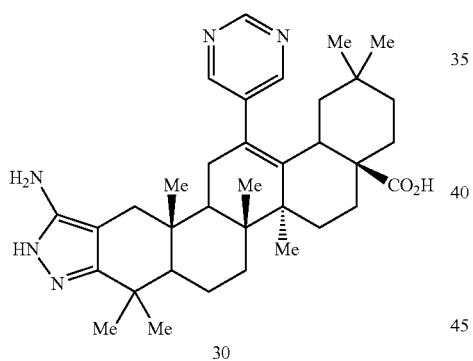

30

(i) Preparation of 30b: (4aS,6aS,6bR,8aR,12aR, 14bS)-Benzyl 11-cyano-2,2,6a,6b,9,9,12a-heptamethyl-10-oxo-14-(pyrimidin-5-yl)-1,2,3,4,4a,5,6,6a, 6b,7,8,8a,9,10,11,12,12a,12b,13,14b-icosahydropicene-4-a-carboxylate A mixture of IIj (200 mg, 0.30 mmol), pyrimidin-5-ylboronic acid (115 mg, 0.91 mmol), Pd(PPh$_3$)$_4$ (34 mg, 0.030 mmol) and K$_2$CO$_3$ (184 mg, 1.33 mmol) in benzene (3.5 mL) and EtOH (1.5 mL) was sealed and heated to 120° C. by microwave for 1 hour. The reaction mixture was diluted with EtOAc (100 mL). The organic phase was washed with brine then dried (MgSO$_4$), filtered and concentrated to dryness. The residue was purified by column chromatography (silica, 0-40% EtOAc in hexanes) to afford the sub-title compound (90 mg, 40%).

(ii) Preparation of 30c: (4aS,6aS,6bR,8aR,13aR, 15bS)-Benzyl 12-amino-2,2,6a,6b,9,9,13a-heptamethyl-15-(pyrimidin-5-yl)-2,3,4,4a,5,6,6a,6b,7,8,8a, 9,11,13,13a,13b,14,15b-octadecahydro-1H-chryseno [1,2-f]indazole-4-a-carboxylate A mixture of 30b (90 mg, 0.13 mmol) and hydrazine (0.04 mL) in EtOH (1.5 mL) was heated at reflux overnight. The reaction mixture was concentrated to dryness under reduced pressure. The residue was purified by column chromatography (silica, 0-30% CMA in CH$_2$Cl$_2$) to afford the sub-title compound (65 mg, 71%).

APCI MS (Positive Mode) m/z 664 [C$_{42}$H$_{55}$N$_5$O$_2$+H]$^+$.

(iii) Preparation of 30: (4aS,6aS,6bR,8aR,13aR, 15bS)-12-Amino-2,2,6a,6b,9,9,13a-heptamethyl-15-(pyrimidin-5-yl)-2,3,4,4a,5,6,6a,6b,7,8,8a,9,11,13, 13a,13b,14,15b-octadecahydro-1H-chryseno[1,2-f] indazole-4-a-carboxylic acid A mixture of 30c (65 mg, 0.098 mmol) and 10% Pd(OH)$_2$/C (30 mg) in MeOH (10 mL) was stirred under a hydrogen balloon for 5 hours. The reaction mixture was filtered through a pad of diatomaceous earth and washed with CMA (25 mL). The filtrate was concentrated to dryness under reduced pressure. The residue was purified by column chromatography (silica, 0-60% CMA in CH$_2$Cl$_2$) to afford the title compound (32 mg, 57%) as a brown solid.

R$_f$ 0.50 (80:18:2 Methylene Chloride/Methanol/concentrated Ammonium Hydroxide).

$^1$H NMR (300 MHz, CD$_3$OD) δ 0.31 (s, 3H), 0.80 (s, 3H), 0.89 (s, 3H), 1.02 (s, 3H), 1.20 (s, 3H), 1.25 (s, 3H), 1.31 (s, 3H), 1.32-2.30 (m, 21H), 2.33 (d, J=14.8 Hz, 1H), 2.88 (m, 1H), 8.78 (s, 1H), 9.04 (s, 1H). mp >300° C. APCI MS (Positive Mode) m/z 572 [C$_{35}$H$_{49}$N$_5$O$_2$+H]$^+$.

EXAMPLE 31

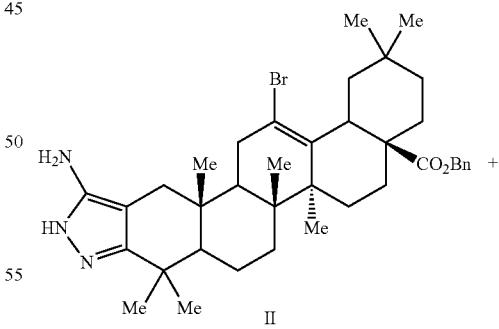

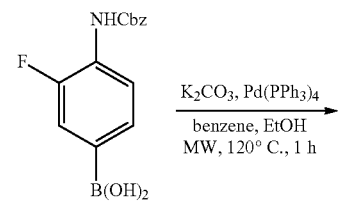

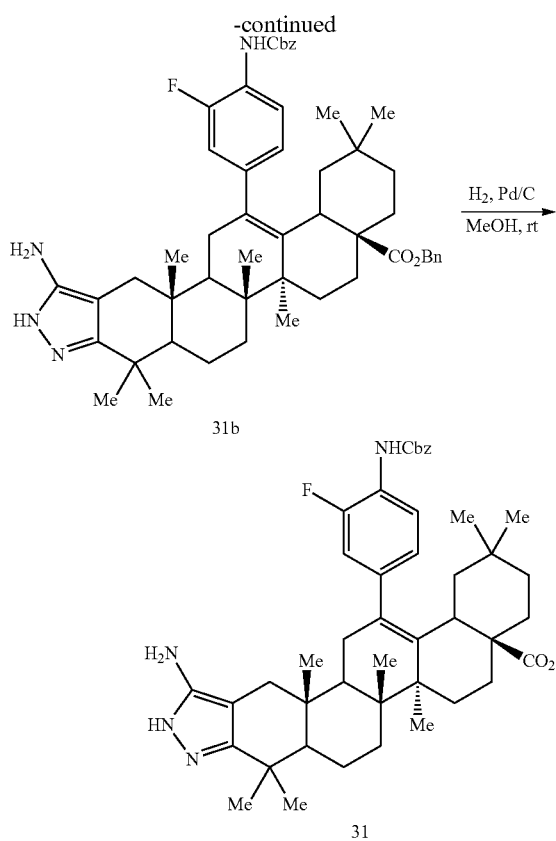

31b

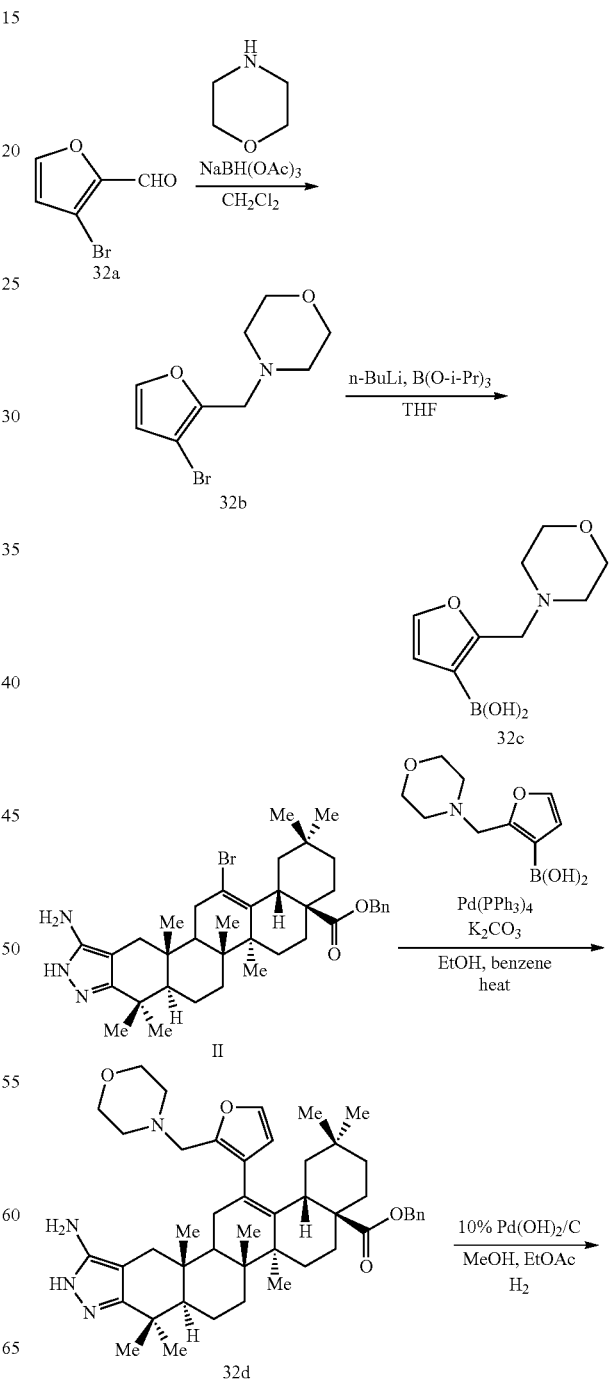

fied by column chromatography (silica, 0-30% CMA in CH₂Cl₂) followed by preparative HPLC to afford the title compound (35 mg, 21%) as as solid.

R$_f$ 0.74 (40:9:1 Methylene Chloride/Methanol/concentrated Ammonium Hydroxide).

$^1$H NMR (300 MHz, CD$_3$OD) δ 0.37-2.43 (m, 41H), 3.07 (dd, J=3.4, 6.5 Hz, 1H), 6.99-7.10 (m, 3H). APCI MS m/z 603 [C$_{37}$H$_{51}$FN$_4$O$_2$+H]$^+$. m.p. 180-200° C. dec. HPLC (Method A)>99% (214 nm) t$_R$=13.4 min.

EXAMPLE 32

(i) Preparation of 31b: (4aS,6aS,6bR,13aR)-Benzyl 12-amino-15-(4-(benzyloxycarbonylamino)-3-fluorophenyl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylate To a mixture of II (200 mg, 0.30 mmol) and 4-(benzyloxycarbonylamino)-3-fluorophenylboronic acid (262 mg, 0.90 mmol) in benzene (4 mL) and EtOH (1 mL) was added K₂CO₃ (166 mg, 1.20 mmol). The mixture was sparged with nitrogen and then Pd(PPh₃)₄ (69 mg, 0.06 mmol) was added. The reaction mixture was heated at 120° C. for 1 hour using microwave irradiation and then solvent was removed under reduced pressure. The residue was dissolved in EtOAc (20 mL) and washed with brine. The organic layer was dried (Na₂SO₄), filtered and concentrated. The residue was purified by column chromatography (silica, 0-10% MeOH in CH₂Cl₂) to afford the sub-title compound (190 mg, 76%).

APCI MS m/z 827 [C$_{52}$H$_{63}$N$_4$O$_4$+H]$^+$.

(ii) Preparation of 31: (4aS,6aS,6bR,13aR)-12-Amino-15-(4-amino-3-fluorophenyl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylic acid A solution of 31b (190 mg, 0.22 mmol) and MeOH (15 mL) was flushed with nitrogen and then 10% Pd/C (300 mg) was added. The mixture was flushed with nitrogen followed by hydrogen. The mixture was stirred under hydrogen at atmospheric pressure overnight. The catalyst was removed by filtration through diatomaceous earth and the filtrate was concentrated under reduced pressure. The residue was puri-

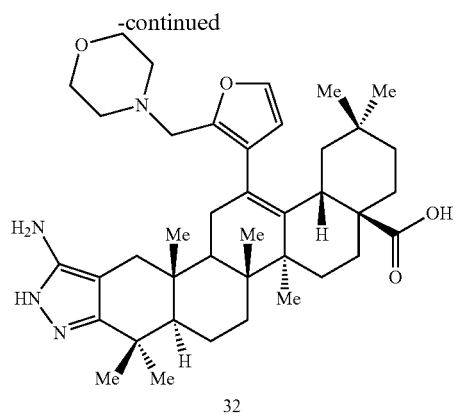

32

(i) Preparation of 32b:
4-((3-Bromofuran-2-yl)methyl)morpholine

To a solution of 3-bromofuran-2-carbaldehyde (500 mg, 2.85 mmol) and morpholine (0.5 mL, 5.71 mmol) in $CH_2Cl_2$ (10 mL) was added sodium triacetoxyborohydride (1.2 g, 5.71 mmol). The mixture was stirred at room temperature for 12 hours. The reaction mixture was diluted with EtOAc (100 mL). The organic phase was washed with aqueous $NaHCO_3$ and brine then dried ($MgSO_4$), filtered and concentrated to dryness. The residue was purified by column chromatography (silica, 0-10% MeOH in $CH_2Cl_2$) to afford the sub-title compound (670 mg, 89%).
$^1$H NMR (300 MHz, $CDCl_3$) δ 2.50 (s, 4H), 3.62 (s, 2H), 3.70 (m, 4H), 6.43 (s, 1H), 7.35 (s, 1H).

(ii) Preparation of 32c:
2-(Morpholinomethyl)furan-3-ylboronic acid

To a solution of 32b (670 mg, 2.54 mmol) in THF (15 mL) was added n-butyllithium (2.5 M in hexanes, 1.30 mL, 3.31 mmol) at −78° C. The mixture was stirred at −78° C. for 20 min. Triisopropyl borate (2.9 mL, 12.7 mmol) was added. The reaction mixture was stirred at −78° C. for 1 hour and quenched with HCl (2 M, 4 mL). The reaction mixture was stirred for 5 min and neutralized by NaOH (2 M) and extracted with EtOAc (100 mL). The organic phase was washed with brine then dried ($MgSO_4$), filtered and concentrated to dryness. The residue was purified by column chromatography (silica, 0-10% MeOH in $CH_2Cl_2$) to afford the sub-title compound (450 mg, 83%).
$^1$H NMR (300 MHz, $CDCl_3$) δ 2.40 (s, 4H), 3.65 (s, 2H), 3.68 (m, 4H), 6.52 (s, 1H), 7.30 (s, 1H).

(iii) Preparation of 32d: (4aS,6aS,6bR,8aR,13aR, 15bS)-Benzyl 12-amino-2,2,6a,6b,9,9,13a-heptamethyl-15-(2-(morpholinomethyl)furan-3-yl)-2,3,4,4a, 5,6,6a,6b,7,8,8a,9,11,13,13a,13b,14,15b-octadecahydro-1H-chryseno[1,2-f]indazole-4-a-carboxylate A mixture of II (200 mg, 0.30 mmol), 32c (250 mg, 1.18 mmol), Pd(PPh$_3$)$_4$ (35 mg, 0.030 mmol) and $K_2CO_3$ (207 mg, 1.50 mmol) in benzene (3.5 mL) and EtOH (1.5 mL) was sealed and heated to 120° C. by microwave for 1 hour. The reaction mixture was diluted with EtOAc (100 mL). The organic phase was washed with brine then dried ($MgSO_4$), filtered and concentrated to dryness. The residue was purified by column chromatography (silica, 0-10% MeOH in $CH_2Cl_2$) to afford the sub-title compound (135 mg, 60%).
APCI MS (Positive Mode) m/z 749 $[C_{47}H_{64}N_4O_4+H]^+$.

(iv) Preparation of 32: (4aS,6aS,6bR,8aR,13aR, 15bS)-12-Amino-2,2,6a,6b,9,9,13a-heptamethyl-15-(2-(morpholinomethyl)furan-3-yl)-2,3,4,4a,5,6,6a, 6b,7,8,8a,9,11,13,13a,13b,14,15b-octadecahydro-1H-chryseno[1,2-f]indazole-4-a-carboxylic acid A mixture of 32d (135 mg, 0.18 mmol) and 10% Pd(OH)$_2$/C (100 mg) in MeOH (12 mL) and EtOAc (3 mL) was stirred under a hydrogen balloon for 6 hours. The reaction mixture was filtered through a pad of diatomaceous earth and washed with CMA (25 mL). The filtrate was concentrated to dryness under reduced pressure. The residue was purified by column chromatography (silica, 0-50% CMA in CMA) to afford the title compound (35 mg, 30%) as a brown solid.
R$_f$ 0.63 (80:18:2 Methylene Chloride/Methanol/concentrated Ammonium Hydroxide).
$^1$H NMR (300 MHz, $CD_3OD$) δ 0.55 (s, 3H), 0.81 (s, 3H), 0.89 (s, 3H), 0.99 (s, 3H), 1.14 (s, 3H), 1.28 (s, 6H), 1.35-2.28 (m, 20H), 2.61 (m, 4H), 2.90 (m, 1H), 3.53 (m, 6H), 6.33 (s, 1H), 7.45 (s, 1H). mp >300° C. dec. APCI MS (Positive Mode) m/z 659 $[C_{40}H_{58}N_4O_4+H]^+$.

EXAMPLE 33

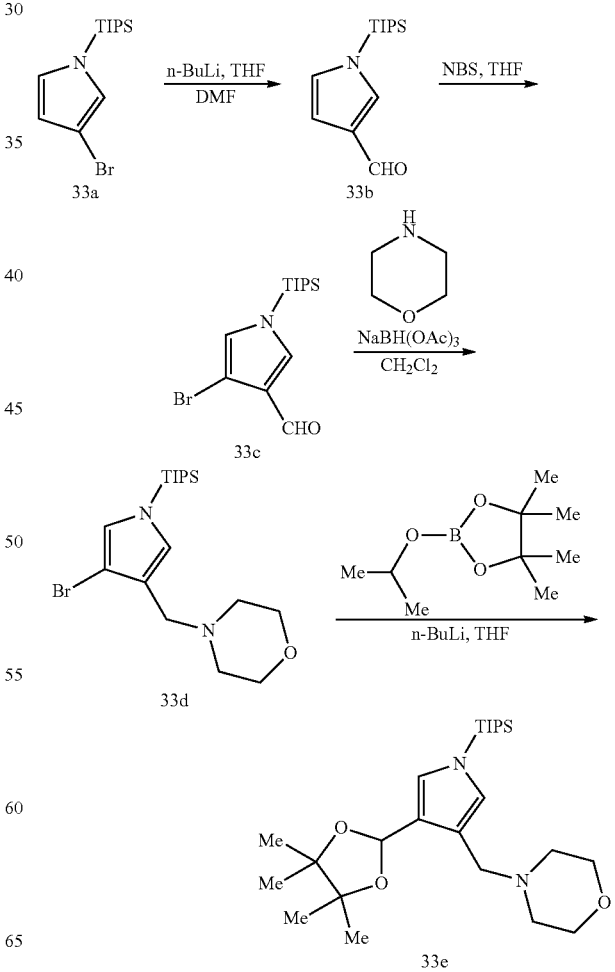

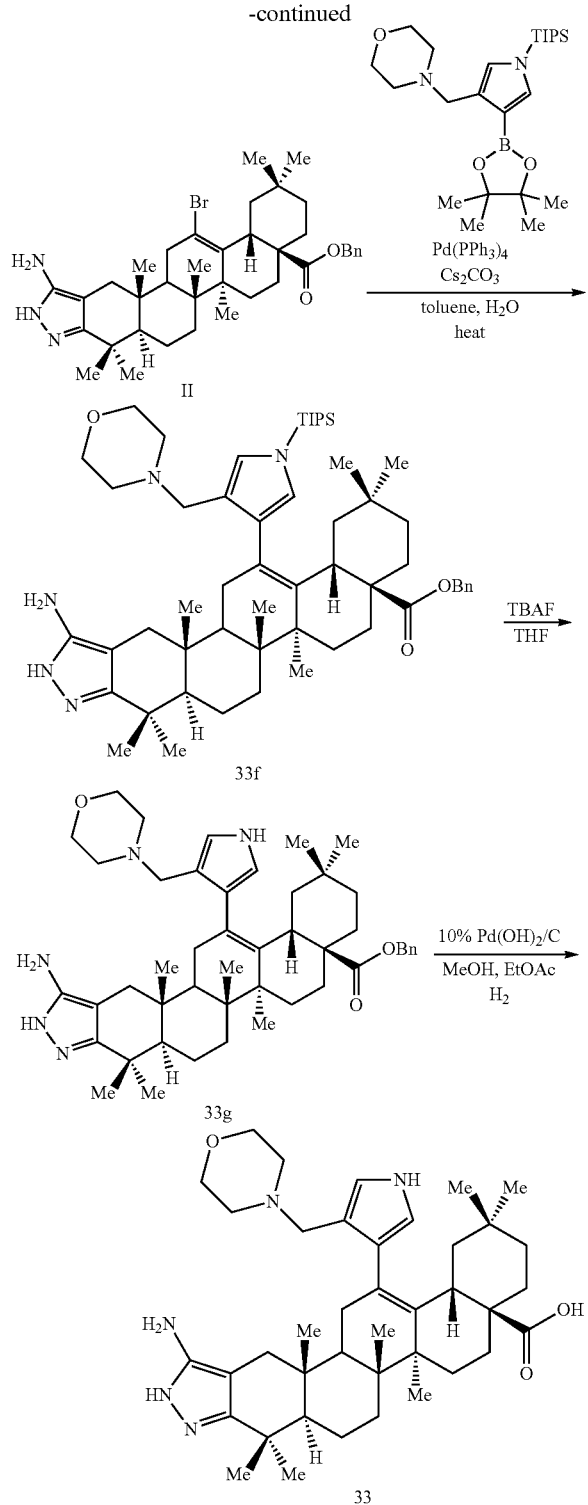

over 1 hour. The reaction mixture was quenched by saturated NH₄Cl and extracted with EtOAc (200 mL). The organic phase was washed with brine then dried (MgSO₄), filtered and concentrated to dryness. The residue was purified by column chromatography (silica, 0-10% EtOAc in hexanes) to afford the sub-title compound (1.65 g, 100%).

¹H NMR (400 MHz, CDCl₃) δ 2.40 (m, 4H), 3.42 (s, 2H), 3.70 (m, 4H), 6.03 (s, 1H), 6.09 (s, 1H), 6.74 (s, 1H), 8.30 (bs, 1H).

(ii) Preparation of 33c: 4-Bromo-1-(triisopropylsilyl)-1H-pyrrole-3-carbaldehyde To a solution of 33b (1.45 g, 5.8 mmol) in THF (40 mL) was added N-bromosuccinimide (1.03 g, 5.8 mmol) at room temperature. The mixture was stirred for 2 hours and quenched with H₂O (5 mL) and extracted with EtOAc (100 mL). The organic phase was washed with brine then dried (MgSO₄), filtered and concentrated to dryness. The residue was purified by column chromatography (silica, 0-10% EtOAc in hexanes) to afford the sub-title compound (1.4 g, 74%).

¹H NMR (400 MHz, CDCl₃) δ 1.15 (d, J=2.5 Hz, 18H), 1.58 (m, 3H), 6.70 (s, 1H), 7.32 (s, 1H), 9.82 (s, 1H).

(iii) Preparation of 33d: 4-((4-Bromo-1-(triisopropylsilyl)-1H-pyrrol-3-yl)methyl)morpholine To a solution of 33c (1.5 g, 4.5 mmol) and morpholine (0.79 mL, 9.0 mmol) in CH₂Cl₂ (30 mL) was added sodium triacetoxyborohydride (1.9 g, 9.0 mmol). The mixture was stirred at room temperature for 12 hours. The reaction mixture was diluted with EtOAc (200 mL). The organic phase was washed with aqueous NaHCO₃ and brine then dried (MgSO₄), filtered and concentrated to dryness. The residue was purified by column chromatography (silica, 0-10% EtOAc in hexanes) to afford the sub-title compound (1.8 g, 91%).

¹H NMR (400 MHz, CDCl₃) δ 1.15 (d, J=2.5 Hz, 18H), 1.58 (m, 3H), 2.40 (m, 4H), 3.40 (s, 2H), 3.72 (m, 4H), 6.61 (s, 1H), 6.65 (s, 1H).

(iv) Preparation of 33e: 4-((4-(4,4,5,5-Tetramethyl-1,3-dioxolan-2-yl)-1-(triisopropylsilyl)-1H-pyrrol-3-yl)methyl)morpholine To a solution of 33d (400 mg, 1.0 mmol) was added n-butyllithium (2.5 M in hexanes, 0.52 mmol, 1.3 mmol) at −78° C. The mixture was stirred for 20 min and 2-isopropoxy-4,4,5,5-tetramethyl-1,3,2-dioxaborolane (0.24 mL, 1.2 mmol) was added. The mixture was stirred at −78° C. for 30 min and warmed to room temperature over 1 hour. The reaction was quenched with H₂O and extracted with EtOAc (100 mL). The organic phase was washed with brine then dried (MgSO₄), filtered and concentrated to dryness. The residue was subjected to column chromatography (silica, 0-50% EtOAc in hexanes) to afford the still impure sub-title compound (448 mg, 100%) which was used without further purification.

(v) Preparation of 33f: (4aS,6aS,6bR,8aR,13aR,15bS)-Benzyl 12-amino-2,2,6a,6b,9,9,13a-heptamethyl-15-(4-(morpholinomethyl)-1-(triisopropylsilyl)-1H-pyrrol-3-yl)-2,3,4,4a,5,6,6a,6b,7,8,8a,9,11,13,13a,13b,14,15b-octadecahydro-1H-chryseno[1,2-f]indazole-4-a-carboxylate A mixture of II (200 mg, 0.30 mmol), 33e (500 mg, 1.06 mmol), Pd(PPh₃)₄ (35 mg, 0.030 mmol) and cesium carbon- (i) Preparation of 33b: 1-(Triisopropylsilyl)-1H-pyrrole-3-carbaldehyde To a solution of 3-bromo-1-(triisopropylsilyl)-1H-pyrrole (2.0 g, 6.61 mmol) in THF (30 mL) was added n-butyllithium (2.5 M in hexanes, 3.4 mL, 8.60 mmol) at −78° C. The mixture was stirred at −78° C. for 10 min then DMF (0.76 mL, 9.92 mmol) was added and the mixture was warmed to 0° C.

ate (390 mg, 1.20 mmol) in toluene (4.5 mL) and H$_2$O (0.3 mL) was sealed and heated to 140° C. by microwave for 1 hour. The reaction mixture was diluted with EtOAc (100 mL). The organic phase was washed with brine then dried (MgSO$_4$), filtered and concentrated to dryness. The residue was purified by column chromatography (silica, 0-10% MeOH in CH$_2$Cl$_2$) to afford the sub-title compound (176 mg, 65%).

(vi) Preparation of 33g: (4aS,6aS,6bR,8aR,13aR, 15bS)-Benzyl 12-amino-2,2,6a,6b,9,9,13a-heptamethyl-15-(4-(morpholinomethyl)-1H-pyrrol-3-yl)-2, 3,4,4a,5,6,6a,6b,7,8,8a,9,11,13,13a,13b,14,15b-octadecahydro-1H-chryseno[1,2-f]indazole-4-a-carboxylate To a solution of 33f (176 mg, 0.19 mmol) in THF (3 mL) was added tetrabutylammonium fluoride (0.38 mL, 1 M in THF, 0.38 mmol). The mixture was stirred at room temperature for 2 hours. The reaction mixture was diluted with EtOAc (100 mL). The organic phase was washed with brine then dried (MgSO$_4$), filtered and concentrated to dryness. The residue was purified by column chromatography (silica, 0-10% MeOH in CH$_2$Cl$_2$) to afford the sub-title compound (60 mg, 42%).

APCI MS (Positive Mode) m/z 748 [C$_{47}$H$_{65}$N$_5$O$_3$+H]$^+$.

(vii) Preparation of 33: (4aS,6aS,6bR,8aR,13aR, 15bS)-12-Amino-2,2,6a,6b,9,9,13a-heptamethyl-15-(4-(morpholinomethyl)-1H-pyrrol-3-yl)-2,3,4,4a,5,6, 6a,6b,7,8,8a,9,11,13,13a,13b,14,15b-octadecahydro-1H-chryseno[1,2-f]indazole-4-a-carboxylic acid A mixture of 33g (60 mg, 0.08 mmol) and 10% Pd(OH)$_2$/C (30 mg) in MeOH (12 mL) and EtOAc (3 mL) was stirred under a hydrogen balloon for 6 hours. The reaction mixture was filtered through a pad of diatomaceous earth and washed with CMA (25 mL). The filtrate was concentrated to dryness under reduced pressure. The residue was purified by column chromatography (silica, 0-70% CMA in CMA) to afford the title compound (35 mg, 67%) as a brown solid.

R$_f$ 0.54 (80:18:2 Methylene Chloride/Methanol/concentrated Ammonium Hydroxide).

$^1$H NMR (400 MHz, CD$_3$OD) δ 0.55 (s, 3H), 0.85 (s, 3H), 0.92 (s, 3H), 1.12 (s, 3H), 1.15 (s, 3H), 1.38 (m, 6H), 1.39-2.20 (m, 21H), 2.26 (d, J=14.4 Hz, 1H), 2.90 (m, 1H), 3.12 (m, 3H), 3.75 (m, 6H), 6.55 (s, 1H), 7.92 (s, 1H). mp >300° C. dec. APCI MS (Positive Mode) m/z 658 [C$_{40}$H$_{59}$N$_5$O$_3$+H]$^+$.

EXAMPLE 34

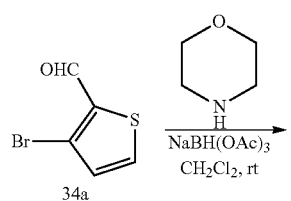

34a

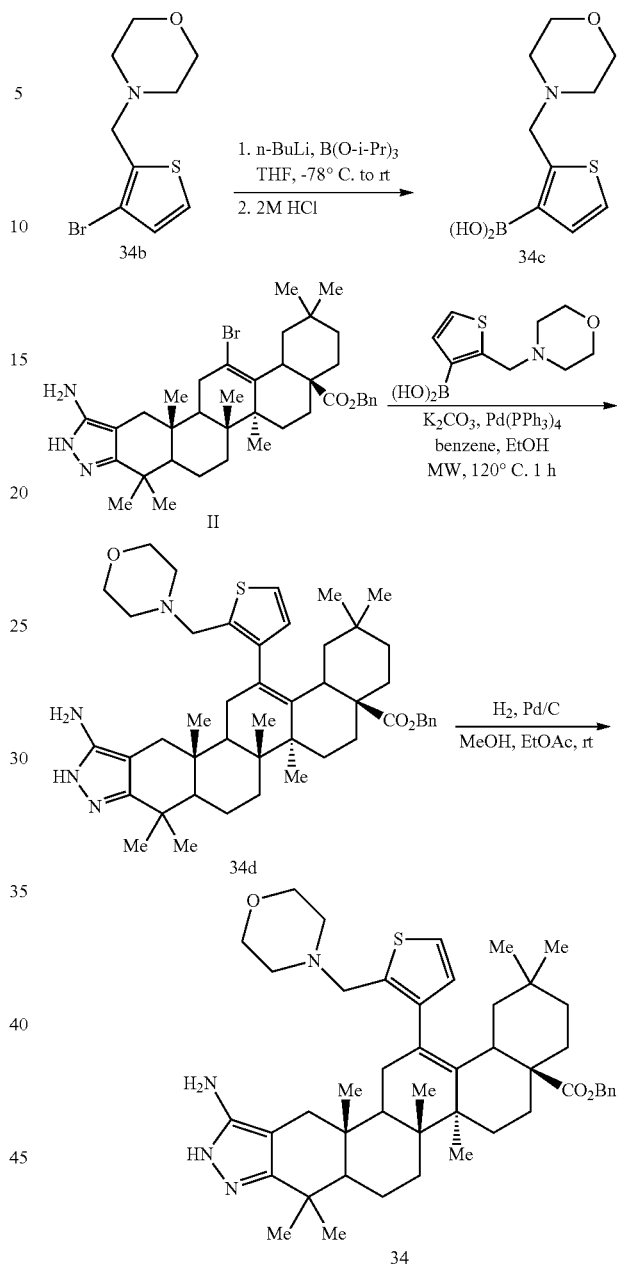

(i) Preparation of 34b:
4-((3-Bromothiophen-2-yl)methyl)morpholine

To a solution of 3-bromothiophene-2-carbaldehyde (500 mg, 2.62 mmol) and morpholine (0.68 mL, 7.85 mmol) and CH$_2$Cl$_2$ (10 mL) was added sodium triacetoxyborohydride (1.11 g, 5.24 mmol). The mixture was stirred at room temperature overnight. The resulting mixture was diluted with EtOAc (100 mL) and the organic layer was washed with brine then dried (Na$_2$SO$_4$), filtered and concentrated. The residue was purified by column chromatography (silica, 0-5% MeOH in CH$_2$Cl$_2$) to afford the sub-title compound (580 mg, 84%).

$^1$H NMR (300 MHz, CDCl$_3$) δ 2.47-2.54 (m, 4H), 3.68-3.71 (m, 4H), 6.90 (d, J=5.2 Hz, 1H), 7.23 (d, J=5.2 Hz, 1H).

(ii) Preparation of 34c: 2-(Morpholinomethyl)thiophen-3-ylboronic acid

To a solution of 34b (500 mg, 1.90 mmol) in THF (10 mL) was added n-butyllithium (1.14 mL, 2.86 mmol) at −78° C. After stifling for 20 min, triisopropyl borate (1.99 mL, 8.69 mmol) was added at −78° C. The mixture was slowly warmed to room temperature and then quenched with aqueous HCl (2.0 M, 2 mL). The reaction mixture was neutralized with 2 M NaOH solution and extracted with EtOAc (3×10 mL) followed by i-PrOH/$CH_2Cl_2$ (1:2, 10 mL×2). The combined extracts were dried ($Na_2SO_4$), filtered and concentrated under reduced pressure. The residue was purified by column chromatography (silica, 0-10% MeOH in $CH_2Cl_2$) to afford the sub-title compound (220 mg, 51%).

$^1$H NMR (300 MHz, $CDCl_3$) δ 2.47-2.49 (m, 4H), 3.52-3.76 (m, 6H), 6.91-6.98 (m, 1H), 7.22-7.24 (m, 1H).

(iii) Preparation of 34d: (4aS,6aS,6bR,13aR)-Benzyl 12-amino-2,2,6a,6b,9,9,13a-heptamethyl-15-(2-(morpholinomethyl)thiophen-3-yl)-2,3,4,4a,5,6,6a,6b,7,8,8a,9,11,13,13a,13b,14,15b-octadecahydro-1H-chryseno[1,2-f]indazole-4-a-carboxylate To a mixture of II (250 mg, 0.38 mmol) and 34c (220 mg, 0.96 mmol) in benzene (4 mL) and EtOH (1 mL) was added $K_2CO_3$ (182 mg, 1.32 mmol). The mixture was sparged with nitrogen and then Pd(PPh$_3$)$_4$ (87 mg, 0.075 mmol) was added. The reaction mixture was heated at 120° C. for 1 hour using microwave irradiation. The solvent was concentrated under reduced pressure. The residue was taken up in EtOAc (20 mL) and washed with brine. The organic layer was dried ($Na_2SO_4$), filtered and concentrated. The residue was purified by column chromatography (silica, 0-10% MeOH in $CH_2Cl_2$) to afford the sub-title compound (190 mg, 66%).

APCI MS m/z 765 $[C_{47}H_{64}N_4O_3S+H]^+$.

(iv) Preparation of 34: (4aS,6aS,6bR,13aR)-12-Amino-2,2,6a,6b,9,9,13a-heptamethyl-15-(2-(morpholinomethyl)thiophen-3-yl)-2,3,4,4a,5,6,6a,6b,7,8,8a,9,11,13,13a,13b,14,15b-octadecahydro-1H-chryseno[1,2-f]indazole-4-a-carboxylic acid A solution of 34d (190 mg, 0.24 mmol), EtOH (2 mL) and MeOH (8 mL) was flushed with nitrogen and then 10% Pd/C (400 mg) was added. The mixture was flushed with nitrogen followed by hydrogen. The mixture was stirred under hydrogen at atmospheric pressure overnight. The catalyst was removed by filtration through diatomaceous earth and the filtrate was concentrated. The residue was purified by column chromatography (silica, 0-50% CMA in $CH_2Cl_2$) followed by preparative HPLC to afford the title compound (18 mg, 11%) as a solid.

$R_f$ 0.13 (90:9:1 Methylene Chloride/Methanol/concentrated Ammonium Hydroxide).

$^1$H NMR (300 MHz, $CD_3OD$) δ 0.40 (s, 3H), 0.80 (s, 3H), 0.92 (s, 3H), 1.05 (s, 3H), 1.10-2.67 (m, 32H), 3.30 (s, 3H), 3.97 (s, 4H), 4.57-4.62 (m, 1H), 6.95 (d, J=4.95 Hz, 1H), 7.67 (d, J=4.95 Hz, 1H). APCI MS m/z 675 $[C_{40}H_{58}N_4O_3S+H]^+$. m.p. 280-300° C. dec. HPLC (Method A) 98.7% (214 nm) $t_R$=12.9 min.

EXAMPLE 35

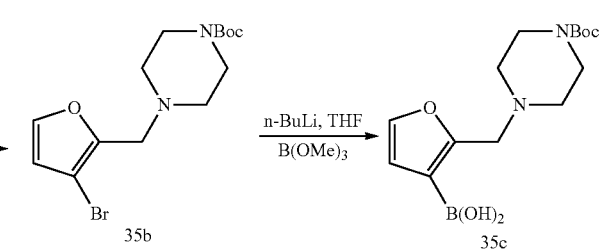

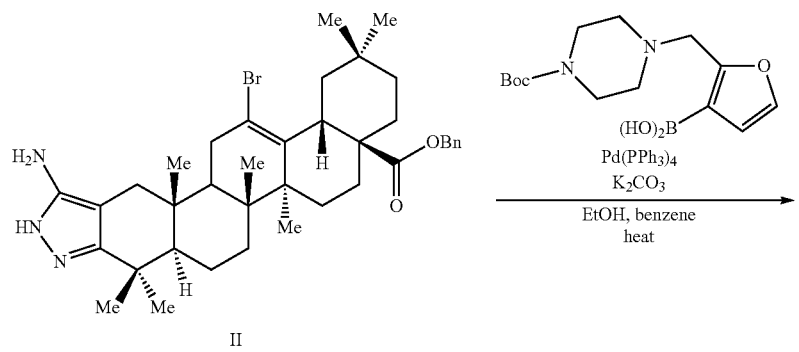

-continued

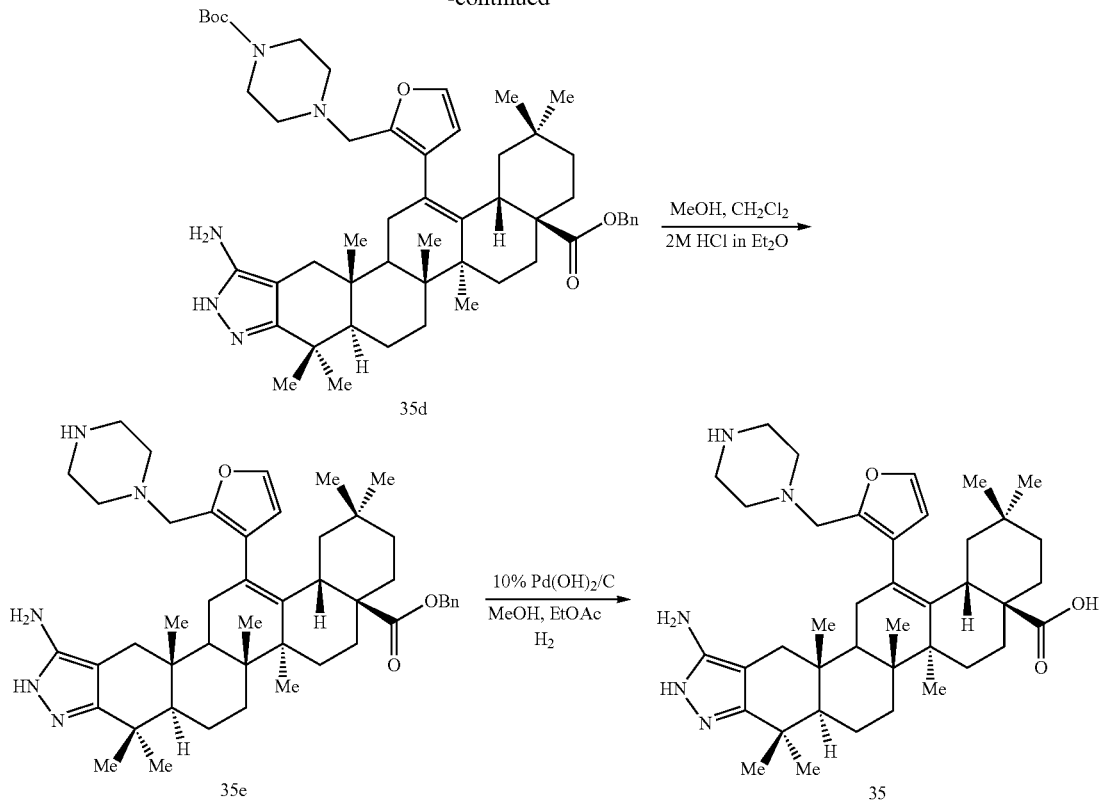

(i) Preparation of 35b: tert-Butyl 4-((3-bromofuran-2-yl)methyl)piperazine-1-carboxylate To a solution of 3-bromofuran-2-carbaldehyde (500 mg, 2.85 mmol) and tert-butyl piperazine-1-carboxylate (1.1 g, 5.71 mmol) in $CH_2Cl_2$ (10 mL) was added sodium triacetoxyborohydride (1.2 g, 5.71 mmol). The mixture was stirred at room temperature for 12 hours. The reaction mixture was diluted with EtOAc (100 mL). The organic phase was washed with aqueous $NaHCO_3$ and brine then dried ($MgSO_4$), filtered and concentrated to dryness. The residue was purified by column chromatography (silica, 0-10% MeOH in $CH_2Cl_2$) to afford the sub-title compound (910 mg, 92%).

$^1$H NMR (300 MHz, $CDCl_3$) δ 1.42 (s, 9H), 2.40 (m, 4H), 3.42 (m, 4H), 3.60 (s, 2H), 6.35 (s, 1H), 7.35 (s, 1H).

(ii) Preparation of 35c: 2-((4-(tert-Butoxycarbonyl)piperazin-1-yl)methyl)furan-3-ylboronic acid To a solution of 35b (910 mg, 2.63 mmol) in THF (20 mL) was added n-butyllithium (2.5 M in hexanes, 1.4 mL, 3.43 mmol) at −78° C. The mixture was stirred at −78° C. for 20 minutes. Triisopropyl borate (3.0 mL, 13.2 mmol) was added. The reaction mixture was stirred at −78° C. for 1 hour and quenched with HCl (2 M, 4 mL). The reaction mixture was stirred for 5 min then neutralized by NaOH (2 M) and extracted with EtOAc (100 mL). The organic phase was washed with brine then dried ($MgSO_4$), filtered and concentrated to dryness. The residue was purified by column chromatography (silica, 0-10% MeOH in $CH_2Cl_2$) to afford the sub-title compound (560 mg, 68%).

$^1$H NMR (300 MHz, $CDCl_3$) δ 1.42 (s, 9H), 2.40 (m, 4H), 3.65 (m, 4H), 3.68 (s, 2H), 6.52 (s, 1H), 7.31 (s, 1H).

(iii) Preparation of 35d: (4aS,6aS,6bR,8aR,13aR,15bS)-Benzyl 12-amino-15-(2-((4-(tert-butoxycarbonyl)piperazin-1-yl)methyl)furan-3-yl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylate A mixture of II (300 mg, 0.45 mmol), 35c (418 mg, 1.35 mmol), $Pd(PPh_3)_4$ (52 mg, 0.045 mmol) and $K_2CO_3$ (248 mg, 1.80 mmol) in benzene (3.5 mL) and EtOH (1.5 mL) was sealed and heated to 120° C. by microwave for 1 hour. The reaction mixture was diluted with EtOAc (100 mL). The organic phase was washed with brine then dried ($MgSO_4$), filtered and concentrated to dryness. The residue was purified by column chromatography (silica, 0-10% MeOH in $CH_2Cl_2$) to afford the sub-title compound (400 mg, 100%).

APCI MS (Positive Mode) m/z 848 $[C_{52}H_{73}N_5O_5+H]^+$.

(iv) Preparation of 35e: (4aS,6aS,6bR,8aR,13aR,15bS)-Benzyl 12-amino-2,2,6a,6b,9,9,13a-heptamethyl-15-(2-(piperazin-1-ylmethyl)furan-3-yl)-2,3,4,4a,5,6,6a,6b,7,8,8a,9,11,13,13a,13b,14,15b-octadecahydro-1H-chryseno[1,2-f]indazole-4-a-carboxylate To a solution of 35d (400 mg, 0.45 mmol) in MeOH (3 mL) and $CH_2Cl_2$ (2 mL) was added HCl (2.3 mL, 2 M in $Et_2O$, 4.6 mmol). The mixture was stirred at room temperature for 12 hours. The reaction mixture was concentrated to dryness. The residue was purified by column chromatography (silica, 0-10% MeOH in $CH_2Cl_2$) to afford the sub-title compound (250 mg, 74%).

APCI MS (Positive Mode) m/z 748 $[C_{47}H_{65}N_5O_3+H]^+$.

(v) Preparation of 35: (4aS,6aS,6bR,8aR,13aR, 15bS)-12-Amino-2,2,6a,6b,9,9,13a-heptamethyl-15-(2-(piperazin-1-ylmethyl)furan-3-yl)-2,3,4,4a,5,6,6a, 6b,7,8,8a,9,11,13,13a,13b,14,15b-octadecahydro-1H-chryseno[1,2-f]indazole-4-a-carboxylic acid A mixture of 35e (250 mg, 0.33 mmol) and 10% Pd(OH)$_2$/C (110 mg) in MeOH (15 mL) and EtOAc (5 mL) was stirred under a hydrogen balloon for 12 hours. The reaction mixture was filtered through a pad of diatomaceous earth and washed with CMA (25 mL). The filtrate was concentrated to dryness under reduced pressure. The residue was purified by column chromatography (silica, 0-10% MeOH in CMA) to afford the title compound (160 mg, 75%) as a brown solid.
R$_f$ 0.20 (80:28:2 Methylene Chloride/Methanol/concentrated Ammonium Hydroxide).
$^1$H NMR (300 MHz, CD$_3$OD) δ 0.55 (s, 3H), 0.78 (s, 3H), 0.86 (s, 3H), 0.94 (s, 3H), 1.12 (s, 3H), 1.21 (s, 3H), 1.24 (s, 3H), 1.35-2.18 (m, 19H), 2.36 (d, J=14.8 Hz, 1H), 2.73 (m, 4H), 3.0 (m, 1H), 3.18 (m, 4H), 3.52 (m, 1H), 3.90 (m, 1H), 6.33 (s, 1H), 7.44 (s, 1H). mp >300° C. APCI MS (Positive Mode) m/z 658 [C$_{40}$H$_{59}$N$_5$O$_3$+H]$^+$.

EXAMPLE 36

(i) Preparation of 36b: 1-((3-Bromofuran-2-yl)methyl)-4-methylpiperazine

To a solution of 3-bromofuran-2-carbaldehyde (500 mg, 2.85 mmol), 1-methylpiperazine dihydrochloride (986 mg, 5.71 mmol) and triethylamine (1.5 mL, 11.4 mmol) in CH$_2$Cl$_2$ (10 mL) was added sodium triacetoxyborohydride (1.2 g, 5.71 mmol). The mixture was stirred at room temperature for 12 hours. The reaction mixture was diluted with EtOAc (100 mL). The organic phase was washed with aqueous NaHCO$_3$ and brine then dried (MgSO$_4$), filtered and concentrated to dryness. The residue was purified by column chromatography (silica, 0-10% MeOH in CH$_2$Cl$_2$) to afford the sub-title compound (570 mg, 78%).
$^1$H NMR (300 MHz, CDCl$_3$) δ 2.25 (s, 3H), 2.40 (m, 4H), 2.60 (m, 4H), 3.60 (s, 2H), 6.35 (s, 1H), 7.35 (s, 1H).

(ii) Preparation of 36c: 2-((4-Methylpiperazin-1-yl)methyl)furan-3-ylboronic acid To a solution of 36b (570 mg, 2.20 mmol) in THF (15 mL) was added n-butyllithium (2.5 M in hexanes, 1.1 mL, 2.80 mmol) at −78° C. The mixture was stirred at −78° C. for 20 minutes. Triisopropyl borate (2.5 mL, 11.0 mmol) was added. The reaction mixture was stirred at −78° C. for 1 hour and quenched with HCl (2 M, 4 mL). The reaction mixture was

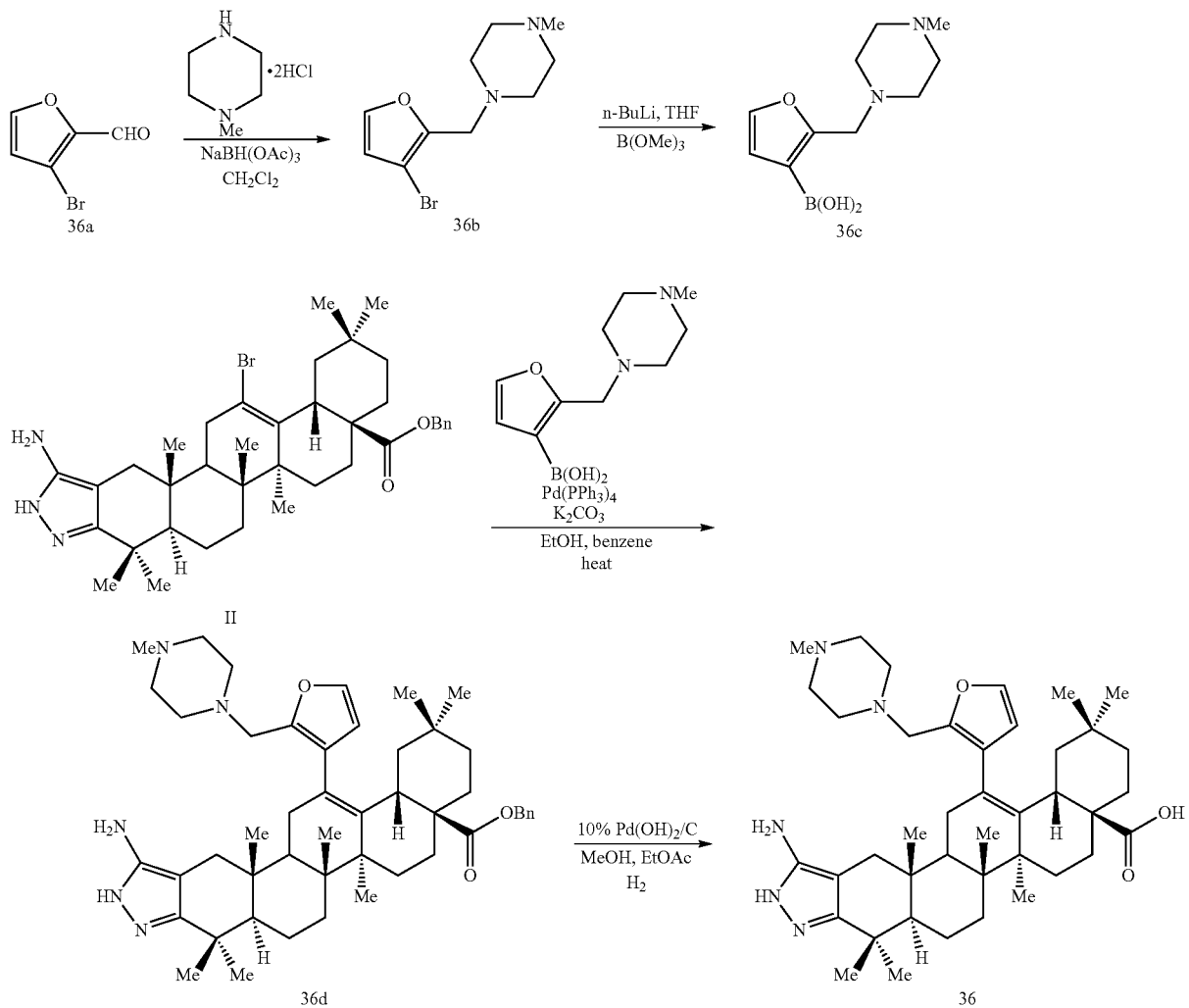

stirred for 5 min then neutralized by NaOH (2 M) and extracted with EtOAc (100 mL). The organic phase was washed with brine then dried (MgSO$_4$), filtered and concentrated to dryness. The residue was purified by column chromatography (silica, 0-15% MeOH in CH$_2$Cl$_2$) to afford the sub-title compound (200 mg, 41%).

$^1$H NMR (300 MHz, CD$_3$OD) δ 2.32 (s, 3H), 2.40 (m, 4H), 2.80 (m, 4H), 3.95 (s, 2H), 6.46 (s, 1H), 7.38 (s, 1H).

(iii) Preparation of 36d: (4aS,6aS,6bR,8aR,13aR, 15bS)-Benzyl 12-amino-2,2,6a,6b,9,9,13a-heptamethyl-15-(2-((4-methylpiperazin-1-yl)methyl)furan-3-yl)-2,3,4,4a,5,6,6a,6b,7,8,8a,9,11,13,13a,13b,14, 15b-octadecahydro-1H-chryseno[1,2-f]indazole-4-a-carboxylate A mixture of II (200 mg, 0.30 mmol), 36c (200 mg, 0.89 mmol), Pd(PPh$_3$)$_4$ (35 mg, 0.030 mmol) and K$_2$CO$_3$ (166 mg, 1.20 mmol) in benzene (3.5 mL) and EtOH (1.5 mL) was sealed and heated to 120° C. by microwave for 1 hour. The reaction mixture was diluted with EtOAc (100 mL). The organic phase was washed with brine then dried (MgSO$_4$), filtered and concentrated to dryness. The residue was purified by column chromatography (silica, 0-50% CMA in CH$_2$Cl$_2$) to afford the sub-title compound (200 mg, 87%).

APCI MS (Positive Mode) m/z 762 [C$_{48}$H$_{67}$N$_5$O$_3$+H]$^+$.

(iv) Preparation of 36: (4aS,6aS,6bR,8aR,13aR, 15bS)-12-Amino-2,2,6a,6b,9,9,13a-heptamethyl-15-(2-((4-methylpiperazin-1-yl)methyl)furan-3-yl)-2,3,4,4a,5,6,6a,6b,7,8,8a,9,11,13,13a,13b,14,15b-octadecahydro-1H-chryseno[1,2-f]indazole-4-a-carboxylic acid A mixture of 36d (200 mg, 0.26 mmol) and 10% Pd(OH)$_2$/C (100 mg) in MeOH (15 mL) and EtOAc (5 mL) was stirred under a hydrogen balloon for 12 hours. The reaction mixture was filtered through a pad of diatomaceous earth and washed with CMA (25 mL). The filtrate was concentrated to dryness under reduced pressure. The residue was purified by column chromatography (silica, 0-70% CMA in CH$_2$Cl$_2$) to afford the title compound (22 mg, 13%) as a brown solid.

R$_f$ 0.30 (80:28:2 Methylene Chloride/Methanol/concentrated Ammonium Hydroxide).

$^1$H NMR (300 MHz, CD$_3$OD) δ 0.55 (s, 3H), 0.78 (s, 3H), 0.86 (s, 3H), 0.99 (s, 3H), 1.12 (s, 3H), 1.28 (s, 6H), 1.35-2.18 (m, 16H), 2.28 (d, J=14.8 Hz, 1H), 2.29 (m, 4H), 2.40 (m, 9H), 2.90 (m, 1H), 3.52 (m, 2H), 3.80 (m, 1H), 6.33 (s, 1H), 7.47 (s, 1H). mp >300° C. APCI MS (Positive Mode) m/z 672 [C$_{41}$H$_{61}$N$_5$O$_3$+H]$^+$.

EXAMPLE 37

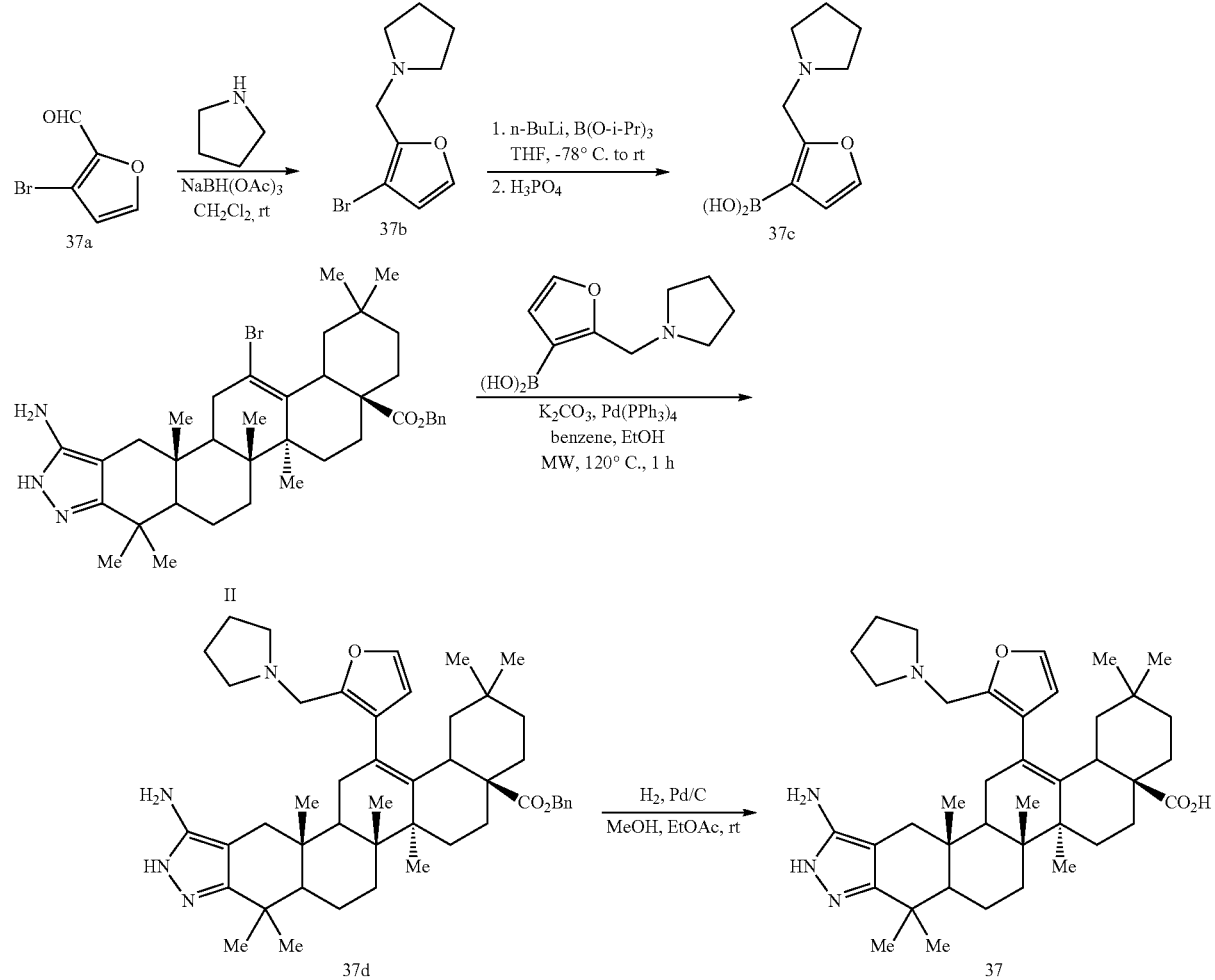

(i) Preparation of 37b:
1-((3-Bromofuran-2-yl)methyl)pyrrolidine

To a solution of 3-bromofuran-2-carbaldehyde (1.5 g, 8.57 mmol) and pyrrolidine (1.42 mL, 17.14 mmol) and $CH_2Cl_2$ (30 mL) was added sodium triacetoxyborohydride (3.63 g, 17.14 mmol). The mixture was stirred at room temperature for 5 hours. The resulting mixture was diluted with EtOAc (300 mL) and the organic layer was washed with saturated $NaHCO_3$ and brine then dried ($Na_2SO_4$), filtered and concentrated. The residue was purified by column chromatography (silica, 0-10% MeOH in $CH_2Cl_2$) to afford the sub-title compound (1.26 g, 65%).

$^1$H NMR (400 MHz, $CDCl_3$) δ 1.74-1.80 (m, 4H), 2.56-2.59 (m, 4H), 3.67 (s, 2H), 6.37 (d, J=2.0 Hz, 1H), 7.34 (d, J=2.0 Hz, 1H).

(ii) Preparation of 37c:
2-(Pyrrolidin-1-ylmethyl)furan-3-ylboronic acid

To a solution of 37b (1.29 g, 5.60 mmol) in THF (20 mL) was added n-butyllithium (4.26 mL, 10.65 mmol) at −78° C. After stirring for 20 min, triisopropylborate (1.99 mL, 8.69 mmol) was added at −78° C. The mixture was slowly warmed to room temperature and then quenched with $H_3PO_4$ (85% in $H_2O$, 3 mL). The reaction mixture was neutralized with 2 N NaOH solution and extracted with EtOAc (3×10 mL) followed by i-PrOH/$CH_2Cl_2$ (2:1, 3×10 mL). The combined extracts were dried ($Na_2SO_4$), filtered and concentrated under reduced pressure. The residue was purified by column chromatography (silica, 0-50% CMA in $CH_2Cl_2$) to afford the sub-title compound (515 mg, 47%).

$^1$H NMR (400 MHz, $CD_3OD$) δ 2.04-2.07 (m, 4H), 3.15-3.18 (m, 4H), 3.29-3.31 (m, 2H), 4.19 (s, 2H), 6.41 (d, J=1.6 Hz, 1H), 7.32 (d, J=1.6 Hz, 1H).

(iii) Preparation of 37d: (4aS,6aS,6bR,13aR)-Benzyl 12-amino-2,2,6a,6b,9,9,13a-heptamethyl-15-(2-(pyrrolidin-1-ylmethyl)furan-3-yl)-2,3,4,4a,5,6,6a,6b,7,8,8a,9,11,13,13a,13b,14,15b-octadecahydro-1H-chryseno[1,2-f]indazole-4-a-carboxylate To a mixture of II (500 mg, 0.75 mmol) and 37c (441 mg, 2.26 mmol) in benzene (4 mL) and EtOH (1 mL) was added $K_2CO_3$ (416 mg, 3.02 mmol). The mixture was sparged with nitrogen and then Pd(PPh$_3$)$_4$ (174 mg, 0.15 mmol) was added. The reaction mixture was heated at 130° C. for 1 hour using microwave irradiation. The solvent was concentrated under reduced pressure. The residue was dissolved in EtOAc (40 mL) and washed with brine (3×15 mL). The organic layer was dried ($Na_2SO_4$), filtered and concentrated. The residue was purified by column chromatography (silica, 0-10% MeOH in $CH_2Cl_2$ followed by 30% CMA in $CH_2Cl_2$) to afford the sub-title compound (260 mg, 47%).

$^1$H NMR (400 MHz, $CD_3OD$) δ 0.51-2.66 (m, 50H), 3.05-3.08 (m, 1H), 3.61-3.87 (m, 3H), 5.0 (d, J=12.20 Hz, 1H), 5.21 (d, J=12.20 Hz, 1H), 6.23 (d, J=1.56 Hz, 1H), 7.31-7.52 (m, 7H). APCI MS m/z 733 [$C_{47}H_{64}N_4O_3$+H]$^+$.

(iv) Preparation of 37: (4aS,6aS,6bR,13aR)-12-Amino-2,2,6a,6b,9,9,13a-heptamethyl-15-(2-(pyrrolidin-1-ylmethyl)furan-3-yl)-2,3,4,4a,5,6,6a,6b,7,8,8a,9,11,13,13a,13b,14,15b-octadecahydro-1H-chryseno[1,2-f]indazole-4-a-carboxylic acid A solution of 37d (260 mg, 0.35 mmol), EtOAc (5 mL) and MeOH (10 mL) was flushed with nitrogen and then 10% Pd/C (130 mg) was added. The mixture was flushed with nitrogen followed by hydrogen. The mixture was stirred under hydrogen at atmospheric pressure overnight. The catalyst was removed by filtration through diatomaceous earth and the filtrate was concentrated. The residue was purified by column chromatography (silica, 0-50% CMA in $CH_2Cl_2$) to afford the title compound (85 mg, 37%).

$R_f$ 0.24 (90:9:1 Methylene Chloride/Methanol/concentrated Ammonium Hydroxide).

$^1$H NMR (300 MHz, $CD_3OD$) δ 0.59 (s, 3H), 0.85 (s, 3H), 0.89 (s, 3H), 1.04-2.32 (m, 36H), 2.75-2.79 (m, 1H), 3.11-3.15 (m, 2H), 3.48 (s, 2H), 4.08-4.19 (m, 2H), 6.38 (d, J=1.5 Hz, 1H), 7.60 (d, J=1.5 Hz, 1H). APCI MS m/z 643 [$C_{40}H_{58}N_4O_3$+H]$^+$. m.p. 260-280° C. dec. HPLC (Method A) 98.4% (214 nm) $t_R$=13.1 min

EXAMPLE 38

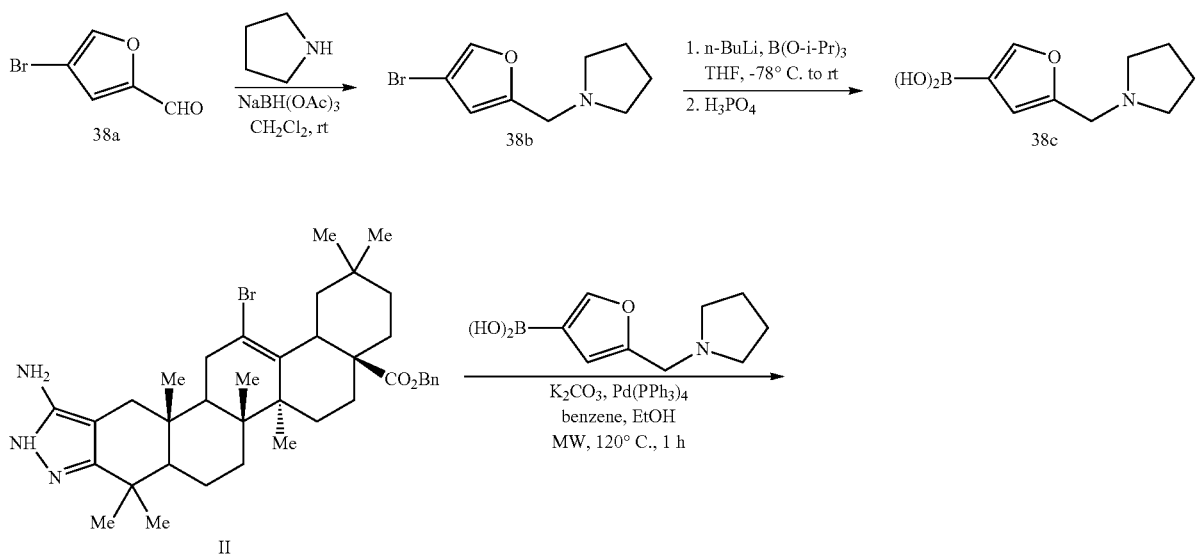

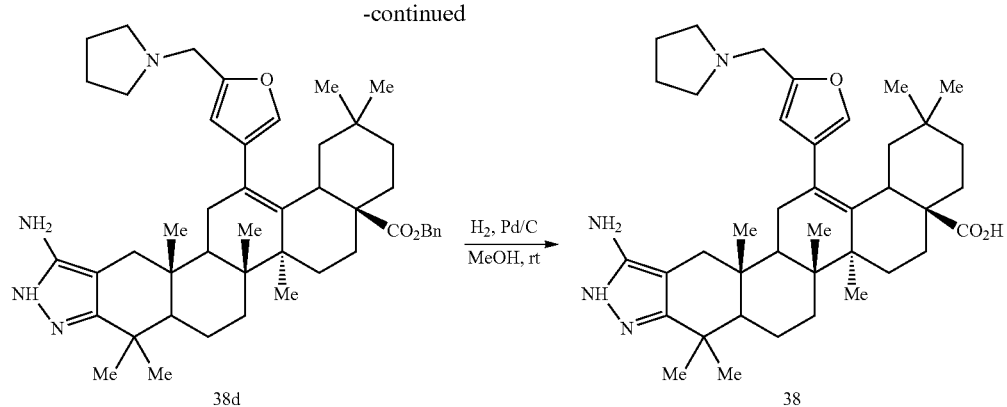

(i) Preparation of 38b:
1-((4-Bromofuran-2-yl)methyl)pyrrolidine

To a solution of 4-bromofuran-2-carbaldehyde (500 mg, 2.85 mmol) and pyrrolidine (0.47 mL, 5.74 mmol) and $CH_2Cl_2$ (10 mL) was added sodium triacetoxyborohydride (1.2 g, 5.71 mmol). The mixture was stirred at room temperature overnight. The resulting mixture was diluted with EtOAc (100 mL) and the organic layer was washed with brine then dried ($Na_2SO_4$), filtered and concentrated. The residue was purified by column chromatography (silica, 0-5% MeOH in $CH_2Cl_2$) to afford the sub-title compound (400 mg, 61%).
$^1H$ NMR (300 MHz, $CDCl_3$) δ 1.77-1.82 (m, 4H), 2.53-2.58 (m, 4H), 3.62 (s, 2H), 6.25 (s, 1H), 7.35 (s, 1H).

(ii) Preparation of 38c:
5-(Pyrrolidin-1-ylmethyl)furan-3-ylboronic acid

To a solution of 38b (400 mg, 1.73 mmol) in THF (10 mL) was added n-butyllithium (0.90 mL, 2.26 mmol) at −78° C. After stifling for 20 min, triisopropylborate (1.99 mL, 8.69 mmol) was added at −78° C. The mixture was slowly warmed to room temperature and then quenched with phosphoric acid. The reaction mixture was neutralized with 2 M NaOH solution and extracted with EtOAc (3×10 mL) followed by i-PrOH/$CH_2Cl_2$ (1:2, 2×10 mL). The combined extracts were dried ($Na_2SO_4$), filtered and concentrated under reduced pressure. The residue was purified by column chromatography (silica, 0-100% CMA in $CH_2Cl_2$) to afford the sub-title compound (197 mg, 58%).
$^1H$ NMR (300 MHz, $CD_3OD$) δ 1.84 (d, J=3.9 Hz, 4H), 2.74 (m, 4H), 3.81 (d, J=4.2 Hz, 2H), 6.46 (d, J=4.2 Hz, 1H), 7.62 (d, J=3.9 Hz, 1H).

(iii) Preparation of 38d: (4aS,6aS,6bR,13aR)-Benzyl 12-amino-2,2,6a,6b,9,9,13a-heptamethyl-15-(5-(pyrrolidin-1-ylmethyl)furan-3-yl)-2,3,4,4a,5,6,6a,6b,7,8,8a,9,11,13,13a,13b,14,15b-octadecahydro-1H-chryseno[1,2-f]indazole-4-a-carboxylate To a mixture of II (200 mg, 0.30 mmol) and 38c (176 mg, 0.96 mmol) in benzene (4 mL) and EtOH (1 mL) was added $K_2CO_3$ (166 mg, 1.20 mmol). The mixture was sparged with nitrogen and then $Pd(PPh_3)_4$ (69 mg, 0.06 mmol) was added. The reaction mixture was heated at 120° C. for 1 hour using microwave irradiation. The solvent was concentrated under reduced pressure. The residue was taken up in EtOAc (20 mL) and washed with brine. The organic layer was dried ($Na_2SO_4$), filtered and concentrated. The residue was purified by column chromatography (silica, 0-10% MeOH in $CH_2Cl_2$) to afford the sub-title compound (200 mg, 90%).
$^1H$ NMR (300 MHz, $CD_3OD$) δ 0.59-3.69 (m, 52H), 5.03 (d, J=12.0 Hz, 1H), 5.21 (d, J=12.3 Hz, 1H), 6.22 (s, 1H), 7.21 (s, 1H), 7.58-7.67 (m, 5H).
APCI MS m/z 733 $[C_{47}H_{64}N_4O_3+H]^+$.

(iv) Preparation of 38: (4aS,6aS,6bR,13aR)-12-Amino-2,2,6a,6b,9,9,13a-heptamethyl-15-(5-(pyrrolidin-1-ylmethyl)furan-3-yl)-2,3,4,4a,5,6,6a,6b,7,8,8a,9,11,13,13a,13b,14,15b-octadecahydro-1H-chryseno[1,2-f]indazole-4-a-carboxylic acid A solution of 38d (200 mg, 0.27 mmol) and MeOH (15 mL) was flushed with nitrogen and then 10% Pd/C (300 mg) was added. The mixture was flushed with nitrogen followed by hydrogen. The mixture was stirred under hydrogen at atmospheric pressure overnight. The catalyst was removed by filtration through diatomaceous earth and the filtrate was concentrated. The residue was purified by column chromatography (silica, 0-80% CMA in $CH_2Cl_2$) followed by preparative HPLC to afford the title compound (16 mg, 9%) as a solid.

$R_f$ 0.30 (40:9:1 Methylene Chloride/Methanol/concentrated Ammonium Hydroxide).
$^1H$ NMR (300 MHz, $CD_3OD$) δ 0.62-2.19 (m, 46H), 2.41 (d, J=15.0 Hz, 2H), 3.53 (m, 2H), 4.45 (s, 2H), 6.64 (s, 1H), 7.57 (s, 1H). APCI MS m/z 643 $[C_{40}H_{58}N_4O_3+H]^+$.
m.p. 220-240° C. dec. HPLC (Method A) 98.6% (214 nm) $t_R$=12.3 min.

EXAMPLE 39

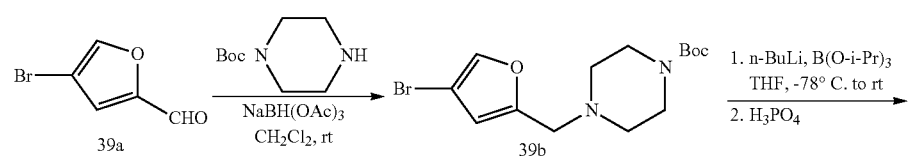

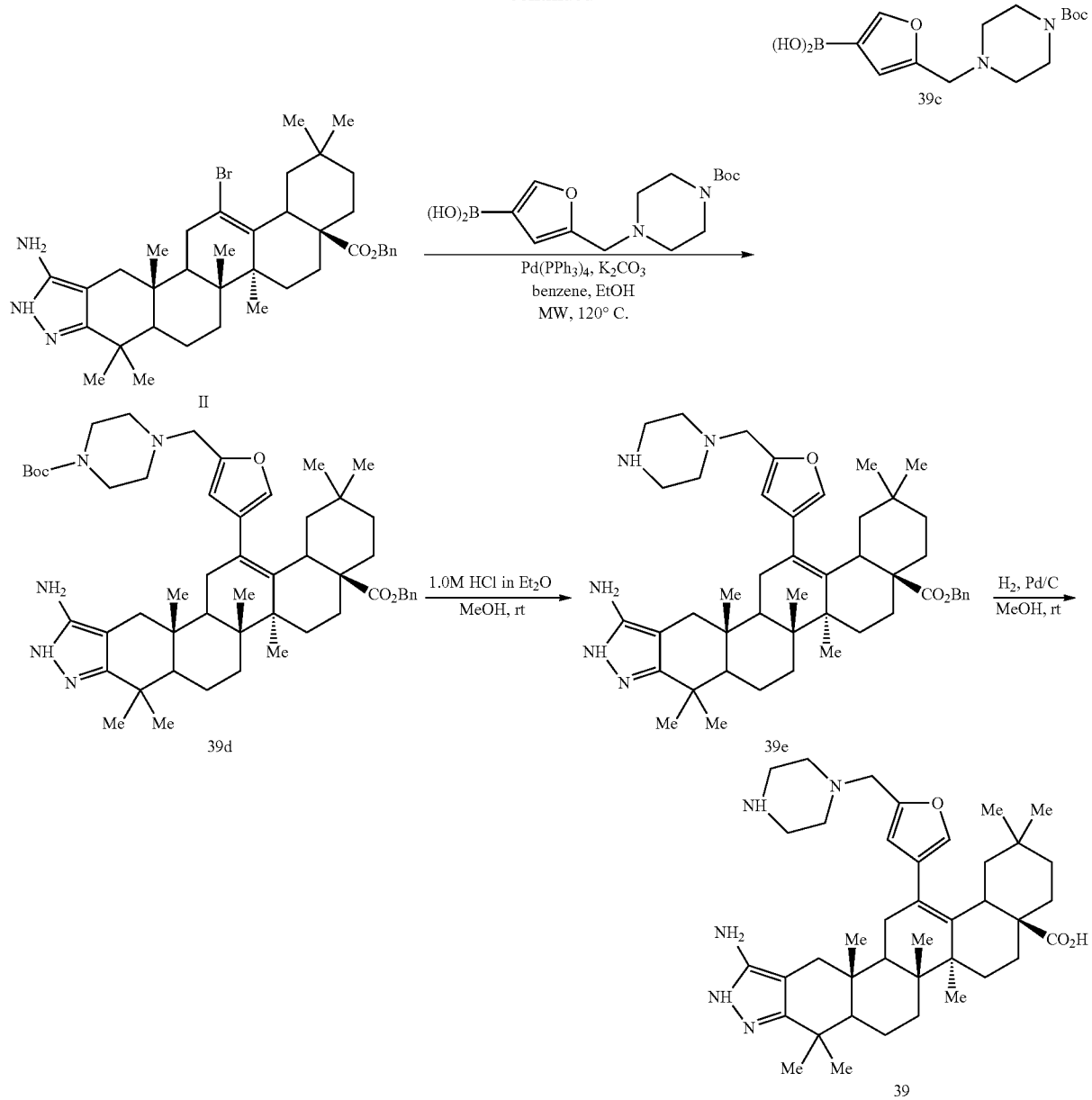

(i) Preparation of 39b: tert-Butyl 4-((4-bromofuran-2-yl)methyl)piperazine-1-carboxylate To a solution of 4-bromofuran-2-carbaldehyde (500 mg, 2.85 mmol) and $CH_2Cl_2$ (10 mL) was added tert-butyl piperazine-1-carboxylate (1.06 g, 5.74 mmol) and sodium triacetoxyborohydride (1.2 g, 5.74 mmol). The mixture was stirred at room temperature overnight. The resultant mixture was diluted with EtOAc (100 mL), washed with brine then dried ($Na_2SO_4$), filtered and concentrated under reduced pressure. The residue was purified by column chromatography (silica, 0-5% MeOH in $CH_2Cl_2$) to afford the sub-title compound (900 mg, 91%).

$^1$H NMR (300 MHz, $CDCl_3$) δ 1.45 (s, 9H), 2.39-2.42 (m, 4H), 3.42-3.45 (m, 4H), 3.52 (s, 2H), 6.27 (s, 1H), 7.38 (s, 1H).

(ii) Preparation of 39c: 5-((4-(tert-Butoxycarbonyl)piperazin-1-yl)methyl)furan-3-ylboronic acid To a solution of 39b (900 mg, 2.60 mmol) and THF (10 mL) was added n-butyllithium (1.35 mL, 3.39 mmol) at −78° C. After stifling for 10 min, triisopropylborate (2.99 mL, 13.04 mmol) was added at −78° C. The mixture was slowly warmed to room temperature and quenched with phosphoric acid. The reaction mixture was neutralized with 2 M NaOH solution and extracted with EtOAc (3×10 mL). The extracts were dried ($Na_2SO_4$), filtered and concentrated under reduced pressure. The residue was purified by column chromatography (silica, 0-5% CMA in $CH_2Cl_2$) to afford the sub-title compound (180 mg, 58%).

$^1$H NMR (300 MHz, $CDCl_3$) δ 1.44 (s, 9H), 3.44 (m, 4H), 3.56 (s, 2H), 3.73 (m, 4H), 6.39 (s, 1H), 7.87 (s, 1H).

(iii) Preparation of 39d: (4aS,6aS,6bR,13aR)-Benzyl 12-amino-15-(5-((4-(tert-butoxycarbonyl)piperazin-1-yl)methyl)furan-3-yl)-2,2,6a,6b,9,9,13a-heptamethyl-2,3,4,4a,5,6,6a,6b,7,8,8a,9,11,13,13a,13b,14,15b-Octadecahydro-1H-chryseno[1,2-f]indazole-4-a-carboxylate To a mixture of II (300 mg, 0.45 mmol) and 39c (420 mg, 1.35 mmol) in benzene (4 mL) and EtOH (1 mL) was added $K_2CO_3$ (249 mg, 1.80 mmol). The mixture was sparged with nitrogen and then Pd(PPh$_3$)$_4$ (105 mg, 0.09 mmol) was added. The reaction mixture was heated at 120° C. for 1 hour using microwave irradiation. The solvent was removed under reduced pressure and the residue was dissolved in EtOAc (20 mL). The solution was washed with brine then dried (Na$_2$SO$_4$), filtered and concentrated. The residue was purified by column chromatography (silica, 0-10% MeOH in CH$_2$Cl$_2$) to afford the sub-title compound (260 mg, 68%).
$^1$H NMR (300 MHz, CDCl$_3$) δ 0.57-2.41 (m, 65H), 3.42-3.48 (m, 6H), 5.04 (d, J=14.7 Hz, 1H), 5.14 (d, J=12.3 Hz, 1H), 6.18 (s, 1H), 7.21 (s, 1H), 7.33-7.35 (m, 5H).
APCI MS m/z 848 $[C_{52}H_{73}N_5O_5+H]^+$.

(iv) Preparation of 39e: (4aS,6aS,6bR,13aR)-Benzyl 12-amino-2,2,6a,6b,9,9,13a-heptamethyl-15-(5-(piperazin-1-ylmethyl)furan-3-yl)-2,3,4,4a,5,6,6a,6b,7,8,8a,9,11,13,13a,13b,14,15b-octadecahydro-1H-chryseno[1,2-f]indazole-4-a-carboxylate To a solution of 39d (260 mg, 0.30 mmol) and MeOH (2 mL) was added HCl (1.0 M in diethyl ether, 10 mL, 10.0 mmol). After stifling overnight at room temperature, the reaction mixture was concentrated. Purification of the residue by column chromatography (silica, 0-80% CMA in CH$_2$Cl$_2$) afforded the sub-title compound (190 mg, 83%).
$^1$H NMR (300 MHz, CD$_3$OD) δ 0.57-2.37 (m, 42H), 2.44 (s, 4H), 2.80 (s, 4H), 3.43 (s, 2H), 4.98-5.03 (m, 1H), 5.15-5.21 (m, 1H), 6.20 (s, 1H), 7.21 (s, 1H), 7.36-7.37 (m, 5H).
APCI MS m/z 748 $[C_{47}H_{65}N_5O_3+H]^+$.

(v) Preparation of 39: (4aS,6aS,6bR,13aR)-12-Amino-2,2,6a,6b,9,9,13a-heptamethyl-15-(5-(piperazin-1-ylmethyl)furan-3-yl)-2,3,4,4a,5,6,6a,6b,7,8,8a,9,11,13,13a,13b,14,15b-octadecahydro-1H-chryseno[1,2-f]indazole-4-a-carboxylic acid A solution of 39e (190 mg, 0.25 mmol) and MeOH (10 mL) was flushed with nitrogen and then 10% Pd/C (190 mg) was added. The mixture was flushed with nitrogen followed by hydrogen. The mixture was stirred under hydrogen at atmospheric pressure overnight. The catalyst was removed by filtration through diatomaceous earth and the filtrate was concentrated under reduced pressure. The residue was purified by column chromatography (silica, 0-70% CMA in CH$_2$Cl$_2$) followed by preparative HPLC to afford the title compound (34 mg, 20%) as a solid.
R$_f$ 0.10 (32:17:1 Methylene Chloride/Methanol/concentrated Ammonium Hydroxide).
$^1$H NMR (300 MHz, CD$_3$OD) δ 0.60-2.44 (m, 42H), 3.14 (s, 4H), 3.39 (s, 4H), 4.06 (s, 2H), 6.64 (s, 1H), 7.48 (s, 1H).
APCI MS m/z 658 $[C_{40}H_{59}N_5O_3+H]^+$. m.p. 220-240° C. dec. HPLC (Method A)>99% (214 nm) t$_R$=13.7 min.

EXAMPLE 40

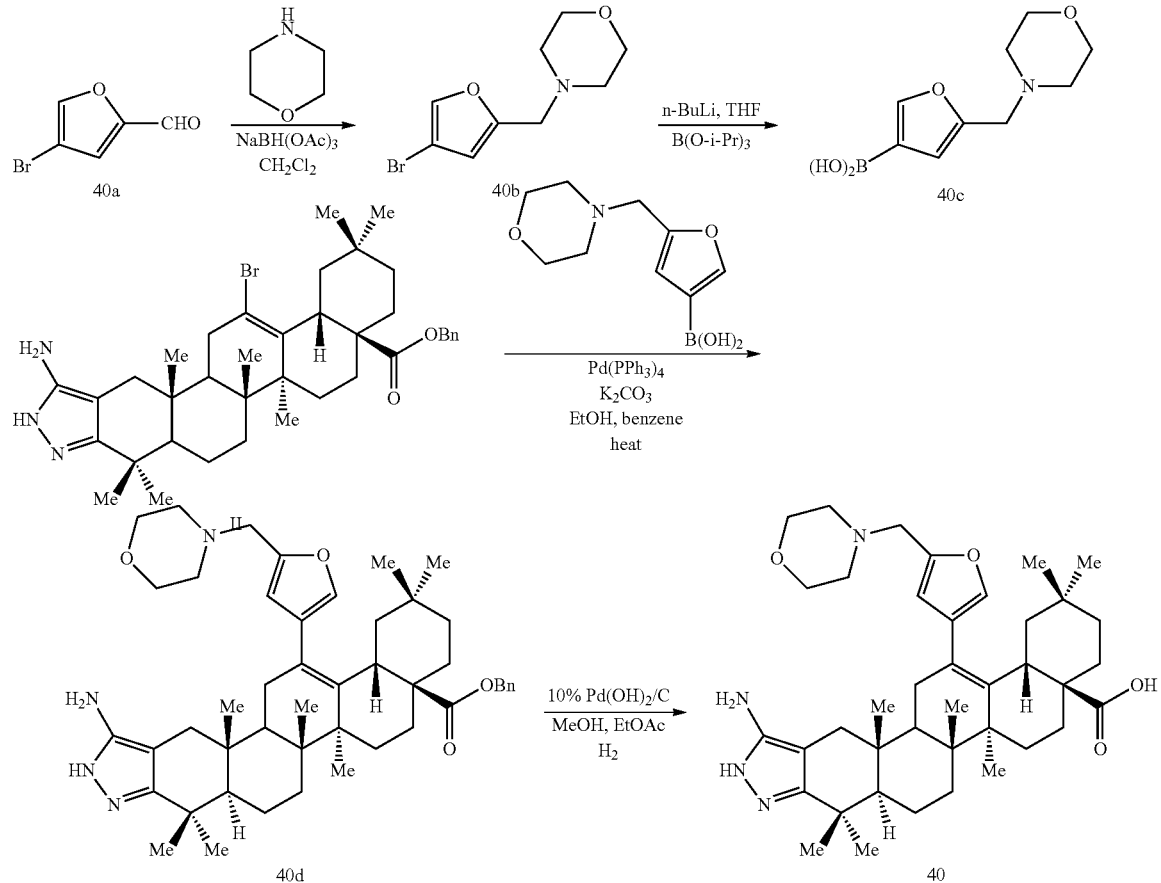

(i) Preparation of 40b:
4-((4-Bromofuran-2-yl)methyl)morpholine

To a solution of 4-bromofuran-2-carbaldehyde (500 mg, 2.85 mmol) and morpholine (0.5 mL, 5.71 mmol) in CH$_2$Cl$_2$ (10 mL) was added sodium triacetoxyborohydride (1.2 g, 5.71 mmol). The mixture was stirred at room temperature for 12 hours. The reaction mixture was diluted with EtOAc (100 mL). The organic phase was washed with aqueous NaHCO$_3$ and brine then dried (MgSO$_4$), filtered and concentrated to dryness. The residue was purified by column chromatography (silica, 0-10% MeOH in CH$_2$Cl$_2$) to afford the sub-title compound (600 mg, 86%).
$^1$H NMR (300 MHz, CDCl$_3$) δ 2.42 (m, 4H), 3.62 (s, 2H), 3.72 (m, 4H), 6.27 (s, 1H), 7.32 (s, 1H).

(ii) Preparation of 40c:
5-(Morpholinomethyl)furan-3-ylboronic acid

To a solution of 40b (300 mg, 1.20 mmol) in THF (6 mL) was added n-butyllithium (2.5 M in hexanes, 0.64 mL, 1.60 mmol) at −78° C. The mixture was stirred at −78° C. for 20 min. Triisopropyl borate (1.3 mL, 6.0 mmol) was added. The reaction mixture was stirred at −78° C. for 1 hour and quenched with HCl (2 M, 4 mL). The reaction mixture was stirred for 5 min and neutralized by NaOH (2 M) and extracted with EtOAc (100 mL). The organic phase was washed with brine then dried (MgSO$_4$), filtered and concentrated to dryness. The residue was purified by column chromatography (silica, 0-10% MeOH in CH$_2$Cl$_2$) to afford the sub-title compound (120 mg, 47%).
$^1$H NMR (300 MHz, CDCl$_3$) δ 2.40 (s, 4H), 3.65 (s, 2H), 3.68 (m, 4H), 6.58 (s, 1H), 7.95 (s, 1H).

(iii) Preparation of 40d: (4aS,6aS,6bR,8aR,13aR, 15bS)-Benzyl 12-amino-2,2,6a,6b,9,9,13a-heptamethyl-15-(5-(morpholinomethyl)furan-3-yl)-2,3,4,4a, 5,6,6a,6b,7,8,8a,9,11,13,13a,13b,14,15b-octadecahydro-1H-chryseno[1,2-f]indazole-4-a-carboxylate A mixture of II (100 mg, 0.18 mmol), 40c (120 mg, 0.56 mmol), Pd(PPh$_3$)$_4$ (20 mg, 0.018 mmol) and K$_2$CO$_3$ (100 mg, 0.72 mmol) in benzene (3.5 mL) and EtOH (1.5 mL) was sealed and heated to 120° C. by microwave for 1 hour. The reaction mixture was diluted with EtOAc (100 mL). The organic phase was washed with brine then dried (MgSO$_4$), filtered and concentrated to dryness. The residue was purified by column chromatography (silica, 0-10% MeOH in CH$_2$Cl$_2$) to afford the sub-title compound (120 mg, 89%).
APCI MS (Positive Mode) m/z 749 [C$_{47}$H$_{64}$N$_4$O$_4$+H]$^+$.

(iv) Preparation of 40: (4aS,6aS,6bR,8aR,13aR, 15bS)-12-Amino-2,2,6a,6b,9,9,13a-heptamethyl-15-(5-(morpholinomethyl)furan-3-yl)-2,3,4,4a,5,6,6a, 6b,7,8,8a,9,11,13,13a,13b,14,15b-octadecahydro-1H-chryseno[1,2-f]indazole-4-a-carboxylic acid A mixture of 40d (120 mg, 0.16 mmol) and 10% Pd(OH)$_2$/C (40 mg) in MeOH (13 mL) and EtOAc (2 mL) was stirred under a hydrogen balloon for 6 hours. The reaction mixture was filtered through a pad of diatomaceous earth and washed with CMA (25 mL). The filtrate was concentrated to dryness under reduced pressure. The residue was purified by column chromatography (silica, 0-60% CMA in CH$_2$Cl$_2$) followed by preparative HPLC to provide the title compound (25 mg, 24%) as an off-white solid.

R$_f$ 0.25 (80:18:2 Methylene Chloride/Methanol/concentrated Ammonium Hydroxide).
$^1$H NMR (300 MHz, CD$_3$OD) δ 0.60 (s, 3H), 0.84 (s, 3H), 0.89 (s, 3H), 0.94 (s, 3H), 1.22 (s, 3H), 1.25 (s, 3H), 1.30 (s, 3H), 1.35-2.28 (m, 20H), 2.38 (d, J=15.0 Hz, 1H), 3.85 (m, 3H), 4.44 (s, 2H), 6.86 (s, 1H), 7.60 (s, 1H). mp >300° C. APCI MS (Positive Mode) m/z 659 [C$_{40}$H$_{58}$N$_4$O$_4$+H]$^+$.

EXAMPLE 41

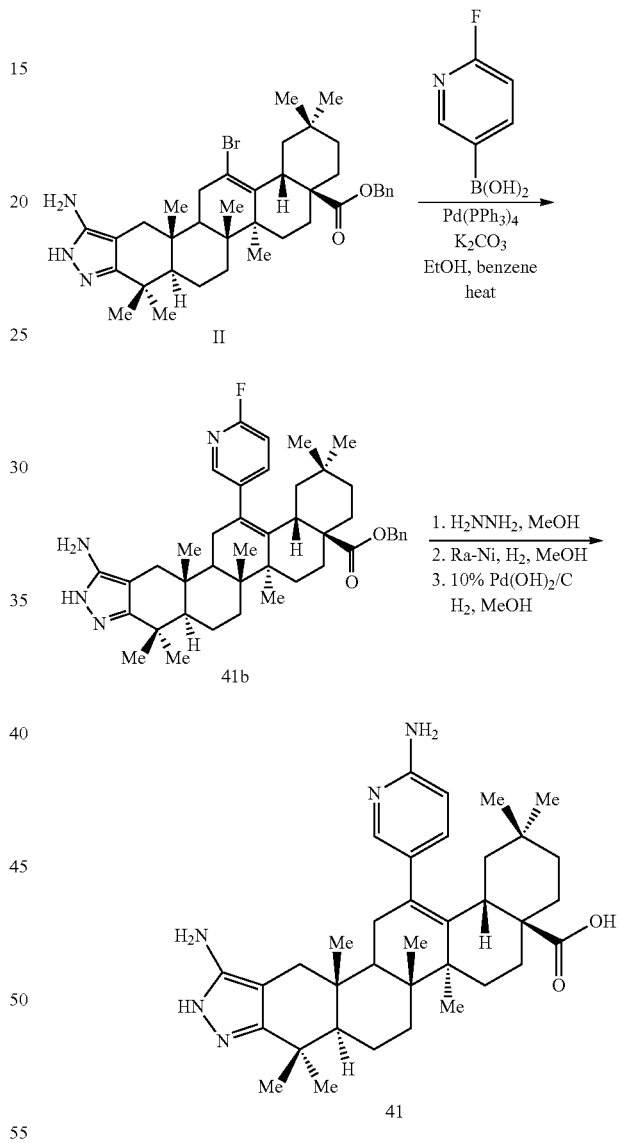

(i) Preparation of 41b: (4aS,6aS,6bR,8aR,13aR, 15bS)-Benzyl 12-amino-15-(6-fluoropyridin-3-yl)-2, 2,6a,6b,9,9,13a-heptamethyl-2,3,4,4a,5,6,6a,6b,7,8, 8a,9,11,13,13a,13b,14,15b-octadecahydro-1H-chryseno[1,2-f]indazole-4-a-carboxylate A mixture of II (400 mg, 2.85 mmol), 6-fluoropyridin-3-ylboronic acid (400 mg, 2.85 mmol), Pd(PPh$_3$)$_4$ (105 mg, 0.090 mmol) and K$_2$CO$_3$ (600 mg, 4.34 mmol) in benzene (4.0 mL) and EtOH (1.0 mL) was sealed and heated to 120° C.

by microwave for 1 hour. The reaction mixture was diluted with EtOAc (100 mL). The organic phase was washed with brine then dried (MgSO$_4$), filtered and concentrated to dryness. The residue was purified by column chromatography (silica, 0-10% MeOH in CH$_2$Cl$_2$) to afford the sub-title compound (500 mg, 81%) as a brown solid.

APCI MS (Positive Mode) m/z 679 [C$_{43}$H$_{55}$FN$_4$O$_2$+H]$^+$.

(ii) Preparation of 41: (4aS,6aS,6bR,8aR,13aR, 15bS)-12-Amino-15-(6-aminopyridin-3-yl)-2,2,6a, 6b,9,9,13a-heptamethyl-2,3,4,4a,5,6,6a,6b,7,8,8a,9, 11,13,13a,13b,14,15b-octadecahydro-1H-chryseno [1,2-f]indazole-4-a-carboxylic acid A mixture of 41b (100 mg, 0.14 mmol) and hydrazine (0.5 mL) in MeOH (4 mL) was sealed and heated to 140° C. by microwave for 5 hours. The mixture was concentrated to dryness. The residue was dissolved in MeOH (20 mL), transferred to a Parr hydrogenation flask and Raney Ni (70 mg) was added. The mixture was placed on a Parr shaker under 40 psi of hydrogen for 12 hours. The mixture was filtered through a pad of diatomaceous earth and the filter cake washed with CMA. The filtrate was concentrated to dryness and the residue dissolved in MeOH (10 mL), transferred to a Parr hydrogenation flask and 10% Pd(OH)$_2$/C (70 mg) was added and the mixture placed on a Parr Shaker under 30 psi of hydrogen for 12 hours. The reaction mixture was filtered through a pad of diatomaceous earth and washed with CMA (25 mL). The filtrate was concentrated to dryness under reduced pressure. The residue was purified by column chromatography (silica, 0-60% CMA in CH$_2$Cl$_2$) to afford the title compound (8 mg, 7%) as a brown solid.

R$_f$ 0.30 (80:18:2 Methylene Chloride/Methanol/concentrated Ammonium Hydroxide).

$^1$H NMR (300 MHz, CD$_3$OD) δ 0.50 (s, 3H), 0.82 (s, 3H), 0.90 (s, 3H), 0.98 (s, 3H), 1.22 (s, 3H), 1.31 (s, 6H), 1.35-2.30 (m, 21H), 6.61 (d, J=8.1 Hz, 1H), 7.47 (d, J=8.1 Hz, 1H), 7.80 (s, 1H). mp >300° C. dec. APCI MS (Positive Mode) m/z 586 [C$_{36}$H$_{51}$N$_5$O$_2$+H]$^+$.

EXAMPLE 42

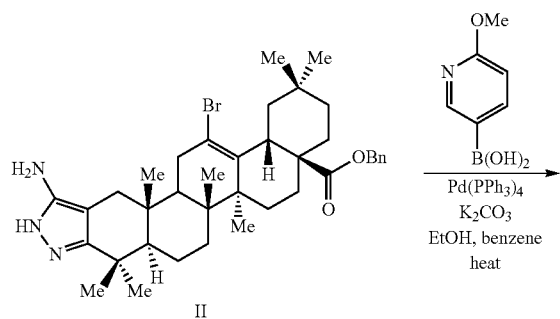

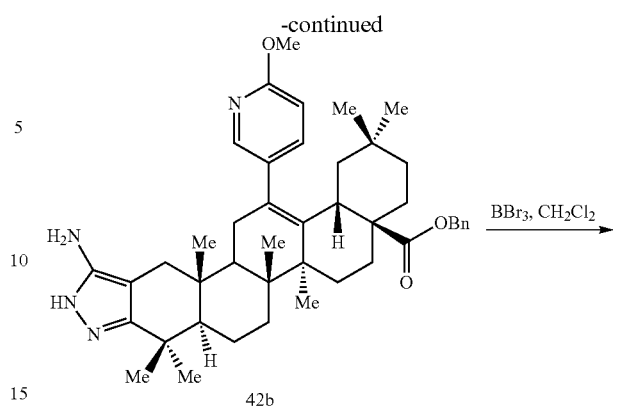

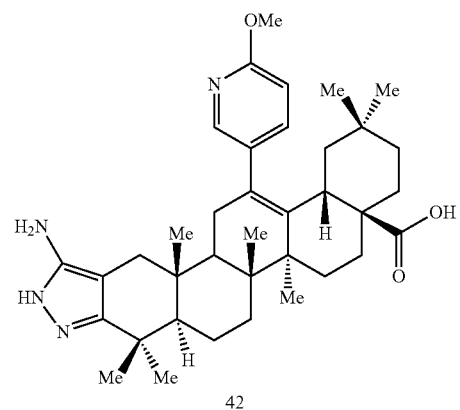

(i) Preparation of 42b: (4aS,6aS,6bR,8aR,13aR, 15bS)-Benzyl 12-amino-15-(6-methoxypyridin-3-yl)-2,2,6a,6b,9,9,13a-heptamethyl-2,3,4,4a,5,6,6a,6b, 7,8,8a,9,11,13,13a,13b,14,15b-octadecahydro-1H-chryseno[1,2-f]indazole-4-a-carboxylate A mixture of II (200 mg, 0.30 mmol), 6-methoxypyridin-3-ylboronic acid (138 mg, 0.90 mmol), Pd(PPh$_3$)$_4$ (34 mg, 0.030 mmol) and K$_2$CO$_3$ (208 mg, 1.50 mmol) in benzene (4.0 mL) and EtOH (1.0 mL) was sealed and heated to 120° C. by microwave for 1 hour. The reaction mixture was diluted with EtOAc (100 mL). The organic phase was washed with brine then dried (MgSO$_4$), filtered and concentrated to dryness. The residue was purified by column chromatography (silica, 0-10% MeOH in CH$_2$Cl$_2$) to afford the sub-title compound (200 mg, 96%) as a brown solid.

APCI MS (Positive Mode) m/z 691 [C$_{44}$H$_{58}$N$_4$O$_3$+H]$^+$.

(ii) Preparation of 42: (4aS,6aS,6bR,8aR,13aR, 15bS)-12-Amino-15-(6-methoxypyridin-3-yl)-2,2, 6a,6b,9,9,13a-heptamethyl-2,3,4,4a,5,6,6a,6b,7,8,8a, 9,11,13,13a,13b,14,15b-octadecahydro-1H-chryseno [1,2-f]indazole-4-a-carboxylic acid To a solution of 42b (107 mg, 0.15 mmol) in CH$_2$Cl$_2$ (2 mL) was added boron tribromide (1 M in THF, 0.93 mL, 0.93 mmol) at −78° C. The mixture was warmed to 0° C. for 6 hours. The reaction mixture was quenched with MeOH (2 mL) and concentrated to dryness under reduced pressure. The residue was purified by column chromatography (silica, 0-4% CMA in CH$_2$Cl$_2$) to afford the title compound (34 mg, 38%).

R$_f$ 0.75 (80:18:2 Methylene Chloride/Methanol/concentrated Ammonium Hydroxide).

$^1$H NMR (300 MHz, CD$_3$OD) δ 0.32 (s, 3H), 0.78 (s, 3H), 0.88 (s, 3H), 1.0 (s, 3H), 1.16 (s, 3H), 1.25 (s, 3H), 1.28 (s, 3H), 1.30-2.25 (m, 19H), 2.32 (d, J=14.7 Hz, 1H), 3.04 (m, 1H), 3.89 (s, 3H), 6.78 (d, J=8.7 Hz, 1H), 7.62 (d, J=10.2, 1H), 8.02 (s, 1H).

mp >300° C. APCI MS (Positive Mode) m/z 601 [C$_{37}$H$_{52}$N$_4$O$_3$+H]$^+$.

EXAMPLE 43

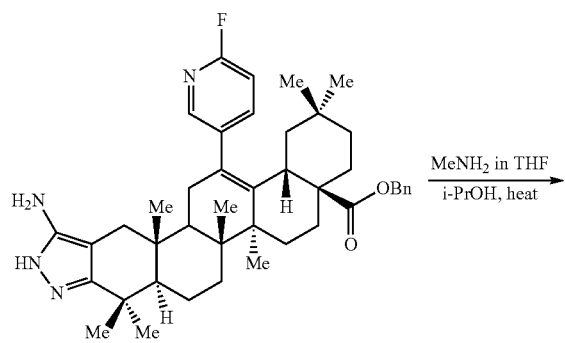

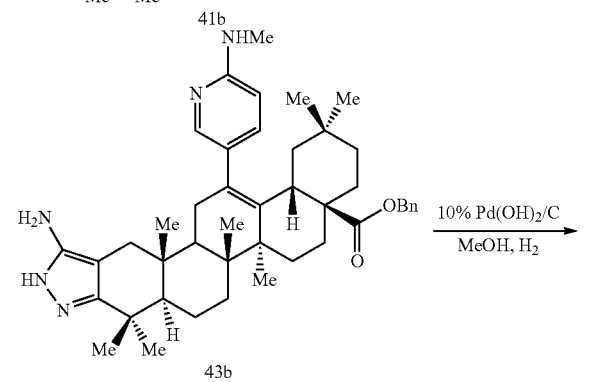

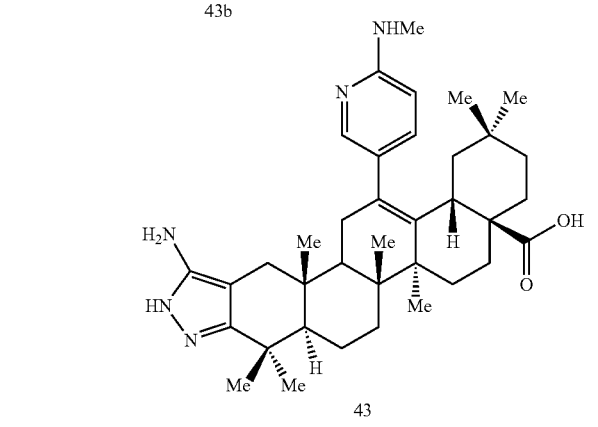

(i) Preparation of 43b: (4aS,6aS,6bR,8aR,13aR, 15bS)-Benzyl 12-amino-2,2,6a,6b,9,9,13a-heptamethyl-15-(6-(methylamino)pyridin-3-yl)-2,3,4,4a,5,6, 6a,6b,7,8,8a,9,11,13,13a,13b,14,15b-octadecahydro-1H-chryseno[1,2-f]indazole-4-a-carboxylate A mixture of 41b (100 mg, 0.14 mmol) and methylamine (1.5 mL, 1 M in THF, 1.5 mmol) in i-PrOH (2 mL) was sealed and heated to 160° C. by microwave for 5 hours. The mixture was concentrated to dryness. The residue was purified by column chromatography (silica, 0-30% CMA in CH$_2$Cl$_2$) to afford the sub-title compound (41 mg, 42%) as a brown solid.

APCI MS (Positive Mode) m/z 690 [C$_{44}$H$_{59}$N$_5$O$_2$+H]$^+$.

(ii) Preparation of 43: (4aS,6aS,6bR,8aR,13aR, 15bS)-12-Amino-2,2,6a,6b,9,9,13a-heptamethyl-15-(6-(methylamino)pyridin-3-yl)-2,3,4,4a,5,6,6a,6b,7, 8,8a,9,11,13,13a,13b,14,15b-octadecahydro-1H-chryseno[1,2-f]indazole-4-a-carboxylic acid A mixture of 43b (32 mg, 0.046 mmol) and 10% Pd(OH)$_2$/C (32 mg) in MeOH (20 mL) was stirred under a hydrogen balloon for 5 hours. The reaction mixture was filtered through a pad of diatomaceous earth and washed with CMA (25 mL). The filtrate was concentrated to dryness under reduced pressure. The residue was purified by column chromatography (silica, 0-70% CMA in CH$_2$Cl$_2$) followed by preparative HPLC to provide the title compound (10 mg, 37%) as an off-white solid.

R$_f$ 0.60 (80:18:2 Methylene Chloride/Methanol/concentrated Ammonium Hydroxide).

$^1$H NMR (300 MHz, CD$_3$OD) δ 0.50 (s, 3H), 0.82 (s, 3H), 0.90 (s, 3H), 0.98 (s, 3H), 1.22 (s, 3H), 1.28 (s, 3H), 1.31 (s, 3H), 1.35-2.30 (m, 21H), 3.02 (m, 1H), 3.03 (s, 3H), 7.05 (d, J=9.3 Hz, 1H), 7.83 (s, 1H), 7.90 (d, J=8.4 Hz, 1H). mp >300° C. APCI MS (Positive Mode) m/z 600 [C$_{37}$H$_{53}$N$_5$O$_2$+H]$^+$.

EXAMPLE 44

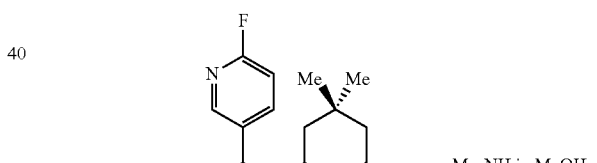

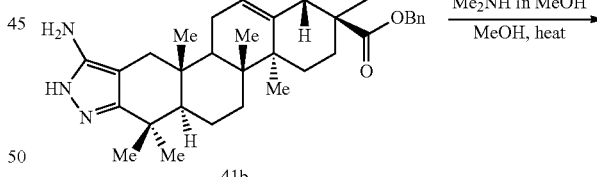

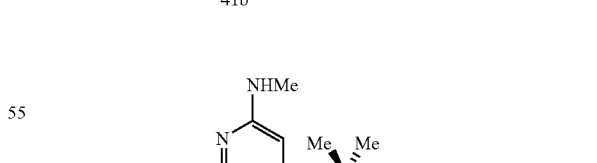

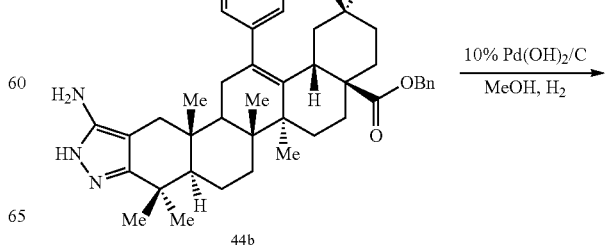

EXAMPLE 45

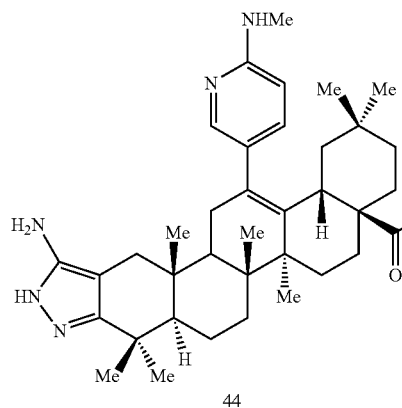
44

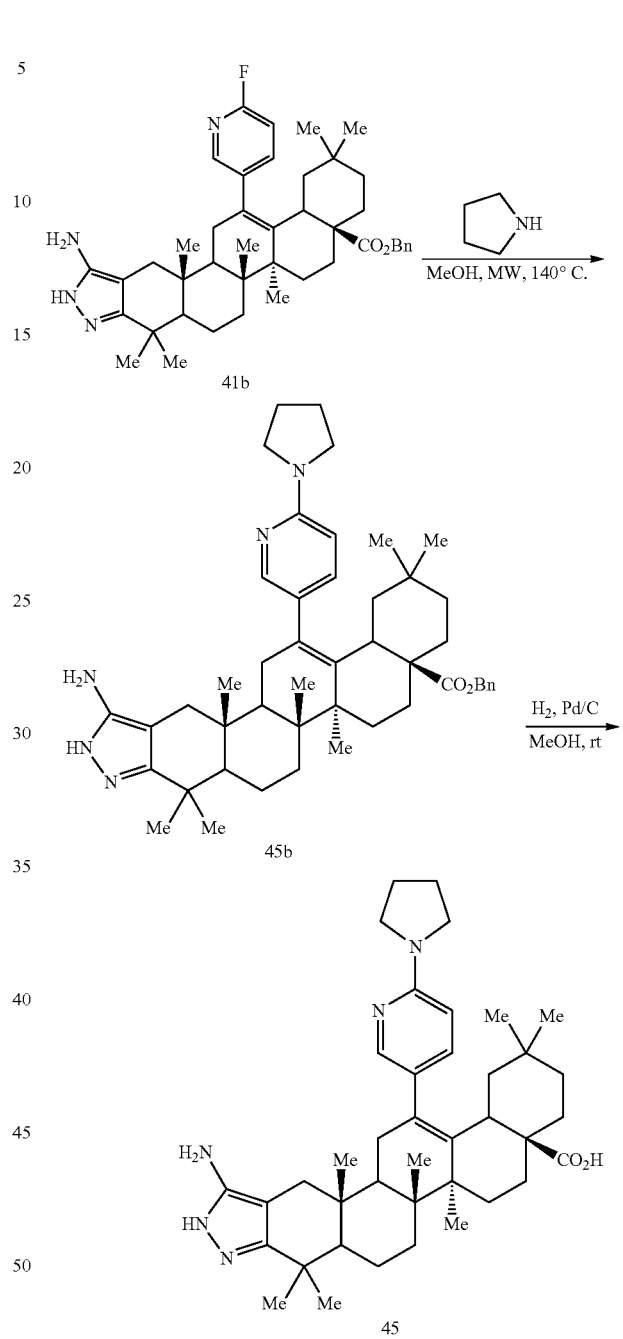

(i) Preparation of 44b: (4aS,6aS,6bR,8aR,13aR,15bS)-Benzyl 12-amino-15-(6-(dimethylamino)pyridin-3-yl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylate A mixture of 41b (150 mg, 0.22 mmol) and dimethylamine (2.0 mL, 1 M in MeOH, 2.0 mmol) in MeOH (1 mL) was sealed and heated to 140° C. by microwave for 7 hours. The mixture was concentrated to dryness. The residue was purified by column chromatography (silica, 0-10% MeOH in $CH_2Cl_2$) to afford the sub-title compound (88 mg, 58%) as a brown solid.

APCI MS (Positive Mode) m/z 690 $[C_{45}H_{61}N_5O_2+H]^+$.

(ii) Preparation of 44: (4aS,6aS,6bR,8aR,13aR,15bS)-12-Amino-15-(6-(dimethylamino)pyridin-3-yl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylic acid A mixture of 44b (88 mg, 0.12 mmol) and 10% $Pd(OH)_2/C$ (40 mg) in MeOH (15 mL) was stirred under a hydrogen balloon for 12 hours. The reaction mixture was filtered through a pad of diatomaceous earth and washed with CMA (25 mL). The filtrate was concentrated to dryness under reduced pressure. The residue was purified by column chromatography (silica, 0-40% CMA in $CH_2Cl_2$) to afford the title compound (35 mg, 26%) as an off-white solid.

$R_f$ 0.75 (80:18:2 Methylene Chloride/Methanol/concentrated Ammonium Hydroxide).

$^1$H NMR (300 MHz, $CD_3OD$) δ 0.38 (s, 3H), 0.78 (s, 3H), 0.87 (s, 3H), 0.99 (s, 3H), 1.15 (s, 3H), 1.25 (s, 3H), 1.26 (s, 3H), 1.35-2.30 (m, 19H), 2.33 (d, J=14.4 Hz, 1H), 3.06 (s, 6H), 3.07 (m, 1H), 6.66 (d, J=8.7 Hz, 1H), 7.50 (d, J=8.7 Hz, 1H), 7.94 (s, 1H).

mp >300° C. dec. APCI MS (Positive Mode) m/z 614 $[C_{38}H_{55}N_5O_2+H]^+$.

(i) Preparation of 45b: (4aS,6aS,6bR,13aR)-Benzyl 12-amino-2,2,6a,6b,9,9,13a-heptamethyl-15-(6-(pyrrolidin-1-yl)pyridin-3-yl)-2,3,4,4a,5,6,6a,6b,7,8,8a,9,11,13,13a,13b,14,15b-octadecahydro-1H-chryseno[1,2-f]indazole-4-a-carboxylate To a solution of 41b (150 mg, 0.22 mmol) in MeOH (4 mL) was added pyrrolidine (1 mL, 12.09 mmol). The mixture was heated at 140° C. for 5 hours using microwave irradiation. The solvent was removed under reduced pressure and the residue was dissolved in EtOAc (20 mL). The solution was washed with brine then dried (Na$_2$SO$_4$), filtered and concentrated to afford the sub-title compound (162 mg, 100%) which was used without further purification.

APCI MS m/z 730 [C$_{47}$H$_{63}$N$_5$O$_2$+H]$^+$.

(ii) Preparation of 45: (4aS,6aS,6bR,13aR)-12-Amino-2,2,6a,6b,9,9,13a-heptamethyl-15-(6-(pyrrolidin-1-yl)pyridin-3-yl)-2,3,4,4a,5,6,6a,6b,7,8,8a,9,11,13,13a,13b,14,15b-octadecahydro-1H-chryseno[1,2-f]indazole-4-a-carboxylic acid A solution of 45b (162 mg, 0.22 mmol) and MeOH (10 mL) was flushed with nitrogen and then 10% Pd/C (200 mg) was added. The mixture was flushed with nitrogen followed by hydrogen. The mixture was stirred under hydrogen at atmospheric pressure overnight. The catalyst was removed by filtration through diatomaceous earth and the filtrate was concentrated. The residue was purified by column chromatography (silica, 0-40% CMA in CH$_2$Cl$_2$) to afford the title compound (52 mg, 37%).

R$_f$ 0.48 (43:6:1 Methylene Chloride/Methanol/concentrated Ammonium Hydroxide).

$^1$H NMR (300 MHz, CD$_3$OD) δ 0.39 (s, 3H), 0.78 (s, 3H), 0.87-2.27 (m, 38H), 2.38 (d, J=14.6 Hz, 1H), 3.08 (m, 1H), 3.43 (m, 4H), 6.50 (d, J=8.7 Hz, 1H), 7.51 (dd, J=2.1 Hz, 2.9 Hz, 1H), 7.90 (s, 1H). m.p. 280-300° C. dec. APCI MS m/z 640 [C$_{40}$H$_{57}$N$_5$O$_2$+H]$^+$.

HPLC (Method A)>99% (214 nm) t$_R$=12.2 min.

EXAMPLE 46

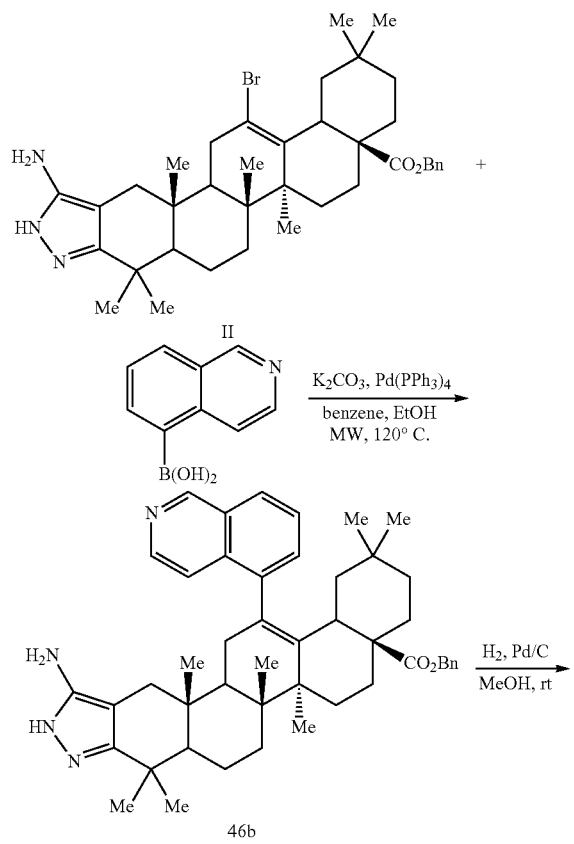

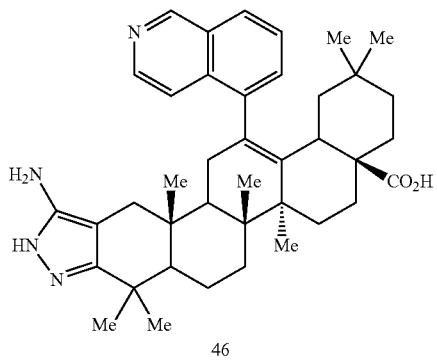

46

(i) Preparation of 46b: (4aS,6aS,6bR,13aR)-Benzyl 12-amino-15-(isoquinolin-5-yl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylate To a mixture of II (200 mg, 0.30 mmol) and isoquinolin-5-ylboronic acid (156 mg, 0.90 mmol) in benzene (4 mL) and EtOH (1 mL) was added K$_2$CO$_3$ (166 mg, 1.20 mmol). The mixture was sparged with nitrogen and then Pd(PPh$_3$)$_4$ (70 mg, 0.06 mmol) was added. The reaction mixture was heated at 120° C. for 1 hour using microwave irradiation and then concentrated. The residue was dissolved in EtOAc (20 mL) and washed with brine. The organic solution was dried (Na$_2$SO$_4$), filtered and concentrated under reduced pressure. The residue was purified by column chromatography (silica, 0-10% MeOH in CH$_2$Cl$_2$) to afford the sub-title compound (180 mg, 84%).

APCI MS m/z 711 [C$_{47}$H$_{58}$N$_4$O$_2$+H]$^+$.

(ii) Preparation of 46: (4aS,6aS,6bR,13aR)-12-Amino-15-(isoquinolin-5-yl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylic acid A solution of 46b (180 mg, 0.25 mmol) and MeOH (15 mL) was flushed with nitrogen and then 10% Pd/C (220 mg) was added. The mixture was flushed with nitrogen followed by hydrogen. The mixture was stirred under hydrogen at atmospheric pressure overnight. The catalyst was removed by filtration through diatomaceous earth and the filtrate was concentrated under reduced pressure. The residue was purified by column chromatography (silica, 0-80% CMA in CH$_2$Cl$_2$) followed by preparative HPLC to afford the title compound (13 mg, 8%) as a solid.

R$_f$ 0.73 (40:9:1 Methylene Chloride/Methanol/concentrated Ammonium Hydroxide).

$^1$H NMR (300 MHz, CD$_3$OD) δ −0.17-2.33 (m, 41H), 2.95 (d, J=11.1 Hz, 1H), 7.94-7.99 (m, 1H), 8.13 (d, J=6.3 Hz, 1H), 8.19 (d, J=7.2 Hz, 1H), 8.32 (d, J=8.4 Hz, 1H), 8.54 (d, J=6.3

Hz, 1H), 9.61 (s, 1H). APCI MS m/z 621 $[C_{40}H_{52}N_4O_2+H]^+$. m.p. >300° C. HPLC (Method A) 93.4% (214 nm) $t_R$=11.6 min.

EXAMPLE 47

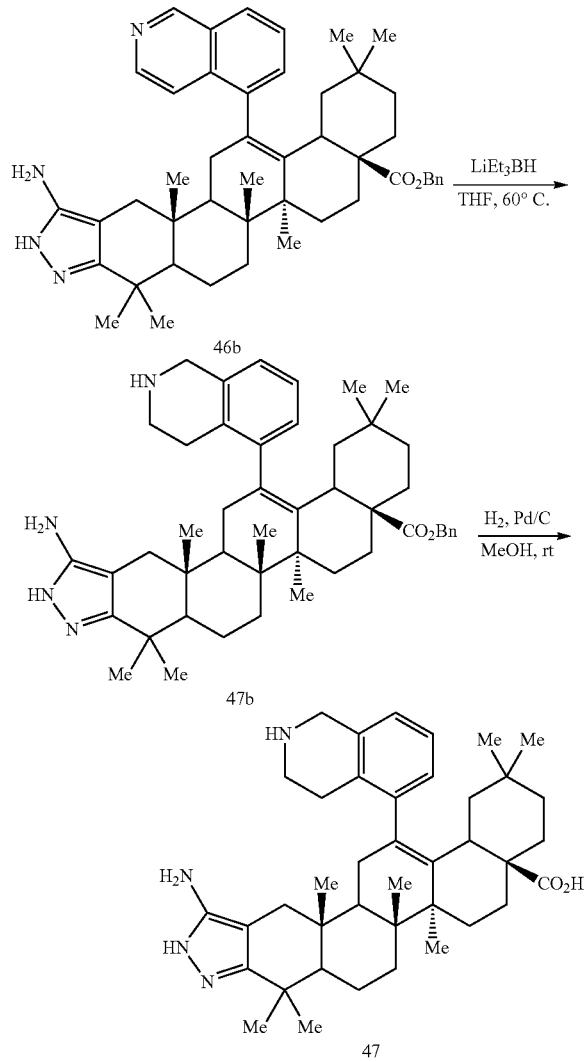

(i) Preparation of 47b: (4aS,6aS,6bR,13aR)-Benzyl 12-amino-2,2,6a,6b,9,9,13a-heptamethyl-15-(1,2,3,4-tetrahydroisoquinolin-5-yl)-2,3,4,4a,5,6,6a,6b,7,8,8a,9,11,13,13a,13b,14,15b-octadecahydro-1H-chryseno[1,2-f]indazole-4-a-carboxylate To a solution of 46b (150 mg, 0.21 mmol) and THF (5 mL) was added lithium triethylborohydride (1.26 mL, 1.26 mmol, 1.0 M in THF). The mixture was heated at 60° C. overnight and then cooled to room temperature. The mixture was taken up in EtOAc (40 mL) and washed with brine (3×15 mL). The organic layer was dried ($Na_2SO_4$), filtered and concentrated. The residue was purified by column chromatography (silica, 0-80% CMA in $CH_2Cl_2$) to afford the sub-title compound (40 mg, 26%).

APCI MS m/z 715 $[C_{47}H_{62}N_4O_2+H]^+$.

(ii) Preparation of 47: (4aS,6aS,6bR,13aR)-12-Amino-2,2,6a,6b,9,9,13a-heptamethyl-15-(1,2,3,4-tetrahydroisoquinolin-5-yl)-2,3,4,4a,5,6,6a,6b,7,8,8a,9,11,13,13a,13b,14,15b-octadecahydro-1H-chryseno[1,2-f]indazole-4-a-carboxylic acid A solution of 47b (40 mg, 0.055 mmol) and MeOH (10 mL) was flushed with nitrogen and then 10% Pd/C (50 mg) was added. The mixture was flushed with nitrogen followed by hydrogen. The mixture was stirred under hydrogen at atmospheric pressure overnight. The catalyst was removed by filtration through diatomaceous earth and the filtrate was concentrated. The residue was purified by column chromatography (silica, 0-80% CMA in $CH_2Cl_2$) to afford the title compound (19 mg, 56%).

$R_f$ 0.28 (40:9:1 Methylene Chloride/Methanol/concentrated Ammonium Hydroxide).

$^1$H NMR (400 MHz, $CD_3OD$) δ 0.24 (s, 3H), 0.75-2.36 (m, 38H), 2.86-3.44 (m, 5H), 4.10-4.20 (m, 2H), 6.98 (d, J=7.42 Hz, 1H), 7.19 (d, J=7.42 Hz, 1H), 7.40 (d, J=7.42 Hz, 1H). APCI MS m/z 625 $[C_{40}H_{56}N_4O_2+H]^+$. m.p. >300° C. dec. HPLC (Method A) 99.1% (214 nm) $t_R$=12.4 min

EXAMPLE 48

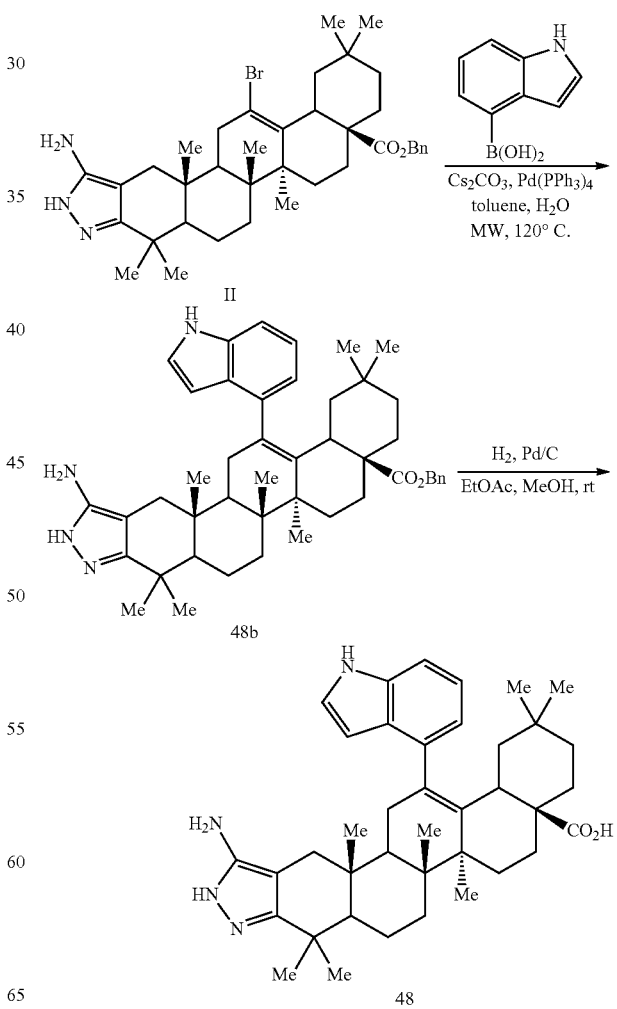

(i) Preparation of 48b: (4aS,6aS,6bR,13aR)-Benzyl 12-amino-15-(1H-indol-4-yl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylate To a mixture of II (200 mg, 0.302 mmol) and 1H-indol-4-ylboronic acid (146 mg, 0.906 mmol) in toluene (4.5 mL) and H$_2$O (0.5 mL) was added cesium carbonate (393 mg, 1.208 mmol). The mixture was sparged with nitrogen and then Pd(PPh$_3$)$_4$ (70 mg, 0.060 mmol) was added. The reaction mixture was heated at 120° C. for 1 hour using microwave irradiation. The solvent was concentrated under reduced pressure. The residue was taken up in EtOAc (20 mL) and washed with brine (3×15 mL). The organic layer was dried (Na$_2$SO$_4$), filtered and concentrated. The residue was purified by column chromatography (silica, 0-10% MeOH in CH$_2$Cl$_2$) to afford the sub-title compound (180 mg, 85%).

APCI MS m/z 699 [C$_{46}$H$_{58}$N$_4$O$_2$+H]$^+$.

(ii) Preparation of 48: (4aS,6aS,6bR,13aR)-12-Amino-15-(1H-indol-4-yl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylic acid A solution of 48b (180 mg, 0.26 mmol), EtOAc (2 mL) and MeOH (8 mL) was flushed with nitrogen and then 10% Pd/C (280 mg) was added. The mixture was flushed with nitrogen followed by hydrogen. The mixture was stirred under hydrogen at atmospheric pressure overnight. The catalyst was removed by filtration through diatomaceous earth and the filtrate was concentrated. The residue was purified by column chromatography (silica, 0-10% MeOH in CH$_2$Cl$_2$) followed by preparative HPLC to afford the title compound (29 mg, 18%) as a solid.

R$_f$ 0.30 (90:9:1 Methylene Chloride/Methanol/concentrated Ammonium Hydroxide).

$^1$H NMR (400 MHz, CD$_3$OD) δ −0.08 (s, 3H), 0.22 (s, 3H), 0.54 (s, 3H), 0.78-2.56 (m, 32H), 6.28 (s, 1H), 7.01-7.24 (m, 5H). APCI MS m/z 609 [C$_{39}$H$_{52}$N$_4$O$_2$+H]$^+$. m.p. 280-300° C. dec. HPLC (Method A) 99.3% (214 nm) t$_R$=16.6 min

EXAMPLE 49

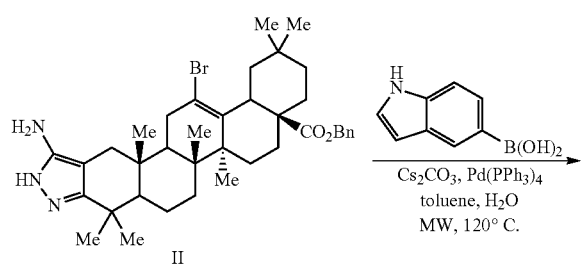

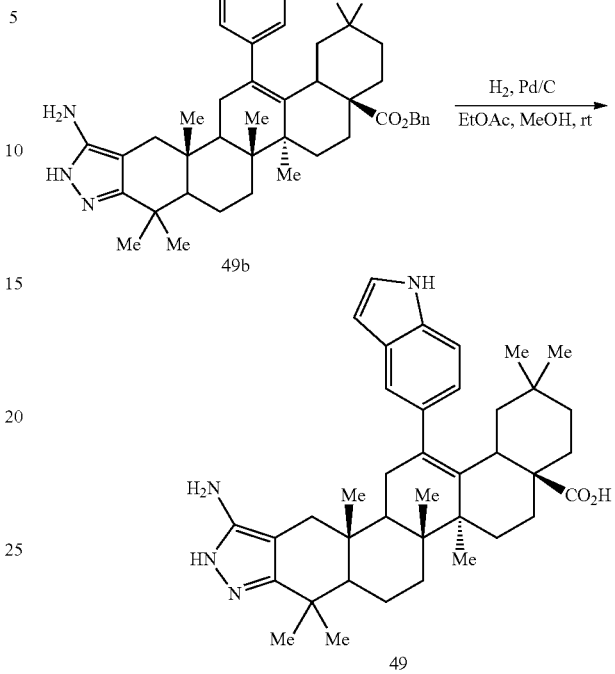

(i) Preparation of 49b: (4aS,6aS,6bR,13aR)-Benzyl 12-amino-15-(1H-indol-5-yl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylate To a mixture of II (200 mg, 0.302 mmol) and 1H-indol-5-ylboronic acid (146 mg, 0.91 mmol) in toluene (4.5 mL) and H$_2$O (0.5 mL) was added cesium carbonate (393 mg, 1.21 mmol). The mixture was sparged with nitrogen and then Pd(PPh$_3$)$_4$ (70 mg, 0.06 mmol) was added. The reaction mixture was heated at 120° C. for 1 hour using microwave irradiation. The solvent was concentrated under reduced pressure. The residue was taken up in EtOAc (20 mL) and washed with brine (3×15 mL). The organic layer was dried (Na$_2$SO$_4$), filtered and concentrated. The residue was purified by column chromatography (silica, 0-10% CMA in CH$_2$Cl$_2$) to afford the sub-title compound (178 mg, 84%).

APCI MS m/z 699 [C$_{46}$H$_{58}$N$_4$O$_2$+H]$^+$.

(ii) Preparation of 49: (4aS,6aS,6bR,13aR)-12-Amino-15-(1H-indol-5-yl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylic acid A solution of 49b (175 mg, 0.25 mmol), EtOAc (5 mL) and MeOH (10 mL) was flushed with nitrogen and then 10% Pd/C (175 mg) was added. The mixture was flushed with nitrogen followed by hydrogen. The mixture was stirred under hydrogen at atmospheric pressure overnight. The catalyst was removed by filtration through diatomaceous earth and the filtrate was concentrated. The residue was purified by column chromatography (silica, 0-6% MeOH in CH$_2$Cl$_2$) followed by preparative HPLC to afford the title compound (18 mg, 12%) as a solid.

$R_f$ 0.30 (90:9:1 Methylene Chloride/Methanol/concentrated Ammonium Hydroxide).
$^1$H NMR (400 MHz, CD$_3$OD) δ 0.10 (s, 3H), 0.70 (s, 3H), 0.89-2.43 (m, 35H), 3.21-3.25 (m, 1H), 6.38-6.39 (m, 1H), 7.04 (s, 1H), 7.18 (s, 1H), 7.32 (d, J=8.26 Hz, 1H), 7.39 (s, 1H). APCI MS m/z 609 [C$_{39}$H$_{52}$N$_4$O$_2$+H]$^+$. m.p. 230-250° C. dec. HPLC (Method A) 96.2% (214 nm) $t_R$=17.1 min
EXAMPLE 50
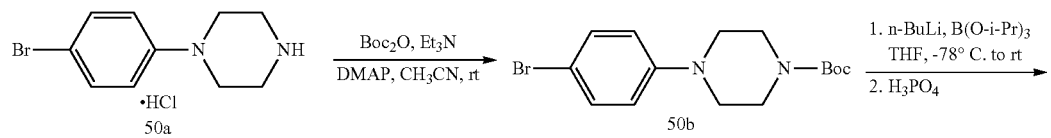
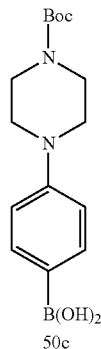
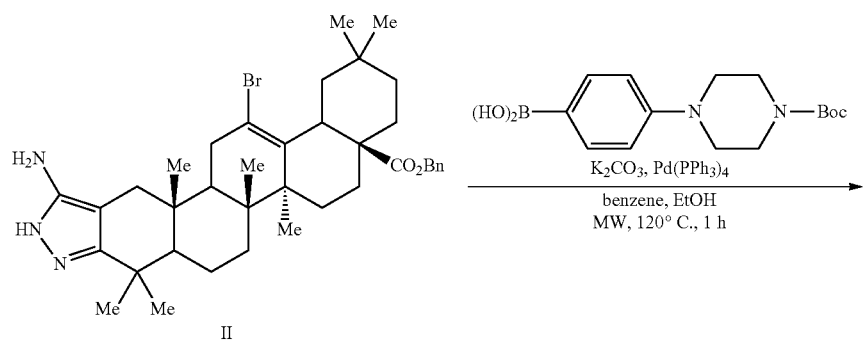
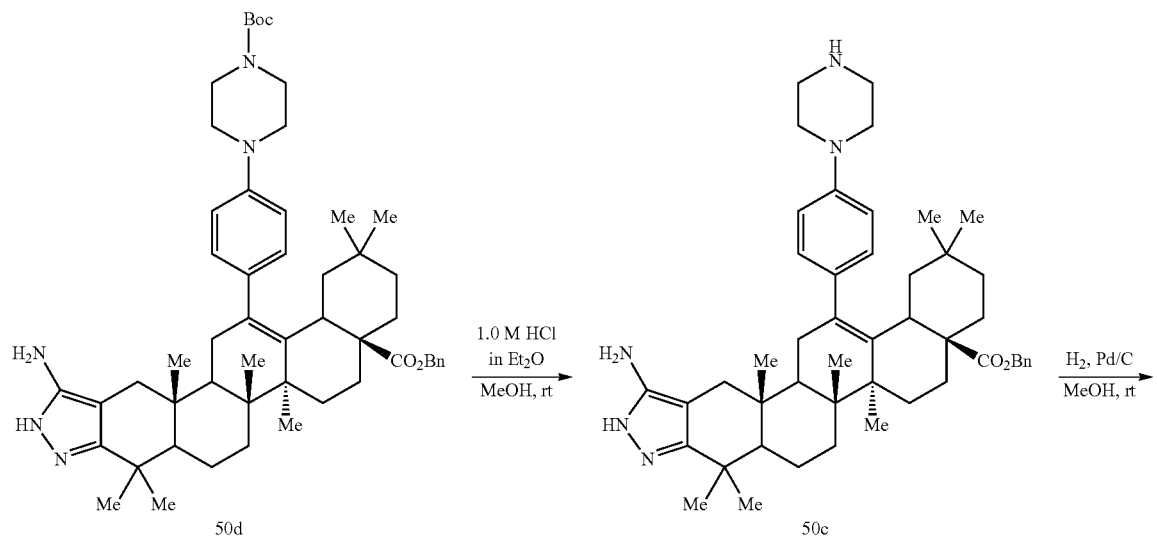

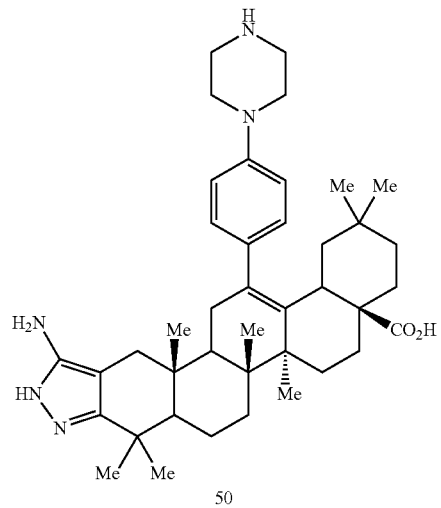

(i) Preparation of 50b: tert-Butyl 4-(4-bromophenyl)piperazine-1-carboxylate To a slurry of 1-(4-bromophenyl)piperazine hydrochloride (3.0 g, 10.8 mmol), DMAP (135 mg, 1.1 mmol) and triethylamine (4.5 mL, 32.4 mmol) in $CH_3CN$ (25 mL) was added di-tert-butyl dicarbonate (2.6 g, 11.9 mmol). The mixture was stirred at room temperature overnight. Water (25 mL) was added to the resultant mixture and stirred for 30 min. The resultant solid was collected by filtration. The solid was washed with $H_2O$ and dried in a vacuum oven at 40° C. to afford the sub-title compound (3.2 g, 87%).

$^1$H NMR ((300 MHz, DMSO-$d_6$) δ 1.48 (s, 9H), 3.15 (m, 4H), 3.54 (m, 4H), 6.95 (d, J=9.0 Hz, 2H), 7.37 (d, J=9.0 Hz, 2H).

(ii) Preparation of 50c: 4-(4-(tert-Butoxycarbonyl) piperazin-1-yl)phenylboronic acid To a solution of 50b (500 mg, 1.46 mmol) and THF (10 mL) was added n-butyllithium (0.76 mL of 2.5 M in hexanes, 1.90 mmol) at −78° C. After stirring for 30 min, triisopropylborate (1.68 mL, 7.33 mmol) was added at −78° C. The mixture was slowly warmed to room temperature and quenched with phosphoric acid. The reaction mixture was neutralized with saturated $NaHCO_3$ and extracted with EtOAc (10 mL×3). The extracts were dried ($Na_2SO_4$), filtered and concentrated under reduced pressure. The residue was purified by column chromatography (silica, 0-10% MeOH in $CH_2Cl_2$) to afford the sub-title compound (180 mg, 58%).

$^1$H NMR (300 MHz, $CD_3OD$) δ −0.50 (s, 9H), 0.93-0.96 (m, 4H), 1.15-1.19 (m, 4H), 4.86-4.89 (m, 4H).

(iii) Preparation of 50d: (4aS,6aS,6bR,13aR)-Benzyl 12-amino-15-(4-(4-(tert-butoxycarbonyl)piperazin-1-yl)phenyl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f] indazole-4-a-carboxylate To a mixture of II (130 mg, 0.19 mmol) and 50c (180 mg, 0.58 mmol) in benzene (4 mL) and EtOH (1 mL) was added $K_2CO_3$ (108 mg, 0.78 mmol). The mixture was sparged with nitrogen and then Pd(PPh$_3$)$_4$ (45 mg, 0.06 mmol) was added. The reaction mixture was heated at 120° C. for 1 hour using microwave irradiation and then concentrated under reduced pressure. The residue was dissolved in EtOAc (20 mL) and the solution was washed with brine then dried ($Na_2SO_4$), filtered and concentrated. The residue was purified by column chromatography (silica, 0-5% MeOH in $CH_2Cl_2$) to afford the sub-title compound (100 mg, 60%).

$^1$H NMR (300 MHz, $CD_3OD$) δ 0.28-3.59 (m, 59H), 5.18 (d, 2H), 6.70-7.07 (m, 9H).

APCI MS m/z 844 $[C_{53}H_{73}N_5O_4+H]^+$.

(iv) Preparation of 50e: (4aS,6aS,6bR,13aR)-Benzyl 12-amino-2,2,6a,6b,9,9,13a-heptamethyl-15-(4-(piperazin-1-yl)phenyl)-2,3,4,4a,5,6,6a,6b,7,8,8a,9,11,13,13a,13b,14,15b-octadecahydro-1H-chryseno[1,2-f]indazole-4-a-carboxylate To a solution of 50d (220 mg, 0.26 mmol) in MeOH (3 mL) was added HCl (1.0 M in diethyl ether, 6 mL, 6.0 mmol). The mixture was stirred at room temperature for 62 hours and then concentrated under reduced pressure. The residue was purified by column chromatography (silica, 0-50% CMA in $CH_2Cl_2$) to afford the sub-title compound (65 mg, 33%).

$^1$H NMR (300 MHz, $CD_3OD$) δ 0.27-2.34 (m, 42H), 2.98-3.06 (m, 8H), 5.02 (d, J=12.3 Hz, 1H), 5.22 (d, J=12.0 Hz, 1H), 6.78 (d, J=8.7 Hz, 2H), 6.99 (d, J=8.7 Hz, 2H), 7.39 (m, 5H). APCI MS m/z 744 $[C_{48}H_{65}N_5O_2+H]^+$.

(v) Preparation of 50: (4aS,6aS,6bR,13aR)-12-Amino-2,2,6a,6b,9,9,13a-heptamethyl-15-(4-(piperazin-1-yl)phenyl)-2,3,4,4a,5,6,6a,6b,7,8,8a,9,11,13,13a,13b,14,15b-octadecahydro-1H-chryseno[1,2-f] indazole-4-a-carboxylic acid A solution of 50e (65 mg, 0.087 mmol) and MeOH (15 mL) was flushed with nitrogen and then 10% Pd/C (90 mg) was added. The mixture was flushed with nitrogen followed by hydrogen. The mixture was stirred under hydrogen at atmospheric pressure overnight. The catalyst was removed by filtration through diatomaceous earth and the filtrate was concentrated. The residue was purified by column chromatography (silica, 0-70% CMA in $CH_2Cl_2$) followed by preparative HPLC to afford the title compound (11 mg, 20%) as a solid.

$R_f$ 0.10 (40:9:1 Methylene Chloride/Methanol/concentrated Ammonium Hydroxide).

$^1$H NMR (300 MHz, CD$_3$OD) δ 0.28-2.42 (m, 41H), 3.10 (d, J=10.2 Hz, 1H), 3.37 (m, 8H), 7.03 (d, J=9.0 Hz, 2H), 7.24 (d, J=7.8 Hz, 2H). APCI MS m/z 654 [C$_{41}$H$_{59}$N$_5$O$_2$+H]$^+$. m.p. 270-290° C. dec. HPLC (Method A)>99% (214 nm) $t_R$=13.2 min.

EXAMPLE 51

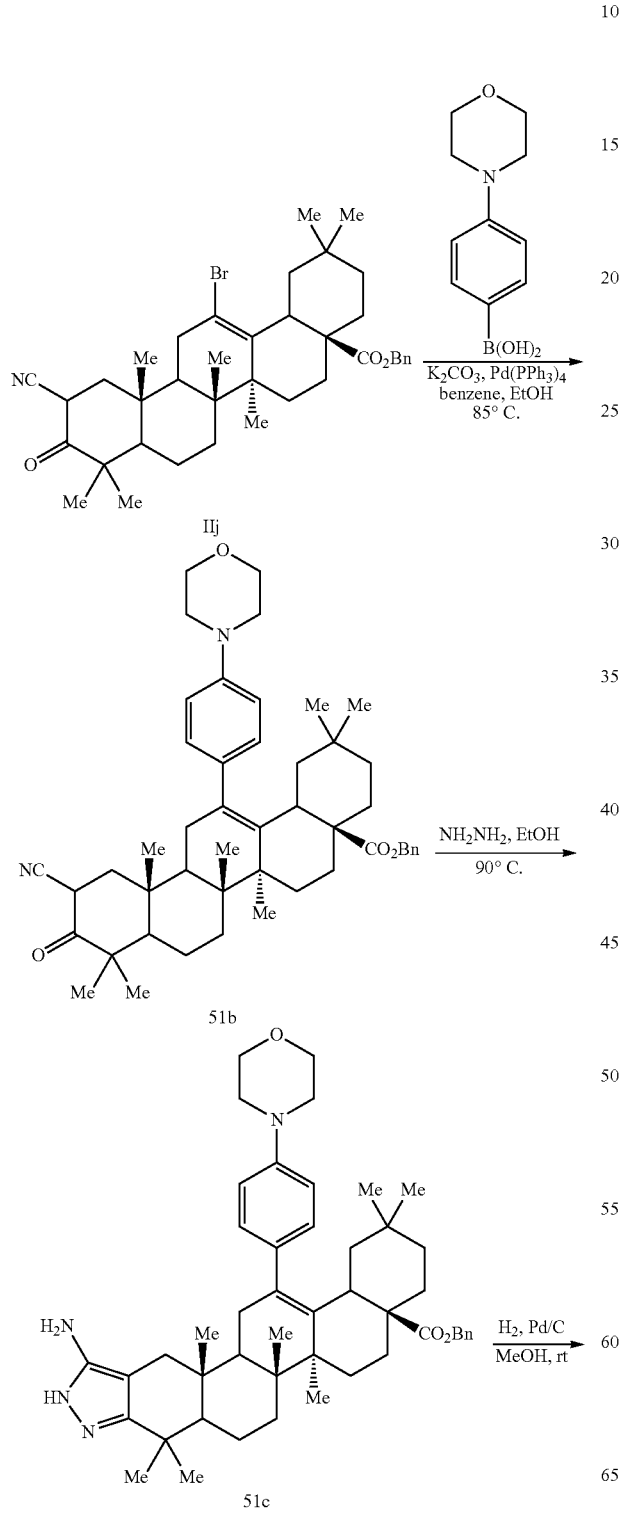

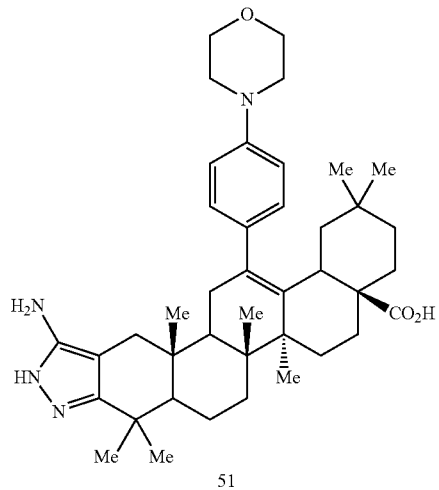

(i) Preparation of 51b: (4aS,6aS,6bR,12aR)-Benzyl 11-cyano-2,2,6a,6b,9,9,12a-heptamethyl-14-(4-morpholinophenyl)-10-oxo-1,2,3,4,4a,5,6,6a,6b,7,8,8a,9,10,11,12,12a,12b,13,14b-icosahydropicene-4-a-carboxylate To a mixture of IIj (300 mg, 0.46 mmol) and 4-morpholinophenylboronic acid (575 mg, 2.78 mmol) in benzene (10 mL) and EtOH (5 mL) was added K$_2$CO$_3$ (511 mg, 3.70 mmol). The mixture was sparged with nitrogen and then Pd(PPh$_3$)$_4$ (107 mg, 0.09 mmol) was added. The mixture was heated at 85° C. overnight and concentrated under reduced pressure. The residue was dissolved in EtOAc (50 mL) and the solution was washed with brine then dried (Na$_2$SO$_4$), filtered and concentrated. The residue was purified by column chromatography (silica, 0-30% EtOAc in hexanes) to afford the sub-title compound (200 mg, 59%).

$^1$H NMR (300 MHz, CDCl$_3$) δ 0.28-2.29 (m, 43H), 3.09-3.10 (m, 4H), 3.85-3.86 (m, 4H), 5.05 (m, 1H), 5.17 (m, 1H), 6.75-6.78 (m, 2H), 7.02-7.06 (m, 2H), 7.25-7.36 (m, 5H).

(ii) Preparation of 51c: (4aS,6aS,6bR,13aR)-Benzyl 12-amino-2,2,6a,6b,9,9,13a-heptamethyl-15-(4-morpholinophenyl)-2,3,4,4a,5,6,6a,6b,7,8,8a,9,11,13,13a,13b,14,15b-octadecahydro-1H-chryseno[1,2-f]indazole-4-a-carboxylate To a solution of 51b (196 mg, 0.26 mmol) and EtOH (5 mL) was added hydrazine (42 µL, 1.34 mmol). The mixture was heated at 90° C. for 60 hours and then concentrated under reduced pressure. The residue was purified by column chromatography (silica, 0-20% CMA in CH$_2$Cl$_2$) to provide the sub-title compound (109 mg, 55%).

$^1$H NMR (300 MHz, CDCl$_3$) δ 0.30-2.24 (m, 43H), 3.07-3.12 (m, 4H), 3.40-3.47 (m, 2H), 3.85-3.88 (m, 4H), 5.10 (d, J=12.3 Hz, 1H), 5.22 (d, J=12.6 Hz, 1H), 6.78 (d, J=8.7 Hz, 1H), 7.06 (d, J=8.4 Hz, 1H), 7.36-7.39 (m, 5H). APCI MS m/z 745 [C$_{48}$H$_{64}$N$_4$O$_3$+H]$^+$.

(iii) Preparation of 51: (4aS,6aS,6bR,13aR)-12-Amino-2,2,6a,6b,9,9,13a-heptamethyl-15-(4-morpholinophenyl)-2,3,4,4a,5,6,6a,6b,7,8,8a,9,11,13,13a,13b,14,15b-octadecahydro-1H-chryseno[1,2-f]indazole-4-a-carboxylic acid A solution of 51c (108 mg, 0.14 mmol) and MeOH (15 mL) was flushed with nitrogen and then 10% Pd/C (55 mg) was added. The mixture was flushed with nitrogen followed by hydrogen. The mixture was stirred under hydrogen at atmospheric pressure overnight.

The catalyst was removed by filtration through diatomaceous earth and the filtrate was concentrated. The residue was purified by column chromatography (silica, 0-10% MeOH in $CH_2Cl_2$) to afford the title compound (26 mg, 27%).

$R_f$ 0.35 (90:9:1 Methylene Chloride/Methanol/concentrated Ammonium Hydroxide).

$^1$H NMR (300 MHz, $CD_3OD$) δ 0.30-2.37 (m, 42H), 3.10 (m, 4H), 3.84 (m, 4H), 6.95 (d, J=7.8 Hz, 2H), 7.16 (d, J=7.5 Hz, 2H). APCI MS m/z 655 $[C_{41}H_{58}N_4O_3+H]^+$. m.p. 250-270° C. dec. HPLC (Method A)>99% (214 nm) $t_R$=13.3 min.

EXAMPLE 52

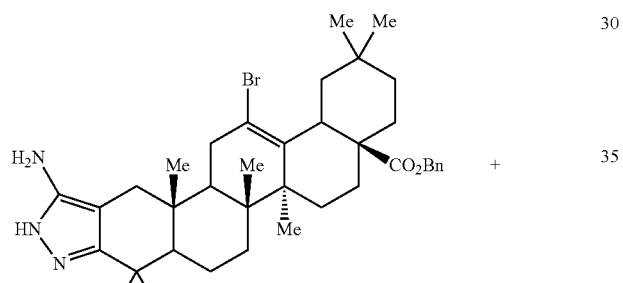

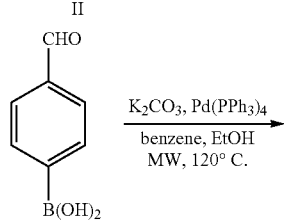

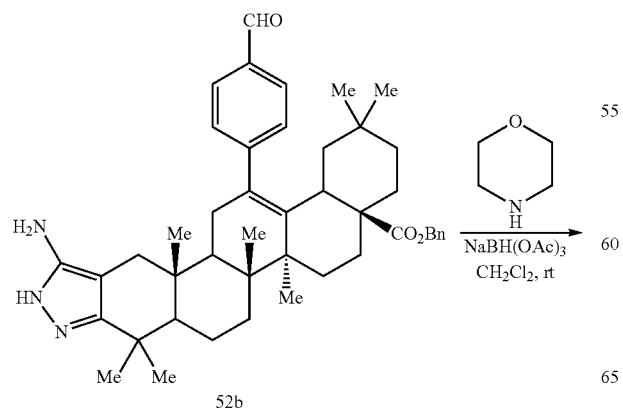

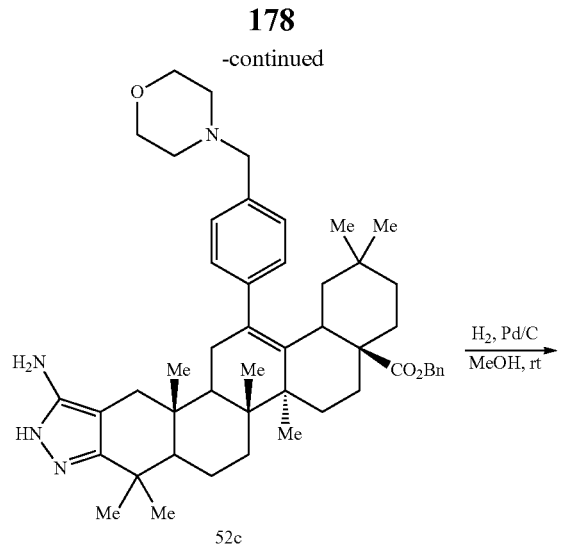

(i) Preparation of 52b: (4aS,6aS,6bR,13aR)-Benzyl 12-amino-15-(4-formylphenyl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylate To a solution of II (250 mg, 0.37 mmol), 4-formylphenylboronic acid (170 mg, 1.13 mmol), benzene (4 mL) and EtOH (1 mL) was added $K_2CO_3$ (208 mg, 1.50 mmol). The mixture was sparged with nitrogen and then $Pd(PPh_3)_4$ (87 mg, 0.07 mmol) was added. The reaction mixture was heated at 120° C. for 1 hour using microwave irradiation and then concentrated under reduced pressure. The residue was dissolved in EtOAc (20 mL) and the solution was washed with brine. The organic layer was dried ($Na_2SO_4$), filtered and concentrated. The residue was purified by column chromatography (silica, 0-10% MeOH in $CH_2Cl_2$) to afford the sub-title compound (224 mg, 86%).

APCI MS m/z 688 $[C_{45}H_{57}N_3O_3+H]^+$.

(ii) Preparation of 52c: (4aS,6aS,6bR,13aR)-Benzyl 12-amino-2,2,6a,6b,9,9,13a-heptamethyl-15-(4-(morpholinomethyl)phenyl)-2,3,4,4a,5,6,6a,6b,7,8,8a,9,11,13,13a,13b,14,15b-octadecahydro-1H-chryseno[1,2-f]indazole-4-a-carboxylate To a solution of 52b (220 mg, 0.32 mmol), morpholine (56 μL, 0.64 mmol) and $CH_2Cl_2$ (10 mL) was added sodium triacetoxyborohydride (136 mg, 0.64 mmol). The mixture was stirred at room temperature overnight. The resultant mixture was diluted with EtOAc (100 mL) and the solution was washed with brine then dried ($Na_2SO_4$), filtered and concentrated under reduced pressure. The residue was purified by column chromatography (silica, 0-20% MeOH in $CH_2Cl_2$) to afford the sub-title compound (80 mg, 33%).

$^1$H NMR (300 MHz, $CD_3OD$) δ 0.28-2.24 (m, 41H), 2.39-2.42 (m, 4H), 3.03 (m, 1H), 3.45 (s, 2H), 3.69-3.70 (m, 4H), 5.03 (d, J=12.6 Hz, 1H), 5.23 (d, J=12.3 Hz, 1H), 7.15-7.18 (m, 4H), 7.37 (s, 5H).

(iii) Preparation of 52: (4aS,6aS,6bR,13aR)-12-Amino-2,2,6a,6b,9,9,13a-heptamethyl-15-(4-(morpholinomethyl)phenyl)-2,3,4,4a,5,6,6a,6b,7,8,8a,9,11,13,13a,13b,14,15b-octadecahydro-1H-chryseno[1,2-f]indazole-4-a-carboxylic acid A solution of 52c (75 mg, 0.09 mmol) and MeOH (10 mL) was flushed with nitrogen and then 10% Pd/C (100 mg) was added. The mixture was flushed with nitrogen followed by hydrogen. The mixture was stirred under hydrogen at atmospheric pressure overnight. The catalyst was removed by filtration through diatomaceous earth and the filtrate was concentrated. The residue was purified by preparative HPLC to afford the title compound (8 mg, 12%).

$R_f$ 0.75 (40:9:1 Methylene Chloride/Methanol/concentrated Ammonium Hydroxide).

$^1$H NMR (300 MHz, $CD_3OD$) δ 0.25-2.39 (m, 45H), 2.99 (m, 1H), 3.73 (s, 2H), 4.02 (s, 2H), 4.38 (s, 2H), 7.47-7.52 (m, 4H). APCI MS m/z 669 $[C_{42}H_{60}N_4O_3+H]^+$. m.p. >300° C. dec. HPLC (Method A)>99% (214 nm) $t_R$=12.1 min.

EXAMPLE 53

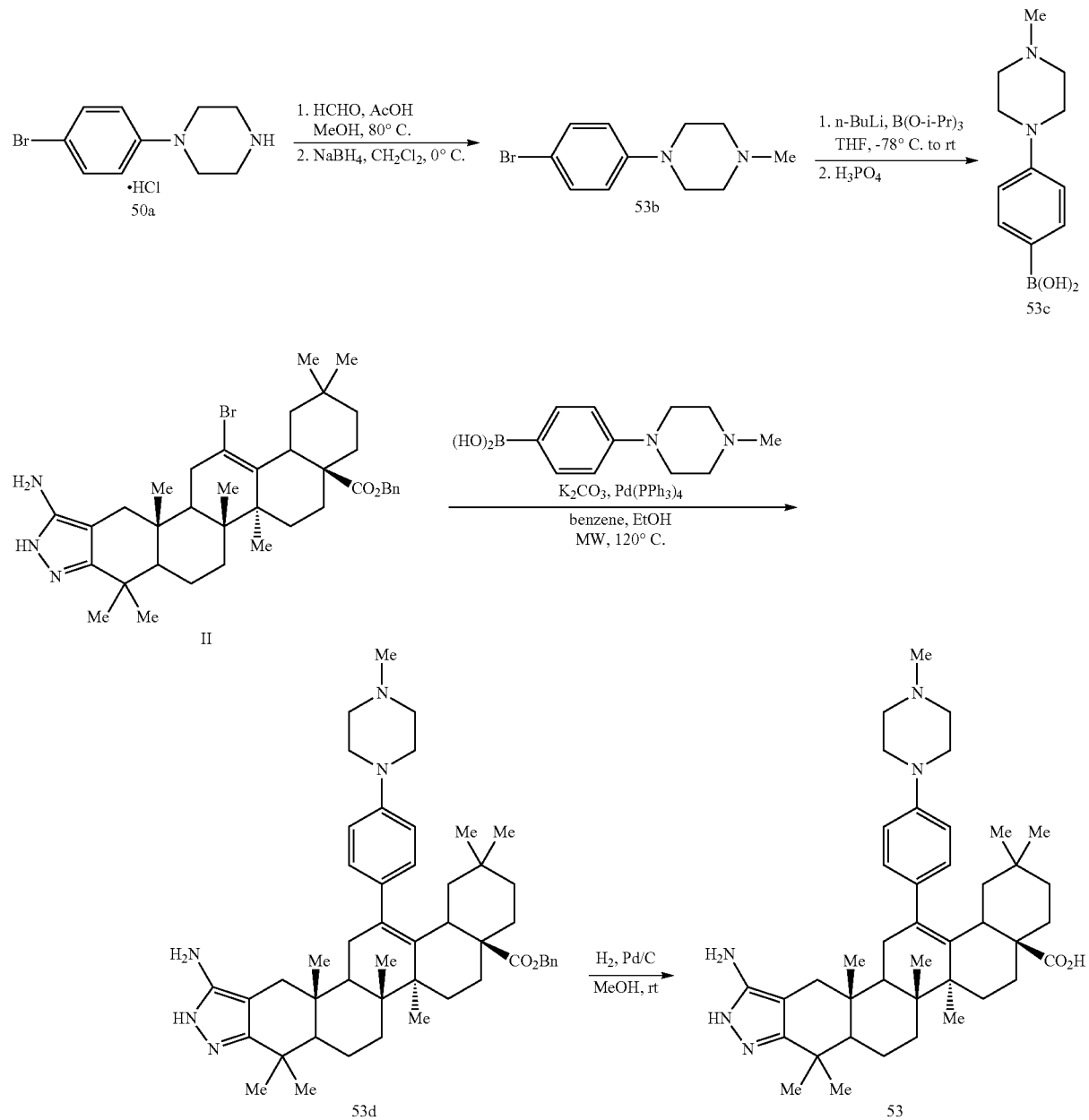

181

(i) Preparation of 53b: 1-(4-Bromophenyl)-4-methylpiperazine

A mixture of 1-(4-bromophenyl)piperazine hydrochloride (1.0 g, 3.61 mmol), formaldehyde (37% aqueous, 3 mL, 39.71 mmol), AcOH (0.23 mL, 3.97 mmol) and MeOH (30 mL) was heated at 80° C. under nitrogen. After 1.5 hours, the mixture was cooled to 0° C. in an ice bath. Methylene chloride (5 mL) was added followed by a slow addition of sodium borohydride (1.91 g, 50.54 mmol) under nitrogen. The mixture was stirred for 1 hour and then poured into a seperatory funnel containing a saturated solution of $NH_4Cl$ (25 mL) and $CH_2Cl_2$ (50 mL). The layers were separated and the aqueous layer was extracted with $CH_2Cl_2$ (2×50 mL). The extracts were dried ($Na_2SO_4$), filtered and concentrated to to give the sub-title compound (900 mg, 97%) which was used without further purification.

$^1$H NMR ((300 MHz, $CDCl_3$) δ 2.34 (s, 3H), 2.55 (m, 4H), 3.17 (m, 4H), 6.79 (d, J=9.0 Hz, 2H), 7.32 (d, J=9.0 Hz, 2H).

(ii) Preparation of 53c: 4-(4-Methylpiperazin-1-yl)phenylboronic acid

To a solution of 53b (390 mg, 1.52 mmol) and THF (10 mL) was added n-butyllithium (0.79 mL of 2.5 M in hexanes, 1.98 mmol) at −78° C. and stirred for 10 min. Triisopropylborate (1.75 mL, 7.64 mmol) was added at −78° C. The mixture was slowly warmed to room temperature and then quenched with phosphoric acid. The reaction mixture was neutralized with saturated $NaHCO_3$ solution and extracted with EtOAc (3×10 mL). The solution was dried ($Na_2SO_4$), filtered and concentrated under reduced pressure. The residue was purified by column chromatography (silica, 0-10% MeOH in $CH_2Cl_2$) to afford the sub-title compound (180 mg, 58%).

$^1$H NMR ((300 MHz, $CD_3OD$) δ 2.32 (s, 3H), 2.55 (m, 4H), 3.03 (s, 1H), 3.21 (m, 3H), 6.69-7.59 (m, 4H).

(iii) Preparation of 53d: (4aS,6aS,6bR,13aR)-Benzyl 12-amino-2,2,6a,6b,9,9,13a-heptamethyl-15-(4-(4-methylpiperazin-1-yl)phenyl)-2,3,4,4a,5,6,6a,6b,7,8,8a,9,11,13,13a,13b,14,15b-octadecahydro-1H-chryseno[1,2-f]indazole-4-a-carboxylate To a mixture of II (160 mg, 0.24 mmol) and 53c (159 mg, 0.72 mmol) in benzene (4 mL) and EtOH (1 mL) was added $K_2CO_3$ (133 mg, 0.96 mmol). The mixture was sparged with nitrogen and then $Pd(PPh_3)_4$ (55 mg, 0.04 mmol) was added. The reaction mixture was heated at 120° C. for 1 hour using microwave irradiation and then concentrated. The residue was dissolved in EtOAc (20 mL) and the solution was washed with brine then dried ($Na_2SO_4$), filtered and concentrated under reduced pressure. The residue was purified by column chromatography (silica, 0-10% MeOH in $CH_2Cl_2$) to afford the sub-title compound (80 mg, 44%).

$^1$H NMR (300 MHz, $CDCl_3$) δ 0.29-3.46 (m, 53H), 5.06 (d, J=12.6 Hz, 1H), 5.22 (d, J=12.6 Hz, 1H), 6.80 (d, J=8.4 Hz, 2H), 7.05 (d, J=8.7 Hz, 2H), 7.35-7.44 (m, 5H).

APCI MS m/z 758 $[C_{49}H_{67}N_5O_2+H]^+$.

(iv) Preparation of 53: (4aS,6aS,6bR,13aR)-12-Amino-2,2,6a,6b,9,9,13a-heptamethyl-15-(4-(4-methylpiperazin-1-yl)phenyl)-2,3,4,4a,5,6,6a,6b,7,8,8a,9,11,13,13a,13b,14,15b-octadecahydro-1H-chryseno[1,2-f]indazole-4-a-carboxylic acid A solution of 53d (75 mg, 0.09 mmol) and MeOH (10 mL) was flushed with nitrogen and then 10% Pd/C (70 mg) was added. The mixture was flushed with nitrogen followed by hydrogen. The mixture was stirred under hydrogen at atmospheric pressure overnight. The catalyst was removed by filtration through diatomaceous earth and the filtrate was concentrated. The residue was purified by column chromatography (silica, 0-40% CMA in $CH_2Cl_2$) followed by preparative HPLC to afford the title compound (6 mg, 5%) as a solid.

$R_f$ 0.37 (40:9:1 Methylene Chloride/Methanol/concentrated Ammonium Hydroxide).

$^1$H NMR (300 MHz, $CD_3OD$) δ 0.28-2.42 (m, 34H), 2.97 (s, 3H), 3.12-3.77 (m, 8H), 3.37 (s, 8H), 7.02 (d, J=8.7 Hz, 2H), 7.24 (d, J=8.1 Hz, 2H). APCI MS m/z 668 $[C_{42}H_{61}N_5O_2+H]^+$. m.p. >300° C. dec. HPLC (Method A)>99% (214 nm) $t_R$=13.9 min.

EXAMPLE 54

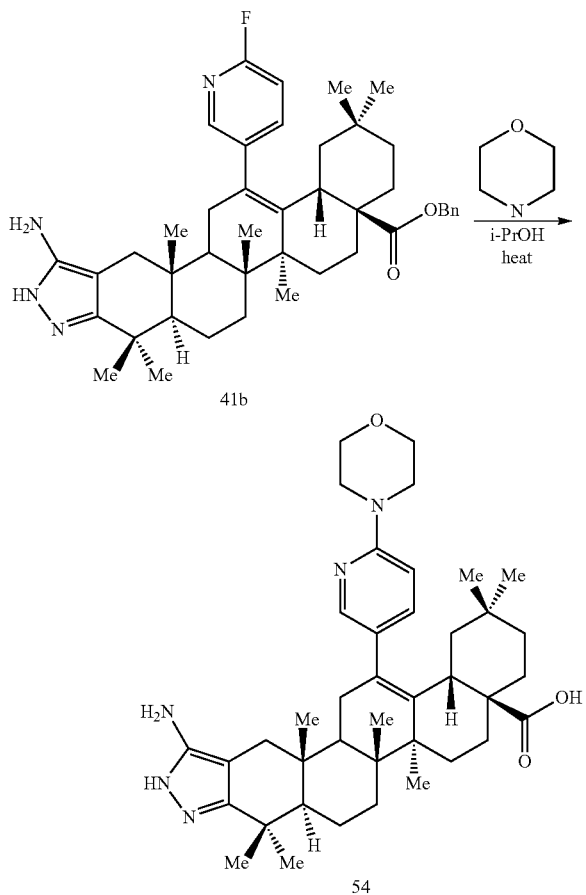

(i) Preparation of 54: (4aS,6aS,6bR,8aR,13aR,15bS)-12-Amino-2,2,6a,6b,9,9,13a-heptamethyl-15-(6-morpholinopyridin-3-yl)-2,3,4,4a,5,6,6a,6b,7,8,8a,9,11,13,13a,13b,14,15b-octadecahydro-1H-chryseno[1,2-f]indazole-4-a-carboxylic acid A mixture of 41b (100 mg, 0.14 mmol) and morpholine (0.5 mL) in i-PrOH (2 mL) was sealed and heated to 160° C. by microwave for 2 hours. The mixture was concentrated to dryness. The residue was purified by column chromatography (silica, 0-30% CMA in $CH_2Cl_2$) followed by preparative HPLC to afford the sub-title compound (10 mg, 11%) as an off-white solid.

$R_f$ 0.75 (80:18:2 Methylene Chloride/Methanol/concentrated Ammonium Hydroxide).

$^1$H NMR (300 MHz, $CD_3OD$) δ 0.46 (s, 3H), 0.82 (s, 3H), 0.90 (s, 3H), 0.99 (s, 3H), 1.22 (s, 3H), 1.25 (s, 3H), 1.29 (s, 3H), 1.35-2.30 (m, 19H), 2.37 (d, J=14.4 Hz, 1H), 3.01 (s, 1H), 3.62 (m, 4H), 3.84 (m, 4H), 7.34 (d, J=9.6 Hz, 1H), 8.00 (s, 2H). mp >300° C.

APCI MS (Positive Mode) m/z 656 $[C_{40}H_{57}N_5O_3+H]^+$.

EXAMPLE 55

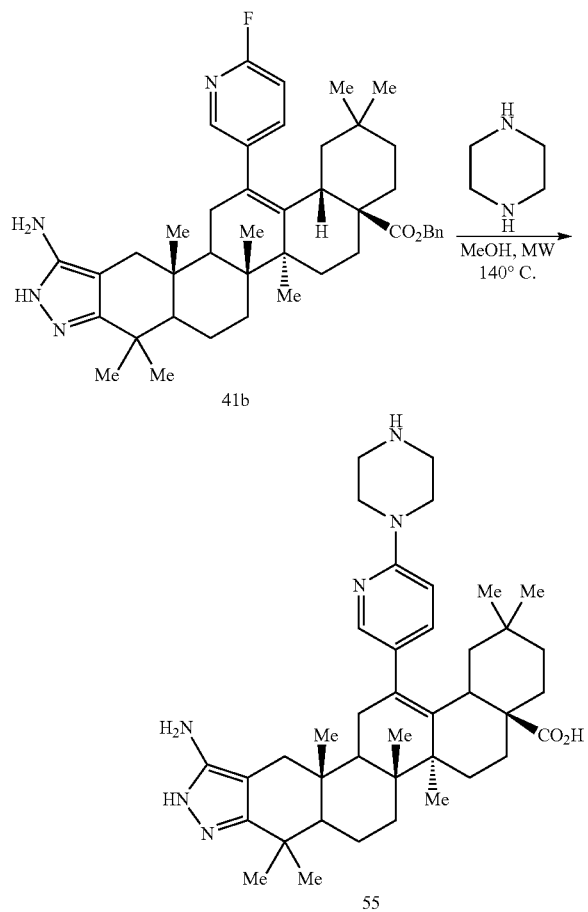

(i) Preparation of 55: (4aS,6aS,6bR,13aR)-12-Amino-2,2,6a,6b,9,9,13a-heptamethyl-15-(6-(piperazin-1-yl)pyridin-3-yl)-2,3,4,4a,5,6,6a,6b,7,8,8a,9,11,13,13a,13b,14,15b-octadecahydro-1H-chryseno[1,2-f]indazole-4-a-carboxylic acid To 41b (150 mg, 0.22 mmol) in MeOH (5 mL) was added piperazine (1.38 g, 20.89 mmol). The reaction mixture was heated at 140° C. for 5 hours and then at 150° C. for an additional 5 hours using microwave irradiation. The solvent was concentrated and then the residue was dissolved in EtOAc/i-PrOH/$CH_2Cl_2$ (1:1:1, 30 mL). The solution was washed with brine, dried ($Na_2SO_4$), filtered and concentrated. The residue was purified by column chromatography (silica, 0-40% CMA in $CH_2Cl_2$) followed by preparative HPLC to afford the title compound (15 mg, 10%) as a solid.

$R_f$ 0.10 (40:9:1 Methylene Chloride/Methanol/concentrated Ammonium Hydroxide).

$^1$H NMR (300 MHz, $CD_3OD$) δ 0.40-2.43 (m, 41H), 2.98 (m, 1H), 3.39-3.41 (m, 4H), 3.85-3.87 (m, 4H), 7.23 (d, J=9.0 Hz, 1H), 7.89 (d, J=3.4 Hz, 1H), 8.12 (s, 1H).

APCI MS m/z 655 $[C_{40}H_{58}N_6O_2+H]^+$. m.p. 240-260° dec. HPLC (Method A) 96.2% (214 nm) $t_R$=10.7 min.

EXAMPLE 56

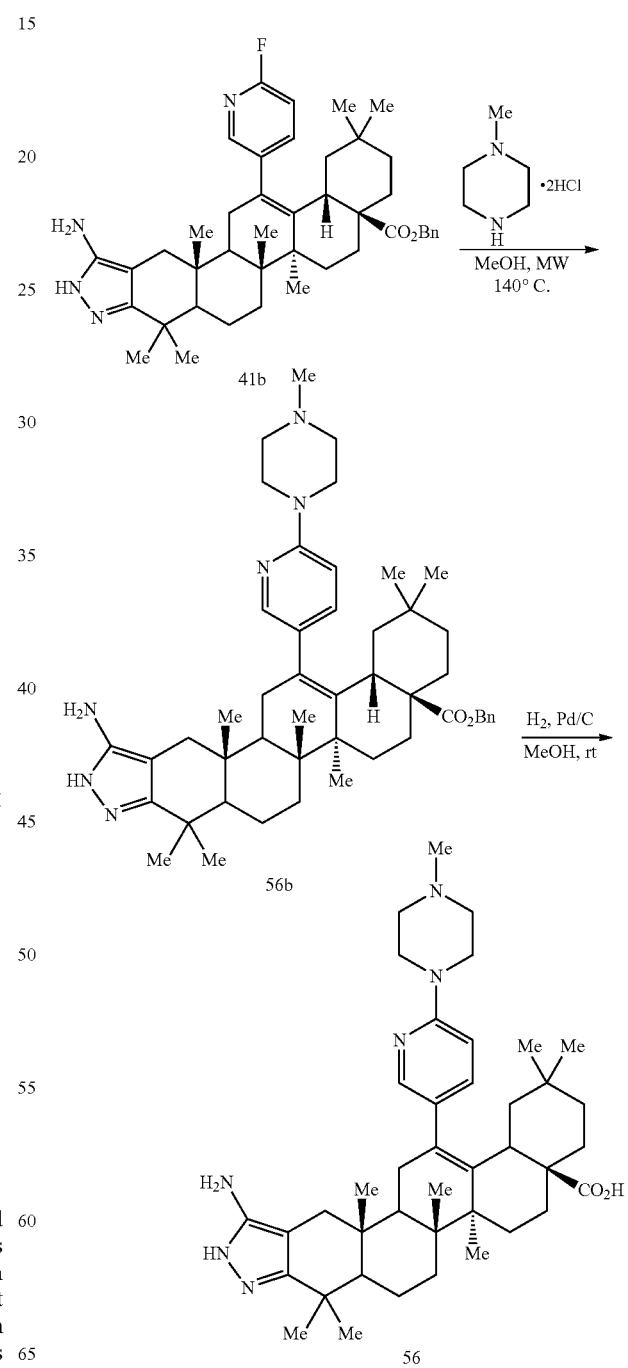

(i) Preparation of 56b: (4aS,6aS,6bR,13aR)-Benzyl 12-amino-2,2,6a,6b,9,9,13a-heptamethyl-15-(6-(4-methylpiperazin-1-yl)pyridin-3-yl)-2,3,4,4a,5,6,6a,6b,7,8,8a,9,11,13,13a,13b,14,15b-octadecahydro-1H-chryseno[1,2-f]indazole-4-a-carboxylate To a solution of 41b (210 mg, 0.30 mmol) in MeOH (4 mL) was added 1-methylpiperazine dihydrochloride (1.5 g, 8.67 mmol). The reaction mixture was heated at 140° C. for 10 hours using microwave irradiation and then concentrated. The residue was dissolved in EtOAc (20 mL) and the solution was washed with brine then dried ($Na_2SO_4$), filtered and concentrated under reduced pressure. The residue was purified by column chromatography (silica, 0-30% CMA in $CH_2Cl_2$) to afford the sub-title compound (90 mg, 38%).

$^1$H NMR (300 MHz, $CD_3OD$) δ 0.34-2.16 (m, 43H), 2.34 (s, 4H), 2.56 (s, 4H), 3.01 (m, 1H), 3.49 (s, 4H), 5.03 (d, J=12.1 Hz, 2H), 5.20 (d, J=12.0 Hz, 2H), 6.65 (d, J=8.4 Hz, 1H), 6.65 (d, J=4.8 Hz, 1H), 7.36-7.38 (m, 6H), 7.98 (s, 1H). APCI MS m/z 759 $[C_{48}H_{66}N_6O_2+H]^+$.

(ii) Preparation of 56: (4aS,6aS,6bR,13aR)-12-Amino-2,2,6a,6b,9,9,13a-heptamethyl-15-(6-(4-methylpiperazin-1-yl)pyridin-3-yl)-2,3,4,4a,5,6,6a,6b,7,8,8a,9,11,13,13a,13b,14,15b-octadecahydro-1H-chryseno[1,2-f]indazole-4-a-carboxylic acid A solution of 56b (70 mg, 0.09 mmol) and MeOH (10 mL) was flushed with nitrogen and then 10% Pd/C (70 mg) was added. The mixture was flushed with nitrogen followed by hydrogen. The mixture was stirred under hydrogen at atmospheric pressure overnight. The catalyst was removed by filtration through diatomaceous earth and the filtrate was concentrated under reduced pressure. The residue was purified by column chromatography (silica, 0-60% CMA in $CH_2Cl_2$) to afford the title compound (42 mg, 69%).

$R_f$ 0.25 (40:9:1 Methylene Chloride/Methanol/concentrated Ammonium Hydroxide).

$^1$H NMR (300 MHz, $CD_3OD$) δ 0.35-2.24 (m, 40H), 2.37 (s, 3H), 2.62 (s, 4H), 3.07 (m, 1H), 3.53 (s, 4H), 4.53 (s, 1H), 6.86 (d, J=8.4 Hz, 1H), 7.75 (d, J=8.1 Hz, 1H), 8.03 (s, 1H). APCI MS m/z 669 $[C_{41}H_{60}N_6O_2+H]^+$. m.p. 280-300° C. dec. HPLC (Method A)>99% (214 nm) $t_R$=10.3 min.

EXAMPLE 57

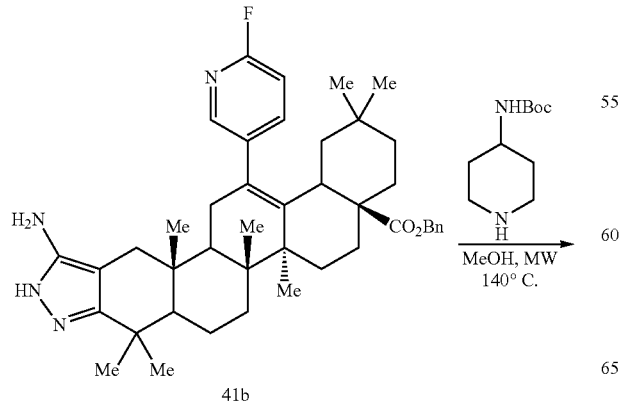

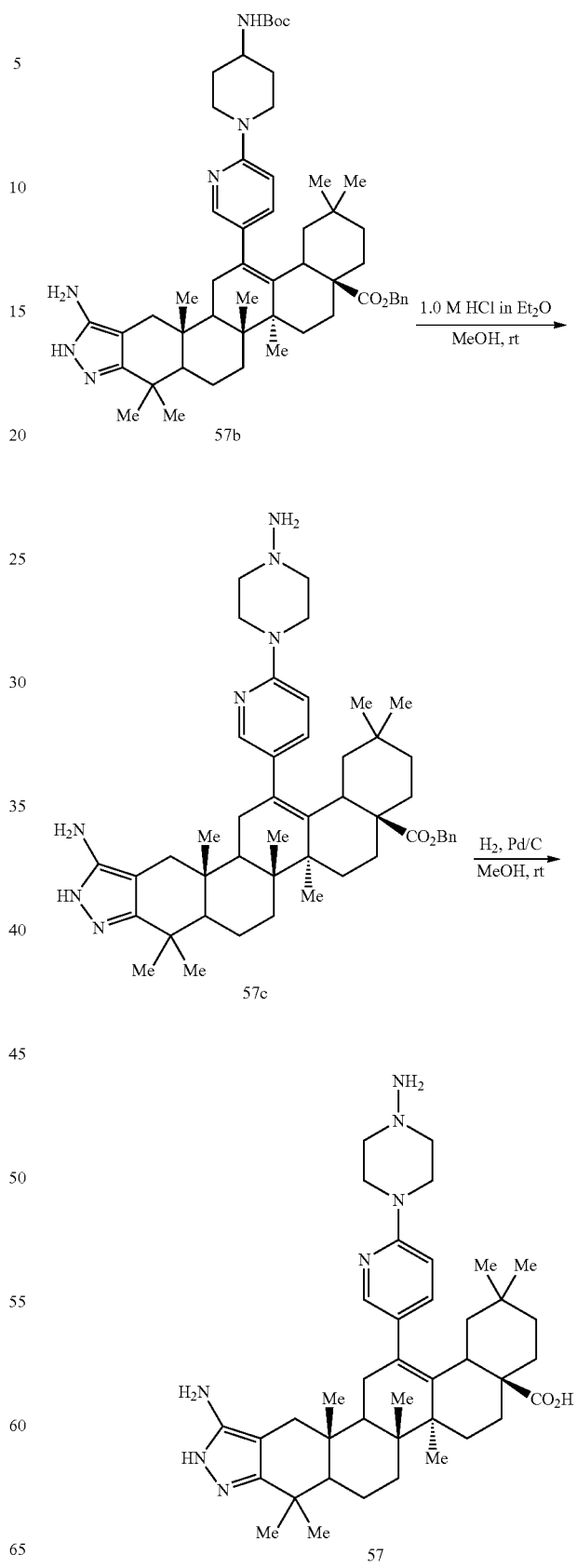

(i) Preparation of 57b: (4aS,6aS,6bR,13aR)-Benzyl 12-amino-15-(6-(4-(tert-butoxycarbonylamino)piperidin-1-yl)pyridin-3-yl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylate To 41b (200 mg, 0.29 mmol) in MeOH (4 mL) was added tert-butyl piperidin-4-ylcarbamate (1.5 g, 7.50 mmol). The reaction mixture was heated at 140° C. for 7 hours using microwave irradiation and then concentrated. The residue was dissolved in EtOAc (20 mL) and the solution was washed with brine then dried ($Na_2SO_4$), filtered and concentrated under reduced pressure. The residue was purified by column chromatography (0-10% MeOH in $CH_2Cl_2$) to afford the sub-title compound (200 mg, 79%).
APCI MS m/z 859 $[C_{53}H_{74}N_6O_4+H]^+$.

(ii) Preparation of 57c: (4aS,6aS,6bR,13aR)-Benzyl 12-amino-15-(6-(4-aminopiperidin-1-yl)pyridin-3-yl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylate To a solution of 57b (190 mg, 0.22 mmol) in MeOH (10 mL) was added HCl (1.0 M in diethyl ether; 10 mL, 10.0 mmol). The mixture was stirred at room temperature for 32 hours and then concentrated under reduced pressure. Purification of the residue by column chromatography (silica, 0-70% CMA in $CH_2Cl_2$) afforded the sub-title compound (100 mg, 59%).
APCI MS m/z 759 $[C_{48}H_{66}N_6O_2+H]^+$.

(iii) Preparation of 57: (4aS,6aS,6bR,13aR)-12-Amino-15-(6-(4-aminopiperidin-1-yl)pyridin-3-yl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylic acid A solution of 57c (100 mg, 0.13 mmol) and MeOH (10 mL) was flushed with nitrogen and then 10% Pd/C (100 mg) was added. The mixture was flushed with nitrogen followed by hydrogen. The mixture was stirred under hydrogen at atmospheric pressure overnight. The catalyst was removed by filtration through diatomaceous earth and the filtrate was concentrated under reduced pressure. The residue was purified by column chromatography (silica, 0-50% CMA in $CH_2Cl_2$) to afford the title compound (25 mg, 29%).
$R_f$ 0.11 (40:9:1 Methylene Chloride/Methanol/concentrated Ammonium Hydroxide).
$^1$H NMR (300 MHz, $CD_3OD$) δ 0.36-2.35 (m, 46H), 3.07 (m, 2H), 3.10 (dd, J=3.4 Hz, 3.9 Hz, 1H), 4.29 (d, J=13.2 Hz, 2H), 6.87 (d, J=8.7 Hz, 1H), 7.61 (m, 1H), 8.03 (s, 1H). APCI MS m/z 669 $[C_{41}H_{60}N_6O_2+H]^+$. m.p. 260-270° C. dec. HPLC (Method A) 95.3% (214 nm) $t_R$=10.8 min.

EXAMPLE 58

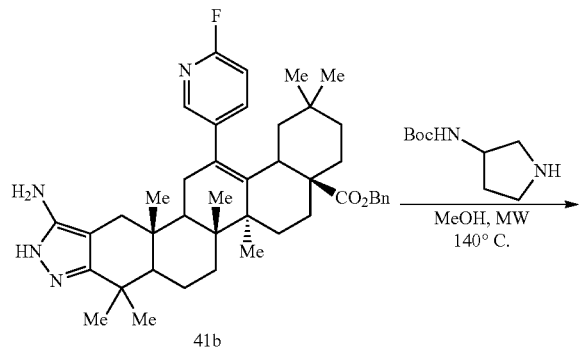

41b

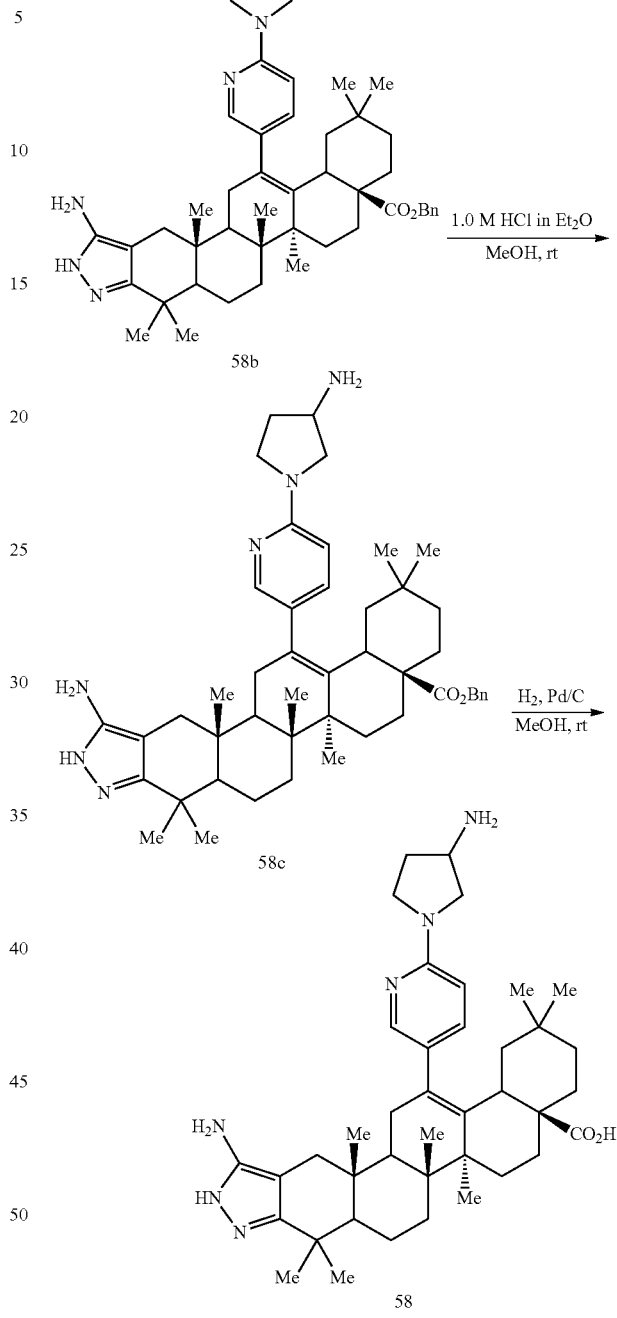

(i) Preparation of 58b: (4aS,6aS,6bR,13aR)-Benzyl 12-amino-15-(6-(3-(tert-butoxycarbonylamino)pyrrolidin-1-yl)pyridin-3-yl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylate To a solution of 41b (246 mg, 0.36 mmol) in MeOH (4 mL) was added tert-butyl pyrrolidin-3-ylcarbamate (1.0 g, 5.36 mmol). The reaction mixture was heated at 140° C. for 6 hours using microwave irradiation. The solvent was removed under reduced pressure and the residue was dissolved in EtOAc (20 mL). The solution was washed with brine then dried (Na$_2$SO$_4$), filtered and concentrated. The residue was purified by column chromatography (silica, 0-10% MeOH in CH$_2$Cl$_2$) to afford the sub-title compound (306 mg, 100%).

APCI MS m/z 845 [C$_{52}$H$_{72}$N$_6$O$_4$+H]$^+$.

(ii) Preparation of 58c: (4aS,6aS,6bR,13aR)-Benzyl 12-amino-15-(6-(3-aminopyrrolidin-1-yl)pyridin-3-yl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylate To a solution of 58b (300 mg, 0.35 mmol) in MeOH (10 mL) was added HCl (1.0 M in diethyl ether, 7.8 mL, 7.80 mmol). The reaction mixture was stirred at room temperature for 24 hours and then concentrated. The residue was purified by column chromatography (silica, 0-40% CMA in CH$_2$Cl$_2$) to afford the sub-title compound (50 mg, 19%).

$^1$H NMR (300 MHz, CD$_3$OD) δ 0.36-2.35 (m, 42H), 3.08-3.68 (m, 7H), 5.05 (d, J=12.0 Hz, 1H), 5.21 (d, J=12.0 Hz, 1H), 6.32 (d, J=8.7 Hz, 1H), 7.30-7.39 (m, 6H), 7.89 (s, 1H).

APCI MS m/z 745 [C$_{47}$H$_{64}$N$_6$O$_2$+H]$^+$.

(iii) Preparation of 58: (4a-8,6a8,6bR,13aR)-12-Amino-15-(6-(3-aminopyrrolidin-1-yl)pyridin-3-yl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylic acid A solution of 58c (50 mg, 0.067 mmol) and MeOH (15 mL) was flushed with nitrogen and then 10% Pd/C (50 mg) was added. The mixture was flushed with nitrogen followed by hydrogen. The mixture was stirred under hydrogen at atmospheric pressure overnight. The catalyst was removed by filtration through diatomaceous earth and the filtrate was concentrated. The residue was purified by column chromatography (silica, 0-70% CMA in CH$_2$Cl$_2$) to afford the title compound (33 mg, 76%).

R$_f$ 0.14 (40:9:1 Methylene Chloride/Methanol/concentrated Ammonium Hydroxide).

$^1$H NMR (300 MHz, CD$_3$OD) δ 0.37-2.36 (m, 44H), 3.10-3.80 (m, 5H), 6.53 (d, J=8.7 Hz, 1H), 7.61 (d, J=8.4 Hz, 1H), 7.93 (s, 1H). APCI MS m/z 655 [C$_{40}$H$_{58}$N$_6$O$_2$+H]$^+$.

m.p. >300° C. HPLC (Method A) 97.4% (214 nm) t$_R$=10.8 min.

EXAMPLE 59

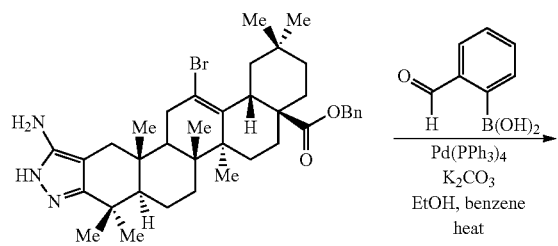

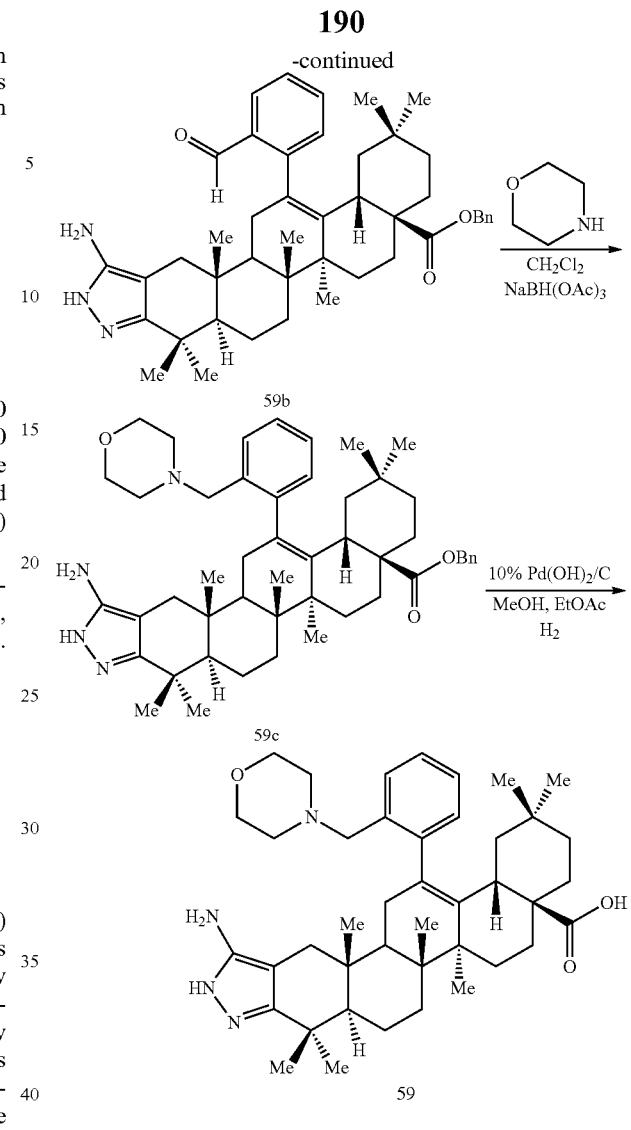

(i) Preparation of 59b: (4aS,6aS,6bR,8aR,13aR,15bS)-benzyl 12-amino-15-(2-formylphenyl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylate A mixture of II (500 mg, 0.75 mmol), 2-formylphenylboronic acid (337 mg, 2.24 mmol) Pd(PPh$_3$)$_4$ (80 mg, 0.069 mmol) and K$_2$CO$_3$ (414 mg, 3.0 mmol) in benzene (3.5 mL) and EtOH (1.5 mL) was sealed and heated to 120° C. by microwave for 1 hour. The reaction mixture was diluted with EtOAc (100 mL). The organic phase was washed with brine then dried (MgSO$_4$), filtered and concentrated to dryness. The residue was purified by column chromatography (silica, 0-10% MeOH in CH$_2$Cl$_2$) to afford the sub-title compound (540 mg) as a brown solid.

APCI MS (Positive Mode) m/z 688 [C$_{45}$H$_{57}$N$_3$O$_3$+H]$^+$.

(ii) Preparation of 59c: (4aS,6aS,6bR,8aR,13aR,15bS)-Benzyl 12-amino-2,2,6a,6b,9,9,13a-heptamethyl-15-(2-(morpholinomethyl)phenyl)-2,3,4,4a,5,6,6a,6b,7,8,8a,9,11,13,13a,13b,14,15b-octadecahydro-1H-chryseno[1,2-f]indazole-4-a-carboxylate To a solution of 59b (140 mg, 0.20 mmol) and morpholine (0.035 mL, 0.40 mmol) in CH$_2$Cl$_2$ (5 mL) was added sodium triacetoxyborohydride (85 mg, 0.40 mmol). The mixture was stirred at room temperature for 12 hours. The reaction mixture was diluted with EtOAc (150 mL). The organic phase was washed with brine then dried (MgSO₄), filtered and concentrated to dryness. The residue was purified by column chromatography (silica, 0-10% MeOH in CH₂Cl₂) to afford the sub-title compound (71 mg, 47%) as a brown solid.

APCI MS (Positive Mode) m/z 759 $[C_{49}H_{66}N_4O_3+H]^+$.

(iii) Preparation of 59: (4aS,6aS,6bR,8aR,13aR, 15bS)-12-Amino-2,2,6a,6b,9,9,13a-heptamethyl-15-(2-(morpholinomethyl)phenyl)-2,3,4,4a,5,6,6a,6b,7,8,8a,9,11,13,13a,13b,14,15b-octadecahydro-1H-chryseno[1,2-f]indazole-4-a-carboxylic acid A mixture of 59c (71 mg, 0.093 mmol) and 10% Pd(OH)₂/C (50 mg) in MeOH (12 mL) and EtOAc (3 mL) was stirred under a hydrogen balloon for 12 hours. The reaction mixture was filtered through a pad of diatomaceous earth and washed with CMA (25 mL). The filtrate was concentrated to dryness under reduced pressure. The residue was purified by column chromatography (silica, 0-70% CMA in CH₂Cl₂) to afford the title compound (20 mg, 33%) as a mixture of rotamers.

$R_f$ 0.80 (80:18:2 Methylene Chloride/Methanol/concentrated Ammonium Hydroxide).

¹H NMR (400 MHz, CD₃OD) δ 0.25 (s, 3H), 0.78 (s, 3H), 0.89 (s, 3H), 1.08 (s, 3H), 1.12 (s, 3H), 1.28 (s, 6H), 1.35-2.30 (m, 23H), 2.28 (d, J=14.8 Hz, 1H), 2.40 (m, 1H), 2.90 (m, 1H), 3.95-4.50 (m, 5H), 7.20-7.62 (m, 4H). mp >300° C. dec. APCI MS (Positive Mode) m/z 669 $[C_{42}H_{60}N_4O_3+H]^+$.

EXAMPLE 60

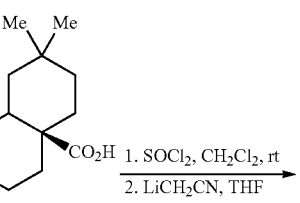

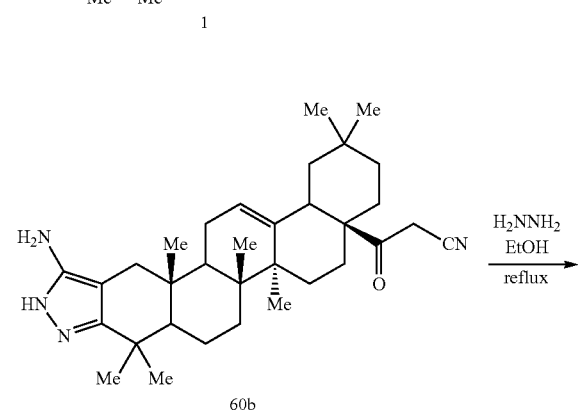

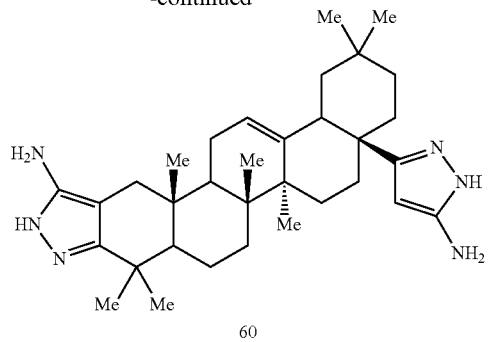

(i) Preparation of 60b: 3-((4aS,6aS,6bR,13aR)-12-Amino-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazol-4-a-yl)-3-oxopropanenitrile To a suspension of 1 (150 mg, 0.30 mmol) and CH₂Cl₂ (7 mL) was added thionyl chloride (0.22 mL, 3.0 mmol) at room temperature. The mixture was stirred for 1 hour, after which time the solvent was removed under reduced pressure. The residue was taken up in toluene (5 mL), concentrated and placed under vacuum at room temperature. A solution of CH₃CN (0.16 mL, 3.0 mmol) and THF (5 mL) was cooled to -78° C. under nitrogen. The solution was treated with n-butyllithium (2.5 M in hexanes, 1.27 mL, 3.2 mmol) while maintaining the internal temperature below -70° C. The previously prepared acid chloride was taken up in THF (2 mL), cooled to -78° C. and slowly added to the lithium salt mixture. The reaction mixture was stirred for 80 minutes and then quenched with 1 N HCl (10 mL). The layers were separated and the aqueous layer was extracted with EtOAc (15 mL) and the combined organic layers were dried (Na₂SO₄) and filtered. The solvent was removed under reduced pressure and the residue was purified by column chromatography (silica, 0-50% CMA in CH₂Cl₂) to provide the sub-title compound (115 mg, 74%) as an off-white solid.

¹H NMR (300 MHz, CD₃OD) δ 0.80 (s, 3H), 0.91-0.96 (m, 9H), 1.12-1.17 (m, 12H), 1.31-1.91 (m, 15H), 2.08-2.12 (m, 3H), 2.39-2.45 (m, 1H), 2.71-2.81 (m, 1H), 5.43-5.45 (m, 1H). ESI MS m/z 517 $[C_{33}H_{48}N_4O+H]^+$. HPLC 97.6% (area %), $t_R$=16.2 min.

(ii) Preparation of 60: (4aS,6aS,6bR,13aR)-4-a-(5-Amino-1H-pyrazol-3-yl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazol-12-amine A solution of 60b (100 mg, 0.19 mmol), hydrazine (31 mg, 0.97 mmol) and EtOH (5 mL) was heated at reflux under nitrogen for 16 hours. A second portion of hydrazine (91 mg, 2.85 mmol) was added and the reaction continued for 72 hours at reflux. The solvent was removed under reduced pressure and the residue was purified by column chromatography (silica, 0-50% CMA in CH₂Cl₂) to provide the title compound (43 mg, 43%) as an off-white solid.

¹H NMR (300 MHz, CD$_3$OD) δ 0.58 (s, 3H), 0.82 (s, 3H), 0.91-1.35 (m, 18H), 1.39-1.91 (m, 15H), 2.13-2.35 (m, 2H), 2.73-2.81 (m, 1H), 5.43-5.48 (m, 2H). ESI MS m/z 531 [C$_{33}$H$_{50}$N$_6$+H]$^+$. HPLC 97.9% (area %), t$_R$=14.2 min.

EXAMPLE 61

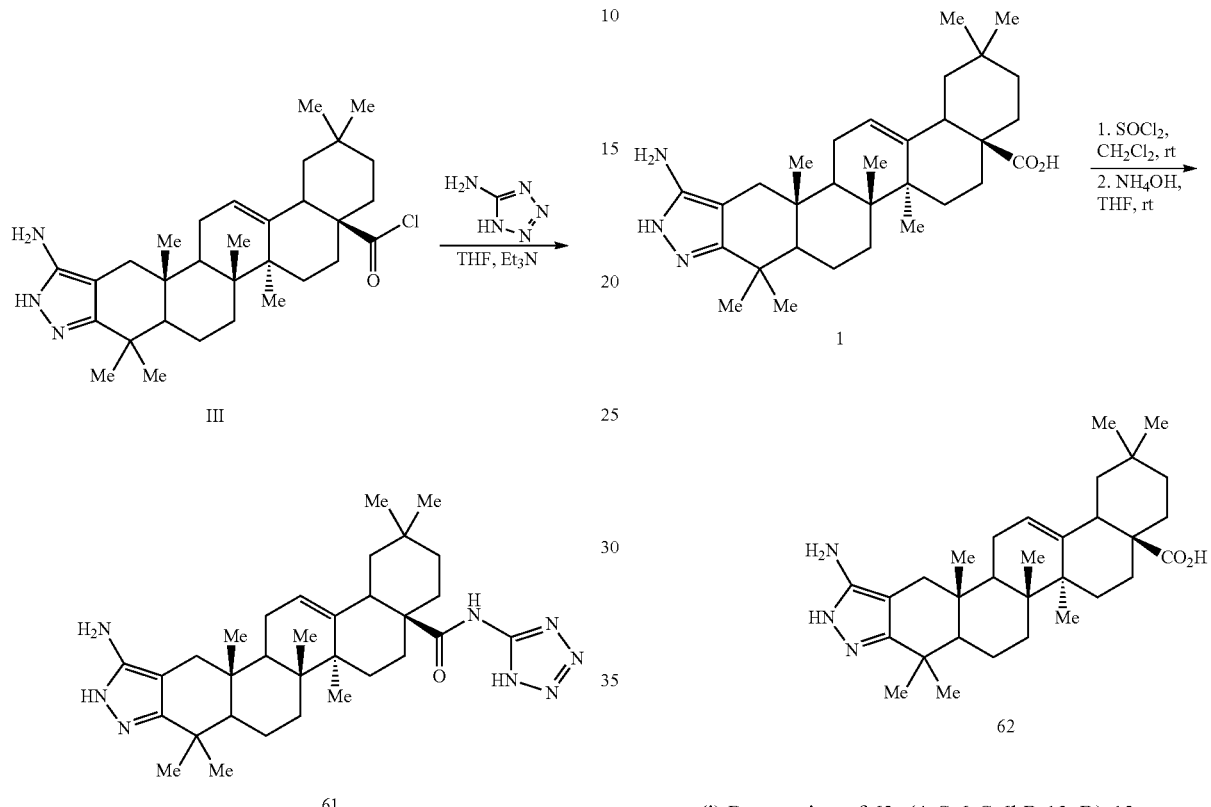

(i) Preparation of 61: (4aS,6aS,6bR,13aR)-12-Amino-2,2,6a,6b,9,9,13a-heptamethyl-N-(1H-tetrazol-5-yl)-2,3,4,4a,5,6,6a,6b,7,8,8a,9,11,13,13a,13b,14,15b-octadecahydro-1H-chryseno[1,2-f]indazole-4-a-carboxamide To a solution of 1H-tetrazol-5-amine hydrate (103 mg, 1.0 mmol) and triethylamine (0.27 mL, 2.0 mmol) in THF (3 mL) was added III (100 mg, 0.20 mmol). The mixture was stirred at room temperature overnight. The reaction mixture was diluted with EtOAc (60 mL). The organic phase was washed with brine, dried (MgSO$_4$), filtered and concentrated to dryness under reduced pressure. The residue was purified by column chromatography (silica, 0-80% CMA in CH$_2$Cl$_2$) followed by preparative HPLC to afford the title compound (35 mg, 32%) as an off-white solid.

R$_f$ 0.40 (80:18:2 Methylene Chloride/Methanol/concentrated Ammonium Hydroxide).

¹H NMR (300 MHz, CD$_3$OD) δ 0.73 (s, 3H), 0.85 (s, 3H), 0.92 (s, 3H), 0.97 (2, 3H), 1.15 (s, 3H), 1.20 (s, 3H), 1.25 (s, 3H), 1.30-1.90 (m, 16H), 2.10 (m, 2H), 2.20 (m, 1H), 2.41 (d, J=15.0 Hz, 1H), 3.05 (m, 1H), 5.46 (s, 1H). mp >300° C. ESI MS (Positive Mode) m/z 561 [C$_{32}$H$_{48}$N$_8$O+H]$^+$.

EXAMPLE 62

(i) Preparation of 62: (4aS,6aS,6bR,13aR)-12-Amino-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxamide To a suspension of 1 (250 mg, 0.51 mmol) and CH$_2$Cl$_2$ (5 mL) was added thionyl chloride (0.4 mL, 5.1 mmol) at room temperature. The mixture was stirred for 3 hours, after which time the solvent was removed under reduced pressure. The residue was taken up in toluene (5 mL), concentrated and placed under vacuum at room temperature for 1 hour. The residue was taken up in THF (5 mL) and concentrated NH$_4$OH (1.4 mL) was added. The mixture was stirred for 1 hour and another portion of NH$_4$OH (1.4 mL) was added. The mixture was stirred at room temperature over night before being quenched with saturated NaHCO$_3$ solution (10 mL). The mixture was extracted with CH$_2$Cl$_2$ (3×15 mL), dried (Na$_2$SO$_4$) and filtered. The solvent was removed under reduced pressure and the residue was purified by column chromatography (silica, 0-3% MeOH in CH$_2$Cl$_2$) to provide the title compound (144 mg, 58%) as an off-white solid.

¹H NMR (500 MHz, CD$_3$OD) δ 0.89-0.98 (m, 12H), 1.02-1.31 (m, 12H), 1.39-1.91 (m, 12H), 2.03-2.11 (m, 3H), 2.42-2.45 (m, 1H), 2.76-2.83 (m, 1H), 5.43-5.45 (m, 1H).

ESI MS m/z 493 [C$_{31}$H$_{48}$N$_4$O+H]$^+$. HPLC 97.9% (area %), t$_R$=14.2 min.

EXAMPLE 63

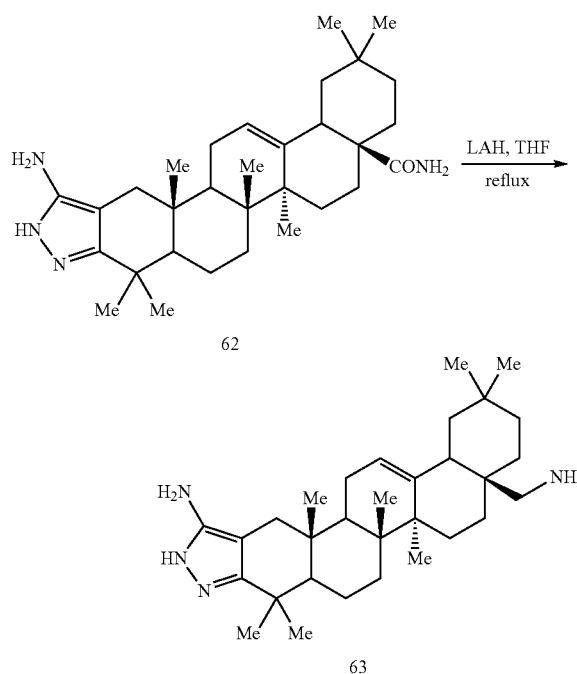

(i) Preparation of 63: (4aS,6aS,6bR,13aR)-4-a-(Aminomethyl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazol-12-amine To a solution of 62 (300 mg, 0.61 mmol) and THF (20 mL) was added lithium aluminum hydride (230 mg, 6.1 mmol) at room temperature. The mixture was heated at reflux for 24 hours, cooled to room temperature, carefully quenched with H$_2$O and EtOAc then extracted with CH$_2$Cl$_2$ (3×20 mL). The organics were dried (Na$_2$SO$_4$) and filtered. The solvent was removed under reduced pressure and the residue was purified by column chromatography (silica, 0-60% CMA in CH$_2$Cl$_2$) to provide the title compound (94 mg, 30%).

$^1$H NMR (300 MHz, CDCl$_3$) δ 0.82-1.03 (m, 12H), 1.15-1.85 (m, 14H), 1.91-2.11 (m, 15H), 2.52-2.60 (m, 2H), 2.83-2.91 (m, 1H), 3.25-3.30 (m, 1H), 3.56-3.63 (m, 1H), 5.23-5.39 (m, 2H), 7.92-7.94 (m, 2H). ESI MS m/z 479 [C$_{31}$H$_{50}$N$_4$+H]$^+$. HPLC 96.6% (area %), t$_R$=11.3 min.

EXAMPLE 64

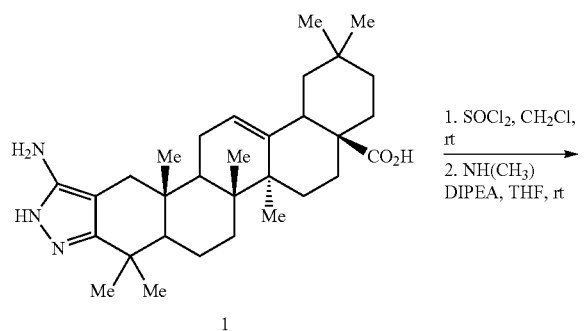

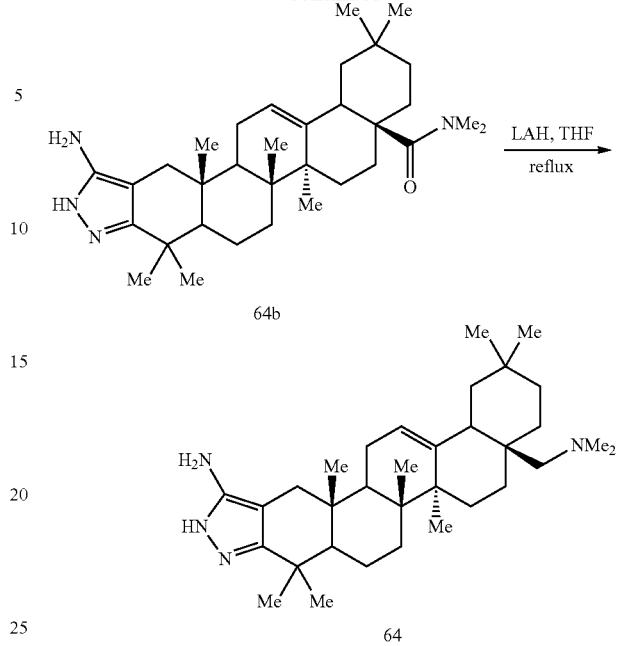

(i) Preparation of 64b: (4aS,6aS,6bR,13aR)-12-Amino-N,N,2,2,6a,6b,9,9,13a-nonamethyl-2,3,4,4a,5,6,6a,6b,7,8,8a,9,11,13,13a,13b,14,15b-octadecahydro-1H-chryseno[1,2-f]indazole-4-a-carboxamide To a suspension of 1 (200 mg, 0.41 mmol) and CH$_2$Cl$_2$ (4 mL) was added thionyl chloride (0.3 mL, 4.1 mmol) at room temperature. The mixture was stirred for 0.5 hours, after which time the solvent was removed under reduced pressure. The residue was taken up in toluene (5 mL), concentrated and placed under vacuum at room temperature for 1 hour. The residue was taken up in THF (4 mL) and N,N-diisopropylethylamine (0.23 mL, 1.2 mmol) was added followed by diethylamine solution (2.0 M in THF, 2.05 mL, 4.1 mmol). The solution was stirred overnight and then quenched with a 2% solution of citric acid. The layers were separated and the aqueous solution was extracted with CH$_2$Cl$_2$ (2×10 mL). The combined extracts were dried (Na$_2$SO$_4$) and filtered. The solvent was removed under reduced pressure and the residue was purified by column chromatography (silica, 0-7% MeOH in CH$_2$Cl$_2$) to provide the sub-title compound (153 mg, 73%) as an off-white solid.

$^1$H NMR (300 MHz, CD$_3$OD) δ 0.83 (s, 3H), 0.91-0.98 (m, 9H), 1.17-1.26 (m, 13H), 1.39-2.25 (m, 16H), 3.01-3.20 (m, 7H), 5.29 (m, 1H). ESI MS m/z 521 [C$_{33}$H$_{52}$N$_4$O+H]$^+$. HPLC 98.4% (area %), t$_R$=17.2 min.

(ii) Preparation of 64: (4aS,6aS,6bR,13aR)-4-a4(Dimethylamino)methyl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazol-12-amine A solution of 64b (129 mg, 0.25 mmol) and THF (12.5 mL) was slowly added to a suspension of lithium aluminum hydride (94 mg, 2.5 mmol) and THF (6.5 mL) at room temperature. The mixture was stirred overnight and then quenched with EtOAc followed by H$_2$O. The layers were separated and the aqueous layer was extracted with EtOAc (3×15 mL). The organics were combined, dried (Na$_2$SO$_4$) and filtered. The solvent was removed under reduced pressure and the residue was purified by column chromatography (silica, 0-7% MeOH in CH$_2$Cl$_2$) to provide the title compound (54 mg, 43%) as a white solid.

$^1$H NMR (300 MHz, CDCl$_3$) δ 0.83-0.95 (m, 12H), 1.02-1.33 (m, 20H), 1.35-2.10 (m, 16H), 2.30-2.41 (m, 3H), 5.21-5.25 (m, 1H). ESI MS m/z 507 [C$_{33}$H$_{54}$N$_4$+H]$^+$. HPLC 96.4% (area %), t$_R$=11.6 min

EXAMPLE 65

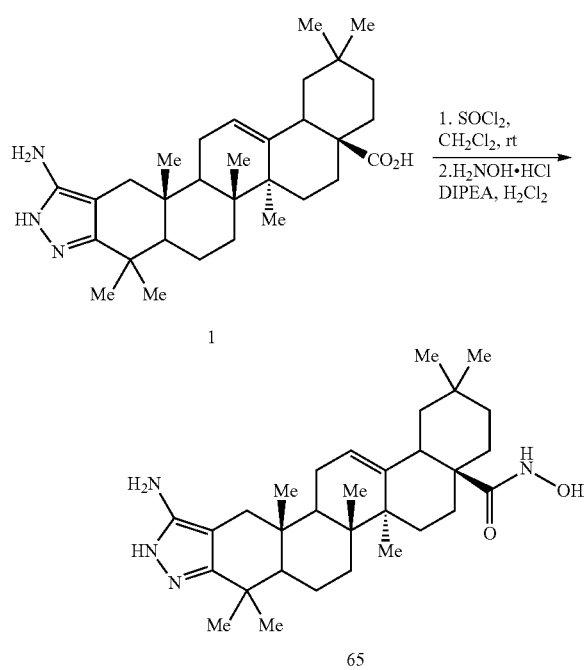

(i) Preparation of 65: (4aS,6aS,6bR,13aR)-12-Amino-N-hydroxy-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxamide To a suspension of 1 (75 mg, 0.15 mmol) in CH$_2$Cl$_2$ (5 mL) was added thionyl chloride (0.1 mL, 1.5 mmol) at room temperature. The mixture was stirred for 0.5 hours, after which time the solvent was removed under reduced pressure. The residue was taken up in toluene (5 mL), concentrated and placed under vacuum at room temperature overnight. The residue was taken up in CH$_2$Cl$_2$ (5 mL) at room temperature. N,N-Diisopropylethylamine (0.2 mL, 1.05 mmol) was added followed by hydroxylamine hydrochloride (52 mg, 0.75 mmol). The mixture was stirred at room temperature for 14 hours. A solution of citric acid (2%, 5 mL) was added and the mixture was extracted with CH$_2$Cl$_2$ (2×5 mL). The combined organic layers were dried (Na$_2$SO$_4$), filtered and concentrated under reduced pressure. The residue was purified by column chromatography (silica, 0-6% MeOH in CH$_2$Cl$_2$) to provided the title compound (144 mg, 58%) as an off-white solid.

$^1$H NMR (500 MHz, CD$_3$OD) δ 0.87-0.95 (m, 12H), 1.05-1.33 (m, 12H), 1.38-1.88 (m, 13H), 2.08-2.15 (m, 3H), 2.43-2.46 (m, 1H), 2.75-2.82 (m, 1H), 5.43-5.45 (m, 1H).

APCI MS m/z 509 [C$_{31}$H$_{48}$N$_4$O+H]$^+$. HPLC 97.4% (area %), t$_R$=13.5 min.

EXAMPLE 66

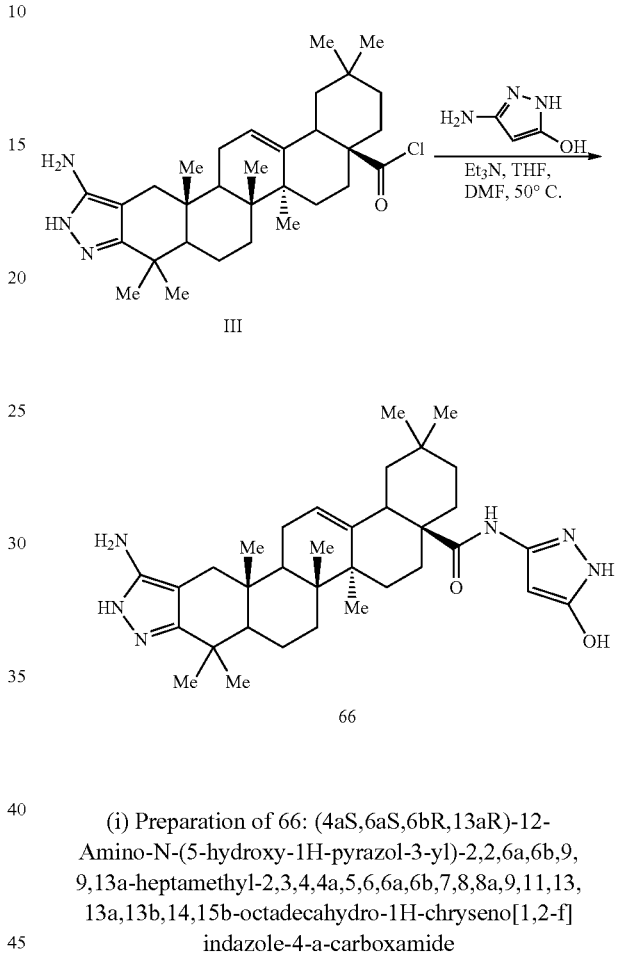

(i) Preparation of 66: (4aS,6aS,6bR,13aR)-12-Amino-N-(5-hydroxy-1H-pyrazol-3-yl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxamide To a solution of III (250 mg, 0.48 mmol) and THF (2 mL) was added triethylamine (0.68 mL, 4.88 mmol) and the solution was stirred for 5 min. To the resultant mixture was added a solution of 3-amino-5-hydroxypyrazole (241 mg, 2.44 mmol) in DMF (6 mL) and the mixture was heated at 50° C. for 3 hours. The mixture was poured into H$_2$O (20 mL) and the precipitate was removed by filtration. The filtrate was concentrated and the residue was purified by column chromatography (silica, 0-50% CMA in CH$_2$Cl$_2$) followed by preparative HPLC to afford the title compound (48 mg, 17%) as a solid.

R$_f$ 0.28 (90:9:1 Methylene Chloride/Methanol/concentrated Ammonium Hydroxide).

$^1$H NMR (300 MHz, CDCl$_3$) δ 0.49-2.97 (m, 42H), 5.36 (s, 1H), 5.76 (s, 1H).

APCI MS m/z 575 [C$_{34}$H$_{50}$N$_6$O$_2$+H]$^+$. m.p. 275-295° C. dec. HPLC (Method A) 97.7% (214 nm) t$_R$=11.5 min.

EXAMPLE 67

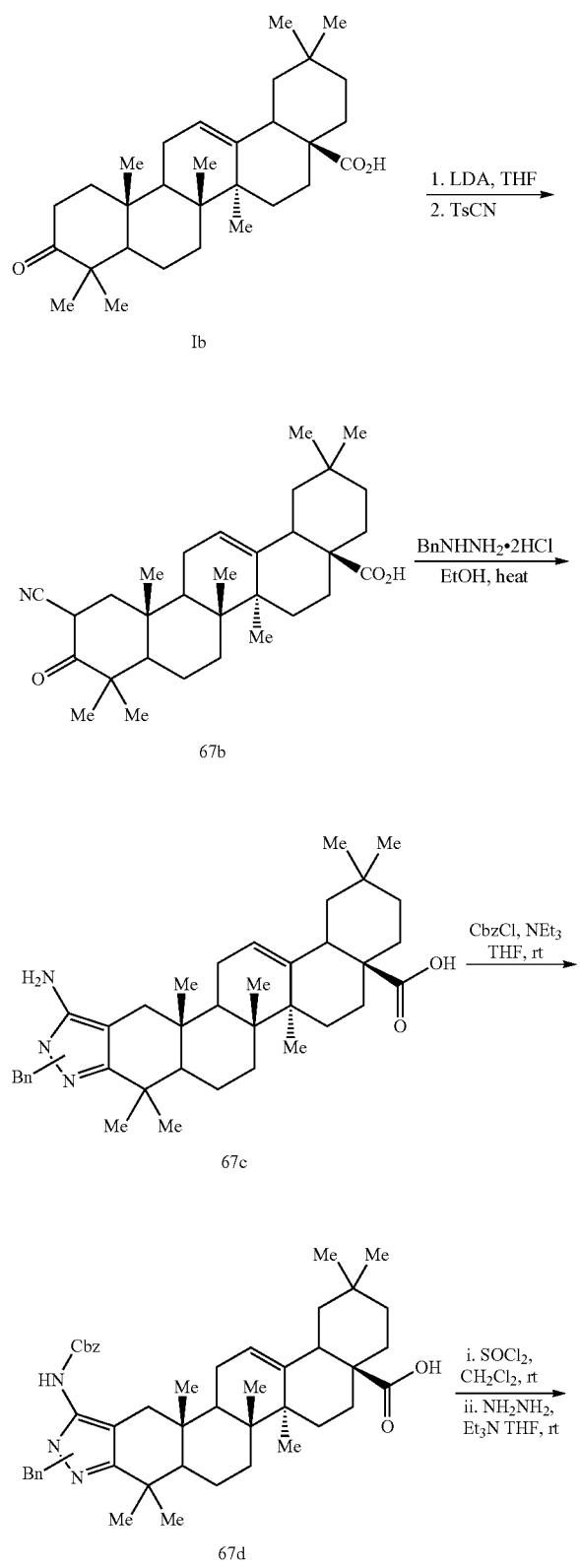

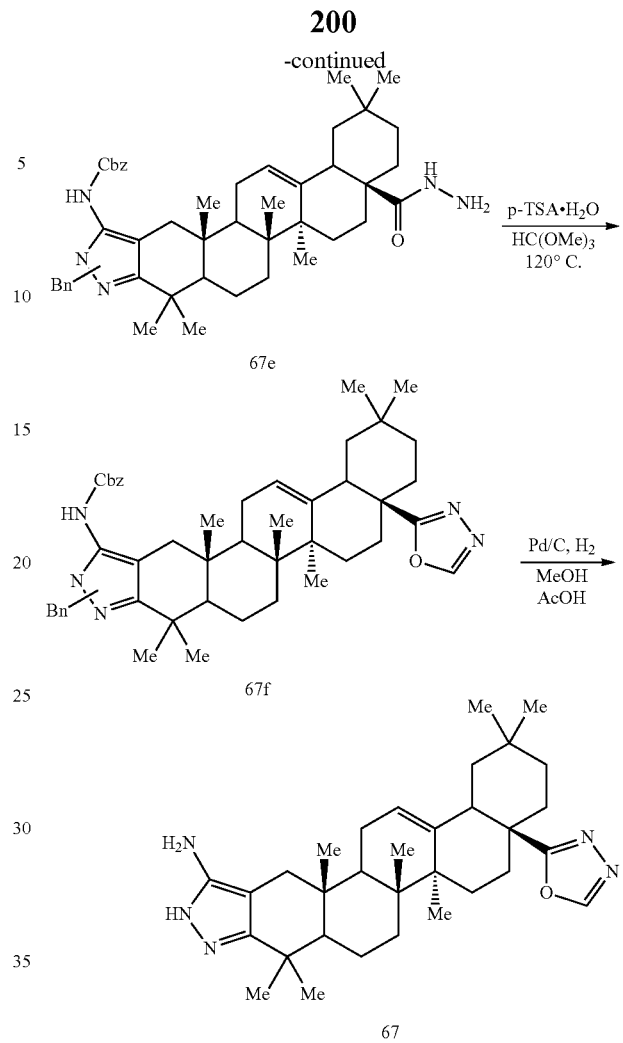

(i) Preparation of 67b: (4aS,6aS,6bR,12aR)-11-Cyano-2,2,6a,6b,9,9,12a-heptamethyl-10-oxo-1,2,3,4,4a,5,6,6a,6b,7,8,8a,9,10,11,12,12a,12b,13,14b-icosahydropicene-4-a-carboxylic acid A solution of diisopropylamine (1.4 mL, 10.2 mmol) and THF (20 mL) was cooled to −78° C. under nitrogen. A solution of n-butyllithium (2.5 M in hexanes, 4.4 mL, 11.0 mmol) was slowly added, maintaining the internal temperature below −70° C. The solution was allowed to stir for 30 min and was then slowly added to a solution of Ib (2.0 g, 4.4 mmol) and THF (250 mL) at −78° C. under nitrogen. This solution was stirred for 30 min after which time a suspension of p-toluenesulfonyl cyanide (1.6 g, 8.8 mmol) and THF (25 mL) was added over 45 min. The solution was stirred for 1 hour and then quenched by the addition of saturated ammonium chloride solution (100 mL) at −78° C. The mixture was allowed to warm to room temperature overnight. The organic layer was separated and the aqueous layer was extracted with EtOAc (3×100 mL). The combined organic layers were dried ($Na_2SO_4$) and filtered. The solvent was removed under reduced pressure and the residue was purified by column chromatography (silica, 0-35% EtOAc in hexanes) to provide the sub-title compound (1.3 g, 60%) as a white solid.

$^1$H NMR (300 MHz, $CDCl_3$) δ 0.77-0.82 (m, 9H), 1.06-1.11 (m, 13H), 1.12-2.03 (m, 19H), 2.09-2.38 (m, 1H), 2.81-2.89 (m, 1H), 5.26-5.35 (m, 1H).

(ii) Preparation of 67c: (4aS,6aS,6bR,13aR)-12-Amino-11-benzyl-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylic acid (and N-benzyl structural isomer)

A solution of 67b (1.3 g, 2.6 mmol), benzylhydrazine dihydrochloride (1.2 g, 6.2 mmol) and EtOH (15 mL) was heated at reflux for 58 hours. The solvent was removed under reduced pressure and the residue was purified by column chromatography (silica, 0-5% MeOH in $CH_2Cl_2$) to provide the sub-title compound (1.1 g, 72%) as yellow solid.
$^1$H NMR (300 MHz, $CDCl_3$) δ 0.78-0.95 (m, 15H), 1.05-2.03 (m, 25H), 2.25-2.35 (m, 1H), 2.81-2.91 (m, 1H), 5.21-5.36 (m, 3H), 7.04-7.11 (m, 2H), 7.21-7.35 (m, 3H).
ESI MS m/z 584 $[C_{38}H_{53}N_3O_2+H]^+$.

(iii) Preparation of 67d: (4aS,6aS,6bR,13aR)-1'-Benzyl-12-(benzyloxycarbonylamino)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxylic acid (and N-benzyl structural isomer)

To a solution of 67c (560 mg, 0.96 mmol) in THF (50 mL) were added triethylamine (0.27 mL, 1.92 mmol) and benzyl chloroformate (0.16 mL, 1.15 mmol) under nitrogen.
The mixture was stirred at room temperature for 16 hours and then quenched with brine (40 mL). The layers were separated and the aqueous layer was extracted with EtOAc (2×20 mL). The solution was dried ($Na_2SO_4$), filtered and concentrated to afford the sub-title compound (108 mg, quant) which was used without further purification.
ESI MS m/z 718 $[C_{46}H_{59}N_3O_4+H]^+$.

(iv) Preparation of 67e: Benzyl (4aS,6aS,6bR,13aR)-11-benzyl-4-a-(hydrazinecarbonyl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazol-12-ylcarbamate (and N-benzyl structural isomer)

To a solution of 67d (744 mg, 1.03 mmol) in $CH_2Cl_2$ (100 mL) was added thionyl chloride (0.76 mL, 10.37 mmol). The mixture was stirred at room temperature for 1.5 hours and then the solvent was removed under reduced pressure. The residue was azeotroped with toluene and then dried under vacuum overnight to afford the intermediate acid chloride (687 mg, 93%). The crude acid chloride (364 mg, 0.49 mmol) was dissolved in THF (10 mL) and then triethylamine (0.34 mL, 2.47 mmol) and hydrazine (0.15 mL, 4.94 mmol) were added. The mixture was stirred at room temperature for 20 hours and concentrated under reduced pressure. The residue was partitioned between EtOAc (20 mL) and $H_2O$ (10 mL). The layers were separated and the organic layer was washed with $H_2O$ and brine. The solution was dried ($Na_2SO_4$), filtered and concentrated. The residue was purified by column chromatography (silica, 0-40% CMA in $CH_2Cl_2$) to afford the sub-title compound (224 mg, 62%).
ESI MS (m/z 733 $[C_{46}H_{61}N_5O_3+H]^+$.

(v) Preparation of 67f: Benzyl (4aS,6aS,6bR,13aR)-11-benzyl-2,2,6a,6b,9,9,13a-heptamethyl-4-a-(1,3,4-oxadiazol-2-yl)-2,3,4,4a,5,6,6a,6b,7,8,8a,9,11,13,13a,13b,14,15b-octadecahydro-1H-chryseno[1,2-f]indazol-12-ylcarbamate (and N-benzyl structural isomer)

A mixture of 67e (100 mg, 0.13 mmol), trimethoxymethane (0.22 mL, 2.04 mmol) and p-toluene sulfonic acid monohydrate (4 mg, 0.02 mmol) was heated at 120° C. overnight. The mixture was concentrated under reduced pressure and the residue was purified by column chromatography (silica, 2:1 hexanes/EtOAc) to afford the sub-title compound (75 mg, 74%).
ESI MS m/z 651 $[C_{47}H_{59}N_5O_3-C_7H_7+H]^+$.

(vi) Preparation of 67: (4aS,6aS,6bR,13aR)-2,2,6a,6b,9,9,13a-Heptamethyl-4-a-(1,3,4-oxadiazol-2-yl)-2,3,4,4a,5,6,6a,6b,7,8,8a,9,11,13,13a,13b,14,15b-octadecahydro-1H-chryseno[1,2-f]indazol-12-amine A solution of 67d (70 mg, 0.09 mmol), acetic acid (0.2 mL) and MeOH (10 mL) was flushed with nitrogen. To the resultant mixture was added 10% Pd/C (150 mg) and the mixture was flushed with nitrogen followed by hydrogen. The mixture was stirred under hydrogen at atmospheric pressure for 23 hours. The catalyst was removed by filtration through diatomaceous earth and the filtrate was concentrated under reduced pressure. The residue was purified by column chromatography (silica, 0-40% CMA in $CH_2Cl_2$) to afford the title compound (6 mg, 12%).
$R_f$ 0.42 (90:9:1 Methylene Chloride/Methanol/concentrated Ammonium Hydroxide).
$^1$H NMR (300 MHz, $CD_3OD$) δ 0.45-2.41 (m, 41H), 3.14 (d, J=10.8 Hz, 1H), 5.44 (s, 1H), 8.84 (s, 1H). ESI MS m/z 518 $[C_{32}H_{47}N_5O+H]^+$. m.p. 255-270° C. dec. HPLC (Method A) 89.0% (214 nm) $t_R$=16.1 min.

EXAMPLE 68

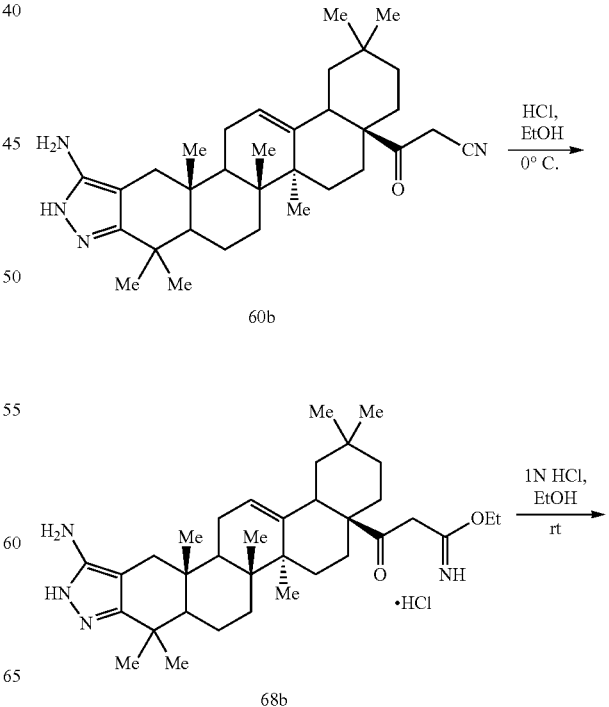

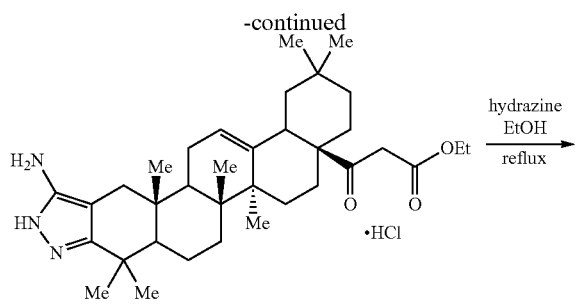

68c

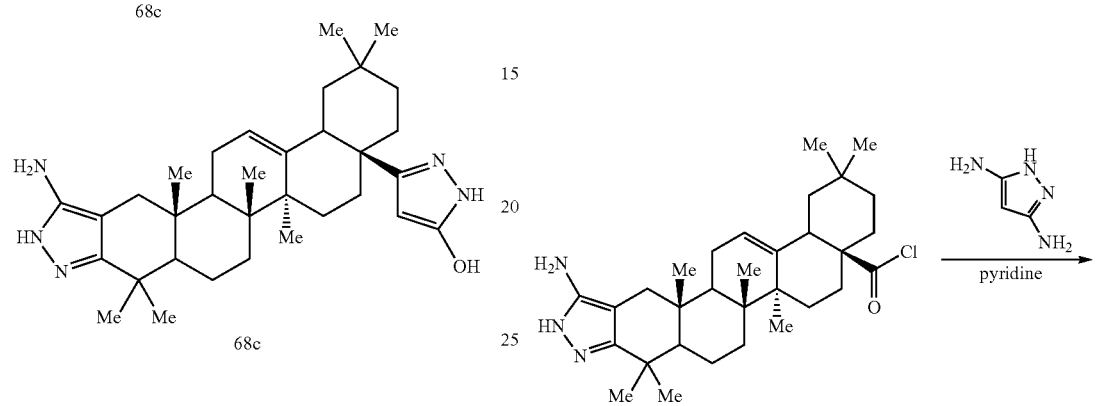

(i) Preparation of 68b: Ethyl 3-((4aS,6aS,6bR,13aR)-12-amino-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazol-4-a-yl)-3-oxopropanimidate hydrochloride A solution of 60b (200 mg, 0.39 mmol) and EtOH (15 mL) was saturated with anhydrous HCl at −5° C. The solution was kept at that temperature for 10 d before removal of the solvent and excess HCl under reduced pressure. The residue was coevaporated with EtOH followed by diethyl ether to provide the sub-title compound (220 mg, 100%) as a tan solid.
APCI MS m/z 563 $[C_{33}H_{54}N_4O_2+H]^+$.

(ii) Preparation of 68c: Ethyl 3-((4aS,6aS,6bR,13aR)-12-amino-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazol-4-a-yl)-3-oxopropanoate hydrochloride To a solution of 68b (220 mg, 0.39 mmol) and EtOH (3 mL) was added 1 N HCl (2 mL) at room temperature. After 24 hours, the solvent was removed under reduced pressure and the residue was purified by column chromatography (silica, 0-65% CMA in $CH_2Cl_2$) to provide the sub-title compound (135 mg, 58%).
$^1$H NMR (500 MHz, $CDCl_3$) δ 0.71-0.95 (m, 12H), 1.13-1.31 (m, 16H), 1.34-2.15 (m, 17H), 2.29-2.33 (m, 1H), 2.71-2.74 (m, 1H), 3.49-3.71 (m, 2H), 4.13-4.21 (m, 2H), 5.43-5.45 (m, 1H).

(iii) Preparation of 68: 3-((4aS,6aS,6bR,13aR)-12-Amino-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazol-4-a-yl)-1H-pyrazol-5-ol A solution of 68c (135 mg, 0.24 mmol), hydrazine (38 mg, 1.2 mmol) and EtOH (5 mL) was heated at reflux under nitrogen for 66 hours and then cooled to room temperature. The solvent was removed under reduced pressure and the residue was purified by column chromatography (silica, 0-55% CMA in $CH_2Cl_2$) to provide the title compound (11 mg, 9%) as a solid.
$^1$H NMR (300 MHz, $CD_3OD$) δ 0.62 (s, 3H), 0.86-1.01 (m, 9H), 1.03-1.39 (m, 15H), 1.41-1.99 (m, 11H), 2.03-2.11 (m, 2H), 2.25-2.45 (m, 2H), 2.74-2.81 (m, 1H), 5.43-5.45 (m, 1H). APCI MS m/z 532 $[C_{33}H_{49}N_5O+H]^+$. HPLC 98.6% (area %), $t_R$=10.2 min.

EXAMPLE 69

(i) Preparation of 69: (4aS,6aS,6bR,13aR)-12-amino-N-(3-amino-1H-pyrazol-5-yl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxamide To a solution of 1H-pyrazole-3,5-diamine (70 mg, 0.54 mmol) prepared by the procedure described in the literature (US82902, 2007) and pyridine (2.0 mL) was added III (100 mg, 0.20 mmol). The mixture was stirred at room temperature overnight. The reaction mixture was concentrated to dryness under reduced pressure. The residue was purified by column chromatography (silica, 0-40% CMA in $CH_2Cl_2$) followed by preparative HPLC to afford the title compound (25 mg, 25%) as an off-white solid.
$R_f$ 0.20 (180:18:2 Methylene Chloride/Methanol/concentrated Ammonium Hydroxide).
$^1$H NMR (300 MHz, DMSO-$d_6$) δ 0.83 (s, 3H), 0.92 (s, 3H), 0.95 (s, 3H), 1.0 (s, 3H), 1.25 (s, 6H), 1.30 (s, 3H), 1.30-1.90 (m, 23H), 2.06 (m, 3H), 2.25 (m, 1H), 2.44 (d, J=15.0 Hz, 1H), 2.62 (m, 1H), 5.35 (s, 1H). mp >300° C. APCI MS (Positive Mode) m/z 574 $[C_{34}H_{51}N_7O+H]^+$.

EXAMPLE 70

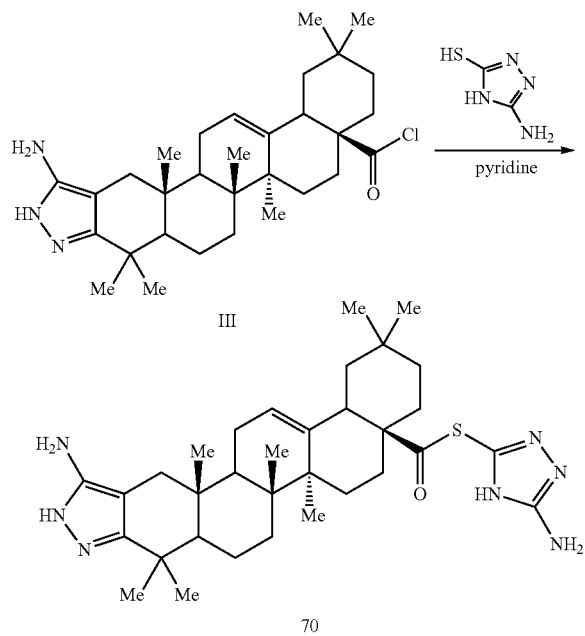

(i) Preparation of 70: (4aS,6aS,6bR,13aR)—S-5-Amino-4H-1,2,4-triazol-3-yl12-amino-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carbothioate To a solution of 5-amino-4H-1,2,4-triazole-3-thiol (1.42 g, 12.2 mmol) in pyridine (30 mL was added III (2.0 g, 3.91 mmol). The mixture was stirred at room temperature for 3 hours. The reaction mixture was concentrated to remove pyridine under reduced pressure. The residue was purified by column chromatography (silica, 0-15% MeOH in CH$_2$Cl$_2$) to afford the title compound (1.41 g, 59%) as an off-white solid.

R$_f$ 0.12 (89:10:1 Methylene Chloride/Methanol/concentrated Ammonium Hydroxide).

$^1$H NMR (300 MHz, CD$_3$OD) δ 0.87 (s, 6H), 0.90 (s, 3H), 0.95 (s, 3H), 1.10 (s, 3H), 1.15 (s, 3H), 1.20 (s, 3H), 1.30-2.20 (m, 19H), 2.38 (d, J=15.0 Hz, 1H), 2.88 (m, 1H), 5.39 (s, 1H). mp 278-296° C. ESI MS (Positive Mode) m/z 59 $[C_{33}H_{49}N_7OS+H]^+$.

EXAMPLE 71

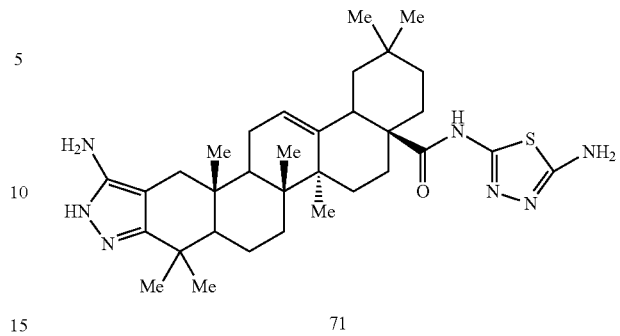

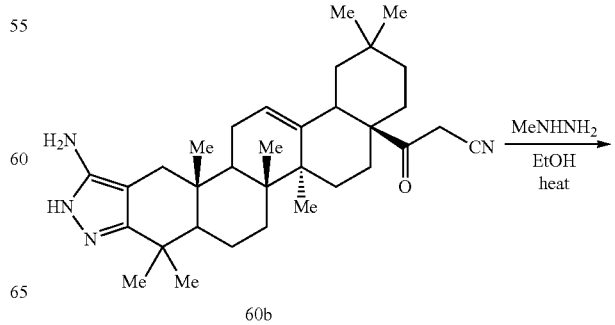

(i) Preparation of 71: (4aS,6aS,6bR,13aR)-12-Amino-N-(5-amino-1,3,4-thiadiazol-2-yl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxamide To a solution of III (500 mg, 0.97 mmol) and pyridine (4 mL) was added 1,3,4-thiadiazole-2,5-diamine (340 mg, 2.92 mmol). The reaction mixture was heated at 60° C. for 20 hours and then poured into H$_2$O (50 mL). The precipitate was collected by filtration and dissolved in CH$_2$Cl$_2$/i-PrOH (2:1, 20 mL). The aqueous layer was extracted with CH$_2$Cl$_2$/i-PrOH (2:1, 2×25 mL). The combined extracts were dried (Na$_2$SO$_4$), filtered and concentrated under reduced pressure. The residue was purified by column chromatography (silica, 0-40% CMA in CH$_2$Cl$_2$) followed by preparative HPLC to afford the title compound (32 mg, 6%) as a solid.

R$_f$ 0.20 (90:9:1 Methylene Chloride/Methanol/concentrated Ammonium Hydroxide)

$^1$H NMR (300 MHz, DMSO-d$_6$) δ 0.77-2.43 (m, 41H), 2.94 (d, J=12 Hz, 1H), 5.32 (s, 1H), 7.46 (s, 1H), 11.50 (s, 1H), 13.20 (s, 1H).

APCI MS m/z 592 $[C_{33}H_{49}N_7OS+H]^+$. m.p. 280-300° C. dec. HPLC (Method A) 95.4% (214 nm) t$_R$=10.2 min.

EXAMPLE 72

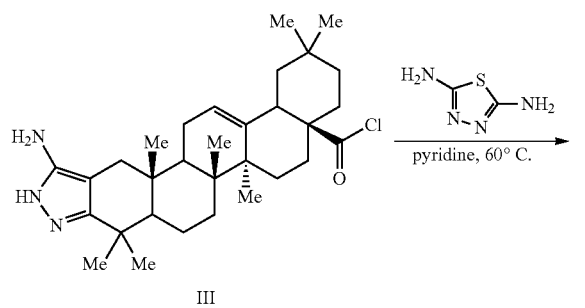

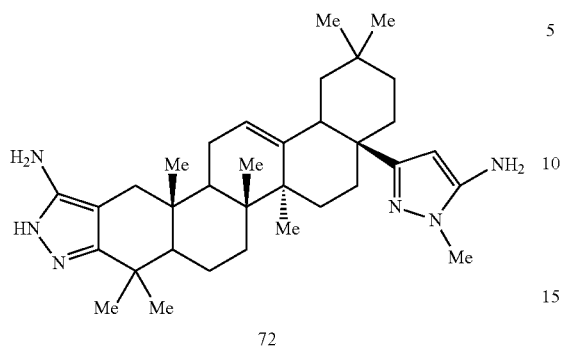

72

(i) Preparation of 72: (4aS,6aS,6bR,8aR,13aR, 15bS)-4-a-(5-Amino-1-methyl-1H-pyrazol-3-yl)-2,2, 6a,6b,9,9,13a-heptamethyl-2,3,4,4a,5,6,6a,6b,7,8,8a, 9,11,13,13a,13b,14,15b-octadecahydro-1H-chryseno [1,2-f]indazol-12-amine A mixture of 60b (282 mg, 0.54 mmol) and methylhydrazine (0.14 mL, 2.73 mmol) in EtOH (4 mL) was sealed and heated to 160° C. by microwave for 3 hours. The reaction mixture was concentrated to dryness. The residue was purified by column chromatography (silica, 0-10% MeOH in CH$_2$Cl$_2$) followed by preparative HPLC to afford title compound (35 mg, 12%) as a white solid.

R$_f$ 0.34 (89:10:1 Methylene Chloride/Methanol/concentrated Ammonium Hydroxide).

$^1$H NMR (300 MHz, CD$_3$OD) δ 0.65 (s, 3H), 0.88 (s, 3H), 0.95 (s, 3H), 0.97 (s, 3H), 1.15 (s, 3H), 1.20 (s, 3H), 1.24 (s, 3H), 1.25-2.10 (m, 19H), 2.38 (m, 2H), 2.78 (m, 1H), 3.68 (s, 3H), 5.47 (m, 1H). mp 195-210° C. dec. APCI MS (Positive Mode) m/z 545 [C$_{34}$H$_{52}$N$_6$+H]$^+$.

(i) Preparation of 73: (2-Amino-1H-imidazol-1-yl) ((4aS,6aS,6bR,13aR)-12-amino-2,2,6a,6b,9,9,13a-heptamethyl-2,3,4,4a,5,6,6a,6b,7,8,8a,9,11,13,13a, 13b,14,15b-octadecahydro-1H-chryseno[1,2-f] indazol-4-a-yl)methanone To a solution of III (200 mg, 0.39 mmol) and pyridine (2 mL) was added 1H-imidazol-2-amine (70 mg, 0.84 mmol). The reaction mixture was stirred at room temperature for 3.5 hours and then poured into H$_2$O (20 mL). The precipitate was collected by filtration and dissolved in CH$_2$Cl$_2$/i-PrOH (2:1, 10 mL). The aqueous layer was extracted with CH$_2$Cl$_2$/i-PrOH (2:1, 2×10 mL). The combined organics were dried (Na$_2$SO$_4$), filtered and concentrated under reduced pressure. The residue was purified by column chromatography (silica, 0-30% CMA in CH$_2$Cl$_2$) to afford the title compound (96 mg, 44%).

R$_f$ 0.50 (90:9:1 Methylene Chloride/Methanol/concentrated Ammonium Hydroxide).

$^1$H NMR (300 MHz, DMSO-d$_6$) δ 0.91-2.49 (m, 41H), 3.00 (d, J=11.1 Hz, 1H), 4.12 (s, 2H), 5.29 (s, 1H), 6.46 (s, 1H), 6.64 (s, 2H), 7.39 (s, 1H), 10.95 (s, 1H). APCI MS m/z 559 [C$_{34}$H$_{50}$N$_6$O+H]$^+$. m.p. 230-250° C. dec. HPLC (Method A) 97.6% (214 nm) t$_R$=9.9 min.

EXAMPLE 73

EXAMPLE 74

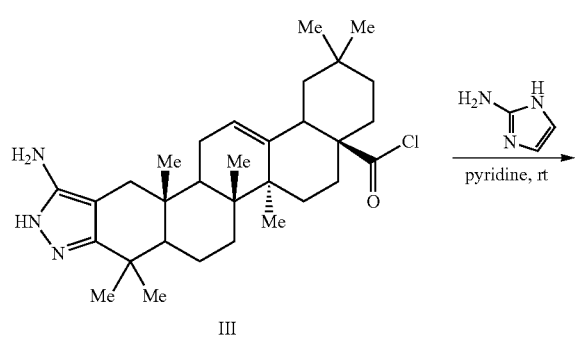

III

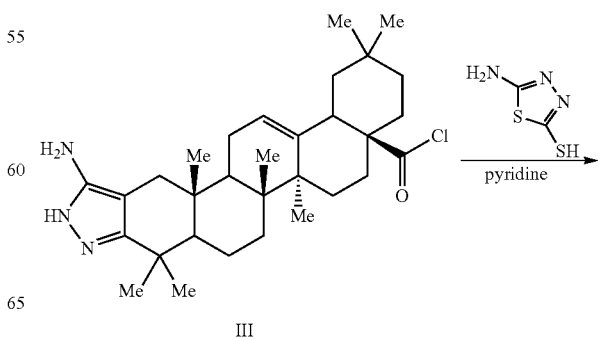

III

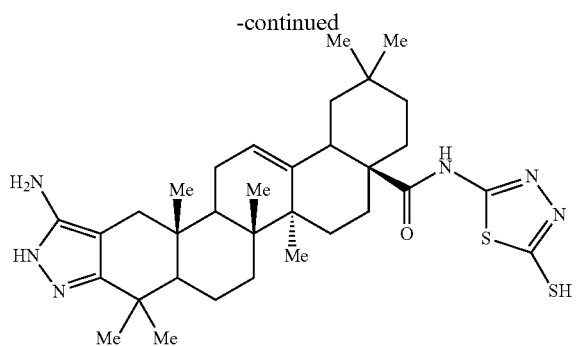

74

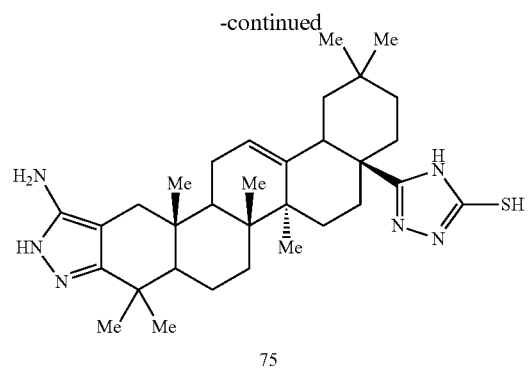

75

(i) Preparation of 74: (4aS,6aS,6bR,13aR)-12-Amino-N-(5-mercapto-1,3,4-thiadiazol-2-yl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxamide To a solution of 5-amino-1,3,4-thiadiazole-2-thiol (200 mg, 2.1 mmol) prepared by the procedure described in the literature (U.S. Pat. No. 3,940,409, 1976) and pyridine (10.0 mL) was added III (215 mg, 0.42 mmol). The mixture was stirred at room temperature overnight. The reaction mixture was concentrated to dryness under reduced pressure. The residue was purified by column chromatography (silica, 0-70% CMA in $CH_2Cl_2$) followed by preparative HPLC to afford the title compound (30 mg, 12%) as an off-white solid.

$R_f$ 0.60 (80:18:2 Methylene Chloride/Methanol/concentrated Ammonium Hydroxide).

$^1$H NMR (300 MHz, $CD_3OD$) δ 0.89 (s, 3H), 0.90 (s, 3H), 0.92 (s, 3H), 0.97 (s, 3H), 1.29 (s, 6H), 1.36 (s, 3H), 1.43-2.30 (m, 19H), 2.43 (d, J=14.7 Hz, 1H), 2.84 (m, 1H), 5.42 (s, 1H). mp >300° C. ESI MS (Positive Mode) m/z 609 $[C_{33}H_{48}N_6OS_2+H]^+$.

EXAMPLE 75

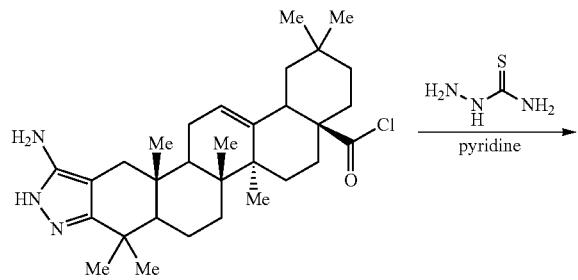

III (i) Preparation of 75b: 2-((4aS,6aS,6bR,13aR)-12-Amino-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carbonyl)hydrazinecarbothioamide To a solution of hydrazinecarbothioamide (914 mg, 10.0 mmol) and pyridine (50.0 mL) was added III (1.0 g, 2.0 mmol). The mixture was stirred at room temperature for 2 hours. The reaction mixture was poured into $H_2O$. Brown precipitates were collected by filtration and washed with $H_2O$, dried in an oven at 40° C. to provide the sub-title compound (900 mg). The crude compound was used without further purification.

ESI MS (Positive Mode) m/z 567 $[C_{32}H_{50}N_6OS+H]^+$.

(ii) Preparation of 75: 5-((4aS,6aS,6bR,13aR)-12-Amino-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazol-4-a-yl)-4H-1,2,4-triazole-3-thiol A mixture of 75b (100 mg) and NaOH (2 M, 2.0 mL) was heated at reflux for 7 d. The reaction mixture was concentrated to dryness under reduced pressure. The residue was triturated with MeOH and $CH_2Cl_2$. The filtrate was concentrated and purified by preparative HPLC to provide the title compound (61 mg, 66%) as an off-white solid.

$R_f$ 0.60 (180:18:2 Methylene Chloride/Methanol/concentrated Ammonium Hydroxide).

$^1$H NMR (300 MHz, $CD_3OD$) δ 0.60 (s, 3H), 0.82 (s, 3H), 0.95 (s, 3H), 0.98 (s, 3H), 1.21 (s, 3H), 1.25 (s, 3H), 1.46 (s, 3H), 1.50-2.05 (m, 18H), 2.25 (m, 1H), 2.40 (d, J=15.0 Hz, 1H), 2.98 (m, 1H), 5.40 (s, 1H). mp >300° C. ESI MS (Positive Mode) m/z 549 $[C_{32}H_{48}N_6S+H]^+$.

EXAMPLE 76

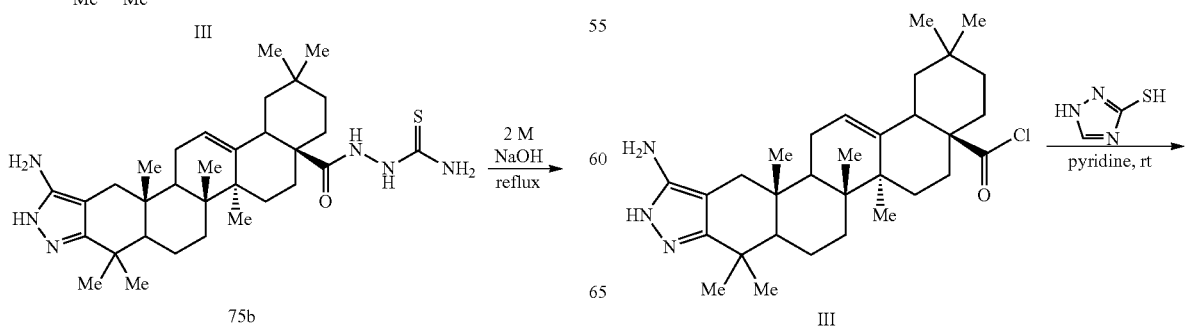

75b                                    III

-continued

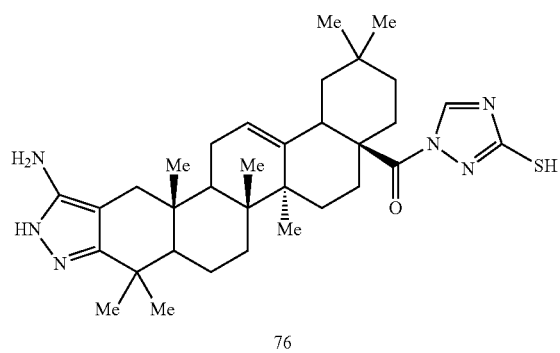

76

(i) Preparation of 76: ((4aS,6aS,6bR,13aR)-12-Amino-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazol-4-a-yl)(3-mercapto-1H-1,2,4-triazol-1-yl)methanone To a solution of III (300 mg, 0.58 mmol) and pyridine (3 mL) was added 1H-1,2,4-triazole-3-thiol (177 mg, 1.75 mmol). The reaction mixture was stirred at room temperature for 1 hour and then poured into H$_2$O (30 mL). The precipitate was dissolved in CH$_2$Cl$_2$/i-PrOH (2:1, 20 mL). The aqueous layer was extracted with CH$_2$Cl$_2$/i-PrOH (2:1, 3×10 mL) and the combined organics were dried (Na$_2$SO$_4$), filtered and concentrated under reduced pressure. The residue was purified by column chromatography (silica, 0-8% MeOH in CH$_2$Cl$_2$) to afford the title compound (110 mg, 33%).

R$_f$ 0.27 (90:9:1 Methylene Chloride/Methanol/concentrated Ammonium Hydroxide)

$^1$H NMR (300 MHz, CD$_3$OD) δ 0.89-2.23 (m, 40H), 2.41 (d, J=14.7 Hz, 1H), 3.00 (dd, J=3.6, 12.9 Hz, 1H), 5.40 (s, 1H), 8.46 (s, 1H). APCI MS m/z 577 [C$_{33}$H$_{48}$N$_6$OS+H]$^+$.

m.p. 260-280° C. dec. HPLC (Method A) 96.2% (214 nm) t$_R$=14.3 min.

EXAMPLE 77

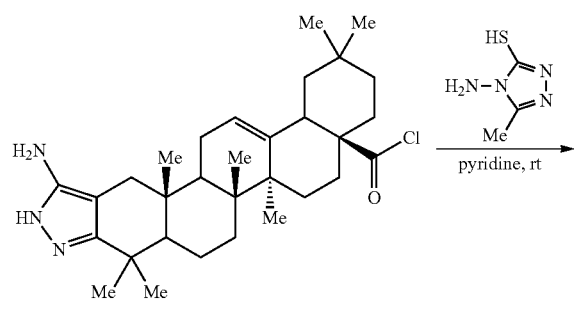

III

-continued

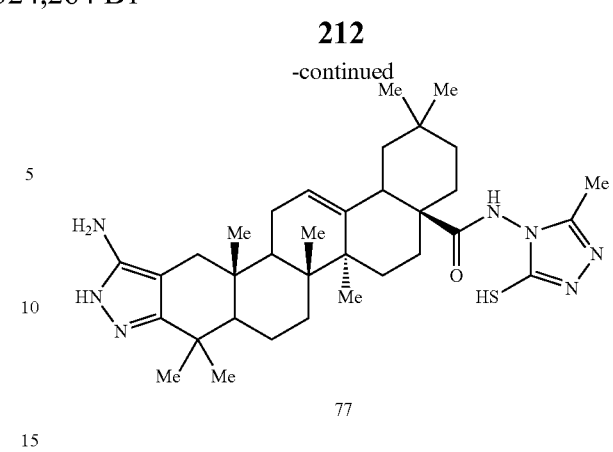

77

(i) Preparation of 77: (4aS,6aS,6bR,13aR)-12-Amino-N-(3-mercapto-5-methyl-4H-1,2,4-triazol-4-yl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxamide To a solution of III (300 mg, 0.58 mmol) and pyridine (3 mL) was added 4-amino-5-methyl-4H-1,2,4-triazole-3-thiol (228 mg, 1.75 mmol). The reaction mixture was stirred at room temperature for 1 hour and then poured into H$_2$O (30 mL). The precipitate was collected by filtration and dried under vacuum overnight. The residue was purified by column chromatography (silica, 0-30% CMA in CH$_2$Cl$_2$) followed by preparative HPLC to afford the title compound (30 mg, 8%) as a solid.

R$_f$ 0.25 (90:9:1 Methylene Chloride/Methanol/concentrated Ammonium Hydroxide)

$^1$H NMR (300 MHz, CD$_3$OD) δ 0.89-2.50 (m, 44H), 2.93-2.97 (m, 1H), 5.36 (s, 1H). APCI MS m/z 606 [C$_{34}$H$_{51}$N$_7$OS+H]$^+$. m.p. 250-270° C. dec. HPLC (Method A) 92.7% (214 nm) t$_R$=13.2 min.

EXAMPLE 78

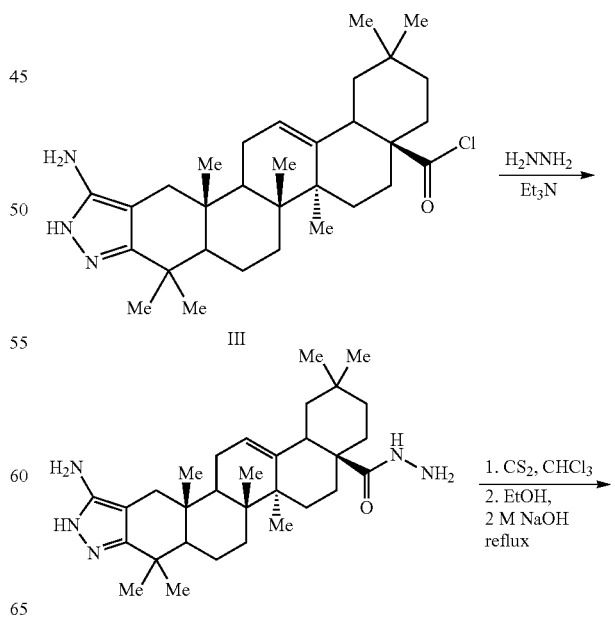

213
-continued

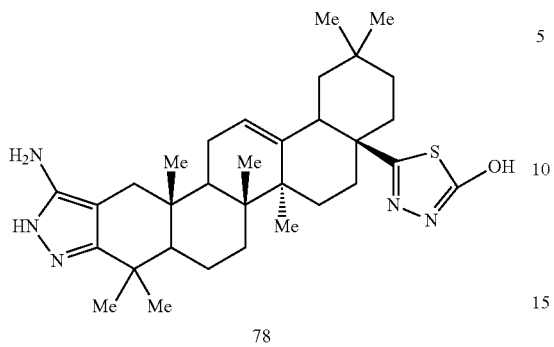

78

(i) Preparation of 78b: (4aS,6aS,6bR,13aR)-12-Amino-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carbohydrazide To a solution of hydrazine (0.15 mL, 4.5 mmol) and triethylamine (0.77 mL) was added III (500 mg, 0.91 mmol). The mixture was stirred at room temperature overnight. The reaction mixture was diluted with EtOAc (100 mL). The organic phase was washed with brine then dried (MgSO$_4$), filtered and concentrated to dryness. The residue was purified by column chromatography on (silica, 0-50% CMA in CH$_2$Cl$_2$) to afford the sub-title compound (360 mg, 78%) as a brown solid.

(ii) Preparation of 78: 5-((4aS,6aS,6bR,13aR)-12-Amino-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazol-4-a-yl)-1,3,4-thiadiazol-2-ol To a solution of 78b (140 mg, 0.27 mmol) in CHCl$_3$ (5 mL) was added carbon disulfide (0.58 mL, 0.96 mmol). The mixture was stirred at room temperature for 4 hours. The reaction mixture was concentrated to dryness under reduced pressure. The residue was dissolved in EtOH (5 mL) and NaOH (2 M, 5 mL) was added. The mixture was heated at reflux for 12 hours. The reaction mixture was concentrated to remove EtOH. Brown solids were collected by filtration and washed with H$_2$O. The residue was purified by column chromatography (silica, 0-50% CMA in CH$_2$Cl$_2$) followed by preparative HPLC to afford the title compound (30 mg, 12%) as an off-white solid.

R$_f$ 0.30 (10:1 Methylene Chloride/Methanol).

$^1$H NMR (300 MHz, DMSO-d$_6$) δ 0.58 (s, 3H), 0.75 (s, 3H), 0.92 (s, 6H), 1.16 (s, 3H), 1.21 (s, 3H), 1.26 (s, 3H), 1.31-1.97 (m, 22H), 2.22 (m, 1H), 2.43 (d, J=15.0 Hz, 1H), 2.83 (m, 1H), 5.35 (s, 1H). mp >300° C. ESI MS (Positive Mode) m/z 550 [C$_{32}$H$_{47}$N$_5$OS+ H]$^+$.

214
EXAMPLE 79

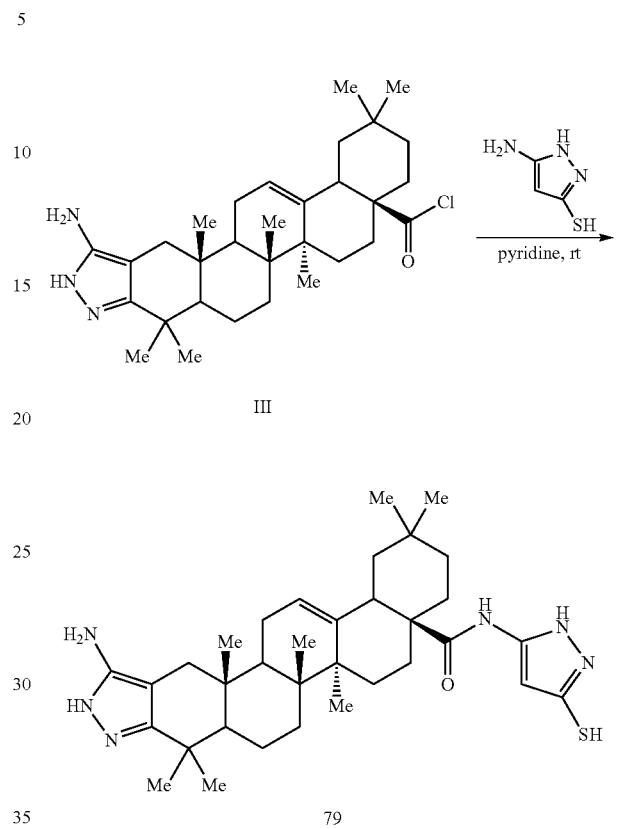

(i) Preparation of 79: (4aS,6aS,6bR,13aR)-12-Amino-N-(3-mercapto-1H-pyrazol-5-yl)-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carboxamide To a solution of 5-amino-1H-pyrazole-3-thiol (459 mg, 4.0 mmol) prepared by the procedure described in the literature (J. Med. Chem. 2008, 51(15), 4672-4684) and pyridine (10.0 mL) was added III (490 mg, 0.95 mmol). The mixture was stirred at room temperature overnight. The reaction mixture was concentrated to dryness under reduced pressure. The residue was purified by column chromatography (silica, 0-70% CMA in CH$_2$Cl$_2$) followed by preparative HPLC to afford the title compound (115 mg, 17%) as an off-white solid.

R$_f$ 0.75 (80:18:2 Methylene Chloride/Methanol/concentrated Ammonium Hydroxide).

$^1$H NMR (300 MHz, CD$_3$OD) δ 0.89 (s, 6H), 0.91 (s, 3H), 0.95 (s, 3H), 1.28 (s, 3H), 1.40 (s, 3H), 1.48 (s, 3H), 1.55-2.20 (m, 19H), 2.43 (d, J=14.4 Hz, 1H), 2.93 (m, 1H), 5.39 (m, 1H), 5.57 (m, 1H). mp >300° C. ESI MS (Positive Mode) m/z 591 [C$_{34}$H$_{50}$N$_6$OS+H]$^+$.

EXAMPLE 80

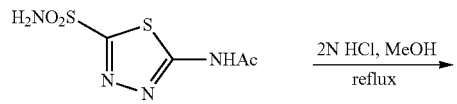

80a

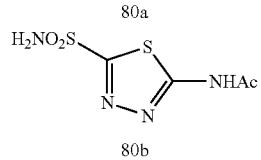

80b

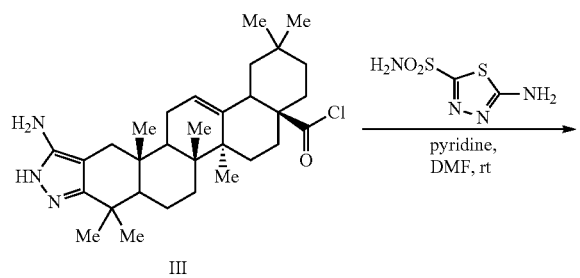

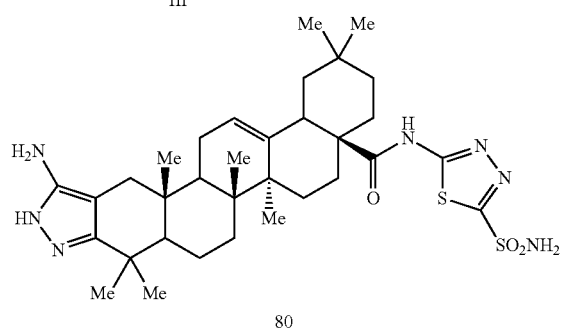

80

(i) Preparation of 80b: 5-Amino-1,3,4-thiadiazole-2-sulfonamide

To a solution of N-(5-sulfamoyl-1,3,4-thiadiazol-2-yl)acetamide (1.0 g, 4.50 mmol) and MeOH (15 mL) was added HCl (2 N, 10 mL). The reaction mixture was heated at reflux for 18 hours and then concentrated under reduced pressure. The residue was purified by column chromatography (silica, 0-10% MeOH in CMA) to afford the sub-title compound (800 mg, 98%).

(ii) Preparation of 80: (4aS,6aS,6bR,13aR)-12-Amino-2,2,6a,6b,9,9,13a-heptamethyl-N-(5-sulfamoyl-1,3,4-thiadiazol-2-yl)-2,3,4,4a,5,6,6a,6b,7,8,8a,9,11,13,13a,13b,14,15b-octadecahydro-1H-chryseno[1,2-f]indazole-4-a-carboxamide To a solution of III (400 mg, 0.78 mmol), pyridine (15 mL) and DMF (1 mL) was added 80b (281 mg, 1.56 mmol). The reaction mixture was stirred at room temperature for 24 hours and then poured into H₂O (15 mL). The precipitate was collected by filtration and dried under vacuum overnight. The residue was purified by column chromatography (silica, 0-60% CMA in CH₂Cl₂) followed by preparative HPLC to afford the title (8 mg, 2%) as a solid.

$R_f$ 0.35 (90:9:1 Methylene Chloride/Methanol/concentrated Ammonium Hydroxide).

$^1$H NMR (300 MHz, Acetone-$d_6$) δ 0.68-2.27 (m, 40H), 2.45 (d, J=15 Hz, 1H), 3.05-3.08 (m, 1H), 5.47 (s, 1H). APCI MS m/z 656 $[C_{33}H_{49}N_7O_3S_2+H]^+$. m.p. 280-300° C. dec. HPLC (Method A)>99% (214 nm) $t_R$=14.0 min.

EXAMPLE 81

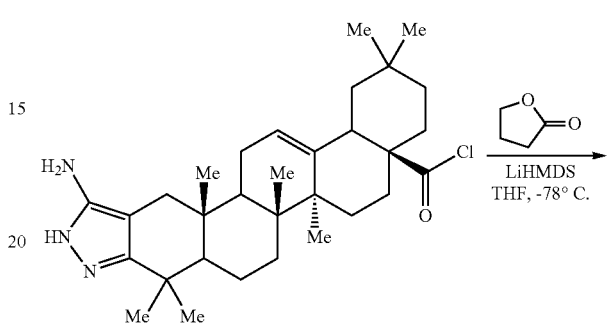

III

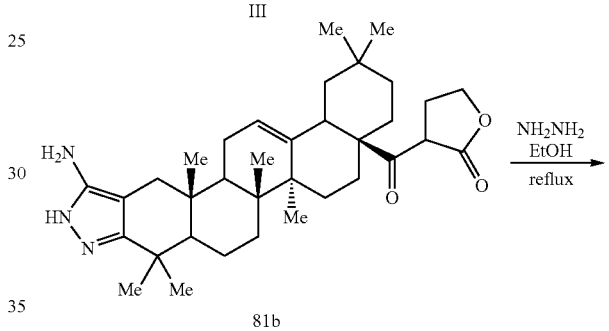

81b

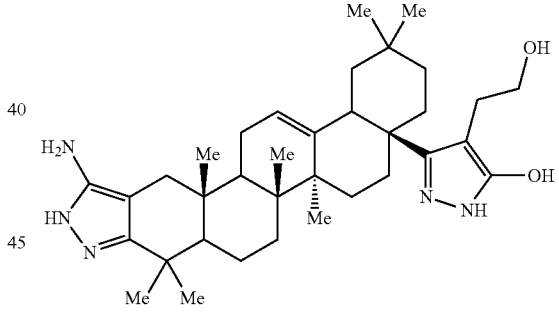

81

(i) Preparation of 81b: 3-((4aS,6aS,6bR,13aR)-12-Amino-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carbonyl) dihydrofuran-2(3H)-one To a solution of lithium bis(trimethylsilyl)amide (2.3 mL, 1 M in THF, 2.3 mmol) was added dihydrofuran-2(3H)-one (0.15 mL, 1.9 mmol) at −78° C. The mixture was stirred for 15 min. The anion solution was added to a solution of III (100 mg, 0.19 mmol) in THF (7 mL) precooled to −78° C. The mixture was stirred at −78° C. for 30 min and deemed incomplete. To a second solution of lithium bis(trimethylsilyl)amide (1.1 mL, 1 M in THF, 1.1 mmol) was added dihydrofuran-2(3H)-one (0.075 mL, 1.0 mmol) at −78° C. The second anion mixture was stirred for 15 min. The anion solution was added to the above reaction mixture at −78° C. The mixture was continued to stir at −78° C. for 30 min. The reaction mixture was quenched with saturated NH₄Cl (60 mL) and extracted with EtOAc (100 mL). The organic phase was washed with brine, dried (MgSO₄), filtered and concentrated to dryness. The residue was purified by column chromatography (silica, 0-30% CMA in CH₂Cl₂) to afford the sub-title compound (150 mg) as a brown solid.

ESI MS (Positive Mode) m/z 562 [$C_{35}H_{51}N_3O_3$+H]⁺.

(ii) Preparation of 81: 3-((4aS,6aS,6bR,13aR)-12-Amino-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazol-4-a-yl)-4-(2-hydroxyethyl)-1H-pyrazol-5-ol A mixture of 81b (150 mg) and hydrazine (0.037 mL) in EtOH (2 mL) was heated at reflux overnight. The reaction mixture was concentrated to dryness under reduced pressure. The residue was purified by column chromatography (silica, 0-60% CMA in CH₂Cl₂) followed by preparative HPLC to afford the title compound (12 mg, 8%) as an off-white solid.

$R_f$ 0.70 (80:18:2 Methylene Chloride/Methanol/concentrated Ammonium Hydroxide).

¹H NMR (300 MHz, CD₃OD) δ 0.50 (s, 3H), 0.86 (s, 3H), 0.95 (s, 3H), 0.98 (s, 3H), 1.23 (s, 3H), 1.28 (s, 3H), 1.32 (s, 3H), 1.35-2.08 (m, 18H), 2.25 (m, 1H), 2.36 (d, J=15.0 Hz, 1H), 2.74 (m, 2H), 2.82 (m, 1H), 3.72 (t, J=6.6 Hz, 2H), 5.51 (s, 1H). mp 251-255° C. APCI MS (Positive Mode) m/z 576 [$C_{35}H_{53}N_5O_2$+H]⁺.

EXAMPLE 82

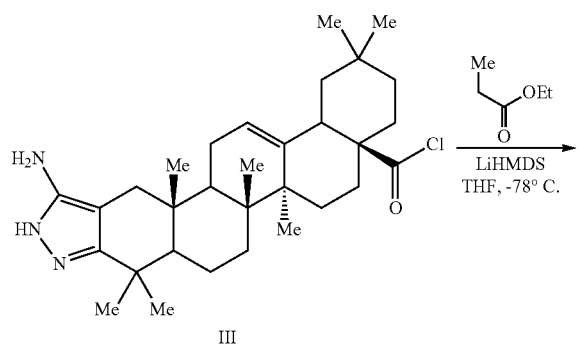

III

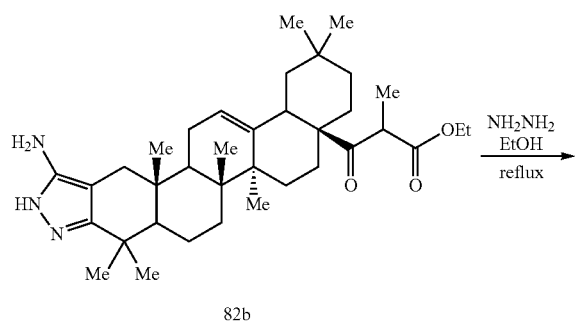

82b

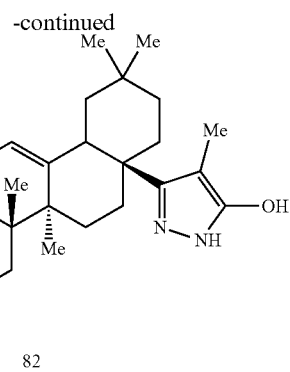

82

(i) Preparation of 82b: Ethyl 3-((4aS,6aS,6bR,13aR)-12-amino-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazol-4-a-yl)-2-methyl-3-oxopropanoate To a solution of lithium bis(trimethylsilyl)amide (3.8 mL, 1 M in THF, 3.8 mmol) was added ethyl propionate (0.22 mL, 1.9 mmol). The mixture was stirred for 30 min. The anion solution was added to a solution of III (100 mg, 0.19 mmol) in THF (3 mL) precooled to −78° C. The mixture was stirred at −78° C. for 1 hour and the reaction was deemed incomplete. To a second solution of lithium bis(trimethylsilyl)amide (1.9 mL, 1 M in THF, 1.9 mmol) was added ethyl propionate (0.33 mL, 1.9 mmol). The second anion mixture was stirred for 30 min. The anion solution was added to the above reaction mixture at −78° C. The mixture was continued to stir at −78° C. for 30 min. The reaction mixture was quenched with saturated NH₄Cl (20 mL) and extracted with EtOAc (100 mL). The organic phase was washed brine, dried (MgSO₄), filtered and concentrated to dryness. The residue was purified by column chromatography (silica, 0-30% CMA in CH₂Cl₂) to afford the sub-title compound (100 mg) as a brown solid.

APCI MS (Positive Mode) m/z 578 [$C_{36}H_{55}N_3O_3$+H]⁺.

(ii) Preparation of 82: 3-((4aS,6aS,6bR,13aR)-12-Amino-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazol-4-a-yl)-4-methyl-1H-pyrazol-5-ol A mixture of 82b (100 mg) and hydrazine (0.06 mL) in EtOH (2 mL) was heated at reflux overnight. The reaction mixture was concentrated to dryness under reduced pressure. The residue was purified by column chromatography (silica, 0-50% CMA in CH₂Cl₂) followed by preparative HPLC to the title compound (7 mg, 7%) as an off-white solid.

$R_f$ 0.70 (80:18:2 Methylene Chloride/Methanol/concentrated Ammonium Hydroxide).

¹H NMR (300 MHz, CD₃OD) δ 0.55 (s, 3H), 0.85 (s, 3H), 0.96 (s, 3H), 1.00 (s, 3H), 1.19 (s, 3H), 1.23 (s, 3H), 1.28 (s, 3H), 1.32-2.08 (m, 21H), 2.39 (m, 1H), 2.44 (d, J=15.0 Hz,

1H), 2.90 (m, 1H), 5.48 (s, 1H). mp >300° C. APCI MS (Positive Mode) m/z 546 $[C_{34}H_{51}N_5O+H]^+$.

EXAMPLE 83

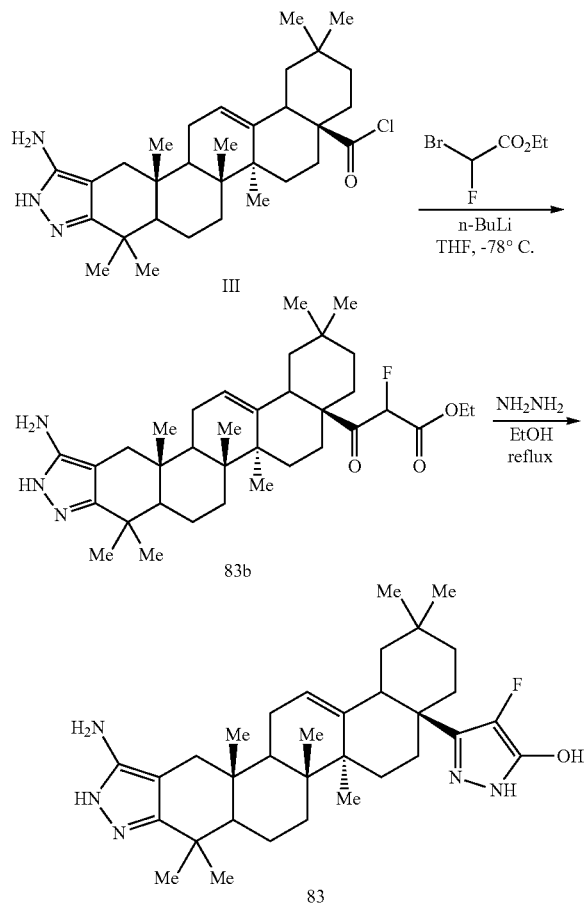

(i) Preparation of 83b: Ethyl 3-((4aS,6aS,6bR,13aR)-12-amino-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazol-4-a-yl)-2-fluoro-3-oxopropanoate To a solution of lithium bis(trimethylsilyl)amide (5.9 mL, 1 M in THF, 5.9 mmol) was added ethyl 2-bromo-2-fluoroacetate (0.46 mL, 3.9 mmol) at −78° C. The mixture was stirred for 10 min. The anion solution was added to a solution of III (200 mg, 0.39 mmol) in THF (4 mL) precooled to −78° C. The mixture was stirred at −78° C. for 1 hour and the reaction was deemed incomplete. To a second solution of n-butyllithium (1.8 mL, 2.5 M in hexanes, 5.9 mmol) was added ethyl 2-bromo-2-fluoroacetate (0.46 mL, 3.9 mmol) at −78° C. The second anion mixture was stirred for 10 min. The anion solution was added to the above reaction mixture at −78° C. The mixture was stirred at −78° C. for 1 hour and warmed to −20° C. over 1 hour. The reaction mixture was quenched with saturated NH₄Cl (20 mL) and extracted with EtOAc (100 mL). The organic phase was washed with brine, dried (MgSO₄), filtered and concentrated to dryness. The residue was purified by column chromatography (silica, 0-30% CMA in CH₂Cl₂) to afford the sub-title compound (110 mg) as a brown solid.

APCI MS (Positive Mode) m/z 582 $[C_{35}H_{52}FN_3O_3+H]^+$.

(ii) Preparation of 83: 3-((4aS,6aS,6bR,13aR)-12-Amino-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazol-4-a-yl)-4-fluoro-1H-pyrazol-5-ol A mixture of 83b (110 mg) and hydrazine (0.05 mL) in EtOH (2 mL) was heated at reflux overnight. The reaction mixture was concentrated to dryness under reduced pressure. The residue was purified by column chromatography (silica, 0-50% CMA in CH₂Cl₂) followed by preparative HPLC to afford the title compound (9 mg, 10%) as an off-white solid.

$R_f$ 0.50 (80:18:2 Methylene Chloride/Methanol/concentrated Ammonium Hydroxide).

¹H NMR (300 MHz, CD₃OD) δ 0.52 (s, 3H), 0.85 (s, 3H), 0.96 (s, 3H), 1.00 (s, 3H), 1.19 (s, 3H), 1.23 (s, 3H), 1.28 (s, 3H), 1.32-2.08 (m, 18H), 2.39 (m, 1H), 2.40 (d, J=15.0 Hz, 1H), 2.90 (m, 1H), 5.42 (s, 1H). mp >300° C. APCI MS (Positive Mode) m/z 550 $[C_{33}H_{48}FN_5O+H]^+$.

EXAMPLE 84

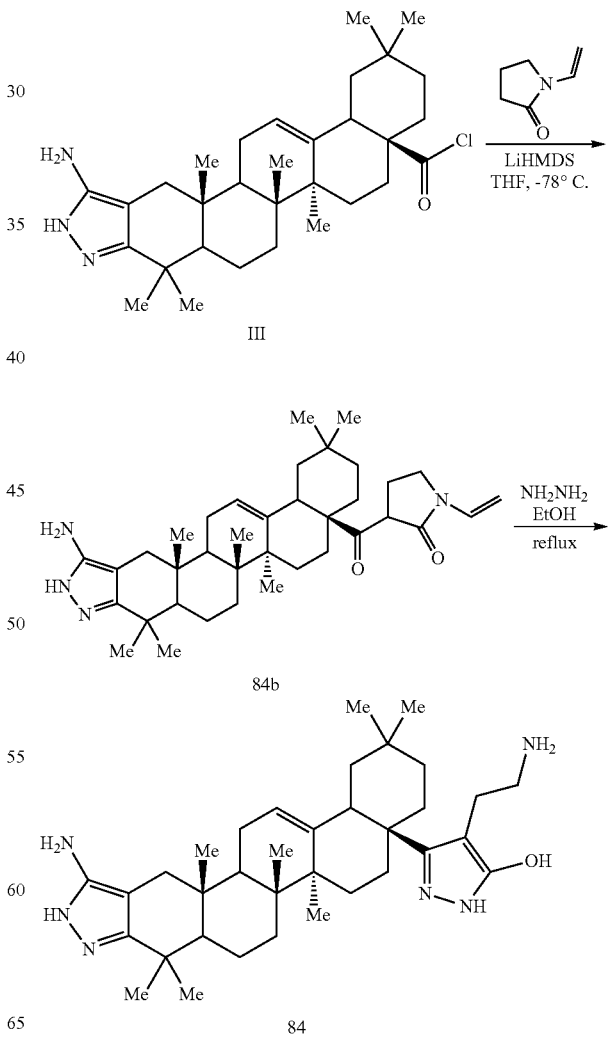

(i) Preparation of 84b: 3-((4aS,6aS,6bR,13aR)-12-Amino-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazole-4-a-carbonyl)-1-vinylpyrrolidin-2-one To a solution of lithium bis(trimethylsilyl)amide (38 mL, 1 M in THF, 38.0 mmol) was added 1-vinyl-2-pyrrolidinone (2.1 mL, 19.0 mmol) at −78° C. The mixture was stirred for 10 min. The anion solution was added to a solution of III (1.0 g, 1.9 mmol) in THF (20 mL) precooled to −78° C. The mixture was stirred at −78° C. for 1 hour. The reaction mixture was quenched with saturated NH$_4$Cl (60 mL) and extracted with EtOAc (100 mL). The organic phase was washed with brine, dried (MgSO$_4$), filtered and concentrated to dryness. The residue was purified by column chromatography (silica, 0-10% MeOH in CH$_2$Cl$_2$) to afford the sub-title compound (350 mg) as a brown solid.

APCI MS (Positive Mode) m/z 587 [C$_{37}$H$_{54}$N$_4$O$_2$+H]$^+$.

(ii) Preparation of 84: 3-((4aS,6aS,6bR,13aR)-12-Amino-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazol-4-a-yl)-4-(2-aminoethyl)-1H-pyrazol-5-ol A mixture of 84b (100 mg) and hydrazine (0.05 mL) in EtOH (2 mL) was sealed and heated to 160° C. by microwave for 3 hours. The reaction mixture was concentrated to dryness under reduced pressure. The residue was purified by column chromatography (silica, 0-80% CMA in CH$_2$Cl$_2$) to afford the title compound (50 mg, 30%) as a brown solid.

R$_f$ 0.27 (80:18:2 Methylene Chloride/Methanol/concentrated Ammonium Hydroxide).

$^1$H NMR (300 MHz, CD$_3$OD) δ 0.50 (s, 3H), 0.86 (s, 3H), 0.95 (s, 3H), 0.98 (s, 3H), 1.09 (s, 3H), 1.21 (s, 6H), 1.35-2.40 (m, 21H), 2.72 (m, 2H), 2.96 (m, 2H), 5.47 (s, 1H).

mp 250-260° C. dec. APCI MS (Positive Mode) m/z 575 [C$_{35}$H$_{54}$N$_6$O+H]$^+$.

EXAMPLE 85 and Example 86

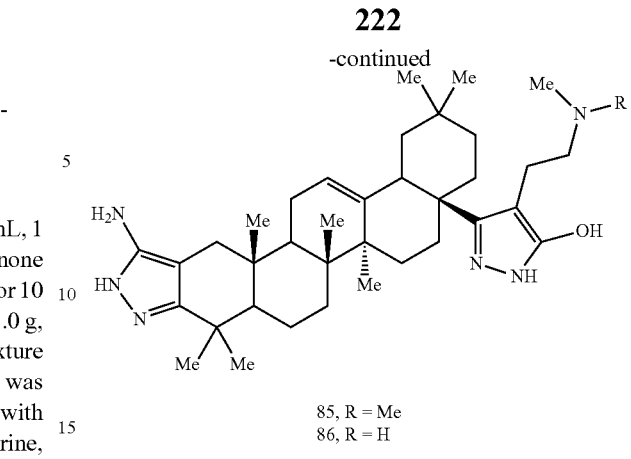

85, R = Me
86, R = H

(i) Preparation of 85 and 86: 3-((4aS,6aS,6bR,13aR)-12-Amino-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazol-4-a-yl)-4-(2-(dimethylamino)ethyl)-1H-pyrazol-5-ol and 3-((4aS,6aS,6bR,13aR)-12-Amino-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazol-4-a-yl)-4-(2-(methylamino)ethyl)-1H-pyrazol-5-ol To a solution of 84 (100 mg, 0.17 mmol) in MeOH (8 mL) was added 37% formaldehyde (0.021 mL, 0.36 mmol) in an ice bath. The mixture was stirred for 5 min. Sodium borohydride (32 mg, 0.84 mmol) was added. The reaction mixture was stirred at 0° C. for 1 hour and concentrated to dryness. The residue was purified by column chromatography (silica, 0-80% CMA in CH$_2$Cl$_2$) to afford 85 (35 mg, 20%) as an off-white solid and 86 (18 mg, 20%) as an off-white solid.

Data for 85:

R$_f$ 0.35 (80:18:2 Methylene Chloride/Methanol/concentrated Ammonium Hydroxide).

$^1$H NMR (300 MHz, CD$_3$OD) δ 0.50 (s, 3H), 0.86 (s, 3H), 0.95 (s, 3H), 0.98 (s, 3H), 1.15 (s, 3H), 1.21 (s, 6H), 1.35-2.35 (m, 20H), 2.35 (s, 6H), 2.67 (m, 4H), 2.90 (m, 1H), 5.48 (s, 1H). mp 260-270° C. dec. APCI MS (Positive Mode) m/z 603 [C$_{37}$H$_{58}$N$_6$O+H]$^+$.

Data for 86:

R$_f$ 0.30 (80:18:2 Methylene Chloride/Methanol/concentrated Ammonium Hydroxide).

$^1$H NMR (300 MHz, CD$_3$OD) δ 0.50 (s, 3H), 0.86 (s, 3H), 0.95 (s, 3H), 0.98 (s, 3H), 1.15 (s, 3H), 1.21 (s, 6H), 1.35-2.08 (m, 20H), 2.30 (s, 2H), 2.71 (m, 3H), 2.83 (m, 3H), 5.49 (s, 1H). mp 260-270° C. dec. APCI MS (Positive Mode) m/z 589 [C$_{36}$H$_{56}$N$_6$O+H]$^+$.

EXAMPLE 87

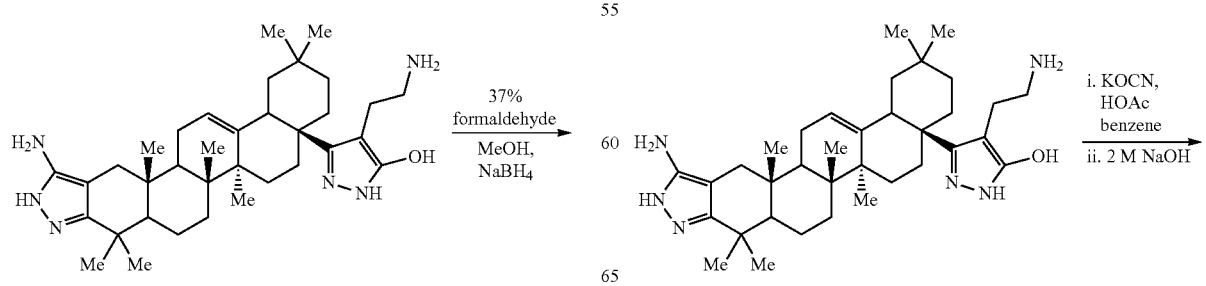

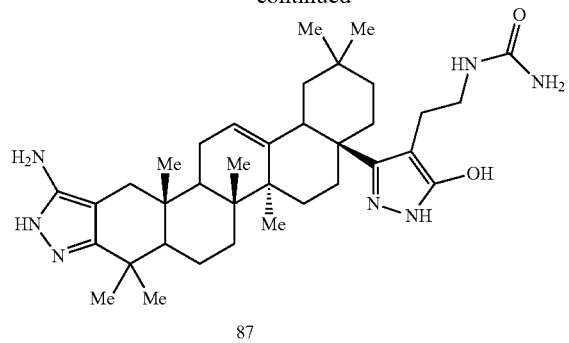

87

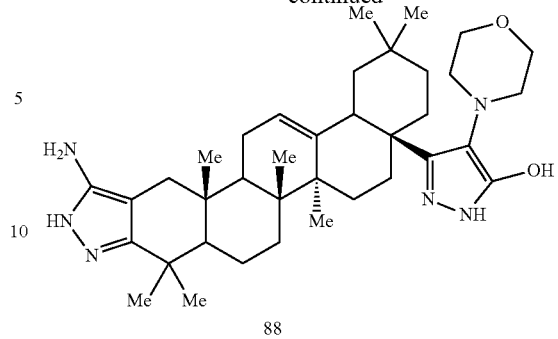

88

(i) Preparation of 87: 1-(2-(3-((4aS,6aS,6bR,13aR)-12-Amino-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazol-4-a-yl)-5-hydroxy-1H-pyrazol-4-yl)ethyl)urea To a solution of 84 (66 mg, 0.11 mmol) and acetic acid (0.2 mL) in THF (2 mL) and benzene (3 mL) was added potassium cyanate (22 mg, 0.26 mmol). The mixture was stirred at room temperature for 12 hours. Sodium hydroxide (2 mL, 2.0 M) was added. The reaction mixture was stirred at room temperature for 3 hours and concentrated to dryness. The residue was purified by column chromatography (silica, 0-10% MeOH in CMA) to afford the title compound (7 mg, 10%) as a brown solid.

$R_f$ 0.50 (80:28:2 Methylene Chloride/Methanol/concentrated Ammonium Hydroxide).

$^1$H NMR (300 MHz, CD$_3$OD) δ 0.51 (s, 3H), 0.87 (s, 3H), 0.96 (s, 3H), 1.00 (s, 3H), 1.12 (s, 3H), 1.28 (s, 3H), 1.32 (s, 3H), 1.35-2.12 (m, 20H), 2.28 (s, 1H), 2.30 (d, J=15.0 Hz, 1H), 2.60 (m, 2H), 2.85 (m, 1H), 5.52 (s, 1H). mp >300° C. APCI MS (Positive Mode) m/z 618 [C$_{36}$H$_{55}$N$_7$O$_2$+H]$^+$.

EXAMPLE 88

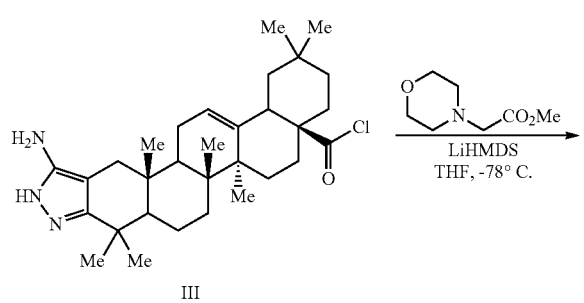

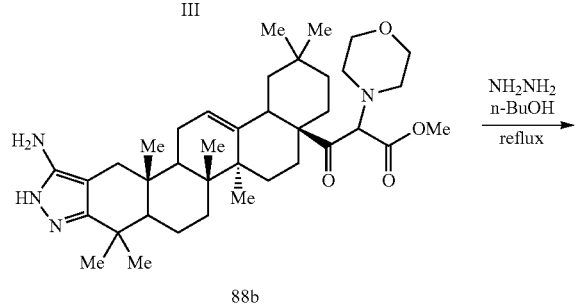

88b (i) Preparation of 88b: Methyl 3-((4aS,6aS,6bR,8aR,13aR,15bS)-12-amino-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazol-4-a-yl)-2-morpholino-3-oxopropanoate To a solution of lithium bis(trimethylsilyl)amide (15.6 mL, 1 M in THF, 15.6 mmol) was added methyl morpholinoacetate (1.8 g, 11.7 mmol) at −78° C. The mixture was stirred for 10 min. The anion solution was added to a solution of III (400 mg, 0.78 mmol) in THF (10 mL) precooled to −10° C. The mixture was stirred at −10° C. for 1 hour. The reaction mixture was quenched with saturated NH$_4$Cl (60 mL) and extracted with EtOAc (100 mL). The organic phase was washed with brine, dried (MgSO$_4$), filtered and concentrated to dryness. The residue was purified by column chromatography (silica, 0-20% CMA in CH$_2$Cl$_2$) to afford the sub-title compound (120 mg) as a brown solid.

APCI MS (Positive Mode) m/z 635 [C$_{38}$H$_{58}$N$_4$O$_4$+H]$^+$.

(ii) Preparation of 88: 3-((4aS,6aS,6bR,13aR)-12-Amino-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazol-4-a-yl)-4-morpholino-1H-pyrazol-5-ol A mixture of 88b (120 mg) and hydrazine (0.05 mL) in n-BuOH (2 mL) was heated at reflux overnight. The reaction mixture was concentrated to dryness under reduced pressure. The residue was purified by column chromatography (silica, 0-30% CMA in CH$_2$Cl$_2$) to afford the title compound (6 mg, 5%) as a brown solid.

$R_f$ 0.42 (80:18:2 Methylene Chloride/Methanol/concentrated Ammonium Hydroxide).

$^1$H NMR (300 MHz, CD$_3$OD) δ 0.53 (s, 3H), 0.84 (s, 3H), 0.94 (s, 3H), 1.12 (s, 3H), 1.21 (s, 3H), 1.23 (s, 6H), 1.32-2.37 (m, 24H), 2.53 (m, 1H), 3.68 (m, 4H), 5.42 (s, 1H). mp >300° C. ESI MS (Positive Mode) m/z 617 [C$_{37}$H$_{56}$N$_6$O$_2$+H]$^+$.

EXAMPLE 89

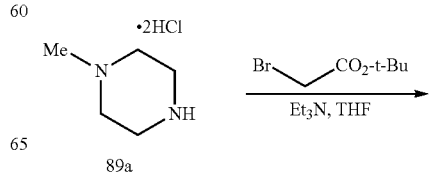

89a

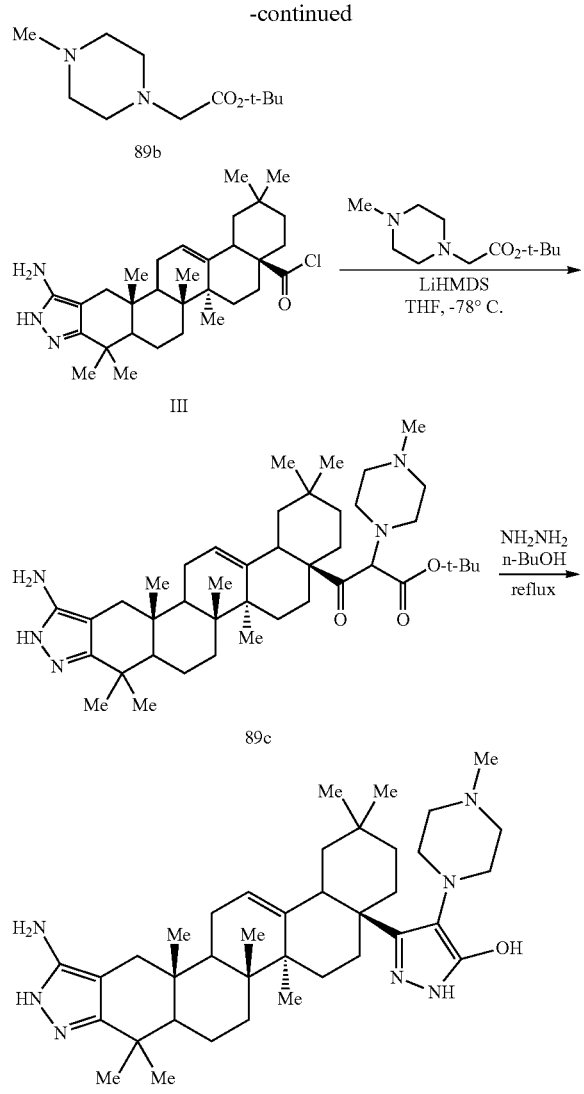

(i) Preparation of 89b: tert-Butyl 2-(4-methylpiperazin-1-yl)acetate

To a suspension of 1-methylpiperazine dihydrochloride (8.5 g, 49.2 mmol) and triethylamine (22.8 mL, 164.0 mmol) in THF (150 mL) was added tert-butyl 2-bromoacetate (8.0 g, 41.0 mmol). The mixture was stirred at room temperature for 12 hours. The reaction mixture was diluted with EtOAc (200 mL) and H$_2$O (100 mL). The organic phase was washed with brine, dried (MgSO$_4$), filtered and concentrated to dryness. The residue was purified by column chromatography (silica, 0-10% MeOH in CH$_2$Cl$_2$) to afford the sub-title compound (6.0 g, 69%).

$^1$H NMR (400 MHz, CDCl$_3$) δ 1.42 (s, 9H), 2.30 (s, 3H), 2.41-2.62 (m, 8H), 3.10 (s, 2H).

(ii) Preparation of 89c: tert-Butyl 3-((4aS,6aS,6bR,13aR)-12-amino-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazol-4-a-yl)-2-(4-methylpiperazin-1-yl)-3-oxopropanoate To a solution of lithium bis(trimethylsilyl)amide (15.6 mL, 1 M in THF, 15.6 mmol) was added 89b (2.5 g, 11.7 mmol) at −78° C. The mixture was stirred for 10 min. The anion solution was added to a solution of III (400 mg, 0.78 mmol) in THF (10 mL) precooled to −10° C. The mixture was stirred at 0° C. for 1.5 hours. The reaction mixture was quenched with saturated NH$_4$Cl (60 mL) and extracted with EtOAc (100 mL). The organic phase was washed with brine, dried (MgSO$_4$), filtered and concentrated to dryness. The residue was purified by column chromatography (silica, 0-20% CMA in CH$_2$Cl$_2$) to afford the sub-title compound (200 mg) as a brown solid.

APCI MS (Positive Mode) m/z 690 [C$_{42}$H$_{67}$N$_5$O$_3$+H]$^+$.

(ii) Preparation of 89: 3-((4aS,6aS,6bR,13aR)-12-Amino-2,2,6a,6b,9,9,13a-heptamethyl-2,3,4,4a,5,6,6a,6b,7,8,8a,9,11,13,13a,13b,14,15b-octadecahydro-1H-chryseno[1,2-f]indazol-4-a-yl)-4-(4-methylpiperazin-1-yl)-1H-pyrazol-5-ol A mixture of 89c (100 mg) and hydrazine (0.02 mL) in n-BuOH (2 mL) was heated at reflux overnight. The reaction mixture was concentrated to dryness under reduced pressure. The residue was purified by column chromatography (silica, 0-40% CMA in CH$_2$Cl$_2$) to afford the title compound (16 mg, 18%) as a brown solid.

R$_f$ 0.70 (80:18:2 Methylene Chloride/Methanol/concentrated Ammonium Hydroxide).

$^1$H NMR (400 MHz, CD$_3$OD) δ 0.54 (s, 3H), 0.84 (s, 3H), 0.91 (s, 3H), 0.95 (s, 3H), 1.01 (s, 3H), 1.10 (s, 3H), 1.11-2.06 (m, 16H), 2.20 (m, 1H), 2.41 (m, 1H), 2.84 (s, 3H), 2.91-3.70 (m, 14H), 5.45 (s, 1H). mp >300° C. APCI MS (Positive Mode) m/z 630 [C$_{38}$H$_{59}$N$_7$O+H]$^+$.

EXAMPLE 90

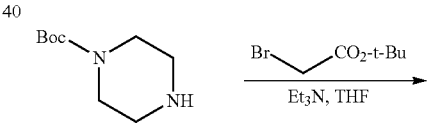

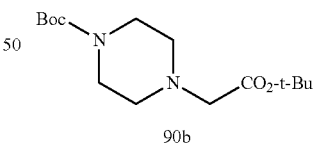

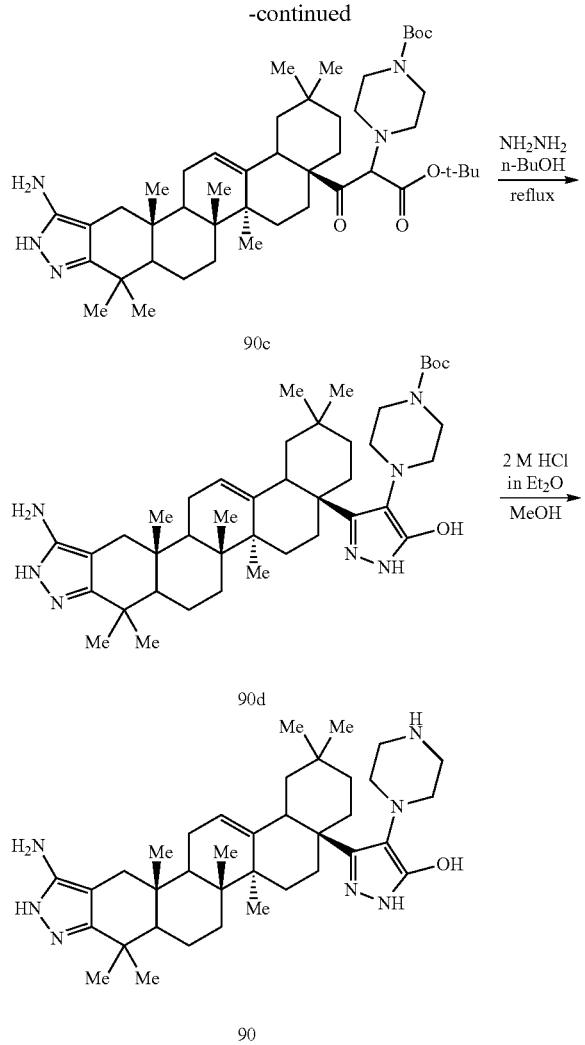

(i) Preparation of 90b: tert-Butyl 4-(2-tert-butoxy-2-oxoethyl)piperazine-1-carboxylate To a suspension of tert-butyl piperazine-1-carboxylate (3.0 g, 16.1 mmol) and triethylamine (4.5 mL, 32.2 mmol) in THF (80 mL) was added tert-butyl 2-bromoacetate (2.4 mL, 16.1 mmol). The mixture was stirred at room temperature for 12 hours. The reaction mixture was diluted with EtOAc (200 mL) and H$_2$O (100 mL). The organic phase was washed with brine, dried (MgSO$_4$), filtered and concentrated to dryness. The residue was purified by column chromatography (silica, 0-5% MeOH in CH$_2$Cl$_2$) to afford the sub-title compound (4.2 g, 87%).

$^1$H NMR (400 MHz, CDCl$_3$) δ 1.42 (s, 18H), 2.50 (m, 4H), 3.10 (s, 2H), 3.47 (m, 4H).

(ii) Preparation of 90c: tert-Butyl 4-(1-((4aS,6aS, 6bR,13aR)-12-amino-2,2,6a,6b,9,9,13a-heptamethyl-2,3,4,4a,5,6,6a,6b,7,8,8a,9,11,13,13a,13b,14, 15b-octadecahydro-1H-chryseno[1,2-f]indazol-4-a-yl)-3-tert-butoxy-1,3-dioxopropan-2-yl)piperazine-1-carboxylate To a solution of lithium bis(trimethylsilyl)amide (19.4 mL, 1 M in THF, 19.4 mmol) was added 90b (3.5 g, 11.7 mmol) at −78° C. The mixture was stirred for 10 min. The anion solution was added to a solution of III (500 mg, 0.97 mmol) in THF (10 mL) precooled to −78° C. The mixture was stirred at 0° C. for 1.5 hours. The reaction mixture was quenched with saturated NH$_4$Cl (60 mL) and extracted with EtOAc (100 mL). The organic phase was washed brine, dried (MgSO$_4$), filtered and concentrated to dryness. The residue was purified by column chromatography (silica, 0-20% CMA in CH$_2$Cl$_2$) to afford the sub-title compound (237 mg) as a brown solid.

ESI MS (Positive Mode) m/z 776 [C$_{46}$H$_{73}$N$_5$O$_5$+H]$^+$.

(iii) Preparation of 90d: tert-Butyl 4-(3-((4aS,6aS, 6bR,13aR)-12-amino-2,2,6a,6b,9,9,13a-heptamethyl-2,3,4,4a,5,6,6a,6b,7,8,8a,9,11,13,13a,13b,14, 15b-octadecahydro-1H-chryseno[1,2-f]indazol-4-a-yl)-5-hydroxy-1H-pyrazol-4-yl)piperazine-1-carboxylate A mixture of 90c (237 mg) and hydrazine (0.059 mL) in n-BuOH (5 mL) was heated at reflux overnight. The reaction mixture was concentrated to dryness under reduced pressure. The residue was purified by column chromatography (silica, 0-40% CMA in CH$_2$Cl$_2$) to afford the sub-title compound (15 mg, 7%) as a brown solid.

(iv) Preparation of 90: 3-((4aS,6aS,6bR,13aR)-12-Amino-2,2,6a,6b,9,9,13a-heptamethyl-2,3,4,4a,5,6, 6a,6b,7,8,8a,9,11,13,13a,13b,14,15b-octadecahydro-1H-chryseno[1,2-f]indazol-4-a-yl)-4-(piperazin-1-yl)-1H-pyrazol-5-ol To a solution of 90d (15 mg) in MeOH (2 mL) was added HCl (0.8 mL, 2 M in diethyl ether) and stirred at room temperature for 5 hours. The reaction mixture was concentrated and purified by preparative HPLC to provide the title compound (4.5 mg, 30%) as an off-white solid.

R$_f$ 0.12 (80:18:2 Methylene Chloride/Methanol/concentrated Ammonium Hydroxide).

$^1$H NMR (400 MHz, CD$_3$OD) δ 0.55 (s, 3H), 0.86 (s, 3H), 0.89 (s, 3H), 0.91 (s, 3H), 1.14 (s, 3H), 1.19 (s, 3H), 1.28 (s, 3H), 1.30-2.06 (m, 23H), 2.20 (m, 1H), 2.41 (d, J=15.0 Hz, 1H), 2.85-3.65 (m, 4H), 5.45 (s, 1H). mp >300° C. APCI MS (Positive Mode) m/z 616 [C$_{37}$H$_{57}$N$_7$O+H]$^+$.

EXAMPLE 91

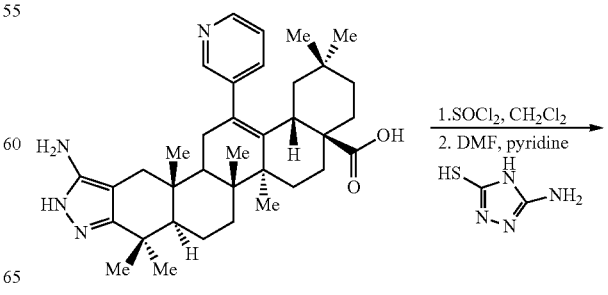

12

229

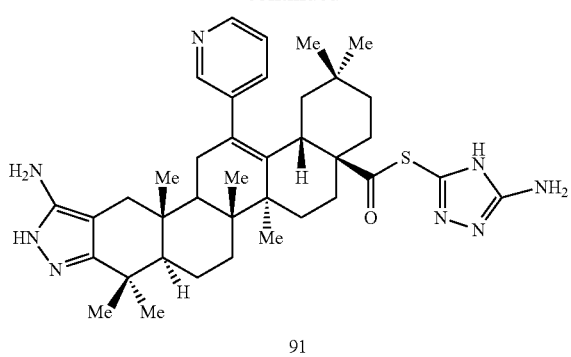

91

(i) Preparation of 91: (4aS,6aS,6bR,8aR,13aR, 15bS)—S-5-Amino-4H-1,2,4-triazol-3-yl 12-amino-2,2,6a,6b,9,9,13a-heptamethyl-15-(pyridin-3-yl)-2,3, 4,4a,5,6,6a,6b,7,8,8a,9,11,13,13a,13b,14,15b-octadecahydro-1H-chryseno[1,2-f]indazole-4-a-carbothioate To a solution of 12 (150 mg, 0.26 mmol) in $CH_2Cl_2$ (10 mL) was added thionyl chloride (0.19 mL, 2.6 mmol). The mixture was stirred at room temperature for 2 hours. The reaction mixture was concentrated to dryness under reduced pressure. The residue was dissolved in pyridine (10 mL) and DMF (2 mL). 5-Amino-4H-1,2,4-triazole-3-thiol (71 mg, 0.60 mmol) was added and stirred at room temperature for 1 hour. The reaction mixture was concentrated to dryness under reduced pressure. The residue was purified by column chromatography (silica, 0-50% CMA in $CH_2Cl_2$) followed by preparative HPLC to afford the title compound (19 mg, 14%) as an off-white solid.

$R_f$ 0.20 (80:18:2 Methylene Chloride/Methanol/concentrated Ammonium Hydroxide).

$^1$H NMR (300 MHz, $CD_3OD$) δ 0.30 (s, 3H), 0.82 (s, 3H), 0.90 (s, 3H), 0.98 (s, 3H), 1.22 (s, 3H), 1.32 (s, 3H), 1.34 (s, 3H), 1.35-2.30 (m, 19H), 2.35 (d, J=15.0 Hz, 1H), 2.75 (m, 1H), 7.91 (dd, J=5.7, 7.5 Hz, 1H), 8.40 (d, J=7.8 Hz, 1H), 8.68 (d, J=4.8 Hz, 1H), 8.79 (s, 1H). mp >300° C. ESI MS (Positive Mode) m/z 669 $[C_{38}H_{52}N_8OS+H]^+$.

EXAMPLE 92

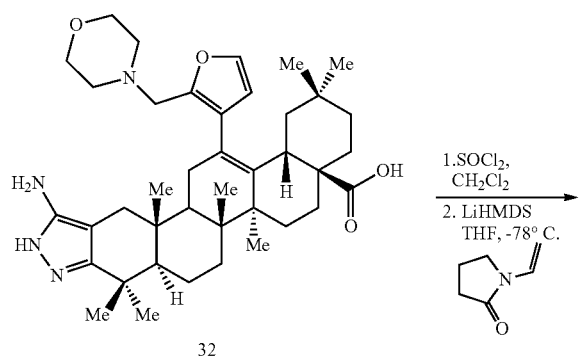

32

230

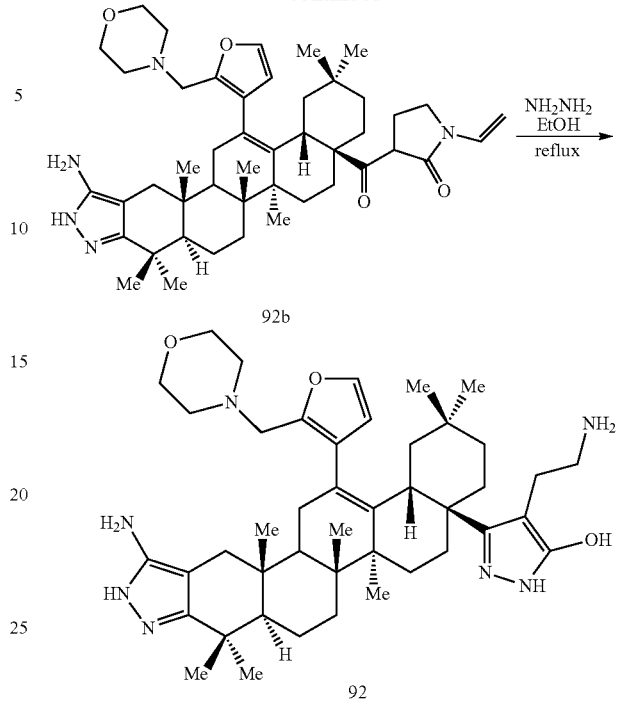

(i) Preparation of 92b: 3-((4aS,6aS,6bR,8aR,13aR, 15bS)-12-Amino-2,2,6a,6b,9,9,13a-heptamethyl-15-(2-(morpholinomethyl)furan-3-yl)-2,3,4,4a,5,6,6a, 6b,7,8,8a,9,11,13,13a,13b,14,15b-octadecahydro-1H-chryseno[1,2-f]indazole-4-a-carbonyl)-1-vinylpyrrolidin-2-one To a solution of 32 (250 mg, 0.37 mmol) in $CH_2Cl_2$ (10 mL) was added thionyl chloride (0.27 mL, 3.7 mmol). The mixture was stirred at room temperature for 2 hours. The reaction mixture was concentrated to dryness under reduced pressure. The residue was dissolved in THF (5 mL) and added to a solution of 1-vinylpyrrolidin-2-one (0.39 mL, 3.7 mmol) and lithium bis(trimethylsilyl)amide (7.4 mL, 1 M in THF, 7.4 mmol) in THF (5 mL) at −78° C. The reaction mixture was stirred at −78° C. for 1 hour. The reaction mixture was quenched with saturated $NH_4Cl$ (10 mL) and extracted with EtOAc (100 mL×2). The organic phase was washed with brine then dried ($MgSO_4$), filtered and concentrated to dryness under reduced pressure. The residue was purified by column chromatography (silica, 0-10% MeOH in $CH_2Cl_2$) to afford the sub-title compound (110 mg, 40%).

$^1$H NMR (300 MHz, $CDCl_3$) δ 0.51 (s, 3H), 0.81 (s, 3H), 0.87 (s, 6H), 1.10 (s, 3H), 1.18 (s, 3H), 1.20 (s, 3H), 1.21-2.60 (m, 29H), 2.95 (m, 1H), 3.35-3.75 (m, 8H), 4.05 (m, 1H), 4.45 (m, 2H), 6.40 (m, 1H), 7.01 (m, 1H), 7.37 (m, 1H).

(ii) Preparation of 92: 3-((4aS,6aS,6bR,8aR,13aR, 15bS)-12-Amino-2,2,6a,6b,9,9,13a-heptamethyl-15-(2-(morpholinomethyl)furan-3-yl)-2,3,4,4a,5,6,6a, 6b,7,8,8a,9,11,13,13a,13b,14,15b-octadecahydro-1H-chryseno[1,2-f]indazol-4-a-yl)-4-(2-aminoethyl)-1H-pyrazol-5-ol A mixture of 92b (110 mg, 0.14 mmol) and hydrazine (0.5 mL) in EtOH (2 mL) was sealed and heated to 160° C. by microwave for 3 hours. The reaction mixture was concentrated to dryness. The residue was purified by column chromatography (silica, 0-70% CMA in $CH_2Cl_2$) to afford the title compound (25 mg, 25%).

$R_f$ 0.54 (80:28:2 Methylene Chloride/Methanol/concentrated Ammonium Hydroxide).

$^1$H NMR (300 MHz, $CD_3OD$) δ 0.60 (s, 6H), 0.84 (s, 3H), 0.86 (s, 3H), 1.12 (s, 3H), 1.22 (s, 3H), 1.28 (s, 3H), 1.35-2.0 (m, 19H), 2.18 (m, 2H), 2.27 (d, J=15.0 Hz, 2H), 2.61-2.72 (m, 6H), 2.97 (m, 2H), 3.50-3.70 (m, 7H), 6.41 (s, 1H), 7.51 (s, 1H). mp 238-240° C. APCI MS (Positive Mode) m/z 740 $[C_{44}H_{65}N_7O_3+H]^+$.

EXAMPLE IV

Table 6, below, lists the inhibitory concentrations of select compounds and antibiotics in the biofilm growth assay against various gram-negative bacterial biofilms. "N" means the number of isolates of bacteria tested. The biofilm growth assay procedure detailed in Example I, above, was followed. *Burkholderia cepacia* used media consisting of M9 salts, 100 μM $CaCl_2$, 1 mM $MgSO_4$, and 0.7% citrate in 0.4% Noble agar. *Salmonella* spp. used media consisting of Nutrient Broth with 0.5% glucose in 0.5% Noble agar. Compound 1 of the invention is the most active compound in Table 6. Compound 1 is superior to tobramycin, ceftazidime, and azithromycin in the biofilm growth assay.

A successful research lead optimization strategy requires examining multiple clinical isolates in parallel based upon the inherent risks of antibacterial development and heterogeneity of biofilms. Past medicinal chemistry efforts focused on identifying superior analogs of approved classes of antibiotics have typically demonstrated that closely related analogs can exhibit varying degrees of antibacterial activities against different isolates and species of bacteria in an unpredictable trend. Hence, accurately selecting the next set of synthetic targets requires microbiological activities from a broad group of bacterial isolates and species of bacteria that would be encountered in clinical and community settings. In addition, significant variability of biofilm formation among different clinical isolates of *P. aeruginosa* has been shown to exist. Therefore, the lead optimization of a biofilm inhibitor may be detrimentally misguided if an unrepresentative group of clinical isolates not exhibiting these different biofilms are used to generate structure activity relationships.

TABLE 6

| Compound | P. aeruginosa (n = 10) | E. coli (n = 10) | B. cepacia (n = 10) | Salmonella spp. (n = 6) |
| --- | --- | --- | --- | --- |
| Oleanolic Acid | 8 | 16 | 0.5 | >64 |
| C644 | 2 | >16 | 0.5 | 16 |
| C649 | 16 | >16 | 1 | >16 |
| Compound 1 | 1 | 1 | 0.25 | 1 |
| Tobramycin | 4 | 16 | >64 | 8 |
| Ceftazidime | 4 | 0.25 | >8 | 0.5 |
| Azithromycin | >16 | — | >16 | >16 |

EXAMPLE V

The bioavailabilities of certain compounds were examined in mice. Administration of the compounds was performed orally and by intraperitoneal (IP) injection using a vehicle as known to those skilled in the art. Many vehicles can be used to examine bioavailability. Prior to administration, each vehicle was optimized based on compound solubility according to the formulation research conducted by Uckun et al. (Arznelmittel-Forschung (Drug Research) 2007; 57(4):218-226). Based upon this publication, vehicles containing approximate ratios of 2:1:1 of propylene glycol:Tween20: PEG400 (Tween20 being a common emulsier used in formulations and food products) and less than 5% ethanol upon administration exhibit good solubility properties and increase serum bioavailability. During these experiments, PEG400 demonstrated a critical role in serum bioavailability. The concentration of PEG400 is modulated depending upon solubility of the compounds and the amount of aqueous phase added (0.02 M citrate and 0.9% NaCl).

Compounds 1, 12, 64, and 68 demonstrated good bioavailability when administered orally or via IP injection at approximately 20 mg/kg to 50 mg/kg exceeding approximately 5 μg/ml in the serum of mice at 30 minutes or 1 hour after administration. Based upon these results, many of the compounds described herein would yield bioavailability including the compounds in Example II, Tables 2 and 3. This example demonstrates that the compounds of the invention can be formulated into tablets, capsules, suppositories, and sterile liquids for parenteral administration as known to those skilled in the art.

EXAMPLE VI

The biofilm growth assay as described in Example I, as amended by the details that follow, was performed using *Pseudomonas syringae*, *Xanthomonas campestris*, and *Pectobacterium atrosepticum* (gram-negative bacterial plant pathogens). A freezer stock of each plant pathogen was grown separately overnight on 1.5% agar plates containing TSB at 30° C. The next day a pipette tip was used to inoculate a round plate composed of M8 salts and 0.7% glucose on 0.5% Noble agar from the overnight TSB plates. Plates were allowed to incubate at 30° C. for approximately 24 to 48 hours. Compound 1 of the invention was examined against these plant pathogens and found to inhibit the spreading biofilms at 0.03 μg/ml against *Pseudomonas syringae*, 0.5 μg/ml against *Xanthomonas campestris*, and 0.06 μg/ml against Pectobacterium atrosepticum. These data demonstrate that the compounds of the invention inhibit spreading biofilms of plant pathogens.

EXAMPLE VII

Inhibition of the Growth of Preformed Biofilms

The Biofilm Growth Assay described in Example I was performed in round plates with the compounds of the invention only in agar on half of the plate. The agar not containing compound was inoculated with bacteria and the formed biofilm moved toward the agar containing compound on the other half of the round plate. Once the spreading biofilm reached the agar containing compound, the biofilm was inhibited from moving or spreading onto the agar with compound. This Biofilm Growth Assay performed on these agar plates demonstrates that the compounds of the invention inhibit the growth of preformed biofilms.

Approximately 0.5% agar not containing a compound of the invention was poured and allowed to dry. Agar on half of the plate was removed and then agar containing a compound of the invention was poured on the empty half of the plate and allowed to dry. Bacteria is inoculated onto the agar not containing compound and allowed in incubate overnight as described in Example I. During incubation bacteria spread as a biofilm until they reach the agar containing compound. The compounds of the invention inhibit the spreading biofilm at the same concentrations at shown in Examples I, II, and III, above.

EXAMPLE VIII

Inhibition of the Growth of Preformed Biofilms

The Biofilm Growth Assay as described in Example VII was performed in round plates with the compounds of the invention in agar on half of the plate and antibiotic disks placed onto the agar containing the compounds of the invention. This assay demonstrates that the compounds of the invention are synergistic with antibiotics like tobramycin and colistin at inhibiting spreading biofilms across the agar.

The Biofilm Growth Assay was performed as described in Example VIII. 2 to 4 antibiotic disks were placed onto the agar containing a compound of the invention in a line parallel to the line that separates the two agars in one round plate. Appropriate negative and positive control plates were performed as known to those skilled in the art. This assay demonstrates that the compounds of the invention in combination with antibiotics inhibit spreading biofilms at approximately 4 times less the concentration than when performed alone as described in Example I.

EXAMPLE IX

Evaluation of Salts

Evaluation of Compound 62 (Table 4) salt formation was performed. HCl, HBr, $H_3PO_4$, p-toluenesulfonic acid, benzenesulfonic acid, methanesulfonic acid, L-tartaric acid, acetic acid, xinafoic acid, L-lactic acid, benzoic acid, adipic acid, oxalic acid, pamoic acid, maleic acid, and laurylsulfuric acid indicated crystallinity. p-toluenesulfonic acid (mono) and $H_3PO_4$ (bis) provided the most desirable physical properties compared to freebase. As stated herein, the invention also includes compounds and their salts.

Evaluation of Compound 64 (Table 4) salt formation was performed. HCl (mono and bis), p-TSA (bis), BSA (bis), MSA (bis), $H_2SO_4$ (mono), and $H_3PO_4$ (mono) provided salts with crystallinity. Bis-MSA and mono-$H_3PO_4$ increased aqueous solubility compared to freebase. As stated herein, the invention also includes compounds and their salts.

EXAMPLE X

A topical gel containing 2% by weight of the compound of the invention with azithromycin for use in treating skin infections can be prepared.

0.25 gram of the compound of the invention is dissolved in 6.75 grams of ethanol. 0.2 grams of azithromycin is dissolved in this solution. 0.25 grams of hydroxypropyl methylcellulose is added with gentle stifling until a homogenous solution is obtained. 4.8 grams of water is then added with gentle shaking.

A formulation without antibiotic can also be prepared using this same procedure.

EXAMPLE XI

Pharmaceutical Formulation for Nebulization of a Compound of the Invention

Solutions were prepared comprising 2 mg/ml and 10 mg/ml of the compound of the invention in ethanol/propylene glycol/water (85:10:5). These solutions were nebulized separately by a ProNeb Ultra nebulizer manufactured by PARI. The nebulized solutions were collected in a cold trap, processed appropriately, and were detected by mass spectrometry. The compound of the invention is expected to be recovered from both formulations to demonstrate that nebulization can be used to deliver this compound to patients with lung infections.

EXAMPLE XII

The compounds shown in the table below were prepared semi-synthetically and tested in the biofilm growth assay as described herein. These compounds with substitutions at $R^1$ and $R^2$ did not inhibit the biofilms of *P. aeruginosa* or *E. coli* at 1 or 2 µg/ml sufficiently to warrant further investigation relative to the compounds noted above.

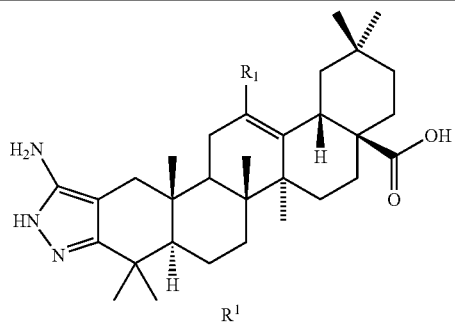

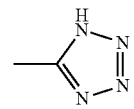

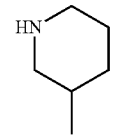

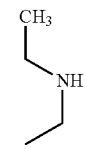

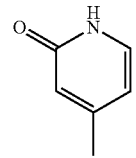

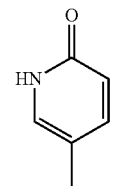

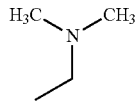

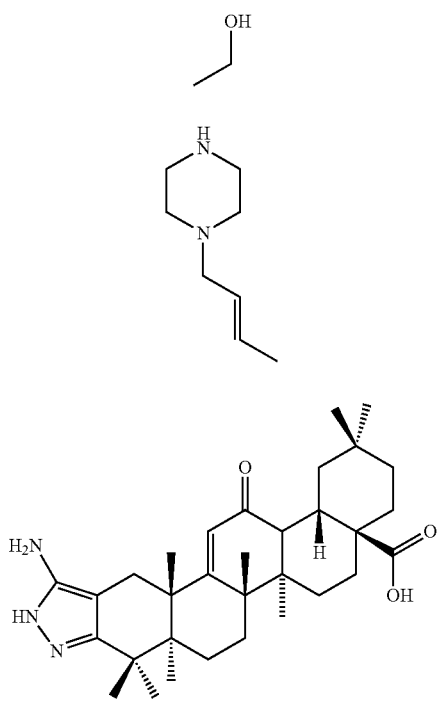
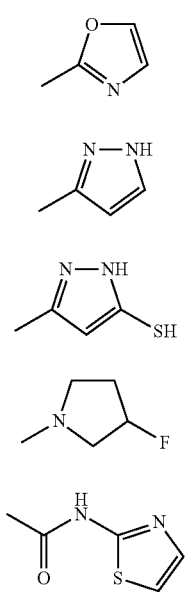
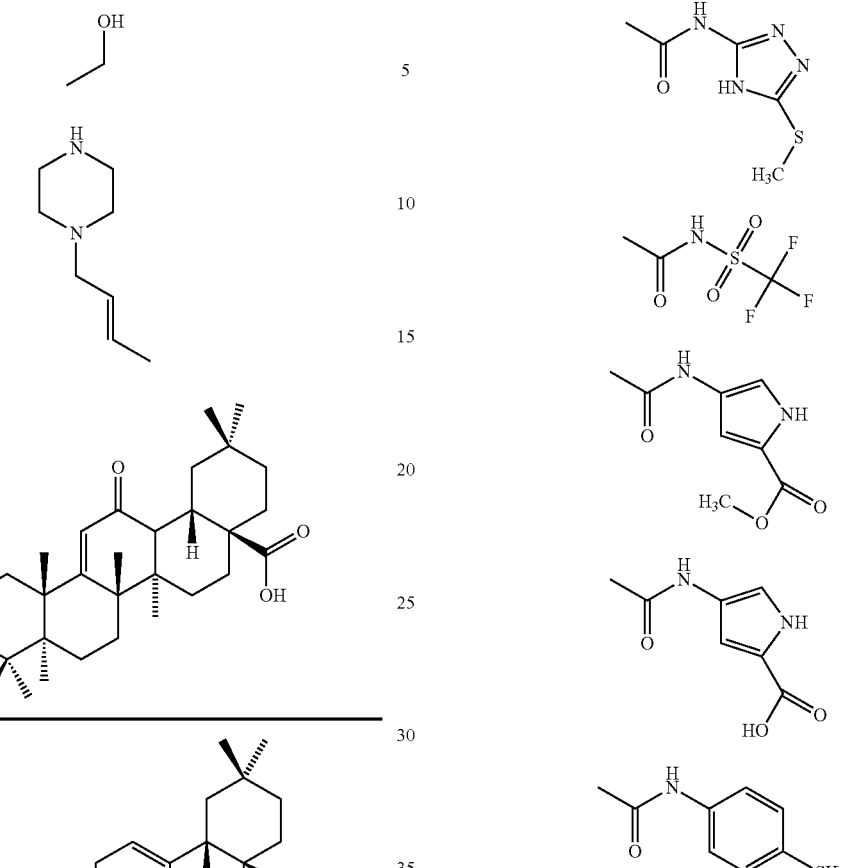

All references, including without limitation all papers, publications, presentations, texts, reports, manuscripts, brochures, internet postings, journal articles, periodicals, and the like, cited in this specification are hereby incorporated by reference. The discussion of the references herein is intended merely to summarize the assertions made by their authors and no admission is made that any reference constitutes prior art. The inventors reserve the right to challenge the accuracy and pertinence of the cited references.

It is intended that all patentable subject matter disclosed herein be claimed and that no such patentable subject matter be dedicated to the public. Thus, it is intended that the claims be read broadly in light of that intent. In addition, unless it is otherwise clear to the contrary from the context, it is intended that all references to "a" and "an" and subsequent corresponding references to "the" referring back to the antecedent basis denoted by "a" or "an" are to be read broadly in the sense of "at least one." Similarly, unless it is otherwise clear to the contrary from the context, the word "or," when used with respect to alternative named elements is intended to be read broadly to mean, in the alternative, any one of the named elements, any subset of the named elements or all of the named elements.

In view of the above, it will be seen that the several advantages of the invention are achieved and other advantageous results obtained. It should be understood that the aforementioned embodiments are for exemplary purposes only and are merely illustrative of the many possible specific embodiments that can represent applications of the principles of the invention. Thus, as various changes could be made in the above methods and compositions without departing from the scope of the invention, it is intended that all matter contained in the above description as shown in the accompanying drawings shall be interpreted as illustrative and not in a limiting sense.

Moreover, one of ordinary skill in the art can make various changes and modifications to the invention to adapt it to various usages and conditions, including those not specifically laid out herein, without departing from the spirit and scope of this invention. Accordingly, those changes and modifications are properly, equitably, and intended to be, within the full range of equivalents of the invention disclosed and described herein.

What is claimed is:

1. A compound corresponding to the following chemical structure:

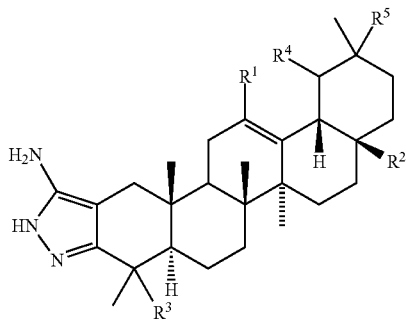

wherein $R^1$ is selected from the group consisting of hydrogen, methyl, halide, lower haloalkyl, nitrile, lower alkyl nitrile, lower alkyl, substituted lower alkyl, lower alkenyl, substituted lower alkenyl, lower alkynyl, substituted lower alkynyl, lower cycloalkyl, lower cycloalkenyl, aryl, substituted aryl, heteroaryl, and substituted heteroaryl; wherein $R^2$ is selected from the group consisting of carboxyl, amide, hydroxyamide, methylamide, —CH$_2$N(CH$_3$)$_2$, —CH$_2$NR$^6$R$^7$,

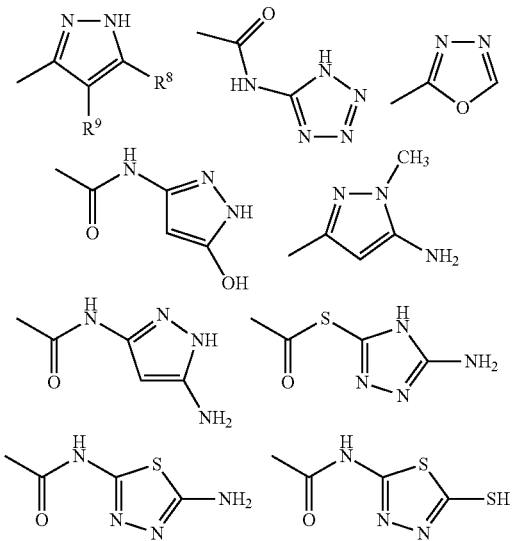

-continued

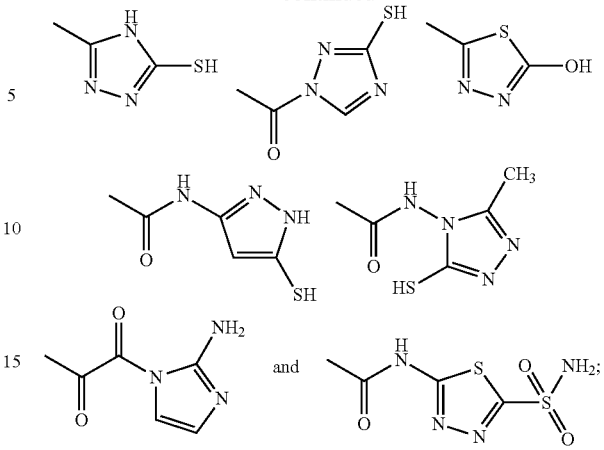

wherein $R^3$ is selected from the group consisting of hydrogen and methyl; wherein one of $R^4$ and $R^5$ is hydrogen and the other is methyl; wherein $R^6$ and $R^7$ are independently selected from the group consisting of hydrogen, methyl, ethyl, propyl, isopropyl, and butyl; wherein $R^8$ is selected from the group consisting of hydroxyl, amino, —N(CH$_3$)$_2$, and —NHCH$_3$; and wherein $R^9$ is selected from the group consisting of hydrogen, halide, lower alkyl, lower alkenyl, lower alkynyl, morpholinyl, piperazinyl, lower alkyl piperazinyl, heterocycloalkyl, lower cycloalkyl, lower cycloalkenyl; and lower alkyl, lower alkenyl, and lower alkynyl optionally substituted with moieties selected from the group consisting of hydroxyl, amino, lower aminoalkyl, halide, lower alkoxy, lower alkoxyalkyl, lower alkoxycarbonyl, lower alkylcarbonylamino, amide, hydroxyamide, —CONHCH$_3$, —NHCONH$_2$, —SO$_2$NH$_2$, —SO$_2$CH$_3$, —NHCOCH$_3$, —NHCSNH$_2$, and —NHSO$_2$CH$_3$; and salts thereof.

2. A compound as set forth in claim 1 wherein the compound corresponds to the following chemical structure:

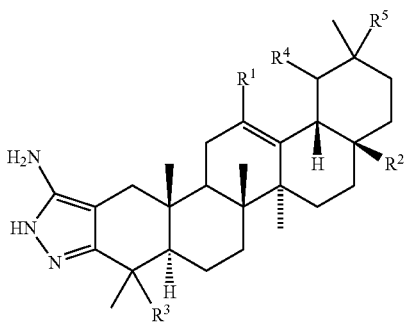

wherein $R^1$ is selected from the group consisting of methyl, halide, lower haloalkyl, nitrile, lower alkyl nitrile, lower alkyl, substituted lower alkyl, lower alkenyl, substituted lower alkenyl, lower alkynyl, substituted lower alkynyl, lower cycloalkyl, lower cycloalkenyl, aryl, substituted aryl, heteroaryl, and substituted heteroaryl; wherein $R^2$ is selected from the group consisting of carboxyl, amide, hydroxyamide, methylamide, —CH$_2$N(CH$_3$)$_2$, —CH$_2$NR$^6$R$^7$,

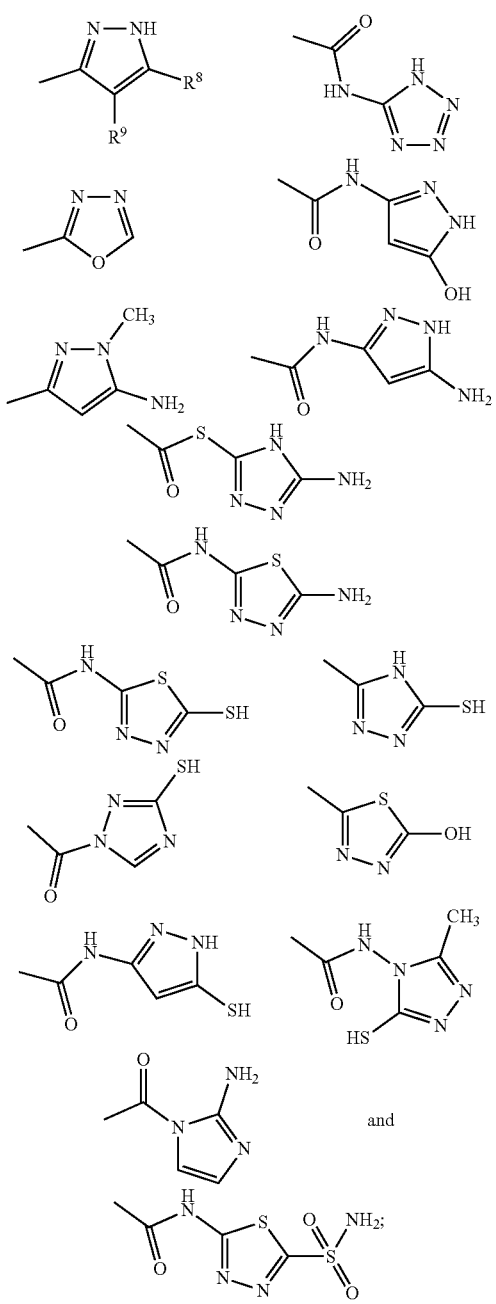

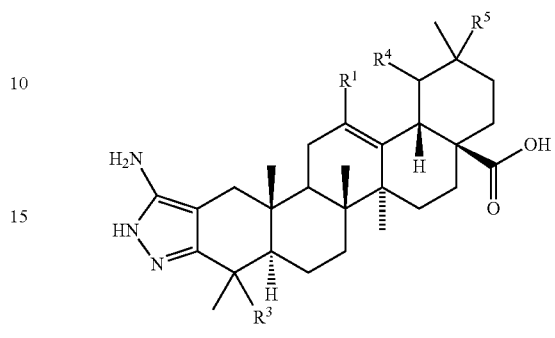

HCH$_3$, —NHCONH$_2$, —SO$_2$NH$_2$, —SO$_2$CH$_3$, —NHCOCH$_3$, —NHCSNH$_2$, and —NHSO$_2$CH$_3$; and salts thereof.

3. A compound as set forth in claim 1 wherein the compound corresponds to the following chemical structure:

wherein R$^3$ is selected from the group consisting of hydrogen and methyl; wherein one of R$^4$ and R$^5$ is hydrogen and the other is methyl; wherein R$^6$ and R$^7$ are independently selected from the group consisting of hydrogen, methyl, ethyl, propyl, isopropyl, and butyl; wherein R$^8$ is selected from the group consisting of hydroxyl, amino, —N(CH$_3$)$_2$, and —NHCH$_3$; and wherein R$^9$ is selected from the group consisting of hydrogen, halide, lower alkyl, lower alkenyl, lower alkynyl, morpholinyl, piperazinyl, lower alkyl piperazinyl, heterocycloalkyl, lower cycloalkyl, lower cycloalkenyl; and lower alkyl, lower alkenyl, and lower alkynyl optionally substituted with moieties selected from the group consisting of hydroxyl, amino, lower aminoalkyl, halide, lower alkoxy, lower alkoxyalkyl, lower alkoxycarbonyl, lower alkylcarbonylamino, amide, hydroxyamide, —CON-wherein R$^1$ is selected from the group consisting of hydrogen, halide, lower alkyl, substituted lower alkyl, lower alkenyl, substituted lower alkenyl, lower cycloalkyl, lower cycloalkenyl, aryl, substituted aryl, heteroaryl, and substituted heteroaryl; wherein R$^3$ is selected from the group consisting of hydrogen and methyl, and wherein one of R$^4$ and R$^5$ is hydrogen and the other is methyl; and salts thereof.

4. A compound as set forth in claim 1 wherein the compound corresponds to the following chemical structure:

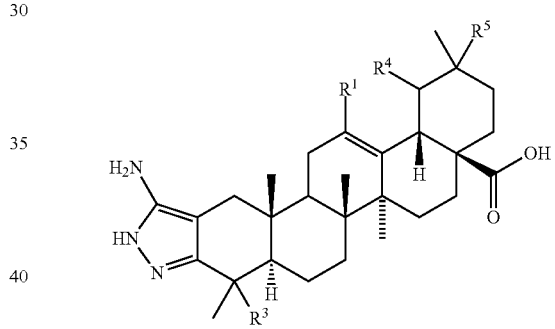

wherein R$^1$ is selected from the group consisting of halide, lower alkyl, substituted lower alkyl, lower alkenyl, substituted lower alkenyl, lower cycloalkenyl, aryl, substituted aryl, heteroaryl, and substituted heteroaryl; wherein R$^3$ is selected from the group consisting of hydrogen and methyl, and wherein one of R$^4$ and R$^5$ is hydrogen and the other is methyl; and salts thereof.

5. A compound as set forth in claim 1 wherein the compound corresponds to the following chemical structure:

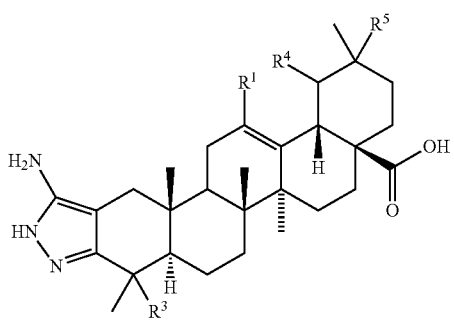

wherein R$^1$ is selected from the group consisting of lower alkenyl, substituted lower alkenyl, lower cycloalkenyl, aryl, substituted aryl, heteroaryl and substituted heteroaryl; wherein R³ is selected from the group consisting of hydrogen and methyl, and wherein one of R⁴ and R⁵ is hydrogen and the other is methyl; and salts thereof.

6. A compound as set forth in claim 1 wherein the compound corresponds to the following chemical structure:

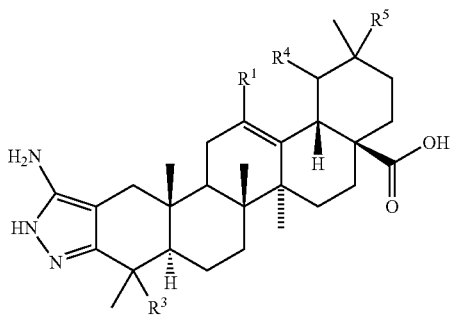

wherein R¹ is selected from the group consisting of aryl, heteroaryl and substituted heteroaryl; wherein R³ is selected from the group consisting of hydrogen and methyl, and wherein one of R⁴ and R⁵ is hydrogen and the other is methyl; and salts thereof.

7. A compound as set forth in claim 1 wherein the compound corresponds to the following chemical structure:

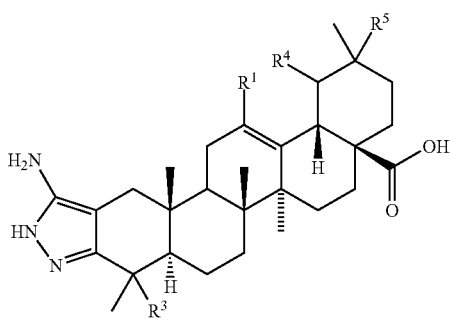

wherein R¹ is selected from the group consisting of heteroaryl, substituted heteroaryl; wherein R³ is selected from the group consisting of hydrogen and methyl, and wherein one of R⁴ and R⁵ is hydrogen and the other is methyl; and salts thereof.

8. A compound as set forth in claim 1 wherein the compound corresponds to the following chemical structure:

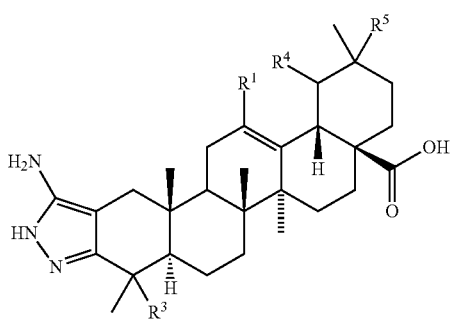

wherein R¹ is selected from the group consisting of heteroaryl optionally substituted with moieties selected from the group consisting of lower alkyl, halide, lower haloalkyl, hydroxyl, amino, lower aminoalkyl, lower alkoxy, and lower alkoxyalkyl; wherein R³ is selected from the group consisting of hydrogen and methyl, and wherein one of R⁴ and R⁵ is hydrogen and the other is methyl; and salts thereof.

9. A compound as set forth in claim 1 wherein the compound corresponds to the following chemical structure:

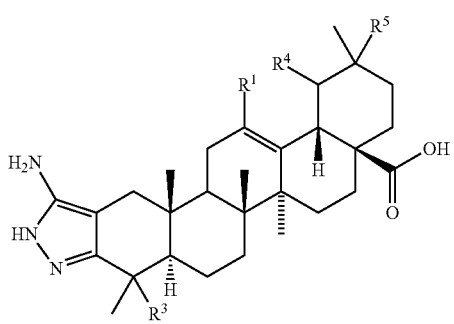

wherein R¹ is selected from the group consisting of pyrrolyl, pyrazolyl, imidazolyl, oxazolyl, isoxazolyl, oxadiazolyl, thiazolyl, isothiazolyl, thienyl, furanyl, furazanyl, pyridinyl, pyrimidinyl, pyridazinyl, indolyl, 3H-indolyl, isoindolyl, indolinyl, indolizinyl, indazolyl, dihydroindolyl, tetrahydroindolyl, purinyl, pyrazinyl, quinolinyl, isoquinolinyl, tetrahydroisoquinolinyl, quinoxalinyl, quinazolinyl, cinnolinyl, pteridinyl, benzimidazolyl, benzopyranyl, benzoxazolyl, benzisoxazolyl, benzofuranyl, isobenzofuranyl, benzothiazolyl, benzisothiazolyl, benzothienyl, furopyridinyl, phthalazinyl, napthyridinyl, pyrazolopyridyl, pyrazolopyrimidinyl, pyrrolopyridinyl, and tetrahydropyrrolopyridinyl optionally substituted from moieties selected from the group consisting of lower alkyl, halide, lower haloalkyl, hydroxyl, amino, lower aminoalkyl, lower hydroxyalkyl, nitrile, lower alkyl nitrile, lower alkyl ethers, lower alkoxy, lower alkoxyalkyl, lower alkoxycarbonyl, lower alkylcarbonylamino, and thioalkyl; wherein R³ is selected from the group consisting of hydrogen and methyl, and wherein one of R⁴ and R⁵ is hydrogen and the other is methyl; and salts thereof.

10. A compound as set forth in claim 1 wherein the compound corresponds to the following chemical structure:

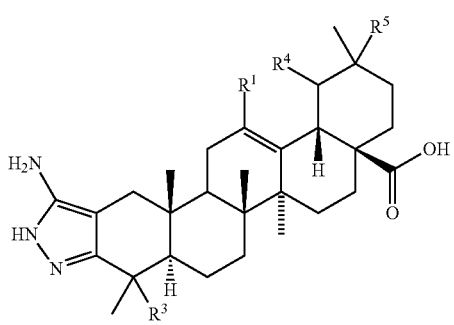

wherein R¹ is selected from the group consisting of pyrrolyl, pyrazolyl, imidazolyl, oxazolyl, isoxazolyl, oxadiazolyl, thiazolyl, isothiazolyl, thienyl, furanyl, furazanyl, pyridinyl, pyrimidinyl, pyridazinyl, indolyl, 3H-indolyl, isoindolyl, indolinyl, indolizinyl, indazolyl, dihydroindolyl, and tetrahydroindolyl optionally substituted from moieties selected from the group consisting of lower alkyl, halide, lower haloalkyl, hydroxyl, amino, lower aminoalkyl, lower hydroxyalkyl, nitrile, lower alkyl nitrile, lower alkyl ethers, lower alkoxy, lower alkoxyalkyl, lower alkoxycarbonyl, lower alkylcarbonylamino, and thioalkyl; wherein $R^3$ is selected from the group consisting of hydrogen and methyl, and wherein one of $R^4$ and $R^5$ is hydrogen and the other is methyl; and salts thereof.

11. A compound as set forth in claim 1 wherein the compound corresponds to the following chemical structure:

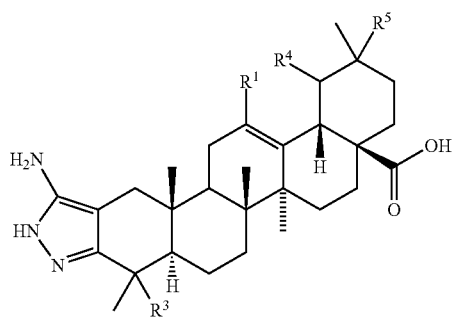

wherein $R^1$ is selected from the group consisting of pyrrolyl, pyrazolyl, imidazolyl, oxazolyl, isoxazolyl, oxadiazolyl, thiazolyl, isothiazolyl, thienyl, furanyl, furazanyl, pyridinyl, pyrimidinyl, pyridazinyl, indolyl, 3H-indolyl, isoindolyl, indolinyl, indolizinyl, indazolyl, dihydroindolyl, and tetrahydroindolyl; wherein $R^3$ is selected from the group consisting of hydrogen and methyl, and wherein one of $R^4$ and $R^5$ is hydrogen and the other is methyl; and salts thereof.

12. A compound as set forth in claim 1 wherein the compound corresponds to the following chemical structure:

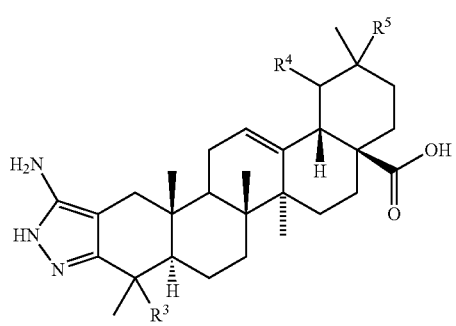

wherein $R^3$ is selected from the group consisting of hydrogen and methyl, and wherein one of $R^4$ and $R^5$ is hydrogen and the other is methyl; and salts thereof.

13. A compound as set forth in claim 1 wherein the compound corresponds to the following chemical structure:

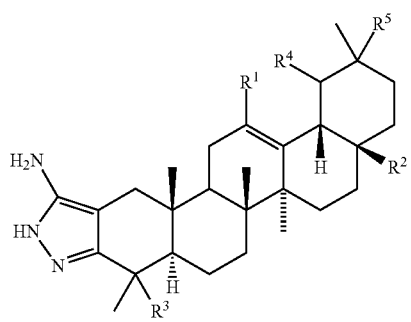

wherein $R^1$ is selected from the group consisting of hydrogen, methyl, halide, lower haloalkyl, nitrile, lower alkyl nitrile, lower alkyl, substituted lower alkyl, lower alkenyl, substituted lower alkenyl, lower alkynyl, substituted lower alkynyl, lower cycloalkyl, lower cycloalkenyl, aryl, substituted aryl, heteroaryl, and substituted heteroaryl;

wherein $R^2$ is selected from the group consisting of amide, hydroxyamide, methylamide, —$CH_2N(CH_3)_2$, —$CH_2NR^6R^7$,

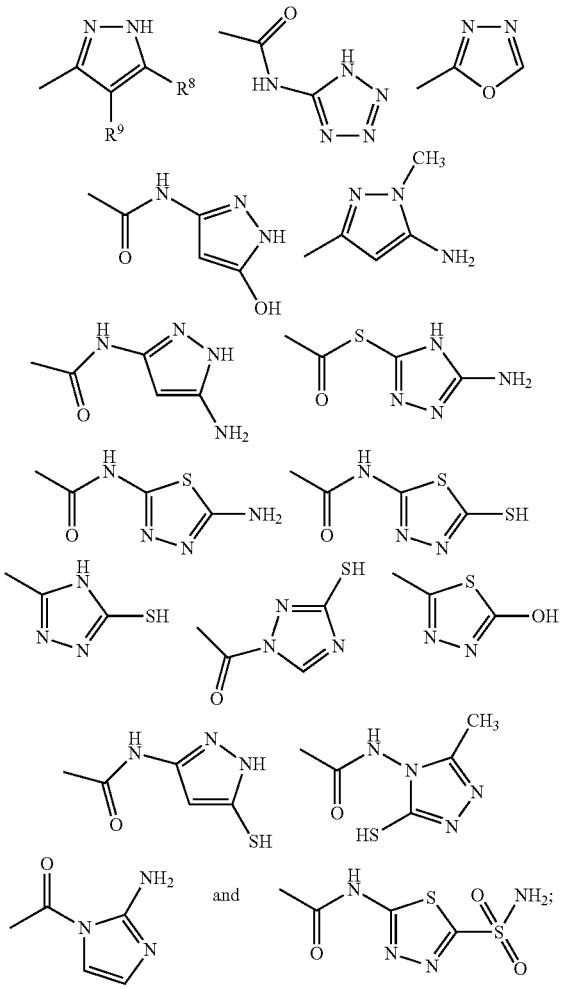

wherein $R^3$ is selected from the group consisting of hydrogen and methyl; wherein one of $R^4$ and $R^5$ is hydrogen and the other is methyl; wherein $R^6$ and $R^7$ are independently selected from the group consisting of hydrogen, methyl, ethyl, propyl, isopropyl, and butyl; wherein $R^8$ is selected from the group consisting of hydroxyl, amino, —$N(CH_3)_2$, and —$NHCH_3$; and wherein $R^9$ is selected from the group consisting of hydrogen, halide, lower alkyl, lower alkenyl, lower alkynyl, morpholinyl, piperazinyl, lower alkyl piperazinyl, heterocycloalkyl, lower cycloalkyl, lower cycloalkenyl; and lower alkyl, lower alkenyl, and lower alkynyl optionally substituted with moieties selected from the group consisting of hydroxyl, amino, lower aminoalkyl, halide, lower alkoxy, lower alkoxyalkyl, lower alkoxycarbonyl, lower alkylcarbonylamino, carboxyl, amide, hydroxyamide, —$CONHCH_3$, —$NHCONH_2$, —$SO_2NH_2$, —$SO_2CH_3$, —$NHCOCH_3$, —$NHCSNH_2$, and —$NHSO_2CH_3$; and salts thereof.

14. A compound as set forth in claim 1 wherein the compound corresponds to the following chemical structure:

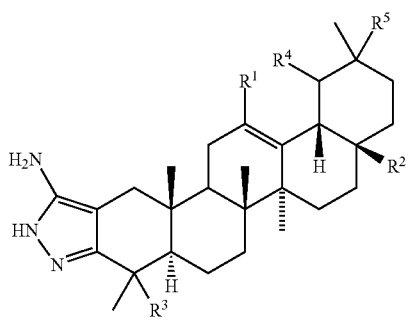

wherein $R^1$ is selected from the group consisting of hydrogen, halide, lower alkyl, substituted lower alkyl, lower alkenyl, substituted lower alkenyl, substituted aryl, lower cycloalkenyl, aryl, heteroaryl, and substituted heteroaryl; wherein $R^2$ is selected from the group consisting of amide, hydroxyamide, methylamide, —$CH_2N(CH_3)_2$, —$CH_2NR^6R^7$,

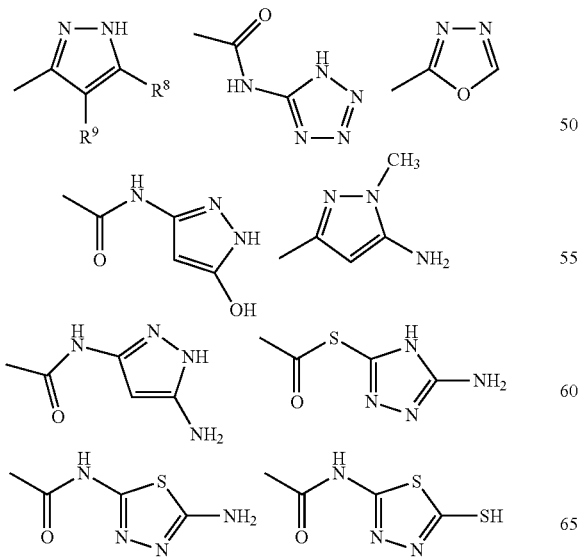

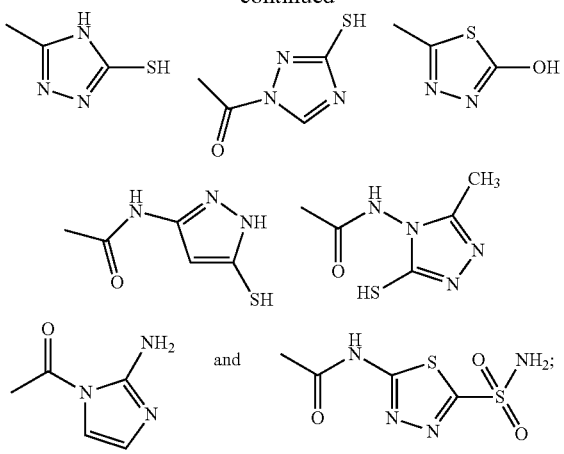

wherein $R^3$ is selected from the group consisting of hydrogen and methyl; wherein one of $R^4$ and $R^5$ is hydrogen and the other is methyl; wherein $R^6$ and $R^7$ are independently selected from the group consisting of hydrogen, methyl, ethyl, propyl, isopropyl, and butyl; wherein $R^8$ is selected from the group consisting of hydroxyl, amino, —$N(CH_3)_2$, and —$NHCH_3$; and wherein $R^9$ is selected from the group consisting of hydrogen, halide, lower alkyl, lower alkenyl, lower alkynyl, morpholinyl, piperazinyl, lower alkyl piperazinyl, heterocycloalkyl, lower cycloalkyl, lower cycloalkenyl; and lower alkyl, lower alkenyl, and lower alkynyl optionally substituted with moieties selected from the group consisting of hydroxyl, amino, lower aminoalkyl, halide, lower alkoxy, lower alkoxyalkyl, lower alkoxycarbonyl, lower alkylcarbonylamino, carboxyl, amide, hydroxyamide, —$CONHCH_3$, —$NHCONH_2$, —$SO_2NH_2$, —$SO_2CH_3$, —$NHCOCH_3$, —$NHCSNH_2$, and —$NHSO_2CH_3$; and salts thereof.

15. A compound as set forth in claim 1 wherein the compound corresponds to the following chemical structure:

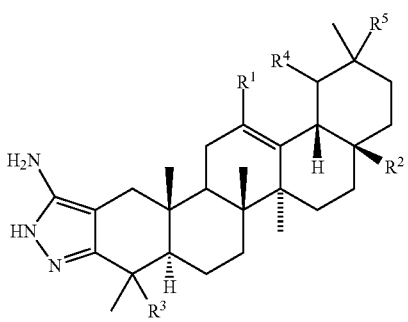

wherein $R^1$ is selected from the group consisting of lower alkenyl, substituted lower alkenyl, aryl, substituted aryl, heteroaryl and substituted heteroaryl; wherein $R^2$ is selected from the group consisting of amide, hydroxyamide, methylamide, —$CH_2N(CH_3)_2$, —$CH_2NR^6R^7$,

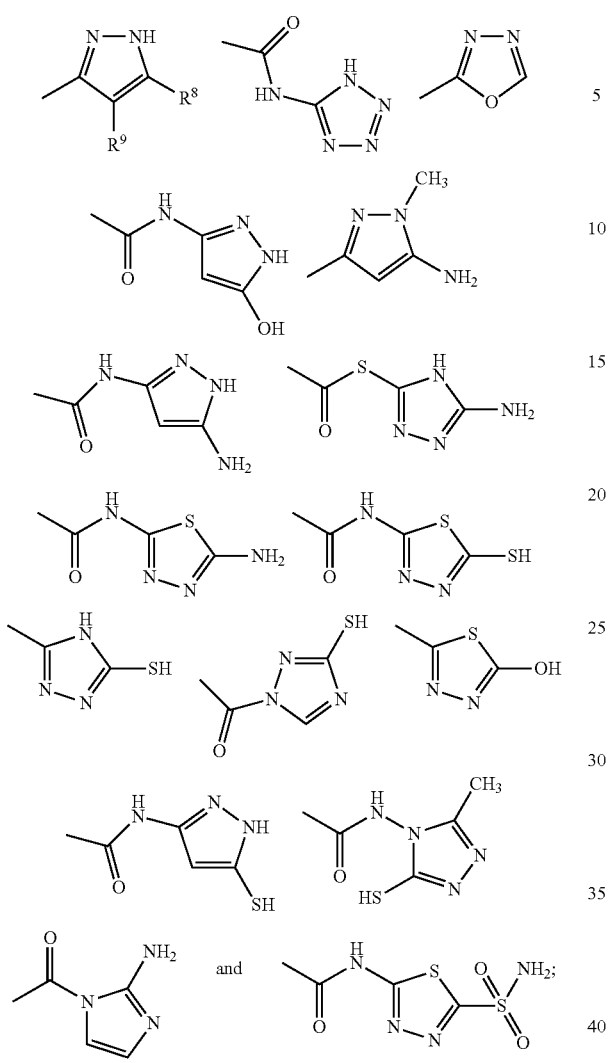

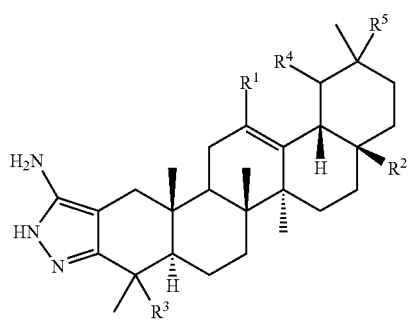

wherein $R^3$ is selected from the group consisting of hydrogen and methyl; wherein one of $R^4$ and $R^5$ is hydrogen and the other is methyl; wherein $R^6$ and $R^7$ are independently selected from the group consisting of hydrogen, methyl, ethyl, propyl, isopropyl, and butyl; wherein $R^8$ is selected from the group consisting of hydroxyl, amino, —N(CH$_3$)$_2$, and —NHCH$_3$; and wherein $R^9$ is selected from the group consisting of hydrogen, halide, lower alkyl, lower alkenyl, lower alkynyl, morpholinyl, piperazinyl, lower alkyl piperazinyl, heterocycloalkyl, lower cycloalkyl, lower cycloalkenyl; and lower alkyl, lower alkenyl, and lower alkynyl optionally substituted with moieties selected from the group consisting of hydroxyl, amino, lower aminoalkyl, halide, lower alkoxy, lower alkoxyalkyl, lower alkoxycarbonyl, lower alkylcarbonylamino, carboxyl, amide, hydroxyamide, —CONHCH$_3$, —NHCONH$_2$, —SO$_2$NH$_2$, —SO$_2$CH$_3$, —NHCOCH$_3$, —NHCSNH$_2$, and —NHSO$_2$CH$_3$; and salts thereof.

16. A compound as set forth in claim 1 wherein the compound corresponds to the following chemical structure:

wherein $R^1$ is selected from the group consisting of heteroaryl and substituted heteroaryl;

wherein $R^2$ is selected from the group consisting of amide, hydroxyamide, methylamide, —CH$_2$N(CH$_3$)$_2$, —CH$_2$NR$^6$R$^7$,

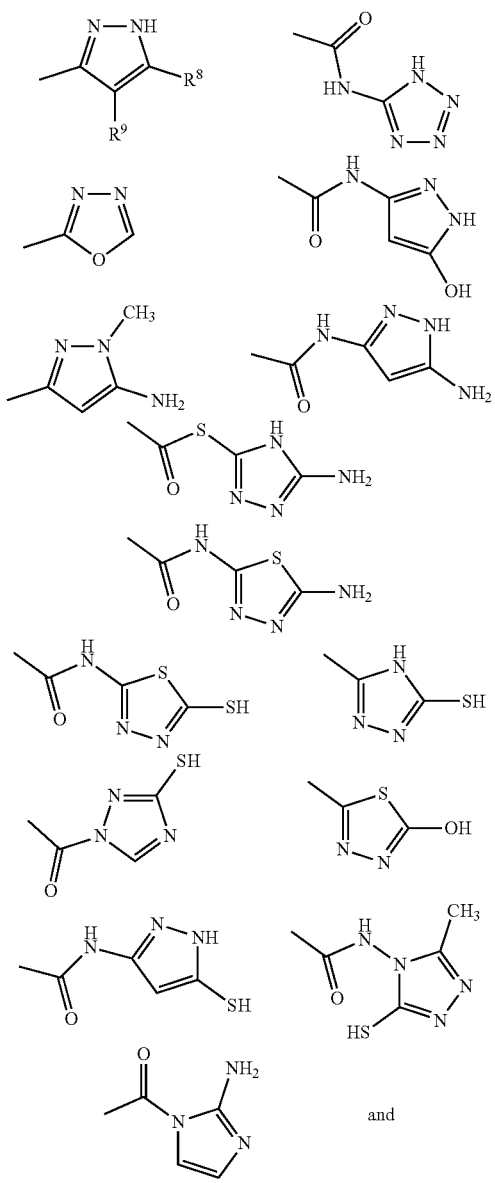

-continued wherein R³ is selected from the group consisting of hydrogen and methyl; wherein one of R⁴ and R⁵ is hydrogen and the other is methyl; wherein R⁶ and R⁷ are independently selected from the group consisting of hydrogen, methyl, ethyl, propyl, isopropyl, and butyl; wherein R⁸ is selected from the group consisting of hydroxyl, amino, —N(CH₃)₂, and —NHCH₃; and wherein R⁹ is selected from the group consisting of hydrogen, halide, lower alkyl, lower alkenyl, lower alkynyl, morpholinyl, piperazinyl, lower alkyl piperazinyl, heterocycloalkyl, lower cycloalkyl, lower cycloalkenyl; and lower alkyl, lower alkenyl, and lower alkynyl optionally substituted with moieties selected from the group consisting of hydroxyl, amino, lower aminoalkyl, halide, lower alkoxy, lower alkoxyalkyl, lower alkoxycarbonyl, lower alkylcarbonylamino, amide, hydroxyamide, —CONHCH₃, —NHCONH₂, —SO₂NH₂, —SO₂CH₃, —NHCOCH₃, —NHCSNH₂, and —NHSO₂CH₃; and salts thereof.

17. A compound as set forth in claim 1 wherein the compound corresponds to the following chemical structure:

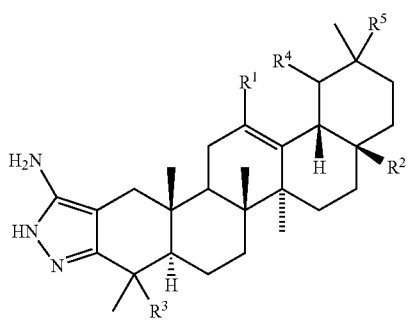

wherein R¹ is selected from the group consisting of substituted heteroaryl; wherein R² is selected from the group consisting of amide, hydroxyamide, methylamide, —CH₂N(CH₃)₂, —CH₂NR⁶R⁷,

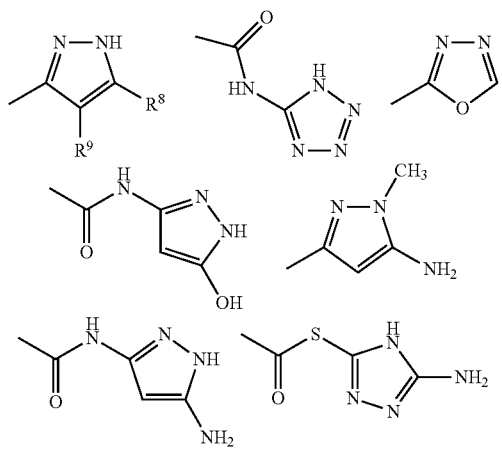

-continued

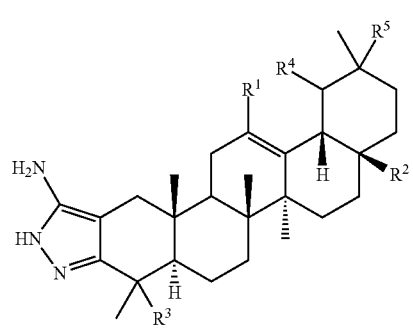
and wherein R³ is selected from the group consisting of hydrogen and methyl; wherein one of R⁴ and R⁵ is hydrogen and the other is methyl; wherein R⁶ and R⁷ are independently selected from the group consisting of hydrogen, methyl, ethyl, propyl, isopropyl, and butyl; wherein R⁸ is selected from the group consisting of hydroxyl, amino, —N(CH₃)₂, and —NHCH₃; and wherein R⁹ is selected from the group consisting of hydrogen, halide, lower alkyl, lower alkenyl, lower alkynyl, morpholinyl, piperazinyl, lower alkyl piperazinyl, heterocycloalkyl, lower cycloalkyl, lower cycloalkenyl; and lower alkyl, lower alkenyl, and lower alkynyl optionally substituted with moieties selected from the group consisting of hydroxyl, amino, lower aminoalkyl, halide, lower alkoxy, lower alkoxyalkyl, lower alkoxycarbonyl, lower alkylcarbonylamino, amide, hydroxyamide, —CONHCH₃, —NHCONH₂, —SO₂NH₂, —SO₂CH₃, —NHCOCH₃, —NHCSNH₂, and —NHSO₂CH₃; and salts thereof.

18. A compound as set forth in claim 1 wherein the compound corresponds to the following chemical structure:

wherein R¹ is selected from the group consisting of heteroaryl optionally substituted with moieties selected from the group consisting of lower alkyl, halide, lower haloalkyl, hydroxyl, amino, lower aminoalkyl, lower hydroxyalkyl, nitrile, lower alkyl nitrile, lower alkoxy, lower alkoxyalkyl, lower alkoxycarbonyl, lower alkylcarbonylamino, and thioalkyl; wherein $R^2$ is selected from the group consisting of amide, hydroxyamide, methylamide, —$CH_2N(CH_3)_2$, —$CH_2NR^6R^7$,

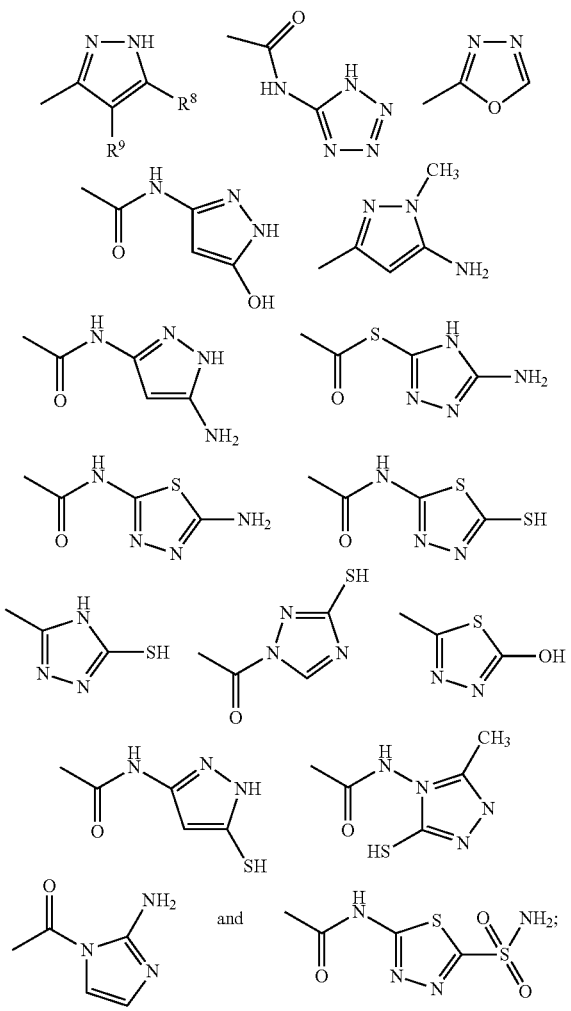

and wherein $R^3$ is selected from the group consisting of hydrogen and methyl; wherein one of $R^4$ and $R^5$ is hydrogen and the other is methyl; wherein $R^6$ and $R^7$ are independently selected from the group consisting of hydrogen, methyl, ethyl, propyl, isopropyl, and butyl; wherein $R^8$ is selected from the group consisting of hydroxyl, amino, —$N(CH_3)_2$, and —$NHCH_3$; and wherein $R^9$ is selected from the group consisting of hydrogen, halide, lower alkyl, lower alkenyl, lower alkynyl, morpholinyl, piperazinyl, lower alkyl piperazinyl, heterocycloalkyl, lower cycloalkyl, lower cycloalkenyl; and lower alkyl, lower alkenyl, and lower alkynyl optionally substituted with moieties selected from the group consisting of hydroxyl, amino, lower aminoalkyl, halide, lower alkoxy, lower alkoxyalkyl, lower alkoxycarbonyl, lower alkylcarbonylamino, amide, hydroxyamide, —$CONHCH_3$, —$NHCONH_2$, —$SO_2NH_2$, —$SO_2CH_3$, —$NHCOCH_3$, —$NHCSNH_2$, and —$NHSO_2CH_3$; and salts thereof.

19. A compound as set forth in claim 1 wherein the compound corresponds to the following chemical structure:

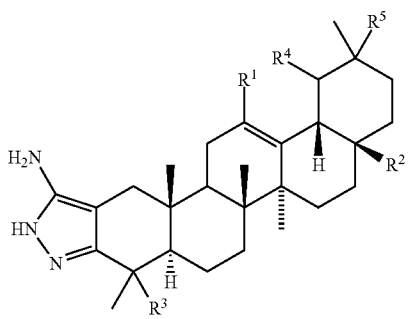

wherein $R^1$ is selected from the group consisting of pyrrolyl, pyrazolyl, imidazolyl, oxazolyl, isoxazolyl, oxadiazolyl, thiazolyl, isothiazolyl, thienyl, furanyl, furazanyl, pyridinyl, pyrimidinyl, pyridazinyl, indolyl, 3H-indolyl, isoindolyl, indolinyl, indolizinyl, indazolyl, dihydroindolyl, tetrahydroindolyl, purinyl, pyrazinyl, quinolinyl, isoquinolinyl, tetrahydroisoquinolinyl, quinoxalinyl, quinazolinyl, cinnolinyl, pteridinyl, benzimidazolyl, benzopyranyl, benzoxazolyl, benzisoxazolyl, benzofuranyl, isobenzofuranyl, benzothiazolyl, benzisothiazolyl, benzothienyl, furopyridinyl, phthalazinyl, napthyridinyl, pyrazolopyridyl, pyrazolopyrimidinyl, pyrrolopyridinyl, and tetrahydropyrrolopyridinyl optionally substituted from moieties selected from the group consisting of lower alkyl, halide, lower haloalkyl, hydroxyl, amino, lower aminoalkyl, lower hydroxyalkyl, nitrile, lower alkyl nitrile, lower alkyl ethers, lower alkoxy, lower alkoxyalkyl, lower alkoxycarbonyl, lower alkylcarbonylamino, and thioalkyl;

wherein $R^2$ is selected from the group consisting of amide, hydroxyamide, methylamide, —$CH_2N(CH_3)_2$, —$CH_2NR^6R^7$,

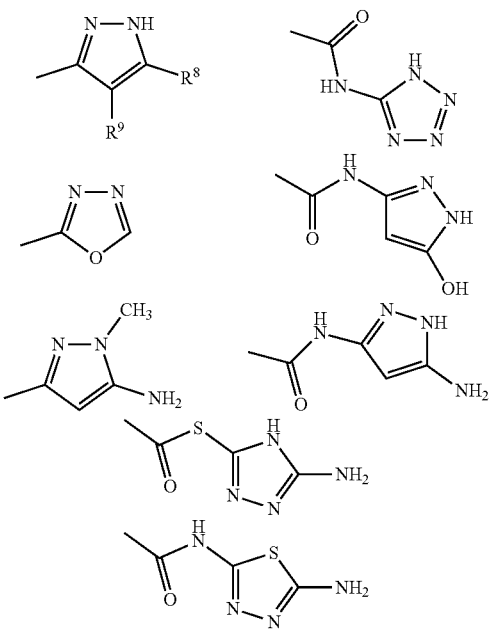

-continued

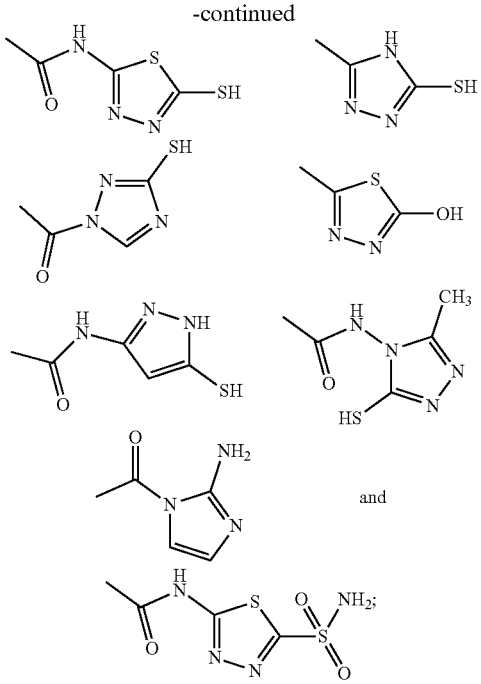

wherein $R^3$ is selected from the group consisting of hydrogen and methyl; wherein one of $R^4$ and $R^5$ is hydrogen and the other is methyl; wherein $R^6$ and $R^7$ are independently selected from the group consisting of hydrogen, methyl, ethyl, propyl, isopropyl, and butyl; wherein $R^8$ is selected from the group consisting of hydroxyl, amino, $-N(CH_3)_2$, and $-NHCH_3$; and wherein $R^9$ is selected from the group consisting of hydrogen, halide, lower alkyl, lower alkenyl, lower alkynyl, morpholinyl, piperazinyl, lower alkyl piperazinyl, heterocycloalkyl, lower cycloalkyl, lower cycloalkenyl; and lower alkyl, lower alkenyl, and lower alkynyl optionally substituted with moieties selected from the group consisting of hydroxyl, amino, lower aminoalkyl, halide, lower alkyl, lower alkoxycarbonyl, lower alkylcarbonylamino, amide, hydroxyamide, $-CONHCH_3$, $-NHCONH_2$, $-SO_2NH_2$, $-SO_2CH_3$, $-NHCOCH_3$, $-NHCSNH_2$, and $-NHSO_2CH_3$; and salts thereof.

20. A compound as set forth in claim 1 wherein the compound corresponds to the following chemical structure:

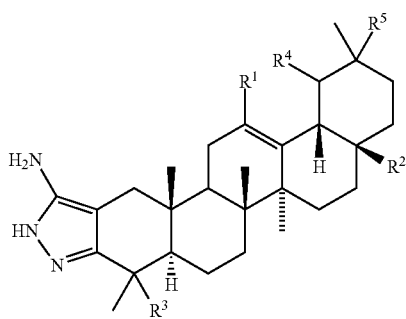

wherein $R^1$ is selected from the group consisting of pyrrolyl, pyrazolyl, imidazolyl, oxazolyl, isoxazolyl, oxadiazolyl, thiazolyl, isothiazolyl, thienyl, furanyl, furazanyl, pyridinyl, pyrimidinyl, pyridazinyl, indolyl, 3H-indolyl, isoindolyl, indolinyl, indolizinyl, indazolyl, dihydroindolyl, and tetrahydroindolyl optionally substituted from moieties selected from the group consisting of lower alkyl, halide, lower haloalkyl, hydroxyl, amino, lower aminoalkyl, lower hydroxyalkyl, nitrile, lower alkyl nitrile, lower alkyl ethers, lower alkoxy, lower alkoxyalkyl, lower alkoxycarbonyl, lower alkylcarbonylamino, and thioalkyl; wherein $R^2$ is selected from the group consisting of amide, hydroxyamide, methylamide, $-CH_2N(CH_3)_2$, $-CH_2NR^6R^7$,

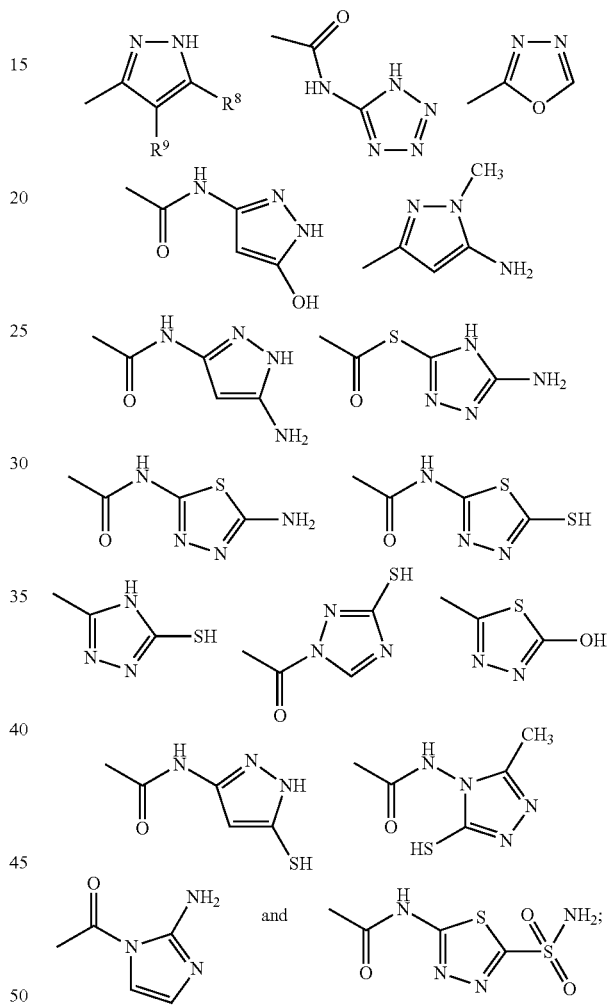

wherein $R^3$ is selected from the group consisting of hydrogen and methyl; wherein one of $R^4$ and $R^5$ is hydrogen and the other is methyl; wherein $R^6$ and $R^7$ are independently selected from the group consisting of hydrogen, methyl, ethyl, propyl, isopropyl, and butyl; wherein $R^8$ is selected from the group consisting of hydroxyl, amino, $-N(CH_3)_2$, and $-NHCH_3$; and wherein $R^9$ is selected from the group consisting of hydrogen, halide, lower alkyl, lower alkenyl, lower alkynyl, morpholinyl, piperazinyl, lower alkyl piperazinyl, heterocycloalkyl, lower cycloalkyl, lower cycloalkenyl; and lower alkyl, lower alkenyl, and lower alkynyl optionally substituted with moieties selected from the group consisting of hydroxyl, amino, lower aminoalkyl, halide, lower alkoxy, lower alkoxyalkyl, lower alkoxycarbonyl, lower alkylcarbonylamino, amide, hydroxyamide, —CONHCH₃, —NHCONH₂, —SO₂NH₂, —SO₂CH₃, —NHCOCH₃, —NHCSNH₂, and —NHSO₂CH₃; and salts thereof.

21. A compound as set forth in claim 1 wherein the compound corresponds to the following chemical structure:

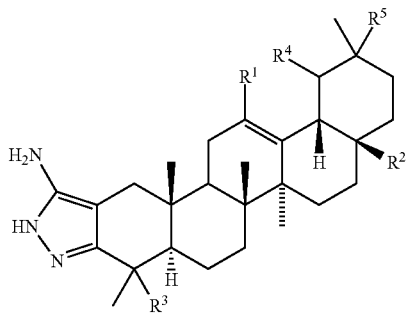

wherein R¹ is selected from the group consisting of pyrrolyl, pyrazolyl, imidazolyl, oxazolyl, isoxazolyl, oxadiazolyl, thiazolyl, isothiazolyl, thienyl, furanyl, furazanyl, pyridinyl, pyrimidinyl, pyridazinyl, indolyl, 3H-indolyl, isoindolyl, indolinyl, indolizinyl, indazolyl, dihydroindolyl, and tetrahydroindolyl; wherein R² is selected from the group consisting of amide, hydroxyamide, methylamide, —CH₂N(CH₃)₂, —CH₂NR⁶R⁷,

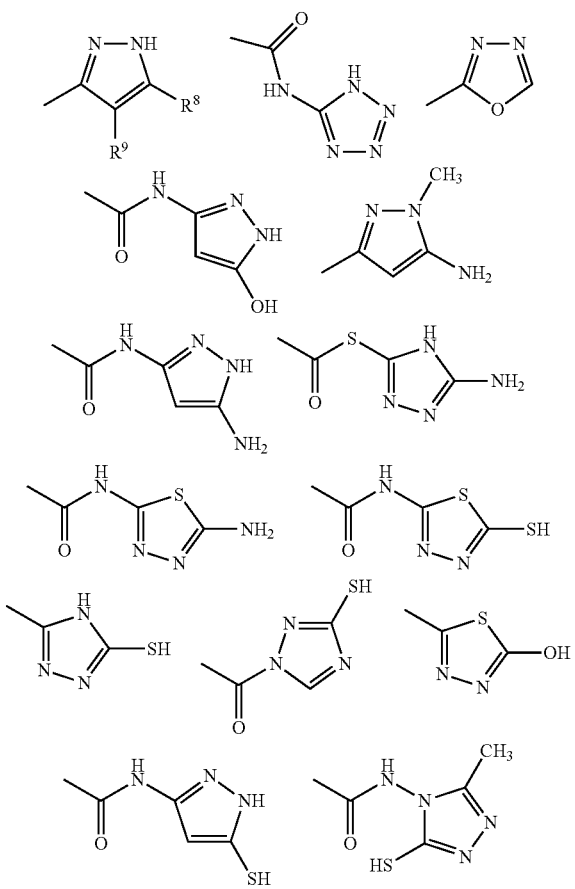

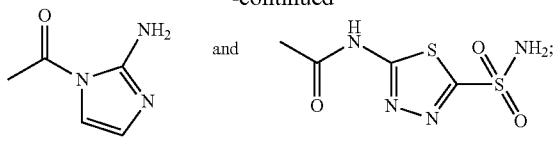

wherein R³ is selected from the group consisting of hydrogen and methyl; wherein one of R⁴ and R⁵ is hydrogen and the other is methyl; wherein R⁶ and R⁷ are independently selected from the group consisting of hydrogen, methyl, ethyl, propyl, isopropyl, and butyl; wherein R⁸ is selected from the group consisting of hydroxyl, amino, —N(CH₃)₂, and —NHCH₃; and wherein R⁹ is selected from the group consisting of hydrogen, halide, lower alkyl, lower alkenyl, lower alkynyl, morpholinyl, piperazinyl, lower alkyl piperazinyl, heterocycloalkyl, lower cycloalkyl, lower cycloalkenyl; and lower alkyl, lower alkenyl, and lower alkynyl optionally substituted with moieties selected from the group consisting of hydroxyl, amino, lower aminoalkyl, halide, lower alkoxy, lower alkoxyalkyl, lower alkoxycarbonyl, lower alkylcarbonylamino, amide, hydroxyamide, —CONHCH₃, —NHCONH₂, —SO₂NH₂, —SO₂CH₃, —NHCOCH₃, —NHCSNH₂, and —NHSO₂CH₃; and salts thereof.

22. A compound as set forth in claim 1 wherein the compound corresponds to the following chemical structure:

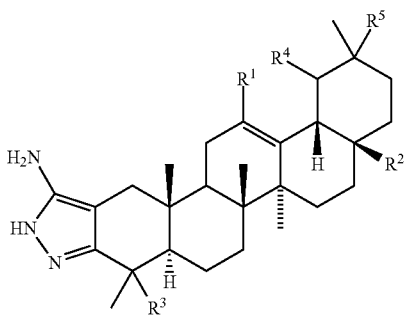

wherein R¹ is selected from the group consisting of hydrogen, pyrrolyl, pyrazolyl, imidazolyl, oxazolyl, isoxazolyl, oxadiazolyl, thiazolyl, isothiazolyl, thienyl, furanyl, furazanyl, pyridinyl, pyrimidinyl, pyridazinyl, indolyl, 3H-indolyl, isoindolyl, indolinyl, indolizinyl, indazolyl, dihydroindolyl, and tetrahydroindolyl; wherein R² is selected from the group consisting of

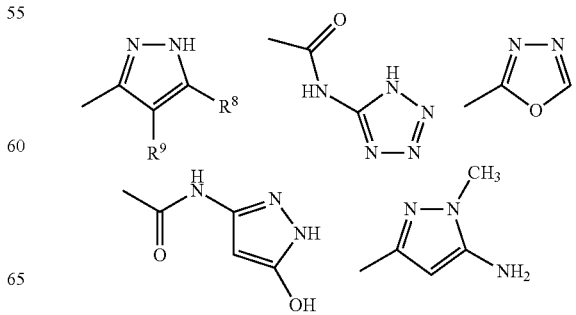

-continued

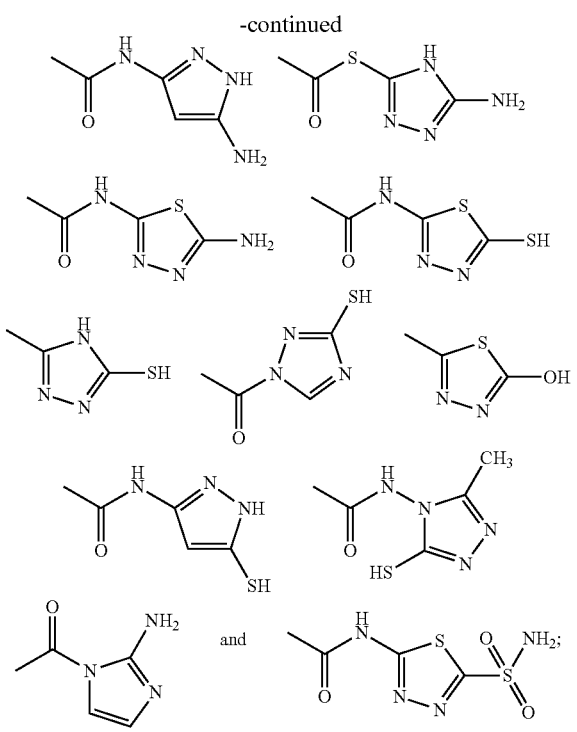

wherein R[1] is selected from the group consisting of hydrogen, methyl, halide, lower haloalkyl, nitrile, lower alkyl nitrile, lower alkyl, substituted lower alkyl, lower alkenyl, substituted lower alkenyl, lower alkynyl, substituted lower alkynyl, lower cycloalkyl, lower cycloalkenyl, aryl, substituted aryl, heteroaryl, and substituted heteroaryl; wherein R[3] is selected from the group consisting of hydrogen and methyl; wherein one of R[4] and R[5] is hydrogen and the other is methyl; wherein R[8] is selected from the group consisting of hydroxyl and amino; and wherein R[9] is selected from the group consisting of hydrogen, halide, lower alkyl, lower alkenyl, lower alkynyl, morpholinyl, piperazinyl, lower alkyl piperazinyl, heterocycloalkyl, lower cycloalkyl, lower cycloalkenyl; and lower alkyl, lower alkenyl, and lower alkynyl optionally substituted with moieties selected from the group consisting of hydroxyl, amino, lower aminoalkyl, halide, lower alkoxy, lower alkoxyalkyl, lower alkoxycarbonyl, lower alkylcarbonylamino, carboxyl, amide, hydroxyamide, —CONHCH$_3$, —NHCONH$_2$, —SO$_2$NH$_2$, —SO$_2$CH$_3$, —NHCOCH$_3$, —NHCSNH$_2$, and —NHSO$_2$CH$_3$; and salts thereof.

24. A compound as set forth in claim 1 wherein the compound corresponds to the following chemical structure:

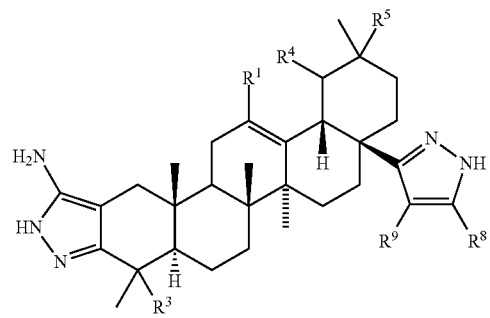

wherein R[1] is selected from the group consisting of hydrogen, halide, lower alkyl, substituted lower alkyl, lower alkenyl, substituted lower alkenyl, lower cycloalkenyl, aryl, substituted aryl, heteroaryl, and substituted heteroaryl; wherein R[3] is selected from the group consisting of hydrogen and methyl; wherein one of R[4] and R[5] is hydrogen and the other is methyl; wherein R[8] is selected from the group consisting of hydroxyl and amino; and wherein R[9] is selected from the group consisting of hydrogen, halide, lower alkyl, lower alkenyl, lower alkynyl, morpholinyl, piperazinyl, lower alkyl piperazinyl, heterocycloalkyl, lower cycloalkyl, lower cycloalkenyl; and lower alkyl, lower alkenyl, and lower alkynyl optionally substituted with moieties selected from the group consisting of hydroxyl, amino, lower aminoalkyl, halide, lower alkoxy, lower alkoxyalkyl, lower alkoxycarbonyl, lower alkylcarbonylamino, carboxyl, amide, hydroxyamide, —CONHCH$_3$, —NHCONH$_2$, —SO$_2$NH$_2$, —SO$_2$CH$_3$, —NHCOCH$_3$, —NHCSNH$_2$, and —NHSO$_2$CH$_3$; and salts thereof.

25. A compound as set forth in claim 1 wherein the compound corresponds to the following chemical structure:

23. A compound as set forth in claim 1 wherein the compound corresponds to the following chemical structure:

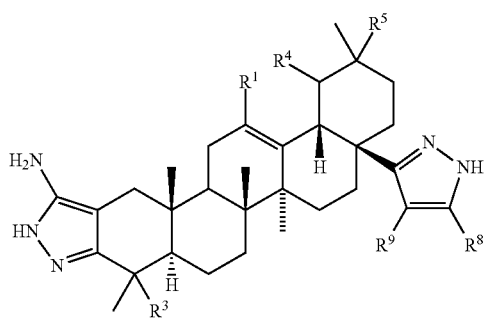

wherein R[1] is selected from the group consisting of hydrogen, methyl, halide, lower haloalkyl, nitrile, lower alkyl

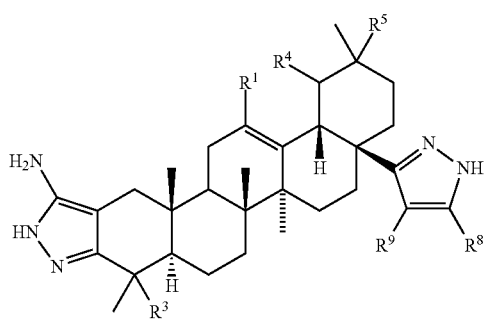

wherein R¹ is selected from the group consisting of lower alkenyl, substituted lower alkenyl, aryl, substituted aryl, heteroaryl and substituted heteroaryl; wherein R³ is selected from the group consisting of hydrogen and methyl; wherein one of R⁴ and R⁵ is hydrogen and the other is methyl; wherein R⁸ is selected from the group consisting of hydroxyl and amino; and wherein R⁹ is selected from the group consisting of hydrogen, halide, lower alkyl, lower alkenyl, lower alkynyl, morpholinyl, piperazinyl, lower alkyl piperazinyl, heterocycloalkyl, lower cycloalkyl, lower cycloalkenyl; and lower alkyl, lower alkenyl, and lower alkynyl optionally substituted with moieties selected from the group consisting of hydroxyl, amino, lower aminoalkyl, halide, lower alkoxy, lower alkoxyalkyl, lower alkoxycarbonyl, lower alkylcarbonylamino, carboxyl, amide, hydroxyamide, —CONHCH₃, —NHCONH₂, —SO₂NH₂, —SO₂CH₃, —NHCOCH₃, —NHCSNH₂, and —NHSO₂CH₃; and salts thereof.

26. A compound as set forth in claim 1 wherein the compound corresponds to the following chemical structure:

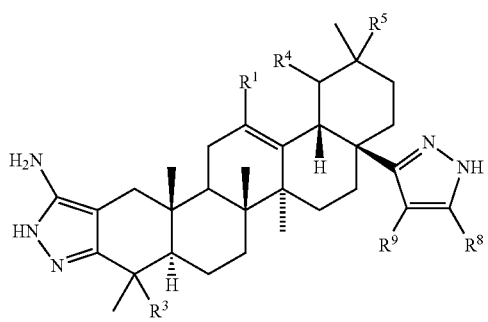

wherein R¹ is selected from the group consisting of heteroaryl and substituted heteroaryl;
wherein R³ is selected from the group consisting of hydrogen and methyl; wherein one of R⁴ and R⁵ is hydrogen and the other is methyl; wherein R⁸ is selected i from the group consisting of hydroxyl and amino; and wherein R⁹ is selected from the group consisting of hydrogen, halide, lower alkyl, lower alkenyl, lower alkynyl, morpholinyl, piperazinyl, lower alkyl piperazinyl, heterocycloalkyl, lower cycloalkyl, lower cycloalkenyl; and lower alkyl, lower alkenyl, and lower alkynyl optionally substituted with moieties selected from the group consisting of hydroxyl, amino, lower aminoalkyl, halide, lower alkoxy, lower alkoxyalkyl, lower alkoxycarbonyl, lower alkylcarbonylamino, carboxyl, amide, hydroxyamide, —CONHCH₃, —NHCONH₂, —SO₂NH₂, —SO₂CH₃, —NHCOCH₃, —NHCSNH₂, and —NHSO₂CH₃; and salts thereof.

27. A compound as set forth in claim 1 wherein the compound corresponds to the following chemical structure:

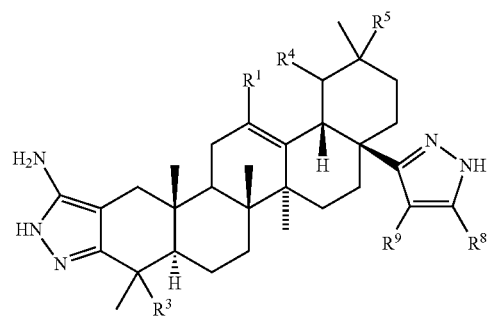

wherein R¹ is selected from the group consisting of substituted heteroaryl; wherein R³ is selected from the group consisting of hydrogen and methyl; wherein one of R⁴ and R⁵ is hydrogen and the other is methyl; wherein R⁸ is selected from the group consisting of hydroxyl and amino; and wherein R⁹ is selected from the group consisting of hydrogen, halide, lower alkyl, lower alkenyl, lower alkynyl, morpholinyl, piperazinyl, lower alkyl piperazinyl, heterocycloalkyl, lower cycloalkyl, lower cycloalkenyl; and lower alkyl, lower alkenyl, and lower alkynyl optionally substituted with moieties selected from the group consisting of hydroxyl, amino, lower aminoalkyl, halide, lower alkoxy, lower alkoxyalkyl, lower alkoxycarbonyl, lower alkylcarbonylamino, carboxyl, amide, hydroxyamide, —CONHCH₃, —NHCONH₂, —SO₂NH₂, —SO₂CH₃, —NHCOCH₃, —NHCSNH₂, and —NHSO₂CH₃; and salts thereof.

28. A compound as set forth in claim 1 wherein the compound corresponds to the following chemical structure:

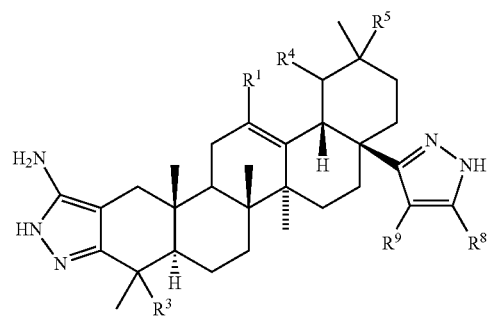

wherein R¹ is selected from the group consisting of heteroaryl optionally substituted with moieties selected from the group consisting of lower alkyl, halide, lower haloalkyl, hydroxyl, amino, lower aminoalkyl, lower hydroxyalkyl, nitrile, lower alkyl nitrile, lower alkoxy, lower alkoxyalkyl, lower alkoxycarbonyl, and lower alkylcarbonylamino; wherein R³ is selected from the group consisting of hydrogen and methyl; wherein one of R⁴ and R⁵ is hydrogen and the other is methyl; wherein R⁸ is selected from the group consisting of hydroxyl and amino; and wherein R⁹ is selected from the group consisting of hydrogen, halide, lower alkyl, lower alkenyl, lower alkynyl, morpholinyl, piperazinyl, lower alkyl piperazinyl, heterocycloalkyl, lower cycloalkyl, lower cycloalkenyl; and lower alkyl, lower alkenyl, and lower alkynyl optionally substituted with moieties selected from the group consisting of hydroxyl, amino, lower aminoalkyl, halide, lower alkoxy, lower alkoxyalkyl, lower alkoxycarbonyl, lower alkylcarbonylamino, carboxyl, amide, hydroxyamide, —CONHCH$_3$, —NHCONH$_2$, —SO$_2$NH$_2$, —SO$_2$CH$_3$, —NHCOCH$_3$, —NHCSNH$_2$, and —NHSO$_2$CH$_3$; and salts thereof.

29. A compound as set forth in claim 1 wherein the compound corresponds to the following chemical structure:

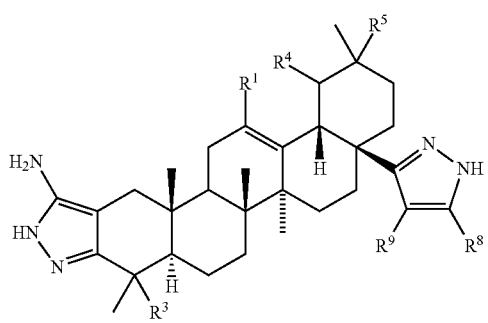

wherein R$^1$ is selected from the group consisting of pyrrolyl, pyrazolyl, imidazolyl, oxazolyl, isoxazolyl, oxadiazolyl, thiazolyl, isothiazolyl, thienyl, furanyl, furazanyl, pyridinyl, pyrimidinyl, pyridazinyl, indolyl, 3H-indolyl, isoindolyl, indolinyl, indolizinyl, indazolyl, dihydroindolyl, tetrahydroindolyl, purinyl, pyrazinyl, quinolinyl, isoquinolinyl, tetrahydroisoquinolinyl, quinoxalinyl, quinazolinyl, cinnolinyl, pteridinyl, benzimidazolyl, benzopyranyl, benzoxazolyl, benzisoxazolyl, benzofuranyl, isobenzofuranyl, benzothiazolyl, benzisothiazolyl, benzothienyl, furopyridinyl, phthalazinyl, napthyridinyl, pyrazolopyridyl, pyrazolopyrimidinyl, pyrrolopyridinyl, and tetrahydropyrrolopyridinyl optionally substituted from moieties selected from the group consisting of lower alkyl, halide, lower haloalkyl, hydroxyl, amino, lower aminoalkyl, lower hydroxyalkyl, nitrile, lower alkyl nitrile, lower alkoxy, lower alkoxyalkyl, lower alkoxycarbonyl, and lower alkylcarbonylamino;

wherein R$^3$ is selected from the group consisting of hydrogen and methyl; wherein one of R$^4$ and R$^5$ is hydrogen and the other is methyl; wherein R$^8$ is selected from the group consisting of hydroxyl and amino; and wherein R$^9$ is selected from the group consisting of hydrogen, fluorine, lower alkyl, lower alkenyl, lower alkynyl, morpholinyl, piperazinyl, lower alkyl piperazinyl, heterocycloalkyl, lower cycloalkyl, lower cycloalkenyl; and lower alkyl, lower alkenyl, and lower alkynyl optionally substituted with moieties selected from the group consisting of hydroxyl, amino, lower aminoalkyl, halide, lower alkoxy, lower alkoxyalkyl, lower alkoxycarbonyl, lower alkylcarbonylamino, carboxyl, amide, hydroxyamide, —CONHCH$_3$, —NHCONH$_2$, —SO$_2$NH$_2$, —SO$_2$CH$_3$, —NHCOCH$_3$, —NHCSNH$_2$, and —NHSO$_2$CH$_3$; and salts thereof.

30. A compound as set forth in claim 1 wherein the compound corresponds to the following chemical structure:

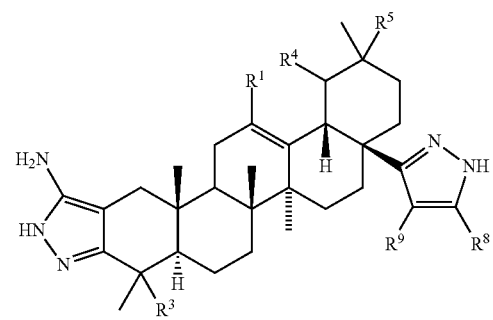

wherein R$^1$ is selected from the group consisting of pyrrolyl, pyrazolyl, imidazolyl, oxazolyl, isoxazolyl, oxadiazolyl, thiazolyl, isothiazolyl, furanyl, pyridinyl, pyrimidinyl, pyridazinyl, indolyl, 3H-indolyl, isoindolyl, indolinyl, indolizinyl, indazolyl, dihydroindolyl, and tetrahydroindolyl optionally substituted from moieties selected from the group consisting of lower alkyl, halide, lower haloalkyl, hydroxyl, amino, lower aminoalkyl, lower hydroxyalkyl, nitrile, lower alkyl nitrile, lower alkoxy, lower alkoxyalkyl, lower alkoxycarbonyl, and lower alkylcarbonylamino;

wherein R$^3$ is selected from the group consisting of hydrogen and methyl; wherein one of R$^4$ and R$^5$ is hydrogen and the other is methyl; wherein R$^8$ is selected from the group consisting of hydroxyl and amino; and wherein R$^9$ is selected from the group consisting of hydrogen, fluorine, lower alkyl, lower alkenyl, lower alkynyl, morpholinyl, piperazinyl, lower alkyl piperazinyl, heterocycloalkyl, lower cycloalkyl, lower cycloalkenyl; and lower alkyl, lower alkenyl, and lower alkynyl optionally substituted with moieties selected from the group consisting of hydroxyl, amino, lower aminoalkyl, halide, lower alkoxy, lower alkoxyalkyl, lower alkoxycarbonyl, lower alkylcarbonylamino, carboxyl, amide, hydroxyamide, —CONHCH$_3$, —NHCONH$_2$, —SO$_2$NH$_2$, —SO$_2$CH$_3$, —NHCOCH$_3$, —NHCSNH$_2$, and —NHSO$_2$CH$_3$; and salts thereof.

31. A compound as set forth in claim 1 wherein the compound corresponds to the following chemical structure:

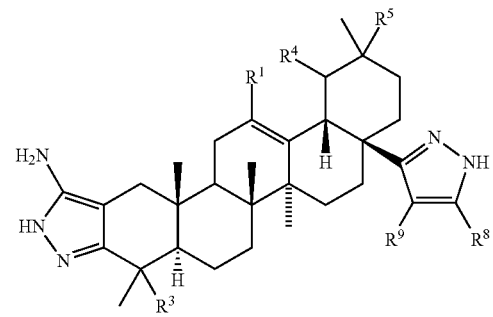

wherein R$^1$ is selected from the group consisting of pyrrolyl, pyrazolyl, imidazolyl, oxazolyl, isoxazolyl, oxadiazolyl, thiazolyl, isothiazolyl, furanyl, pyridinyl, pyrimidinyl, pyridazinyl, indolyl, 3H-indolyl, isoindolyl, indolinyl, indolizinyl, indazolyl, dihydroindolyl, and tetrahydroindolyl; wherein R$^3$ is selected from the group consisting of hydrogen and methyl; wherein one of R$^4$ and R$^5$ is hydrogen and the other is methyl; wherein R$^8$ is selected from the group consisting of hydroxyl and amino; and wherein R⁹ is selected from the group consisting of hydrogen, fluorine, lower alkyl, lower alkenyl, lower alkynyl, morpholinyl, piperazinyl, lower alkyl piperazinyl, heterocycloalkyl, lower cycloalkyl, lower cycloalkenyl; and lower alkyl, lower alkenyl, and lower alkynyl optionally substituted with moieties selected from the group consisting of hydroxyl, amino, lower aminoalkyl, halide, lower alkoxy, lower alkoxyalkyl, lower alkoxycarbonyl, lower alkylcarbonylamino, carboxyl, amide, hydroxyamide, —CONHCH₃, —NHCONH₂, —SO₂NH₂, —SO₂CH₃, —NHCOCH₃, —NHCSNH₂, and —NHSO₂CH₃; and salts thereof.

32. A compound as set forth in claim 1 wherein the compound corresponds to the following chemical structure:

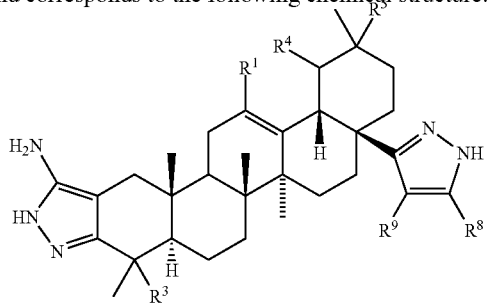

wherein R¹ is selected from the group consisting of hydrogen, pyrrolyl, pyrazolyl, imidazolyl, oxazolyl, isoxazolyl, oxadiazolyl, thiazolyl, isothiazolyl, furanyl, pyridinyl, pyrimidinyl, pyridazinyl, indolyl, 3H-indolyl, isoindolyl, indolinyl, indolizinyl, indazolyl, dihydroindolyl, and tetrahydroindolyl; wherein R³ is selected from the group consisting of hydrogen and methyl; wherein one of R⁴ and R⁵ is hydrogen and the other is methyl; wherein R⁸ is selected from the group consisting of hydroxyl and amino; and wherein R⁹ is selected from the group consisting of hydrogen, fluorine, lower alkyl, lower alkenyl, lower alkynyl, morpholinyl, piperazinyl, lower alkyl piperazinyl, heterocycloalkyl, lower cycloalkyl, lower cycloalkenyl; and lower alkyl, lower alkenyl, and lower alkynyl optionally substituted with moieties selected from the group consisting of hydroxyl, amino, lower aminoalkyl, halide, lower alkoxy, lower alkoxyalkyl, lower alkoxycarbonyl, lower alkylcarbonylamino, carboxyl, amide, hydroxyamide, —CONHCH₃, —NHCONH₂, —SO₂NH₂, —SO₂CH₃, —NHCOCH₃, —NHCSNH₂, and —NHSO₂CH₃; and salts thereof.

33. A compound as set forth in claim 1 wherein the compound corresponds to the following chemical structure:

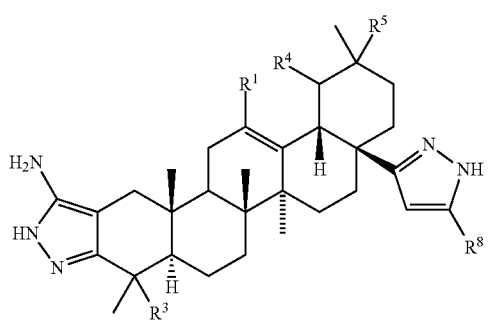

wherein R¹ is selected from the group consisting of hydrogen, methyl, halide, lower haloalkyl, nitrile, lower alkyl nitrile, lower alkyl, substituted lower alkyl, lower alkenyl, substituted lower alkenyl, lower alkynyl, substituted lower alkynyl, lower cycloalkyl, lower cycloalkenyl, aryl, substituted aryl, heteroaryl, and substituted heteroaryl; wherein R³ is selected from the group consisting of hydrogen and methyl; wherein one of R⁴ and R⁵ is hydrogen and the other is methyl; and wherein R⁸ is selected from the group consisting of hydroxyl and amino; and salts thereof.

34. A compound as set forth in claim 1 wherein the compound corresponds to the following chemical structure:

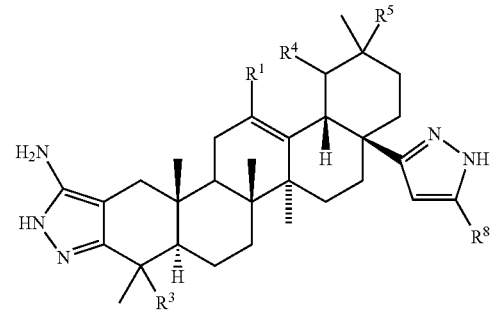

wherein R¹ is selected from the group consisting of hydrogen, halide, lower alkyl, substituted lower alkyl, lower alkenyl, substituted lower alkenyl, lower cycloalkenyl, aryl, substituted aryl, heteroaryl, and substituted heteroaryl; wherein R³ is selected from the group consisting of hydrogen and methyl; wherein one of R⁴ and R⁵ is hydrogen and the other is methyl; and wherein R⁸ is selected from the group consisting of hydroxyl and amino; and salts thereof.

35. A compound as set forth in claim 1 wherein the compound corresponds to the following chemical structure:

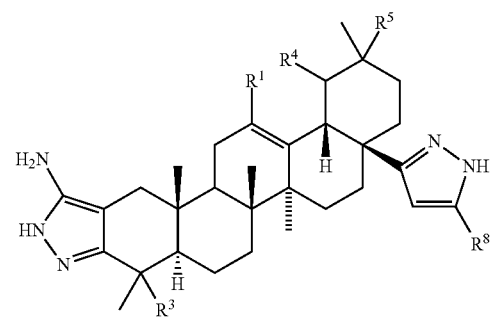

wherein R¹ is selected from the group consisting of lower alkenyl, substituted lower alkenyl, aryl, substituted aryl, heteroaryl and substituted heteroaryl; wherein R³ is selected from the group consisting of hydrogen and methyl; wherein one of R⁴ and R⁵ is hydrogen and the other is methyl; and wherein R⁸ is selected from the group consisting of hydroxyl and amino; and salts thereof.

36. A compound as set forth in claim 1 wherein the compound corresponds to the following chemical structure:

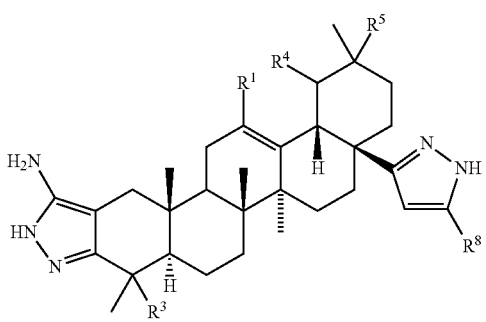

wherein R¹ is selected from the group consisting of aryl, heteroaryl and substituted heteroaryl; wherein R³ is selected from the group consisting of hydrogen and methyl; wherein one of R⁴ and R⁵ is hydrogen and the other is methyl; and wherein R⁸ is selected from the group consisting of hydroxyl and amino; and salts thereof.

37. A compound as set forth in claim 1 wherein the compound corresponds to the following chemical structure:

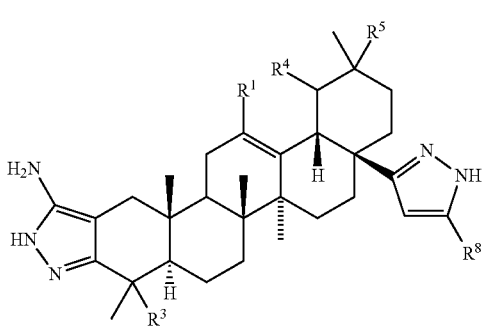

wherein R¹ is selected from the group consisting of heteroaryl and substituted heteroaryl;
wherein R³ is selected from the group consisting of hydrogen and methyl;
wherein one of R⁴ and R⁵ is hydrogen and the other is methyl; and wherein R⁸ is selected from the group consisting of hydroxyl and amino; and salts thereof.

38. A compound as set forth in claim 1 wherein the compound corresponds to the following chemical structure:

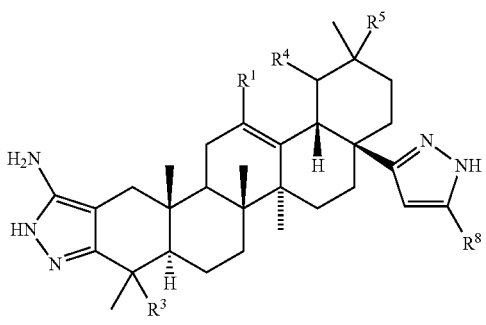

wherein R¹ is selected from the group consisting of heteroaryl optionally substituted with moieties selected from the group consisting of lower alkyl, halide, lower haloalkyl, hydroxyl, amino, lower aminoalkyl, lower hydroxyalkyl, nitrile, lower alkyl nitrile, lower alkoxy, lower alkoxyalkyl, lower alkoxycarbonyl, and lower alkylcarbonylamino; wherein R³ is selected from the group consisting of hydrogen and methyl; wherein one of R⁴ and R⁵ is hydrogen and the other is methyl; and wherein R⁸ is selected from the group consisting of hydroxyl and amino; and salts thereof.

39. A compound as set forth in claim 1 wherein the compound corresponds to the following chemical structure:

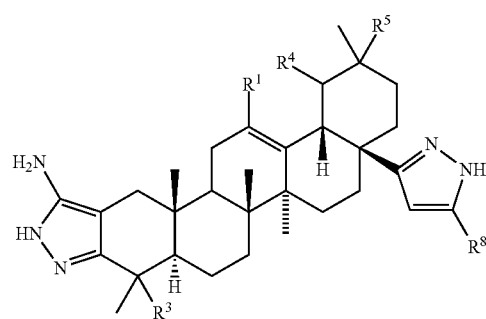

wherein R¹ is selected from the group consisting of pyrrolyl, pyrazolyl, imidazolyl, oxazolyl, isoxazolyl, oxadiazolyl, thiazolyl, isothiazolyl, thienyl, furanyl, furazanyl, pyridinyl, pyrimidinyl, pyridazinyl, indolyl, 3H-indolyl, isoindolyl, indolinyl, indolizinyl, indazolyl, dihydroindolyl, tetrahydroindolyl, purinyl, pyrazinyl, quinolinyl, isoquinolinyl, tetrahydroisoquinolinyl, quinoxalinyl, quinazolinyl, cinnolinyl, pteridinyl, benzimidazolyl, benzopyranyl, benzoxazolyl, benzisoxazolyl, benzofuranyl, isobenzofuranyl, benzothiazolyl, benzisothiazolyl, benzothienyl, furopyridinyl, phthalazinyl, napthyridinyl, pyrazolopyridyl, pyrazolopyrimidinyl, pyrrolopyridinyl, and tetrahydropyrrolopyridinyl optionally substituted from moieties selected from the group consisting of lower alkyl, halide, lower haloalkyl, hydroxyl, amino, lower aminoalkyl, lower hydroxyalkyl, nitrile, lower alkyl nitrile, lower alkyl ethers, lower alkoxy, lower alkoxyalkyl, lower alkoxycarbonyl, lower alkylcarbonylamino, and thioalkyl; wherein R³ is selected from the group consisting of hydrogen and methyl; wherein one of R⁴ and R⁵ is hydrogen and the other is methyl; and wherein R⁸ is selected from the group consisting of hydroxyl and amino; and salts thereof.

40. A compound as set forth in claim 1 wherein the compound corresponds to the following chemical structure:

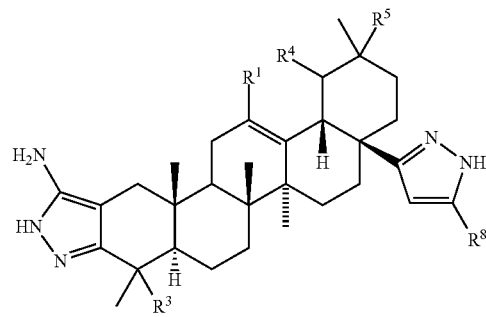

wherein R¹ is selected from the group consisting of pyrrolyl, pyrazolyl, imidazolyl, oxazolyl, isoxazolyl, oxadiazolyl, thiazolyl, isothiazolyl, furanyl, pyridinyl, pyrimidinyl, pyridazinyl, indolyl, 3H-indolyl, isoindolyl, indolinyl, indolizinyl, indazolyl, dihydroindolyl, and tetrahydroindolyl optionally substituted from moieties selected from the group consisting of lower alkyl, halide, lower haloalkyl, hydroxyl, amino, lower aminoalkyl, lower hydroxyalkyl, nitrile, lower alkyl nitrile, lower alkyl ethers, lower alkoxy, lower alkoxyalkyl, lower alkoxycarbonyl, lower alkylcarbonylamino, and thioalkyl; wherein R³ is selected from the group consisting of hydrogen and methyl; wherein one of R⁴ and R⁵ is hydrogen and the other is methyl; and wherein R⁸ is selected from the group consisting of hydroxyl and amino; and salts thereof.

41. A compound as set forth in claim 1 wherein the compound corresponds to the following chemical structure:

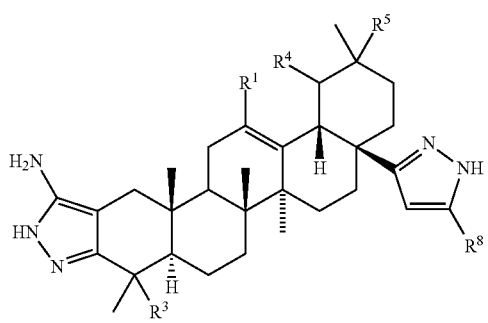

wherein R¹ is selected from the group consisting of pyrrolyl, pyrazolyl, imidazolyl, oxazolyl, isoxazolyl, oxadiazolyl, thiazolyl, isothiazolyl, furanyl, pyridinyl, pyrimidinyl, pyridazinyl, indolyl, 3H-indolyl, isoindolyl, indolinyl, indolizinyl, indazolyl, dihydroindolyl, and tetrahydroindolyl; wherein R³ is selected from the group consisting of hydrogen and methyl; wherein one of R⁴ and R⁵ is hydrogen and the other is methyl; and wherein R⁸ is selected from the group consisting of hydroxyl and amino; and salts thereof.

42. A compound as set forth in claim 1 wherein the compound corresponds to the following chemical structure:

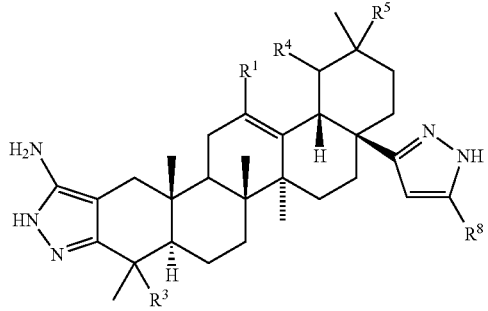

wherein R¹ is selected from the group consisting of hydrogen, pyrrolyl, pyrazolyl, imidazolyl, oxazolyl, isoxazolyl, oxadiazolyl, thiazolyl, isothiazolyl, furanyl, pyridinyl, pyrimidinyl, pyridazinyl, indolyl, 3H-indolyl, isoindolyl, indolinyl, indolizinyl, indazolyl, dihydroindolyl, and tetrahydroindolyl; wherein R³ is selected from the group consisting of hydrogen and methyl; wherein one of R⁴ and R⁵ is hydrogen and the other is methyl; and wherein R⁸ is selected from the group consisting of hydroxyl and amino; and salts thereof.

43. A compound as set forth in claim 1 wherein the compound corresponds to the following chemical structure:

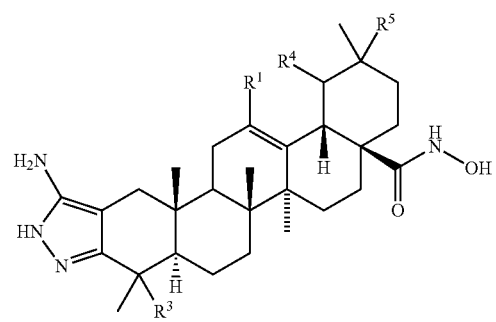

wherein R¹ is selected from the group consisting of hydrogen, methyl, halide, lower alkyl, substituted lower alkyl, lower alkenyl, substituted lower alkenyl, aryl, substituted aryl, heteroaryl, and substituted heteroaryl; wherein R³ is selected from the group consisting of hydrogen and methyl; wherein one of R⁴ and R⁵ is hydrogen and the other is methyl; and wherein R⁸ is selected from the group consisting of hydroxyl and amino; and salts thereof.

44. A compound as set forth in claim 1 wherein the compound corresponds to the following chemical structure:

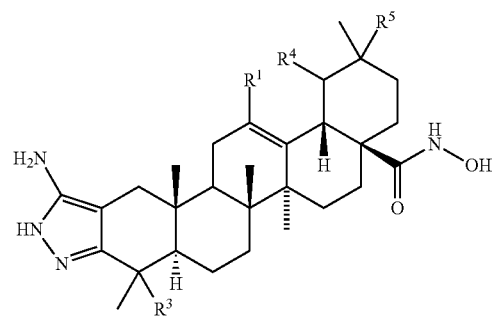

wherein R¹ is selected from the group consisting of lower alkyl, lower alkenyl, halide, aryl, substituted aryl, heteroaryl, and substituted heteroaryl; wherein R³ is selected from the group consisting of hydrogen and methyl; wherein one of R⁴ and R⁵ is hydrogen and the other is methyl; and wherein R⁸ is selected from the group consisting of hydroxyl and amino; and salts thereof.

45. A compound as set forth in claim 1 wherein the compound corresponds to the following chemical structure:

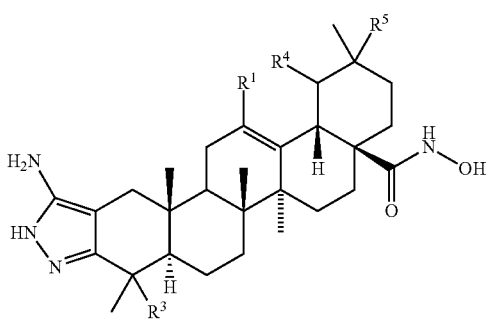

wherein R¹ is selected from the group consisting of heteraryl and substituted heteroaryl; wherein R³ is selected from the group consisting of hydrogen and methyl; wherein one of R⁴ and R⁵ is hydrogen and the other is methyl; and wherein R⁸ is selected from the group consisting of hydroxyl and amino; and salts thereof.

46. A compound as set forth in claim 1 wherein the compound corresponds to the following chemical structure:

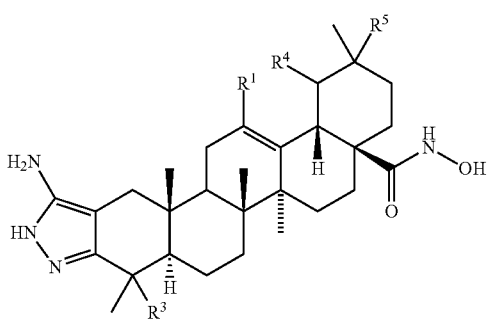

wherein R¹ is selected from the group consisting of hydrogen, pyrrolyl, pyrazolyl, imidazolyl, oxazolyl, isoxazolyl, oxadiazolyl, thiazolyl, isothiazolyl, furanyl, pyridinyl, pyrimidinyl, pyridazinyl, indolyl, 3H-indolyl, isoindolyl, indolinyl, indolizinyl, indazolyl, dihydroindolyl, and tetrahydroindolyl; wherein R³ is selected from the group consisting of hydrogen and methyl; wherein one of R⁴ and R⁵ is hydrogen and the other is methyl; and wherein R⁸ is selected from the group consisting of hydroxyl and amino; and salts thereof.

47. A method for reducing the formation or growth of a biofilm comprising contacting the biofilm with an effective amount of a compound or composition comprising a compound corresponding to the following chemical structure:

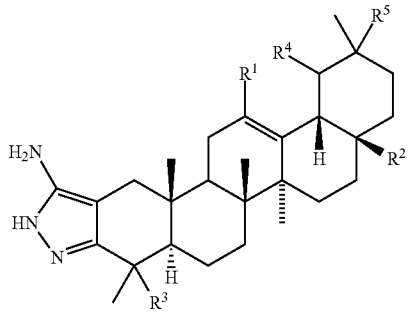

wherein R¹ is selected from the group consisting of hydrogen, methyl, halide, lower haloalkyl, nitrile, lower alkyl nitrile, lower alkyl, substituted lower alkyl, lower alkenyl, substituted lower alkenyl, lower alkynyl, substituted lower alkynyl, lower cycloalkyl, lower cycloalkenyl, aryl, substituted aryl, heteroaryl, and substituted heteroaryl; wherein R² is selected from the group consisting of carboxyl, amide, hydroxyamide, methylamide, —CH₂N(CH₃)₂, —CH₂NR⁶R⁷,

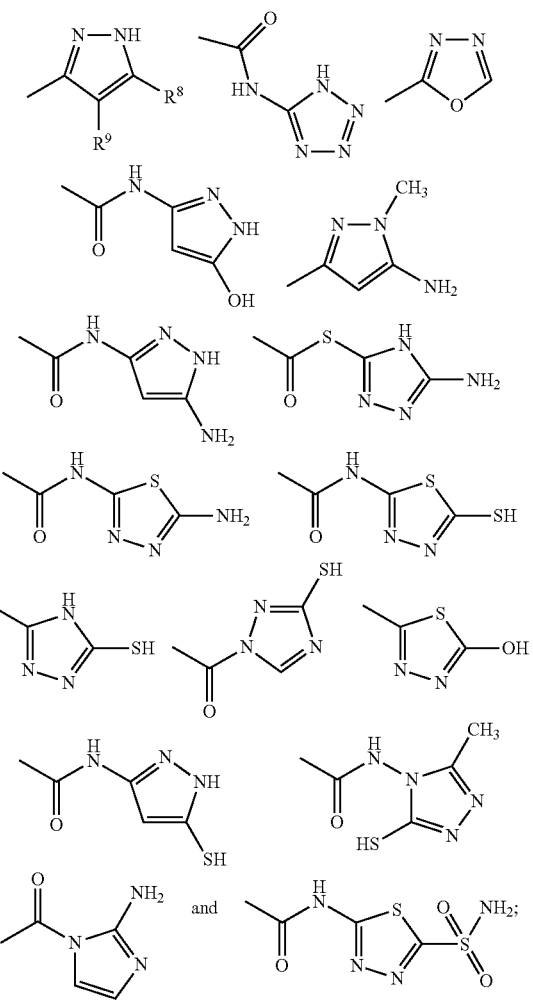

wherein R³ is selected from the group consisting of hydrogen and methyl; wherein one of R⁴ and R⁵ is hydrogen and the other is methyl; wherein R⁶ and R⁷ are independently selected from the group consisting of hydrogen, methyl, ethyl, propyl, isopropyl, and butyl; wherein R⁸ is selected from the group consisting of hydroxyl, amino, —N(CH₃)₂, and —NHCH₃; and wherein R⁹ is selected from the group consisting of hydrogen, halide, lower alkyl, lower alkenyl, lower alkynyl, morpholinyl, piperazinyl, lower alkyl piperazinyl, heterocycloalkyl, lower cycloalkyl, lower cycloalkenyl; and lower alkyl, lower alkenyl, and lower alkynyl substituted with moieties selected from the group consisting of hydroxyl, amino, lower aminoalkyl, halide, lower alkoxy, lower alkoxyalkyl, lower alkoxycarbonyl, lower alkylcarbonylamino, carboxyl, amide, hydroxyamide, —CON- HCH$_3$, —NHCONH$_2$, —SO$_2$NH$_2$, —SO$_2$CH$_3$, —NH-COCH$_3$, —NHCSNH$_2$, and —NHSO$_2$CH$_3$; and salts thereof.

48. A method for reducing the formation or growth of a biofilm as set forth in claim 47 wherein the compound corresponds to the following chemical structure:

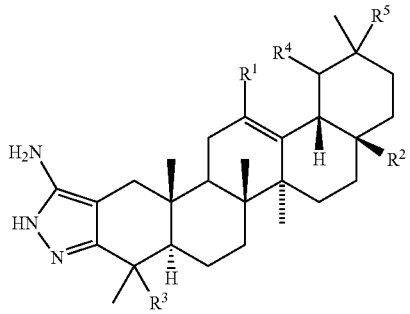

wherein R$^1$ is selected from the group consisting of halide, lower haloalkyl, nitrile, lower alkyl nitrile, lower alkyl, substituted lower alkyl, lower alkenyl, substituted lower alkenyl, lower alkynyl, substituted lower alkynyl, lower cycloalkenyl, aryl, substituted aryl, heteroaryl, and substituted heteroaryl; wherein R$^2$ is selected from the group consisting of carboxyl, amide, hydroxyamide, methylamide, —CH$_2$N(CH$_3$)$_2$, —CH$_2$NR$^6$R$^7$,

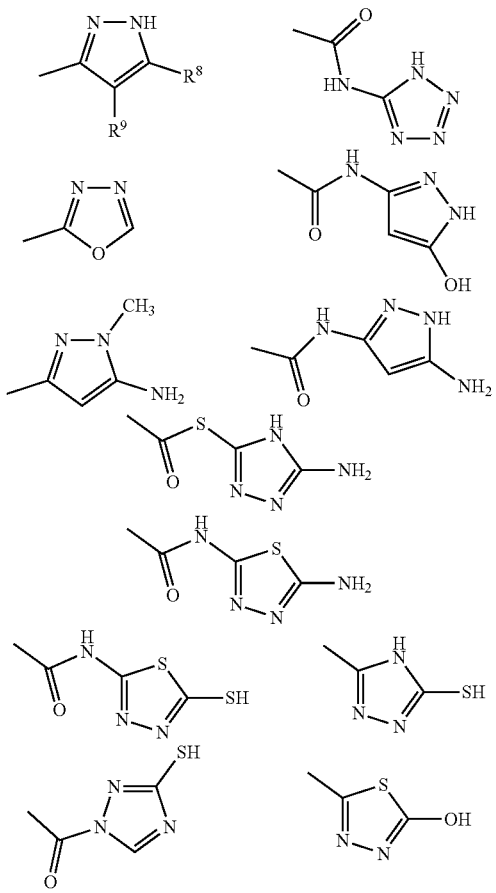

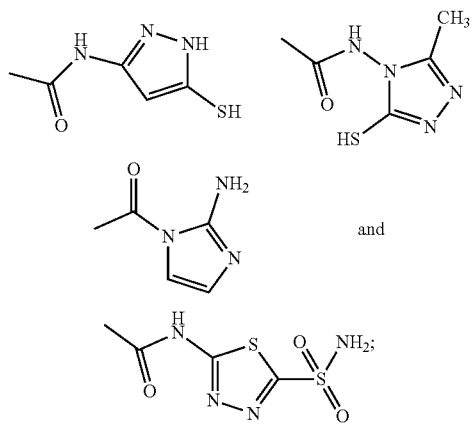

wherein R$^3$ is selected from the group consisting of hydrogen and methyl; wherein one of R$^4$ and R$^5$ is hydrogen and the other is methyl; wherein R$^6$ and R$^7$ are independently selected from the group consisting of hydrogen, methyl, ethyl, propyl, isopropyl, and butyl; wherein R$^8$ is selected from the group consisting of hydroxyl, amino, —N(CH$_3$)$_2$, and —NHCH$_3$; and wherein R$^9$ is selected from the group consisting of hydrogen, halide, lower alkyl, lower alkenyl, lower alkynyl, morpholinyl, piperazinyl, lower alkyl piperazinyl, heterocycloalkyl, lower cycloalkyl, lower cycloalkenyl; and lower alkyl, lower alkenyl, and lower alkynyl substituted with moieties selected from the group consisting of hydroxyl, amino, lower aminoalkyl, halide, lower alkoxy, lower alkoxyalkyl, lower alkoxycarbonyl, lower alkylcarbonylamino, carboxyl, amide, hydroxyamide, —CONHCH$_3$, —NHCONH$_2$, —SO$_2$NH$_2$, —SO$_2$CH$_3$, —NHCOCH$_3$, —NHCSNH$_2$, and —NHSO$_2$CH$_3$; and salts thereof.

49. A method for reducing the formation or growth of a biofilm as set forth in claim 47 wherein the compound corresponds to the following chemical structure:

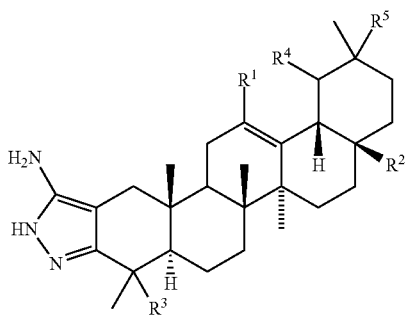

wherein R$^1$ is selected from the group consisting of hydrogen, methyl, halide, lower haloalkyl, nitrile, lower alkyl nitrile, lower alkyl, substituted lower alkyl, lower alkenyl, substituted lower alkenyl, lower alkynyl, substituted lower alkynyl, aryl, substituted aryl, heteroaryl, and substituted heteroaryl; wherein R$^2$ is selected from the group consisting of amide, hydroxyamide, methylamide, —CH$_2$N(CH$_3$)$_2$, —CH$_2$NR$^6$R$^7$,

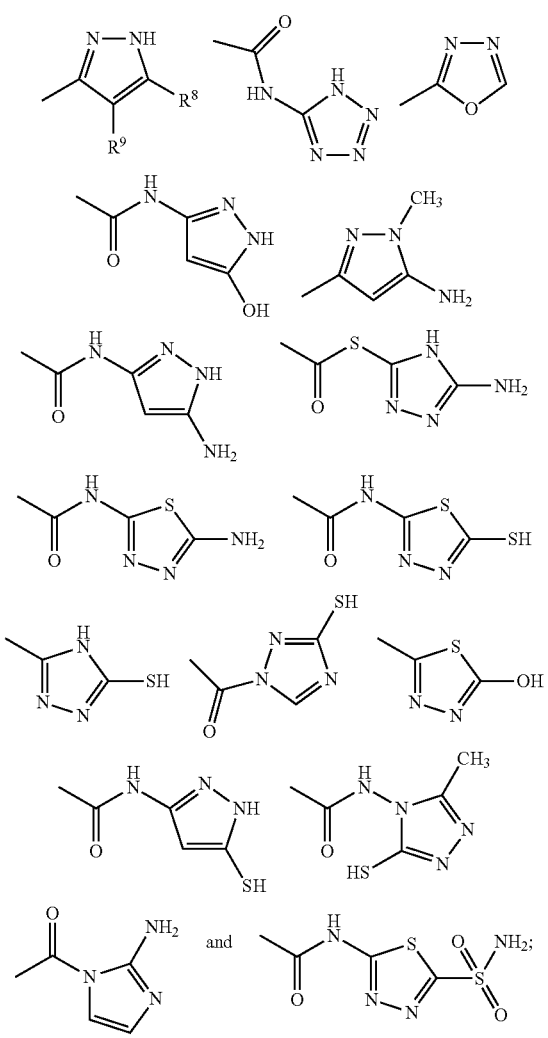

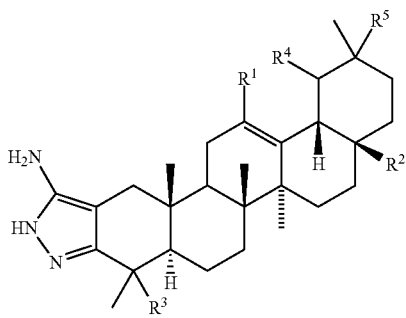

wherein R¹ is selected from the group consisting of hydrogen, methyl, halide, lower haloalkyl, nitrile, lower alkyl nitrile, lower alkyl, substituted lower alkyl, lower alkenyl, substituted lower alkenyl, lower alkynyl, substituted lower alkynyl, aryl, substituted aryl, heteroaryl, and substituted heteroaryl; wherein R² is selected from the group consisting of

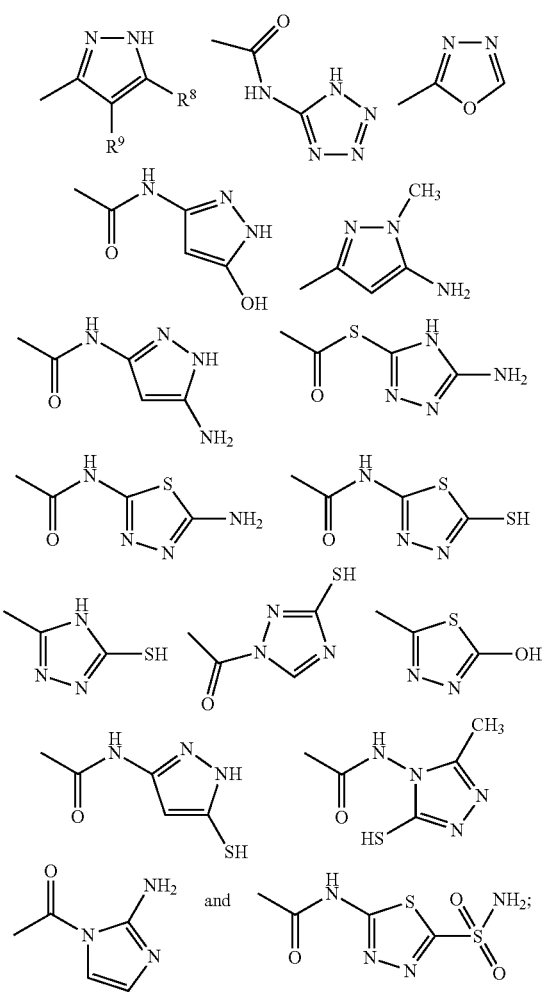

wherein R³ is selected from the group consisting of hydrogen and methyl; wherein one of R⁴ and R⁵ is hydrogen and the other is methyl; wherein R⁶ and R⁷ are independently selected from the group consisting of hydrogen, methyl, ethyl, propyl, isopropyl, and butyl; wherein R⁸ is selected from the group consisting of hydroxyl, amino, —N(CH₃)₂, and —NHCH₃; and wherein R⁹ is selected from the group consisting of hydrogen, halide, lower alkyl, lower alkenyl, lower alkynyl, morpholinyl, piperazinyl, lower alkyl piperazinyl, heterocycloalkyl, lower cycloalkyl, lower cycloalkenyl; and lower alkyl, lower alkenyl, and lower alkynyl substituted with moieties selected from the group consisting of hydroxyl, amino, lower aminoalkyl, halide, lower alkoxy, lower alkoxyalkyl, lower alkoxycarbonyl, lower alkylcarbonylamino, carboxyl, amide, hydroxyamide, —CONHCH₃, —NHCONH₂, —SO₂NH₂, —SO₂CH₃, —NHCOCH₃, —NHCSNH₂, and —NHSO₂CH₃; and salts thereof.

50. A method for reducing the formation or growth of a biofilm as set forth in claim 47 wherein the compound corresponds to the following chemical structure:

wherein R³ is selected from the group consisting of hydrogen and methyl; wherein one of R⁴ and R⁵ is hydrogen and the other is methyl; wherein R⁶ and R⁷ are independently selected from the group consisting of hydrogen, methyl, ethyl, propyl, isopropyl, and butyl; wherein R⁸ is selected from the group consisting of hydroxyl, amino, —N(CH₃)₂, and —NHCH₃; and wherein R⁹ is selected from the group consisting of hydrogen, halide, lower alkyl, lower alkenyl, lower alkynyl, morpholinyl, piperazinyl, lower alkyl piperazinyl, heterocycloalkyl, lower cycloalkyl, lower cycloalkenyl; and lower alkyl, lower alkenyl, and lower alkynyl substituted with moieties selected from the group consisting of hydroxyl, amino, lower aminoalkyl, halide, lower alkoxy, lower alkoxyalkyl, lower alkoxycarbonyl, lower alkylcarbonylamino, carboxyl, amide, hydroxyamide, —CONHCH₃, —NHCONH₂, —SO₂NH₂, —SO₂CH₃, —NHCOCH₃, —NHCSNH₂, and —NHSO₂CH₃; and salts thereof.

51. A method for reducing the formation or growth of a biofilm as set forth in claim 47 wherein the compound corresponds to the following chemical structure:

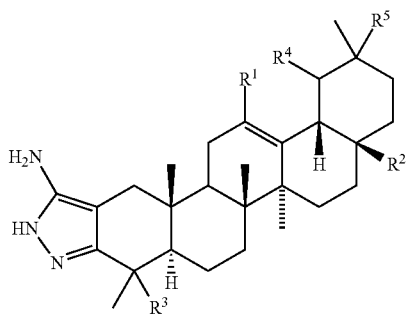

wherein R¹ is selected from the group consisting of halide, lower alkenyl, substituted lower alkenyl, substituted aryl, heteroaryl, and substituted heteroaryl; wherein R² is selected from the group consisting of carboxyl, amide, hydroxyamide, methylamide, —CH₂N(CH₃)₂, —CH₂NR⁶R⁷,

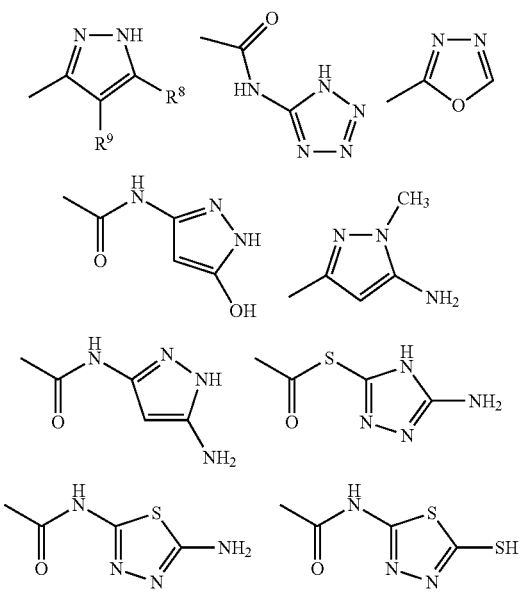

-continued

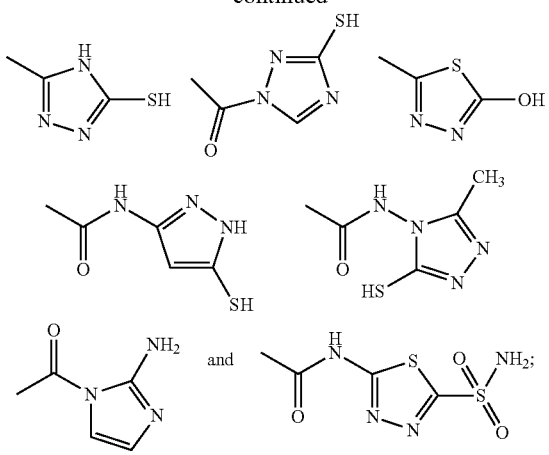

wherein R³ is selected from the group consisting of hydrogen and methyl; wherein one of R⁴ and R⁵ is hydrogen and the other is methyl; wherein R⁶ and R⁷ are independently selected from the group consisting of hydrogen, methyl, ethyl, propyl, isopropyl, and butyl; wherein R⁸ is selected from the group consisting of hydroxyl, amino, —N(CH₃)₂, and —NHCH₃; and wherein R⁹ is selected from the group consisting of hydrogen, halide, lower alkyl, lower alkenyl, lower alkynyl, morpholinyl, piperazinyl, lower alkyl piperazinyl, heterocycloalkyl, lower cycloalkyl, lower cycloalkenyl; and lower alkyl, lower alkenyl, and lower alkynyl substituted with moieties selected from the group consisting of hydroxyl, amino, lower aminoalkyl, halide, lower alkoxy, lower alkoxyalkyl, lower alkoxycarbonyl, lower alkylcarbonylamino, amide, hydroxyamide, —CONHCH₃, —NHCONH₂, —SO₂NH₂, —SO₂CH₃, —NHCOCH₃, —NHCSNH₂, and —NHSO₂CH₃; and salts thereof.

52. A method for reducing the formation or growth of a biofilm as set forth in claim 47 wherein the compound corresponds to the following chemical structure:

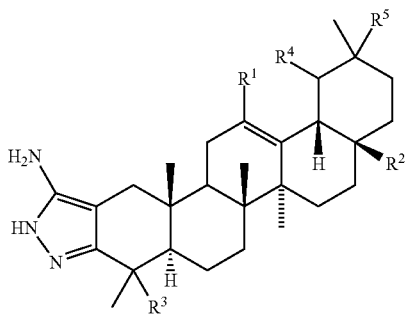

wherein R¹ is selected from the group consisting of heteroaryl and substituted heteroaryl; wherein R² is selected from the group consisting of carboxyl, amide, hydroxyamide, methylamide, —CH₂N(CH₃)₂, —CH₂NR⁶R⁷,

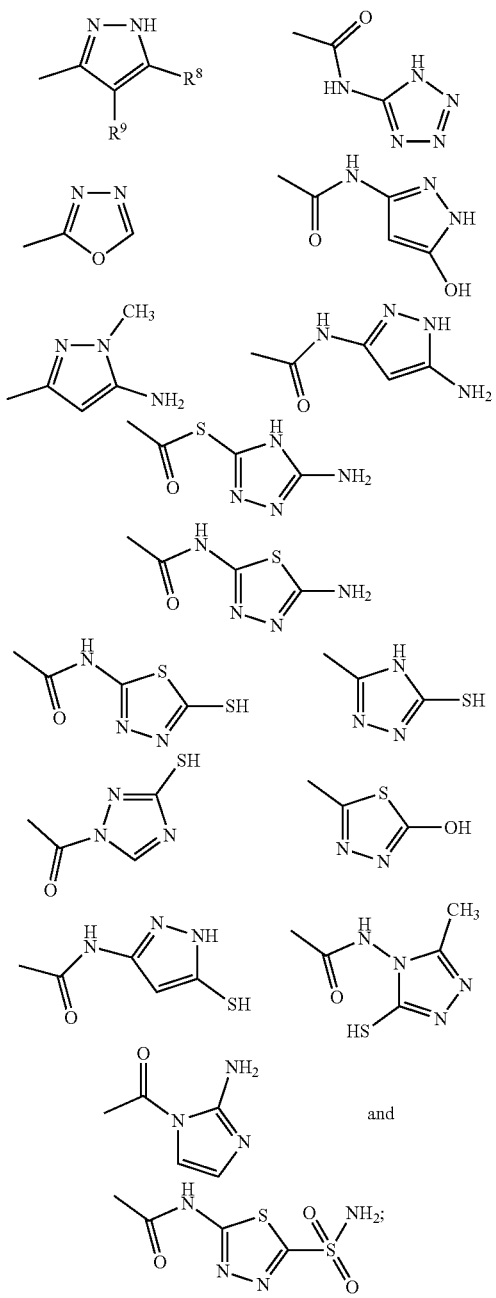

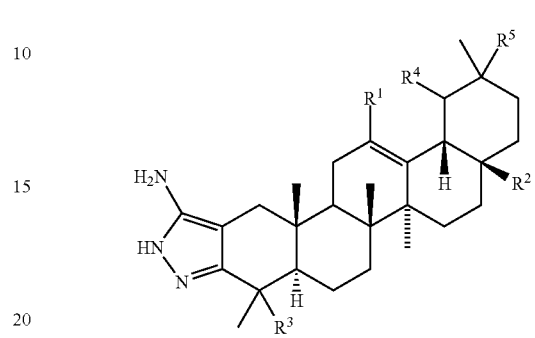

HCH$_3$, —NHCONH$_2$, —SO$_2$NH$_2$, —SO$_2$CH$_3$, —NH-COCH$_3$, —NHCSNH$_2$, and —NHSO$_2$CH$_3$; and salts thereof.

53. A method for reducing the formation or growth of a biofilm as set forth in claim 47 wherein the compound corresponds to the following chemical structure:

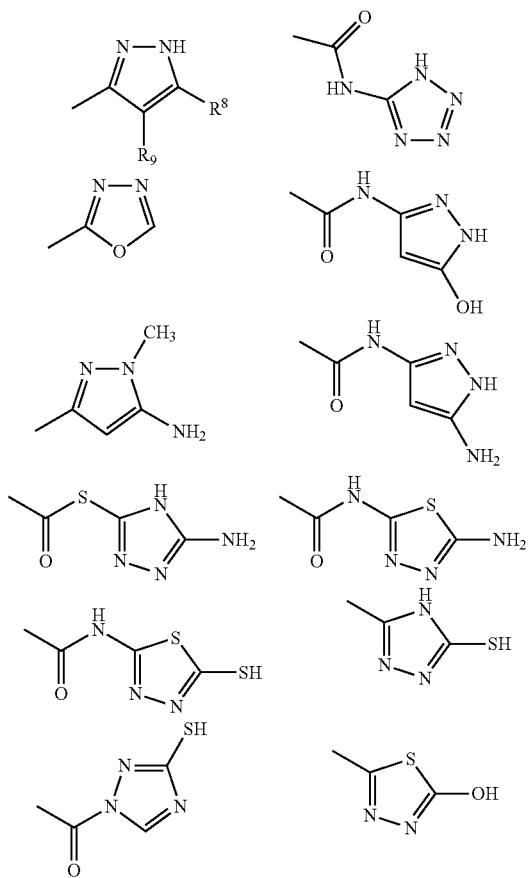

wherein R$^1$ is selected from the group consisting of heteroaryl optionally substituted with moieties selected from the group consisting of lower alkyl, halide, lower haloalkyl, hydroxyl, amino, lower aminoalkyl, nitrile, lower alkyl nitrile, lower alkyl ethers, lower alkoxy, lower alkoxyalkyl, lower alkoxycarbonyl, lower alkylcarbonylamino, and thioalkyl; wherein R$^2$ is selected from the group consisting of carboxyl, amide, hydroxyamide, methylamide, —CH$_2$N(CH$_3$)$_2$, —CH$_2$NR$^6$R$^7$, wherein R$^3$ is selected from the group consisting of hydrogen and methyl; wherein one of R$^4$ and R$^5$ is hydrogen and the other is methyl; wherein R$^6$ and R$^7$ are independently selected from the group consisting of hydrogen, methyl, ethyl, propyl, isopropyl, and butyl; wherein R$^8$ is selected from the group consisting of hydroxyl, amino, —N(CH$_3$)$_2$, and —NHCH$_3$; and wherein R$^9$ is selected from the group consisting of hydrogen, halide, lower alkyl, lower alkenyl, lower alkynyl, morpholinyl, piperazinyl, lower alkyl piperazinyl, heterocycloalkyl, lower cycloalkyl, lower cycloalkenyl; and lower alkyl, lower alkenyl, and lower alkynyl substituted with moieties selected from the group consisting of hydroxyl, amino, lower aminoalkyl, halide, lower alkoxy, lower alkoxyalkyl, lower alkoxycarbonyl, lower alkylcarbonylamino, carboxyl, amide, hydroxyamide, —CON-

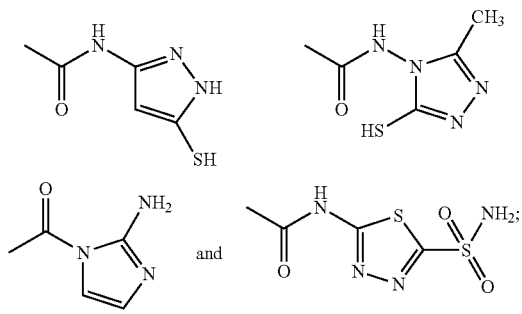

wherein R³ is selected from the group consisting of hydrogen and methyl; wherein one of R⁴ and R⁵ is hydrogen and the other is methyl; wherein R⁶ and R⁷ are independently selected from the group consisting of hydrogen, methyl, ethyl, propyl, isopropyl, and butyl; wherein R⁸ is selected from the group consisting of hydroxyl, amino, —N(CH₃)₂, and —NHCH₃; and wherein R⁹ is selected from the group consisting of hydrogen, halide, lower alkyl, lower alkenyl, lower alkynyl, morpholinyl, piperazinyl, lower alkyl piperazinyl, heterocycloalkyl, lower cycloalkyl, lower cycloalkenyl; and lower alkyl, lower alkenyl, and lower alkynyl substituted with moieties selected from the group consisting of hydroxyl, amino, lower aminoalkyl, halide, lower alkoxy, lower alkoxyalkyl, lower alkoxycarbonyl, lower alkylcarbonylamino, carboxyl, amide, hydroxyamide, —CONHCH₃, —NHCONH₂, —SO₂NH₂, —SO₂CH₃, —NHCOCH₃, —NHCSNH₂, and —NHSO₂CH₃; and salts thereof.

54. A method for reducing the formation or growth of a biofilm as set forth in claim 47 wherein the compound corresponds to the following chemical structure:

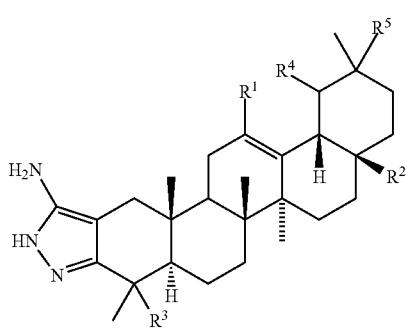

wherein R¹ is selected from the group consisting of heteroaryl; wherein R² is selected from the group consisting of carboxyl, amide, hydroxyamide, methylamide, —CH₂N(CH₃)₂, —CH₂NR⁶R⁷,

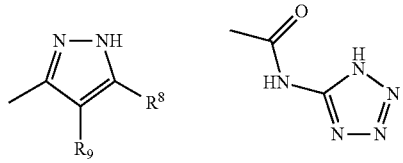

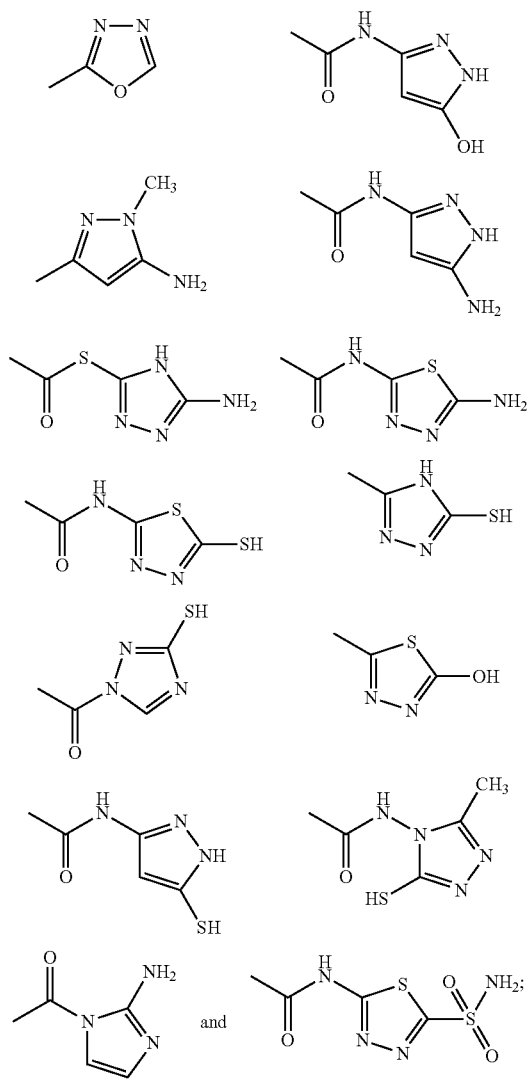

wherein R³ is selected from the group consisting of hydrogen and methyl; wherein one of R⁴ and R⁵ is hydrogen and the other is methyl; wherein R⁶ and R⁷ are independently selected from the group consisting of hydrogen, methyl, ethyl, propyl, isopropyl, and butyl; wherein R⁸ is selected from the group consisting of hydroxyl, amino, —N(CH₃)₂, and —NHCH₃; and wherein R⁹ is selected from the group consisting of hydrogen, halide, lower alkyl, lower alkenyl, lower alkynyl, morpholinyl, piperazinyl, lower alkyl piperazinyl, heterocycloalkyl, lower cycloalkyl, lower cycloalkenyl; and lower alkyl, lower alkenyl, and lower alkynyl substituted with moieties selected from the group consisting of hydroxyl, amino, lower aminoalkyl, halide, lower alkoxy, lower alkoxyalkyl, lower alkoxycarbonyl, lower alkylcarbonylamino, carboxyl, amide, hydroxyamide, —CONHCH₃, —NHCONH₂, —SO₂NH₂, —SO₂CH₃, —NHCOCH₃, —NHCSNH₂, and —NHSO₂CH₃; and salts thereof.

55. A method for reducing the formation or growth of a biofilm as set forth in claim 47 wherein the compound corresponds to the following chemical structure:

281

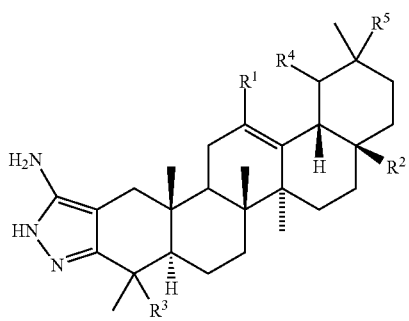

wherein R¹ is selected from the group consisting of heteroaryl; wherein R² is selected from the group consisting of

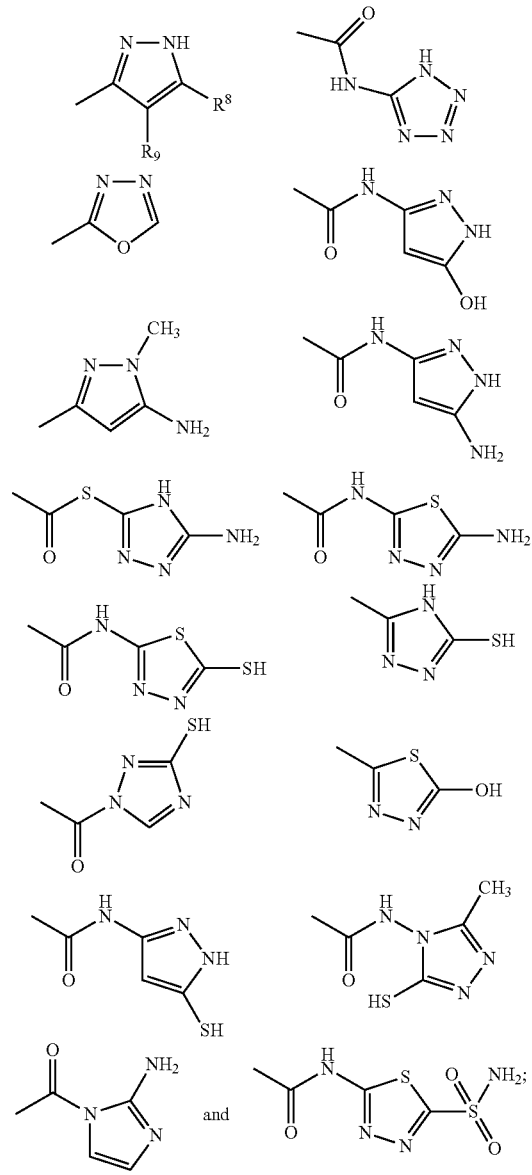

wherein R³ is selected from the group consisting of hydrogen and methyl; wherein one of R⁴ and R⁵ is hydrogen and the other is methyl; wherein R⁶ and R⁷ are independently selected from the group consisting of hydrogen, methyl, ethyl, propyl, isopropyl, and butyl; wherein R⁸ is selected from the group consisting of hydroxyl, amino, —N(CH₃)₂, and —NHCH₃; and wherein R⁹ is selected from the group consisting of hydrogen, halide, lower alkyl, lower alkenyl, lower alkynyl, morpholinyl, piperazinyl, lower alkyl piperazinyl, heterocycloalkyl, lower cycloalkyl, lower cycloalkenyl; and lower alkyl, lower alkenyl, and lower alkynyl substituted with moieties selected from the group consisting of hydroxyl, amino, lower aminoalkyl, halide, lower alkoxy, lower alkoxyalkyl, lower alkoxycarbonyl, lower alkylcarbonylamino, carboxyl, amide, hydroxyamide, —CONHCH₃, —NHCONH₂, —SO₂NH₂, —SO₂CH₃, —NHCOCH₃, —NHCSNH₂, and —NHSO₂CH₃; and salts thereof.

56. A method for reducing the formation or growth of a biofilm as set forth in claim 47 wherein the compound corresponds to the following chemical structure:

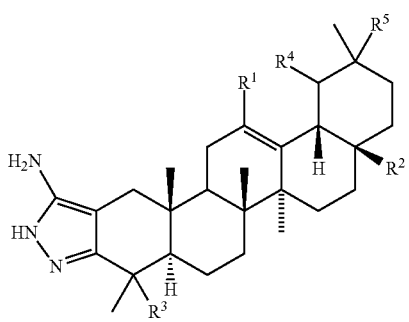

wherein R¹ is selected from the group consisting of hydrogen, methyl, halide, lower alkyl, and lower alkenyl; wherein R² is selected from the group consisting of amide, hydroxyamide, methylamide, —CH₂N(CH₃)₂, —CH₂NR⁶R⁷,

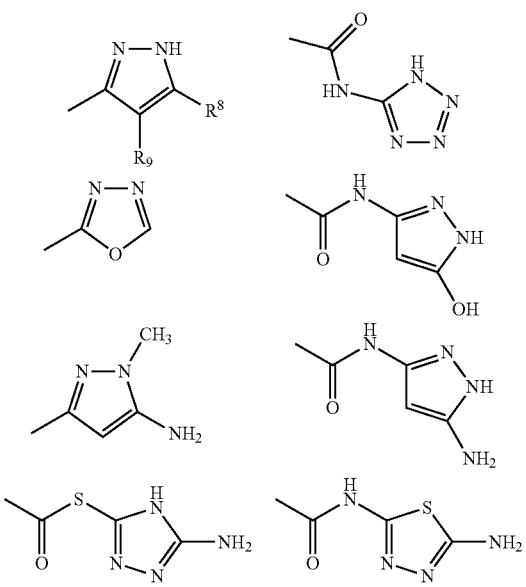

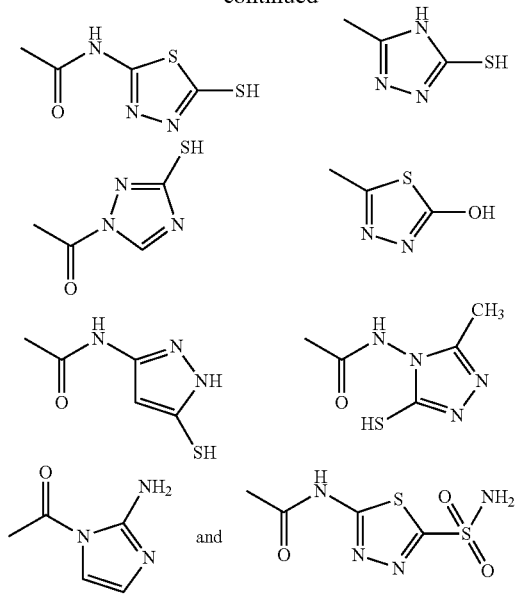

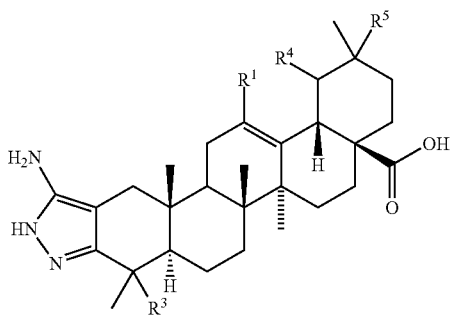

wherein $R^3$ is selected from the group consisting of hydrogen and methyl; wherein one of $R^4$ and $R^5$ is hydrogen and the other is methyl; wherein $R^6$ and $R^7$ are independently selected from the group consisting of hydrogen, methyl, ethyl, propyl, isopropyl, and butyl; wherein $R^8$ is selected from the group consisting of hydroxyl, amino, —N(CH$_3$)$_2$, and —NHCH$_3$; and wherein $R^9$ is selected from the group consisting of hydrogen, halide, lower alkyl, lower alkenyl, lower alkynyl, morpholinyl, piperazinyl, lower alkyl piperazinyl, heterocycloalkyl, lower cycloalkyl, lower cycloalkenyl; and lower alkyl, lower alkenyl, and lower alkynyl substituted with moieties selected from the group consisting of hydroxyl, amino, lower aminoalkyl, halide, lower alkoxy, lower alkoxyalkyl, lower alkoxycarbonyl, lower alkylcarbonylamino, carboxyl, amide, hydroxyamide, —CONHCH$_3$, —NHCONH$_2$, —SO$_2$NH$_2$, —SO$_2$CH$_3$, —NHCOCH$_3$, —NHCSNH$_2$, and —NHSO$_2$CH$_3$; and salts thereof.

57. A method for reducing the formation or growth of a biofilm as set forth in claim 47 wherein the compound corresponds to the following chemical structure:

wherein $R^1$ is selected from the group consisting of heteroaryl optionally substituted with moieties selected from the group consisting of lower alkyl, halide, lower haloalkyl, hydroxyl, amino, lower aminoalkyl, nitrile, lower alkyl nitrile, lower alkyl ethers, lower alkoxy, lower alkoxyalkyl, lower alkoxycarbonyl, lower alkylcarbonylamino, and thioalkyl; wherein $R^3$ is selected from the group consisting of hydrogen and methyl; and wherein one of $R^4$ and $R^5$ is hydrogen and the other is methyl; and salts thereof.

58. A method for reducing the formation or growth of a biofilm as set forth in claim 47 wherein the compound corresponds to the following chemical structure:

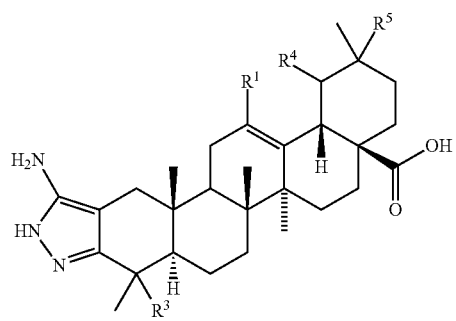

wherein $R^1$ is selected from the group consisting of heteroaryl; wherein $R^3$ is selected from the group consisting of hydrogen and methyl; and wherein one of $R^4$ and $R^5$ is hydrogen and the other is methyl; and salts thereof.

59. A method for reducing the formation or growth of a biofilm as set forth in claim 47 wherein the compound corresponds to the following chemical structure:

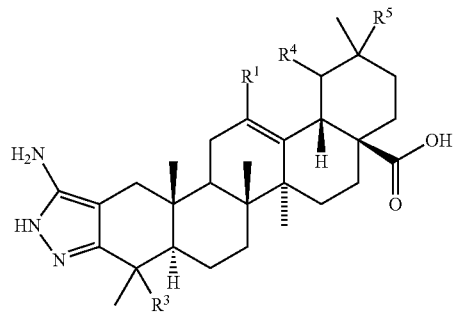

wherein $R^1$ is selected from the group consisting of halide, methyl, lower alkyl, and lower alkenyl; and wherein $R^3$ is selected from the group consisting of hydrogen and methyl; wherein one of $R^4$ and $R^5$ is hydrogen and the other is methyl; and salts thereof.

60. A method for reducing the formation or growth of a biofilm as set forth in claim 47 wherein the compound corresponds to the following chemical structure:

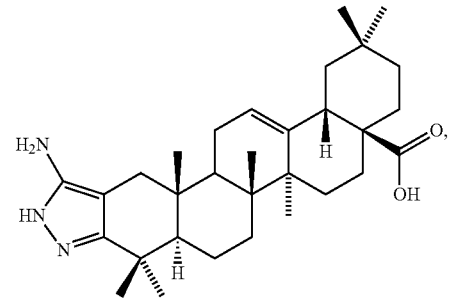

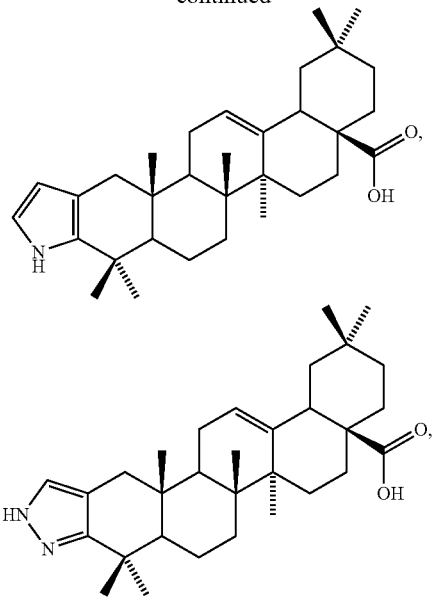

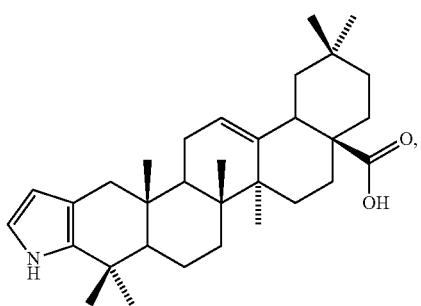

and salts thereof.

61. A method for reducing the formation or growth of a biofilm as set forth in claim 47 wherein the compound corresponds to the following chemical structure:

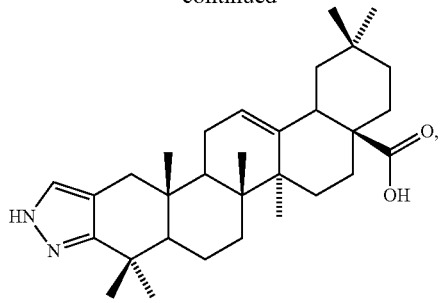

and salts thereof.

62. A method for reducing the formation or growth of a biofilm as set forth in claim 47 wherein the compound corresponds to the following chemical structure:

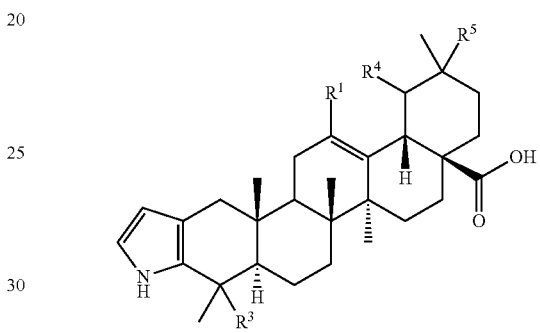

wherein $R^1$ is selected from the group consisting of hydrogen, methyl, halide, nitrile, lower alkyl, substituted lower alkyl, lower alkenyl, substituted lower alkenyl, lower alkynyl, substituted lower alkynyl, aryl, substituted aryl, heteroaryl, and substituted heteroaryl; wherein $R^3$ is selected from the group consisting of hydrogen and methyl; and wherein one of $R^4$ and $R^5$ is hydrogen and the other is methyl; and salts thereof.

* * * * *